US006828422B1

(12) United States Patent
Achim et al.

(10) Patent No.: US 6,828,422 B1
(45) Date of Patent: Dec. 7, 2004

(54) PROTEIN/(POLY)PEPTIDE LIBRARIES

(75) Inventors: Knappik Achim, Gräfelfing (DE); Peter Pack, München (DE); Ge Liming, München (DE); Moroney Simon, München (NZ); Plückthun Andreas, Zürich (CH)

(73) Assignee: Morphosys AG, Munich (DE)

( * ) Notice: Subject to any disclaimer, the term of this patent is extended or adjusted under 35 U.S.C. 154(b) by 0 days.

(21) Appl. No.: 09/490,324

(22) Filed: Jan. 24, 2000

Related U.S. Application Data

(62) Division of application No. 09/025,769, filed on Feb. 18, 1998, now Pat. No. 6,300,064, which is a continuation of application No. PCT/EP96/03647, filed on Aug. 19, 1996.

(30) Foreign Application Priority Data

Aug. 18, 1995 (EP) ............................................. 95113021

(51) Int. Cl.[7] ......................... C07K 16/00; C12P 21/08; C12P 21/06; C12Q 1/68
(52) U.S. Cl. .................... 530/380; 530/386; 530/387.1; 530/387.3; 530/350; 435/6; 435/69.7; 435/69.1
(58) Field of Search ................................ 530/350, 380, 530/386, 387.1, 387.3; 435/6, 69.7, 69.1

(56) References Cited

U.S. PATENT DOCUMENTS

| | | | |
|---|---|---|---|
| 5,476,786 A | | 12/1995 | Huston |
| 5,693,493 A | * | 12/1997 | Robinson et al. .......... 435/69.1 |
| 5,693,761 A | * | 12/1997 | Queen et al. ............ 536/23.53 |
| 5,840,479 A | | 11/1998 | Little et al. |

OTHER PUBLICATIONS

John De Kruif et al., "Selection and Application of Human Single Chain Fv Antibody Fragments from a Semi–synthetic Phage Antibody Display Library with Designed CDR3 Regions", J. Mol. Biol. (1995) 248, pp. 97–105.

Robert Schier et al., "Identification of functional and structural amino–acid residues by parsimonious mutagenesis", Gene, 169 (1996) pp. 147–155.

Lisa J. Garrard et al., "Selection of an anti–IGF–1 Fab from a Fab phage library created by mutagenesis of multiple CDR loops", Gene, 128 (1993) pp. 103–109.

Carlos F. Barbas, III, "Semisynthetic combinatorial antibody libraries: A chemical solution to the diversity problem", Proc. Natl. Acad. Sci. USA, vol. 89, May 1992, pp. 4457–4461.

\* cited by examiner

*Primary Examiner*—Mary K. Zeman
*Assistant Examiner*—Lori A. Clow
(74) *Attorney, Agent, or Firm*—Heller Ehrman White and McAuliffe LLP

(57) ABSTRACT

The present invention relates to synthetic DNA sequences which encode one or more collections of homologous proteins/(poly)peptides, and methods for generating and applying libraries of these DNA sequences. In particular, the invention relates to the preparation of a library of human-derived antibody genes by the use of synthetic consensus sequences which cover the structural repertoire of antibodies encoded in the human genome. Furthermore, the invention relates to the use of a single consensus antibody gene as a universal framework for highly diverse antibody libraries.

59 Claims, 220 Drawing Sheets

FIG. 2A

Figure 1:
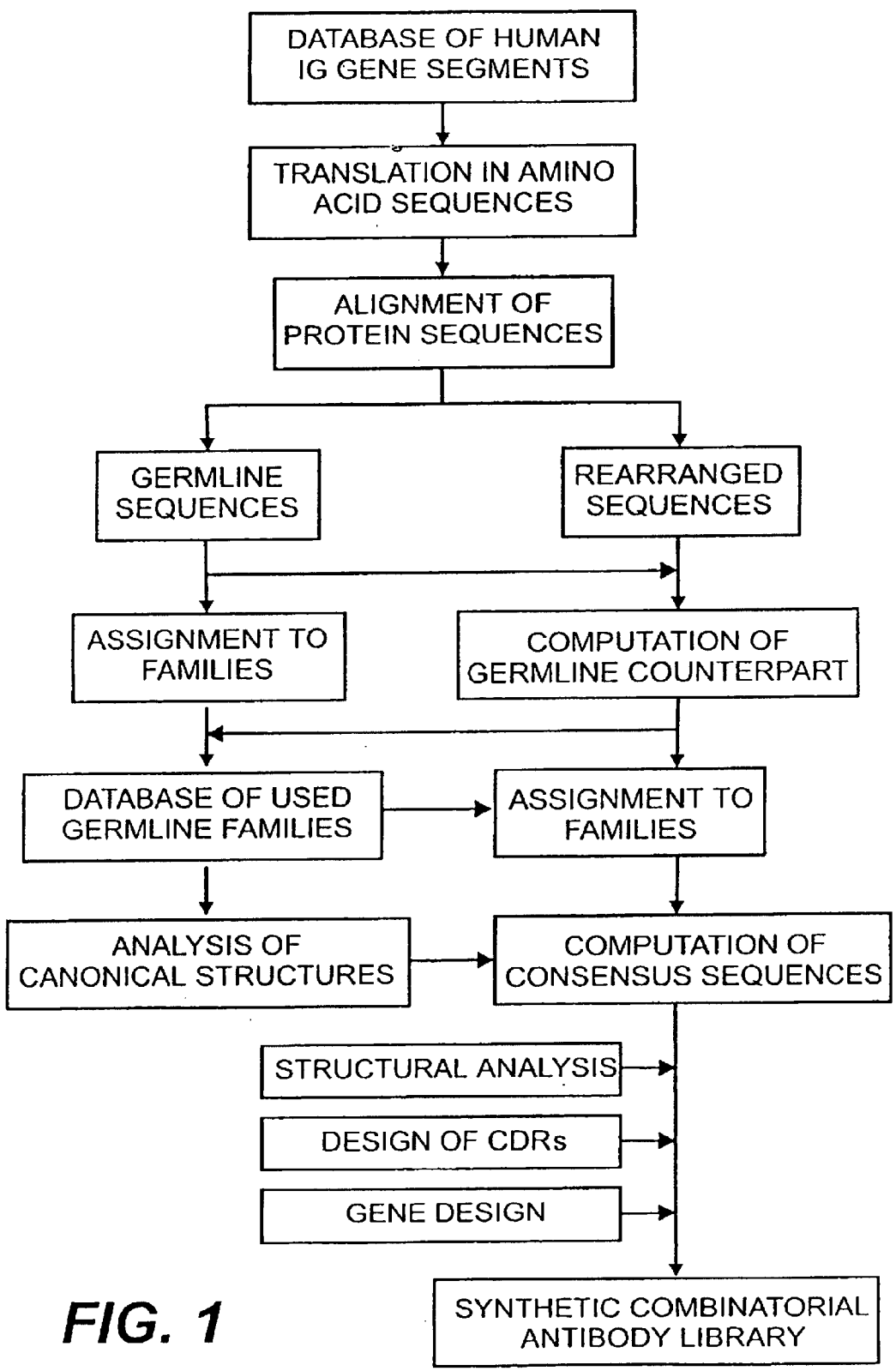
Figure 7E:
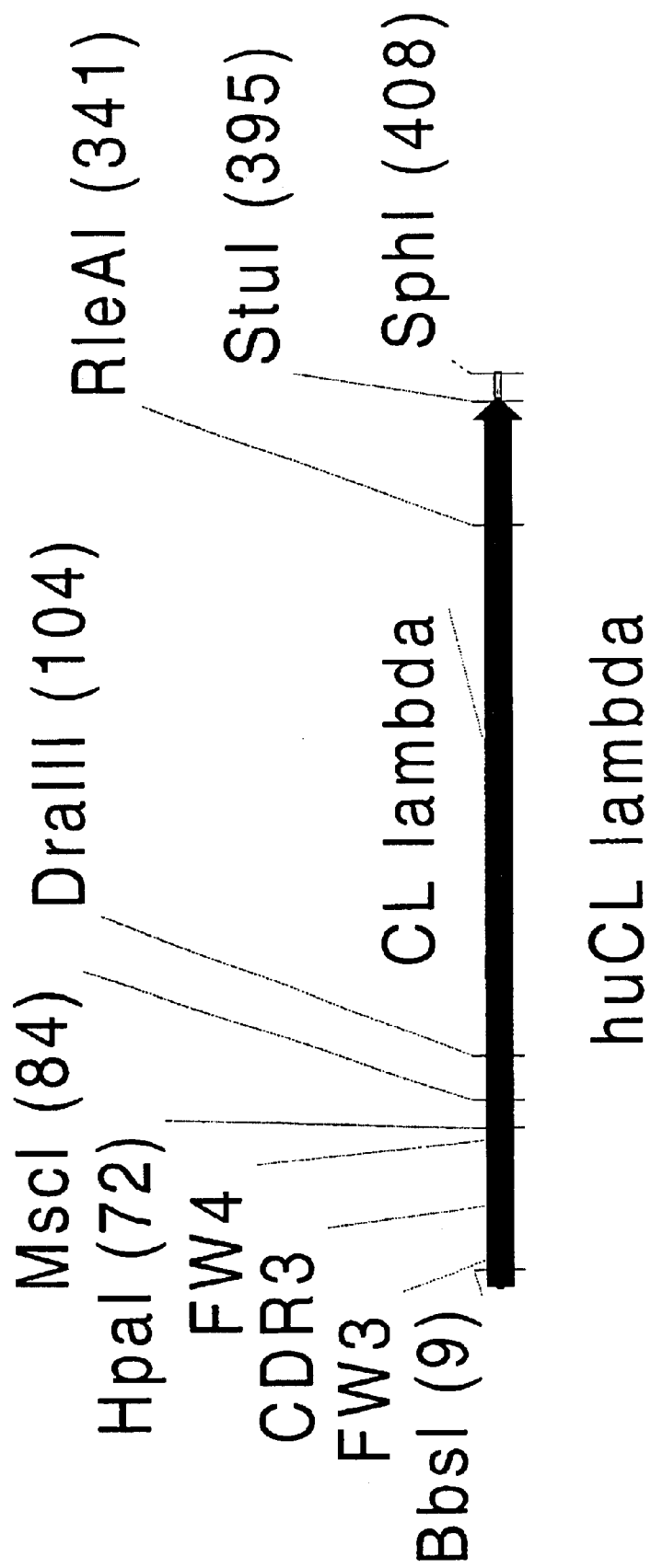

| | framework 1 | | CDRI | |
|---|---|---|---|---|
| | 1 2 3 4 5 6 7 8 9 10 11 12 13 14 15 16 17 18 19 20 21 22 23 | | 24 25 26 27 A B C | |
| Vκ1 | D I Q M T Q S P S S L S A S V G D R V T I T C R A S Q | - | - | - |
| Vκ2 | D I V M T Q S P L S L P V T P G E P A S I S C R S S Q | S | L | L |
| Vκ3 | D I V L T Q S P A T L S L S P G E R A T L S C R A S Q | S | - | - |
| Vκ4 | D I V M T Q S P D S L A V S L G E R A T I N C R S S Q | S | V | L |

| | CDR I | | framework 2 | | CDR II | |
|---|---|---|---|---|---|---|
| | 28 29 30 31 32 33 34 | | 35 36 37 38 39 40 41 42 43 44 45 46 47 48 49 | | 50 51 52 53 54 | |
| Vκ5 | - - - G I S S | Y L A W Y Q Q K P G K A P K L L I Y | A A S S L |
| Vκ6 | H S - N G Y N | Y L D W Y L Q K P G Q S P Q L L I Y | L G S N R |
| Vκ7 | - - - V S S S | Y L A W Y Q Q K P G Q A P R L L I Y | G A S S R |
| Vκ8 | Y S S N N K N | Y L A W Y Q Q K P G Q P P K L L I Y | W A S T R |

FIG. 2B

| CDRII | framework 3 | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
| Vk1 Q | S | G | V | P | S | R | F | S | G | S | G | S | G | T | D | F | T | L | T | I | S | S | L | Q | P | E | D | F | A |
| Vk2 A | S | G | V | P | D | R | F | S | G | S | G | S | G | T | D | F | T | L | K | I | S | R | V | E | A | E | D | V | G |
| Vk3 A | T | G | V | P | A | R | F | S | G | S | G | S | G | T | D | F | T | L | T | I | S | S | L | E | P | E | D | F | A |
| Vk4 E | S | G | V | P | D | R | F | S | G | S | G | S | G | T | D | F | T | L | T | I | S | S | L | Q | A | E | D | V | A |

| framework 3 | CDRIII | framework 4 | | | | | | | | | | | | | | | | | | | | | | |
|---|---|---|---|---|---|---|---|---|---|---|---|---|---|---|---|---|---|---|---|---|---|---|---|---|
| 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 |
| Vk1 T | Y | Y | C | Q | Q | H | Y | T | T | P | P | T | F | G | Q | G | T | K | V | E | I | K | R | T |
| Vk2 V | Y | Y | C | Q | Q | H | Y | T | T | P | P | T | F | G | Q | G | T | K | V | E | I | K | R | T |
| Vk3 V | Y | Y | C | Q | Q | H | Y | T | T | P | P | T | F | G | Q | G | T | K | V | E | I | K | R | T |
| Vk4 V | Y | Y | C | Q | Q | H | Y | T | T | P | P | T | F | G | Q | G | T | K | V | E | I | K | R | T |

```
         framework 1                                              CDRI
    1 2 3 4 5 6 7 8 9 10 11 12 13 14 15 16 17 18 19 20 21 22 23 24 25 26 27 28
vλ1 Q S V L T Q P P S -  V  S  G  A  P  G  Q  R  V  T  I  S  C  S  G  S  S  N  I
vλ2 Q S A L T Q P A S -  V  S  G  S  P  G  Q  S  I  T  I  S  C  T  G  T  S  S  D  V
vλ3 S Y E L T Q P P S -  V  S  V  A  P  G  Q  T  A  R  I  S  C  S  G  D  A  -  -  L CDRI              framework 2                              CDR II
    29 30 31 32 33 34 35 36 37 38 39 40 41 42 43 44 45 46 47 48 49 50 51 52 53 54 55 56 57
vλ1 G  S  N  -  Y  V  S  W  Y  Q  Q  L  P  G  T  A  P  K  L  L  I  Y  D  N  N  Q  R  P  S  G
vλ2 G  G  Y  N  Y  V  S  W  Y  Q  Q  H  P  G  K  A  P  K  L  M  I  Y  D  V  S  N  R  P  S  G
vλ3 G  D  K  -  Y  A  S  W  Y  Q  Q  K  P  G  Q  A  P  V  L  V  I  Y  D  D  S  D  R  P  S  G
```

*FIG. 2C*

FIG. 2D framework 3 (positions 58–87):

| | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
|---|---|---|---|---|---|---|---|---|---|---|---|---|---|---|---|---|---|---|---|---|---|---|---|---|---|---|---|---|---|---|
| vλ1 | V | P | D | R | F | S | G | S | K | S | G | T | S | A | S | L | A | I | T | G | L | Q | S | E | D | E | A | D | Y | Y |
| vλ2 | V | S | N | R | F | S | G | S | K | S | G | N | T | A | S | L | T | I | S | G | L | Q | A | E | D | E | A | D | Y | Y |
| vλ3 | I | P | E | R | F | S | G | S | N | S | G | N | T | A | T | L | T | I | S | G | T | Q | A | E | D | E | A | D | Y | Y |

CDRIII / framework 4 (positions 88–107):

| | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|
| vλ1 | C | Q | Q | H | Y | T | T | P | P | V | F | G | G | G | T | K | L | T | V | L G |
| vλ2 | C | Q | Q | H | Y | T | T | P | P | V | F | G | G | G | T | K | L | T | V | L G |
| vλ3 | C | Q | Q | H | Y | T | T | P | P | V | F | G | G | G | T | K | L | T | V | L G |

FIG. 2E framework 1 (positions 1–30):

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|
| VH1A | Q | V | Q | L | V | Q | S | G | A | E | V | K | K | P | G | S | S | V | K | V | S | C | K | A | S | G | G | T | F | S |
| VH1B | Q | V | Q | L | V | Q | S | G | A | E | V | K | K | P | G | A | S | V | K | V | S | C | K | A | S | G | Y | T | F | T |
| VH2  | Q | V | Q | L | K | E | S | G | P | A | L | V | K | P | T | Q | T | L | T | L | T | C | T | F | S | G | F | S | L | S |
| VH3  | E | V | Q | L | V | E | S | G | G | G | L | V | Q | P | G | G | S | L | R | L | S | C | A | A | S | G | F | T | F | S |
| VH4  | Q | V | Q | L | Q | E | S | G | P | G | L | V | K | P | S | E | T | L | S | L | T | C | T | V | S | G | G | S | I | S |
| VH5  | E | V | Q | L | V | Q | S | G | A | E | V | K | K | P | G | E | S | L | K | I | S | C | K | G | S | G | Y | S | F | T |
| VH6  | Q | V | Q | L | Q | Q | S | G | P | G | L | V | K | P | S | Q | T | L | S | L | T | C | A | I | S | G | D | S | V | S |

CDR I (31, B, 32–35) / framework 2 (36–49) / CDR II (50, 51, 52, A, 53–57):

| | 31 | B | 32 | 33 | 34 | 35 | 36 | 37 | 38 | 39 | 40 | 41 | 42 | 43 | 44 | 45 | 46 | 47 | 48 | 49 | 50 | 51 | 52 | A | 53 | 54 | 55 | 56 | 57 |
|---|---|---|---|---|---|---|---|---|---|---|---|---|---|---|---|---|---|---|---|---|---|---|---|---|---|---|---|---|---|
| VH1A | S | – | – | Y | A | I | S | W | V | R | Q | A | P | G | Q | G | L | E | W | M | G | G | I | I | P | – | I | F | G | T | A |
| VH1B | S | – | – | Y | Y | M | H | W | V | R | Q | A | P | G | Q | G | L | E | W | M | G | W | I | N | P | – | N | S | G | G | T |
| VH2  | T | S | G | V | G | V | G | W | I | R | Q | P | P | G | K | A | L | E | W | L | A | L | I | D | – | W | D | D | D | K |
| VH3  | S | – | – | Y | A | M | S | W | V | R | Q | A | P | G | K | G | L | E | W | V | S | A | I | S | G | – | S | G | G | S | T |
| VH4  | S | – | – | Y | Y | W | S | W | I | R | Q | P | P | G | K | G | L | E | W | I | G | Y | I | Y | Y | – | S | G | S | T |
| VH5  | S | – | – | Y | W | I | G | W | V | R | Q | M | P | G | K | G | L | E | W | M | G | I | I | Y | P | – | G | D | S | D | T |

VH6: S N S A A W N W I R Q S P G R G L E W L G R T Y Y R - S K W Y N

| | CDRII | | | | | | | | | framework 3 | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 |
| VH1A | N | Y | A | Q | K | F | Q | G | R | V | T | I | T | A | D | E | S | T | S | T | A | Y | M | E | L | S | S | L | R | S | E |
| VH1B | N | Y | A | Q | K | F | Q | G | R | V | T | I | T | A | D | E | S | T | S | T | A | Y | M | E | L | S | S | L | R | S | E |
| VH2 | Y | Y | S | T | S | L | K | T | R | L | T | T | I | S | K | D | T | S | K | N | Q | V | V | L | T | M | T | N | M | D | P V |
| VH3 | Y | Y | A | D | S | V | K | G | R | F | T | I | S | R | D | N | S | K | N | T | L | Y | L | Q | M | N | S | L | R | A | E |
| VH4 | N | Y | N | P | S | L | K | S | R | V | T | I | S | V | D | T | S | K | N | Q | F | S | L | K | L | S | S | V | T | A | A |
| VH5 | R | Y | S | P | S | F | Q | G | Q | V | T | I | S | A | D | K | S | I | S | T | A | Y | L | Q | W | S | S | L | K | A | S |
| VH6 | D | Y | A | V | S | V | K | S | R | I | T | I | N | P | D | T | S | K | N | Q | F | S | L | Q | L | N | S | V | T | P | E |

| | framework 3 | | | | | | | | | | CDRIII | | | | | | | | | framework 4 | | | | | | | | | | |
|---|---|---|---|---|---|---|---|---|---|---|---|---|---|---|---|---|---|---|---|---|---|---|---|---|---|---|---|---|---|---|
| | 86 | 87 | 88 | 89 | 90 | 91 | 92 | 93 | 94 | 95 | 96 | 97 | 98 | 99 | 100 | 100A | 100B | 100C | 101 | 102 | 103 | 104 | 105 | 106 | 107 | 108 | 109 | 110 | 111 | 112 | 113 |
| VH1A | D | T | A | V | Y | Y | C | A | R | W | G | G | D | G | F | Y | A | M | D | Y | W | G | Q | G | T | L | V | T | V | S | S |
| VH1B | D | T | A | V | Y | Y | C | A | R | W | G | G | D | G | F | Y | A | M | D | Y | W | G | Q | G | T | L | V | T | V | S | S |
| VH2 | D | T | A | T | Y | Y | C | A | R | W | G | G | D | G | F | Y | A | M | D | Y | W | G | Q | G | T | L | V | T | V | S | S |
| VH3 | D | T | A | V | Y | Y | C | A | R | W | G | G | D | G | F | Y | A | M | D | Y | W | G | Q | G | T | L | V | T | V | S | S |
| VH4 | D | T | A | V | Y | Y | C | A | R | W | G | G | D | G | F | Y | A | M | D | Y | W | G | Q | G | T | L | V | T | V | S | S |

FIG. 2F

VH5  DTAMYYCARWGGDGFYAMDYWGQGTLVTVSS
VH6  DTAVYYCARWGGDGFYAMDYWGQGTLVTVSS

*FIG. 2G*

```
D   I   Q   M   T   Q   S   P   S   S   L   S   A   S   V   G   D
EcoRV                   BanII
~~~~~
GATATCCAGA TGACCCAGAG CCCGTCTAGC CTGAGCGCGA GCGTGGGTGA
CTATAGGTCT ACTGGGTCTC GGGCAGATCG GACTCGCGCT CGCACCCACT

R   V   T   I   T   C   R   A   S   Q   G   I   S   S   Y   L
                            PstI
                            ~~~~~
TCGTGTGACC ATTACCTGCA GAGCGAGCCA GGGCATTAGC AGCTATCTGG
AGCACACTGG TAATGGACGT CTCGCTCGGT CCCGTAATCG TCGATAGACC

A   W   Y   Q   Q   K   P   G   K   A   P   K   L   L   I   Y   A
        KpnI                    SexAI                       AseI
        ~~~~~                   ~~~~~                       ~~~~~
CGTGGTACCA GCAGAAACCA GGTAAAGCAC CGAAACTATT AATTTATGCA
GCACCATGGT CGTCTTTGGT CCATTTCGTG GCTTTGATAA TTAAATACGT

A   S   S   L   Q   S   G   V   P   S   R   F   S   G   S   G   S
                                SanDI                           BamHI
                                ~~~~~                           ~~~~~
GCCAGCAGCT TGCAAAGCGG GGTCCCGTCC CGTTTTAGCG GCTCTGGATC
CGGTCGTCGA ACGTTTCGCC CCAGGGCAGG GCAAAATCGC CGAGACCTAG
```

*FIG. 3A*

```
G  T  D  F  T  L  T  I  S  S  L  Q  P  E  D  F
                                      Eco57I
                                      ~~~~~~~    BbsI
                                                 ~~~~~~~
CGGCACTGAT TTTACCCTGA CCATTAGCAG CCTGCAACCT GAAGACTTTG
GCCGTGACTA AAATGGGACT GGTAATCGTC GGACGTTGGA CTTCTGAAAC
BamHI
~

A  T  Y  Y  C  Q  Q  H  Y  T  T  P  P  T  F  G  Q
                                                 MscI
                                                 ~~~~~~~
CGACCTATTA TTGCCAGCAG CATTATACCA CCCCGCCCGAC CTTTGGCCAG
GCTGGATAAT AACGGTCGTC GTAATATGGT GGGGCGGGCTG GAAACCGGTC

G  T  K  V  E  I  K  R  T
                    BsiWI
                    ~~~~~
GGTACGAAAG TTGAAATTAA ACGTACG
CCATGCTTTC AACTTTAATT TGCATGC
```

FIG. 3B

```
D   I   V   M   T   Q   S   P   L   S   L   P   V   T   P   G   E
EcoRV           BanII
~~~~~~          ~~~~~~
GATATCGTGA TGACCCAGAGC CCCACTGAGC CTGCCAGTGA CTCCGGGCGA
CTATAGCACT ACTGGGTCTC GGGTGACTCG GACGGTCACT GAGGCCCGCT

P   A   S   I   S   C   R   S   S   Q   S   L   L   H   S   N
              PstI
              ~~~~~~
GCCTGCGAGC ATTAGCTGCA GAAGCAGCCA AAGCCTGCTG CATAGCAACG
CGGACGCTCG TAATCGACGT CTTCGTCGGT TTCGGACGAC GTATCGTTGC

G   Y   N   Y   L   D   W   Y   L   Q   K   P   G   Q   S   P   Q
              KpnI                                SexAI
              ~~~~~~                              ~~~~~~
GCTATAACTA TCTGGATTGG TACCTTCAAA AACCAGGTCA AAGCCCGCAG
CGATATTGAT AGACCTAACC ATGGAAGTTT TTGGTCCAGT TTCGGGCGTC
```

*FIG. 3C*

```
 L   L   I   Y   L   G   S   N   R   A   S   G   V   P   D   R   F
CTATTAATTT ATCTGGCAGC CAACCGTGCC AGTGGGGTCC CGGATCGTTT
GATAATTAAA TAGACCCGTC GTTGGCACGG TCACCCCAGG GCCTAGCAAA
                                      ~~~~~~~~~~~
                                          SanDI

S   G   S   G   S   G   T   D   F   T   L   K   I   S   R   V
TAGCGGCTCT GGATCCGGCA CCGATTTTAC CCTGAAAATT AGCCGTGTGG
ATCGCCGAGA CCTAGGCCGT GGCTAAAATG GGACTTTTAA TCGGCACACC
            ~~~~~~
            BamHI

E   A   E   D   V   G   V   Y   Y   C   Q   Q   H   Y   T   T   P
AAGCTGAAGA CGTGGGCGTG TATTATTGCC AGCAGCATTA TACCACCCCG
TTCGACTTCT GCACCCGCAC ATAATAACGG TCGTCGTAAT ATGGTGGGGC
    ~~~~~~
    Eco57I
       ~~~~~~
       BbsI
```

FIG. 3D

```
P  T  F  G  Q     G  T  K  V  E     I  K  R  T
            MscI                          BsiWI
            ~~~~~~~~                      ~~~~~~
CCGACCTTTG GCCAGGGTAC GAAAGTTGAA ATTAAACGTA CG
GGCTGGAAAC CGGTCCCATG CTTTCAACTT TAATTTGCAT GC
```

FIG. 3E

```
 D   I   V   L   T   Q   S   P   A   T   L   S   L   S   P   G   E
EcoRV                   BanII
GATATCGTGC TGACCCAGAG CCCGGGCGACC CTGAGCCTGT CTCCGGGCGA
CTATAGCACG ACTGGGTCTC GGGCCCGCTGG GACTCGGACA GAGGCCCGCT

R   A   T   L   S   C   R   A   S   Q   S   V   S   S   Y
                        PstI
ACGTGGCGACC CTGAGCTGCA GAGCGAGCCA GAGCGTGAGC AGCAGCTATC
TGCACCGCTGG GACTCGACGT CTCGCTCGGT CTCGCACTCG TCGTCGATAG

L   A   W   Y   Q   Q   K   P   G   Q   A   P   R   L   L   I   Y
           KpnI                         SexAI                AseI
```

FIG. 3F

```
TGGGCGTGGTA CCAGCAGAAA CCAGGTCAAG CACCGCGTCT ATTAATTTAT
ACCGCACCAT GGTCGTCTTT GGTCCAGTTC GTGGCGCAGA TAATTAAATA

G  A  S  S   R  A  T     G  V  P    A  R  F  S    G  S  G
                                     SanDI              BamHI
                                     ~~~~~~~           ~

GGCGCGAGCA GCCGTGCAAC TGGGGTCCCG GCGGCGTTTTA GCGGCTCTGG
CCGCGCTCGT CGGCACGTTG ACCCCAGGGC CGCCGCAAAAT CGCCGAGACC

S  G  T  D   F  F  T  L   T  I  S    S  L  E    P  E  D
                                                  Eco57I
                                                  ~~~~~~~

BamHI
~~~~
ATCCGGCACG GATTTACCC TGACCATTAG CAGCCTGGAA CCTGAAGACT
TAGGCCGTGC CTAAAATGGG ACTGGTAATC GTCGGACCTT GGACTTCTGA
                                           BbsI
                                           ~~~~
```

FIG. 3G

```
 F   A   V   Y   Y   C   Q   Q   H   Y   T   T   P   P   T   F   G
                                                                MscI
                                                                ~~~
TTGCGGTGTA TTATTGCCAG CAGCATTATA CCACCCCGCC GACCTTTGGC
AACGCCACAT AATAACGGTC GTCGTAATAT GGTGGGGCGG CTGGAAACCG

Q   G   T   K   V   E   I   K   R   T
MscI                             BsiWI
 ~                               ~~~~~~
CAGGGTACGA AAGTTGAAAT TAAACGTACG
GTCCCATGCT TTCAACTTTA ATTTGCATGC
```

FIG. 3H

```
D  I  V  M  T  Q  S  P  D  S  L  A  V  S  L  G  E
      EcoRV                  BanII
      ~~~~~                  ~~~~~
GATATCGTGA TGACCCAGAGAG CCCGGATAGC CTGGCGGTGA GCCTGGGCGA
CTATAGCACT ACTGGGTCTC GGGCCTATCG GACCGCCACT CGGACCCGCT

R  A  T  I  N  C  R  S  S  Q  S  V  L  Y  S  S
               PstI
               ~~~~~
ACGTGCGACC ATTAACTGCA GAAGCAGCCA GAGCGTGCTG TATAGCAGCA
TGCACGCTGG TAATTGACGT CTTCGTCGGT CTCGCACGAC ATATCGTCGT

N  N  K  N  Y  L  A  W  Y  Q  Q  K  P  G  Q  P  P
                  KpnI               SexAI
                  ~~~~~               ~~~~~
ACAACAAAAA CTATCTGGCG TGGTACCAGC AGAAACCAGG TCAGCCCGCCG
TGTTGTTTTT GATAGACCGC ACCATGGTCG TCTTTGGTCC AGTCGGGCGGC
```

FIG. 31

```
K  L  L  I  Y  W  A  S  T  R  E  S  G  V  P  D  R
AAACTATTAA TTTATTGGGC ATCCACCCGT GAAAGCGGGG TCCCGGATCG
TTTGATAATT AAATAACCCG TAGGTGGGCA CTTTCGCCCC AGGGCCTAGC
           AseI                                SanDI

F  S  G  S  G  S  G  T  D  F  T  L  T  I  S  S
TTTTAGCGGC TCTGGATCCG GCACTGATTT TACCCTGACC ATTTCGTCCC
AAAATCGCCG AGACCTAGGC CGTGACTAAA ATGGGACTGG TAAAGCAGGG
                BamHI

L  Q  A  E  D  V  A  V  Y  Y  C  Q  Q  H  Y  T  T
      Eco57I
       BbsI
```

FIG. 3J

```
TGCAAGCTGA AGACGTGGCG GTGTATTATT GCCAGCAGCA TTATACCACC
ACGTTCGACT TCTGCACCGC CACATAATAA CGGTCGTCGT AATATGGTGG
  P  P  T  F  G  Q  G     T  K  V  E  I  K  R    T
                  MscI                         BsiWI
                  ~~~~~~                       ~~~~~~

CCGCCGACCT TTGGCCAGGG TACGAAAGTT GAAATTAAAC GTACG
GGCGGCTGGA AACCGGTCCC ATGCTTTCAA CTTTAATTTG CATGC
```

*FIG. 3K*

```
Q  S  V  L  T  Q  P  P  S  V  S  G  A  P  G  Q  R

CAGAGCGTGC TGACCCAGCC GCCTTCAGTG AGTGGGCCAC CAGGTCAGCG
GTCTCGCACG ACTGGGTCGG CGGAAGTCAC TCACCGGCGTG GTCCAGTCGC
                                 Eco57I          SexAI

V  T  I  S  C  S  G  S  S  S  N  I  G  S  N  Y

TGTGACCATC TCGTGTAGCG GCAGCAGCAG CAACATTGGC AGCAACTATG
ACACTGGTAG AGCACATCGC CGTCGTCGTC GTTGTAACCG TCGTTGATAC
           BssSI

V  S  W  Y  Q  Q  L  P  G  T  A  P  K  L  L  I  Y

TGAGCTGGTA CCAGCAGTTG CCCGGGACGG CGCCGAAACT GCTGATTTAT
ACTCGACCAT GGTCGTCAAC GGGCCCTGCC GCGGCTTTGA CGACTAAATA
           KpnI       XmaI  BbeI
```

*FIG. 4A*

```
D   N   N   Q   R   P   S         G   V   P   D   R   F   S   G   S   K
                  Bsu36I                                        BamHI
                  ~~~~~~                                        ~~~~~~
GATAACAACC AGCGTCCCTC AGGCGTGCCG GATCGTTTTA GCGGATCCAA
CTATTGTTGG TCGCAGGGAG TCCGCACGGC CTAGCAAAAT CGCCTAGGTT

S   G   T   S   A   S   L   A   I   T   G   L   Q   S   E   D
                                                          BbsI
                                                          ~~~~
AGCGGCACC  TCGGCGAGCC TTGCGATTAC AGGGCCTGCAA AGCGAAGACG
TCGCCGTGG  AGCCGCTCGG AACGCTAATG TCCCGGACGTT TCGCTTCTGC

E   A   D   Y         Y   C   Q         Q   H   Y   T         P   P         V   F   G
AAGCGGATTA TTATTGCCAG CAGCATTATA CCACCCCGCC TGTGTTTGGC
TTCGCCTAAT AATAACGGTC GTCGTAATAT GGTGGGGCGG ACACAAACCG
```

*FIG. 4B*

```
G  G  G  T  K    L    T  V  L  G
              HpaI         MscI
              ~~~~~        ~~~
GGGGGCACGA AGTTAACCGT TCTTGGC
CCCCCGTGCT TCAATTGGCA AGAACCG
```

FIG. 4C

```
Q  S  A  L  T  Q  P  A  S  V  S  G  S  P  G  Q  S

CAGAGGCGCAC TGACCCCAGCC AGCTTCAGTG AGCGGCTCAC CAGGTCAGAG
GTCTCGCCGTG ACTGGGGTCGG TCGAAGTCAC TCGCCGAGTG GTCCAGTCTC
                                  Eco57I
                                  ~~~~~
                                                      SexAI
                                                      ~~~~~

I  T  I  S  C  T  G  T  S  S  D  V  G  G  Y  N
         BssSI
         ~~~~~

CATTACCATC TCGTGTACGG GTACTAGCAG CGATGTGGGC GGCTATAACT
GTAATGGTAG AGCACATGCC CATGATCGTC GCTACACCCG CCGATATTGA

Y  V  S  W  Y  Q  Q  H  P  G  K  A  P  K  L  M  I
         KpnI              XmaI        BbeI
         ~~~~~             ~~~~~       ~~~~~

ATGTGAGCTG GTACCAGCAG CATCCCGGGA AGGCGCCGAA ACTGATGATT
TACACTCGAC CATGGTCGTC GTAGGGCCCT TCCGCGGCTT TGACTACTAA
```

FIG. 4D

```
Y  D  V  S  N  R  P  S  G  V  S  N  R  F  S  G  S
                  Bsu36I                        BamHI
                  ~~~~~~~                       ~~~~~
TATGATGTGA GCAACCGTCC CTCAGGGCGTG AGCAACCGTT TTAGCGGATC
ATACTACACT CGTTGGCAGG GAGTCCGCAC TCGTTGGCAA AATCGCCTAG

K  S  G  N  T  A  S  L  T  I  S  G  L  Q  A  E
BamHI                                         BbsI
~                                             ~~~~~
CAAAAGCGGC AACACCGCGA GCCTGACCAT TAGCGGCCTG CAAGCCGAAG
GTTTTCGCCG TTGTGGCGCT CGGACTGGTA ATCGCCGGAC GTTCGGCCTTC

D  E  A  D  Y  Y  C  Q  Q  H  Y  T  T  P  P  V  F
BbsI
~
ACGAAGCGGA TTATTATTGC CAGCAGCATT ATACCACCCC GCCTGTGTTT
TGCTTCGCCT AATAATAACG GTCGTCGTAA TATGGTGGGG CGGACACAAA
```

*FIG. 4E*

```
 G  G  G  T   K   L   T      V   L   G
                  HpaI           MscI
                 ~~~~~           ~~~
GGCGGGGGCA CGAAGTTAAC CGTTCTTGGC
CCGCCCCCGT GCTTCAATTG GCAAGAACCG
```

FIG. 4F

```
  S   Y   E   L   T   Q   P   P   S   V   S   V   A   P   G   Q   T
AGCTATGAAC TGACCCAGCC GCCTTCAGTG AGCGGTTGCAC CAGGTCAGAC
TCGATACTTG ACTGGGTCGG CGGAAGTCAC TCGCAACGTG GTCCAGTCTG
                                  Eco57I              SexAI
                                  ~~~~~               ~~~~~

A   R   I   S   C   S   G   D   A   L   G   D   K   Y   A   S
CGGCGTATC TCGTGTAGCG GCGATGCGCT GGGGCGATAAA TACGCGAGCT
GCCGCATAG AGCACATCGC CGCTACGCGA CCCGCTATTT ATGCGCTCGA
          BssSI

W   Y   Q   Q   K   P   G   Q   A   P   V   L   V   I   Y   D   D
          KpnI    XmaI    BbeI
          ~~~~    ~~~~    ~~~~
```

FIG. 4G

```
GGTACCAGCA GAAACCCGGG CAGGCGCCAG TTCTGGTGAT TTATGATGAT
CCATGGTCGT CTTTGGGCCC GTCCGCGGTC AAGACCACTA AATACTACTA
 S   D   R   P   S   G   I   P   E   R   F   S   G   S   N   S   G
                   Bsu36I                           BamHI
                   ~~~~~~                           ~~~~~~

TCTGACCGTC CCTCAGGCAT CCCGGAACGC TTTAGCGGAT CCAACAGCGG
AGACTGGCAG GGAGTCCGTA GGGCCTTGCG AAATCGCCTA GGTTGTCGCC
 N   T   A   T   L   T   I   S   G   T   Q   A   E   D   E   A
                                                 BbsI
                                                 ~~~~~~
```

FIG. 4H

```
CAACACCGCG ACCCTGACCA TTAGCGGCAC TCAGGCGGAA GACGAAGCGG
GTTGTGGCGC TGGGACTGGT AATCGCCGTG AGTCCGCCTT CTGCTTCGCC

D  Y  Y  C    Q  Q  H    Y  T  T  P    P  V  F    G  G  G
ATTATTATTG CCAGCAGCAT TATACCACCC CGCCTGTGTT TGGCGGCGGC
TAATAATAAC GGTCGTCGTA ATATGGTGGG GCGGACACAA ACCGCCGCCG

T  K  L  T   V  L  G
   HpaI       MscI
 ~~~~~~~~    ~~~~~~
ACGAAGTTAA CCGTTCTTGG C
TGCTTCAATT GGCAAGAACC G
```

*FIG. 41*

```
Q  V  Q  L   V  Q  S   G  A  E   V  K  K  P   G  S  S
      MfeI
CAGGTGCAAT TGGTTCAGTC TGGCGCGGAA GTGAAAAAAC CGGGGCAGCAG
GTCCACGTTA ACCAAGTCAG ACCGCGCCTT CACTTTTTTG GCCCGTCGTC

V  K  V   S  C  K  A   S  G  G   T  F  S   S  Y  A
                          BspEI
CGTGAAAGTG AGCTGCAAAG CCTCCGGAGG CACTTTTAGC AGCTATGCGA
GCACTTTCAC TCGACGTTTC GGAGGCCTCC GTGAAAATCG TCGATACGCT

I  S  W  V   R  Q  A   P  G  Q   G  L  E  W   M  G  G
                 BstXI                      XhoI
TTAGCTGGGT GCGCCAAGCC CCTGGGCAGG GTCTCGAGTG GATGGGCGGC
AATCGACCCA CGCGGTTCGG GGACCCGTCC CAGAGCTCAC CTACCCGCCG
```

FIG. 5A

```
  I   P   I   F   G   T    A   N   Y    A   Q   K   F    Q   G   R
ATTATTCCGA TTTTGGCACA GGCGAACTAC GGGCAGAAGT TTCAGGGCCG
TAATAAGGCT AAAAACCGTG CCGCTTGATG CGCGTCTTCA AAGTCCCGGC

V   T   I    T   A   D   E    S   T   S    T   A   Y   M   E   L
GGTGACCATT ACCGCGGATG AAAGCACCAG CACCGCGTAT ATGGAACTGA
CCACTGGTAA TGGCGCCTAC TTTCGTGGTC GTGGCGCATA TACCTTGACT
    BstEII                                    EagI

S   S   L   R    S   E   D    T   A   V    Y   Y   C   A   R   W   G
GCAGCCTGCG TAGCGAAGAT ACGGCCGTGT ATTATTGCGC GCGTTGGGGC
CGTCGGACGC ATCGCTTCTA TGCCGGCACA TAATAACGCG CGCAACCCCG
                                              BssHII
```

FIG. 5B

```
 G  D  G  F     Y  A  M  D  Y  W     G  Q  G        T  L  V  T
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG
                                       StyI
                                      ~~~~~

V  S  S
    BlpI
   ~~~~
GGTTAGCTCA G
CCAATCGAGT C
```

FIG. 5C

```
Q  V  Q  L  V  Q  S  G  A  E  V  K  K  P  G  A  S
   MfeI
   ~~~~
CAGGTGCAAT TGGTTCAGAG CGGGCGGGAA GTGAAAAAAC CGGGCGCGAG
GTCCACGTTA ACCAAGTCTC GCCCGCCCTT CACTTTTTTG GCCCGCGCTC

V  K  V  S  C  K  A  S  G  Y  T  F  T  S  Y  Y
                          BspEI
                          ~~~~~
CGTGAAAGTG AGCTGCAAAG CCTCCGGATA TACCTTTACC AGCTATTATA
GCACTTTCAC TCGACGTTTC GGAGGCCTAT ATGGAAATGG TCGATAATAT

M  H  W  V  R  Q  A  P  G  Q  G  L  E  W  M  G  W
                 BstXI                 XhoI
                 ~~~~~~~~~~~~~         ~~~~~
TGCACTGGGT CCGCCAAGCC CCTGGGCCAGG GTCTCGAGTG GATGGGCTGG
ACGTGACCCA GGCGGTTCGG GGACCCGTCC CAGAGCTCAC CTACCCGACC
```

FIG. 5D

```
  I  N  P  N           S  G  G        T  N  Y     A  Q  K  F  Q  G  R
ATTAACCCGA ATAGCGGCGG CACGAACTAC GCGCAGAAAGT TTCAGGGCCG
TAATTGGGCT TATCGCCGCC GTGCTTGATG CGCGTCTTCA AAGTCCCGGC

V  T  M     T  R  D  T  S  I  S        T  A  Y     M  E  L
GGTGACCATG ACCCGTGATA CCAGCATTAG CACCGCGTAT ATGGAACTGA
CCACTGGTAC TGGGCACTAT GGTCGTAATC GTGGCGCATA TACCTTGACT
BstEII
~~~~~~                              EagI
                                    ~~~~

S  S  L  R     S  E  D     T  A  V     Y  Y  C  A  R  W  G
GCAGCCTGCG TAGCGAAGAT ACGGCCGTGT ATTATTGCGC GCGTTGGGGC
CGTCGGACGC ATCGCTTCTA TGCCGGCACA TAATAACGCG CGCAACCCCG
                                         BssHII
                                         ~~~~~
```

FIG. 5E

```
G  D  G  F  Y  A  M  D  Y  W  G  Q  G  T  L  V  T
                                   StyI
                                   ~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

V  S  S
   BlpI
   ~~~~
GGTTAGCTCA G
CCAATCGAGT C
```

FIG. 5F

```
Q  V  Q  L  K  E  S  G  P  A  L  V  K  P  T  Q  T
      MfeI
CAGGTGCAAT TGAAAGAAAG CGGCCCCGGCC CTGGTGAAAC CGACCCAAAC
GTCCACGTTA ACTTTCTTTC GCCGGGGCCGG GACCACTTTG GCTGGGTTTG

L  T  L  T  C  T  F  S  G  F  S  L  S  T  S  G
                       BspEI
CCTGACCCTG ACCTGTACCT TTTCCGGATT TAGCCTGTCC ACGTCTGGCG
GGACTGGGAC TGGACATGGA AAAGGCCTAA ATCGGACAGG TGCAGACCGC

V  G  V  G  W  I  R  Q  P  P  G  K  A  L  E  W  L
                              BstXI          XhoI
TTGGCGTGGG CTGGATTCGC CAGCCGCCTG GGAAAGCCCT CGAGTGGCTG
AACCGCACCC GACCTAAGCG GTCGGCGGAC CCTTTCGGGA GCTCACCGAC
```

*FIG. 5G*

```
A  L  I  D  W  D  D  D  K  Y  Y  S  T  S  L  K  T
                                              MluI
                                              ~~~~
GCTCTGATTG ATTGGGATGA TGATAAGTAT TATAGCACCA GCCTGAAAAC
CGAGACTAAC TAACCCTACT ACTATTCATA ATATCGTGGT CGGACTTTTG

R  L  T  I  S  K  D  T  S  K  N  Q  V  V  L  T
MluI                      NspV
~~~~                      ~~~~~~~
GCGTCTGACC ATTAGCAAAG ATACTTCGAA AAATCAGGTG GTGCTGACTA
CGCAGACTGG TAATCGTTTC TATGAAGCTT TTTAGTCCAC CACGACTGAT

M  T  N  M  D  P  V  D  T  A  T  Y  Y  C  A  R  W
                                              BssHII
                                              ~~~~~~~
TGACCAACAT GGACCCGGTG GATACGGCCA CCTATTATTG CGCGCGTTGG
ACTGGTTGTA CCTGGGCCAC CTATGCCGGT GGATAATAAC GCGCGCAACC
```

*FIG. 5H*

```
 G  G  D  G  F  Y  A  M  D  Y  W  G  Q  G  T  L  V
GGGGCGGATG GCTTTTATGC GATGGATTAT TGGGGCCAAG GCACCCTGGT
CCGCCGCTAC CGAAAATACG CTACCTAATA ACCCCGGTTC CGTGGGACCA
                                  StyI
                                  ~~~~~

T  V  S  S
GACGGTTAGC TCAG
CTGCCAATCG AGTC
    BlpI
    ~~~~
```

FIG. 5I

```
E  V  Q  L    V  E  S    G  G  G    L  V  Q  P    G  G  S
         MfeI
GAAGTGCAAT TGGTGGAAAG CGGCGGCGGC CTGGTGCAAC CGGGCGGCAG
CTTCACGTTA ACCACCTTTC GCCGCCGCCG GACCACGTTG GCCCGCCGTC

L  R  L    S  C  A  A    S  G  F    T  F  S    S  Y  A
                           BspEI
CCTGCGTCTG AGCTGCGCGG CCTCCGGATT TACCTTTAGC AGCTATGCGA
GGACGCAGAC TCGACGCGCC GGAGGCCTAA ATGGAAATCG TCGATACGCT

M  S  W  V    R  Q  A    P  G  K  G    L  E  W    V  S  A
                BstXI                      XhoI
TGAGCTGGGT GCGCCAAGCC CCTGGGAAGG GTCTCGAGTG GGTGAGCGCG
ACTCGACCCA CGCGGTTCGG GGACCCTTCC CAGAGCTCAC CCACTCGCGC
```

FIG. 5J

```
  I  S  G  S     G  G  S     T  Y  Y     A  D  S  V     K  G  R
ATTAGCGGGTA   GCGGCGGCAG   CACCTATTAT   GCGGATAGCG   TGAAAGGCCG
TAATCGCCCAT   CGCCGCCGTC   GTGGATAATA   CGCCTATCGC   ACTTTCCGGC

F  T  I     S  R  D  N     S  K  N     T  L  Y  L  Q  M
                  PmlI          NspV
                  ~~~~          ~~~~
TTTTACCATT   TCACGTGATA   ATTCGAAAAA   CACCCTGTAT   CTGCAAATGA
AAAATGGTAA   AGTGCACTAT   TAAGCTTTTT   GTGGGACATA   GACGTTTACT

N  S  L  R     A  E  D     T  A  V  Y  Y  C  A  R  W  G
                  EagI                       BssHII
                  ~~~~                       ~~~~~~
ACAGCCTGCG   TGCGGAAGAT   ACGGCCGTGT   ATTATTGCGC   GCGTTGGGGC
TGTCGGACGC   ACGCCTTCTA   TGCCGGCACA   TAATAACGCG   CGCAACCCCG
```

*FIG. 5K*

```
G  D  G  F  Y  A  M  D  Y  W  G  Q  G  T  L  V  T
                                  StyI
                                  ~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

V  S  S
BlpI
~~~~~~
GGTTAGCTCA G
CCAATCGAGT C
```

*FIG. 5L*

```
Q  V  Q  L  Q  E  S  G  P  G  L  V  K  P  S  E  T
      MfeI
CAGGTGCAAT TGCAAGAAAG TGGTCCGGGC CTGGTGAAAC CGAGCGAAAC
GTCCACGTTA ACGTTCTTTC ACCAGGCCCG GACCACTTTG GCTCGCTTTG

L  S  L  T  C  T  V  S  G  G  S  I  S  S  Y  Y
                              BspEI
CCTGAGCCTG ACCTGCACCG TTTCCGGAGG CAGCATTAGC AGCTATTATT
GGACTCGGAC TGGACGTGGC AAAGGCCTCC GTCGTAATCG TCGATAATAA

W  S  W  I  R  Q  P  P  G  K  G  L  E  W  I  G  Y
          BstXI                              XhoI
```

FIG. 5M

```
GGAGCTGGAT  TCGCCAGCCG  CCTGGGAAGG  GTCTCGAGTG  GATTGGCTAT
CCTCGACCTA  AGCGGTCGGC  GGACCCTTCC  CAGAGCTCAC  CTAACCGATA
 I   Y   S   G   S   T   N   Y   N   P   S   L   K   S   R   V
                                                    BstEII
                                                    ~~~~~~

ATTTATTATA  GCGGCAGCAC  CAACTATAAT  CCGAGCCTGA  AAAGCCGGGT
TAAATAATAT  CGCCGTCGTG  GTTGATATTA  GGCTCGGACT  TTTCGGCCCA
 T   I   S   V   D   T   S   K   N   Q   F   S   L   K   L   S
BstEII               NspV
~~~~~~               ~~~~

GACCATTAGC  GTTGATACTT  CGAAAAACCA  GTTTAGCCTG  AAACTGAGCA
CTGGTAATCG  CAACTATGAA  GCTTTTTGGT  CAAATCGGAC  TTTGACTCGT
 S   V   T   A   A   D   T   A   V   Y   Y   C   A   R   W   G   G
                   EagI                        BssHII
                   ~~~~                        ~~~~~~
```

FIG. 5N

```
GCGTGACGGC GGCGGATACG GCCGTGTATT ATTGCGCGGC TTGGGGCGGC
CGCACTGCCG CCGCCTATGC CGGCACATAA TAACGCGCCG AACCCCGCCG

D  G  F  Y  A  M  D  Y  W  G  Q  G  T  L  V  T  V
                                  StyI
                                  ~~~~
GATGGCTTTT ATGCGATGGA TTATTGGGGC CAAGGCACCC TGGTGACGGT
CTACCGAAAA TACGCTACCT AATAACCCCG GTTCCGTGGG ACCACTGCCA

S  S
BlpI
~~~~
TAGCTCAG
ATCGAGTC
```

FIG. 50

```
E  V  Q  L  V  Q  S  G  A  E  V  K  K  P  G  E  S
   MfeI
   ~~~~~~~
GAAGTGCAAT TGGTTCAGAG CGGGCGGAA CGGGCGGGAA GTGAAAAAAC CGGGCGAAAG
CTTCACGTTA ACCAAGTCTC GCCCGCCCTT GCCCGCCCTT CACTTTTTTG GCCCGCTTTC

L  K  I  S  C  K  G  S  G  Y  S  F  T  S  Y  W
                              BspEI
                              ~~~~~~~
CCTGAAAATT AGCTGCAAAG GTTCCGGATA TTCCTTTACG AGCTATTGGA
GGACTTTTAA TCGACGTTTC CAAGGCCTAT AAGGAAATGC TCGATAACCT

I  G  W  V  R  Q  M  P  G  K  G  L  E  W  M  G  I
              BstXI                   XhoI
              ~~~~~~~~~~~~~~          ~~~~~~
TTGGCTGGGT GCGCCAGATG CCTGGGAAGG GTCTCGAGTG GATGGGCATT
AACCGACCCA CGCGGTCTAC GGACCCTTCC CAGAGCTCAC CTACCCGTAA
```

FIG. 5P

```
 I   Y   P   G   D   S   D       T   R   Y       S   P   S   F       Q   G   Q
ATTTATCCGG GCGATAGCGA TACCCGTTAT TCTCCGAGCT TTCAGGGCCA
TAAATAGGCC CGCTATCGCT ATGGGCAATA AGAGGCTCGA AAGTCCCGGT

V   T   I       S   A   D   K       S   I   S       T   A   Y   L   Q   W
BstEII
~~~~~~
GGTGACCATT AGCGCGGATA AAAGCATTAG CACCGCGTAT CTTCAATGGA
CCACTGGTAA TCGCGCCTAT TTTCGTAATC GTGGCGCATA GAAGTTACCT

S   S   L   K       A   S   D       T   A   M   Y   Y   C   A   R   W       G
                                                          BssHII
                                                          ~~~~~~~
GCAGCCTGAA AGCGAGCCGAT ACGGCCATGT ATTATTGCGC GCGTTGGGGC
CGTCGGACTT TCGCTCGCTA TGCCGGTACA TAATAACGCG CGCAACCCCG
```

FIG.5Q

```
G  D  G  F  Y  A  M  D  Y  W  G  Q  G  T  L  V  T
                                   StyI
                                   ~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

V  S  S
   BlpI
   ~~~~~~
GGTTAGCTCA G
CCAATCGAGT C
```

*FIG.5R*

```
Q  V  Q  L  Q  Q  S  G  P  G  L  V  K  P  S  Q  T
      MfeI
CAGGTGCAAT TGCAACAGTC TGGTCCGGGC CTGGTGAAAC CGAGCCAAAC
GTCCACGTTA ACGTTGTCAG ACCAGGCCCG GACCACTTTG GCTCGGTTTG
      ~~~~~~~

L  S  L  T  C  A  I  S  G  D  S  V  S  S  N  S
                          BspEI
                          ~~~~~~
CCTGAGCCTG ACCTGTGCGA TTTCCGGAGA TAGCGTGAGC AGCAACAGCG
GGACTCGGAC TGGACACGCT AAAGGCCTCT ATCGCACTCG TCGTTGTCGC

A  A  W  N  W  I  R  Q  S  P  G  R  G  L  E  W  L
                       BstXI                 XhoI
                       ~~~~~~~~~~~            ~~~~~~
CGGCGTGGAA CTGGATTCGC CAGTCTCCTG GGCGTGGCCT CGAGTGGCTG
GCCGCACCTT GACCTAAGCG GTCAGAGGAC CCGCACCGGA GCTCACCGAC
```

*FIG.5S*

```
G   R   T   Y   Y   R   S       K   W   Y       N   D   Y   A       V   S   V
GGCCGTACCT ATTATCGTAG CAAATGGTAT AACGATTATG CGGTGAGCGT
CCGGCATGGA TAATAGCATC GTTTACCATA TTGCTAATAC GCCACTCGCA

K   S   R       I   T   I   N       P   D   T       S   K   N   Q   F   S
GAAAAGCCGG ATTACCATCA ACCCGGATAC TTCGAAAAAC CAGTTTAGCC
CTTTTCGGCC TAATGGTAGT TGGGCCTATG AAGCTTTTTG GTCAAATCGG
          BsaBI                             NspV
          ~~~~~~~~~~                        ~~~~~~~~

L   Q   L   N       S   V   T       P   E   D   T       A   V   Y       Y   C   A
TGCAACTGAA CAGCCGTGACC CCGGAAGATA CGGCCGTGTA TTATTGCGCG
ACGTTGACTT GTCGCACTGG GGCCTTCTAT GCCGGCACAT AATAACGCGC
                                 EagI                BssHII
                                 ~~~~~~~~             ~~~~~~~
```

FIG. 5T

```
R   W   G   G   D   G   F   Y   A   M   D   Y   W   G   Q   G   T
BssHII                                                    StyI
~~                                                        ~~~~~
CGTTGGGGCG GCGATGGCTT TTATGCGATG GATTATTGGG GCCAAGGCAC
GCAACCCCGC CGCTACCGAA AATACGCTAC CTAATAACCC CGGTTCCGTG

L   V   T   V   S   S
            BlpI
            ~~~~~
CCTGGTGACG GTTAGCTCAG
GGACCACTGC CAATCGAGTC
```

FIG. 5U

O1K1 5'- GAATGCATACGCTGATATCCAGATGACCCAGAG-CCCGTCTAGCCTGAGC -3'
O1K2 5'- CGCTCTGCAGGTAATGGTCACACGATCACCCAC-GCTCGCGCTCAGGCTAGACGGGC -3'
O1K3 5'- GACCATTACCTGCAGAGCGAGCCAGGGCATTAG-CAGCTATCTGGCGTGGTACCAGCAG -3'
O1K4 5'- CTTTGCAAGCTGCTGGCTGCATAAATTAATAGT-TTCGGTGCTTTACCTGGTTTCTGCTGGTACCACGCCAG -3'
O1K5 5'- CAGCCAGCAGCTTGCAAAGCGGGGTCCCGTCCC-GTTTTAGCGGCTCTGGATCCGGCACTGATTTTAC -3'
O1K6 5'- GATAATAGGTCGCAAAGTCTTCAGGTTGCAGGC-TGCTAATGGTCAGGGTAAAATCAGTGCCGGATCC -3'
O2K1 5'- CGATATCGTGATGACCCAGAGCCCACTGAGCCT-GCCAGTGACTCCGGGCGAGCC -3'
O2K2 5'- GCCGTTGCTATGCAGCAGGCTTTGGCTGCTTCT-GCAGCTAATGCTCGCAGGCTCGCCCGGAGTCAC -3'
O2K3 5'- CTGCTGCATAGCAACGGCTATAACTATCTGGAT-TGGTACCTTCAAAAACCAGGTCAAAGCCC -3'
O2K4 5'- CGATCCGGGACCCCACTGGCACGGTTGCTGCCC-AGATAAATTAATAGCTGCGGGCTTTGACCTGGTTTTTG -3'
O2K5 5'- AGTGGGGTCCCGGATCGTTTTAGCGGCTCTGGA-TCCGGCACCGATTTTACCCTGAAAATTAGCCGTGTG -3'
O2K6 5'- CCATGCAATAATACACGCCCACGTCTTCAGCTT-CCACACGGCTAATTTTCAGGG -3'
O3K1 5'- GAATGCATACGCTGATATCGTGCTGACCCAGAG CCCGG -3'
O3K2 5'- CGCTCTGCAGCTCAGGGTCGCACGTTCGCCCGG-AGACAGGCTCAGGGTCGCCGGGCTCTGGGTCAGC -3'
O3K3 5'- CCCTGAGCTGCAGAGCGAGCCAGAGCGTGAGCA-GCAGCTATCTGGCGTGGTACCAG -3'

*FIG. 6A*

O3K4  5'- GCACGGCTGCTCGCGCCATAAATTAATAGACGC-GGTGCTTGACCTGGTTTCTGCTGGTACCACGCCAGATAG -3'

O3K5  5'- GCGCGAGCAGCCGTGCAACTGGGGTCCCGGCGC-GTTTTAGCGGCTCTGGATCCGGCACGGATTTTAC -3'

O3K6  5'- GATAATACACCGCAAAGTCTTCAGGTTCCAGGC-TGCTAATGGTCAGGGTAAAATCCGTGCCGGATC -3'

O4K1  5'- GAATGCATACGCTGATATCGTGATGACCCAGAG-CCCGGATAGCCTGGCG -3'

O4K2  5'- GCTTCTGCAGTTAATGGTCGCACGTTCGCCCAG-GCTCACCGCCAGGCTATCCGGGC -3'

O4K3  5'- CGACCATTAACTGCAGAAGCAGCCAGAGCGTGC-TGTATAGCAGCAACAACAAAAACTATCTGGCGTGGTACCAG 3'

O4K4  5'- GATGCCCAATAAATTAATAGTTTCGGCGGCTGA-CCTGGTTTCTGCTGGTACCACGCCAGATAG -3'

O4K5  5'- AAACTATTAATTTATTGGGCATCCACCCGTGAA-AGCGGGGTCCCGGATCGTTTTAGCGGCTCTGGATCCGGCAC- 3'

O4K6  5'- GATAATACACCGCCACGTCTTCAGCTTGCAGGG-ACGAAATGGTCAGGGTAAAATCAGTGCCGGATCCAGAGCC- 3'

O1L1  5'- GAATGCATACGCTCAGAGCGTGCTGACCCAGCC-GCCTTCAGTGAGTGG -3'

O1L2  5'- CAATGTTGCTGCTGCTGCCGCTACACGAGATGG-TCACACGCTGACCTGGTGCGCCACTCACTGAAGGCGGC -3'

O1L3  5'- GGCAGCAGCAGCAACATTGGCAGCAACTATGTG-AGCTGGTACCAGCAGTTGCCCGGGAC -3'

O1L4  5'- CCGGCACGCCTGAGGGACGCTGGTTGTTATCAT-AAATCAGCAGTTTCGGCGCCGTCCCGGGCAACTGC -3

O1L5 5'- CCCTCAGGCGTGCCGGATCGTTTTAGCGGATCC-AAAAGCGGCACCAGCGCGAGCCTTGCG -3'

FIG.6B

O1L6  5'- CCGCTTCGTCTTCGCTTTGCAGGCCCGTAATCG-
CAAGGCTCGCGCTGG -3'
O2L1  5'- GAATGCATACGCTCAGAGCGCACTGACCCAGCC-
AGCTTCAGTGAGCGGC -3'
O2L2  5'- CGCTGCTAGTACCCGTACACGAGATGGTAATGC-
TCTGACCTGGTGAGCCGCTCACTGAAGCTGG -3'
O2L3  5'- GTACGGGTACTAGCAGCGATGTGGGCGGCTATA-
ACTATGTGAGCTGGTACCAGCAGCATCCCGG -3'
O2L4  5'- CGCCTGAGGGACGGTTGCTCACATCATAAATCA-
TCAGTTTCGGCGCCTTCCCGGGATGCTGCTGGTAC -3'
O2L5  5'- CAACCGTCCCTCAGGCGTGAGCAACCGTTTTAG-
CGGATCCAAAAGCGGCAACACCGCGAGCC -3'
O2L6  5'- CCGCTTCGTCTTCCGCTTGCAGGCCGCTAATGG-
TCAGGCTCGCGGTGTTGCCG -3'
O3L1  5'- GAATGCATACGCTAGCTATGAACTGACCCAGCC-
GCCTTCAGTGAGCG -3'
O3L2  5'- CGCCCAGCGCATCGCCGCTACACGAGATACGCG-
CGGTCTGACCTGGTGCAACGCTCACTGAAGGCGGC -3'
O3L3  5'- GGCGATGCGCTGGGCGATAAATACGCGAGCTGG-
TACCAGCAGAAACCCGGGCAGGCGC -3'
O3L4  5'- GCGTTCCGGGATGCCTGAGGGACGGTCAGAATC-
ATCATAAATCACCAGAACTGGCGCCTGCCCGGGTTTC -3'
O3L5  5'- CAGGCATCCCGGAACGCTTTAGCGGATCCAACA-
GCGGCAACACCGCGACCCTGACCATTAGCGG -3'
O3L6  5'- CCGCTTCGTCTTCCGCTGAGTGCCGCTAATGG-
TCAGGGTC -3'
O1246H1   5'- GCTCTTCACCCCTGTTACCAAAGCCCAG-
GTGCAATTG -3'
O1AH2 5'- GGCTTTGCAGCTCACTTTCACGCTGCTGCCCGGT-
TTTTTCACTTCCGCGCCAGACTGAACCAATTGCACCTGGGC-
TTTG -3'

*FIG. 6C*

O1AH3 5'- GAAAGTGAGCTGCAAAGCCTCCGGAGGCACTTT-TAGCAGCTATGCGATTAGCTGGGTGCGCCAAGCCCCTGGGCAGGGTC -3'

O1AH4 5'- GCCCTGAAACTTCTGCGCGTAGTTCGCCGTGCCA-AAAATCGGAATAATGCCGCCCATCCACTCGAGACCCTGCCC-AGGGGC -3'

O1AH5 5'- GCGCAGAAGTTTCAGGGCCGGGTGACCATTACC-GCGGATGAAAGCACCAGCACCGCGTATATGGAACTGAGCAGCCTGCG -3'

O1ABH6 5'- GCGCGCAATAATACACGGCCGTATCTTCGCT-ACGCAGGCTGCTCAGTTCC -3'

O1BH2 5'- GGCTTTGCAGCTCACTTTCACGCTCGCGCCCGGT-TTTTTCACTTCCGCGCCGCTCTGAACCAATTGCACCTGGGC-TTTG -3'

O1BH3 5'- GAAAGTGAGCTGCAAAGCCTCCGGATATACCTT-TACCAGCTATTATATGCACTGGGTCCGCCAAGCCCCTGGGCAGGGTC -3'

O1BH4 5'- GCCCTGAAACTTCTGCGCGTAGTTCGTGCCGCC-GCTATTCGGGTTAATCCAGCCCATCCACTCGAGACCCTGCCCAGGGGC -3'

O1BH5 5'- GCGCAGAAGTTTCAGGGCCGGGTGACCATGACC-CGTGATACCAGCATTAGCACCGCGTATATGGAACTGAGCAGCCTGCG -3'

O2H2 5'- GGTACAGGTCAGGGTCAGGGTTTGGGTCGGTTT-CACCAGGGCCGGGCCGCTTTCTTTCAATTGCACCTGGGCTTTG -3'

O2H3 5'- CTGACCCTGACCTGTACCTTTTCCGGATTTAGC-CTGTCCACGTCTGGCGTTGGCGTGGGCTGGATTCGCCAGCCGCCTGGGAAAG -3

O2H4 5'- GCGTTTTCAGGCTGGTGCTATAATACTTATCAT-CATCCCAATCAATCAGAGCCAGCCACTCGAGGGCTTTCCCAGGCGGCTGG -3'

FIG. 6D

O2H5 5'- GCACCAGCCTGAAAACGCGTCTGACCATTAGCA-AAGATACTTCGAAAAATCAGGTGGTGCTGACTATGACCAACATGG -3'

O2H6 5'- GCGCGCAATAATAGGTGGCCGTATCCACCGGGT-CCATGTTGGTCATAGTCAGC -3'

O3H1 5'- CGAAGTGCAATTGGTGGAAAGCGGCGGCGGCCT-GGTGCAACCGGGCGGCAG -3'

O3H2 5'- CATAGCTGCTAAAGGTAAATCCGGAGGCCGCGC-AGCTCAGACGCAGGCTGCCGCCCGGTTGCAC -3'

O3H3 5'- GATTTACCTTTAGCAGCTATGCGATGAGCTGGG-TGCGCCAAGCCCCTGGGAAGGGTCTCGAGTGGGTGAG -3'

O3H4 5'- GGCCTTTCACGCTATCCGCATAATAGGTGCTGC-CGCCGCTACCGCTAATCGCGCTCACCCACTCGAGACCC -3'

O3H5 5'- CGGATAGCGTGAAAGGCCGTTTTACCATTTCAC-GTGATAATTCGAAAAACACCCTGTATCTGCAAATGAACAG -3'

O3H6 5'- CACGCGCAATAATACACGGCCGTATCTTCCG-CACGCAGGCTGTTCATTTGCAGATACAGG -3'

O4H2 5'- GGTCAGGCTCAGGGTTTCGCTCGGTTTCACCAG-GCCCGGACCACTTTCTTGCAATTGCACCTGGGCTTTG -3'

O4H3 5'- GAAACCCTGAGCCTGACCTGCACCGTTTCCGGAGG-CAGCATTAGCAGCTATTATTGGAGCTGGATTCGCCAGCCGC -3'

O4H4 5'- GATTATAGTTGGTGCTGCCGCTATAATAAATAT-AGCCAATCCACTCGAGACCCTTCCCAGGCGGCTGGCGAATCCAG -3'

O4H5 5'- CGGCAGCACCAACTATAATCCGAGCCTGAAAAG-CCGGGTGACCATTAGCGTTGATACTTCGAAAACCAGTTTAGCCTG -3'

O4H6 5'- GCGCGCAATAATACACGGCCGTATCCGCCGCCG-TCACGCTGCTCAGTTTCAGGCTAAACTGGTTTTTCG -3'

FIG. 6E

O5H1  5'- GCTCTTCACCCCTGTTACCAAAGCCGAAGTGCAATTG -3'
O5H2  5'- CCTTTGCAGCTAATTTTCAGGCTTTCGCCCGGTTTTTTCACTTCCGCGCCGCTCTGAACCAATTGCACTTCGGCTTTGG -3'
O5H3  5'- CCTGAAAATTAGCTGCAAAGGTTCCGGATATTCCTTTACGAGCTATTGGATTGGCTGGGTGCGCCAGATGCCTGG -3'
O5H4  5'- CGGAGAATAACGGGTATCGCTATCGCCCGGATAAATAATGCCCATCCACTCGAGACCCTTCCCAGGCATCTGGCGCAC -3'
O5H5  5'- CGATACCCGTTATTCTCCGAGCTTTCAGGGCCAGGTGACCATTAGCGCGGATAAAGCATTAGCACCGCGTATCTTC -3'
O5H6  5'- GCGCGCAATAATACATGGCCGTATCGCTCGCTTTCAGGCTGCTCCATTGAAGATACGCGGTGCTAATG -3'
O6H2  5'- GAAATCGCACAGGTCAGGCTCAGGGTTTGGCTCGGTTTCACCAGGCCCGGACCAGACTGTTGCAATTGCACCTGGGCTTTG -3'
O6H3  5'- GCCTGACCTGTGCGATTTCCGGAGATAGCGTGAGCAGCAACAGCGCGGCGTGGAACTGGATTCGCCAGTCTCCTGGGCG -3'
O6H4  5'- CACCGCATAATCGTTATACCATTTGCTACGATAATAGGTACGGCCCAGCCACTCGAGGCCACGCCCAGGAGACTGGCG -3'
O6H5  5'- GGTATAACGATTATGCGGTGAGCGTGAAAAGCCGGATTACCATCAACCCGGATACTTCGAAAAACCAGTTTAGCCTGC -3'
O6H6  5'- GCGCGCAATAATACACGGCCGTATCTTCCGGGGTCACGCTGTTCAGTTGCAGGCTAAACTGGTTTTTC -3'
OCLK1 5'- GGCTGAAGACGTGGGCGTGTATTATTGCCAGCAGCATTATACCACCCCGCCGACCTTTGGCCAGGGTAC -3'

FIG. 6F

OCLK2 5'- GCGAAAAATAAACACGCTCGGAGCAGCCACCG-TACGTTTAATTTCAACTTTCGTACCCTGGCCAAAGGTC -3'
OCLK3 5'- GAGCGTGTTTATTTTTCCGCCGAGCGATGAACA-ACTGAAAAGCGGCACGGCGAGCGTGGTGTGCCTGCTG -3'
OCLK4 5'- CAGCGCGTTGTCTACTTTCCACTGAACTTTCGC-TTCACGCGGATAAAAGTTGTTCAGCAGGCACACCACGC -3'
OCLK5 5'- GAAAGTAGACAACGCGCTGCAAAGCGGCAACAG-CCAGGAAAGCGTGACCGAACAGGATAGCAAAGATAG -3'
OCLK6 5'- GTTTTTCATAATCCGCTTTGCTCAGGGTCAGGG-TGCTGCTCAGAGAATAGGTGCTATCTTTGCTATCCTGTTCG -3'
OCLK7 5'- GCAAAGCGGATTATGAAAAACATAAAGTGTATG-CGTGCGAAGTGACCCATCAAGGTCTGAGCAGCCCGGTG -3'
OCLK8 5'- GGCATGCTTATCAGGCCTCGCCACGATTAAAAG-ATTTAGTCACCGGGCTGCTCAGAC -3'
OCH1 5'- GGCGTCTAGAGGCCAAGGCACCCTGGTGACGGT-TAGCTCAGCGTCGAC -3'
OCH2 5'- GTGCTTTTGCTGCTCGGAGCCAGCGGAAACACG-CTTGGACCTTTGGTCGACGCTGAGCTAACC -3'
OCH3 5'- CTCCGAGCAGCAAAAGCACCAGCGGCGGCACGG-CTGCCCTGGGCTGCCTGGTAAAGATTATTTCC -3'
OCH4 5'- CTGGTCAGCGCCCCGCTGTTCCAGCTCACGGTG-ACTGGTTCCGGGAAATAATCTTTAACCAGGCA -3'
OCH5 5'- AGCGGGGCGCTGACCAGCGGCGTGCATACCTTT-CCGGCGGTGCTGCAAAGCAGCGGCTG -3'
OCH6 5'- GTGCCTAAGCTGCTGCTCGGCACGGTCACAACG-CTGCTCAGGCTATACAGGCCGCTGCTTTGCAG -3'
OCH7 5'- GAGCAGCAGCTTAGGCACTCAGACCTATATTTG-CAACGTGAACCATAAACCGAGCAACACC -3'
OCH8 5'- GCGCGAATTCGCTTTTCGGTTCCACTTTTTTAT-CCACTTTGGTGTTGCTCGGTTTATGG -3'

*FIG. 6G*

```
          V   A   A   P   S       V   F   I   F   P   P   S       D   E   Q
BsiWI
~~~~~~
CGTACGGGTGG CTGCTCCGAG       CGTGTTTATT TTTCCGCCGA       GCGATGAACA
GCATGCCACC  GACGAGGCTC       GCACAAATAA AAAGGCGGCT       CGCTACTTGT

L   K   S       G   T   A   S       V   V   C       L   L   N       N   F   Y
ACTGAAAAGC GGCACGGGCGA GCGTGGTGTG       CCTGCTGAAC AACTTTTATC
TGACTTTTCG CCGTGCCCGCT CGCACCACAC       GGACGACTTG TTGAAAATAG

P   R   E   A       K   V   Q       W   K   V   D       N   A   L       Q   S       G
CGCGTGAAGC GAAAGTTCAG       TGGAAAGTAG ACAACGCGCT       GCAAAGCGGC
GCGCACTTCG CTTTCAAGTC       ACCTTTCATC TGTTGCGCGA       CGTTTCGCCG

N   S   Q   E       S   V   T       E   Q   D       S   K   D   S       T   Y   S
AACAGCCAGG AAAGCGTGAC       CGAACAGGAT AGCAAAGATA       GCACCTATTC
TTGTCGGTCC TTTCGCACTG       GCTTGTCCTA TCGTTTCTAT       CGTGGATAAG
```

*FIG. 7A*

```
L  S  S  T  L  T  L     S  K  A     D  Y  E  K  H  H  K
TCTGAGCAGC ACCCTGACCC TGAGCAAAGC GGATTATGAA AAACATAAAG
AGACTCGTCG TGGGACTGGG ACTCGTTTCG CCTAATACTT TTTGTATTTC

V  Y  A  C     E  V  T     H  Q  G  L     S  S  P     V  T  K
TGTATGCGGTG CGAAGTGACC CATCAAGGTC TGAGCAGCCC GGTGACTAAA
ACATACGCAC GCTTCACTGG GTAGTTCCAG ACTCGTCGGG CCACTGATTT

S  F  N  R     G  E  A  *
                         StuI            SphI
                         ~~~~~~~         ~~~~~~~
TCTTTTAATC GTGGCGAGGC CTGATAAGCA TGC
AGAAAATTAG CACCGCTCCG GACTATTCGT ACG
```

*FIG. 7B*

```
       A   S   T   K   G   P   S   V   F   P   L   A   P   S   S
     BlpI    SalI
     ~~~~~~  ~~~~~~
     GCTCAGCGTC GACCAAAGGT CCAAGCGTGT TTCCGCTGGC TCCGAGCAGC
     CGAGTCGCAG CTGGTTTCCA GGTTCGCACA AAGGCGACCG AGGCTCGTCG

K   S   T   S   G   G   T   A   A   L   G   C   L   V   K   D   Y
     AAAAGCACCA GCGGCGGCAC GGCTGCCCTG GGCTGCCTGG TTAAAGATTA
     TTTTCGTGGT CGCCGCCGTG CCGACGGGAC CCGACGGACC AATTTCTAAT

F   P   E   P   V   T   V   S   W   N   S   G   A   L   T   S
     TTTCCCGGAA CCAGTCACCG TGAGCTGGAA CAGCGGGGCG CTGACCAGCG
     AAAGGGCCTT GGTCAGTGGC ACTCGACCTT GTCGCCCCGC GACTGGTCGC

G   V   H   T   F   P   A   V   L   Q   S   S   G   L   Y   S   L
     GCGTGCATAC CTTTCCGGCG GTGCTGCAAA GCAGCGGCCT GTATAGCCTG
     CGCACGTATG GAAAGGCCGC CACGACGTTT CGTCGCCGGA CATATCGGAC
```

*FIG. 7C*

```
      S   S   V   V   T   V   P       S   S   S       L   G   T   Q       T   Y   I
    AGCAGCGTTG TGACCGTGCC GAGCAGCAGC TTAGGCACTC AGACCTATAT
    TCGTCGCAAC ACTGGCACGG CTCGTCGTCG AATCCGTGAG TCTGGATATA

C   N   V       N   H   K   P   S   N   T       K   V   D       K   K   V
    TTGCAACGTG AACCATAAAC CGAGCAACAC CAAAGTGGAT AAAAAAGTGG
    AACGTTGCAC TTGGTATTTG GCTCGTTGTG GTTTCACCTA TTTTTTCACC

E   P   K   S       E   F   *       HindIII
                          EcoRI          ~~~~~~
                          ~~~~~~
    AACCGAAAAG CGAATTCTGA TAAGCTT
    TTGGCTTTTC GCTTAAGACT ATTCGAA
```

FIG. 7D

```
       BbsI
       ~~~~~~
  1    GAAGACGAAG CGGATTATTA TTGCCAGCAG CATTATACCA CCCCGCCTGT
       CTTCTGCTTC GCCTAATAAT AACGGTCGTC GTAATATGGT GGGGCGGACA

HpaI                MscI           DraIII
                       ~~~~~~              ~~~~~~         ~~~~~~
 51    GTTTGGCGGC GGCACGAAGT TAACCGTTCT TGGCCAGCCG AAAGCCGCAC
       CAAACCGCCG CCGTGCTTCA ATTGGCAAGA ACCGGTCGGC TTTCGGCGTG

DraIII
       ~~~~~~
101    CGAGTGTGAC GCTGTTTCCG CCGAGCAGCG AAGAATTGCA GGCGAACAAA
       GCTCACACTG CGACAAAGGC GGCTCGTCGC TTCTTAACGT CCGCTTGTTT

151    GCGACCCTGG TGTGCCTGAT TAGCCGACTTT TATCCGGGAG CCGTGACAGT
       CGCTGGGACC ACACGGACTA ATCGCTGAAA ATAGGCCCTC GGCACTGTCA
```

*FIG. 7F*

```
201  GGCCTGGAAG  GCAGATAGCA  GCCCCGTCAA  GGCGGGAGTG  GAGACCACCA
     CCGGACCTTC  CGTCTATCGT  CGGGGCAGTT  CCGCCCTCAC  CTCTGGTGGT

251  CACCCTCCAA  ACAAAGCAAC  AACAAGTACG  CGGCCAGCAG  CTATCTGAGC
     GTGGGAGGTT  TGTTTCGTTG  TTGTTCATGC  GCCGGTCGTC  GATAGACTCG
                                         RleAI
                                         ~~~~~

301  CTGACGCCCTG  AGCAGTGGAA  GTCCCACAGA  AGCTACAGCT  GCCAGGTCAC
     GACTGCGGGAC  TCGTCACCTT  CAGGGTGTCT  TCGATGTCGA  CGGTCCAGTG
                                                     StuI
                                                     ~~~~~
```

*FIG. 7G*

351  GCATGAGGGG AGCACCGTGG AAAAACCGT TGCGCCGACT GAGGCCTGAT
     CGTACTCCCC TCGTGGCACC TTTTTTGGCA ACGCGGCTGA CTCCGGACTA
          SphI
          ~~~~~
401  AAGCATGC
     TTCGTACG

FIG. 7H

M24: assembly PCR

M24-A:

GAAGACAAGCGGATTATTATTGCCAGCAGCATTATACCACCCGCCTGTGTTGGCGGCG-
GCACGAAGTTAACCGTTC

M24-B:

CAATTCTTCGCTGCTCGGGCGGGAAACAGCGTCACACTCGGTGCGGCTTTCGGCTGGCCAA-
GAACGGTTAACTTCGTGCCGC

M24-C:

CGCCGAGCAGCGGAAGAATTGCAGGCGAACAAAGCGACCCTGGTGTGCCTGATTAGCGACT-
TTTATCCCGGGAGCCCGTGACA

FIG. 71

M24-D:
TGTTTGGAGGGTGTGGTGGTCTCCACTCCCGCCTTGACGGGGCTGCTATCTGCCTTCCAG-
GCCACTGTCACGGCTCCCGG

M24-E:
CCACACCCTCCAAACAACAAAGCAACAACAAGTACGCGGCCAGCAGCTATCTGAGCCTGACGC-
CTGAGCAGTGGAAGTCCCACAGAAGCTACAGCTG

M24-F:
GCATGCTTATCAGGCCTCAGTCGGGCGCAACGGTTTTTCCACGGTGCTCCCCTCATGCGT-
GACCTGGGCAGCTGTAGCTTC

FIG. 7J

```
M   K   Q   S   T   I   A   L   A   L   L   P   L   L   F   T   P
ATGAAACAAA GCACTATTGC ACTGGCACTC TTACCGTTGC TCTTCACCCC
TACTTTGTTT CGTGATAACG TGACCGTGAG AATGGCAACG AGAAGTGGGG
                                           ~~~~~~~
                                           SapI

V   T   K   A   D   Y   K   D   E   V   Q   L   V   E   S   G
                                           ~~~~~~~~
                                           MfeI
TGTTACCAAA GCCGACTACA AAGATGAAGT GCAATTGGTG GAAAGCGGCG
ACAATGGTTT CGGCTGATGT TTCTACTTCA CGTTAACCAC CTTTCGCCGC

G   G   L   V   Q   P   G   G   S   L   R   L   S   C   A   A   S
                                                           ~~~~~
                                                           BspEI
GCGGCCTGGT GCAACCGGGC GGCAGCCTGC GTCTGAGCTG CGCGGCCTCC
CGCCGGACCA CGTTGGCCCG CCGTCGGACG CAGACTCGAC GCGCCGGAGG

G   F   T   F   S   S   Y   A   M   S   W   V   R   Q   A   P   G
~~~                                                 ~~~~~~~~
BspEI                                               BstXI
GCGGCCTGGT TTAGCAGCTA TGCCGATGAGC TGGGTGCGCC AAGCCCCTGG
CCTAAATGGA AATCGTCGAT ACGCTACTCG ACCCACGCGG TTCGGGGACC
```

*FIG. 8A*

```
K  G  L  E  W  V  S     A  I  S     G  S  G     G  G  S     T
         XhoI
GAAGGGTCTC GAGTGGGTGA GCGCGATTAG CGGTAGCGGC GGCAGCACCT
CTTCCCAGAG CTCACCCACT CGCGCTAATC GCCATCGCCG CCGTCGTGGA

Y  Y  A  D  S  V  K     G  R  F  T  I  S  R     D  N  S
                                    PmlI          NspV
ATTATGCGGA TAGCGTGAAA GGCCGTTTTA CCATTTCACG TGATAATTCG
TAATACGCCT ATCGCACTTT CCGGCAAAAT GGTAAAGTGC ACTATTAAGC

K  N  T  L  Y  L  Q     M  N  S     L  R  A  E     D  T  A
NspV                                                     EagI
AAAAACACCC TGTATCTGCA AATGAACAGC CTGCGTGCGG AAGATACGGC
TTTTTGTGGG ACATAGACGT TTACTTGTCG GACGCACGCC TTCTATGCCG

V  Y  Y     C  A  R  W     G  G  D     G  F  Y  A  M  D
EagI        BssHII
CGTGTATTAT TGCGCGCGTT GGGGCGGCGA TGGCTTTTAT GCGATGGATT
```

FIG. 8B

```
GCACATAATAACGCGGCAA CCCCGCCGCT ACCGAAAATA CGCTACCTAA
 Y  W  G  Q  G  T  L  V  T  V  S  S  A  G  G  G  G  S
                                      BlpI
                                      ~~~~~

ATTGGGGCCA AGGCACCCTG GTGACGGTTA GCTCAGCGGG TGGCGGTTCT
TAACCCCGGT TCCGTGGGAC CACTGCCAAT CGAGTCGCCC ACCGCCAAGA

G  G  G  S  G  G  G  G  S  G  G  G  G  S  D  I
                                            EcoRV
                                            ~~~~~

GGCGGCGGTG GGAGCGGGTG CGGTGGTTCT GGCGGTGGTG GTTCCGATAT
CCGCCGCCAC CCTCGCCCAC GCCACCAAGA CCGCCACCAC CAAGGCTATA

V  M  T  Q  S  P  L  S  L  P  V  T  P  G  E  P
 EcoRV          BanII
 ~              ~~~~~

CGTGATGACC CAGAGCCCAC TGAGCCTGCC AGTGACTCCG GGCGAGCCTG
GCACTACTGG GTCTCGGGTG ACTCGGACGG TCACTGAGGC CCGCTCGGAC

A  S  I  S  C  R  S  S  Q  S  L  L  H  S  N  G  Y
          PstI
          ~~~~~

CGAGCATTAG CTGCAGAAGC AGCCAAAGCC TGCTGCATAG CAACGGCTAT
GCTCGTAATC GACGTCTTCG TCGGTTTCGG ACGACGTATC GTTGCCGATA
```

FIG. 8C

```
N  Y  L  D  W  Y  L  Q  K  P  G  Q  S  P  Q  L  L
         KpnI              SexAI                  AseI
AACTATCTGG ATTGGTACCT TCAAAAACCA GGTCAAAGCC CGCAGCTATT
TTGATAGACC TAACCATGGA AGTTTTTGGT CCAGTTTCGG GCGTCGATAA

I  Y  L  G  S  N  R  A  S  G  V  P  D  R  F  S
AseI                          EcoO109I
AATTTATCTG GGCAGCAACC GTGCCAGTGG GGTCCCGGAT CGTTTTAGCG
TTAAATAGAC CCGTCGTTGG CACGGTCACC CCAGGGCCTA GCAAAATCGC

G  S  G  S  G  T  D  F  T  L  K  I  S  R  V  E  A
      BamHI
GCTCTGGATC CGGCACCGAT TTTACCCTGA AAATTAGCCG TGTGGAAGCT
CGAGACCTAG GCCGTGGCTA AAATGGGACT TTTAATCGGC ACACCTTCGA

E  D  V  G  V  Y  Y  C  Q  Q  H  Y  T  T  P  P  T
BbsI
GAAGACGTGG GCGTGTATTA TTGCCAGCAG CATTATACCA CCCCGCCGAC
CTTCTGCACC CGCACATAAT AACGGTCGTC GTAATATGGT GGGGCGGCTG
```

FIG. 8D

```
F   G   Q   G   G   T   K   V   E   I   K   R   T   E   F
    MscI                                        BsiWI EcoRI
    ~~~~                                        ~~~~~ ~~~~~
CTTTGGCCAG GGTACGAAAG TTGAAATTAA ACGTACGGAA TTC
GAAACCGGTC CCATGCTTTC AACTTTAATT TGCATGCCTT AAG
```

FIG. 8E

| | 92 | 93 | 94 | 95 | 96 | 97 | 98 | 99 | 100 | 100A | 100B | 100C | 100D | 100E | 101 | 102 | 103 |
|---|---|---|---|---|---|---|---|---|---|---|---|---|---|---|---|---|---|
| A | C | A | R | W | G | G | D | G | F | Y | A | - | - | M | D | Y | W |
| B | C | A | R | F | G | K | M | N | Y | - | - | - | - | - | D | Y | W |
|   | C | A | R | H | R | T | E | W | H | - | - | - | - | - | D | Y | W |
|   | C | A | R | V | R | E | L | Y | H | - | - | - | - | - | D | Y | W |
|   | C | A | R | K | F | L | K | A | R | - | - | - | - | - | D | Y | W |
|   | C | A | R | W | N | E | T | G | Y | - | - | - | - | - | D | Y | W |
|   | C | A | R | I | N | I | A | Q | P | - | - | - | - | - | D | Y | W |
|   | C | A | R | T | A | N | T | R | - | - | - | - | - | - | D | Y | W |
|   | C | A | R | W | Y | G | R | N | S | - | - | - | - | - | D | Y | W |
|   | C | A | R | S | V | T | D | S | K | - | - | - | - | - | D | Y | W |
|   | C | A | R | V | K | P | F | A | A | - | - | - | - | - | D | Y | W |
|   | C | A | R | M | A | S | Q | Y | D | - | - | - | - | - | D | Y | W |
|   | C | A | R | M | Q | E | E | W | M | - | - | - | - | - | D | Y | W |

| | 92 | 93 | 94 | 95 | 96 | 97 | 98 | 99 | 100 | 100A | 100B | 100C | 100D | 100E | 101 | 102 | 103 | Frequency |
|---|---|---|---|---|---|---|---|---|---|---|---|---|---|---|---|---|---|---|
| | C | A | R | K | R | M | M | Q | N | P | R | F | R | F | D | V | W | 1 |
| | C | A | R | R | S | K | Q | K | R | K | M | R | R | F | D | V | W | 3 |
| | C | A | R | R | N | G | K | R | H | L | R | H | R | F | D | V | W | 1 |
| | C | A | R | R | K | M | R | K | R | I | K | R | R | F | D | V | W | 2 |
| | C | A | R | Y | R | I | I | M | K | W | K | N | S | F | D | V | W | 1 |
| | C | A | R | L | I | E | V | H | P | S | F | D | Q | M | D | V | W | 1 |
| | C | A | R | R | K | P | P | F | L | K | K | A | V | F | D | Y | W | 1 |
| | C | A | R | R | K | M | H | R | Y | S | T | V | K | F | D | Y | W | 2 |
| | C | A | R | R | K | R | M | R | S | R | R | K | R | F | D | V | W | 1 |
| | C | A | R | R | K | N | S | R | R | R | M | D | M | R | D | V | W | 1 |
| | C | A | R | R | G | P | R | R | G | A | R | N | N | F | D | V | W | 1 |
| | C | A | R | R | M | K | K | K | K | R | R | P | R | F | D | V | W | 1 |
| | C | A | R | R | K | V | V | H | F | P | K | K | K | F | D | V | W | 1 |
| | C | A | R | R | W | H | H | I | A | Y | R | A | I | Q | D | V | W | 1 |
| | C | A | R | R | T | L | T | T | G | P | R | R | Q | F | D | V | W | 1 |
| | C | A | R | K | K | L | K | R | Y | S | F | S | R | F | D | Y | W | 1 |

FIG. 22

| Position | | | | | | | | | FREQUENCY |
|---|---|---|---|---|---|---|---|---|---|
| 92 | C | C | C | C | C | C | C | C | |
| 93 | A | A | A | A | A | A | A | A | |
| 94 | R | R | R | R | R | R | R | R | |
| 95 | Q | - | M | L | R | S | V | D | |
| 96 | R | W | A | Q | L | W | D | W | |
| 97 | Y | R | D | A | I | H | D | P | |
| 98 | R | D | L | Y | E | N | F | T | |
| 99 | S | F | D | L | Q | S | Q | L | |
| 100 | K | N | N | K | A | Q | T | I | |
| 100A | I | S | Y | P | R | F | E | F | |
| 100B | K | Y | W | H | D | T | N | W | |
| 100C | G | D | V | H | H | Q | E | Y | |
| 100D | H | P | Q | W | V | S | W | W | |
| 100E | F | M | F | M | M | F | M | F | |
| 101 | D | D | D | D | D | D | D | D | |
| 102 | V | Y | Y | Y | Y | V | Y | Y | |
| 103 | W | W | W | W | W | W | W | W | |
| FREQUENCY | 16 | 1 | 1 | 1 | 1 | 1 | 1 | 1 | |

FIG. 23

| | 92 | 93 | 94 | 95 | 96 | 97 | 98 | 99 | 100 | 100A | 100B | 100C | 100Ca | 100D | 100E | 101 | 102 | 103 | FREQUENCY |
|---|---|---|---|---|---|---|---|---|---|---|---|---|---|---|---|---|---|---|---|
| | C | A | R | G | F | G | F | F | E | – | – | – | – | – | – | D | Y | W | 4 |
| | C | A | R | Q | F | D | E | D | S | F | V | R | – | R | F | D | V | W | 4 |
| | C | A | R | H | L | K | E | S | G | K | S | R | – | Q | M | D | V | W | 2 |
| | C | A | R | E | Q | D | E | Y | S | A | H | R | – | H | M | D | Y | W | 1 |
| | C | A | R | N | H | F | W | A | D | W | P | R | R | Q | M | D | V | W | 1 |
| | C | A | R | E | Z | E | E | V | R | M | H | L | – | D | M | D | Y | W | 2 |
| | C | A | R | Q | F | S | W | T | K | W | V | R | – | K | F | D | Y | W | 1 |
| | C | A | R | K | K | R | E | S | V | T | R | R | – | K | F | D | V | W | 13 |
| | C | A | R | R | W | R | Q | Y | K | H | D | W | – | R | M | D | V | W | 3 |
| | C | A | R | D | Y | H | M | E | F | S | K | R | – | F | F | D | Y | W | 1 |
| | C | A | R | Q | F | E | E | E | K | – | – | – | – | – | – | D | Y | W | 1 |
| | C | A | R | Q | F | E | E | T | K | Q | R | R | – | L | M | D | Y | W | 1 |

| unique restriction site | Isoschizomers |
|---|---|
| AatII | / |
| AflII | BfrI, BspTI, Bst98I |
| AscI | / |
| AseI | VspI, AsnI, PshBI |
| BamHI | BstI |
| BbeI | EheI, KasI, NarI |
| BbsI | BpuAI, BpiI |
| BglII | / |
| BlpI | Bpu1102I, CelII, BlpI |
| BsaBI | MamI, Bsh1365I, BsrBRI |
| BsiWI | Pfl23II, SplI, SunI |
| BspEI | AccIII, BseAI, BsiMI, Kpn2I, MroI |
| BsrGI | Bsp1407I, SspBI |
| BssHII | PauI |
| BstEII | BstPI, Eco91I, EcoO65I |
| BstXI | / |
| Bsu36I | AocI, CvnI, Eco81I |
| DraIII | / |
| DsmAI | |
| EagI | BstZI, EclXI, Eco52I, XmaIII |
| Eco57I | / |
| EcoO109I | DraII |
| EcoRI | / |
| EcoRV | Eco32I |
| FseI | / |
| HindIII | / |
| HpaI | / |
| KpnI | Acc65I, Asp718I |
| MluI | / |
| MscI | BalI, MluNI |

*FIG. 25B*

| unique restriction site | Isoschizomers |
|---|---|
| MunI | MfeI |
| NheI | / |
| NsiI | Ppu10I, EcoT22I, Mph1103I |
| NspV | Bsp119I, BstBI, Csp45I, LspI, SfuI |
| PacI | / |
| PmeI | / |
| PmlI | BbrPI, Eco72I, PmaCI |
| Psp5II | PpuMI |
| PstI | / |
| RsrII | (RsriI), CpoI, CspI |
| SanDI | / |
| SapI | / |
| SexAI | / |
| SpeI | / |
| SfiI | / |
| SphI | BbuI, PaeI, NspI |
| StuI | AatI, Eco147I |
| StyI | Eco130I, EcoT14I |
| XbaI | BspLU11II |
| XhoI | PaeR7I |
| XmaI | AvaI, SmaI, Cfr9I, PspAI |

*FIG. 25C*

| No | module/flan-king restriction sites | functional element | sites to be removed | sites to be inserted | template | reference |
|---|---|---|---|---|---|---|
| M1 | AatII-lacp/o-XbaI | lac promotor/operator | 2x VspI (AseI) | AatII | vector pASK30 | Skerra et al. (1991) Bio/Technology 9, 273-278 |
| M2 | BglII-lox-AatII | Cre/lox recombination site | 2x VspI (AseI) | lox, BglII | (synthetic) | Hoess et al. (1986) Nucleic Acids Res. 2287-2300 |
| M3 | XbaI-lox'-SphI | Cre/lox' recombination site | none | lox', SphI | (synthetic) | see M2 |
| M7-I | EcoRI-gIIIlong-HindIII | gIIIp of filamentous phage with N-terminal myctail/amber codon | SphI, BamHI | none | vector pIG10 | Ge et al., (1994) Expressing antibodies in E. coli. In: Antibody engineering: A practical approach. IRL Press, New York, pp 229-266 |

FIG. 26A

| | | | | |
|---|---|---|---|---|
| M7-II | EcoRI-gIIIss-HindIII | truncated gIIIp of filamentous phage with N-terminal Gly-Ser linker | SphI | vector pIG10 | see M7-I |
| M7-III | EcoRI-gIIIss-HindIII | truncated gIIIp of filamentous phage with N-terminal myctail/amber codon | SphI, BbsI | vector pIG10 | see M7-I |
| M8 | SphI-lox-HindIII | Cre/lox recombination site | none | lox | see M3 |
| M9-II | HindIII-lpp-PacI | lpp-terminator | none | (synthetic) | see M1 |
| M10-II | PacI/FseI-bla-BsrGI | beta-lactamase/bla (ampR) | VspI, Eco57I, BssSI | (synthetic) | see M1 |
| M11-II | BsrGI-f1 ori-NheI | origin of single-stranded replication | DraIII (BanII not removed) | pASK30 | see M1 |
| M11-III | BsrGI-f1 ori-NheI | origin of single-stranded replication | DraIII, BanII | pASK30 | see M1 |

*FIG. 26B*

| | | | | |
|---|---|---|---|---|
| M12 | NheI-p15A-BglII | origin of double-stranded replication | BssSI, VspI, NspV | pACYC184 | Rose, R.E. (1988) Nucleic Acids Res. 16, 355 |
| M13 | BglII-lox-BglII | Cre/lox recombination site | none | NheI, BglII | see M3 |
| M14-Ext2 | BglII-ColEI-NheI | origin of double-stranded replication | Eco57I (BssSI not removed) | BglII, lox, XmnI | Yanisch-Perron, C. (1985) Gene 33, 103-119 |
| M17 | AatII-cat-BglII | chloramphenicol-acetyltransferase/ cat (camR) | BspEI, MscI, StyI/NcoI | BglII, NheI | Cardoso, M. & Schwarz, S. (1992) J. Appl. Bacteriol. 72, 289-293 |
| M19 | XbaI-phoA-EcoRI | signal sequence of phosphatase A | (synthetic) | (synthetic) | see M1 |
| M20 | XbaI-phoA-FLAG-EcoRI | signal sequence of phosphatase A + FLAG detection tag | (synthetic) | (synthetic) | Knappik, A & Plückthun, A. (1994) BioTechniques 17, 754-761 |

FIG. 26C

| | | | | |
|---|---|---|---|---|
| M21 | XbaI-stII-SapI | heat-stable enterotoxin II signal sequence | (synthetic) | Lee et al. (1983) Infect. Immunol. 264-268 |
| M41 | AflII-lacI-NheI | lac-repressor | BstXI, MluI,BbsI, BanII, BstEII, HpaI, BbeI, VspI | pASK30 | see M1 |
| M42 | EcoRI-Histail-HindIII | poly-histidine tail | | (synthetic) | Lindner et al., (1992) Methods: a companion to methods in enzymology 4, 41-56 |

FIG. 26D

```
                HindIII       PacI                        BsrGI
              ----------                ----------      ----------
  1   ACATGTAAGC TTCCCCCCCC CCTTAATTAA CCCCCCCCC  TGTACACCCC
      TGTACATTCG AAGGGGGGGG GGAATTAATT GGGGGGGGG  ACATGTGGGG NheI              BglII              AatII   XbaI
         ----------        ----------         ----------
 51   CCCCCCGCTA GCCCCCCCC CCAGATCTCC CCCCCCCGA CGTCCCCCCT
      GGGGGGCGAT CGGGGGGGG GGTCTAGAGG GGGGGGGCT GCAGGGGGGA XbaI          SphI                  EcoRI AatII
      ----------    ----------             ----------
101   CTAGACCCCC CCCCCGCATG CCCCCCCC CGAATTCGAC GTC
      GATCTGGGGG GGGGGCGTAC GGGGGGGG GCTTAAGCTG CAG
```

FIG. 27B

```
  1  CAGGTGGCAC  TTTTCGGGGA  AATGTGCGCG  GAACCCCTAT  TTGTTTATTT
     GTCCACCGTG  AAAAGCCCCT  TTACACGCGC  CTTGGGGATA  AACAAATAAA
     BssSI
     ~~~~~

51  TTCTAAATAC  ATTCAAATAT  GTATCCGCTC  ATGAGACAAT  AACCCTGATA
     AAGATTTATG  TAAGTTTATA  CATAGGCGAG  TACTCTGTTA  TTGGGACTAT

101  AATGCTTCAA  TAATATTGAA  AAAGGAAGAG  TATGAGTATT  CAACATTTCC
     TTACGAAGTT  ATTATAACTT  TTTCCTTCTC  ATACTCATAA  GTTGTAAAGG

151  GTGTCGCCCT  TATTCCCTTT  TTTGCGGCAT  TTTGCCTTCC  TGTTTTTGCT
     CACAGCGGGA  ATAAGGGAAA  AAACGCCGTA  AAACGGAAGG  ACAAAAACGA

Eco57I
                                         ~~~~~~~

201  CACCCCAGAAA  CGCTGGTGAA  AGTAAAAGAT  GCTGAAGATC  AGTTGGGTGC
     GTGGGTCTTT  GCGACCACTT  TCATTTTCTA  CGACTTCTAG  TCAACCCACG
                                                               BssSI
                                                               ~~~~~

251  ACGAGTGGGT  TACATCGAAC  TGGATCTCAA  CAGCGGTAAG  ATCCTTGAGA
     TGCTCACCCA  ATGTAGCTTG  ACCTAGAGTT  GTCGCCATTC  TAGGAACTCT
     BssSI
     ~~~~~
```

*FIG. 28B*

```
                XmnI
                ~~~~~~~~~~~
301  GTTTTCGCCC CGAAGAACGT TTTCCAATGA TGAGCACTTT TAAAGTTCTG
     CAAAAGCGGG GCTTCTTGCA AAAGGTTACT ACTCGTGAAA ATTTCAAGAC

351  CTATGTGGCG CGGTATTATC CCGTATTGAC GCCGGGCAAG AGCAACTCGG
     GATACACCGC GCCATAATAG GGCATAACTG CGGCCCGTTC TCGTTGAGCC

401  TCGCCGCATA CACTATTCTC AGAATGACTT GGTTGAGTAC TCACCAGTCA
     AGCGGCGTAT GTGATAAGAG TCTTACTGAA CCAACTCATG AGTGGTCAGT

451  CAGAAAAGCA TCTTACGGAT GGCATGACAG TAAGAGAATT ATGCAGTGCT
     GTCTTTTCGT AGAATGCCTA CCGTACTGTC ATTCTCTTAA TACGTCACGA

501  GCCATAACCA TGAGTGATAA CACTGCGGCC AACTTACTTC TGACAACGAT
     CGGTATTGGT ACTCACTATT GTGACGCCGG TTGAATGAAG ACTGTTGCTA

551  CGGAGGACCG AAGGAGCTAA CCGCTTTTTT GCACAACATG GGGGATCATG
     GCCTCCTGGC TTCCTCGATT GGCGAAAAAA CGTGTTGTAC CCCCTAGTAC

601  TAACTCGCCT TGATCGTTGG GAACCGGAGC TGAATGAAGC CATACCAAAC
     ATTGAGCGGA ACTAGCAACC CTTGGCCTCG ACTTACTTCG GTATGGTTTG

651  GACGAGCGTG ACACCACGAT GCCTGTAGCA ATGGCAACAA CGTTGCGCAA
```

FIG. 28C

```
                                                                     AseI
                                                                     ------
     CTGCTCGCAC TGTGGTGCTA CGGACATCGT TACCGTTGTT GCAACGCGTT

701  ACTATTAACT GGCGAACTAC TTACTCTAGC TTCCCGGCAA CAATTAATAG
     TGATAATTGA CCGCTTGATG AATGAGATCG AAGGGCCGTT GTTAATTATC

751  ACTGGATGGA GGCGGATAAA GTTGCAGGAC CACTTCTGCG CTCGGCCCTT
     TGACCTACCT CCGCCTATTT CAACGTCCTG GTGAAGACGC GAGCCGGGAA

801  CCGGCTGGCT GGTTTATTGC TGATAAATCT GGAGCCGGTG AGCGTGGGTC
     GGCCGACCGA CCAAATAACG ACTATTTAGA CCTCGGCCAC TCGCACCCAG

851  TCGCGGTATC ATTGCAGCAC TGGGGCCAGA TGGTAAGCCC TCCCGTATCG
     AGCGCCATAG TAACGTCGTG ACCCCGGTCT ACCATTCGGG AGGGCATAGC

901  TAGTTATCTA CACGACGGGG AGTCAGGCAA CTATGGATGA ACGAAATAGA
     ATCAATAGAT GTGCTGCCCC TCAGTCCGTT GATACCTACT TGCTTTATCT

951  CAGATCGCTG AGATAGGTGC CTCACTGATT AAGCATTGGT AACTGTCAGA
     GTCTAGCGAC TCTATCCACG GAGTGACTAA TTCGTAACCA TTGACAGTCT

1001 CCAAGTTTAC TCATATATAC TTTAGATTGA TTTAAAACTT CATTTTTAAT
     GGTTCAAATG AGTATATATG AATCTAACT AAATTTTGAA GTAAAAATTA
```

*FIG. 28D*

```
1051  TTAAAAGGAT CTAGGTGAAG ATCCTTTTTG ATAATCTCAT GACCAAAATC
      AATTTTCCTA GATCCACTTC TAGGAAAAAC TATTAGAGTA CTGGTTTTAG

1101  CCTTAACGTG AGTTTTCGTT CCACTGAGCG TCAGACCCCG TAGAAAGAT
      GGAATTGCAC TCAAAAGCAA GGTGACTCGC AGTCTGGGGC ATCTTTTCTA

1151  CAAAGGATCT TCTTGAGATC CTTTTTTTCT GCGCGTAATC TGCTGCTTGC
      GTTTCCTAGA AGAACTCTAG GAAAAAAAGA CGCGCATTAG ACGACGAACG

1201  AAACAAAAAA ACCACCGCTA CCAGCGGGTGG TTTGTTTTGCC GGATCAAGAG
      TTTGTTTTTT TGGTGGCGAT GGTCGCCACC AAACAAACGG CCTAGTTCTC

1251  CTACCAACTC TTTTTCCGAA GGTAACTGGC TTCAGCAGAG CGCAGATACC
      GATGGTTGAG AAAAAGGCTT CCATTGACCG AAGTCGTCTC GCGTCTATGG
                                         Eco57I
                                         - - - - - -

1301  AAATACTGTC CTTCTAGTGT AGCCGTAGTT AGGCCACCAC TTCAAGAACT
      TTTATGACAG GAAGATCACA TCGGCATCAA TCCGGTGGTG AAGTTCTTGA

1351  CTGTAGCACC GCCTACATAC CTCGCTCTGC TAATCCTGTT ACCAGTGGCT
      GACATCGTGG CGGATGTATG GAGCGAGACG ATTAGGACAA TGGTCACCGA
```

*FIG. 28E*

```
1401  GCTGCCAGTG  GCGATAAGTC  GTGTCTTACC  GGGTTGGACT  CAAGACGATA
      CGACGGTCAC  CGCTATTCAG  CACAGAATGG  CCCAACCTGA  GTTCTGCTAT

1451  GTTACCGGAT  AAGGCGCAGC  GGTCGGGCTG  AACGGGGGGT  TCGTGCACAC
      CAATGGCCTA  TTCCGCGTCG  CCAGCCCGAC  TTGCCCCCCA  AGCACGTGTG

1501  AGCCCAGCTT  GGAGCGAACG  ACCTACACCG  AACTGAGATA  CCTACAGCGT
      TCGGGTCGAA  CCTCGCTTGC  TGGATGTGGC  TTGACTCTAT  GGATGTCGCA

1551  GAGCTATGAG  AAAGCGCCAC  GCTTCCCGAA  GGGAGAAAGG  CGGACAGGTA
      CTCGATACTC  TTTCGCGGTG  CGAAGGGCTT  CCCTCTTTCC  GCCTGTCCAT

1601  TCCGGTAAGC  GGCAGGGTCG  GAACAGGAGA  GCGCACGAGG  GAGCTTCCAG
      AGGCCATTCG  CCGTCCCAGC  CTTGTCCTCT  CGCGTGCTCC  CTCGAAGGTC
                                                     BssSI
                                                     ~~~~~~

1651  GGGGAAACGC  CTGGTATCTT  TATAGTCCTG  TCGGGTTTCG  CCACCTCTGA
      CCCCTTTGCG  GACCATAGAA  ATATCAGGAC  AGCCCAAAGC  GGTGGAGACT

1701  CTTGAGCGTC  GATTTTTGTG  ATGCTCGTCA  GGGGGGCGGA  GCCTATGGAA
      GAACTCGCAG  CTAAAAACAC  TACGAGCAGT  CCCCCCGCCT  CGGATACCTT

1751  AAACGCCAGC  AACGCGGCCT  TTTTACGGTT  CCTGGCCTTT  TGCTGGCCTT
```

FIG. 28F

```
                 TTTGCGGGTCG TTGCGCCGGA AAAATGCCAA GGACCGGAAA ACGACCGGAA
                                              PacI                        BsrGI
                              HindIII         ------                      ------
1801  TTGCTCACAT GTAAGCTTCC CCCCCCCTT AATTAACCCC CCCCCCTGTA
      AACGAGTGTA CATTCGAAGG GGGGGGGAA TTAATTGGGG GGGGGGACAT
      BsrGI         NheI                BglII              AatII
      ------        ------              ------             ------
1851  CACCCCCCCC CCGCTAGCCC CCCCCCCAG ATCTCCCCCC CCCCGACGTC
      GTGGGGGGGG GGCGATCGGG GGGGGGGTC TAGAGGGGGG GGGGCTGCAG
                                         SphI                    EcoRI
                                         ------                  ------
1901  CCCCCTCTAG ACCCCCCCCC CGCATGCCCC CCCCCCCGAA TTCACGT
      GGGGAGATC TGGGGGGGGG GCGTACGGGG GGGGGGGCTT AAGTGCA
```

FIG. 28G

```
     AatII
     ------
  1  GACGTCTTAA TGTGAGTTAG CTCACTCATT AGGCACCCCA GGCTTTACAC
     CTGCAGAATT ACACTCAATC GAGTGAGTAA TCCGTGGGGT CCGAAATGTG

51  TTTATGCTTC CGGCTCGTAT GTTGTGTGGA ATTGTGAGCG GATAACAATT
     AAATACGAAG GCCGAGCATA CAACACACCT TAACACTCGC CTATTGTTAA

XbaI
                                    ----
101  TCACACAGGA AACAGCTATG ACCATGATTA CGAATTTCTA GA
     AGTGTGTCCT TTGTCGATAC TGGTACTAAT GCTTAAAGAT CT
```

FIG. 29B

```
     EcoRI
     ------
  1  GAATTCGAGC AGAAGCTGAT CTCTGAGGAG GATCTGTAGG GTGGTGGCTC
     CTTAAGCTCG TCTTCGACTA GAGACTCCTC CTAGACATCC CACCACCGAG

51  TGGTTCCGGT GATTTTGATT ATGAAAAGAT GGCAAACGCT AATAAGGGG
     ACCAAGGCCA CTAAAACTAA TACTTTTCTA CCGTTTGCGA TTATTCCCC

101  CTATGACCGA AAATGCCGAT GAAAACGCGC TACAGTCTGA CGCTAAAGGC
     GATACTGGCT TTTACGGCTA CTTTTGCGCG ATGTCAGACT GCGATTTCCG

151  AAACTTGATT CTGTCGCTAC TGATTACGGT GCTGCTATCG ATGGTTTCAT
     TTTGAACTAA GACAGCGATG ACTAATGCCA CGACGATAGC TACCAAAGTA

201  TGGTGACGTT TCCGGCCTTG CTAATGGTAA TGGTGCTACT GGTGATTTTG
     ACCACTGCAA AGGCCGGAAC GATTACCATT ACCACGATGA CCACTAAAAC

251  CTGGCTCTAA TTCCCAAATG GCTCAAGTCG GTGACGGTGA TAATTCACCT
     GACCGAGATT AAGGGTTTAC CGAGTTCAGC CACTGCCACT ATTAAGTGGA
        XmnI
        ------
301  TTAATGAATA ATTTCCGTCA ATATTTACCT TCCCTCCCTC AATCGGTTGA
     AATTACTTAT TAAAGGCAGT TATAAATGGA AGGGAGGGAG TTAGCCAACT
```

*FIG. 30B*

```
351  ATGTCGCCCT TTTGTCTTTG GCGCTGGTAA ACCATATGAA TTTTCTATTG
     TACAGCGGGA AAACAGAAAC CGCCGACCATT TGGTATACTT AAAAGATAAC

401  ATTGTGACAA AATAAACTTA TTCCGTGGTG TCTTTGCGTT TCTTTTATAT
     TAACACTGTT TTATTTGAAT AAGGCACCAC AGAAACGCAA AGAAAATATA

451  GTTGCCACCT TTATGTATGT ATTTTCTACG TTTGCTAACA TACTGCGTAA
     CAACGGTGGA AATACATACA TAAAAGATGC AAACGATTGT ATGACGCATT
                          HindIII
                          ------

501  TAAGGAGTCT TGATAAGCTT
     ATTCCTCAGA ACTATTCGAA
```

*FIG. 30C*

```
        HindIII
        ------
  1  GGGGGGGGG AAGCTTGACC TGTGAAGTGA AAAATGGCGC AGATTGTGCG
     CCCCCCCCC TTCGAACTGG ACACTTCACT TTTTACCGCG TCTAACACGC PacI                            FseI
                        ------                          ------
 51  ACATTTTTTT TGTCTGCCGT TTAATTAAAG GGGGGGGGGG GCCGGCCTGG
     TGTAAAAAAA ACAGACGGCA AATTAATTTC CCCCCCCCCC CGGCCGGACC BsrGI
       ------
101  GGGGGGTGT ACAGGGGGGG GGG
     CCCCCCACA TGTCCCCCCC CCC
```

FIG. 31B

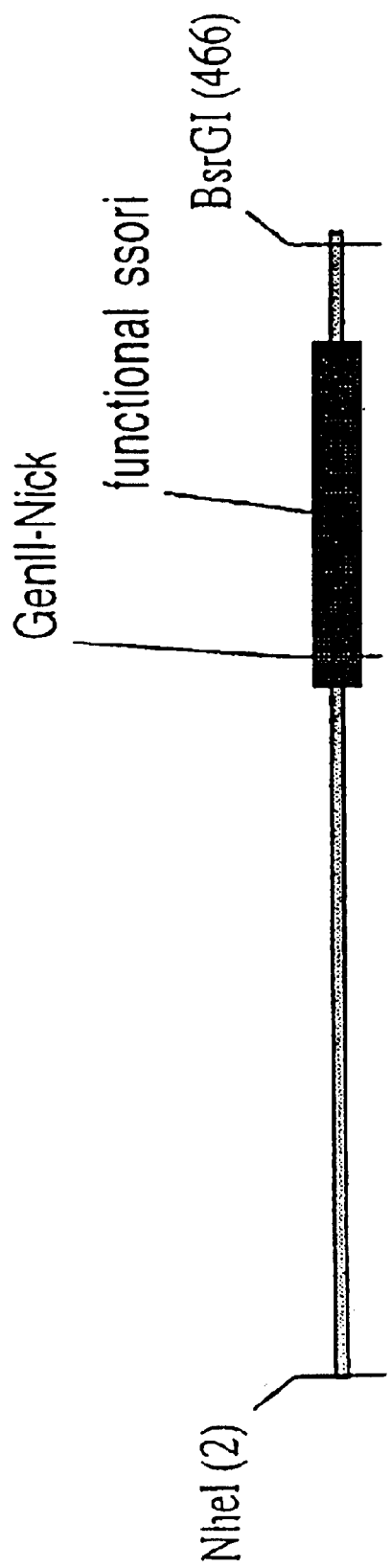

```
      NheI
      ~~~~~~~
  1   GCTAGCACGC  GCCCTGTAGC  GGCGCATTAA  GCGCGGCGGG  TGTGGTGGTT
      CGATCGTGCG  CGGGACATCG  CCGCGTAATT  CGCGCCGCCC  ACACCACCAA

51   ACGCGCAGCG  TGACCGCTAC  ACTTGCCAGC  GCCCTAGCGC  CCGCTCCTTT
      TGCGCGTCGC  ACTGGCGATG  TGAACGGTCG  CGGGATCGCG  GGCGAGGAAA

101   CGCTTTCTTC  CCTTCCTTTC  TCGCCACGTT  CGCCGGCTTT  CCCCGTCAAG
      GCGAAAGAAG  GGAAGGAAAG  AGCGGTGCAA  GCGGCCGAAA  GGGGCAGTTC

151   CTCTAAATCG  GGGCATCCCT  TTAGGGTTCC  GATTTAGTGC  TTTACGGCAC
      GAGATTTAGC  CCCGTAGGGA  AATCCCAAGG  CTAAATCACG  AAATGCCGTG

201   CTCGACCCCA  AAAAACTTGA  TTAGGGTGAT  GGTTCTCGTA  GTGGGCCATC
      GAGCTGGGGT  TTTTTGAACT  AATCCCACTA  CCAAGAGCAT  CACCCGGTAG

251   GCCCTGATAG  ACGGTTTTTC  GCCCTTTGAC  GTTGGAGTCC  ACGTTCTTTA
      CGGGACTATC  TGCCAAAAAG  CGGGAAACTG  CAACCTCAGG  TGCAAGAAAT

301   ATAGTGGACT  CTTGTTCCAA  ACTGGAACAA  CACTCAACCC  TATCTCGGTC
      TATCACCTGA  GAACAAGGTT  TGACCTTGTT  GTGAGTTGGG  ATAGAGCCAG

351   TATTCTTTTG  ATTTATAAGG  GATTTTGCCG  ATTTCGGCCT  ATTGGTTAAA
```

*FIG. 32B*

```
            ATAAGAAAAC TAAATATTCC CTAAAACGGC TAAAGCCGGA TAACCAATTT
401  AAATGAGCTG ATTTAACAAA AATTTAACGC GAATTTAAAC AAAATATTAA
     TTTACTCGAC TAAATTGTTT TTAAATTGCG CTTAAAATTG TTTTATAATT

BsrGI
                         ~~~~~~
451  CGTTTACAAT TTCATGTACA
     GCAAATGTTA AAGTACATGT
```

*FIG. 32C*

M14-EXT2
733 bp

```
     BglII
     ------
  1  AGATCTGACC AAAATCCCTT AACGTGAGTT TTCGTTCCAC TGAGCGTCAG
     TCTAGACTGG TTTTAGGGAA TTGCACTCAA AAGCAAGGTG ACTCGCAGTC

51  ACCCCGTAGA AAAGATCAAA GGATCTTCTT GAGATCCTTT TTTTCTGCGC
     TGGGGCATCT TTTCTAGTTT CCTAGAAGAA CTCTAGGAAA AAAAGACGCG

101  GTAATCTGCT GCTTGCAAAC AAAAAAACCA CCGCTACCAG CGGTGGTTTG
     CATTAGACGA CGAACGTTTG TTTTTTTGGT GGCGATGGTC GCCACCAAAC

151  TTTGCCGGAT CAAGAGCTAC CAACTCTTTT TCCGAAGGTA ACTGGCTACA
     AAACGGCCTA GTTCTCGATG GTTGAGAAAA AGGCTTCCAT TGACCGATGT

201  GCAGAGCGCA GATACCAAAT ACTGTTCTTC TAGTGTAGCC GTAGTTAGGC
     CGTCTCGCGT CTATGGTTTA TGACAAGAAG ATCACATCGG CATCAATCCG

251  CACCACTTCA AGAACTCTGT AGCACCGCCT ACATACCTCG CTCTGCTAAT
     GTGGTGAAGT TCTTGAGACA TCGTGGCGGA TGTATGGAGC GAGACGATTA

301  CCTGTTACCA GTGGCTGCTG CCAGTGGCGA TAAGTCGTGT CTTACCGGGT
     GGACAATGGT CACCGACGAC GGTCACCGCT ATTCAGCACA GAATGGCCCA

351  TGGACTCAAG ACGATAGTTA CCGGATAAGG CGCAGCGGTC GGGCTGAACG
```

FIG. 33B

```
       ACCTGAGTTC  TGCTATCAAT  GGCCTATTCC  GCGTCGCCAG  CCCGACTTGC
401    GGGGTTCGT   GCACACAGCC  CAGCTTGGAG  CGAACGACCT  ACACCGAACT
       CCCCCAAGCA  CGTGTGTCGG  GTCGAACCTC  GCTTGCTGGA  TGTGGCTTGA
451    GAGATACCTA  CAGCGTGAGC  TATGAGAAAG  CGCCACGCTT  CCCGAAGGGA
       CTCTATGGAT  GTCGCACTCG  ATACTCTTTC  GCGGTGCGAA  GGGCTTCCCT
501    GAAAGGCGGA  CAGGTATCCG  GTAAGCGGCA  GGGTCGGAAC  AGGAGAGCGC
       CTTTCCGCCT  GTCCATAGGC  CATTCGCCGT  CCCAGCCTTG  TCCTCTCGCG
                                                       BssSI
551    ACGAGGGAGC  TTCCAGGGGG  AAACGCCTGG  TATCTTTATA  GTCCTGTCGG
       TGCTCCCTCG  AAGGTCCCCC  TTTGCGGACC  ATAGAAATAT  CAGGACAGCC
       BssSI
601    GTTTCGCCAC  CTCTGACTTG  AGCGTCGATT  TTTGTGATGC  TCGTCAGGGG
       CAAAGCGGTG  GAGACTGAAC  TCGCAGCTAA  AAACACTACG  AGCAGTCCCC
651    GGCGGAGCCT  ATGGAAAAAC  GCCAGCAACG  CGGCCTTTTT  ACGGTTCCTG
       CCGCCTCGGA  TACCTTTTTG  CGGTCGTTGC  GCCGGAAAAA  TGCCAAGGAC
```

*FIG. 33C*

```
                                    NheI
                                   -------
701  GCCTTTTGCT GGCCTTT.GC TCACATGGCT AGC
     CGGAAAACGA CCGGAAAACG AGTGTACCGA TCG
```

FIG. 33D

```
     AatII
     ------
  1  GGGACGTCGG GTGAGGTTCC AACTTTCACC ATAATGAAAT AAGATCACTA
     CCCTGCAGCC CACTCCAAGG TTGAAAGTGG TATTACTTTA TTCTAGTGAT

51  CCGGGGCGTAT TTTTTGAGTT ATCGAGATTT TCAGGAGCTA AGGAAGCTAA
     GGCCCGCATA AAAAACTCAA TAGCTCTAAA AGTCCTCGAT TCCTTCGATT

101  AATGGAGAAA AAAATCACTG GATATACCAC CGTTGATATA TCCCAATGGC
     TTACCTCTTT TTTTAGTGAC CTATATGGTG GCAACTATAT AGGGTTACCG

151  ATCGTAAAGA ACATTTGAG GCATTTCAGT CAGTTGCTCA ATGTACCTAT
     TAGCATTTCT TGTAAAACTC CGTAAAGTCA GTCAACGAGT TACATGGATA

201  AACCAGACCG TTCAGCTGGA TATTACGGCC TTTTTAAAGA CCGTAAAGAA
     TTGGTCTGGC AAGTCGACCT ATAATGCCGG AAAAATTTCT GGCATTTCTT

251  AAATAAGCAC AAGTTTTATC CGGCCTTTAT TCACATTCTT GCCCGCCTGA
     TTTATTCGTG TTCAAAATAG GCCGGAAATA AGTGTAAGAA CGGGCGGACT

301  TGAATGCTCA CCCGGAGTTC CGTATGGCAA TGAAAGACGG TGAGCTGGTG
     ACTTACGAGT GGGCCTCAAG GCATACCGTT ACTTTCTGCC ACTCGACCAC

351  ATATGGGATA GTGTTCACCC TTGTTACACC GTTTTCCATG AGCAAACTGA
```

FIG. 34B

```
     TATACCCTAT CACAAGTGGG AACAATGTGG CAAAAGGTAC TCGTTTGACT
401  AACGTTTTCA TCGCTCTGGA GTGAATACCA CGACGATTTC CGGCAGTTTC
     TTGCAAAAGT AGCGAGACCT CACTTATGGT GCTGCTAAAG GCCGTCAAAG
451  TACACATATA TTCGCAAGAT GTGGCGTGTT ACGGTGAAAA CCTGGCCTAT
     ATGTGTATAT AAGCGTTCTA CACCGCACAA TGCCACTTTT GGACCGGATA
501  TTCCCTAAAG GGTTTATTGA GAATATGTTT TTCGTCTCAG CCAATCCCTG
     AAGGGATTTC CCAAATAACT CTTATACAAA AAGCAGAGTC GGTTAGGGAC
551  GGTGAGTTTC ACCAGTTTTG ATTTAAACGT AGCCAATATG GACAACTTCT
     CCACTCAAAG TGGTCAAAAC TAAATTTGCA TCGGTTATAC CTGTTGAAGA
601  TCGCCCCCGT TTTCACTATG GGCAAATATT ATACGCAAGG CGACAAGGTG
     AGCGGGGGCA AAAGTGATAC CCGTTTATAA TATGCGTTCC GCTGTTCCAC
651  CTGATGCCGC TGGCGATTCA GGTTCATCAT GCCGTTTGTG ATGGCTTCCA
     GACTACGGCG ACCGCTAAGT CCAAGTAGTA CGGCAAACAC TACCGAAGGT
701  TGTCGGCAGA ATGCTTAATG AATTACAACA GTACTGCGAT GAGTGGCAGG
     ACAGCCGTCT TACGAATTAC TTAATGTTGT CATGACGCTA CTCACCGTCC
751  GCGGGGCGTA ATTTTTTAA GGCAGTTATT GGTGCCCTT AAACGCCTGG
```

FIG. 34C

```
                CGCCCCGGCAT TAAAAAAATT CCGTCAATAA CCCACGGGAA TTTGCGGACC
                     BglII
                     ~~~~~
       801       TGCTAGATCT TCC
                 ACGATCTAGA AGG
```

*FIG. 34D*

```
     EcoRI
     ~~~~
  1  AATTCGAGCA GAAGCTGATC TCTGAGGAGG ATCTGTAGGG TGGTGGCTCT
     TTAAGCTCGT CTTCGACTAG AGACTCCTCC TAGACATCCC ACCACCGAGA

51  GGTTCCGGTG ATTTTGATTA TGAAAAGATG GCAAACGCTA ATAAGGGGGC
     CCAAGGCCAC TAAAACTAAT ACTTTTCTAC CGTTTGCGAT TATTCCCCCG

101  TATGACCGAA AATGCCGATG AAAACGCGCT ACAGTCTGAC GCTAAAGGCA
     ATACTGGCTT TTACGGCTAC TTTTGCGCGA TGTCAGACTG CGATTTCCGT

151  AACTTGATTC TGTCGCTACT GATTACGGTG CTGCTATCGA TGGTTTCATT
     TTGAACTAAG ACAGCGATGA CTAATGCCAC GACGATAGCT ACCAAAGTAA

201  GGTGACGTTT CCGGCCCTGC TAATGGTAAT GGTGCTACTG GTGATTTTGC
     CCACTGCAAA GGCCGGGAACG ATTACCATTA CCACGATGAC CACTAAAACG

251  TGGCTCTAAT TCCCAAATGG CTCAAGTCGG TGACGGTGAT AATTCACCTT
     ACCGAGATTA AGGGTTTACC GAGTTCAGCC ACTGCCACTA TTAAGTGGAA
           XmnI
           ~~~~~
           ~~~~~
           ~~~~~
301  TAATGAATAA TTTCCGTCAA TATTTACCTT CCCTCCCTCA ATCGGTTGAA
     ATTACTTATT AAAGGCAGTT ATAAATGGAA GGGAGGGAGT TAGCCAACTT
```

*FIG. 35B*

```
351   TGTCGCCCTT  TTGTCTTTGG  CGCTGGTAAA  CCATATGAAT  TTTCTATTGA
      ACAGCGGGAA  AACAGAAACC  GCGACCATTT  GGTATACTTA  AAAGATAACT

401   TTGTGACAAA  ATAAACTTAT  TCCGTGGTGT  CTTTGCGTTT  CTTTTATATG
      AACACTGTTT  TATTTGAATA  AGGCACCACA  GAAACGCAAA  GAAAATATAC

451   TTGCCACCTT  TATGTATGTA  TTTTCTACGT  TTGCTAACAT  ACTGCGTAAT
      AACGGTGGAA  ATACATACAT  AAAAGATGCA  AACGATTGTA  TGACGCATTA
                                HindIII
                                ------

501   AAGGAGTCTT  GATAAGCTTG  ACCTGTGAAG  TGAAAAATGG  CGCAGATTGT
      TTCCTCAGAA  CTATTCGAAC  TGGACACTTC  ACTTTTTACC  GCGTCTAACA
                                            PacI
                                          --------

551   GCGACATTTT  TTTTGTCTGC  CGTTAATTA  AAGGGGGGGG  GGGGCCGCC
      CGCTGTAAAA  AAAACAGACG  GCAAATTAAT  TTCCCCCCCC  CCCCGGCCGG
         BsrGI                                          FseI
         -----                                          ----

601   TGGGGGGGG  TGTACATGAA  ATTGTAAACG  TTAATATTTT  GTTAAAATTC
      ACCCCCCCC  ACATGTACTT  TAACATTTGC  AATTATAAAA  CAATTTTAAG
```

FIG. 35C

```
651  GCGTTAAATT  TTTGTTAAAT  CAGCTCATTT  TTTAACCAAT  AGGCCGAAAT
     CGCAATTTAA  AAACAATTTA  GTCGAGTAAA  AAATTGGTTA  TCCGGCTTTA

701  CGGCAAAATC  CCTTATAAAT  CAAAAGAATA  GACCGAGATA  GGGTTGAGTG
     GCCGTTTTAG  GGAATATTTA  GTTTTCTTAT  CTGGCTCTAT  CCCAACTCAC

751  TTGTTCCAGT  TTGGAACAAG  AGTCCACTAT  TAAAGAACGT  GGACTCCAAC
     AACAAGGTCA  AACCTTGTTC  TCAGGTGATA  ATTTCTTGCA  CCTGAGGTTG

801  GTCAAAGGGC  GAAAAACCGT  CTATCAGGGC  GATGGCCCAC  TACGAGAACC
     CAGTTTCCCG  CTTTTTGGCA  GATAGTCCCG  CTACCGGGTG  ATGCTCTTGG

851  ATCACCCTAA  TCAAGTTTTT  TGGGGTCGAG  GTGCCGTAAA  GCACTAAATC
     TAGTGGGATT  AGTTCAAAAA  ACCCCAGCTC  CACGGCATTT  CGTGATTTAG
                BanII
                ~~~~~~

901  GGAACCCTAA  AGGGAGCCCC  CGATTTAGAG  CTTGACGGGG  AAAGCCCGGCG
     CCTTGGGATT  TCCCTCGGGG  GCTAAATCTC  GAACTGCCCC  TTTCGGCCGC

951  AACGTGGCGA  GAAAGGAAGG  GAAGAAAGCG  AAAGGAGCGG  GCGCTAGGGC
     TTGCACCGCT  CTTTCCTTCC  CTTCTTTCGC  TTTCCTCGCC  CGCGATCCCG
```

*FIG. 35D*

```
1001  GCTGGCAAGT  GTAGCGGTCA  CGCTGCGCGT  AACCACCACA  CCCGCCGCGC
      CGACCGTTCA  CATCGCCAGT  GCGACGCGCA  TTGGTGGTGT  GGGCGGCGCG
                                                  NheI
                                                 -------
1051  TTAATGCGCC  GCTACAGGGC  GCGTGCTAGC  CATGTGAGCA  AAAGGCCAGC
      AATTACGCGG  CGATGTCCCG  CGCACGATCG  GTACACTCGT  TTTCCGGTCG

1101  AAAGGCCAG   GAACCGTAAA  AAGGCCGCGT  TGCTGGCGTT  TTTCCATAGG
      TTTCCGGTC   CTTGGCATTT  TTCCGGCGCA  ACGACCGCAA  AAAGGTATCC

1151  CTCCGCCCCC  CTGACGAGCA  TCACAAAAAT  CGACGCTCAA  GTCAGAGGTG
      GAGGCGGGGG  GACTGCTCGT  AGTGTTTTTA  GCTGCGAGTT  CAGTCTCCAC

1201  GCGAAACCCG  ACAGGACTAT  AAAGATACCA  GGCGTTTCCC  CCTGGAAGCT
      CGCTTTGGGC  TGTCCTGATA  TTTCTATGGT  CCGCAAAGGG  GGACCTTCGA
          BssSI
         -------
1251  CCCTCGTGCG  CTCTCCTGTT  CCGACCCTGC  CGCTTACCGG  ATACCTGTCC
      GGGAGCACGC  GAGAGGACAA  GGCTGGGACG  GCGAATGGCC  TATGGACAGG

1301  GCCTTTCTCC  CTTCGGGAAG  CGTGGCGCTT  TCTCATAGCT  CACGCTGTAG
      CGGAAAGAGG  GAAGCCCTTC  GCACCGCGAA  AGAGTATCGA  GTGCGACATC
```

FIG. 35E

```
1351  GTATCTCAGT TCGGTGTAGG TCGTTCGCTC CAAGCTGGGC TGTGTGCACG
      CATAGAGTCA AGCCACATCC AGCAAGCGAG GTTCGACCCG ACACACGTGC

1401  AACCCCCCGT TCAGCCCGAC CGCTGCGCCT TATCCGGTAA CTATCGTCTT
      TTGGGGGGCA AGTCGGGCTG GCGACGCGGA ATAGGCCATT GATAGCAGAA

1451  GAGTCCAACC CGGTAAGACA CGACTTATCG CCACTGGCAG CAGCCACTGG
      CTCAGGTTGG GCCATTCTGT GCTGAATAGC GGTGACCGTC GTCGGTGACC

1501  TAACAGGATT AGCAGAGCGA GGTATGTAGG CGGTGCTACA GAGTTCTTGA
      ATTGTCCTAA TCGTCTCGCT CCATACATCC GCCACGATGT CTCAAGAACT

1551  AGTGGTGGCC TAACTACGGC TACACTAGAA GAACAGTATT TGGTATCTGC
      TCACCACCGG ATTGATGCCG ATGTGATCTT CTTGTCATAA ACCATAGACG

1601  GCTCTGCTGT AGCCAGTTAC CTTCGGAAAA AGAGTTGGTA GCTCTTGATC
      CGAGACGACA TCGGTCAAATG GAAGCCTTTT TCTCAACCAT CGAGAACTAG

1651  CGGCAAACAA ACCACCGCTG GTAGCGGTGG TGCAAGCAGC
      GCCGTTTGTT TGGTGGCGAC CATCGCCACC ACGTTCGTCG

1701  AGATTACGCG CAGAAAAAAA GGATCTCAAG AAGATCCTTT GATCTTTTCT
      TCTAATGCGC GTCTTTTTTT CCTAGAGTTC TTCTAGGAAA CTAGAAAAGA
```

*FIG. 35F*

```
1751   ACGGGGTCTG ACGCTCAGTG GAACGAAAAC TCACGTTAAG GGATTTTGGT
       TGCCCCAGAC TGCGAGTCAC CTTGCTTTTG AGTGCAATTC CCTAAAACCA
           BglII
           -------
1801   CAGATCTAGC ACCAGGCGTT TAAGGGCACC AATAACTGCC TTAAAAAAT
       GTCTAGATCG TGGTCCGCAA ATTCCCGTGG TTATTGACGG AATTTTTTA

1851   TACGCCCCGC CCTGCCACTC ATCGCAGTAC TGTTGTAATT CATTAAGCAT
       ATGCGGGGCG GGACGGTGAG TAGCGTCATG ACAACATTAA GTAATTCGTA

1901   TCTGCCGACA TGGAAGCCAT CACAAACGGC ATGATGAACC TGAATCGCCA
       AGACGGCTGT ACCTTCGGTA GTGTTTGCCG TACTACTTGG ACTTAGCGGT

1951   GCGGCATCAG CACCTTGTCG CCTTGCGTAT AATATTTGCC CATAGTGAAA
       CGCCGTAGTC GTGGAACAGC GGAACGCATA TTATAAACGG GTATCACTTT

2001   ACGGGGGCGA AGAAGTTGTC CATATTGGCT ACGTTTAAAT CAAAACTGGT
       TGCCCCCGCT TCTTCAACAG GTATAACCGA TGCAAATTTA GTTTTGACCA

2051   GAAACTCACC CAGGGATTGG CTGAGACGAA AAACATATTC TCAATAAACC
       CTTTGAGTGG GTCCCTAACC GACTCTGCTT TTTGTATAAG AGTTATTTGG
```

*FIG. 35G*

```
2101  CTTTAGGGAA ATAGGCCAGG TTTTCACCGT AACACGCCAC ATCTTGCGAA
      GAAATCCCTT TATCCGGTCC AAAAGTGGCA TTGTGCGGTG TAGAACGCTT

2151  TATATGTGTA GAAACTGCCG GAAATCGTCG TGGTATTCAC TCCAGAGCGA
      ATATACACAT CTTTGACGGC CTTTAGCAGC ACCATAAGTG AGGTCTCGCT

2201  TGAAAACGTT TCAGTTTGCT CATGGAAAAC GGTGTAACAA GGGTGAACAC
      ACTTTTGCAA AGTCAAACGA GTACCTTTTG CCACATTGTT CCCACTGTG

2251  TATCCCATAT CACCAGCTCA CCGTCTTTCA TTGCCATACG GAACTCCGGG
      ATAGGGTATA GTGGTCGAGT GGCAGAAAGT AACGGTATGC CTTGAGGCCC

2301  TGAGCATTCA TCAGGCGGGC AAGAATGTGA ATAAAGGCCG GATAAAACTT
      ACTCGTAAGT AGTCCGCCCG TTCTTACACT TATTTCCGGC CTATTTTGAA

2351  GTGCTTATTT TTCTTTACGG TCTTTAAAAA GGCCGTAATA TCCAGCTGAA
      CACGAATAAA AAGAAATGCC AGAAATTTTT CCGGCATTAT AGGTCGACTT

2401  CGGTCTGGTT ATAGGTACAT TGAGCAACTG ACTGAAATGC CTCAAAATGT
      GCCAGACCAA TATCCATGTA ACTCGTTGAC TGACTTTACG GAGTTTTACA

2451  TCTTTACGAT GCCATTGGGA TATATCAACG GTGGTATATC CAGTGATTTT
      AGAAATGCTA CGGTAACCCT ATATAGTTGC CACCATATAG GTCACTAAAA
```

*FIG. 35H*

```
2501  TTTCTCCATT TTAGCTTCCT TAGCTCCTGA AAATCTCGAT AACTCAAAAA
      AAAGAGGTAA AATCGAAGGA ATCGAGGACT TTTAGAGCTA TTGAGTTTTT

2551  ATACGCCCGG TAGTGATCTT ATTTCATTAT GGTGAAAGTT GGAACCTCAC
      TATGCGGGCC ATCACTAGAA TAAAGTAATA CCACTTTCAA CCTTGGAGTG
          AatII

2601  CCGACGTCTA ATGTGAGTTA GCTCACTCAT TAGGCACCCC AGGCTTTACA
      GGCTGCAGAT TACACTCAAT CGAGTGAGTA ATCCGTGGGG TCCGAAATGT

2651  CTTTATGCTT CCGGCTCGTA TGTTGTGTGG AATTGTGAGC GGATAACAAT
      GAAATACGAA GGCCGAGCAT ACAACACACC TTAACACTCG CCTATTGTTA
                                                 XbaI    SphI

2701  TTCACACAGG AAACAGCTAT GACCATGATT ACGAATTTCT AGAGCATGCG
      AAGTGTGTCC TTTGTCGATA CTGGTACTAA TGCTTAAAGA TCTCGTACGC
      EcoRI

2751  GGGGG
      CCCCC
```

FIG. 35I

M 2:

```
       AatII
       ------
  1  GACGTCTTAA TGTGAGTTAG CTCACTCATT AGGCACCCCA GGCTTTACAC
     CTGCAGAATT ACACTCAATC GAGTGAGTAA TCCGTGGGGT CCGAAATGTG

51  TTTATGCTTC CGGCTCGTAT GTTGTGTGGA ATTGTGAGCG GATAACAATT
     AAATACGAAG GCCGAGCATA CAACACACCT TAACACTCGC CTATTGTTAA
                                           XmnI
                                           ------
                              XbaI
                              ------
101  TCACACAGGA AACAGCTATG ACCATGTCTA GAATAACTTC GTATAATGTA
     AGTGTGTCCT TTGTCGATAC TGGTACAGAT CTTATTGAAG CATATTACAT
                        SphI
                        ------
151  CGCTATACGA AGTTATCGCA TGC
     GCGATATGCT TCAATAGCGT ACG
```

FIG. 35K

M3
47 bp

M 3:

```
    BglII                                                      AatII
    |-----|                                                    |-----|
1   AGATCTCATA ACTTCGTATA ATGTATGCTA TACGAAGTTA TGACGTC
    TCTAGAGTAT TGAAGCATAT TACATACGAT ATGCTTCAAT ACTGCAG
```

FIG. 35M

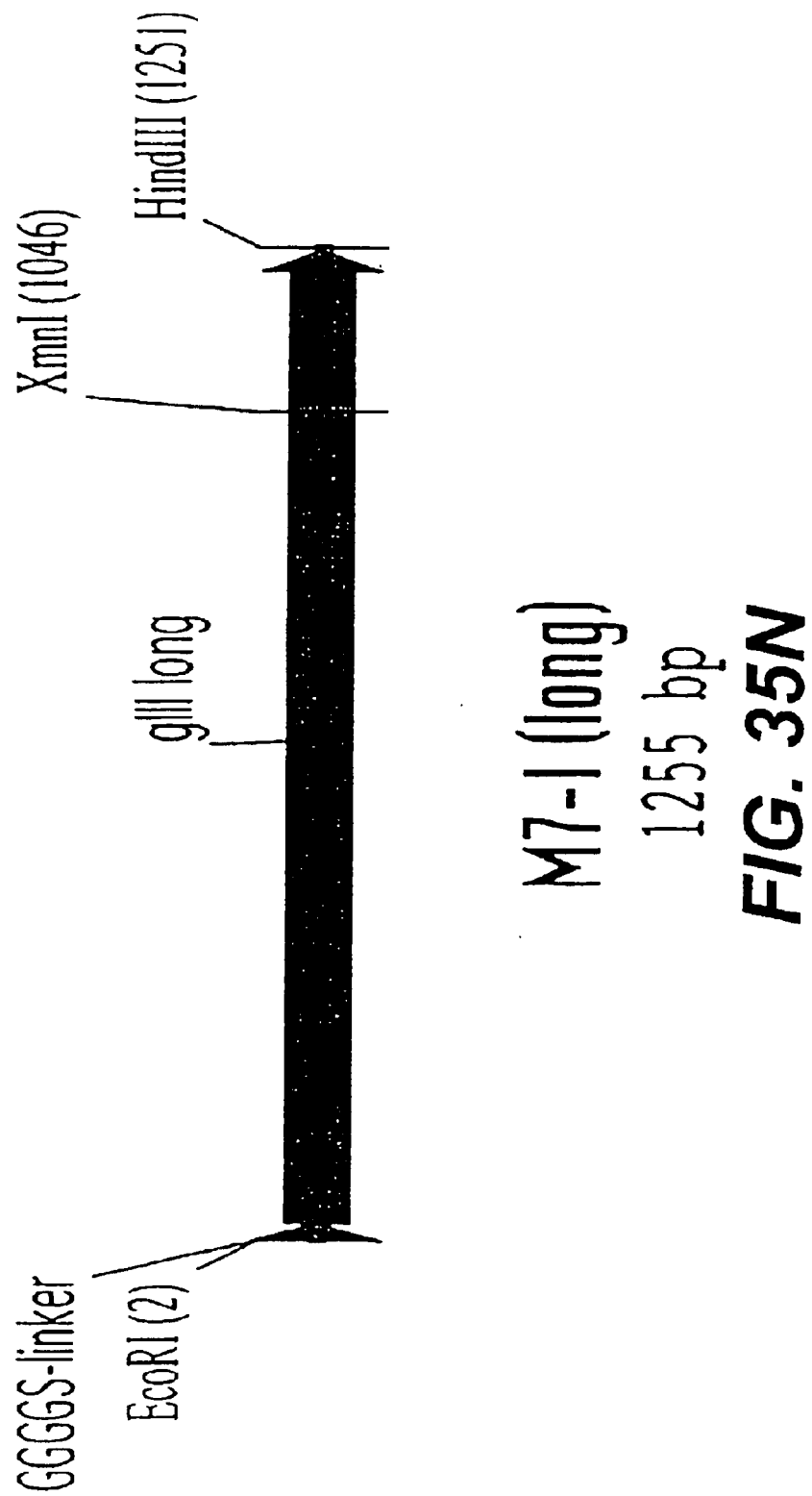

M 7-I (long):

EcoRI
------

```
  1  GAATTCGGTG GTGGTGGATC TGCGTGCGCT GAAACGGTTG AAAGTTGTTT
     CTTAAGCCAC CACCACCTAG ACGCACGCGA CTTTGCCAAC TTTCAACAAA

51  AGCAAAATCC CATACAGAAA ATTCATTTAC TAACGTCTGG AAAGACGACA
     TCGTTTTAGG GTATGTCTTT TAAGTAAATG ATTGCAGACC TTTCTGCTGT

101  AAACTTTAGA TCGTTACGCT AACTATGAGG GCTGTCTGTG GAATGCTACA
     TTTGAAATCT AGCAATGCGA TTGATACTCC CGACAGACAC CTTACGATGT

151  GGCGTTGTAG TTTGTACTGG TGACGAAACT CAGTGTTACG GTACATGGGT
     CCGCAACATC AAACATGACC ACTGCTTTGA GTCACAATGC CATGTACCCA

201  TCCTATTGGG CTTGCTATCC CTGAAAATGA GGGTGGTGGC TCTGAGGGTG
     AGGATAACCC GAACGATAGG GACTTTTACT CCCACCACCG AGACTCCCAC

251  GCGGTTCTGA GGGTGGCGGT TCTGAGGGTG GCGGTACTAA ACCTCCTGAG
     CGCCAAGACT CCCACCGCCA AGACTCCCAC CGCCATGATT TGGAGGACTC

301  TACGGTGATA CACCTATTCC GGGCTATACT TATATCAACC CTCTCGACGG
     ATGCCACTAT GTGGATAAGG CCCGATATGA ATATAGTTGG GAGAGCTGCC
```

*FIG. 350*

```
351  CACTTATCCG  CCTGGTACTG  AGCAAAACCC  CGCTAATCCT  AATCCTTCTC
     GTGAATAGGC  GGACCATGAC  TCGTTTTGGG  GCGATTAGGA  TTAGGAAGAG

401  TTGAGGAGTC  TCAGCCTCTT  AATACTTTCA  TGTTTCAGAA  TAATAGGTTC
     AACTCCTCAG  AGTCGGAGAA  TTATGAAAGT  ACAAAGTCTT  ATTATCCAAG

451  CGAAATAGGC  AGGGGGCATT  AACTGTTTAT  ACGGGCACTG  TTACTCAAGG
     GCTTTATCCG  TCCCCCGTAA  TTGACAAATA  TGCCCGTGAC  AATGAGTTCC

501  CACTGACCCC  GTTAAAACTT  ATTACCAGTA  CACTCCTGTA  TCATCAAAAG
     GTGACTGGGG  CAATTTTGAA  TAATGGTCAT  GTGAGGACAT  AGTAGTTTTC

551  CCATGTATGA  CGCTTACTGG  AACGGTAAAT  TCAGAGACTG  CGCTTTCCAT
     GGTACATACT  GCGAATGACC  TTGCCATTTA  AGTCTCTGAC  GCGAAAGGTA

601  TCTGGCTTTA  ATGAGGATTT  ATTTGTTTGT  GAATATCAAG  GCCAATCGTC
     AGACCGAAAT  TACTCCTAAA  TAAACAAACA  CTTATAGTTC  CGGTTAGCAG

651  TGACCTGCCT  CAACCTCCTG  TCAATGCTGG  CGGCGGCTCT  GGTGGTGGTT
     ACTGGACGGA  GTTGGAGGAC  AGTTACGACC  GCCGCCGAGA  CCACCACCAA

701  CTGGTGGCGG  CTCTGAGGGT  GGTGGCTCTG  AGGGTGGCGG  TTCTGAGGGT
     GACCACCGCC  GAGACTCCCA  CCACCGAGAC  TCCCACCGCC  AAGACTCCCA
```

FIG. 35P

```
 751  GGCGGCTCTG AGGGAGGCGG TTCCGGTGGT GGCTCTGTGT CCGGTGATTT
      CCGCCGAGAC TCCCTCCGCC AAGGCCACCA CCGAGACACA GGCCACTAAA

801  TGATTATGAA AAGATGGCAA ACGCTAATAA ACGCTAATAA ACCGAAAATG
      ACTAATACTT TTCTACCGTT TGCGATTATT CCCCCGATAC TGGCTTTTAC

851  CCGATGAAAA CGCGCTACAG TCTGACGCTA AAGGCAAACT TGATTCTGTC
      GGCTACTTTT GCGCGATGTC AGACTGCGAT TTCCGTTTGA ACTAAGACAG

901  GCTACTGATT ACGGTGCTGC TATCGATGGT TTCATTGGTG ACGTTTCCGG
      CGATGACTAA TGCCACGACG ATAGCTACCA AAGTAACCAC TGCAAAGGCC

951  CCTTGCTAAT GGTAATGGTG CTACTGGTGA TTTTGCTGGC TCTAATTCCC
      GGAACGATTA CCATTACCAC GATGACCACT AAAACGACCG AGATTAAGGG

XmnI
                                                 |-------|
1001  AAATGGCTCA AGTCGGTGAA GGTGATAATT CACCTTTAAT GAATAATTTC
      TTTACCGAGT TCAGCCACTT CCACTATTAA GTGGAAATTA CTTATTAAAG

1051  CGTCAATATT TACCTTCCAT CCCTCAATCG GTTGAATGTC GCCCTTTGT
      GCAGTTATAA ATGGAAGGTA GGGAGTTAGC CAACTTACAG CGGGAAAACA
```

*FIG. 35Q*

```
1101  CTTTGGCGCT GGTAAACCCT ATGAATTTTC TATTGATTGT GACAAAATAA
      GAAACCGCGA CCATTTGGGA TACTTAAAAG ATAACTAACA CTGTTTTATT

1151  ACTTATTCCG TGGTGTCTTT GCGTTTCTTT TATATGTTGC CACCTTTATG
      TGAATAAGGC ACCACAGAAA CGCAAAGAAA ATATACAACG GTGGAAATAC
                                                  HindIII 1201  TATGTATTTT CTACGTTTGC TAACATACTG CGTAATAAGG AGTCTTGATA
      ATACATAAAA GATGCAAACG ATTGTATGAC GCATTATTCC TCAGAACTAT HindI
      ----
1251  AGCTT
      TCGAA
```

FIG. 35R

M 7-II (ss-TAG):

EcoRI

```
  1  CGGGAATTCG GAGGCGGTTC CGGTGGTGGC TCTGGTTCCG GTGATTTTGA
     GCCCTTAAGC CTCCGCCAAG GCCACCACCG AGACCAAGGC CACTAAAACT

51  TTATGAAAAG ATGGCAAACG CTAATAAGGG GGCTATGACC GAAAATGCCG
     AATACTTTTC TACCGTTTGC GATTATTCCC CCGATACTGG CTTTTACGGC

101  ATGAAAACGC GCTACAGTCT GACGCTAAAG GCAAACTTGA TTCTGTCGCT
     TACTTTTGCG CGATGTCAGA CTGCGATTTC CGTTTGAACT AAGACAGCGA

151  ACTGATTACG GTGCTGCTAT CGATGGTTTC ATTGGTGACG TTTCCGGCCT
     TGACTAATGC CACGACGATA GCTACCAAAG TAACCACTGC AAAGGCCGGA

201  TGCTAATGGT AATGGTGCTA CTGGTGATTT TGCTGGCTCT AATTCCCAAA
     ACGATTACCA TTACCACGAT GACCACTAAA ACGACCGAGA TTAAGGGTTT

XmnI

251  TGGCTCAAGT CGGTGACGGT GATAATTCAC CTTTAATGAA TAATTTCCGT
     ACCGAGTTCA GCCACTGCCA CTATTAAGTG GAAATTACTT ATTAAAGGCA
```

FIG. 35T

```
301  CAATATTTAC CTTCCCTCCC TCAATCGGTT GAATGTCGCC CTTTGTCTT
     GTTATAAATG GAAGGGAGGG AGTTAGCCAA CTTACAGCGG GAAAACAGAA

351  TGGCGCTGGT AAACCATATG AATTTCTAT  TGATTGTGAC AAAATAAACT
     ACCGCGACCA TTTGGTATAC TTAAAAGATA ACTAACACTG TTTTATTTGA

401  TATTCCGTGG TGTCTTTGCG TTTCTTTTAT ATGTTGCCAC CTTTATGTAT
     ATAAGGCACC ACAGAAACGC AAAGAAAATA TACAACGGTG GAAATACATA

HindIII
                                                ------
451  GTATTTTCTA CGTTTGCTAA CATACTGCGT AATAAGGAGT CTTGATAAGC
     CATAAAAGAT GCAAACGATT GTATGACGCA TTATTCCTCA GAACTATTCG 501  Hi
     -
     TT
     AA
```

FIG. 35U

M8
47 bp

M 8:

```
     SphI                                              HindIII
     ------                                            ------
1    GCATGCCATA ACTTCGTATA ATGTACGCTA TACGAAGTTA TAAGCTT
     CGTACGGTAT TGAAGCATAT TACATGCGAT ATGCTTCAAT ATTCGAA
```

FIG. 35W

M 10-II:

```
        BsrGI
       --------
  1  GGGGGTGTAC ATTCAAATAT GTATCCGCTC ATGAGACAAT AACCCTGATA
     CCCCCACATG TAAGTTTATA CATAGGCGAG TACTCTGTTA TTGGGACTAT

51  AATGCTTCAA TAATATTGAA AAAGGAAGAG TATGAGTATT CAACATTTCC
     TTACGAAGTT ATTATAACTT TTTCCTTCTC ATACTCATAA GTTGTAAAGG

101  GTGTCGCCCT TATTCCCTTT TTTGCGGCAT TTTGCCTTCC TGTTTTTGCT
     CACAGCGGGA ATAAGGGAAA AAACGCCGTA AAACGGAAGG ACAAAAACGA

151  CACCCAGAAA CGCTGGTGAA AGTAAAAGAT GCTGAGGATC AGTTGGGTGC
     GTGGGTCTTT GCGACCACTT TCATTTTCTA CGACTCCTAG TCAACCCACG

201  GCGAGTGGGT TACATCGAAC TGGATCTCAA CAGCGGTAAG ATCCTTGAGA
     CGCTCACCCA ATGTAGCTTG ACCTAGAGTT GTCGCCATTC TAGGAACTCT
                          XmnI
                         ---------

251  GTTTTCGCCC CGAAGAACGT TTTCCAATGA TGAGCACTTT TAAAGTTCTG
     CAAAAGCGGG GCTTCTTGCA AAAGGTTACT ACTCGTGAAA ATTTCAAGAC
```

FIG. 35Y

```
301  CTATGTGGCG CGTATTATC  CCGTATTGAC GCCGGGCAAG AGCAACTCGG
     GATACACCGC GCCATAATAG GGCATAACTG CGGCCCCGTTC TCGTTGAGCC

351  TCGCCGCATA CACTATTCTC AGAATGACTT GGTTGAGTAC TCACCAGTCA
     AGCGGCGTAT GTGATAAGAG TCTTACTGAA CCAACTCATG AGTGGTCAGT

401  CAGAAAAGCA TCTTACGGAT GGCATGACAG TAAGAGAATT ATGCAGTGCT
     GTCTTTTCGT AGAATGCCTA CCGTACTGTC ATTCTCTTAA TACGTCACGA

451  GCCATAACCA TGAGTGATAA CACTGCGGCC AACTTACTTC TGACAACGAT
     CGGTATTGGT ACTCACTATT GTGACGCCGG TTGAATGAAG ACTGTTGCTA

501  CGGAGGACCG AAGGAGCTAA CCGCTTTTTT GCACAACATG GGGGATCATG
     GCCTCCTGGC TTCCTCGATT GGCGAAAAAA CGTGTTGTAC CCCCTAGTAC

551  TAACTCGCCT TGATCGTTGG GAACCGGAGC TGAATGAAGC CATACCAAAC
     ATTGAGCGGA ACTAGCAACC CTTGGCCTCG ACTTACTTCG GTATGGTTTG

601  GACGAGCGTG ACACCACGAT GCCTGTAGCA ATGGCAACAA CGTTGCGCAA
     CTGCTCGCAC TGTGGTGCTA CGGACATCGT TACCGTTGTT GCAACGCGTT

651  ACTATTAACT GGCGAACTAC TTACTCTAGC TTCCCGGCAA CAGTTAATAG
     TGATAATTGA CCGCTTGATG AATGAGATCG AAGGGCCGTT GTCAATTATC
```

*FIG. 35Z*

```
 701  ACTGGATGGA GGCGGATAAA GTTGCAGGAC CACTTCTGCG CTCGGCCCTT
      TGACCTACCT CCGCCTATTT CAACGTCCTG GTGAAGACGC GAGCCGGGAA

751  CCGGCTGGCT GGTTTATTGC TGATAAATCT GGAGCCGGTG AGCCGTGGGTC
      GGCCGACCGA CCAAATAACG ACTATTTAGA CCTCGGCCAC TCGCACCCAG

801  TCGCGGTATC ATTGCAGCAC TGGGGCCAGA TGGTAAGCCC TCCCGTATCG
      AGCGCCATAG TAACGTCGTG ACCCCGGTCT ACCATTCGGG AGGGCATAGC

851  TAGTTATCTA CACGACGGGG AGTCAGGCAA ACGAAATAGA
      ATCAATAGAT GTGCTGCCCC TCAGTCCGTT TGCTTTATCT

901  CAGATCGCTG AGATAGGTGC CTCACTGATT AAGCATTGGG TAACTGTCAG
      GTCTAGCGAC TCTATCCACG GAGTGACTAA TTCGTAACCC ATTGACAGTC

951  ACCAAGTTTA CTCATATATA CTTTAGATTG ATTTAAAACT TCATTTTAA
      TGGTTCAAAT GAGTATATAT GAAATCTAAC TAAATTTTGA AGTAAAAATT

1001  TTTAAAAGGA TCTAGGTGAA GATCCTTTTT GATAATCTCA TGACCAAAAT
      AAATTTTCCT AGATCCACTT CTAGGAAAAA CTATTAGAGT ACTGGTTTTA

1051  CCCTTAACGT GAGTTTTCGT TCCACTGAGC GTCAGACCCC GTAGAAAAGA
      GGGAATTGCA CTCAAAAGCA AGGTGACTCG CAGTCTGGGG CATCTTTTCT
```

*FIG. 35AA*

```
                                                         FseI              PacI
                                                  ------------           ------
1101  TCAAAGGATC  TTCTTTGAGAT  CCTTTTTGAT  AATGGCCGGC  CCCCCCCTT
      AGTTTCCTAG  AAGAACTCTA   GGAAAAACTA  TTACCGGCCG  GGGGGGGAA

PacI
      ------
1151  AATTAAGGGG  GGG
      TTAATTCCCC  CCC
```

*FIG. 35BB*

```
M11-II:

NheI
     ------
  1  GCTAGCACGC GCCCTGTAGC GGCGCATTAA GCGCGGCGGG TGTGGTGGTT
     CGATCGTGCG CGGGACATCG CCGCGTAATT CGCGCCGCCC ACACCACCAA

51  ACGCGCAGCG TGACCGCTAC ACTTGCCAGC GCCCTAGCGC CCGCTCCTTT
     TGCGCGTCGC ACTGGCGATG TGAACGGTCG CGGGATCGCG GGCGAGGAAA

101  CGCTTTCTTC CCTTCCTTTC TCGCCACGTT CGCCCGGCTTT CCCCGTCAAG
     GCGAAAGAAG GGAAGGAAAG AGCGGTGCAA GCGGCCCGAAA GGGGCAGTTC
                           BanII
                           ------
151  CTCTAAATCG GGGCTCCCT TTAGGGTTCC GATTTAGTGC TTTACGGCAC
     GAGATTTAGC CCCCGAGGGA AATCCCAAGG CTAAATCACG AAATGCCGTG

201  CTCGACCCCA AAAAACTTGA TTAGGGTGAT GGTTCTCGTA GTGGGCCATC
     GAGCTGGGGT TTTTTGAACT AATCCCACTA CCAAGAGCAT CACCCGGTAG

251  GCCCTGATAG GCCCTTTGAC GTTGGAGTCC ACGTTCTTTA
     CGGGACTATC CGGGAAACTG CAACCTCAGG TGCAAGAAAT
```

FIG. 35DD

```
301  ATAGTGGACT CTTGTTCCAA ACTGGAACAA CACTCAACCC TATCTCGGTC
     TATCACCTGA GAACAAGGTT TGACCTTGTT GTGAGTTGGG ATAGAGCCAG

351  TATTCTTTTG ATTTATAAGG GATTTTGCCG ATTTCGGCCT ATTGGTTAAA
     ATAAGAAAAC TAAATATTCC CTAAAACGGC TAAAGCCGGA TAACCAATTT

401  AAATGAGCTG ATTTAACAAA AATTTAACGC GAATTTTAAC AAAATATTAA
     TTTACTCGAC TAAATTGTTT TTAAATTGCG CTTAAAATTG TTTTATAATT

BsrGI
              ------
451  CGTTTACAAT TTCATGTACA
     GCAAATGTTA AAGTACATGT
```

*FIG. 35EE*

M 12:
BglII
~~~~~~

1  AGATCTAATA AGATGATCTT CTTGAGATCG TTTTGGTCTG CGCGTAATCT
     TCTAGATTAT TCTACTAGAA GAACTCTAGC AAAACCAGAC GCGCATTAGA

51  CTTGCTCTGA AAACGAAAAA ACCGCCTTGC AGGGCGGTTT TTCGTAGGTT
     GAACGAGACT TTTGCTTTTT TGGCGGAACG TCCCGCCAAA AAGCATCCAA

101  CTCTGAGCTA CCAACTCTTT GAACCGAGGT AACTGGCTTG GAGGAGCGCA
     GAGACTCGAT GGTTGAGAAA CTTGGCTCCA TTGACCGAAC CTCCTCGCGT

151  GTCACTAAAA CTTGTCCTTT CAGTTTAGCC TTAACCGGCG CATGACTTCA
     CAGTGATTTT GAACAGGAAA GTCAAATCGG AATTGGCCGC GTACTGAAGT

201  AGACTAACTC CTCTAAATCA ATTACCAGTG GCTGCTGCCA GTGGTGCTTT
     TCTGATTGAG GAGATTTAGT TAATGGTCAC CGACGACGGT CACCACGAAA

251  TGCATGTCTT TCCGGGTTGG ACTCAAGACG ATAGTTACCG GATAAGGCGC
     ACGTACAGAA AGGCCCAACC TGAGTTCTGC TATCAATGGC CTATTCCGCG

301  AGCGGGTCGGA CTGAACGGGG GGTTCGTGCA TACAGTCCAG CTTGGAGCGA
     TCGCCCAGCCT GACTTGCCCC CCAAGCACGT ATGTCAGGTC GAACCTCGCT

*FIG. 35GG*

```
351  ACTGCCTACC CGGAACTGAG TGTCAGGCGT GGAATGAGAC AAACGCGGCC
     TGACGGATGG GCCTTGACTC ACAGTCCGCA CCTTACTCTG TTTGCGCCGG

AgeI
                          ~~~~~~~~
401  ATAACAGCGG AATGACACCG GTAAACCGAA AGGCAGGAAC AGGAGAGCGC
     TATTGTCGCC TTACTGTGGC CATTTGGCTT TCCGTCCTTG TCCTCTCGCG

451  AGGAGGGAGC CGCCAGGGGG AAACGCCTGG TATCTTTATA GTCCTGTCGG
     TCCTCCCTCG GCGGTCCCCC TTTGCGGACC ATAGAAATAT CAGGACAGCC

501  GTTTCGCCAC CACTGATTTG AGCGTCAGAT TTCGTGATGC TTGTCAGGGG
     CAAAGCGGTG GTGACTAAAC TCGCAGTCTA AAGCACTACG AACAGTCCCC

551  GGCGGAGCCT ATGGAAAAAC GGCTTTGCCG CGGCCCCTCT ACTTCCCTGT
     CCGCCTCGGA TACCTTTTTG CCGAAACGGC GCCGGGAGAG TGAAGGGACA

601  TAAGTATCTT CCTGGCATCT TCCAGGAAAT CTCCGCCCCG TTCGTAAGCC
     ATTCATAGAA GGACCGTAGA AGGTCCTTTA GAGGCGGGGC AAGCATTCGG

651  ATTTCCGCTC GCCGCAGTCG AACGACCGAG CGTAGCGAGT CAGTGAGCGA
     TAAAGGCGAG CGGCGTCAGC TTGCTGGCTC GCATCGCTCA GTCACTCGCT
```

*FIG. 35HH*

```
                                                                       AgeI
                                                                       ~~~~
701  GGAAGCGGAA TATATCCTGT ATCACATATT CTGCTGACGC ACCGGTGCAG
     CCTTCGCCTT ATATAGGACA TAGTGTATAA GACGACTGCG TGGCCACGTC

XmnI
                         ~~~~~~~~~~~
751  CCTTTTTTCT CCTGCCACAT GAAGCACTTC ACTGACACCC TCATCAGTGC
     GGAAAAAAGA GGACGGTGTA CTTCGTGAAG TGACTGTGGG AGTAGTCACG

NheI
                         ~~~~~
801  CAACATAGTA AGCCAGTATA CACTCCGCTA GC
     GTTGTATCAT TCGGTCATAT GTGAGGCGAT CG
```

*FIG. 35II*

```
M 13:
       BglII                              XmnI          BglII
       ------                             ------        ------
    1  AGATCTCATA ACTTCGTATA ATGTATGCTA TACGAAGTTA TTCAGATCT
       TCTAGAGTAT TGAAGCATAT TACATACGAT ATGCTTCAAT AAGTCTAGA
```

FIG. 35KK

M 19:

```
     XbaI  SphI                                                     
     ------ ----                                                    
  1  TCTAGAGCAT GCGTAGGAGA AAATAAAATG AAACAAAGCA CTATTGCACT
     AGATCTCGTA CGCATCCTCT TTTATTTTAC TTTGTTTCGT GATAACGTGA

SapI                              EcoRI
                       ------                            -----
 51  GGCACTCTTA CCGTTGCTCT TCACCCCTGT TACCAAAGCC GAATTC
     CCGTGAGAAT GGCAACGAGA AGTGGGGACA ATGGTTTCGG CTTAAG
```

FIG. 35MM

M 20:

```
     XbaI  SphI
     ----- ----
  1  TCTAGAGCAT GCGTAGGAGA AAATAAAATG AAACAAAGCA CTATTGCACT
     AGATCTCGTA CGCATCCTCT TTTATTTTAC TTTGTTTCGT GATAACGTGA
                                SapI
                                ----
 51  GGCACTCTTA CCGTTGCTCT TCACCCCTGT TACCAAAGCC GACTACAAAG
     CCGTGAGAAT GGCAACGAGA AGTGGGGACA ATGGTTTCGG CTGATGTTTC
            MunI  EcoRI
            ----  -----
101  ATGAAGTGCA ATTGGAATTC
     TACTTCACGT TAACCTTAAG
```

*FIG. 3500*

M21
96 bp

M 21:

```
     XbaI
     ------
  1  TCTAGAGGTT GAGGTGATTT TATGAAAAAG AATATCGCAT TTCTTCTTGC
     AGATCTCCAA CTCCACTAAA ATACTTTTTC TTATAGCGTA AAGAAGAACG

NsiI                    EcoRI
                           ------                  ------
 51  ATCTATGTTC GTTTTTCTA TTGCTACAAA TGCATACGCT GAATTC
     TAGATACAAG CAAAAAAGAT AACGATGTTT ACGTATGCGA CTTAAG
```

FIG. 35QQ

M 41:

```
       NheI
       ------
  1    GCTAGCATCG AATGGCGCAA AACCTTTCGC GGTATGGCAT GATAGCGCCC
       CGATCGTAGC TTACCGCGTT TTGGAAAGCG CCATACCGTA CTATCGCGGG

51    GGAAGAGAGT CAATTCAGGG TGGTGAATGT GAAACCAGTA ACGTTATACG
       CCTTCTCTCA GTTAAGTCCC ACCACTTACA CTTTGGTCAT TGCAATATGC

101    ATGTCGCAGA GTATGCCCGGT GTCTCTTATC AGACCGTTTC CCGGCGTGGTG
       TACAGCGTCT CATACGGCCA CAGAGAATAG TCTGGCAAAG GGCGCACCAC

151    AACCAGGCCA GCCACGTTTC TGCCGAAAACG CGGGAAAAAG TGGAAGCGGC
       TTGGTCCGGT CGGTGCAAAG ACGCTTTTGC GCCCTTTTTC ACCTTCGCCG

201    GATGGCGGAG CTGAATTACA TTCCTAACCG CGTGGCACAA CAACTGGCGG
       CTACCGCCTC GACTTAATGT AAGGATTGGC GCACCGTGTT GTTGACCGCC

251    GCAAACAGTC GTTGCTGATT GGCGTTGCCA CCTCCAGTCT GGCCCTGCAC
       CGTTTGTCAG CAACGACTAA CCGGCAACGGT GGAGGTCAGA CCGGGACGTG

301    GCGCCGTCGC AAATTGTCGC GGCGATTAAA TCTCGCGCCG ATCAACTGGG
       CGCGGCAGCG TTTAACAGCG CCGCTAATTT AGAGCGCGGC TAGTTGACCC
```

FIG. 35SS

```
351  TGCCAGCGTG GTCGTGTCGA TGGTAGAACG AAGCGGCGTC GAAGCCTGTA
     ACGGTCGCAC CAGCACAGCT ACCATCTTGC TTCGCCGCAG CTTCGGACAT

401  AAGCGGCGGT GCACAATCTT CTCGCGCAAC GTGTCAGTGG GCTGATTATT
     TTCGCCGCCA CGTGTTAGAA GAGCGCGTTG CACAGTCACC CGACTAATAA

451  AACTATCCGC TGGATGACCA GGATGCTATT GCTGTGGAAG CTGCCTGCAC
     TTGATAGGCG ACCTACTGGT CCTACGATAA CGACACCTTC GACGGACGTG

501  TAATGTTCCG GCGTTATTTC TTGATGTCTC TGACCAGACA CCCATCAACA
     ATTACAAGGC CGCAATAAAG AACTACAGAG ACTGGTCTGT GGGTAGTTGT

551  GTATTATTTT CTCCCATGAG GACGGTACGC GACTGGGCGT GGAGCATCTG
     CATAATAAAA GAGGGTACTC CTGCCATGCG CTGACCCGCA CCTCGTAGAC

601  GTCGCATTGG GCCACCAGCA AATCGCGCTG TTAGCTGGCC CATTAAGTTC
     CAGCGTAACC CGGTGGTCGT TTAGCGCGAC AATCGACCGG GTAATTCAAG

651  TGTCTCGGCG CGTCTGCGTC TGGCTGGCTG GCATAAATAT CTCACTCGCA
     ACAGAGCCGC GCAGACGCAG ACCGACCGAC CGTATTTATA GAGTGAGCGT

701  ATCAAATTCA GCCGATAGCG GAACGGGAAG GCCGACTGGAG TGCCATGTCC
     TAGTTTAAGT CGGCTATCGC CTTGCCCTTC CGCTGACCTC ACGGTACAGG
```

FIG. 35TT

```
 751  GGTTTTCAAC AAACCATGCA AATGCTGAAT GAGGGCATCG TTCCCACTGC
      CCAAAAGTTG TTTGGTACGT TTACGACTTA CTCCCGTAGC AAGGGTGACG

801  GATGCTGGTT GCCAACGATC AGATGGCGCT GGGCGCAATG CGTGCCATTA
      CTACGACCAA CGGTTGCTAG TCTACCGCGA CCCGCGTTAC GCACGGTAAT

851  CCGAGTCCGG GCTGCGCGTT GGTGCGGACA TCTCGGTAGT GGGATACGAC
      GGCTCAGGCC CGACGCGCAA CCACGCCTGT AGAGCCATCA CCCTATGCTG

901  GATACCGAGG ACAGCTCATG TTATATCCCG CCGCTGACCA CCATCAAACA
      CTATGGCTCC TGTCGAGTAC AATATAGGGC GGCGACTGGT GGTAGTTTGT

951  GGATTTTCGC CTGCTGGGGC AAACCAGCGT GGACCCGCTTG CTGCAACTCT
      CCTAAAAGCG GACGACCCCG TTTGGTCGCA CCTGGCGAAC GACGTTGAGA

1001  CTCAGGGCCA GGCGGTGAAG GGCAATCAGC TGTTGCCCGT CTCACTGGTG
      GAGTCCCGGT CCGCCACTTC CCGTTAGTCG ACAACGGGCA GAGTGACCAC

1051  AAAAGAAAAA CCACCCTGGC TCCCAATACG CAAACCGCCT CTCCCCGCGC
      TTTTCTTTTT GGTGGGACCG AGGGTTATGC GTTTGGCGGA GAGGGGCGCG

1101  GTTGGCCGAT TCACTGATGC AGCTGGCACG ACAGGTTTCC CGACTGGAAA
      CAACCGGCTA AGTGACTACG TCGACCGTGC TGTCCAAAGG GCTGACCTTT
```

*FIG. 35UU*

```
1151  GCGGGCAGTG AGGCTACCCG ATAAAAGCGG CTTCCTGACA GGAGGCCGTT
      CGCCCGTCAC TCCGATGGGC TATTTTCGCC GAAGGACTGT CCTCCGGCAA
                                        AflII
                                        ------

1201  TTGTTTTGCA GCCCACTTAA G
      AACAAAACGT CGGGTGAATT C
```

Figure 35A:
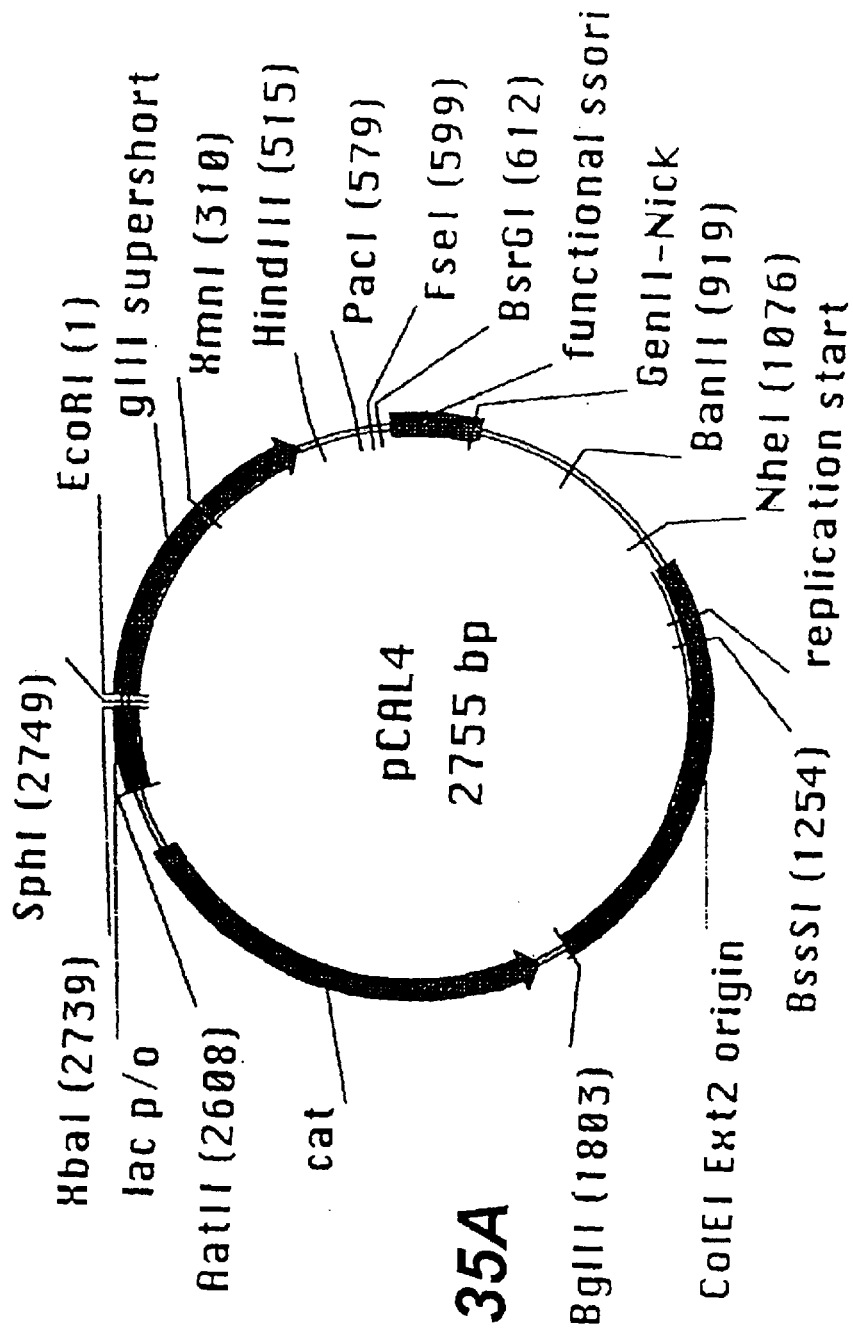
Figure 35J:
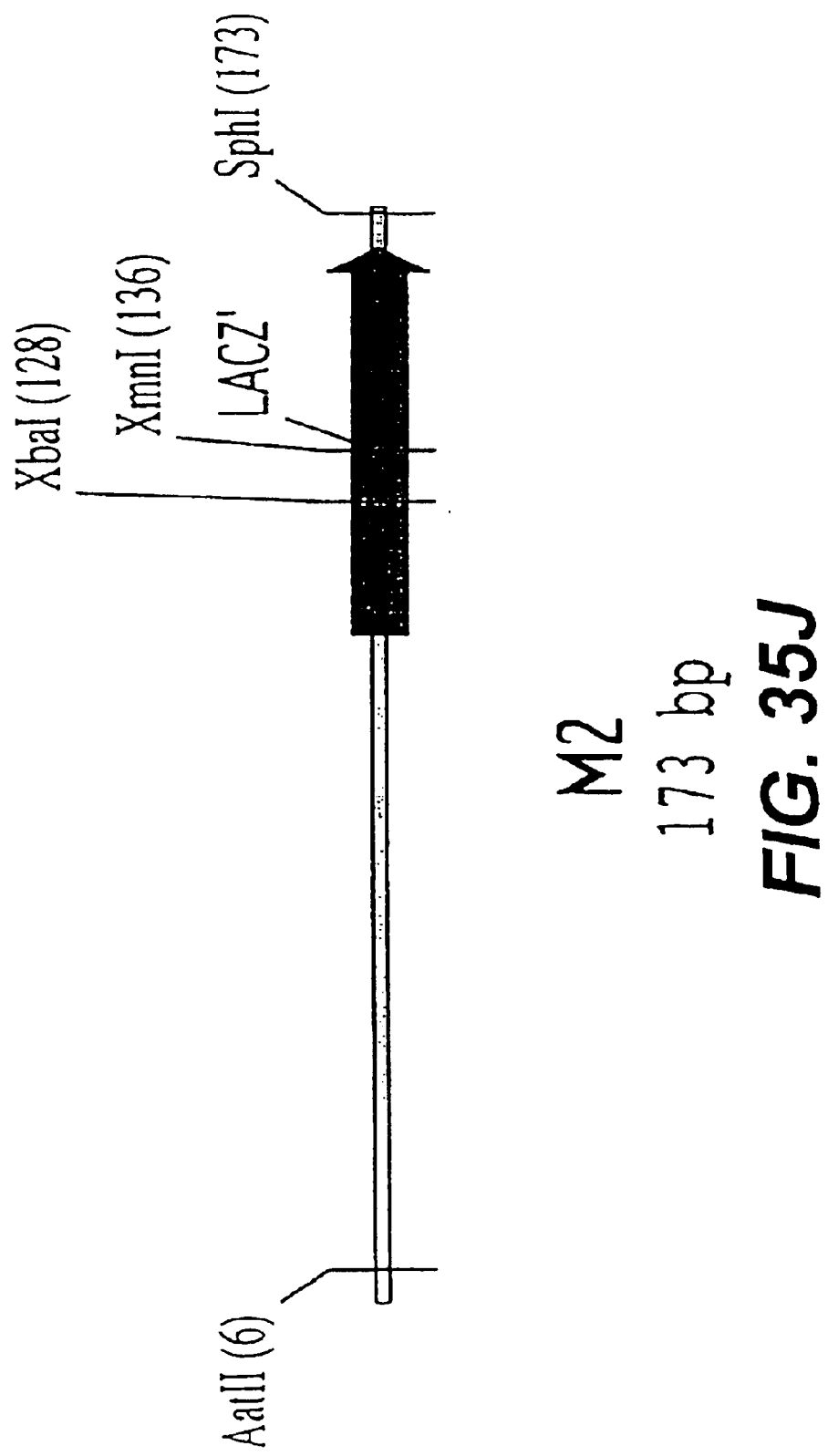
Figure 35L:
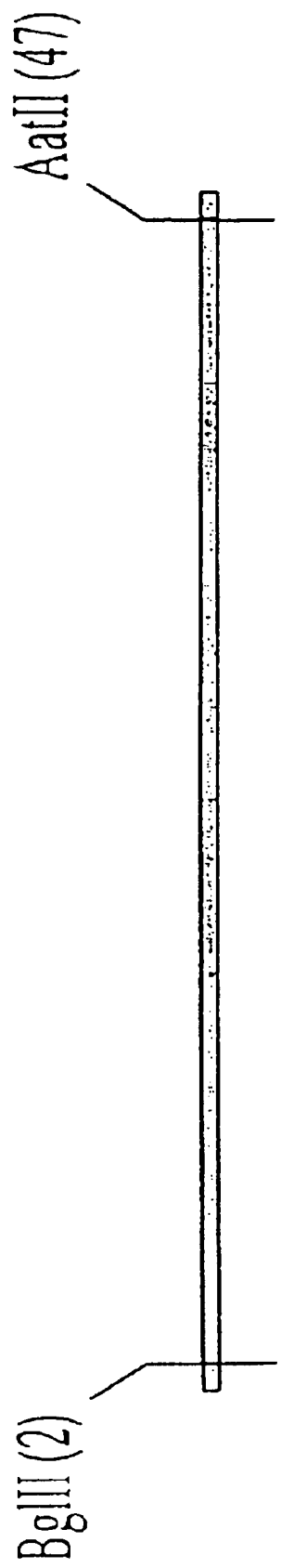
Figure 35S:
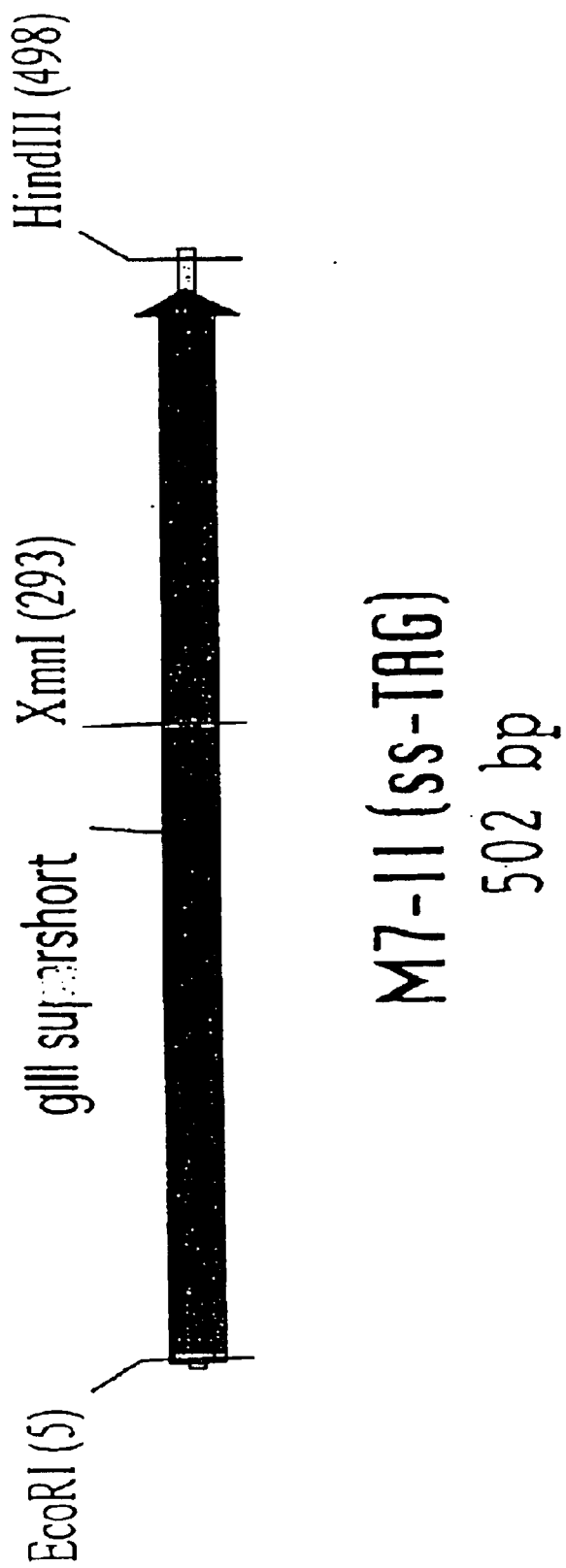
Figure 35V:
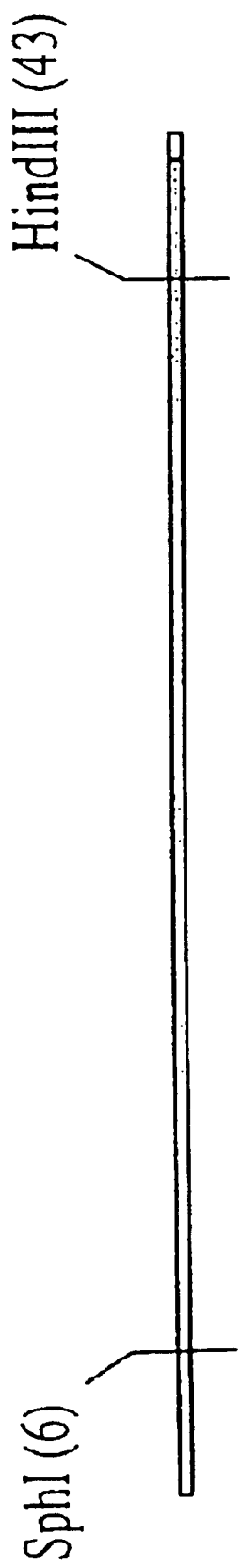

FIG. 35VV pCAL0-1:
BglII
~~~~~

```
  1  GATCTAGCAC CAGGCGTTTA AGGGCACCAA TAACTGCCTT AAAAAAATTA
     CTAGATCGTG GTCCGCAAAT TCCCGTGGTT ATTGACGGAA TTTTTTTAAT

51  CGCCCCGCCC TGCCACTCAT CGCAGTACTG TTGTAATTCA TTAAGCATTC
     GCGGGGCGGG ACGGTGAGTA GCGTCATGAC AACATTAAGT AATTCGTAAG

101  TGCCGACATG GAAGCCATCA CAAACGGCAT GATGAACCTG AATCGCCAGC
     ACGGCTGTAC CTTCGGTAGT GTTTGCCGTA CTACTTGGAC TTAGCGGTCG

151  GGCATCAGCA CCTTGTCGCC TTGCGTATAA TATTTGCCCA TAGTGAAAAC
     CCGTAGTCGT GGAACAGCGG AACGCATATT ATAAACGGGT ATCACTTTTG

201  GGGGGCGAAG AAGTTGTCCA TATTGGCTAC GTTTAAATCA AAACTGGTGA
     CCCCCGCTTC TTCAACAGGT ATAACCGATG CAAATTTAGT TTTGACCACT

251  AACTCACCCA GGGATTGGCT GAGACGAAAA ACATATTCTC AATAAACCCT
     TTGAGTGGGT CCCTAACCGA CTCTGCTTTT TGTATAAGAG TTATTTGGGA

301  TTAGGGAAAT AGGCCAGGTT TTCACCGTAA CACGCCACAT CTTGCGAATA
     AATCCCTTTA TCCGGTCCAA AAGTGGCATT GTGCGGTGTA GAACGCTTAT
```

FIG. 35XX

```
351  TATGTGTAGA AACTGCCGGA AGTCGTCGTG GTATTCACTC CAGAGCGATG
     ATACACATCT TTGACGGCCT TTAGCAGCAC CATAAGTGAG GTCTCGCTAC

401  AAAACGTTTC AGTTTGCTCA TGGAAAACGG TGTAACAAGG GTGAACACTA
     TTTTGCAAAG TCAAACGAGT ACCTTTTGCC ACATTGTTCC CACTTGTGAT

451  TCCCATATCA CCAGCTCACC GTCTTTCATT GCCATACGGA ACTCCGGGTG
     AGGGTATAGT GGTCGAGTGG CAGAAAGTAA CGGTATGCCT TGAGGCCCAC

501  AGCATTCATC AGGCGGGCAA GAATGTGAAT AAAGGCCGGA TAAAACTTGT
     TCGTAAGTAG TCCGCCCGTT CTTACACTTA TTTCCGGCCT ATTTTGAACA

551  GCTTATTTTT CTTTACGGTC TTTAAAAAGG CCGTAATATC CAGCTGAACG
     CGAATAAAAA GAAATGCCAG AAATTTTTCC GGCATTATAG GTCGACTTGC

601  GTCTGGTTAT AGGTACATTG AGCAAACTGAC TGAAATGCCT CAAAATGTTC
     CAGACCAATA TCCATGTAAC TCGTTGACTG ACTTTACGGA GTTTTACAAG

651  TTTACGATGC CATTGGGATA TATCAACGGT GGTATATCCA GTGATTTTTT
     AAATGCTACG GTAACCCTAT ATAGTTGCCA CCATATAGGT CACTAAAAAA

701  TCTCCATTTT AGCTTCCTTA GCTCCTGAAA ATCTCGATAA CTCAAAAAAT
     AGAGGTAAAA TCGAAGGAAT CGAGGACTTT TAGAGCTATT GAGTTTTTA
```

FIG. 35YY

```
751   ACGCCCGGTA GTGATCTTAT TTCATTATGG TGAAAGTTGG AACCTCACCC
      TGCGGGCCAT CACTAGAATA AAGTAATACC ACTTTCAACC TTGGAGTGGG
                 AatII
                 -------

801   GACGTCTAAT GTGAGTTAGC TCACTCATTA GGCACCCCAG GCTTTACACT
      CTGCAGATTA CACTCAATCG AGTGAGTAAT CCGTGGGGTC CGAAATGTGA

851   TTATGCTTCC GGCTCGTATG TTGTGTGGAA TTGTGAGCGG ATAACAATTT
      AATACGAAGG CCGAGCATAC AACACACCTT AACACTCGCC TATTGTTAAA
                                                 XbaI
                                                 -------

901   CACACAGGAA ACAGCTATGA CCATGATTAC GAATTCTAG ACCCCCCCCC
      GTGTGTCCTT TGTCGATACT GGTACTAATG CTTAAAGATC TGGGGGGGGG
      SphI                                      HindIII
      -------                                   -------

951   CGCATGCCAT AACTTCGTAT AATGTACGCT ATACGAAGTT ATAAGCTTGA
      GCGTACGGTA TTGAAGCATA TTACATGCGA TATGCTTCAA TATTCGAACT

1001  CCTGTGAAGT GAAAAATGGC GCAGATTGTG CGACATTTTT TTTGTCTGCC
      GGACACTTCA CTTTTTACCG CGTCTAACAC GCTGTAAAAA AAACAGACGG
```

FIG. 35ZZ

```
                PacI                              FseI                              BsrGI
              ~~~~~~~                          ~~~~~~~~                           ~~~~~~
1051  GTTTAATTAA AGGGGGGGGG GGCCCGGCCT GGGGGGGGGT GTACATGAAA
      CAAATTAATT TCCCCCCCCC CCCGGCCGGA CCCCCCCCCA CATGTACTTT

1101  TTGTAAACGT TAATATTTTG TTAAAATTCG CGTTAAATTT TTGTTAAATC
      AACATTTGCA ATTATAAAAC AATTTTAAGC GCAATTTAAA AACAATTTAG

1151  AGCTCATTTT TTAACCAATA GGCCGAAATC GGCAAAATCC CTTATAAATC
      TCGAGTAAAA AATTGGTTAT CCGGCTTTAG CCGTTTTAGG GAATATTTAG

1201  AAAAGAATAG ACCGAGATAG GGTTGAGTGT TGTTCCAGTT TGGAACAAGA
      TTTTCTTATC TGGCTCTATC CCAACTCACA ACAAGGTCAA ACCTTGTTCT

1251  GTCCACTATT AAAGAACGTG GACTCCAACG TCAAAGGGCG AAAAACCGTC
      CAGGTGATAA TTTCTTGCAC CTGAGGTTGC AGTTTCCCGC TTTTTGGCAG

1301  TATCAGGGCG ATGGCCCACT ACGAGAACCA TCACCCTAAT CAAGTTTTTT
      ATAGTCCCGC TACCGGGTGA TGCTCTTGGT AGTGGGATTA GTTCAAAAAA

BanII
                                                    ~~~~~~
1351  GGGGTCGAGG TGCCGTAAAG CACTAAATCG GAACCCTAAA GGGAGCCCCC
      CCCCAGCTCC ACGGCATTTC GTGATTTAGC CTTGGGATTT CCCTCGGGGG
```

*FIG. 35AAA*

```
1401  GATTTAGAGC  TTGACGGGGA  AAGCCGGCGA  ACGTGGCGAG  AAAGGAAGGG
      CTAAATCTCG  AACTGCCCCT  TTCGGCCGCT  TGCACCGCTC  TTTCCTTCCC

1451  AAGAAAGCGA  AAGGAGCGGG  CGCTAGGGCG  CTGGCAAGTG  TAGCGGTCAC
      TTCTTTCGCT  TTCCTCGCCC  GCGATCCCGC  GACCGTTCAC  ATCGCCAGTG

1501  GCTGCGCGTA  ACCACCACAC  CCGCCGCGCT  TAATGCGCCG  CTACAGGGCG
      CGACGCGCAT  TGGTGGTGTG  GGCGGCGCGA  ATTACGCGGC  GATGTCCCGC
                  NheI

1551  CGTGCTAGCG  GAGTGTATAC  TGGCTTACTA  TGTTGGCACT  GATGAGGGTG
      GCACGATCGC  CTCACATATG  ACCGAATGAT  ACAACCGTGA  CTACTCCCAC
                       XmnI                              AgeI

1601  TCAGTGAAGT  GCTTCATGTG  GCAGGAGAAA  AAAGGCTGCA  CCGGTGCGTC
      AGTCACTTCA  CGAAGTACAC  CGTCCTCTTT  TTTCCGACGT  GGCCACGCAG

1651  AGCAGAATAT  GTGATACAGG  ATATATTCCG  CTTCCTCGCT  CACTGACTCG
      TCGTCTTATA  CACTATGTCC  TATATAAGGC  GAAGGAGCGA  GTGACTGAGC

1701  CTACGCTCGG  TCGTTCGACT  GCGGCGAGCG  GAAATGGCTT  ACGAACGGGG
```

FIG. 35BBB

```
      GATGCCAGCC AGCAAGCTGA CGCCGCTCGC CTTTACCGAA TGCTTGCCCC
1751  CGGAGATTTC CTGGAAGATG CCAGGAAGAT ACTTAACAGG GAAGTGAGAG
      GCCTCTAAAG GACCTTCTAC GGTCCTTCTA TGAATTGTCC CTTCACTCTC
1801  GGCCGCGGCA AAGCCGTTTT TCCATAGGCT CCGCCCCCCT GACAAGCATC
      CCGGCGCCGT TTCGGCAAAA AGGTATCCGA GGCGGGGGGA CTGTTCGTAG
1851  ACGAAATCTG ACGCTCAAAT CAGTGGTGGC GAAACCCGAC AGGACTATAA
      TGCTTTAGAC TGCGAGTTTA GTCACCACCG CTTTGGGCTG TCCTGATATT
1901  AGATACCAGG CGTTCCCCCC TGGCGGCTCC CTCCTGCGCT CTCCTGTTCC
      TCTATGGTCC GCAAAGGGGG ACCGCCGAGG GAGGACGCGA GAGGACAAGG
                  AgeI
                  ------
1951  TGCCTTTCGG TTTACCGGTG TCATTCCGCT GTTATGGCCG CGTTTGTCTC
      ACGGAAAGCC AAATGGCCAC AGTAAGGCGA CAATACCGGC GCAAACAGAG
2001  ATTCCACGCC TGACACTCAG TTCCGGGTAG GCAGTTCGCT CCAAGCTGGA
      TAAGGTGCGG ACTGTGAGTC AAGGCCCATC CGTCAAGCGA GGTTCGACCT
2051  CTGTATGCAC GAACCCCCCG TTCAGTCCGA CCGCTGCGCC TTATCCGGTA
      GACATACGTG CTTGGGGGGC AAGTCAGGCT GGCGACGCGG AATAGGCCAT
```

*FIG. 35CCC*

```
2101  ACTATCGTCT TGAGTCCAAC CCGGAAAGAC ATGCAAAAGC ACCACTGGCA
      TGATAGCAGA ACTCAGGTTG GGCCTTTCTG TACGTTTTCG TGGTGACCGT

2151  GCAGCCACTG GTAATTGATT TAGAGGAGTT AGTCTTGAAG TCATGCGCCG
      CGTCGGTGAC CATTAACTAA ATCTCCTCAA TCAGAACTTC AGTACGCGGC

2201  GTTAAGGCTA AACTGAAAGG ACAAGTTTTA GTGACTGCGC TCCTCCAAGC
      CAATTCCGAT TTGACTTTCC TGTTCAAAAT CACTGACGCG AGGAGGTTCG

2251  CAGTTACCTC GGTTCAAAGA GTTGGTAGCT CAGAGAACCT ACGAAAAACC
      GTCAATGGAG CCAAGTTTCT CAACCATCGA GTCTCTTGGA TGCTTTTTGG

2301  GCCCTGCAAG GCGGTTTTTT CGTTTTCAGA GCAAGAGATT ACGCGCAGAC
      CGGGACGTTC CGCCAAAAAA GCAAAAGTCT CGTTCTCTAA TGCGCGTCTG

BglII
                                              ~
2351  CAAAACGATC TCAAGAAGAT CATCTTATTA
      GTTTTGCTAG AGTTCTTCTA GTAGAATAAT
```

*FIG. 35DDD*

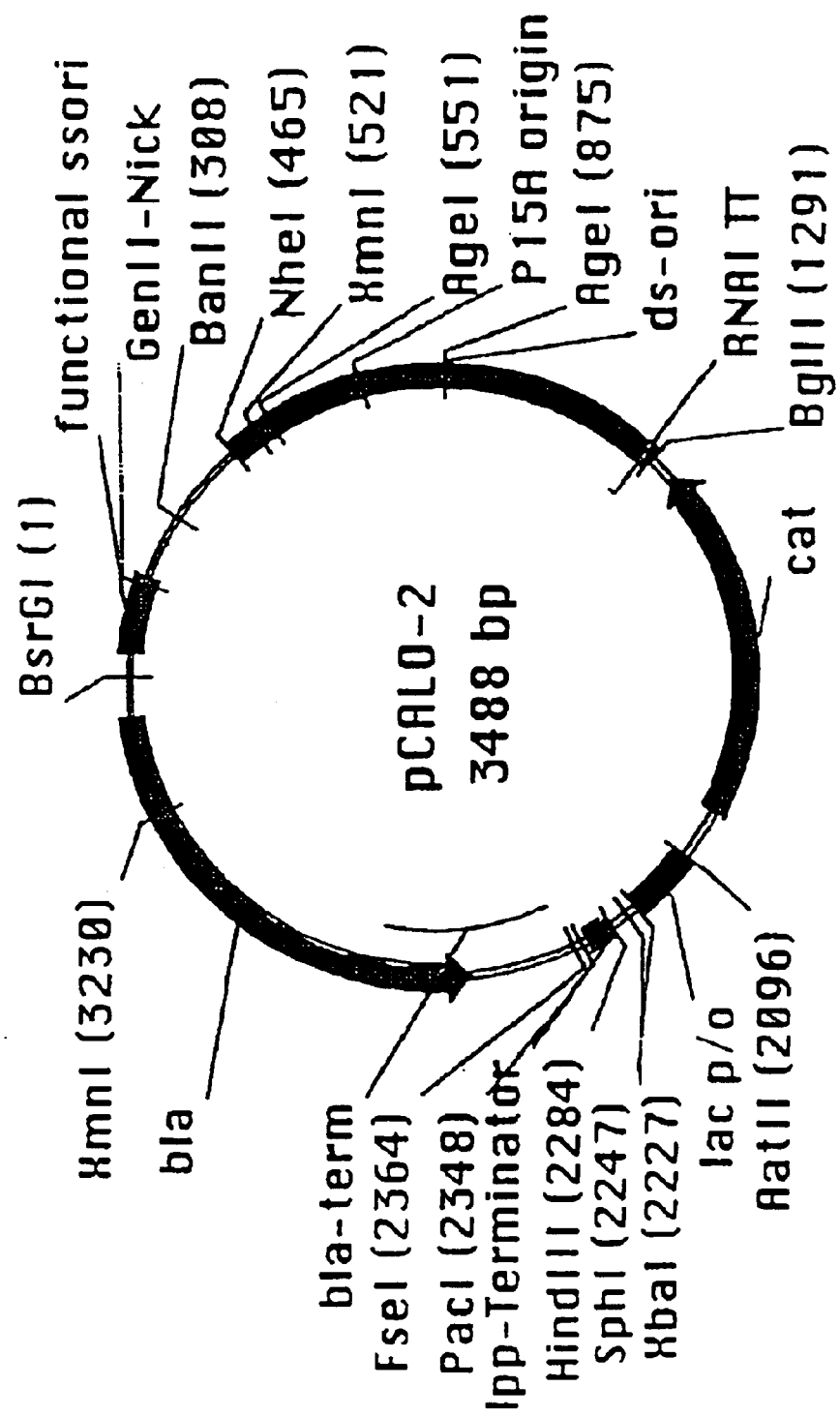
FIG. 35EEE pCAL0-2:
BsrGI
~~~~

```
  1  GTACATGAAA TTGTAAACGT TAATATTTTG TTAAAATTCG CGTTAAATTT
     CATGTACTTT AACATTTGCA ATTATAAAAC AATTTTAAGC GCAATTTAAA

51  TTGTTAAATC AGCTCATTTT TTAACCAATA GGCCGAAATC GGCAAAATCC
     AACAATTTAG TCGAGTAAAA AATTGGTTAT CCGGCTTTAG CCGTTTTAGG

101  CTTATAAATC AAAAGAATAG ACCGAGATAG GGTTGAGTGT TGTTCCAGTT
     GAATATTTAG TTTTCTTATC TGGCTCTATC CCAACTCACA ACAAGGTCAA

151  TGGAACAAGA GTCCACTATT AAAGAACGTG GACTCCAACG TCAAAGGGCG
     ACCTTGTTCT CAGGTGATAA TTTCTTGCAC CTGAGGTTGC AGTTTCCCGC

201  AAAACCGTC TATCAGGGCG ATGGCCCACT ACGAGAACCA TCACCCTAAT
     TTTTGGCAG ATAGTCCCGC TACCGGGTGA TGCTCTTGGT AGTGGGATTA

251  CAAGTTTTTT GGGGTCGAGG TGCCGTAAAG CACTAAATCG GAACCCTAAA
     GTTCAAAAAA CCCCAGCTCC ACGGCATTTC GTGATTTAGC CTTGGGATTT
           BanII
           ~~~~~

301  GGGAGCCCCC GATTTAGAGC TTGACGGGGA AAGCCGGGCGA ACGTGGCGAG
```

*FIG. 35FFF*

```
      CCCTCGGGGG CTAAATCTCG AACTGCCCCT TTCGGCCGCT TGCACCGCTC
351   AAAGGAAGGG AAGAAAGCGA AGGAGCGGG  CGCTAGGGCG CTGGCAAGTG
      TTTCCTTCCC TTCTTTCGCT TTCCTCGCCC GCGATCCCGC GACCGTTCAC
401   TAGCGGTCAC GCTGCGCGTA ACCACCACAC CCGCCCGCGCT TAATGCGCCG
      ATCGCCAGTG CGACGCGCAT TGGTGGTGTG GGCGGGCGCGA ATTACGCGGC
                 NheI
451   CTACAGGGCG CGTGCTAGCG GAGTGTATAC TGGCTTACTA TGTTGGCACT
      GATGTCCCGC GCACGATCGC CTCACATATG ACCGAATGAT ACAACCGTGA
                                XmnI                 AgeI
501   GATGAGGGTG TCAGTGAAGT GCTTCATGTG GCAGGAGAAA AAAGGCTGCA
      CTACTCCCAC AGTCACTTCA CGAAGTACAC CGTCCTCTTT TTTCCGACGT
      AgeI
551   CCGGTGCGTC AGCAGAATAT GTGATACAGG ATATATTCCG CTTCCTCGCT
      GGCCACGCAG TCGTCTTATA CACTATGTCC TATATAAGGC GAAGGAGCGA
601   CACTGACTCG CTACGCTCGG TCGTTCGACT GCGGCGAGCG GAAATGGCTT
```

FIG. 35GGG

```
     GTGACTGAGC GATGCGAGCC AGCAAGCTGA CGCCGCTCGC CTTTACCGAA
651  ACGAACGGGG CGGAGATTTC CTGGAAGATG CCAGGAAGAT ACTTAACAGG
     TGCTTGCCCC GCCTCTAAAG GACCTTCTAC GGTCCTTCTA TGAATTGTCC
701  GAAGTGAGAG GGCCGCGGCA AAGCCGTTTT TCCATAGGCT CCGCCCCCT
     CTTCACTCTC CCGGCGCCGT TTCGGCAAAA AGGTATCCGA GGCGGGGGA
751  GACAAGCATC ACGAAATCTG ACGCTCAAAT CAGTGGTGGC GAAACCCGAC
     CTGTTCGTAG TGCTTTAGAC TGCGAGTTTA GTCACCACCG CTTTGGGCTG
801  AGGACTATAA AGATACCAGG CGTTTCCCCC TGGCGGCTCC CTCCTGCGCT
     TCCTGATATT TCTATGGTCC GCAAAGGGGG ACCGCCGAGG GAGGACGCGA
                                      AgeI
                                      ~~~~~
851  CTCCTGTTCC TGCCTTTCGG TTTACCGGTG TCATTCCGCT GTTATGCCG
     GAGGACAAGG ACGGAAAGCC AAATGGCCAC AGTAAGGCGA CAATACCGGC
901  CGTTTGTCTC ATTCCACGCC TGACACTCAG TTCCGGGTAG GCAGTTCGCT
     GCAAACAGAG TAAGGTGCGG ACTGTGAGTC AAGGCCCATC CGTCAAGCGA
951  CCAAGCTGGA CTGTATGCAC GAACCCCCCG TTCAGTCCGA CCGCTGCGCC
     GGTTCGACCT GACATACGTG CTTGGGGGGC AAGTCAGGCT GGCGACGCGG
```

FIG. 35HHH

```
1001  TTATCCGTA  ACTATCGTCT  TGAGTCCAAC  CCGGAAAGAC  ATGCAAAAGC
      AATAGGCCAT  TGATAGCAGA  ACTCAGGTTG  GGCCTTTCTG  TACGTTTTCG

1051  ACCACTGGCA  GCAGCCACTG  GTAATTGATT  TAGAGGAGTT  AGTCTTGAAG
      TGGTGACCGT  CGTCGGTGAC  CATTAACTAA  ATCTCCTCAA  TCAGAACTTC

1101  TCATGCGCCG  GTTAAGGCTA  AACTGAAAGG  ACAAGTTTTA  GTGACTGCGC
      AGTACGCGGC  CAATTCCGAT  TTGACTTTCC  TGTTCAAAAT  CACTGACGCG

1151  TCCTCCAAGC  CAGTTACCTC  GGTTCAAAGA  GTTGGTAGCT  CAGAGAACCT
      AGGAGGTTCG  GTCAATGGAG  CCAAGTTTCT  CAACCATCGA  GTCTCTTGGA

1201  ACGAAAAACC  GCCCTGCAAG  GCGGTTTTTT  CGTTTTCAGA  GCAAGAGATT
      TGCTTTTTGG  CGGGACGTTC  CGCCAAAAAA  GCAAAAGTCT  CGTTCTCTAA

BglII
                                                      ~~~~~~

1251  ACGCGCAGAC  CAAAACGATC  TCAAGAAGAT  CATCTTATTA  GATCTAGCAC
      TGCGCGTCTG  GTTTTGCTAG  AGTTCTTCTA  GTAGAATAAT  CTAGATCGTG

1301  CAGGCGTTTA  AGGCACCAA   TAACTGCCTT  AAAAAAATTA  CGCCCCGCCC
      GTCCGCAAAT  TCCGTGGTT   ATTGACGGAA  TTTTTTTAAT  GCGGGGCGGG
```

FIG. 35III

```
1351  TGCCACTCAT  CGCAGTACTG  TTGTAATTCA  TTAAGCATTC  TGCCGACATG
      ACGGTGAGTA  GCGTCATGAC  AACATTAAGT  AATTCGTAAG  ACGGCTGTAC

1401  GAAGCCATCA  CAAACGGCAT  GATGAACCTG  AATCGCCAGC  GGCATCAGCA
      CTTCGGTAGT  GTTTGCCGTA  CTACTTGGAC  TTAGCGGTCG  CCGTAGTCGT

1451  CCTTGTCGCC  TTGCGTATAA  TATTTGCCCA  TAGTGAAAAC  GGGGGCGAAG
      GGAACAGCGG  AACGCATATT  ATAAACGGGT  ATCACTTTTG  CCCCCGCTTC

1501  AAGTTGTCCA  TATTGGCTAC  GTTTAAATCA  AAACTGGTGA  AACTCACCCA
      TTCAACAGGT  ATAACCGATG  CAAATTTAGT  TTTGACCACT  TTGAGTGGGT

1551  GGGATTGGCT  GAGACGAAAA  ACATATTCTC  AATAAACCCT  TTAGGGAAAT
      CCCTAACCGA  CTCTGCTTTT  TGTATAAGAG  TTATTTGGGA  AATCCCTTTA

1601  AGGCCAGGTT  TTCACCGTAA  CACGCCACAT  CTTGCGAATA  TATGTGTAGA
      TCCGGTCCAA  AAGTGGCATT  GTGCGGTGTA  GAACGCTTAT  ATACACATCT

1651  AACTGCCGGA  AATCGTCGTG  GTATTCACTC  CAGAGCGATG  AAAACGTTTC
      TTGACGGCCT  TTAGCAGCAC  CATAAGTGAG  GTCTCGCTAC  TTTTGCAAAG

1701  AGTTTGCTCA  TGGAAAACGG  TGTAACAAGG  GTGAACACTA  TCCCATATCA
      TCAAACGAGT  ACCTTTTGCC  ACATTGTTCC  CACTTGTGAT  AGGGTATAGT
```

*FIG. 35JJJ*

```
1751  CCAGCTCACC  GTCTTTCATT  GCCATACGGA  ACTCCGGGTG  AGCATTCATC
      GGTCGAGTGG  CAGAAAGTAA  CGGTATGCCT  TGAGGCCCAC  TCGTAAGTAG

1801  AGGCGGGCAA  GAATGTGAAT  AAAGGCCGGA  TAAAACTTGT  GCTTATTTTT
      TCCGCCCGTT  CTTACACTTA  TTTCCGGCCT  ATTTTGAACA  CGAATAAAAA

1851  CTTTACGGTC  TTTAAAAAGG  CCGTAATATC  CAGCTGAACG  GTCTGGTTAT
      GAAATGCCAG  AAATTTTTCC  GGCATTATAG  GTCGACTTGC  CAGACCAATA

1901  AGTACATTG   AGCAACTGAC  TGAAATGCCT  CAAAATGTTC  TTTACGATGC
      TCCATGTAAC  TCGTTGACTG  ACTTTACGGA  GTTTTACAAG  AAATGCTACG

1951  CATTGGGATA  TATCAACGGT  GGTATATCCA  GTGATTTTTT  TCTCCATTTT
      GTAACCCTAT  ATAGTTGCCA  CCATATAGGT  CACTAAAAAA  AGAGGTAAAA

2001  AGCTTCCTTA  GCTCCCTGAAA  ATCTCGATAA  CTCAAAAAAT  ACGCCCGGTA
      TCGAAGGAAT  CGAGGACTTT  TAGAGCTATT  GAGTTTTTTA  TGCGGGCCAT

AatII
                                                     ~~~~~~

2051  GTGATCTTAT  TTCATTATGG  TGAAAGTTGG  AACCTCACCC  GACGTCTAAT
      CACTAGAATA  AAGTAATACC  ACTTTCAACC  TTGGAGTGGG  CTGCAGATTA

2101  GTGAGTTAGC  TCACTCATTA  GGCACCCCAG  GCTTTACACT  TTATGCTTCC
```

FIG. 35KKK

```
      CACTCAATCG AGTGAGTAAT CCGTGGGGTC CGAAATGTGA AATACGAAGG
2151  GGCTCGTATG TTGTGTGGAA TTGTGAGCGG ATAACAATTT CACACAGGAA
      CCGAGCATAC AACACACCTT AACACTCGCC TATTGTTAAA GTGTGTCCTT
                            XbaI                  SphI
                            ------                -------
2201  ACAGCTATGA CCATGATTAC GAATTCCTAG ACCCCCCCCC CGCATGCCAT
      TGTCGATACT GGTACTAATG CTTAAAGATC TGGGGGGGGG GCGTACGGTA
                                        HindIII
                                        -------
2251  AACTTCGTAT AATGTACGCT ATACGAAGTT ATAAGCTTGA CCTGTGAAGT
      TTGAAGCATA TTACATGCGA TATGCTTCAA TATTCGAACT GGACACTTCA
                                                   PacI
                                                   -------
2301  GAAAAATGGC GCAGATTGTG CGACATTTTT TTTGTCTGCC GTTTAATTAA
      CTTTTTACCG CGTCTAACAC GCTGTAAAAA AAACAGACGG CAAATTAATT
            FseI
            -------
2351  GGGGGGGGGC CGGCCATTAT CAAAAAGGAT CTCAAGAAGA TCCTTTGATC
      CCCCCCCCCG GCCGGTAATA GTTTTTCCTA GAGTTCTTCT AGGAAACTAG

FIG. 35LLL
```

```
2401  TTTTCTACGG  GGTCTGACGC  TCAGTGGAAC  GAAAACTCAC  GTTAAGGAT
      AAAAGATGCC  CCAGACTGCG  AGTCACCTTG  CTTTTGAGTG  CAATTCCCTA

2451  TTTGGTCATG  AGATTATCAA  AAAGGATCTT  CACCTAGATC  CTTTTAAATT
      AAACCAGTAC  TCTAATAGTT  TTCCTAGAA   GTGGATCTAG  GAAAATTTAA

2501  AAAAATGAAG  TTTTAAATCA  ATCTAAAGTA  TATATGAGTA  AACTTGGTCT
      TTTTTACTTC  AAAATTTAGT  TAGATTTCAT  ATATACTCAT  TTGAACCAGA

2551  GACAGTTACC  CAATGCTTAA  TCAGTGAGGC  ACCTATCTCA  GCGATCTGTC
      CTGTCAATGG  GTTACGAATT  AGTCACTCCG  TGGATAGAGT  CGCTAGACAG

2601  TATTTCGTTC  ATCCATAGTT  GCCTGACTCC  CCGTCGTGTA  GATAACTACG
      ATAAAGCAAG  TAGGTATCAA  CGGACTGAGG  GGCAGCACAT  CTATTGATGC

2651  ATACGGGAGG  GCTTACCATC  TGGCCCCAGT  GCTGCAATGA  TACCGCGAGA
      TATGCCCTCC  CGAATGGTAG  ACCGGGGTCA  CGACGTTACT  ATGGCGCTCT

2701  CCCACGCTCA  CCGGCTCCAG  ATTTATCAGC  AATAAACCAG  CCAGCCGGAA
      GGGTGCGAGT  GGCCGAGGTC  TAAATAGTCG  TTATTTGGTC  GGTCGGCCTT

2751  GGGCCGAGCG  CAGAAGTGGT  CCTGCAACTT  TATCCGCCTC  CATCCAGTCT
      CCCGGCTCGC  GTCTTCACCA  GGACGTTGAA  ATAGGCGGAG  GTAGGTCAGA
```

*FIG. 35MMM*

```
2801  ATTAACTGTT  GCCGGGAAGC  TAGAGTAAGT  AGTTCGCCAG  TTAATAGTTT
      TAATTGACAA  CGGCCCTTCG  ATCTCATTCA  TCAAGCGGTC  AATTATCAAA

2851  GCGCAACGTT  GTTGCCATTG  CTACAGGCAT  CGTGGTGTCA  CGCTCGTCGT
      CGCGTTGCAA  CAACGGTAAC  GATGTCCGTA  GCACCACAGT  GCGAGCAGCA

2901  TTGGTATGGC  TTCATTCAGC  TCCGGTTCCC  AACGATCAAG  GCGAGTTACA
      AACCATACCG  AAGTAAGTCG  AGGCCAAGGG  TTGCTAGTTC  CGCTCAATGT

2951  TGATCCCCCA  TGTTGTGCAA  AAAAGCGGTT  AGCTCCTTCG  GTCCTCCGAT
      ACTAGGGGGT  ACAACACGTT  TTTTCGCCAA  TCGAGGAAGC  CAGGAGGCTA

3001  CGTTGTCAGA  AGTAAGTTGG  CCGCAGTGTT  ATCACTCATG  GTTATGGCAG
      GCAACAGTCT  TCATTCAACC  GGCGTCACAA  TAGTGAGTAC  CAATACCGTC

3051  CACTGCATAA  TTCTCTTACT  GTCATGCCAT  CCGTAAGATG  CTTTTCTGTG
      GTGACGTATT  AAGAGAATGA  CAGTACGGTA  GGCATTCTAC  GAAAAGACAC

3101  ACTGGTGAGT  ACTCAACCAA  GTCATTCTGA  GAATAGTGTA  TGCGGCGACC
      TGACCACTCA  TGAGTTGGTT  CAGTAAGACT  CTTATCACAT  ACGCCGCTGG

3151  GAGTTGCTCT  TGCCCGGCGT  CAATACGGGA  TAATACCGCG  CCACATAGCA
      CTCAACGAGA  ACGGGCCGCA  GTTATGCCCT  ATTATGGCGC  GGTGTATCGT
```

*FIG. 35NNN*

```
                              XmnI
                         ~~~~~~~~~~~~~
3201  GAACTTTAAA AGTGCTCATC ATTGGAAAAC GTTCTTCGGG GCGAAAACTC
      CTTGAAATTT TCACGAGTAG TAACCTTTTG CAAGAAGCCC CGCTTTTGAG

3251  TCAAGGATCT TACCGCTGTT GAGATCCAGT TCGATGTAAC CCACTCGCGC
      AGTTCCTAGA ATGGCGACAA CTCTAGGTCA AGCTACATTG GGTGAGCGCG

3301  ACCCAACTGA TCCTCAGCAT CTTTTACTTT CACCAGCGTT TCTGGGTGAG
      TGGGTTGACT AGGAGTCGTA GAAAATGAAA GTGGTCGCAA AGACCCACTC

3351  CAAAAACAGG AAGGCAAAAT GCCGCAAAAA AGGGAATAAG GGCGACACGG
      GTTTTTGTCC TTCCGTTTTA CGGCGTTTTT TCCCTTATTC CCGCTGTGCC

3401  AAATGTTGAA TACTCATACT CTTCCTTTTT CAATATATT GAAGCATTTA
      TTTACAACTT ATGAGTATGA GAAGGAAAAA GTTATAATAA CTTCGTAAAT

BsrGI
3451  TCAGGGTTAT TGTCTCATGA GCGGATACAT ATTTGAAT
      AGTCCCAATA ACAGAGTACT CGCCTATGTA TAAACTTA
```

FIG. 35OOO

Figure 35X:
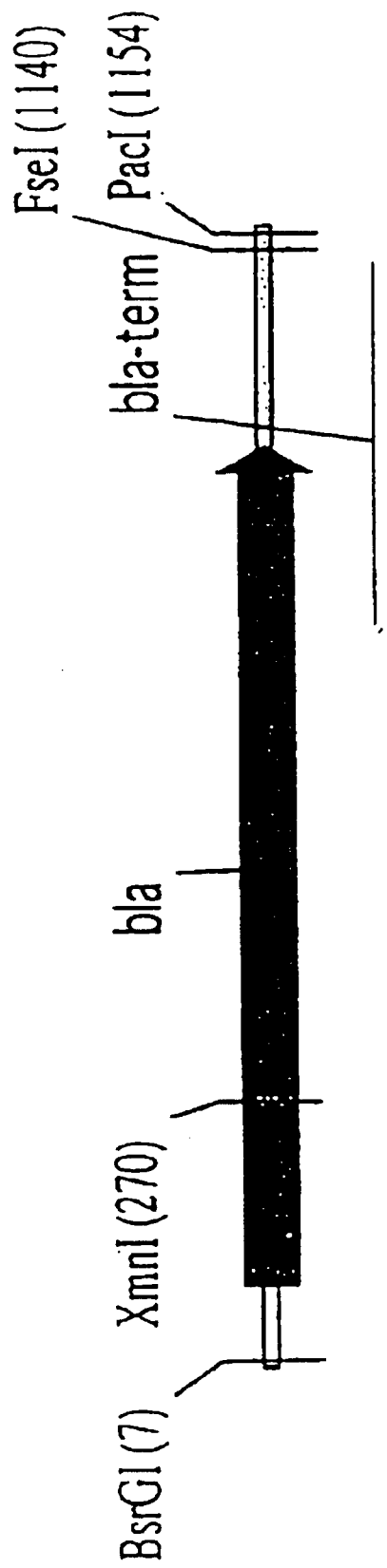
Figure 35C:
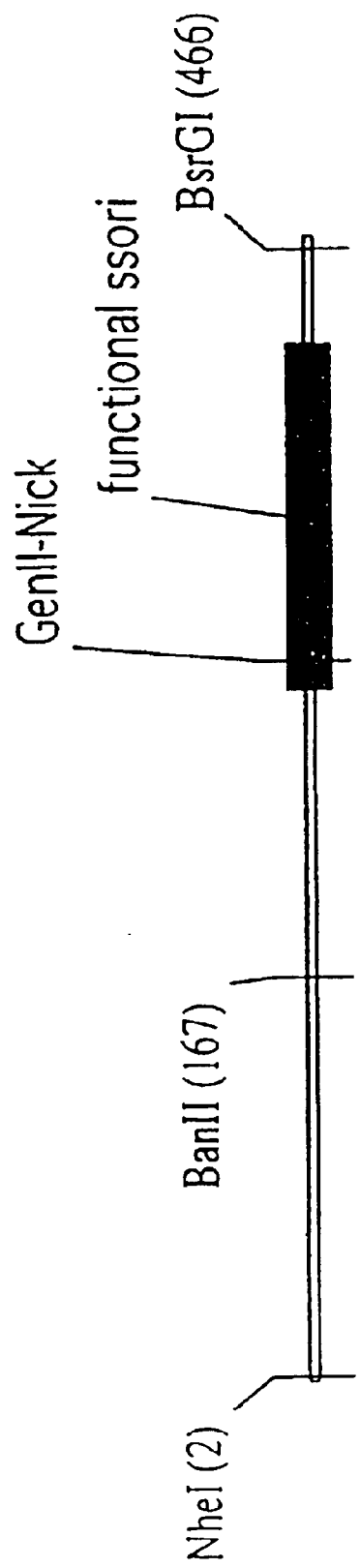
Figure 35F:
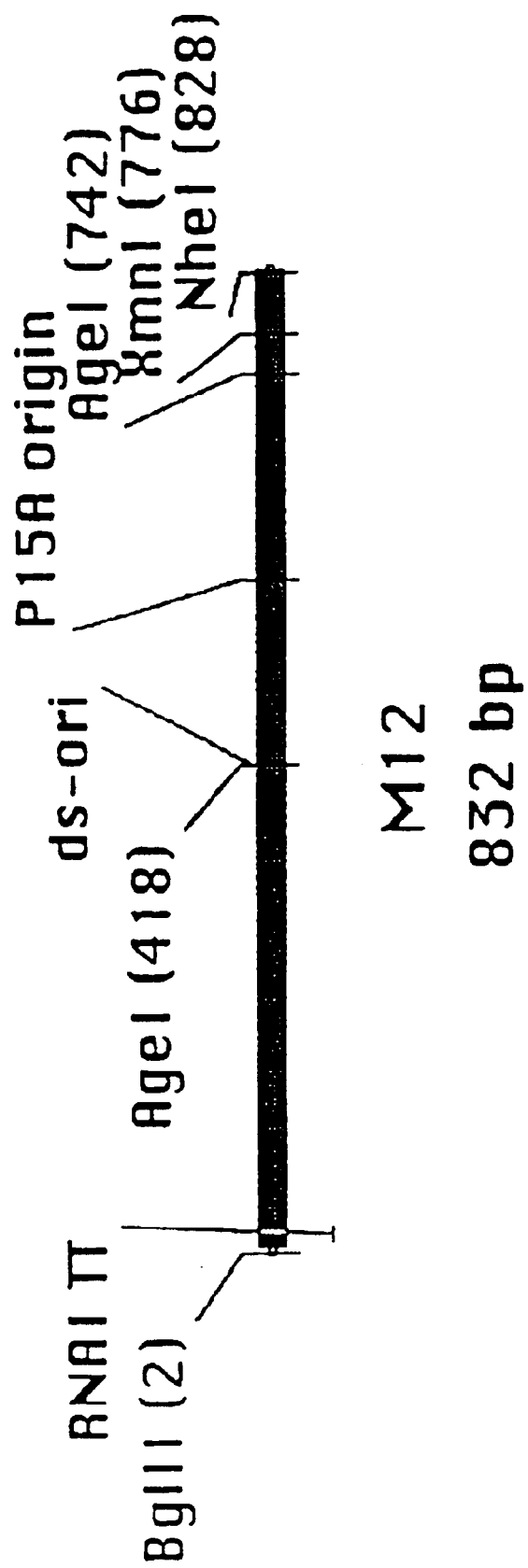
Figure 35J:
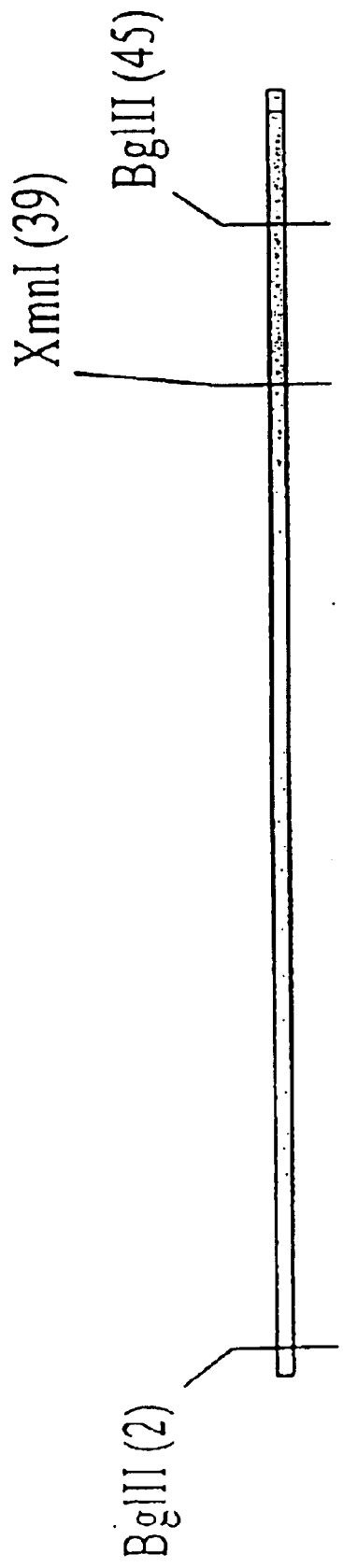
Figure 35L:
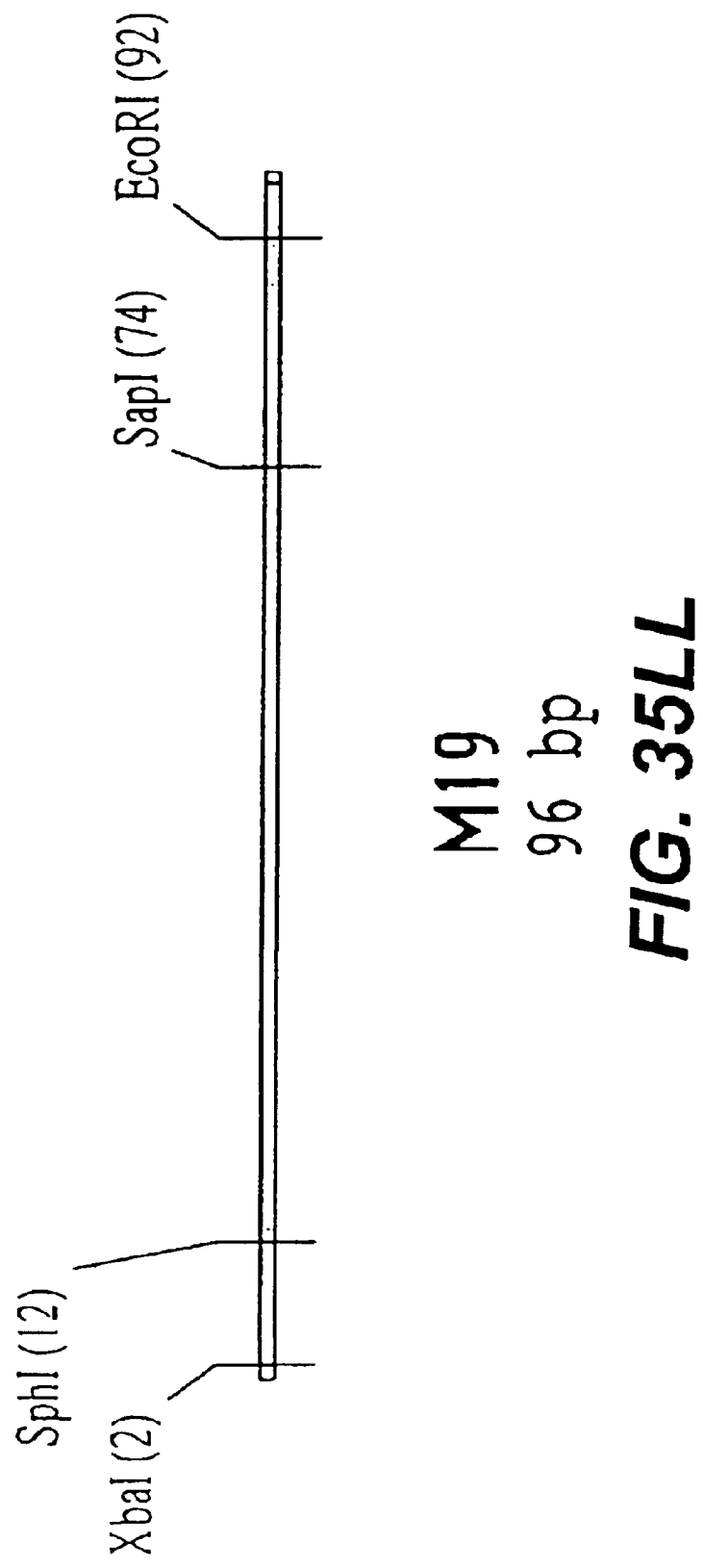
Figure 35N:
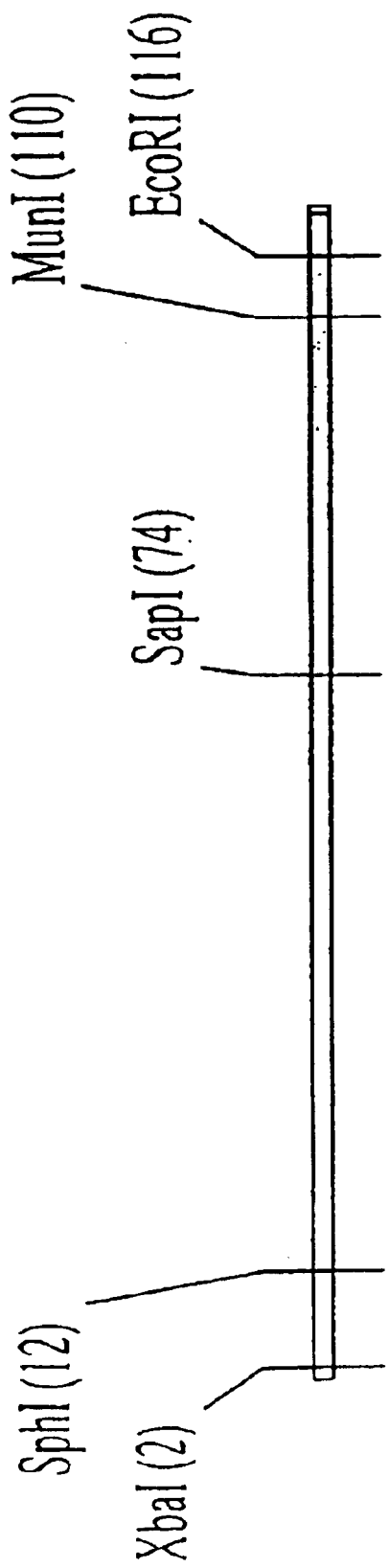
Figure 35P:
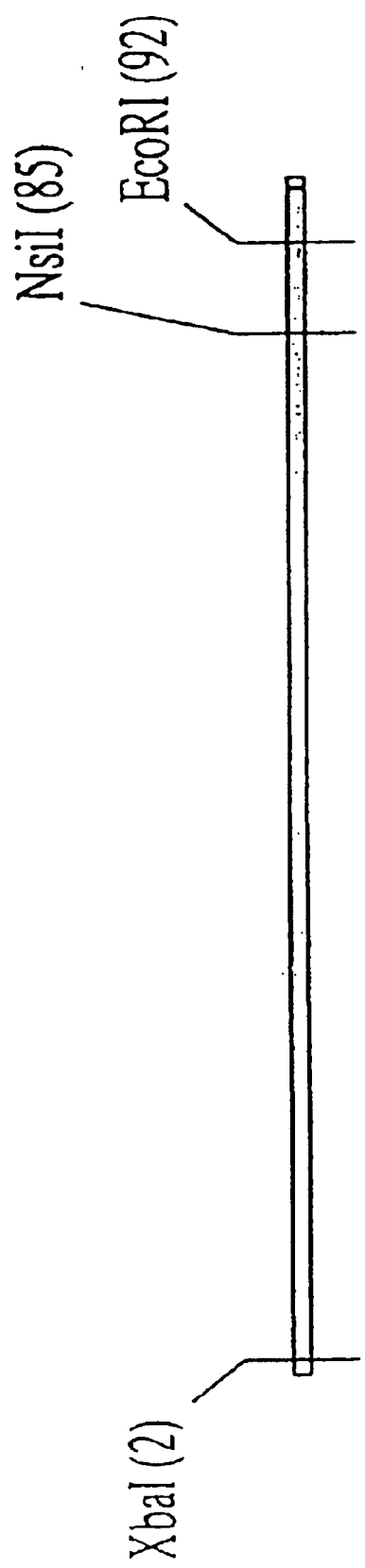
Figure 35R:
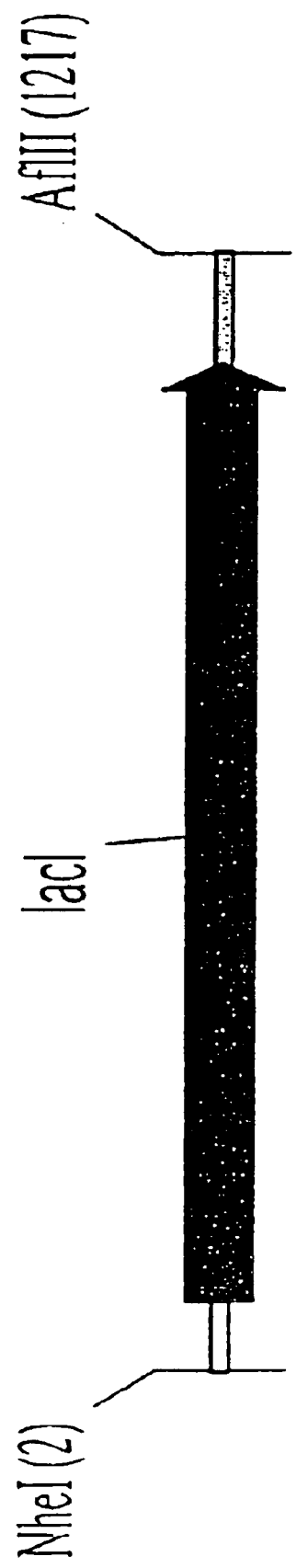
Figure 35W:
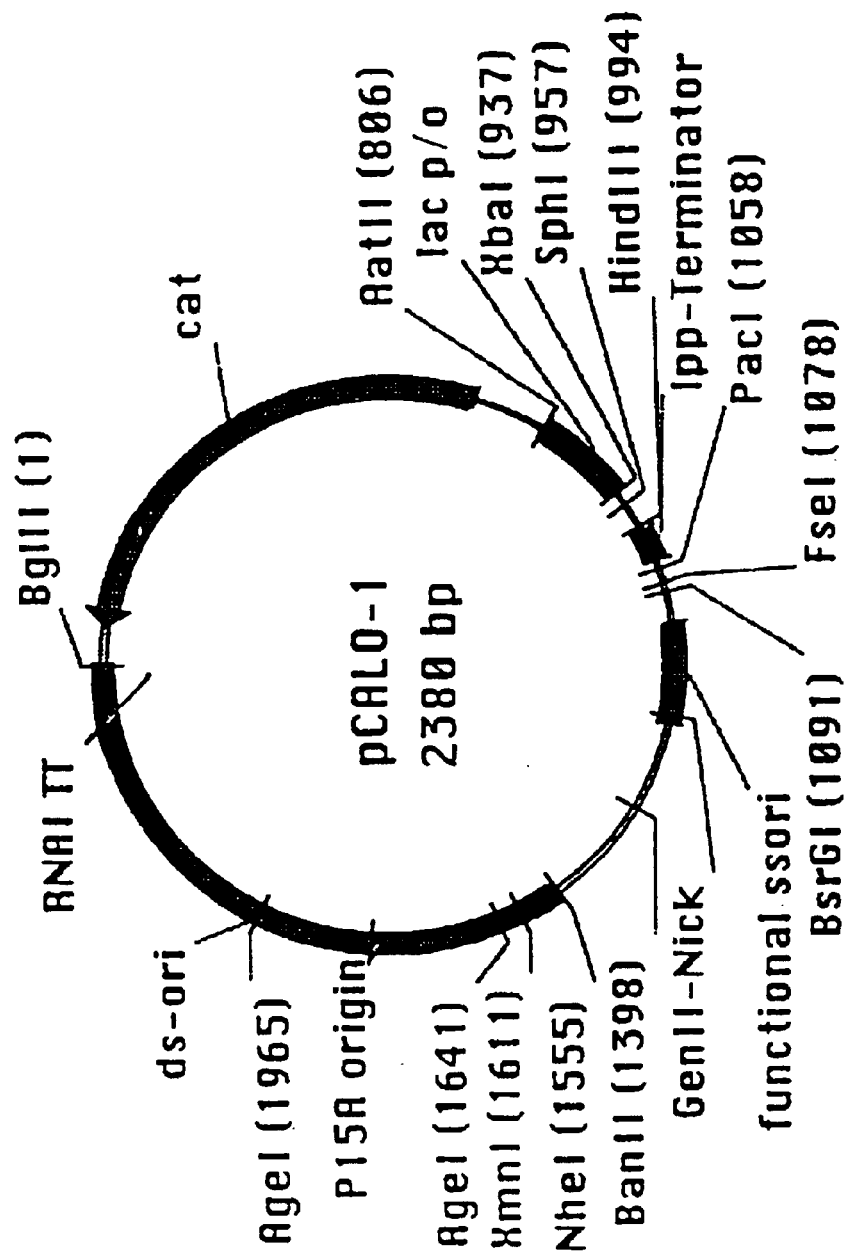
Figure 36A:
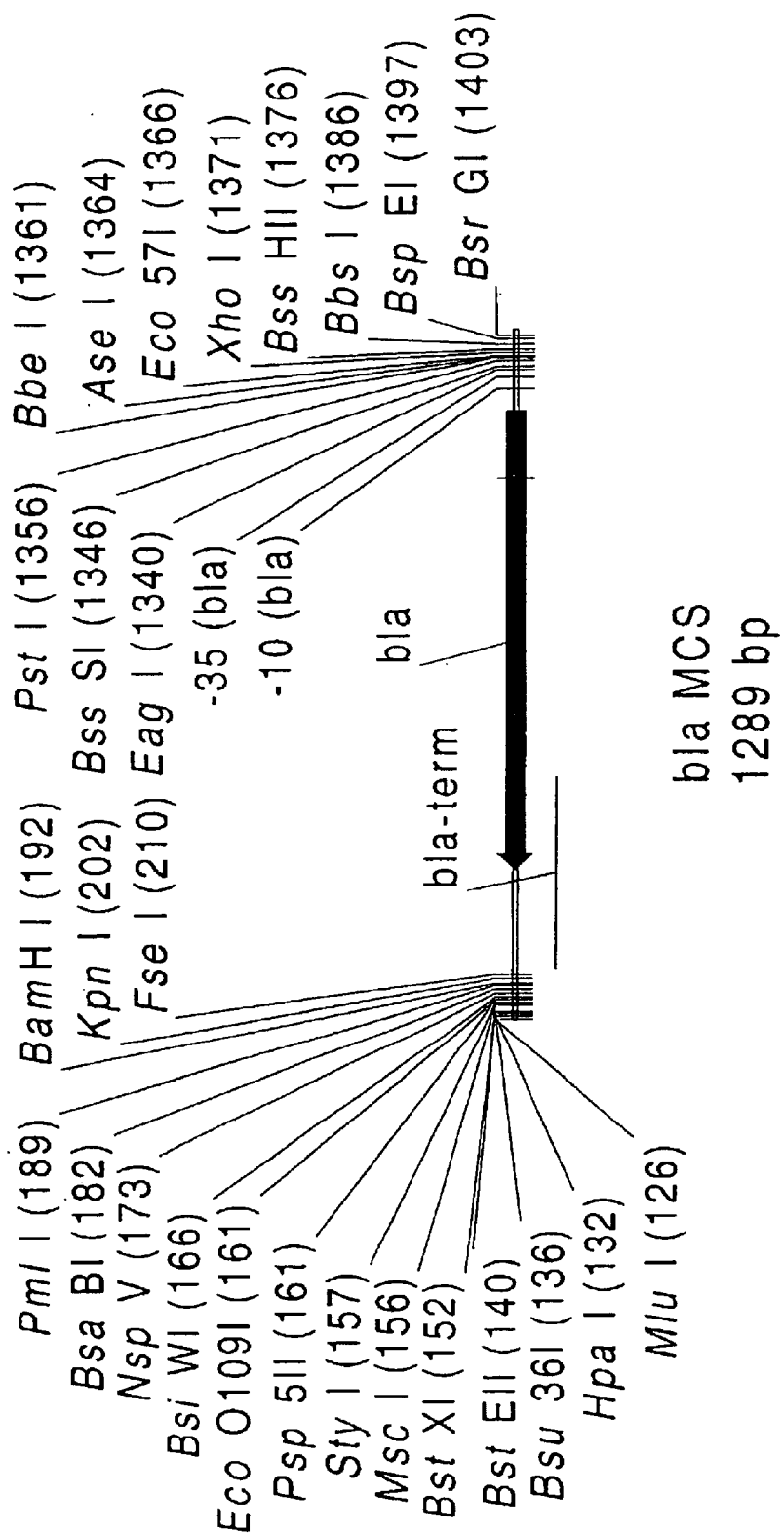

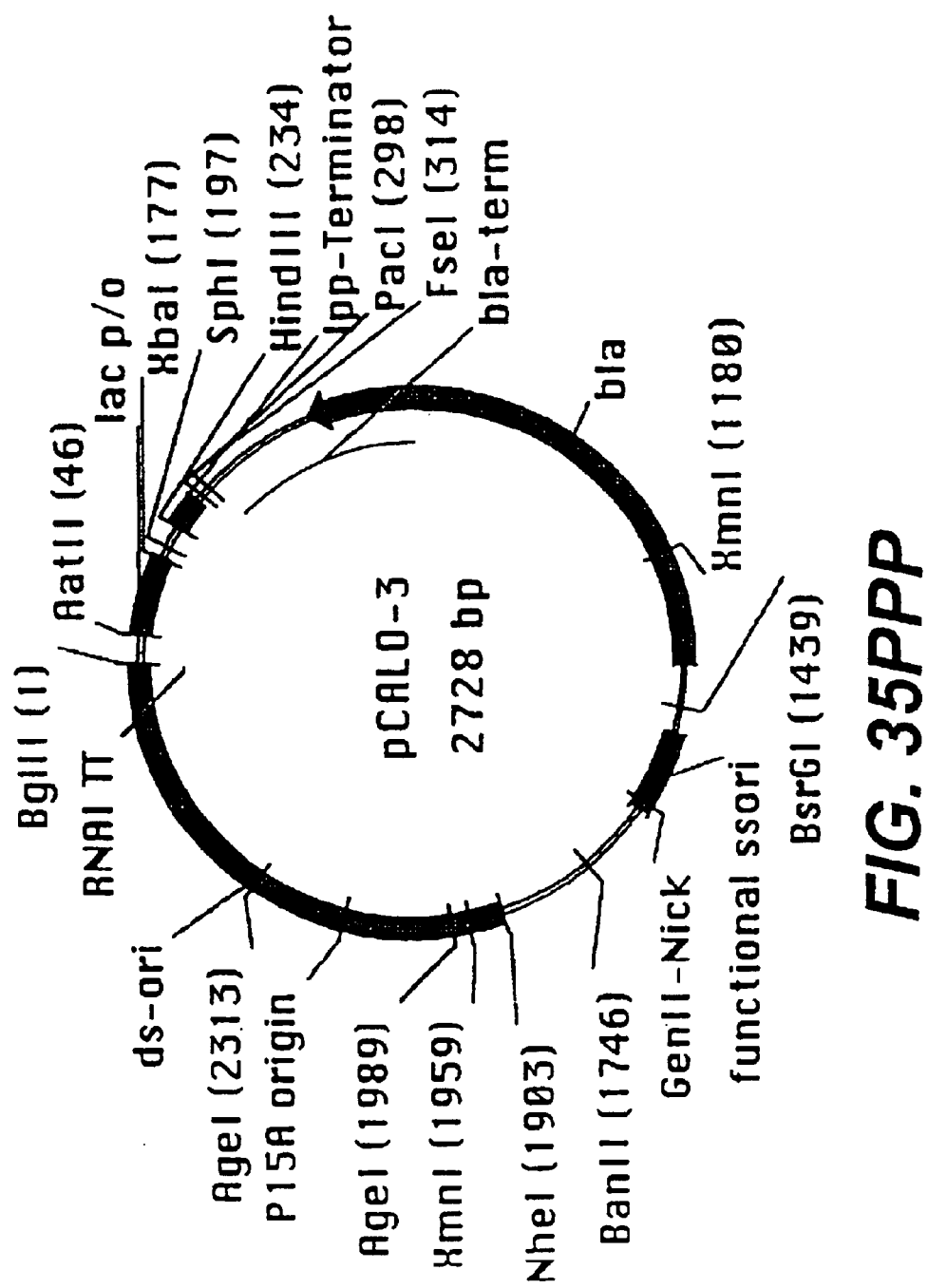
FIG. 35PPP pCAL0-3:

```
     BglII
     ~~~~~
  1  GATCTCATAA CTTCGTATAA TGTATGCTAT ACGAAGTTAT                   AatII
                                                                   ~~~~~
                                                       GACGTCTAAT
     CTAGAGTATT GAAGCATATT ACATACGATA TGCTTCAATA       CTGCAGATTA

51  GTGAGTTAGC TCACTCATTA GGCACCCCAG GCTTTACACT TTATGCTTCC
     CACTCAATCG AGTGAGTAAT CCGTGGGGTC CGAAATGTGA AATACGAAGG

101  GGCTCGTATG TTGTGTGGAA TTGTGAGCGG ATAACAATTT CACACAGGAA
     CCGAGCATAC AACACACCTT AACACTCGCC TATTGTTAAA GTGTGTCCTT

XbaI                              SphI
                                  ~~~~~                             ~~~~~
151  ACAGCTATGA CCATGATTAC GAATTCTAG   ACCCCCCCCC CGCATGCCAT
     TGTCGATACT GGTACTAATG CTTAAAGATC  TGGGGGGGGG GCGTACGGTA

HindIII
                                     ~~~~~~~
201  AACTTCGTAT AATGTACGCT ATACGAAGTT ATAAGCTTGA CCTGTGAAGT
     TTGAAGCATA TTACATGCGA TATGCTTCAA TATTCGAACT GGACACTTCA PacI
```

FIG. 35QQQ

```
251  GAAAAATGGC GCAGATTGTG CGACATTTTT TTTGTCTGCC GTTTAATTAA
     CTTTTTACCG CGTCTAACAC GCTGTAAAAA AAACAGACGG CAAATTAATT
                FseI
                --------

301  GGGGGGGGGC CGGCCATTAT CAAAAAGGAT CTCAAGAAGA TCCTTTGATC
     CCCCCCCCCG GCCGGTAATA GTTTTTCCTA GAGTTCTTCT AGGAAACTAG

351  TTTTCTACGG GGTCTGACGC TCAGTGGAAC GAAAACTCAC GTTAAGGGAT
     AAAAGATGCC CCAGACTGCG AGTCACCTTG CTTTTGAGTG CAATTCCCTA

401  TTTGGTCATG AGATTATCAA AAAGGATCTT CACCTAGATC CTTTTAAATT
     AAACCAGTAC TCTAATAGTT TTTCCTAGAA GTGGATCTAG GAAAATTTAA

451  AAAAATGAAG TTTTAAATCA ATCTAAAGTA TATATGAGTA AACTTGGTCT
     TTTTTACTTC AAAATTTAGT TAGATTTCAT ATATACTCAT TTGAACCAGA

501  GACAGTTACC CAATGCTTAA TCAGTGAGGC ACCTATCTCA GCGATCTGTC
     CTGTCAATGG GTTACGAATT AGTCACTCCG TGGATAGAGT CGCTAGACAG

551  TATTTCGTTC ATCCATAGTT GCCTGACTCC CCGTCGTGTA GATAACTACG
     ATAAAGCAAG TAGGTATCAA CGGACTGAGG GGCAGCACAT CTATTGATGC
```

*FIG. 35RRR*

```
601  ATACGGGAGG GCTTACCATC TGGCCCCAGT GCTGCAATGA TACCGCGAGA
     TATGCCCTCC CGAATGGTAG ACCGGGGTCA CGACGTTACT ATGGCGCTCT

651  CCCACGCTCA CCGGCTCCAG ATTTATCAGC AATAAACCAG CCAGCCGGAA
     GGGTGCGAGT GGCCGAGGTC TAAATAGTCG TTATTTGGTC GGTCGGCCTT

701  GGGCCCGAGCG CAGAAGTGT CCTGCAACTT TATCCGCCTC CATCCAGTCT
     CCCGGCTCGC GTCTTCACCA GGACGTTGAA ATAGGCGGAG GTAGGTCAGA

751  ATTAAACTGTT GCCGGGAAGC TAGAGTAAGT AGTTCGCCAG TTAATAGTTT
     TAATTGACAA CGGCCCTTCG ATCTCATTCA TCAAGCGGTC AATTATCAAA

801  GCGCAACGTT GTTGCCATTG CTACAGGCAT CGTGGTGTCA CGCTCGTCGT
     CGCGTTGCAA CAACGGTAAC GATGTCCGTA GCACCACAGT GCGAGCAGCA

851  TTGGTATGGC TTCATTCAGC TCCGGTTCCC AACGATCAAG GCGAGTTACA
     AACCATACCG AAGTAAGTCG AGGCCAAGGG TTGCTAGTTC CGCTCAATGT

901  TGATCCCCCA TGTTGTGCAA AAAAGCCGGTT AGCTCCTTCG GTCCTTCCGAT
     ACTAGGGGGT ACAACACGTT TTTTCGCCAA TCGAGGAAGC CAGGAGGCTA

951  CGTTGTCAGA AGTAAGTTGG CCGCAGTGTT ATCACTCATG GTTATGGCAG
     GCAACAGTCT TCATTCAACC GGCGTCACAA TAGTGAGTAC CAATACCGTC
```

FIG. 35SSS

```
1001  CACTGCATAA TTCTCTTACT GTCATGCCAT CCGTAAGATG CTTTTCTGTG
      GTGACGTATT AAGAGAATGA CAGTACGGTA GGCATTCTAC GAAAAGACAC

1051  ACTGGTGAGT ACTCAACCAA GTCATTCTGA GAATAGTGTA TGCGGCGACC
      TGACCACTCA TGAGTTGGTT CAGTAAGACT CTTATCACAT ACGCCGCTGG

1101  GAGTTGCTCT TGCCCGGCGT CAATACGGGA TAATACCGCG CCACATAGCA
      CTCAACGAGA ACGGGCCGCA GTTATGCCCT ATTATGGCGC GGTGTATCGT
                                 XmnI
                            ~~~~~~~~~~~~
1151  GAACTTTAAA AGTGCTCATC ATTGGAAAAC GTTCTTCGGG GCGAAAACTC
      CTTGAAATTT TCACGAGTAG TAACCTTTTG CAAGAAGCCC CGCTTTTGAG

1201  TCAAGGATCT TACCGCTGTT GAGATCCAGT TCGATGTAAC CCACTCCGCG
      AGTTCCTAGA ATGGCGACAA CTCTAGGTCA AGCTACATTG GGTGAGGCGC

1251  ACCCAACTGA TCCTCAGCAT CTTTTACTTT CACCAGCGTT TCTGGGTGAG
      TGGGTTGACT AGGAGTCGTA GAAAATGAAA GTGGTCGCAA AGACCCACTC

1301  CAAAAACAGG AAGGCAAAAT GCCGCAAAAA AGGGAATAAG GGCGACACGG
      GTTTTTGTCC TTCCGTTTTA CGGCGTTTTT TCCCTTATTC CCGCTGTGCC

1351  AAATGTTGAA TACTCATACT CTTCCTTTTT CAATATTATT GAAGCATTTA
```

FIG. 35TTT

```
       TTTACAACTT ATGAGTATGA GAAGGAAAAA GTTATAATAA CTTCGTAAAT
                                                  BsrGI
                                                  ~~~~~~~~
1401   TCAGGGTTAT TGTCTCATGA GCGGATACAT ATTGAATGT ACATGAAATT
       AGTCCCAATA ACAGAGTACT CGCCTATGTA TAAACTTACA TGTACTTTAA

1451   GTAAACGTTA ATATTTTGTT AAAATTCGCG TTAAATTTTT GTTAAATCAG
       CATTTGCAAT TATAAAACAA TTTTAAGCGC AATTTAAAAA CAATTTAGTC

1501   CTCATTTTTT AACCAATAGG CCGAAATCGG CAAAATCCCT TATAAATCAA
       GAGTAAAAAA TTGGTTATCC GGCTTTAGCC GTTTTAGGGA ATATTTAGTT

1551   AAGAATAGAC CGAGATAGGG TTGAGTGTTG TTCCAGTTTG GAACAAGAGT
       TTCTTATCTG GCTCTATCCC AACTCACAAC AAGGTCAAAC CTTGTTCTCA

1601   CCACTATTAA AGAACGTGGA CTCCAACGTC AAAGGGCGAA AAACCGTCTA
       GGTGATAATT TCTTGCACCT GAGGTTGCAG TTTCCCGCTT TTTGGCAGAT

1651   TCAGGGCGAT GGCCCACTAC GAGAACCATC ACCCTAATCA AGTTTTTTGG
       AGTCCCGCTA CCGGGTGATG CTCTTGGTAG TGGGATTAGT TCAAAAAACC
                                                 BanII
                                                 ~~~~~~
```

FIG. 35UUU

```
1701  GGTCGAGGTG  CCGTAAAGCA  CTAAATCGGA  ACCCTAAAGG  GAGCCCCCGA
      CCAGCTCCAC  GGCATTTCGT  GATTTAGCCT  TGGGATTTCC  CTCGGGGGCT

1751  TTTAGAGCTT  GACGGGGAAA  GCCGGCGAAC  GTGGCGAGAA  AGGAAGGGAA
      AAATCTCGAA  CTGCCCCTTT  CGGCCGCTTG  CACCGCTCTT  TCCTTCCCTT

1801  GAAAGCGAAA  GGAGCGGGCG  CTAGGGCGCT  GGCAAGTGTA  GCGGTCACGC
      CTTTCGCTTT  CCTCGCCCGC  GATCCCGCGA  CCGTTCACAT  CGCCAGTGCG

1851  TGCGCGTAAC  CACCACACCC  GCCGCGCTTA  ATGCGCCGCT  ACAGGGGCCG
      ACGCGCATTG  GTGGTGTGGG  CGGCGCGAAT  TACGCGGCGA  TGTCCCGCGC
                NheI

1901  TGCTAGCGGA  GTGTATACTG  GCTTACTATG  TTGGCACTGA  TGAGGGTGTC
      ACGATCGCCT  CACATATGAC  CGAATGATAC  AACCGTGACT  ACTCCCACAG
                XmnI                                AgeI

1951  AGTGAAGTGC  TTCATGTGGC  AGGAGAAAAA  AGGCTGCACC  GGTGCGTCAG
      TCACTTCACG  AAGTACACCG  TCCTCTTTTT  TCCGACGTGG  CCACGCAGTC

2001  CAGAATATGT  GATACAGGAT  ATATTCCGCT  TCCTCGCTCA  CTGACTCCGCT
      GTCTTATACA  CTATGTCCTA  TATAAGGCGA  AGGAGCGAGT  GACTGAGCGA
```

FIG. 35VVV

```
2051  ACGCTCGGTC GTTCGACTGC GGCGAGCGGA AATGGCTTAC GAACGGGGCG
      TGCGAGCCAG CAAGCTGACG CCGCTCGCCT TTACCGAATG CTTGCCCCGC

2101  GAGATTTCCT GGAAGATGCC AGGAAGATAC TTAACAGGGA AGTGAGAGGG
      CTCTAAAGGA CCTTCTACGG TCCTTCTATG AATTGTCCCT TCACTCTCCC

2151  CCGCGGCAAA GCCGTTTTC  CATAGGCTCC GCCCCCCTGA CAAGCATCAC
      GGCGCCGTTT CGGCAAAAAG GTATCCGAGG CGGGGGGACT GTTCGTAGTG

2201  GAAATCTGAC GCTCAAATCA GTGGTGGCGA AACCCGACAG GACTATAAAG
      CTTTAGACTG CGAGTTTAGT CACCACCGCT TTGGGCTGTC CTGATATTTC

2251  ATACCAGGCG TTTCCCCCTG GCGGCTCCCT CCTGCGCTCT CCTGTTCCTG
      TATGGTCCGC AAAGGGGGAC CGCCGAGGGA GGACGCGAGA GGACAAGGAC
                  AgeI
                  ------

2301  CCTTTCGGTT TACCGGTGTC ATTCCGCTGT TATGGCCGCG TTTGTCTCAT
      GGAAAGCCAA ATGGCCACAG TAAGGCGACA ATACCGGCGC AAACAGAGTA

2351  TCCACGCCTG ACACTCAGTT CCGGGTAGGC AGTTCGCTCC AAGCTGGACT
      AGGTGCGGAC TGTGAGTCAA GGCCCATCCG TCAAGCGAGG TTCGACCTGA
```

*FIG. 35WWW*

```
2401  GTATGCACGA ACCCCCGTT  CAGTCCGACC GCTGCGCCTT ATCCGGTAAC
      CATACGTGCT TGGGGGGCAA GTCAGGCTGG CGACGCGGAA TAGGCCATTG

2451  TATCGTCTTG AGTCCAACCC GGAAAGACAT GCAAAAGCAC CACTGGCAGC
      ATAGCAGAAC TCAGGTTGGG CCTTTCTGTA CGTTTTCGTG GTGACCGTCG

2501  AGCCACTGGT AATTGATTTA GAGGAGTTAG TCTTGAAGTC ATGCGCCGGT
      TCGGTGACCA TTAACTAAAT CTCCTCAATC AGAACTTCAG TACGCGGCCA

2551  TAAGGCTAAA CTGAAAGGAC AAGTTTTAGT GACTGCGCTC CTCCAAGCCA
      ATTCCGATTT GACTTTCCTG TTCAAAATCA CTGACGCGAG GAGGTTCGGT

2601  GTTACCTCGG TTCAAAGAGT TGGTAGCTCA GAGAACCTAC GAAAAACCGC
      CAATGGAGCC AAGTTTCTCA ACCATCGAGT CTCTTGGATG CTTTTTGGCG

2651  CCTGCAAGGC GGTTTTTCG  TTTTCAGAGC AAGAGATTAC GCGCAGACCA
      GGACGTTCCG CCAAAAAAGC AAAAGTCTCG TTCTCTAATG CGCGTCTGGT
                                BglII

2701  AAACGATCTC AAGAAGATCA TCTTATTA
      TTTGCTAGAG TTCTTCTAGT AGAATAAT
```

*FIG. 35XXX*

M1: PCR using template

NoVspAatII: TAGACGTC

M2: synthesis

BloxA-A: TATGAGATCTCATAACTTCGTATAATGTACGCTATACG-
AAGTTAT

BloxA-B: TAATAACTTCGTATAGCATACATTATACGAAGTTATG-
AGATCTCA

M3: PCR, NoVspAatII as second oligo

XloxS-muta: CATTTTTTGCCCTCGTTATCTACGCATGCGATAACTTCGTA-
TAGCGTACATTATACGAAGTTATTCTAGACATGGTCATAGCTGTTTCCTG

M7-I: PCR gIIINEW-fow: GGGGGGGAATTCGGTGGTGGTGGATCTGCGTGCGCTG-
AAACGGTTGAAAGTTG gIIINEW-rev: CCCCCCCAAGCTTATCAAGACTCCTTATTACG

M7-II: PCR gIIIss-fow: GGGGGGGGGAATTCGGAGGCGGTTCCGGTGGTGGC

M7-III: PCR gIIIsupernew-fow: GGGGGGGGGAATTCGAGCAGAAGCTGATCTCT-
GAGGAGGATCTGTAGGGTGGTGGCTCTGGTTCCGGTGATTTTG

FIG. 35YYY

M8: synthesis lox514-A: CCATAACTTCGTATAATGTACGCTATACGAAGTTATA lox514-B: AGCTTATAACTTCGTATAGCGTACATTATACGAAGT-
TATGGCATG

M9II: synthesis

M9II-fow: AGCTTGACCTGTGAAGTGAAAAATGGCGCAGATT-
GTGCGACATTTTTTTTGTCTGCCGTTTAATTAAAGGGGGGGT M9II-rev: GTACACCCCCCCCCAGGCCGGCCCCCCCCCCCCTTTAA-
TTAAACGGCAGACAAAAAAAATGTCGCACAATCTGCG

M10II: assembly PCR with template bla-fow: GGGGGGGGTGTACATTCAAATATGTATCCGCTCATG bla-seq4: GGGTTACATCGAACTGGATCTC bla1-muta: CCAGTTCGATGTAACCCACTCGCGCACCCAACTGATC-
CTCAGCATCTTTTACTTTCACC blaII-muta: ACTCTAGCTTCCCGGCAACAGTTAATAGACTGGATG-
GAGGCGG bla-NEW: CTGTTGCCGGGAAGCTAGAGTAAG bla-rev: CCCCCCCTTAATTAAGGGGGGGGGGCCGGCCATTATCAAA-
AAGGATCTCAAGAAGATCC

M11II/III: PCR, site-directed mutagenesis

FIG. 35ZZZ f1-fow: GGGGGGGGGCTAGCACGCGCCCTGTAGCGGCGCATTAA f1-rev: CCCCCCCTGTACATGAAATTGTAAACGTTAATATTTTG f1-t133.muta: GGGCGATGGCCCACTACGAGAACCATCACCCTAATC

M12: assembly PCR using template p15-fow: GGGGGGAGATCTAATAAGATGATCTTCTTGAG p15-NEWI: GAGTTGGTAGCTCAGAGAACCTACGAAAAACCGCCCTG-CAAGGCG p15-NEWII: GTAGGTTCTCTGAGCTACCAACTC p15-NEWIII: GTTTCCCCCTGGCGGCTCCCTCCTGCGCTCTCCTGTTCCT-GCC p15-NEWIV: AGGAGGGAGCCGCCAGGGGGAAAC p15-rev: GACATCAGCGCTAGCGGAGTGTATAC

M13: synthesis

BloxXB-A: GATCTCATAACTTCGTATAATGTATGCTATACGAAGTTA-TTCA

BloxXB-B: GATCTGAATAACTTCGTATAGCATACATTATACGAAGTTA-TGAGA

M14-Ext2: PCR, site-directed mutagenesis

ColEXT2-fow: GGGGGGGAGATCTGACCAAAATCCCTTAACGTGAG

Col-mutal: GGTATCTGCGCTCTGCTGTAGCCAGTTACCTTCGG

FIG. 35AAAA

Col-rev: CCCCCCCGCTAGCCATGTGAGCAAAAGGCCAGCAA

M17: assembly PCR using template
CAT-1: GGGACGTCGGGTGAGGTTCCAAC
CAT-2: CCATACGGAACTCCGGGTGAGCATTCATC
CAT-3: CCGGAGTTCCGTATGG
CAT-4: ACGTTTAAATCAAAACTGG
CAT-5: CCAGTTTTGATTTAAACGTAGCCAATATGGACAACTTCTTC-GCCCCCGTTTTCACTATGGGCAAATATT
CAT-6: GGAAGATCTAGCACCAGGCGTTTAAG M41: assembly PCR using template
LAC1: GAGGCCGGCCATCGAATGGCGCAAAAC
LAC2: CGCGTACCGTCCTCATGGGAGAAAATAATAC
LAC3: CCATGAGGACGGTACGCGACTGGGCGTGGAGCATCTGGTCGCA-TTGGGTCACCAGCAAATCCGCTGTTAGCTGGCCCATTAAG
LAC4: GTCAGCGGCGGGATATAACATGAGCTGTCCTCGGTATCGTCG
LAC5: GTTATATCCCGCCGCTGACCACCATCAAAC
LAC6: CATCAGTGAATCGGCCAACGCGCGGGGAGAGGCGGTTTGCGT4TTG-GGAGCCAGGGTGGTTTTTC
LAC7: GGTTAATTAACCTCACTGCCCGCTTTCCAGTCGGGAAACCTGTCGTGCC-AGCTGCATCAGTGAATCGGCCAAC
M41-MCS-fow: CTAGACTAGTGTTTAAACCGGACCGGGGGGGGGCTT-AAGGGGGGGGGGGG

FIG. 35BBBB

M41-MCS-rev: CTAGCCCCCCCCCCCCTTAAGCCCCCCCCCGGTCCGGT-TTAAACACTAGT

M41-fow: CTAGACTAGTGTTTAAACCGGACCGGGGGGGGGCTTAA-GGGGGGGGGGGG

M41-rev: CCCCCCCTTAAGTGGGCTGCAAAACAAAACGGCCTCC-TGTCAGGAAGCCGCTTTTATCGGGTAGCCTCACTGCCCGCTTTCC

M41-A2: GTTGTTGTGCCACGCGGTTAGGAATGTAATTCAGCTCCGC

M41-B1: AACCGCGTGGCACAACAAC

M41-B2: CTTCGTTCTACCATCGACACGACCACGCTGGCACCCAGTTG

M41-C1: GTGTCGATGGTAGAACGAAG

M41-CII: CCACAGCAATAGCATCCTGGTCATCCAGCGGATAGTT-AATAATCAGCCCACTGACACGTTGCGCGAG

M41-DI: GACCAGGATGCTATTGCTGTGG

M41-DII: CAGCGCGATTTGCTGGTGGCCCAATGCGACCAGATGC

M41-EI: CACCAGCAAATCGCGCTG

M41-EII: CCCGGACTCGGTAATGGCACGCATTGCGCCCAGCGCC

M41-FI: GCCATTACCGAGTCCGGG

<u>M42: synthesis</u>

Eco-H5-Hind-fow: AATTCCACCATCATCACCATTGACGTCTA

Eco-H5-Hind-rev: AGCTTAGACGTCAATGGTGATGATGGTGG

FIG. 35CCCC

```
                                                    StyI
                                                  ~~~~~~~
                                                    PspSII                    BsiWI NspV
                                                  --------                    ----- ----
            MluI Bsu36I                  BstXI         EcoO109I
            ---- ------                  -----    --------
                   HpaI   BstEII              MscI                             
                   ----   ------              ----
126    CGCGTTAACC TCAGGTGACC AAGCCCCTGG CCAAGGTCCC CGGTACCAGG CCGGCCATTA TCAAAAAGGA GTACGTTCGA
       GCGCAATTGG AGTCCACTGG TTCGGGGACC GGTTCCAGGG GCCATGGTCC GGCCGGTAAT AGTTTTTCCT CATGCAAGCT
                  PmlI
                  ----
              NspVBsaBI       BamHI KpnI           FseI
              --------        ----- ----           ----
176    AGATTACCAT CACGTGGATC CGGTACCAGG CCGGCCATTA GGGTCTGACG CTCAGTGGAA
       TCTAATGGTA GTGCACCTAG GCCATGGTCC GGCCGGTAAT CCCAGACTGC GAGTCACCTT

226    TCTCAAGAAG ATCCTTTGAT CTTTTCTACG GGGTCTGACG CTCAGTGGAA
       AGAGTTCTTC TAGGAAACTA GAAAAGATGC CCCAGACTGC GAGTCACCTT

276    CGAAAACTCA CGTTAAGGGA TTTTGGTCAT GAGATTATCA AAAAGGATCT
       GCTTTTGAGT GCAATTCCCT AAAACCAGTA CTCTAATAGT TTTTCCTAGA
```

FIG. 36B

```
326  TCACCTAGAT CCTTTTAAAT TAAAAATGAA GTTTTAAATC AATCTAAAGT
     AGTGGATCTA GGAAAATTTA ATTTTTACTT CAAAATTTAG TTAGATTCA

376  ATATATGAGT AAACTTGGTC TGACAGTTAC CAATGCTTAA TCAGTGAGGC
     TATATACTCA TTTGAACCAG ACTGTCAATG GTTACGAATT AGTCACTCCG

426  ACCTATCTCA GCGATCTGTC TATTTCGTTC ATCCATAGTT GCCTGACTCC
     TGGATAGAGT CGCTAGACAG ATAAAGCAAG TAGGTATCAA CGGACTGAGG

476  CCGTCGTGTA GATAACTACG ATACGGGAGG GCTTACCATC TGGCCCCAGT
     GGCAGCACAT CTATTGATGC TATGCCCTCC CGAATGGTAG ACCGGGGTCA

526  GCTGCAATGA TACCGCGAGA CCCACGCTCA CCGGCTCCAG ATTTATCAGC
     CGACGTTACT ATGGCGCTCT GGGTGCGAGT GGCCGAGGTC TAAATAGTCG

576  AATAAACCAG CCAGCCGGAA GGGCCGAGCG CAGAAGTGGT CCTGCAACTT
     TTATTTGGTC GGTCGGCCTT CCCGGCTCGC GTCTTCACCA GGACGTTGAA

626  TATCCGCCTC CATCCAGTCT ATTAACTGTT GCCGGGAAGC TAGAGTAAGT
     ATAGGCGGAG GTAGGTCAGA TAATTGACAA CGGCCCTTCG ATCTCATTCA

676  AGTTCGCCAG TTAATAGTTT GCGCAACGTT GTTGCCATTG CTACAGGCAT
     TCAAGCGGTC AATTATCAAA CGCGTTGCAA CAACGGTAAC GATGTCCGTA
```

*FIG. 36C*

```
 726   CGTGGTGTCA CGCTCGTCGT TTGGTATGGC TTCATTCAGC TCCGGTTCCC
       GCACCACAGT GCGAGCAGCA AACCATACCG AAGTAAGTCG AGGCCAAGG

776   AACGATCAAG GCGAGTTACA TGATCCCCCA TGTTGTGCAA AAAAGCGGTT
       TTGCTAGTTC CGCTCAATGT ACTAGGGGGT ACAACACGTT TTTTCGCCAA

826   AGCTCCTTCG GTCCTCCGAT CGTTGTCAGA AGTAAGTTGG CCGCAGTGTT
       TCGAGGAAGC CAGGAGGCTA GCAACAGTCT TCATTCAACC GGCGTCACAA

876   ATCACTCATG GTTATGGCAG CACTGCATAA TTCTCTTACT GTCATGCCAT
       TAGTGAGTAC CAATACCGTC GTGACGTATT AAGAGAATGA CAGTACGGTA

926   CCGTAAGATG CTTTTCTGTG ACTGGTGAGT ACTCAACCAA GTCATTCTGA
       GGCATTCTAC GAAAAGACAC TGACCACTCA TGAGTTGGTT CAGTAAGACT

976   GAATAGTGTA TGCGGCGACC GAGTTGCTCT TGCCCGGCGT CAATACGGGA
       CTTATCACAT ACGCCGCTGG CTCAACGAGA ACGGGCCGCA GTTATGCCCT

1026   TAATACCGCG CCACATAGCA GAACTTTAAA AGTGCTCATC ATTGAAAAAC
       ATTATGGCGC GGTGTATCGT CTTGAAATTT TCACGAGTAG TAACCTTTTG

1076   GTTCTTCGGG GCGAAAACTC TCAAGGATCT TACCGCTGTT GAGATCCAGT
       CAAGAAGCCC CGCTTTTGAG AGTTCCTAGA ATGGCGACAA CTCTAGGTCA
```

*FIG. 36D*

```
1126  TCGATGTAAC  CCACTCGTGC  ACCCAACTGA  TCTTCAGCAT  CTTTTACTTT
      AGCTACATTG  GGTGAGCACG  TGGGTTGACT  AGAAGTCGTA  GAAAATGAAA
                      BssSI                  Eco57I
                      -----                  ------

1176  CACCAGCGTT  TCTGGGTGAG  CAAAAACAGG  AAGGCAAAAT  GCCGCAAAAA
      GTGGTCGCAA  AGACCCACTC  GTTTTTGTCC  TTCCGTTTTA  CGGCGTTTTT

1226  AGGGAATAAG  GGCGACACGG  AAATGTTGAA  TACTCATACT  CTTCCTTTTT
      TCCCTTATTC  CCGCTGTGCC  TTTACAACTT  ATGAGTATGA  GAAGGAAAAA

1276  CAATATTATT  GAAGCATTTA  TCAGGGTTAT  TGTCTCATGA  GCGGATACAT
      GTTATAATAA  CTTCGTAAAT  AGTCCCAATA  ACAGAGTACT  CGCCTATGTA
                                   PstI                      XhoI
                                   ----                      ----
                      EagI  BssSI            BbeI  AseI       BssHII
                      ----  -----            ----  ----       ------

1326  ATTTGAATGT  ACTCGGCCGC  ACGAGCTGCA  GGCGCCATTA  ATGGCTCGAG
      TAAACTTACA  TGAGCCGGCG  TGCTCGACGT  CCGCGGTAAT  TACCGAGCTC
          BspEI  BsrGI
          -----  -----
      BssHII
      ------
```

*FIG. 36E*

1376 CGCGCTTCAG CGCTTTGTCT TCCGGATGTA CATGAAATT
     GCGCGAAGTC GCGAAACAGA AGGCCTACAT GTACTTTAA
         Eco57I        BbsI

FIG. 36F

```
              1                    10
O_K3L_5    5'- G C C C T G C A A G C G │G A A G A C│
                                       │    Bbsl   │
                                            E    D
Vk1 & Vk3  5'- G C C C T G C A A G C G │G A A G A C│

E    D
Vk2        5'- G C C C T G C A A G C G │G A A G A C│

E    D
Vk4        5'- G C C C T G C A A G C G │G A A G A C│
```

FIG. 37A

```
              20              30              40
  -3'
          F       A        ▓      Y       Y    C             Q
      T  T  T G C G ▓▓▓▓ T A  T  T A T T G  C           C A
                     ▓▓▓▓
          V       G        V      Y       Y    C
      G  T  G G C G T G T A  T  T A T T G  C           C A
          V       A        V      Y       Y    C
      G  T  G G C G G T G T A  T  T A T T G  C         C A
```

|   |     |
|---|-----|
| A |     |
| C |     |
| D |     |
| E |     |
| F | T T T |
| G |     |
| H | C A T |
| I |     |
| K |     |
| L | C T T |
| M | A T G |
| N |     |
| P |     |
| Q | C A G |
| R |     |
| S |     |
| T |     |
| V |     |
| W |     |
| Y |     |

80% Q

FIG. 37B

```
                              50                      60
                                                       3'- G G A

T
         G                                             A C C T

T
         G                                             A C C T
                                                           T
         G                                             A C C T
```

| G C T |       |       | G C T |       | G C T |
|-------|-------|-------|-------|-------|-------|
|       |       |       |       |       |       |
| G A T | G A T | G A T | G A T |       | G A T |
| G A G |       |       | G A G |       | G A G |
| T T T |       |       | T T T |       | T T T |
| G G T | G G T | G G T | G G T |       | G G T |
| C A T |       |       | C A T |       | C A T |
| A T T |       |       | A T T |       | A T T |
| A A G |       |       | A A G |       | A A G |
| C T T |       |       | C T T |       | C T T |
| A T G |       |       | A T G |       | A T G |
| A A T | A A T | A A T | A A T |       | A A T |
|       |       |       | C C T | C C T | C C T |
| C A G |       |       | C A G |       | C A G |
| C G T |       |       | C G T |       | C G T |
| T C T | T C T | T C T | T C T | T C T | T C T |
| A C T |       |       | A C T |       | A C T |
| G T T |       |       | G T T |       | G T T |
| T G G |       |       | T G G |       | T G G |
| T A T | T A T |       | T A T |       | T A T |
| 50% Y |       |       |       | 80% P |       |

FIG. 37C

```
                       70                    80 81
        A A C C G G T A A G C T T T C G  G  -5' O_K3L_3
           ┌──────────┐
           │   MscI   │
         F │  G    Q  │
        T │T G G C C A│ T T C G A A A G C  C  -3'

```
            30              40                  50
     Y   Y   C   Q   S           D
    -ATTATTGCCAGAGC          GAC
                          A           GCT GCT -
                          C
                          D           GAT GAT
                          E           GAG GAG
                          F           TTT TTT
                          G           GGT GGT
                          H           CAT CAT
                          I           ATT ATT
                          K           AAG AAG
                          L           CTT CTT
                          M           ATG ATG
                          N           AAT AAT
                          P           CCT CCT
                          Q           CAG CAG
                          R CGT       CGT CGT
                          S           TCT TCT
                          T           ACT ACT
                          V           GTT GTT
                          W TGG
                          Y TAT       TAT TAT
                            3    1    18  18
                            3    1    18  18
                            3    1    18  18
```

FIG. 38B

|  | 60 | | | 70 | 80 |
|---|---|---|---|---|---|

```
                                G   G   G   T   K   L
                               G G C G G C G G C A C G A A G T T A
```

|  | gap | gap |  |
|---|---|---|---|
| -G C T | G C T | G C T | G C T |
| G A T | G A T | G A T | G A T |
| G A G | G A G | G A G | G A G |
| T T T | T T T | T T T | T T T |
| G G T | G G T | G G T | G G T |
| C A T | C A T | C A T | C A T |
| A T T | A T T | A T T | A T T |
| A A G | A A G | A A G | A A G |
| C T T | C T T | C T T | C T T |
| A T G | A T G | A T G | A T G |
| A A T | A A T | A A T | A A T |
| C C T | C C T | C C T | C C T |
| C A G | C A G | C A G | C A G |
| C G T | C G T | C G T | C G T |
| T C T | T C T | T C T | T C T |
| A C T | A C T | A C T | A C T |
| G T T | G T T | G T T | G T T |
|  |  |  | T G G |
| T A T | T A T | T A T | T A T | Variability |
| 18 |  |  | 19 | 3.32E+05 |
| 18 | 18 |  | 19 | 5.98E+06 |
| 18 | 18 | 18 | 19 | 1.08E+08 |

FIG. 38C

```
            90              100          108
     T  V  L  G  Q   E  F
ACCGTTCTTGGCAG GAATTC GAGCC-3'
       3'-CCGGTCCTTAAGCTCGG-5'
```

FIG. 38D

| % soluble | κ1 | κ2 | κ3 | κ4 | λ1 | λ2 | λ3 |
|---|---|---|---|---|---|---|---|
| H1A | 61% | 58% | 52% | 42% | 90% | 61% | 60% |
| H1B | 39% | 48% | 66% | 48% | 47% | 39% | 36% |
| H2 | 47% | 57% | 46% | 49% | 37% | 36% | 45% |
| H3 | 85% | 67% | 76% | 61% | 80% | 71% | 83% |
| H4 | 69% | 52% | 51% | 44% | 45% | 33% | 42% |
| H5 | 49% | 49% | 46% | 67% | 54% | 46% | 47% |
| H6 | 90% | 58% | 54% | 47% | 45% | 50% | 51% |

| Total amount compared to H3κ2 | κ1 | κ2 | κ3 | κ4 | λ1 | λ2 | λ3 |
|---|---|---|---|---|---|---|---|
| H1A | 289% | 94% | 166% | 272% | 20% | 150% | 78% |
| H1B | 219% | 122% | 89% | 139% | 117% | 158% | 101% |
| H2 | 186% | 223% | 208% | 182% | 126% | 60% | 97% |
| H3 | 50% |  | 71% | 54% | 59% | 130% | 47% |
| H4 | 37% | 55% | 60% | 77% | 195% | 107% | 251% |
| H5 | 98% | 201% | 167% | 83% | 93% | 128% | 115% |
| H6 | 65% | 117% | 89% | 109% | 299% | 215% | 278% |

*FIG. 40A*

| Soluble amount compared to H3κ2 | κ1 | κ2 | κ3 | κ4 | λ1 | λ2 | λ3 |
|---|---|---|---|---|---|---|---|
| H1A | 191% | 88% | 1221% | 1222% | 26% | 211% | 76% |
| H1B | 124% | 95% | 83% | 107% | 79% | 142% | 59% |
| H2 | 126% | 204% | 139% | 130% | 66% | 50% | 70% |
| H3 | 63% | — | 81% | 49% | 69% | 143% | 61% |
| H4 | 40% | 47% | 49% | 54% | 95% | 55% | 125% |
| H5 | 69% | 158% | 116% | 80% | 72% | 84% | 84% |
| H6 | 85% | 122% | 87% | 77% | 162% | 162% | 212% |

| | McPC |
|---|---|
| soluble | 38% |
| %H3κ2 total | 1117% |
| %H3κ2 soluble | 69% |

*FIG. 40B*

PROTEIN/(POLY)PEPTIDE LIBRARIES

This application is a divisional of Ser. No. 09/025,769, filed 18 Feb. 1998 now U.S. Pat. No. 6,300,064, which is a continuation of PCT EP96/03647 filed 19 Aug. 1996.

FIELD OF THE INVENTION

The present invention relates to synthetic DNA sequences which encode one or more collections of homologous proteins(poly)peptides, and methods for generating and applying libraries of these DNA sequences. In particular, the invention relates to the preparation of a library of human-derived antibody genes by the use of synthetic consensus sequences which cover the structural repertoire of antibodies encoded in the human genome. Furthermore, the invention relates to the use of a single consensus antibody gene as a universal framework for highly diverse antibody libraries.

BACKGROUND TO THE INVENTION

All current recombinant methods which use libraries of proteins/(poly)peptides, e.g. antibodies, to screen for members with desired properties, e.g. binding a given ligand, do not provide the possibility to improve the desired properties of the members in an easy and rapid manner. Usually a library is created either by inserting a random oligonucleotide sequence into one or more DNA sequences cloned from an organism, or a family of DNA sequences is cloned and used as the library. The library is then screened, e.g. using phage display, for members which show the desired property. The sequences of one or more of these resulting molecules are then determined. There is no general procedure available to improve these molecules further on.

Winter (EP 0 368 684 B1) has provided a method for amplifying (by PCR), cloning, and expressing antibody variable region genes. Starting with these genes he was able to create libraries of functional antibody fragments by randomizing the CDR3 of the heavy and/or the light chain. This process is functionally equivalent to the natural process of VJ and VDJ recombination which occurs during the development of B-cells in the immune system.

However the Winter invention does not provide a method for optimizing the binding affinities of antibody fragments further on, a process which would be functionally equivalent to the naturally occurring phenomenon of "affinity maturation", which is provided by the present invention. Furthermore, the Winter invention does not provide for artificial variable region genes, which represent a whole family of structurally similar natural genes, and which can be assembled from synthetic DNA oligonucleotides. Additionally, Winter does not enable the combinatorial assembly of portions of antibody variable regions, a feature which is provided by the present invention. Furthermore, this approach has the disadvantage that the genes of all antibodies obtained in the screening procedure have to be completely sequenced, since, except for the PCR priming regions, no additional sequence information about the library members is available. This is time and labor intensive and potentially leads to sequencing errors.

The teaching of Winter as well as other approaches have tried to create large antibody libraries having high diversity in the complementarity determining regions (CDRs) as well as in the frameworks to be able to find antibodies against as many different antigens as possible. It has been suggested that a single universal framework may be useful to build antibody libraries, but no approach has yet been successful.

Another problem lies in the production of reagents derived from antibodies. Small antibody fragments show exciting promise for use as therapeutic agents, diagnostic reagents, and for biochemical research. Thus, they are needed in large amounts, and the expression of antibody fragments, e.g. Fv, single-chain Fv (scFv), or Fab in the periplasm of *E. coli* (Skerra & Plückthun, 1988; Better et al., 1988) is now used routinely in many laboratories. Expression yields vary widely, however. While some fragments yield up to several mg of functional, soluble protein per liter and OD of culture broth in shake flask culture (Carter et al., 1992, Plückthun et al. 1996), other fragments may almost exclusively lead to insoluble material, often found in so-called inclusion bodies. Functional protein may be obtained from the latter in modest yields by a laborious and time-consuming refolding process. The factors influencing antibody expression levels are still only poorly understood. Folding efficiency and stability of the antibody fragments, protease lability and toxicity of the expressed proteins to the host cells often severely limit actual production levels, and several attempts have been tried to increase expression yields. For example, Knappik & Plückthun (1995) could show that expression yield depends on the antibody sequence. They identified key residues in the antibody framework which influence expression yields dramatically. Similarly, Ullrich et al. (1995) found that point mutations in the CDRs can increase the yields in periplasmic antibody fragment expression. Nevertheless, these strategies are only applicable to a few antibodies. Since the Winter invention uses existing repertoires of antibodies, no influence on expressibility of the genes is possible.

Furthermore, the findings of Knappik & Plückthun and Ullrich demonstrate that the knowledge about antibodies, especially about folding and expression is still increasing. The Winter invention does not allow to incorporate such improvements into the library design.

The expressibility of the genes is important for the library quality as well, since the screening procedure relies in most cases on the display of the gene product on a phage surface, and efficient display relies on at least moderate expression of the gene.

These disadvantages of the existing methodologies are overcome by the present invention, which is applicable for all collections of homologous proteins. It has the following novel and useful features illustrated in the following by antibodies as an example:

Artificial antibodies and fragments thereof can be constructed based on known antibody sequences, which reflect the structural properties of a whole group of homologous antibody genes. Therefore it is possible to reduce the number of different genes without any loss in the structural repertoire. This approach leads to a limited set of artificial genes, which can be synthesized de novo, thereby allowing introduction of cleavage sites and removing unwanted cleavages sites. Furthermore, this approach enables (i), adapting the codon usage of the genes to that of highly expressed genes in any desired host cell and (ii), analyzing all possible pairs of antibody light (L) and heavy (H) chains in terms of interaction preference, antigen preference or recombinant expression titer, which is virtually impossible using the complete collection of antibody genes of an organism and all combinations thereof.

The use of a limited set of completely synthetic genes makes it possible to create cleavage sites at the boundaries of encoded structural sub-elements. Therefore, each gene is built up from modules which represent structural sub-elements on the protein/(poly)peptide level. In the case of antibodies, the modules consist of "framework" and "CDR"

modules. By creating separate framework and CDR modules, different combinatorial assembly possibilities are enabled. Moreover, if two or more artificial genes carry identical pairs of cleavage sites at the boundaries of each of the genetic sub-elements, pre-built libraries of sub-elements can be inserted in these genes simultaneously, without any additional information related to any particular gene sequence. This strategy enables rapid optimization of, for example, antibody affinity, since DNA cassettes encoding libraries of genetic sub-elements can be (i), pre-built, stored and reused and (ii), inserted in any of these sequences at the right position without knowing the actual sequence or having to determine the sequence of the individual library member.

Additionally, new information about amino acid residues important for binding, stability, or solubility and expression could be integrated into the library design by replacing existing modules with modules modified according to the new observations.

The limited number of consensus sequences used for creating the library allows to speed up the identification of binding antibodies after screening. After having identified the underlying consensus gene sequence, which could be done by sequencing or by using fingerprint restriction sites, just those part(s) comprising the random sequence(s) have to be determined. This reduces the probability of sequencing errors and of false-positive results.

The above mentioned cleavage sites can be used only if they are unique in the vector system where the artificial genes have been inserted. As a result, the vector has to be modified to contain none of these cleavage sites. The construction of a vector consisting of basic elements like resistance gene and origin of replication, where cleavage sites have been removed, is of general interest for many cloning attempts. Additionally, these vector(s) could be part of a kit comprising the above mentioned artificial genes and pre-built libraries.

The collection of artificial genes can be used for a rapid humanization procedure of non-human antibodies, preferably of rodent antibodies. First, the amino acid sequence of the non-human, preferably rodent antibody is compared with the amino acid sequences encoded by the collection of artificial genes to determine the most homologous light and heavy framework regions. These genes are then used for insertion of the genetic sub-elements encoding the CDRs of the non-human, preferably rodent antibody.

Surprisingly, it has been found that with a combination of only one consensus sequence for each of the light and heavy chains of a scFv fragment an antibody repertoire could be created yielding antibodies against virtually every antigen. Therefore, one aspect of the present invention is the use of a single consensus sequence as a universal framework for the creation of useful (poly)peptide libraries and antibody consensus sequences useful therefor.

DETAILED DESCRIPTION OF THE INVENTION

The present invention enables the creation of useful libraries of (poly)peptides. In a first embodiment, the invention provides for a method of setting up nucleic acid sequences suitable for the creation of said libraries. In a first step, a collection of at least three homologous proteins is identified and then analyzed. Therefore, a database of the protein sequences is established where the protein sequences are aligned to each other. The database is used to define subgroups of protein sequences which show a high degree of similarity in both the sequence and, it information is available, in the structural arrangement. For each of the subgroups a (poly)peptide sequence comprising at least one consensus sequence is deduced which represents the members of this subgroup; the complete collection of (poly) peptide sequences represent therefore the complete structural repertoire of the collection of homologous proteins. These artificial (poly)peptide sequences are then analyzed, if possible, according to their structural properties to identify unfavorable interactions between amino acids within said (poly)peptide sequences or between said or other (poly) peptide sequences, for example, in multimeric proteins. Such interactions are then removed by changing the consensus sequence accordingly. The (poly)peptide sequences are then analyzed to identify sub-elements such as domains, loops, helices or CDRs. The amino acid sequence is back-translated into a corresponding coding nucleic acid sequence which is adapted to the codon usage of the host planned for expressing said nucleic acid sequences. A set of cleavage sites is set up in a way that each of the sub-sequences encoding the sub-elements identified as described above, is flanked by two sites which do not occur a second time within the nucleic acid sequence. This can be achieved by either Identifying a cleavage site already flanking a sub-sequence of by changing one or more nucleotides to create the cleavage site, and by removing that site from the remaining part of the gene. The cleavage sites should be common to all corresponding sub-elements or sub-sequences, thus creating a fully modular arrangement of the sub-sequences in the nucleic acid sequence and of the sub-elements in the corresponding (poly)peptide.

In a further embodiment, the invention provides for a method which sets up two or more sets of (poly)peptides, where for each set the method as described above is performed, and where the cleavage sites are not only unique within each set but also between any two sets. This method can be applied for the creation of (poly)peptide libraries comprising for example two α-helical domains from two different proteins, where said library is screened for novel hetero-association domains.

In yet a further embodiment, at least two of the sets as described above, are derived from the same collection of proteins or at least a part of it. This describes libraries comprising for example, but not limited to, two domains from antibodies such as VH and VL, or two extracellular loops of transmembrane receptors.

In another embodiment, the nucleic acid sequences set up as described above, are synthesized. This can be achieved by any one of several methods well known to the practitioner skilled in the art, for example, by total gene synthesis or by PCR-based approaches.

In one embodiment, the nucleic acid sequences are cloned into a vector. The vector could be a sequencing vector, an expression vector or a display (e.g. phage display) vector, which are well known to those skilled in the art. Any vector could comprise one nucleic acid sequence, or two or more nucleic sequences, either in different or the same operon. In the last case, they could either be cloned separately or as contiguous sequences.

In one embodiment, the removal of unfavorable interactions as described above, leads to enhanced expression of the modified (poly)peptides.

In a preferred embodiment, one or more sub-sequences of the nucleic acid sequences are replaced by different sequences. This can be achieved by excising the sub-sequences using the conditions suitable for cleaving the cleavage sites adjacent to or at the end of the sub-sequence, for example, by using a restriction enzyme at the corresponding restriction site under the conditions well known to those skilled in the art, and replacing the sub-sequence by a different sequence compatible with the cleaved nucleic acid sequence. In a further preferred embodiment, the different sequences replacing the initial sub-sequence(s) are genomic or rearranged genomic sequences, for example in grafting CDRs from non-human antibodies onto consensus antibody sequences for rapid humanization of non-human antibodies. In the most preferred embodiment, the different sequences are random sequences, thus replacing the sub-sequence by a collection of sequences to introduce variability and to create a library. The random sequences can be assembled in various ways, for example by using a mixture of mononucleotides or preferably a mixture of trinucleotides (Virnekäs et al., 1994) during automated oligonucleotide synthesis, by error-prone PCR or by other methods well known to the practitioner in the art. The random sequences may be completely randomized or biased towards or against certain codons according to the amino acid distribution at certain positions in known protein sequences. Additionally, the collection of random sub-sequences may comprise different numbers of codons, giving rise to a collection of sub-elements having different lengths.

In another embodiment, the invention provides for the expression of the nucleic acid sequences from a suitable vector and under suitable conditions well known to those skilled in the art.

In a further preferred embodiment, the (poly)peptides expressed from said nucleic acid sequences are screened and, optionally, optimized. Screening may be performed by using one of the methods well known to the practitioner in the art, such as phage-display, selectively infective phage, polysome technology to screen for binding, assay systems for enzymatic activity or protein stability. (Poly)peptides having the desired property can be identified by sequencing of the corresponding nucleic acid sequence or by amino acid sequencing or mass spectrometry. In the case of subsequent optimization, the nucleic acid sequences encoding the initially selected (poly)peptides can optionally be used without sequencing. Optimization is performed by repealing the replacement of sub-sequences by different sequences, preferably by random sequences, and the screening step one or more times.

The desired property the (poly)peptides are screened for is preferably, but not exclusively, selected from the group of optimized affinity or specificity for a target molecule, optimized enzymatic activity, optimized expression yields, optimized stability and optimized solubility.

In one embodiment, the cleavage sites flanking the sub-sequences are sites recognized and cleaved by restriction enzymes, with recognition and cleavage sequences being either identical or different, the restricted sites either having blunt or sticky ends.

The length of the sub-elements is preferably, but not exclusively ranging between 1 amino acid, such as one residue in the active site of an enzyme or a structure-determining residue, and 150 amino acids, as for whole protein domains. Most preferably, the length ranges between 3 and 25 amino acids, such as most commonly found in CDR loops of antibodies.

The nucleic acid sequences could be RNA or, preferably, DNA.

In one embodiment, the (poly)peptides have an amino acid pattern characteristic of a particular species. This can for example be achieved by deducing the consensus sequences from a collection of homologous proteins of just one species, most preferably from a collection of human proteins. Since the (poly)peptides comprising consensus sequences are artificial, they have to be compared to the protein sequence(s) having the closest similarity to ensure the presence of said characteristic amino acid pattern.

In one embodiment, the invention provides for the creation of libraries of (poly)peptides comprising at least part of members or derivatives of the immunoglobulin superfamily, preferably of member or derivatives of the immnoglobulins. Most preferably, the invention provides for the creation of libraries of human antibodies, wherein said (poly)peptides are or are derived from heavy or light chain variable regions wherein said structural sub-elements are framework regions (FR) 1, 2, 3, or 4 or complementary determining regions (CDR) 1, 2, or 3. In a first step, a database of published antibody sequences of human origin is established where the antibody sequences are aligned to each other. The database is used to define subgroups of antibody sequences which show a high degree of similarity in both the sequence and the canonical fold of CDR loops (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed e.g. by total gene synthesis or by the use of synthetic genetic subunits. These genetic subunits correspond to structural sub-elements on the (poly)peptide level. On the DNA level, these genetic subunits are defined by cleavage sites at the start and the end of each of the sub-elements, which are unique in the vector system. All genes which are members of the collection of consensus sequences are constructed such that they contain a similar pattern of corresponding genetic sub-sequences. Most preferably, said (poly)peptides are or are derived from the HuCAL consensus genes: Vκ1, Vκ2, Vκ3, Vκ4, Vλ1, Vλ2, Vλ3, VH1A, VH1B, VH2, VH3, VH4, VH5, VH6, Cκ, Cλ, CH1 or any combination of said HuCAL consensus genes.

This collection of DNA molecules can then be used to create libraries of antibodies or antibody fragments, preferably Fv, disulphide-linked Fv, single-chain Fv (scFv), or Fab fragments, which may be used as sources of specificities against new target antigens. Moreover, the affinity of the antibodies can be optimized using pre-built library cassettes and a general procedure. The invention provides a method for identifying one or more genes encoding one or more antibody fragments which binds to a target, comprising the steps of expressing the antibody fragments, and then screening them to isolate one or more antibody fragments which bind to a given target molecule. Preferably, an scFv fragment library comprising the combination of HuCAL VH3 and HuCAL Vλ2 consensus genes and at least a random sub-sequence encoding the heavy chain CDR3 sub-element is screened for binding antibodies. If necessary, the modular design of the genes can then be used to excise from the genes encoding the antibody fragments one or more genetic sub-sequences encoding structural sub-elements, and replacing them by one or more second sub-sequences encoding structural sub-elements. The expression and screening steps can then be repeated until an antibody having the desired affinity is generated.

Particularly preferred is a method in which one or more of the genetic subunits (e.g. the CDRs) are replaced by a random collection of sequences (the library) using the said cleavage sites. Since these cleavage sites are (i) unique in the vector system and (ii) common to all consensus genes, the same (pre-built) library can be inserted into all artificial antibody genes. The resulting library is then screened against any chosen antigen. Binding antibodies are selected, collected and used as starting material for the next library. Here, one or more of the remaining genetic subunits are randomized as described above.

A further embodiment of the present invention relates to fusion proteins by providing for a DNA sequence which encodes both the (poly)peptide, as described above, as well as an additional moiety. Particularly preferred are moieties which have a useful therapeutic function. For example, the additional moiety may be a toxin molecule which is able to kill cells (Vitetta et al., 1993). There are numerous examples of such toxins, well known to the one skilled in the art, such as the bacterial toxins Pseudomonas exotoxin A, and diphtheria toxin, as well as the plant toxins ricin, abrin, modeccin, saporin, and gelonin. By fusing such a toxin for example to an antibody fragment, the toxin can be targeted to, for example, diseased cells, and thereby have a beneficial therapeutic effect. Alternatively, the additional moiety may be a cytokine, such as IL-2 (Rosenberg & Lotze, 1986), which has a particular effect (in this case a T-cell proliferative effect) on a family of cells. In a further embodiment, the additional moiety may confer on its (poly)peptide partner a means of detection and/or purification. For example, the fusion protein could comprise the modified antibody fragment and an enzyme commonly used for detection purposes, such as alkaline phosphatase (Blake et al., 1984). There are numerous other moieties which can be used as detection or purification tags, which are well known to the practitioner skilled in the art. Particularly preferred are peptides comprising at least five histidine residues (Hochuli et al., 1988), which are able to bind to metal ions, and can therefore be used for the purification of the protein to which they are fused (Lindner et al., 1992). Also provided for by the invention are additional moieties such as the commonly used C-myc and FLAG-tags (Hopp et al., 1988; Knappik & Plückthun, 1994).

By engineering one or more fused additional domains, antibody fragments or any other (poly)peptide can be assembled into larger molecules which also fall under the scope of the present invention. For example, mini-antibodies (Pack, 1994) are dimers comprising two antibody fragments, each fused to a self-associating dimerization domain. Dimerization domains which are particularly preferred include those derived from a leucine zipper (Pack & Plückthun, 1992) or helix-turn-helix motif (Pack et al., 1993).

All of the above embodiments of the present invention can be effected using standard techniques of molecular biology known to anyone skilled in the art.

In a further embodiment, the random collection of subsequences (the library) is inserted into a singular nucleic acid sequence encoding one (poly)peptide, thus creating a (poly)peptide library based on one universal framework. Preferably a random collection of CDR sub-sequences is inserted into a universal antibody framework, for example into the HuCAL H3κ2 single-chain Fv fragment described above.

In further embodiments, the invention provides for nucleic acid sequencers), vector(s) containing the nucleic acid sequence(s), host cell(s) containing the vector(s), and (poly)peptides, obtainable according to the methods described above.

In a further preferred embodiment, the invention provides for modular vector systems being compatible with the modular nucleic acid sequences encoding the (poly) peptides. The modules of the vectors are flanked by restriction sites unique within the vector system and essentially unique with respect to the restriction sites incorporated into the nucleic acid sequences encoding the (poly)peptides, except for example the restriction sites necessary for cloning the nucleic acid sequences into the vector. The list of vector modules comprises origins of single-stranded replication, origins of double-stranded replication for high- and low copy number plasmids, promotor/operator, repressor or terminator elements, resistance genes, potential recombination sites, gene III for display on filamentous phages, signal sequences, purification and detection tags, and sequences of additional moieties. The vectors are preferably, but not exclusively, expression vectors or vectors suitable for expression and screening of libraries.

In another embodiment, the invention provides for a kit, comprising one or more of the list of nucleic acid sequence (s), recombinant vector(s), (poly)peptide(s), and vector(s) according lo the methods described above, and suitable host cell(s) for producing the (poly)peptide(s).

In a preferred embodiment, the invention provides for the creation of libraries of human antibodies. In a first step, a database of published antibody sequences of human origin is established. The database is used to define subgroups of antibody sequences which show a high degree of similarity in both the sequence and the canonical fold (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed by the use of synthetic genetic subunits. These genetic subunits correspond to structural sub-elements on the protein level. On the DNA level, these genetic subunits are defined by cleavage sites at the start and the end of each of the subelements, which are unique in the vector system. All genes which are members of the collection of consensus sequences are constructed such that they contain a similar pattern of said genetic subunits.

This collection of DNA molecules can then be used to create libraries of antibodies which may be used as sources of specificities against new target antigens. Moreover, the affinity of the antibodies can be optimised using pre-built library cassettes and a general procedure. The invention provides a method for identifying one or more genes encoding one or more antibody fragments which binds to a target, comprising the steps of expressing the antibody fragments, and then screening them to isolate one or more antibody fragments which bind to a given target molecule. If necessary, the modular design of the genes can then be used to excise from the genes encoding the antibody fragments one or more genetic sub-sequences encoding structural sub-elements, and replacing them by one or more second sub-sequences encoding structural sub-elements. The expression and screening steps can then be repeated until an antibody having the desired affinity is generated.

Particularly preferred is a method in which one or more of the genetic subunits (e.g. the CDR's) are replaced by a random collection of sequences (the library) using the said cleavage sites. Since these cleavage sites are (i) unique in the vector system and (ii) common to all consensus genes, the same (pre-built) library can be inserted into all artificial antibody genes. The resulting library is then screened against any chosen antigen. Binding antibodies are eluted, collected and used as starting material for the next library. Here, one or more of the remaining genetic subunits are randomised as described above.

DEFINITIONS

Protein

The term protein comprises monomeric polypeptide chains as well as homo- or heteromultimeric complexes of two or more polypeptide chains connected either by covalent interactions (such as disulphide bonds) or by non-covalent interactions (such as hydrophobic or electrostatic interactions).

Analysis of Homologous Proteins

The amino acid sequences of three or more proteins are aligned to each other (allowing for introduction of gaps) in a way which maximizes the correspondence between identical or similar amino acid residues at all positions. These aligned sequences are termed homologous it the percentage of the sum of identical and/or similar residues exceeds a defined threshold. This threshold is commonly regarded by those skilled in the art as being exceeded when at least 15% of the amino acids in the aligned genes are identical, and at least 30% are similar. Examples for families of homologous proteins are: immunoglobulin superfamily, scavenger receptor superfamily, fibronectin superfamilies (e.g. type II and III), complement control protein superfamily, cytokine receptor superfamily, cystine knot proteins, tyrosine kinases, and numerous other examples well known to one of ordinary skill in the art.

Consensus Sequence

Using a matrix of at least three aligned amino acid sequences, and allowing for gaps in the alignment, it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

Removing Unfavorable Interactions

The consensus sequence is per se in most cases artificial and has to be analyzed in order to change amino acid residues which, for example, would prevent the resulting molecule to adapt a functional tertiary structure or which would block the interaction with other (poly)peptide chains in multimeric complexes. This can be done either by (i) building a three-dimensional model of the consensus sequence using known related structures as a template, and identifying amino acid residues within the model which may interact unfavorably with each other, or (ii) analyzing the matrix of aligned amino acid sequences in order to detect combinations of amino acid residues within the sequences which frequently occur together in one sequence and are therefore likely lo interact with each other, These probable interaction-pairs are then tabulated and the consensus is compared with these "interaction maps". Missing or wrong interactions in the consensus are repaired accordingly by introducing appropriate changes in amino acids which minimize unfavorable interactions.

Identification of Structural Sub-elements

Structural sub-elements are stretches of amino acid residues within a protein/(poly)peptide which correspond to a defined structural or functional part of the molecule. These can be loops (e.g. CDR loops of an antibody) or any other secondary or functional structure within the protein/(poly) peptide (domains, α-helices, β-sheets, framework regions of antibodies, etc.). A structural sub-element can be identified using known structures of similar or homologous (poly) peptides; or by using the above mentioned matrices of aligned amino acid sequences. Here the variability at each position is the basis for determining stretches of amino acid residues which belong to a structural sub-element (e.g. hypervariable regions of an antibody).

Sub-sequence

A sub-sequence is defined as a genetic module which is flanked by unique cleavage sites and encodes at least one structural sub-element. It is not necessarily identical to a structural sub-element.

Cleavage Site

A short DNA sequence which is used as a specific target for a reagent which cleaves DNA in a sequence-specific manner (e.g. restriction endonucleases).

Compatible Cleavage Sites

Cleavage sites are compatible with each other, if they can be efficiently ligated without modification and, preferably, also without adding an adapter molecule.

Unique Cleavage Sites

A cleavage site is defined as unique if it occurs only once in a vector containing at least one of the genes of interest, or if a vector containing at least one of the genes of interest could be treated in a way that only one of the cleavage sites could be used by the cleaving agent.

Corresponding (poly)Peptide Sequences

Sequences deduced from the same part of one group of homologous proteins are called corresponding (poly)peptide sequences.

Common Cleavage Sites

A cleavage site in at least two corresponding sequences, which occurs at the same functional position (i.e. which flanks a defined subsequence), which can be hydrolyzed by the same cleavage tool and which yields identical compatible ends is termed a common cleavage site.

Excising Genetic Sub-sequences

A method which uses the unique cleavage sites and the corresponding cleavage reagents to cleave the target DNA at the specified positions in order to isolate, remove or replace the genetic sub-sequence flanked by these unique cleavage sites.

Exchanging Genetic Sub-sequences

A method by which an existing sub-sequence is removed using the flanking cleavage sites of this sub-sequence, and a new sub-sequence or a collection of sub-sequences, which contain ends compatible with the cleavage sites thus created, is inserted.

Expression of Genes

The term expression refers to in vivo or in vitro processes, by which the information of a gene is transcribed into mRNA and then translated into a protein/(poly)peptide. Thus, the term expression refers to a process which occurs inside cells, by which the information of a gene is transcribed into mRNA and then into a protein. The term expression also includes all events of post-translational modification and transport, which are necessary for the (poly)peptide to be functional.

Screening of Protein/(poly)peptide Libraries

Any method which allows isolation of one or more proteins/(poly)peptides having a desired property from other proteins/(poly)peptides within a library.

Amino Acid Pattern Characteristic for a Species

A (poly)peptide sequence is assumed to exhibit an amino acid pattern characteristic for a species if it is deduced from a collection of homologous proteins from just this species.

Immunoglobulin Superfamily (IgSF)

The IgSF is a family of proteins comprising domains being characterized by the immunoglobulin fold. The IgSF comprises for example T-cell receptors and the immunoglobulins (antibodies).

Antibody Framework

A framework of an antibody variable domain is defined by Kabat et al. (1991) as the part of the variable domain which serves as a scaffold for the antigen binding loops of this variable domain.

Antibody CDR

The CDRs (complementarity determining regions) of an antibody consist of the antigen binding loops, as defined by Kabat et al. (1991). Each of the two variable domains of an antibody Fv fragment contain three CDRs.

HuCAL

Acronym for Human Combinatorial Antibody Library. Antibody Library based on modular consensus genes according to the invention (see Example 1).

Antibody Fragment

Any portion of an antibody which has a particular function, e.g. binding of antigen. Usually, antibody fragments are smaller than whole antibodies. Examples are Fv, disulphide-linked Fv, single-chain Fv (scFv), or Fab fragments. Additionally, antibody fragments are often engineered to include new functions or properties.

Universal Framework

One single framework which can be used to create the full variability of functions, specificities or properties which is originally sustained by a large collection of different frameworks, is called universal framework.

Binding of an Antibody to its Target

The process which leads to a light and specific association between an antibody and a corresponding molecule or ligand is called binding. A molecule or ligand or any part of a molecukle or ligand which is recognized by an antibody is called the target.

Replacing Genetic Sub-sequences

A method by which an existing sub-sequence is removed using the flanking cleavage sites of this sub-sequence, and a new sub-sequence or collection of sub-sequences, which contains ends compatible with the cleavage sites thus created, is inserted.

Assembling of Genetic Sequences

Any process which is used to combine synthetic or natural genetic sequences in a specific manner in order to get longer genetic sequences which contain at least parts of the used synthetic or natural genetic sequences.

Analysis of Homologous Genes

The corresponding amino acid sequences of two or more genes are aligned to each other in a way which maximizes the correspondence between identical or similar amino acid residues at all positions. These aligned sequences are termed homologous if the percentage of the sum of identical and/or similar residues exceeds a defined threshold. This threshold is commonly regarded by those skilled in the art as being exceeded when at least 15 percent of the amino acids in the aligned genes are identical, and at least 30 percent are similar.

LEGENDS TO FIGURES AND TABLES

FIG. 1: Flow chart outlining the process of construction of a synthetic human antibody library based on consensus sequences.

FIGS. 2A–2G: Alignment of consensus sequences designed for each subgroup (amino acid residues are shown with their standard one-letter abbreviation). (2A–2B) (SEQ ID NOS 28–31, respectively) kappa sequences, (2C–2D) (SEQ ID NOS 32–34, respectively) lambda sequences and (2E–2G) (SEQ ID NOS 35–41, respectively), heavy chain sequences. The positions are numbered according to Kabat (1991). In order to maximize homology in the alignment, gaps (−) have been introduced in the sequence at certain positions.

FIGS. 3A–3K: Gene sequences (SEQ ID NOS 42, 44, 46 and 48, respectively) of the synthetic V kappa consensus genes. The corresponding amino acid sequences (SEQ ID NOS 43, 45, 47 and 49, respectively) (see FIGS. 2A–2B) as well as the unique cleavage sites are also shown.

FIGS. 4A–4I: Gene sequences (SEQ ID NOS 50, 52 and 54, respectively) of the synthetic V lambda consensus genes. The corresponding amino acid sequences (SEQ ID NOS 51, 53 and 55, respectively) (see FIGS. 2C–2D) as well as the unique cleavage sites are also shown.

FIGS. 5A–5U: Gene sequences (SEQ ID NOS 56, 58, 60, 62, 64, 66 and 68, respectively) of the synthetic V heavy chain consensus genes. The corresponding amino acid sequences (SEQ ID NOS 57, 59, 61, 63, 65, 67 and 69, respectively) (see FIGS. 2E–2G) as well as the unique cleavage sites are also shown.

FIGS. 6A–6G: Oligonucleotides (SEQ ID NOS 70–164, respectively) used for construction of the consensus genes. The oligos are named according to the corresponding consensus gene, e.g. the gene Vκ1 was constructed using the six oligonucleotides O1K1 to O1K6. The oligonucleotides used for synthesizing the genes encoding the constant domains Cκ (OCLK1 to 8) and CH1 (OCH1 to 8) are also shown.

FIGS. 7A–7D: Sequences of the synthetic genes (SEQ ID NOS 165 and 167, respectively) encoding the constant domains Cκ (7A–7B) and CH1(7C–7D). The corresponding amino acid sequences (SEQ ID NOS 166 and 168, respectively) as well as unique cleavage sites introduced in these genes are also shown.

FIGS. 7E–7H: Functional map and sequence (SEQ ID NOS 169–170, respectively) of module M24 comprising the synthetic Cλ gene segment (huCL lambda).

FIGS. 7I–7J: Oligonucleotides (SEQ ID NOS 171–176) used for synthesis of module M24.

FIGS. 8A–8E: Sequence (SEQ ID NOS 177–178, respectively) and restriction map of the synthetic gene encoding the consensus single-chain fragment VH3-Vκ2. The signal sequence (amino acids 1 to 21) was derived from the E. coli phoA gene (Skerra & Plückthun, 1988). Between the phoA signal sequence and the VH3 domain, a short sequence stretch encoding 4 amino acid residues (amino acid 22 to 25) has been inserted in order to allow detection of the single-chain fragment in Western blot or ELISA using the monoclonal antibody M1 (Knappik & Plückthun, 1994) The last 6 basepairs of the sequence were introduced for cloning purposes (EcoRI site).

Figure 9:
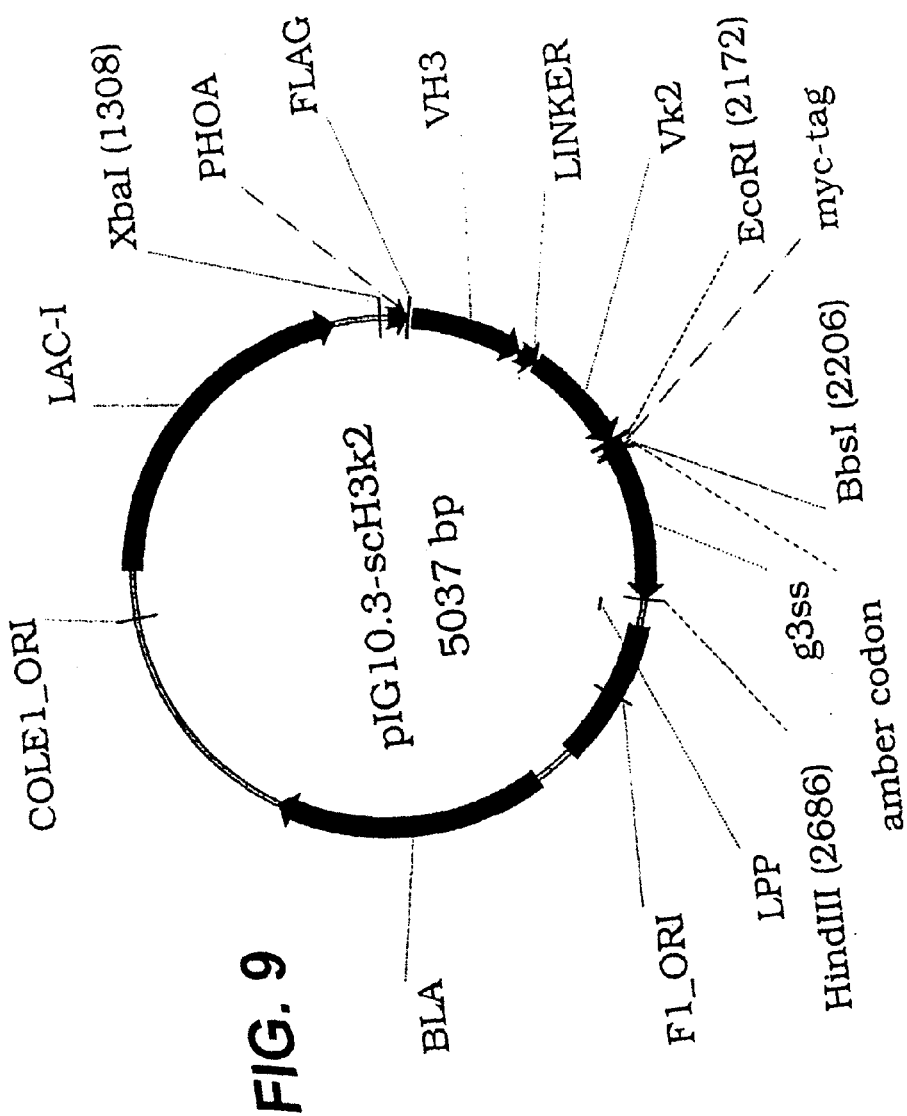

FIG. 9: Plasmid map of the vector pIG10.3 used for phage display of the H3κ2 scFv fragment. The vector is derived from pIG10 and contains the gene for the lac operon repressor, lac, the artificial operon encoding the H3κ2-gene3ss fusion under control of the lac promoter, the lpp terminator of transcription, the single-strand replication origin of the E. coli phage 11 (F1_ORI), a gene encoding β-lactamase (bla) and the ColEI derived origin of replication.

FIGS. 10A–10B: Sequencing results of independent clones from the initial library, translated into the corresponding amino acid sequences. (A) (SEQ ID NO: 179) Amino acid sequence of the VH3 consensus heavy chain CDR3 (position 93 to 102, Kabat numbering). (B) (SEQ ID NOS 180–191, respectively) Amino acid sequences of 12 clones of the 10-mer library. (C) (SEQ ID NOS 192–202, respectively) Amino acid sequences of 11 clones of the 15-mer library, *: single base deletion.

Figure 11:
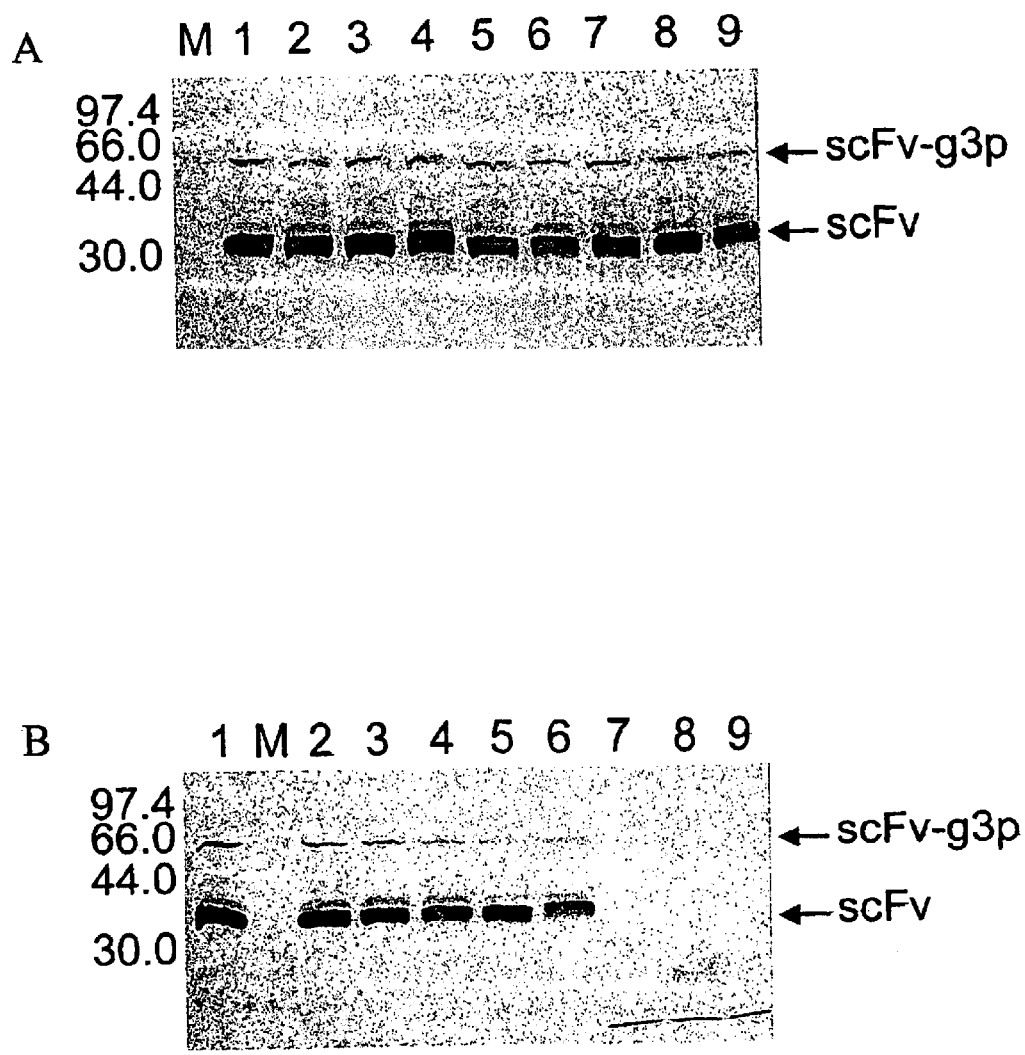

FIG. 11: Expression test of individual library members. (A) Expression of 9 independent clones of the 10-mer library. (B) Expression of 9 independent clones of the 15-mer library. The lane designated with M contains the size marker. Both the gp3-scFv fusion and the scFv monomer are indicated.

Figure 12:
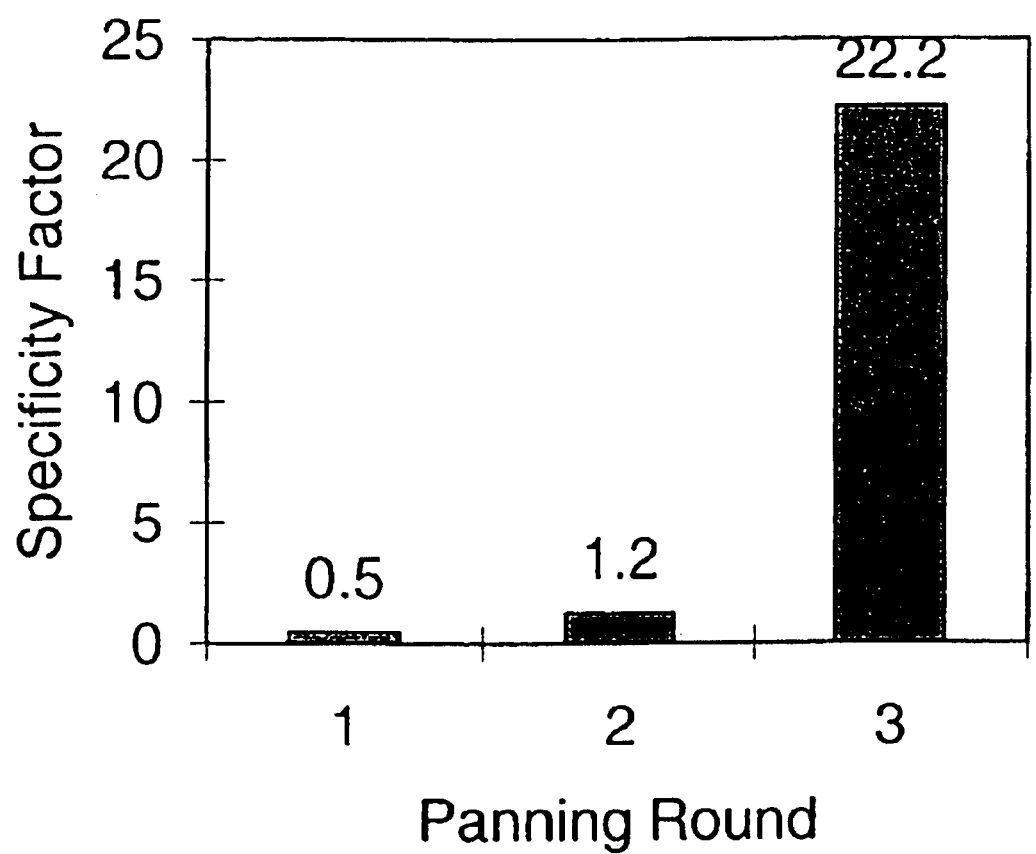

FIG. 12: Enrichment of specific phage antibodies during the panning against FITC-BSA. The initial as well as the subsequent fluorescein-specific sub-libraries were panned against the blocking buffer and the ratio of the phage eluted from the FITC-BSA coated well vs. that from the powder milk coated well from each panning round is presented as the "specificity factor".

Figure 13:
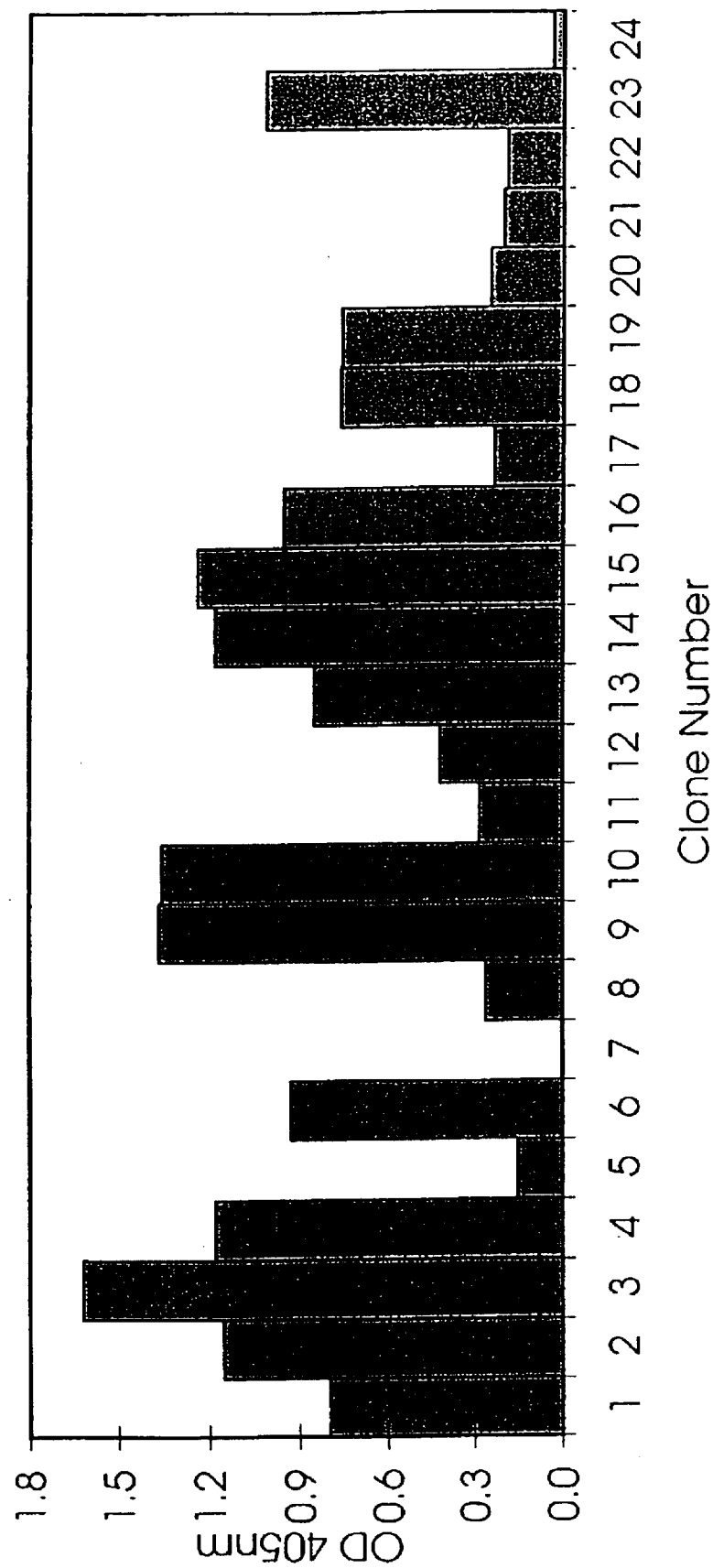

FIG. 13: Phage ELISA of 24 independent clones after the third round of panning tested for binding on FITC-BSA.

Figure 14:
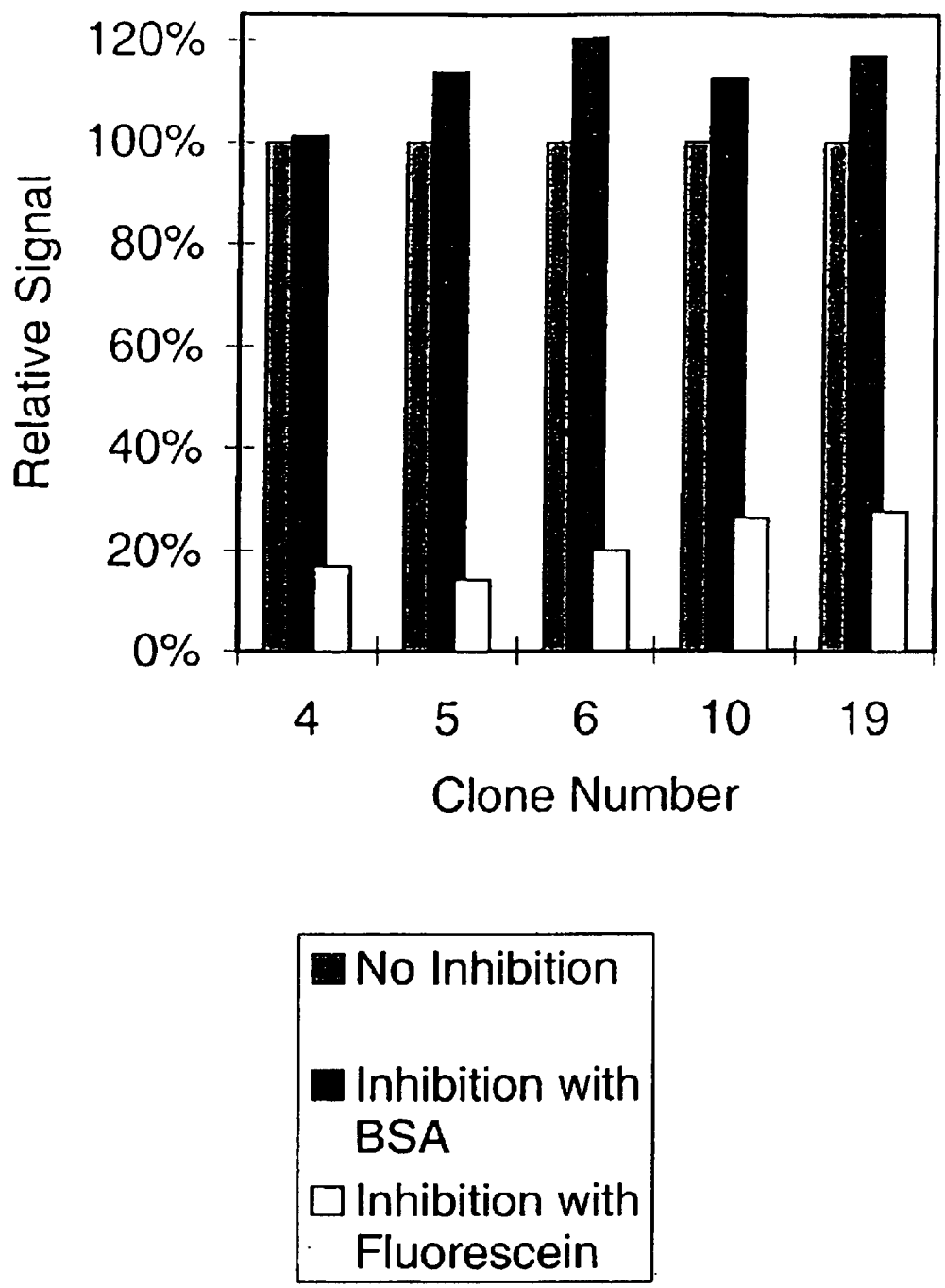

FIG. 14: Competition ELISA of selected FITC-BSA binding clones. The ELISA signals ($OD_{405nm}$) of scFv binding without inhibition are taken as 100%.

FIG. 15: Sequences results of the heavy chain CDR3s of independent clones after 3 rounds of planning against FITC-BSA, translated into the corresponding amino acid sequences (SEQ ID NOS 203–218, respectively) (position 93 to 102. Kabat numbering).

Figure 16:
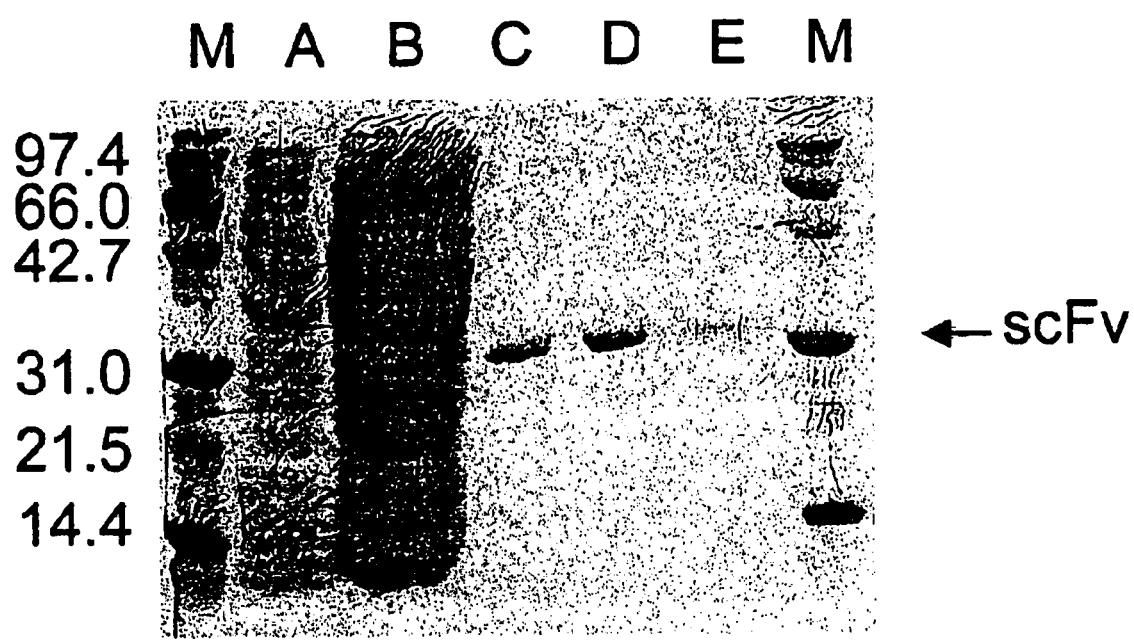

FIG. 16: Coomassie-Blue stained SDS-PAGE of the purified anti-fluorescein scFv fragments: M: molecular weight marker, A: total soluble cell extract after induction, B: fraction of the flow-through, C, D and E: purified scFv fragments 1HA-3E4, 1HA-3E5 and 1HA-3E10, respectively.

Figure 17:
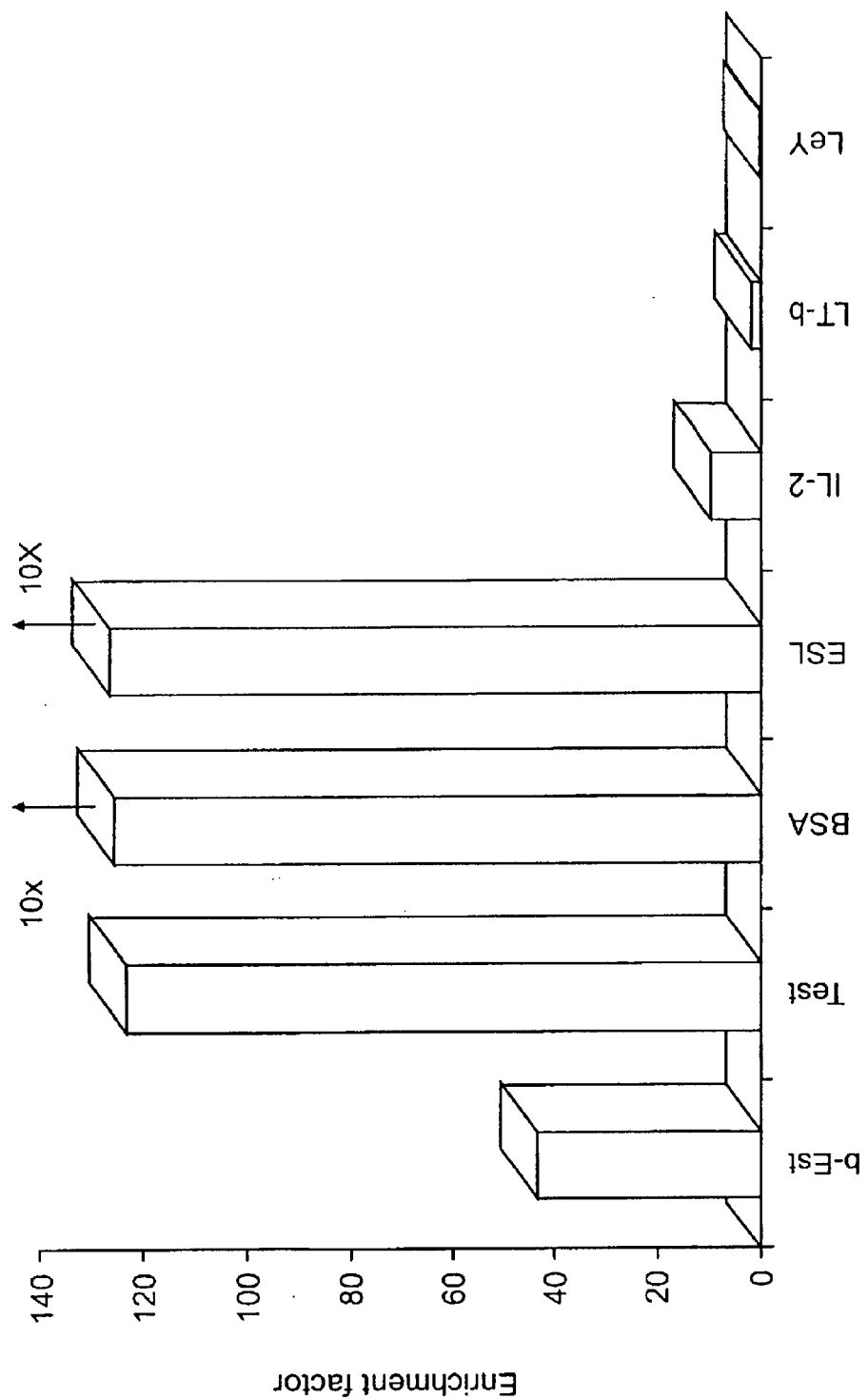

FIG. 17: Enrichment of specific phage antibodies during the panning against β-estradiol-BSA, testosterone-BSA, BSA, ESL-1, inlerleukin-2, lymphotoxin-β, and LeY-BSA after three rounds of panning.

Figure 18:
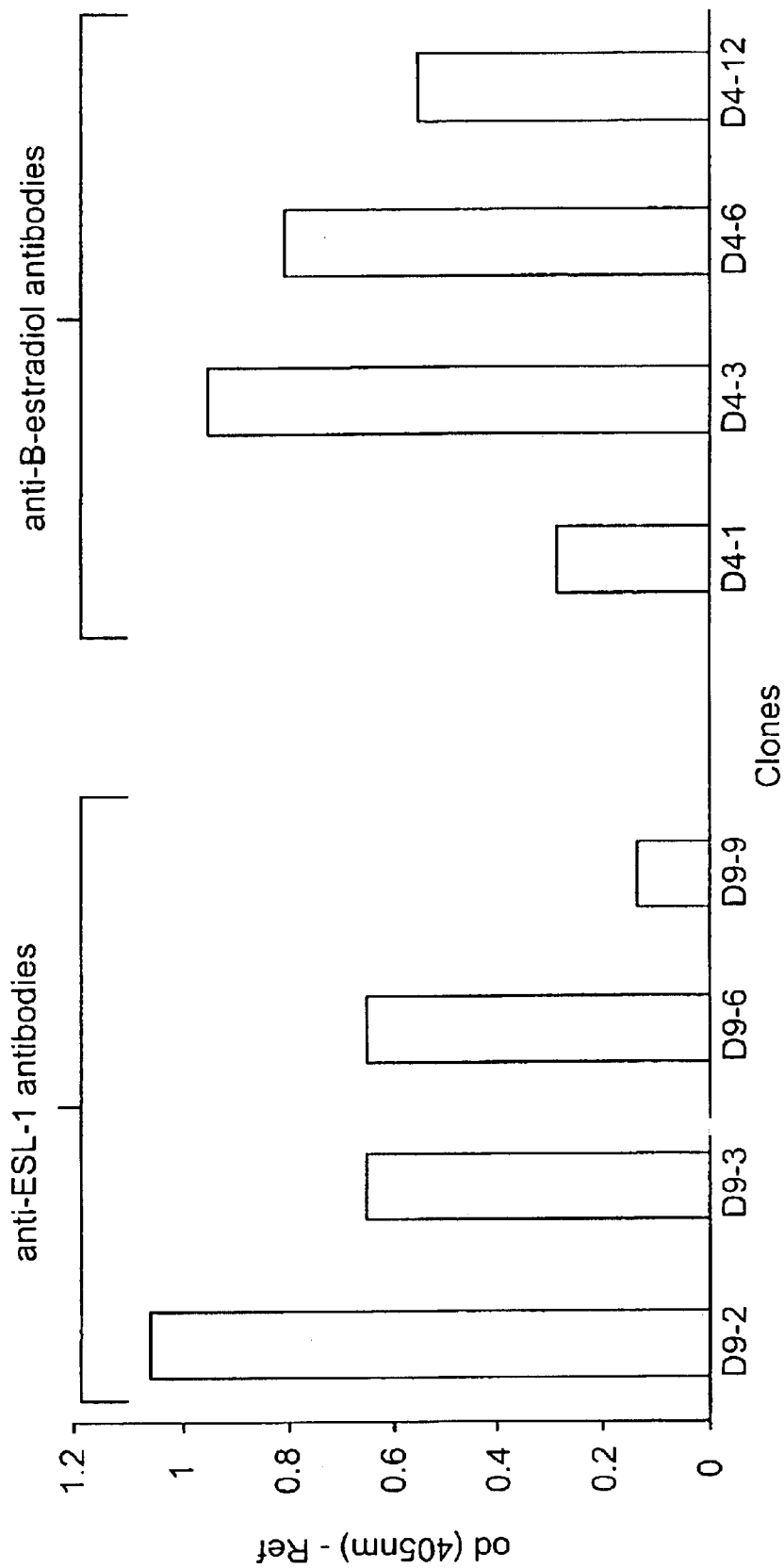

FIG. 18: ELISA of selected ESL-1 and β-estradiol binding clones

Figure 19:
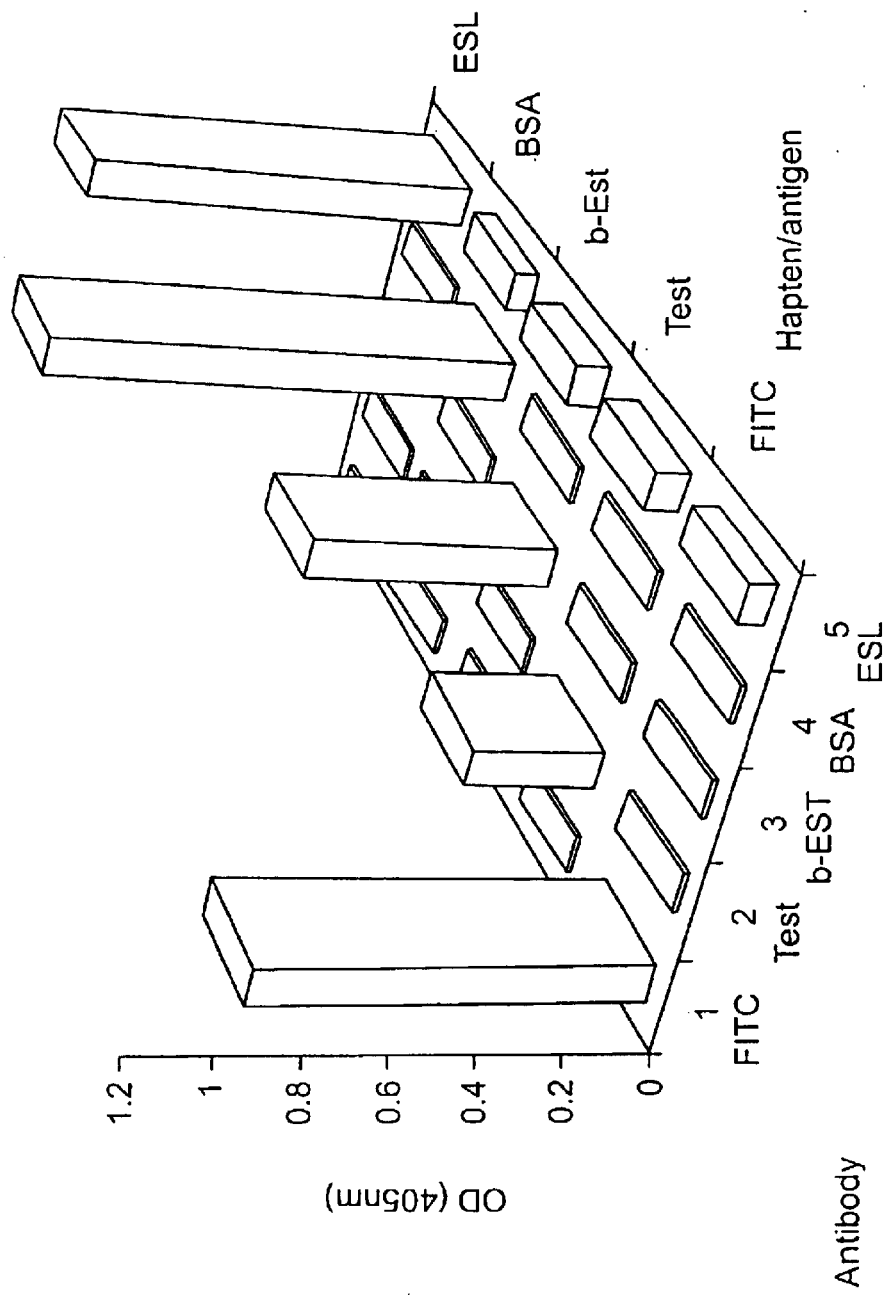

FIG. 19: Selectivity and cross-reactivity of HuCAL antibodies: in the diagonal specific binding of HuCAL antibodies can be seen, off-diagonal signals show non-specific cross-reactivity.

Figure 20:
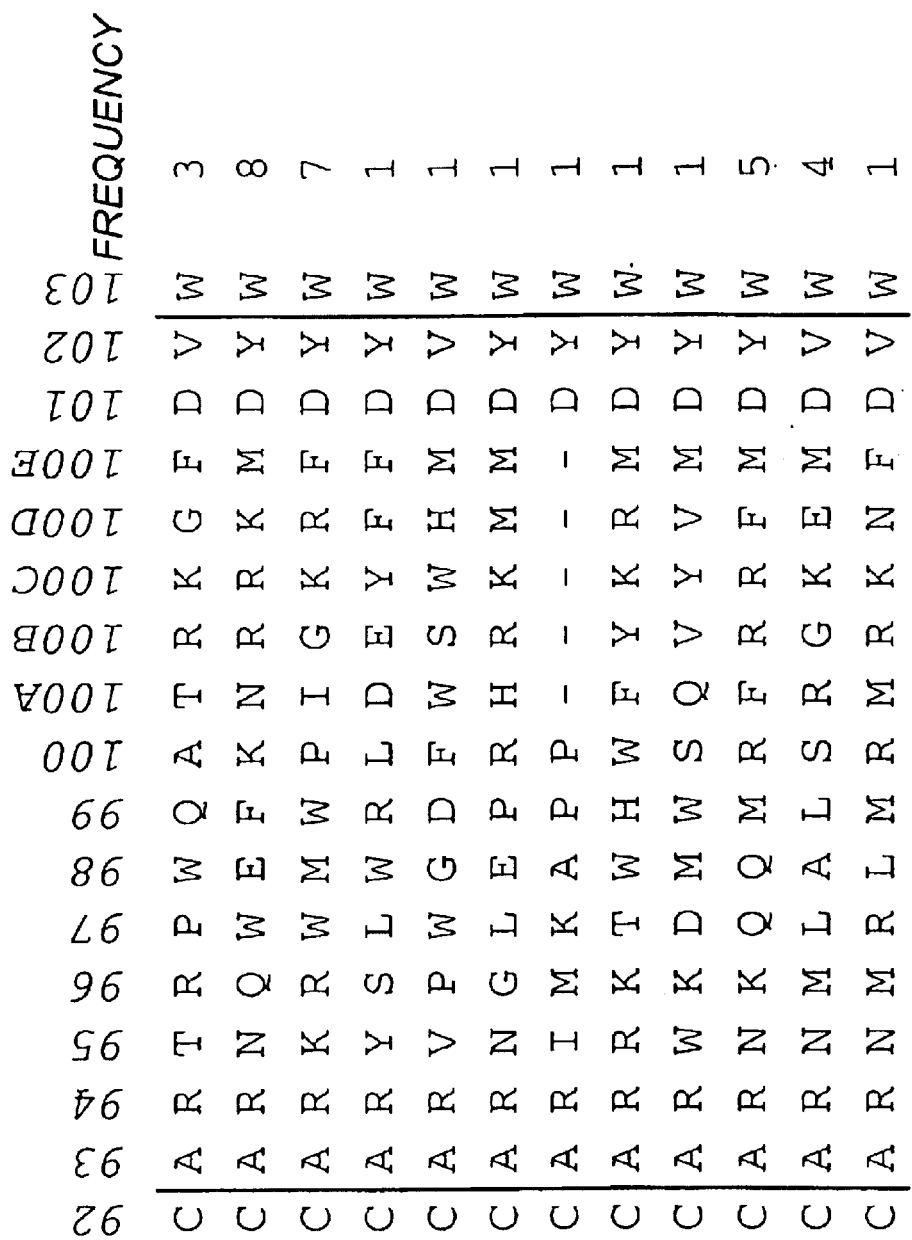

FIG. 20: Sequencing results of the heavy chain CDR3s of independent clones after 3 rounds of panning against β-estradiol-BSA, translated into the corresponding amino acid sequences (SEQ ID NOS 219–230 respectively) (position 93 to 102, Kabat numbering). One clone is derived from the 10 mer library.

Figure 21:
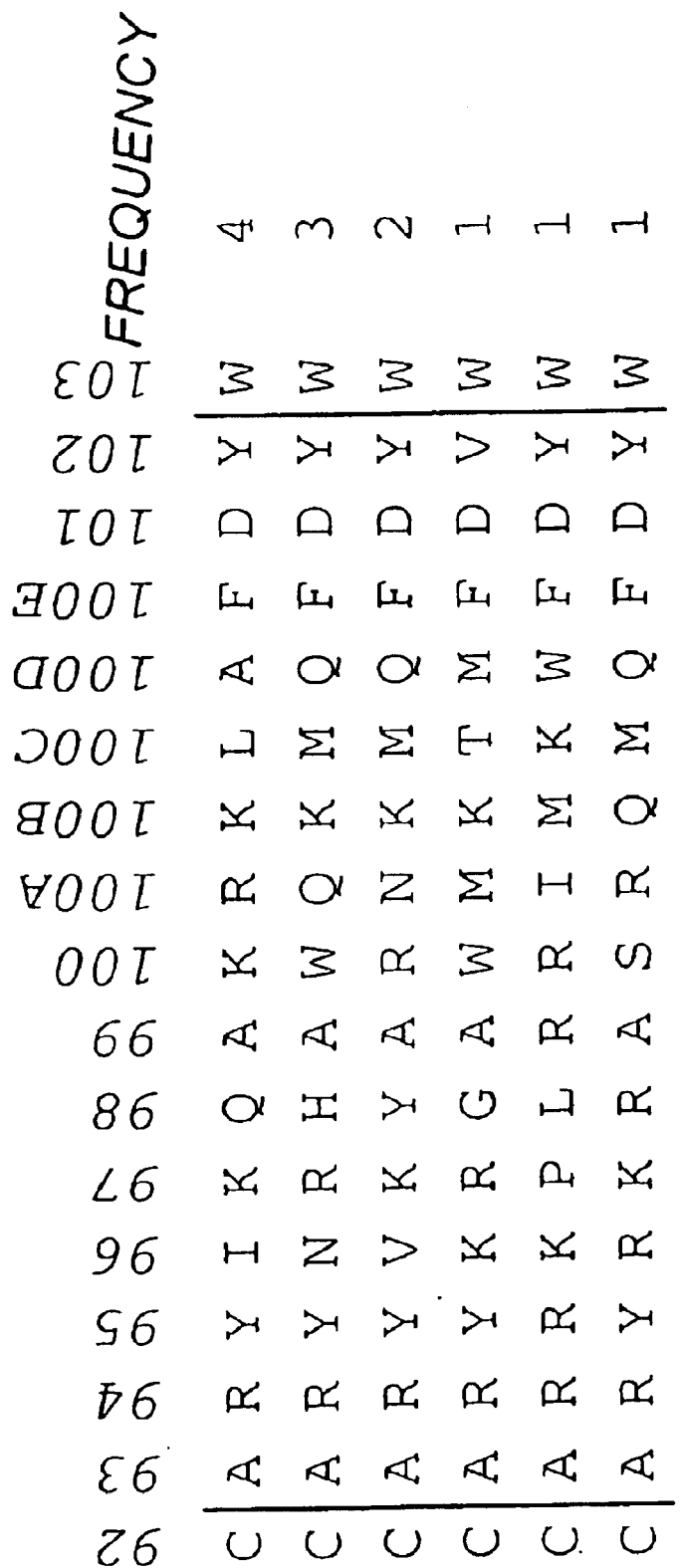

FIG. 21: Sequencing results of the heavy chain CDR3s of independent clones after 3 rounds of panning against testosterone-BSA, translated into the corresponding amino acid sequences (SEQ ID NOS 231–236, respectively) (position 93 to 102, Kabat numbering).

FIG. 22: Sequencing results of the heavy chain CDR3s of independent clones after 3 rounds of panning against lymphotoxin-β, translated into the corresponding amino acid sequences (SEQ ID NOS 237–244, respectively) (position 93 to 102, Kabat numbering). One clone comprises a 14 mer CDR, presumably introduced by incomplete coupling of the trinucleolide mixture during oligonucleotide synthesis.

FIG. 23: Sequencing results of the heavy chain CDR3s of independent clones after 3 rounds of panning agains ESL-1, translated into the corresponding amino acid sequences (SEQ ID NOS 245–256, respectively) (position 93 to 102, Kabat numbering). Two clones are derived from the 10 mer library. One clone comprises a 16 mer CDR, presumably introduced by chain elongation during oligonucleotide synthesis using trinucleotides.

Figure 24:
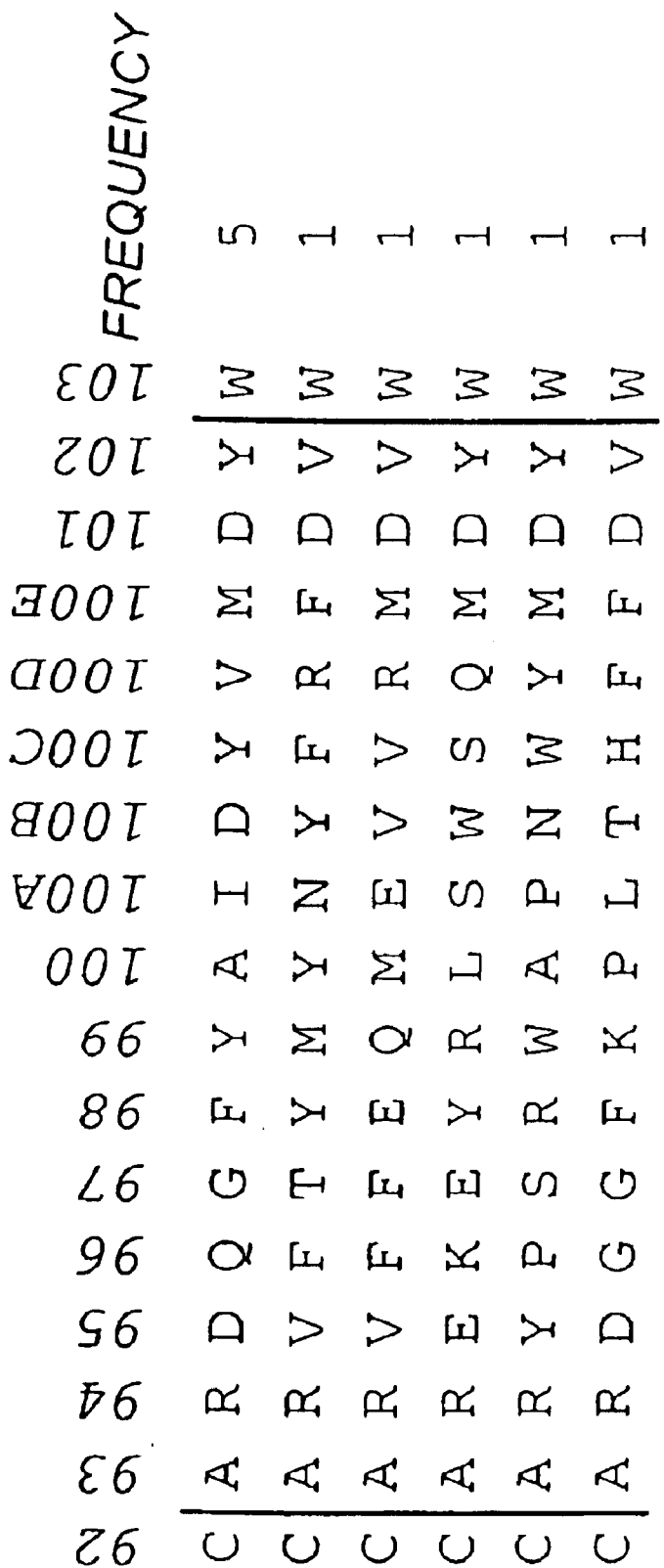

FIG. 24: Sequencing results of the heavy chain CDR3s of independent clones after 3 rounds of panning against BSA, translated into the corresponding amino acid sequences (SEQ ID NOS 257–262, respectively) (position 93 to 102, Kabat numbering).

Figure 25A:
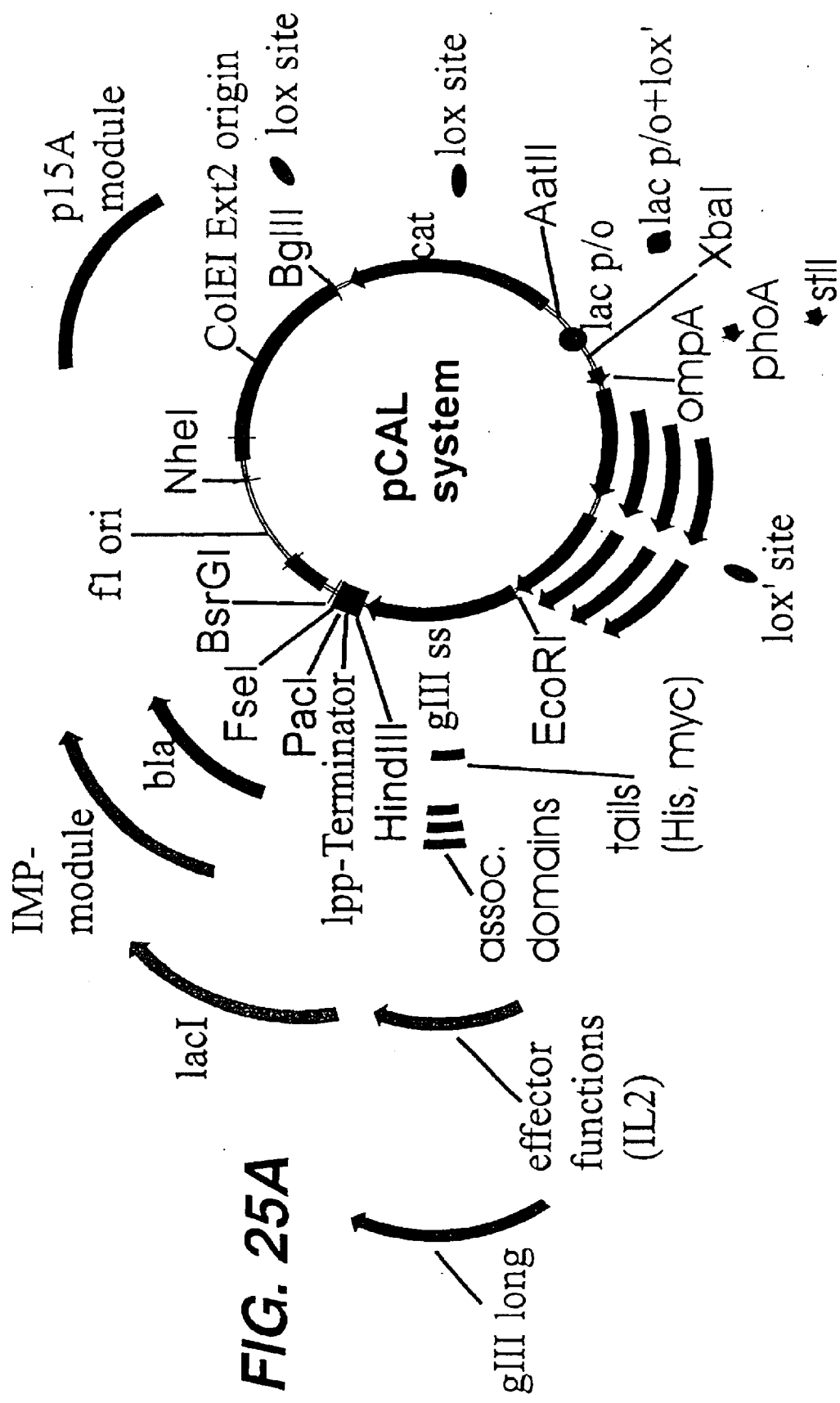

FIG. 25A: Schematic representation of the modular pCAL vector system.

FIGS. 25B–25C: List of restriction sites already used in or suitable for the modular HuCAL genes and pCAL vector system.

FIG. 26: List of the nodular vector elements for the pCAL vector series: shown are only those restriction sites which are part of the modular system.

Figure 27A:
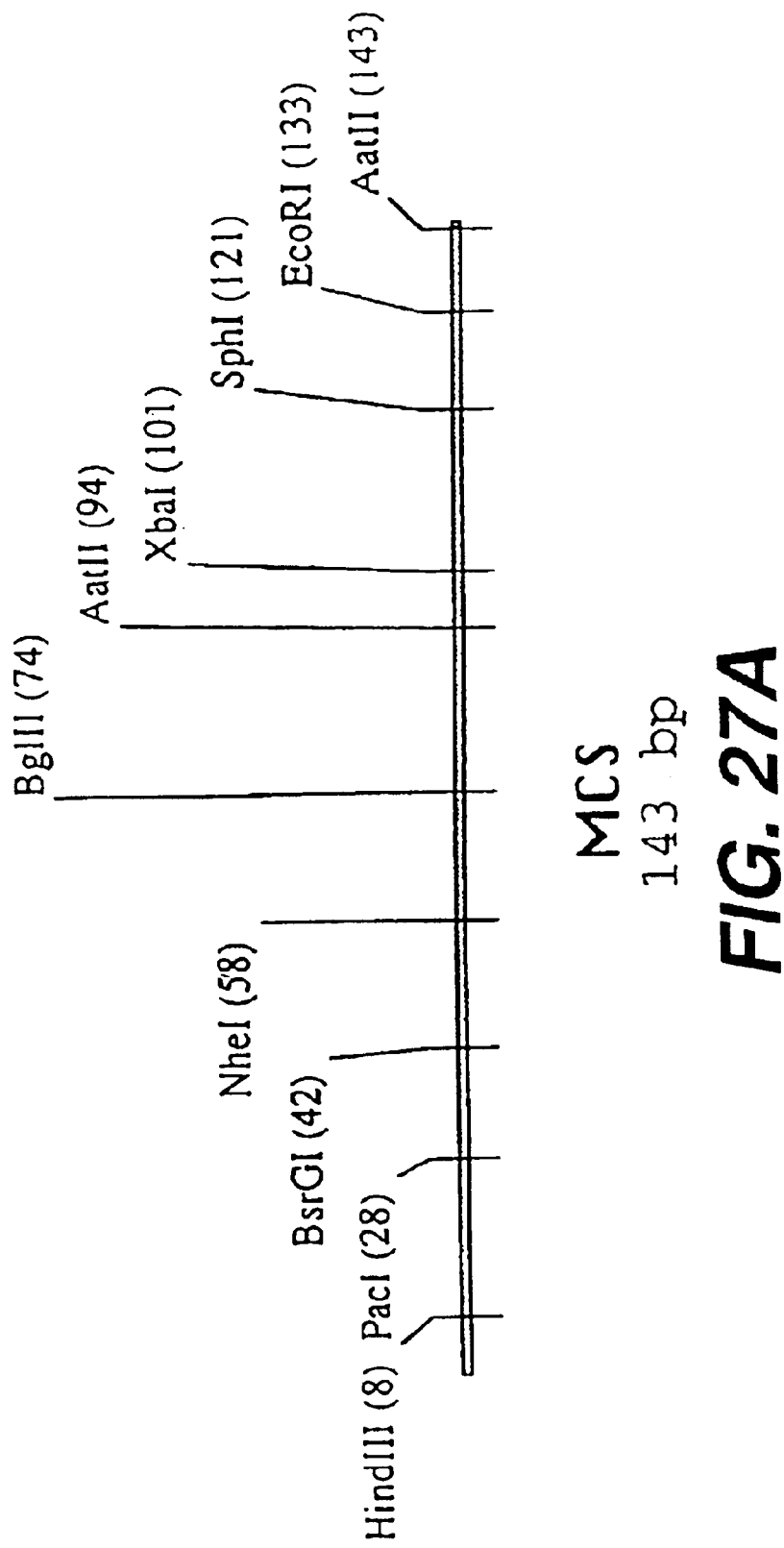
Figure 28A:
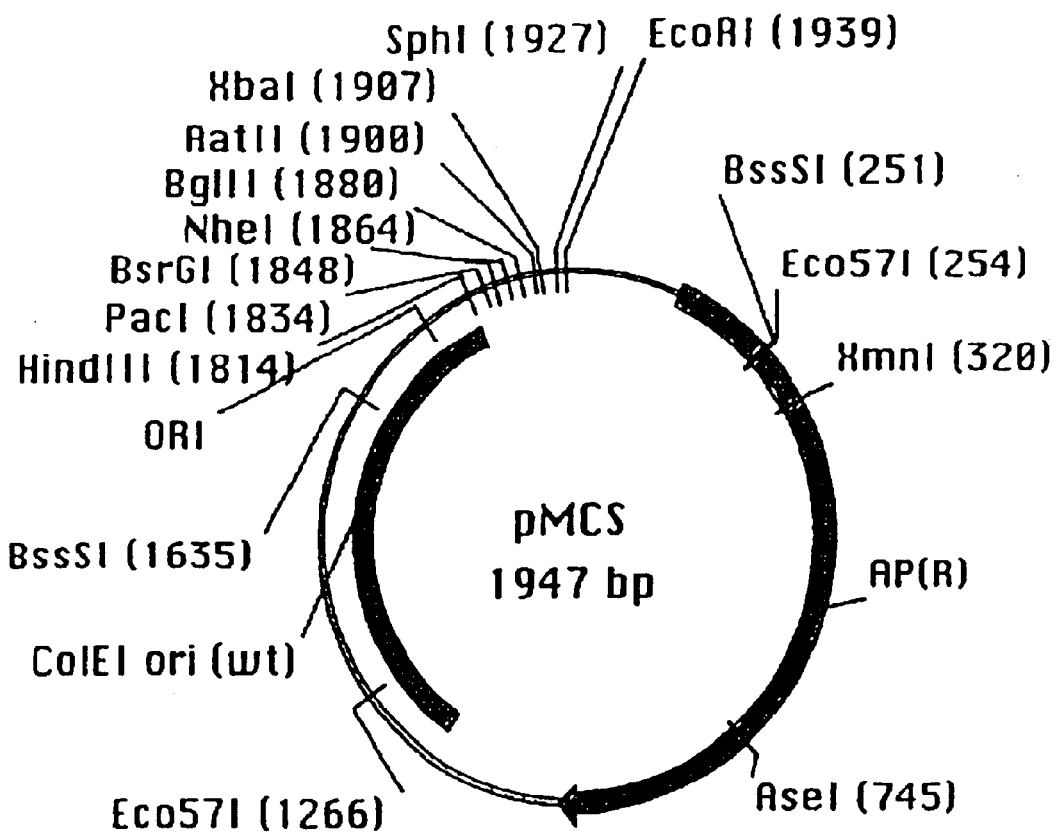

FIGS. 27A–27B: Functional map and sequence (SEQ ID NO: 263) of the multi-cloning site module (MCS).

FIGS. 28A–28G: Functional map and sequence (SEQ ID NO: 264–265, respectively) of the pMCS cloning vector series.

Figure 29A:
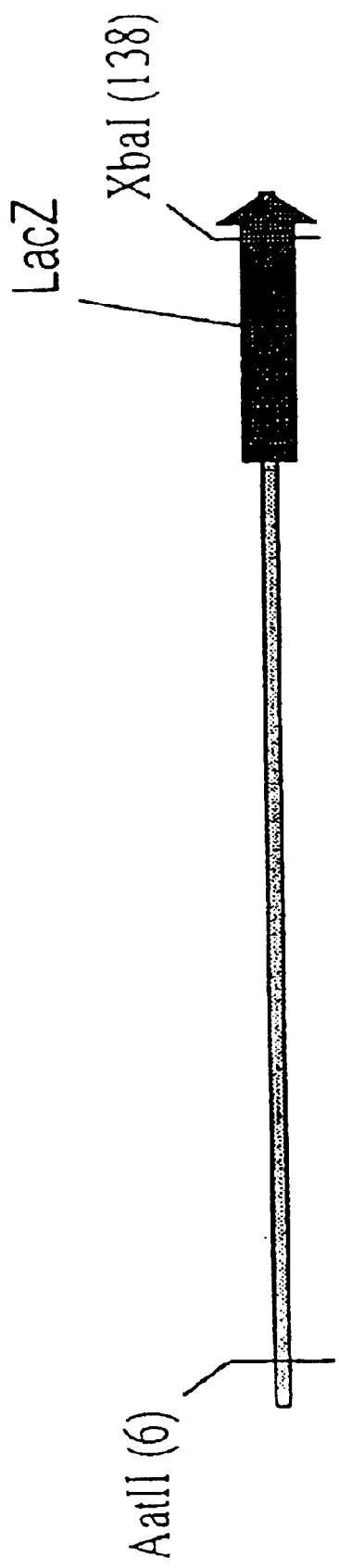

FIGS. 29A–29B: Functional map and sequence (SEQ ID NO: 266) of the pCAL module M1 (see FIGS. 26A–26D).

Figure 30A:
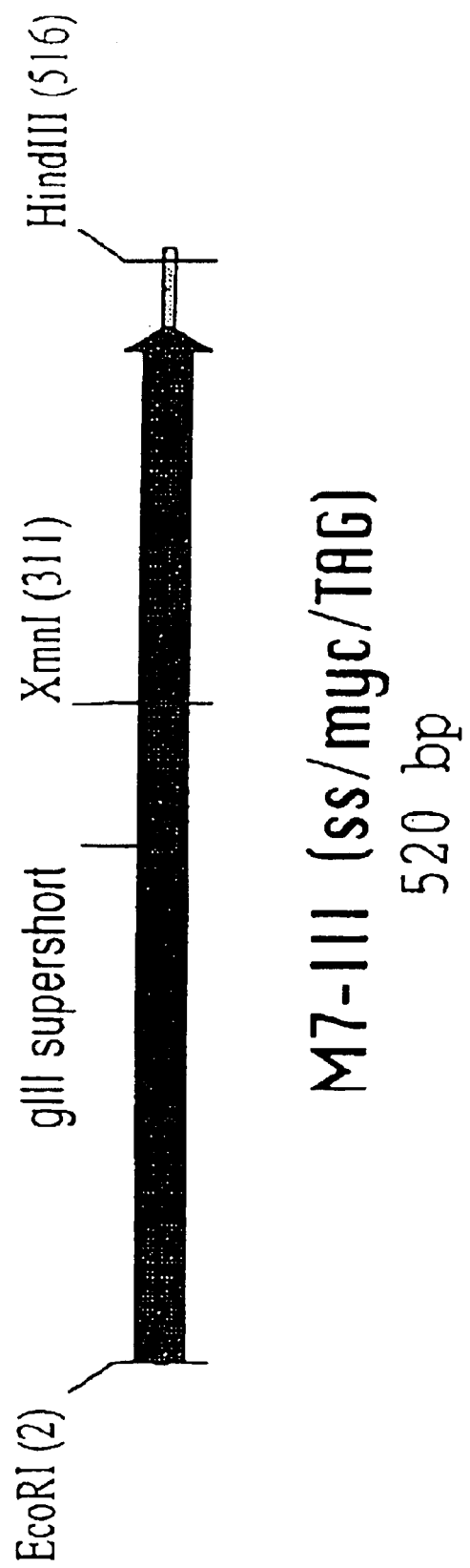

FIGS. 30A–30C: Functional map and sequence (SEQ ID NOS 267–268, respectively) of the pCAL module M7-III (see FIGS. 26A–26D).

Figure 31A:
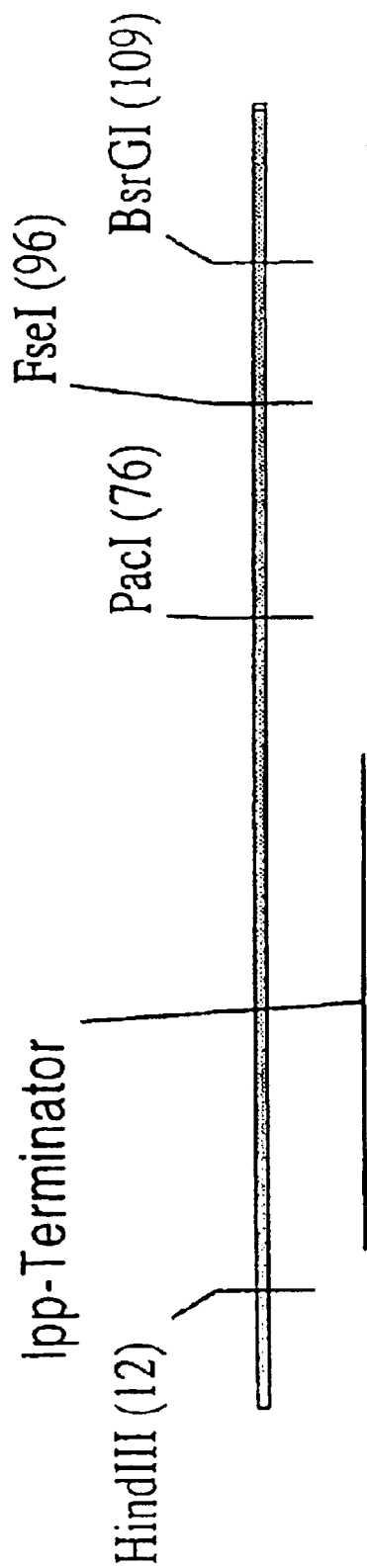
Figure 33A:
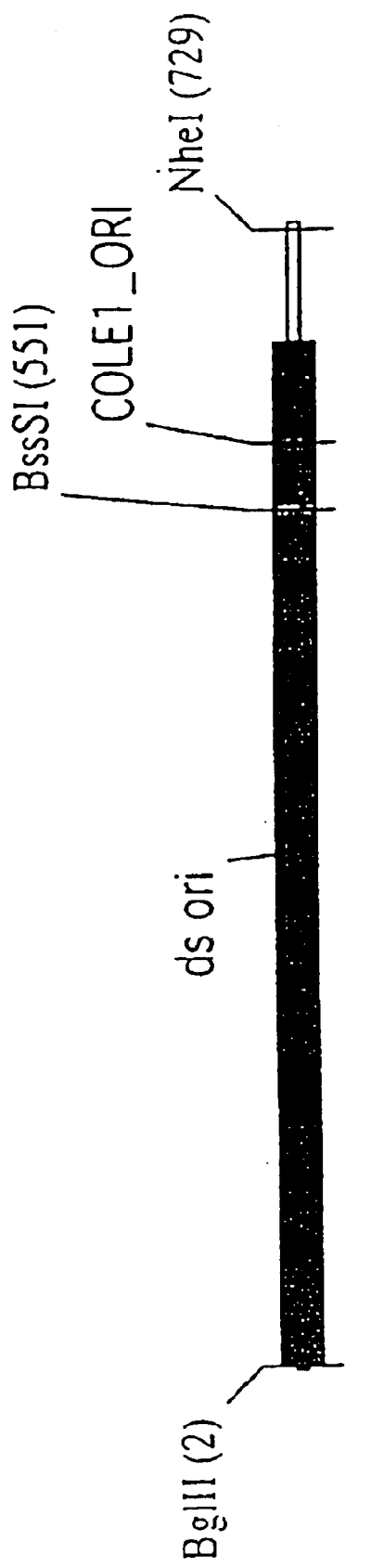
Figure 34A:
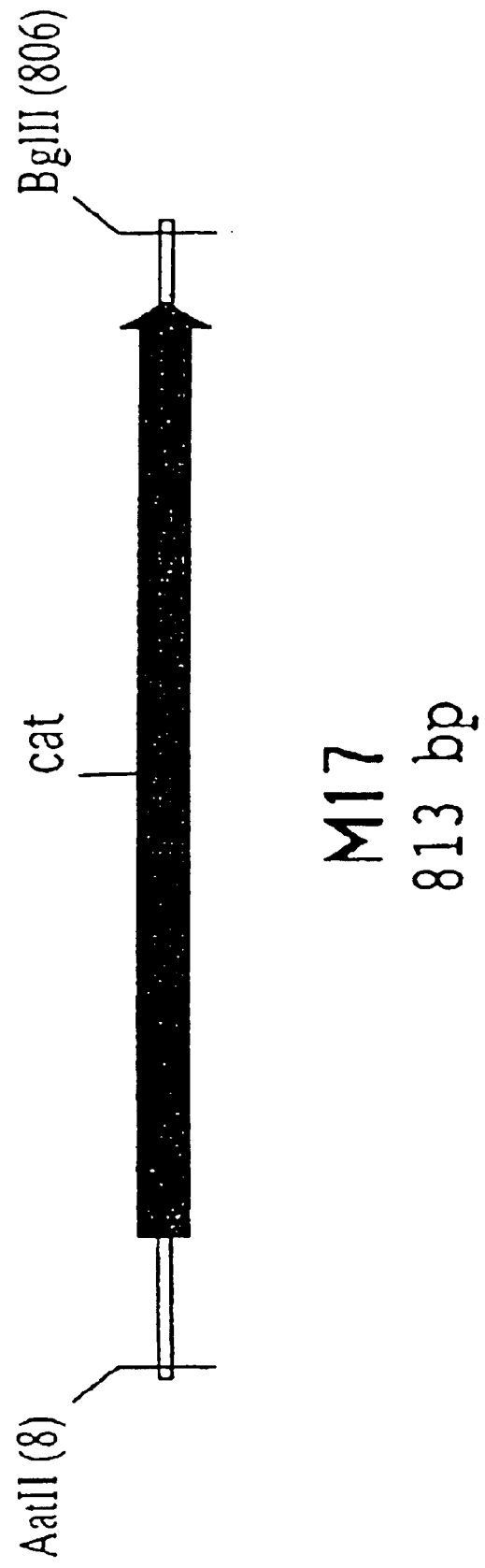

FIGS. 31A–31B: Functional map and sequence (SEQ ID NO: 269) of the pCAL module M9-II (see FIGS. 26A–26D).

FIGS. 32A–32C: Functional map and sequence (SEQ ID NO: 270) of the pCAL module M11-II (see FIGS. 26A–26D).

FIGS. 33A–33D: Functional map and sequence (SEQ ID NO: 271) of the pCAL module M14-Ext2 (see FIGS. 26A–26D).

FIGS. 34A–34D: Functional map and sequence (SEQ IO NOS 272–273, respectively) of the pCAL module M17 (see FIGS. 26A–26D).

FIGS. 35A–35I: Functional map and sequence (SEQ ID NOS 274–276, respectively) module vector pCAL4.

FIGS. 35J–35XXX: Functional maps and sequences (SEQ ID NOS 277–300, respectively) of additional pCAL modules (M2, M3, M7I, M7II, M8, M10II, M11II, M12, M13, M19, M20, M21, M41) and of low-copy number plasmid vectors (pCALO1 to pCALO3).

FIGS. 35YYY–35CCCC: List of oligonucleotides and primers (SEQ ID NOS 301–360, respectively) used for synthesis of pCAL vector modules.

FIGS. 36A–36F: Functional map and sequence (SEQ ID NOS 361–362, respectively) of the β-lactamase cassette for replacement of CDRs for CDR library cloning.

FIGS. 37A–37D: Oligo and primer (SEQ ID NOS 363–367, respectively) design for Vκ CDR3 libraries.

FIGS. 38A–38D: Oligo and primer (SEQ ID NOS 368–371, respectively) design for Vλ CDR3 libraries.

Figure 39:
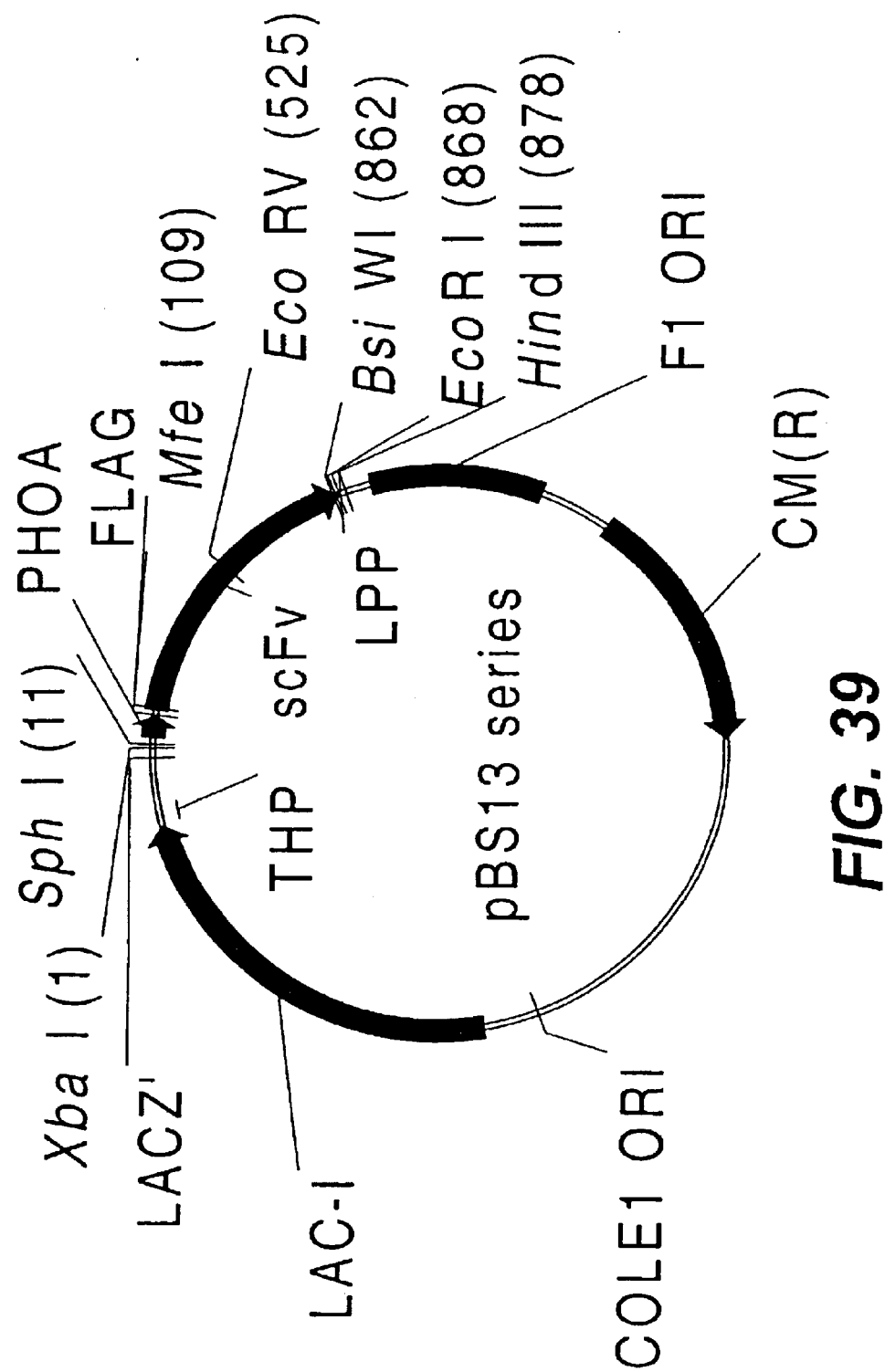

FIG. 39: Functional map of the pBS13 expression vector series.

FIGS. 40A–40B: Expression of all 49 HuCAL scFvs obtained by combining each of the 7 VH genes with each of the 7 VL genes (pBS 13, 30° C.): Values are given for the percentage of soluble vs. insoluble material, the total and the soluble amount compared to the combination H3P2, which was set to 100%. In addition, the corresponding values for the McPC603 scFv are given.

Table 1: Summary of human immunoglobulin germline sequences used for computing the germline membership of rearranged sequences. (A) kappa sequences, (B) lambda sequences and (C), heavy chain sequences. (1) The germline name used in the various calculations, (2) the references number for the corresponding sequence (see appendix for sequence related citations), (3) the family where each sequence belongs to and (4), the various names found in literature for germline genes with identical amino acid sequences.

Table 2: Rearranged human sequences used for the calculation of consensus sequences. (A) kappa sequences, (B) lambda sequences and (C), heavy chain sequences. The table summarized the name of the sequence (1), the length of the sequence in amino acids (2), the germline family (3) as well as the computed germline counterpart (4). The number of amino acid exchanges between the rearranged sequence and the germline sequence is tabulated in (5), and the percentage of different amino acids is given in (6). Column (7) gives the references number for the corresponding sequence (see appendix for sequence related citations).

Table 3: Assignment of rearranged V sequences lo their germline counterparts. (A) kappa sequences, (B) lambda sequences and (C), heavy chain sequences. The germline genes are tabulated according to their family (1), and the number of rearranged genes found for every germline gene is given in (2).

Table 4: Computation of the consensus sequence of the rearranged V kappa sequences. (A) (SEQ ID NO: 14), V kappa subgroup 1, (B) (SEQ ID NO: 15), V kappa subgroup 2, (C) (SEQ ID NO: 16), V kappa subgroup 3 and (D) (SEQ ID. NO: 17), V kappa subgroup 4. The number of each amino acid found at each position is tabulated together with the statistical analysis data. (1) Amino acids are given with their standard one-letter abbreviations (and B means D or N, Z means E or Q and X means any amino acid). The statistical analysis summarizes the number of sequences found at each position (2), the number of occurrences of the most common amino acid (3), the amino acid residue which is most common at this position (4), the relative frequency of the occurrence of the most common amino acid (5) and the number of different amino acids found at each position (6).

Table 5: Computation of the consensus sequence of the rearranged V lambda sequences. (A) (SEQ ID NO: 18), V lambda subgroup 1, (B) (SEQ ID NO: 19), V lambda subgroup 2, and (C) (SEO ID NO: 20), V lambda subgroup 3. The number of each amino acid found at each position is tabulated together with the statistical analysis of the data. Abbreviations are the same as in Table 4.

Table 6: Computation of the consensus sequence of the rearranged V heavy chain sequences. (A) (SEQ ID NO: 21), V heavy chain subgroup 1A, (B) (SEQ ID NO: 22), V heavy chain subgroup 1B. (C) (SEQ ID NO: 23), V heavy chain subgroup 2, (D) (SEQ ID NO: 24), V heavy chain subgroup 3, (E) (SEQ ID NO: 25), V heavy chain subgroup 4, (F) (SEQ ID NO: 26), V heavy chain subgroup 5, and (G) (SEQ ID NO: 27), V heavy chain subgroup 6. The number of each amino acid found at each position is tabulated together with the statistical analysis of the data. Abbreviations are the same as in Table 4.

EXAMPLES

Example 1

Design of a Synthetic Human Combinatorial Antibody Library (HuCAL)

The following example describes the design of a fully synthetic human combinatorial antibody library (HuCAL), based on consensus sequences of the human immunoglobulin repertoire, and the synthesis of the consensus genes. The general procedure is outlined in FIG. 1.

1.1 Sequence Database 1.1.1 Collection and Alignment of Human Immunoglobulin Sequences In a first step, sequences of variable domains of human immunoglobulins have been collected and divided into three sub bases: V heavy chain (VH), V kappa (Vκ) and V lambda (Vλ). For each sequence, the gene sequence was then translated into the corresponding amino acid sequence. Subsequently, all amino acid sequences were aligned according to Kabat et al. (1991). In the case of Vλ sequences, the numbering system of Chuchana et al. (1990) was used. Each of the three main databases was then divided into two further sub bases: the first sub base contained all sequences derived from rearranged V genes, where more than 70 positions of the sequence were known. The second sub bass contained all germline gene segments (without the D- and J-minigenes; pseudogenes with internal stop codons were also removed). In all cases, where germline sequences with identical amino acid sequence but different names were found, only one sequence was used (see Table 1). The final databases of rearranged sequences contained 386, 149 and 674 entries for Vκ, Vλ and VH, respectively. The final databases of germline sequences contained 48, 26 and 141 entries for Vκ, Vλ and VH, respectively.

1.1.2 Assignment of Sequences to Subgroups

The sequences in the three germline databases where then grouped according to sequence homology (see also Tomlinson et al., 1992, Williams & Winter, 1993, and Cox et al., 1994). In the case of Vκ, 7 families could be established. Vλ was divided into 8 families and VH into 6 families. The VH germline genes of the VH7 family (Van Dijk et al., 1993) were grouped into the VH1 family, since the genes of the two families are highly homologous. Each family contained different numbers of germline genes, varying from 1 (for example VH6) to 47 (VH3).

1.2 Analysis of Sequences 1.2.1 Computation of Germline Membership

For each of the 1209 amino acid sequences in the databases of rearranged genes, the nearest germline counterpart, i.e. the germline sequence with the smallest number of amino acid differences was then calculated. After the germline counterpart was found, the number of somatic mutations which occurred in the rearranged gene and which ted to amino acid exchanges could be tabulated. In 140 cases, the germline counterpart could not be calculated exactly, because more than one germline gene was found with an identical number of amino acid exchanges. These rearranged sequences were removed from the database. In a few cases, the number of amino acid exchanges was found to be unusually large (>20 for VL and >25 for VH), indicating either heavily mutated rearranged genes or derivation from germline genes not present in the database. Since it was not possible to distinguish between these two possibilities, these sequences were also removed from the database. Finally, 12 rearranged sequences were removed from the database because they were found to have very unusual CDR lengths and composition or unusual amino acids at canonical positions (see below). In summary, 1023 rearranged sequences out of 1209 (85%) could be clearly assigned to their germline counterparts (see Table 2).

After this calculation, every rearranged gene could be arranged in one of the families established for the germline genes. Now the usage of each germline gene, i.e. the number of rearranged genes which originate from each germline gene, could be calculated (see Table 2). It was found that the usage was strongly biased towards a subset of germline genes, whereas most of the germline genes were not present as rearranged genes in the database and therefore apparently not used in the immune system (Table 3). This observation had already been reported in the case of Vκ (Cox, et al., 1994). All germline gene families, where no or only very few rearranged counterparts could be assigned, were removed from the database, leaving 4 Vκ, 3 Vλ, and 6 VH families.

1.2.2 Analysis of CDR Conformations

The conformation of the antigen binding loops of antibody molecules, the CDRs, is strongly dependent on both the length of the CDRs and the amino acid residues located at the so-called canonical positions (Chothia & Lesk, 1987). It has been found that only a few canonical structures exist, which determine the structural repertoire of the immunoglobulin variable domains (Chothia et al., 1989). The canonical amino acid positions can be found in CDR as well as framework regions. The 13 used germline families defined above (7 VL and 6 VH) were now analyzed for their canonical structures in order to define the structural repertoire encoded in these families.

In 3 of the 4 Vκ families (Vκ1, 2 and 4), one different type of CDR1 conformation could be defined for every family. The family Vκ3 showed two types of CDR1 conformation: one type which was identical to Vκ1 and one type only found in Vκ3. All Vκ CDR2s used the same type of canonical structure. The CDR3 conformation is not encoded in the germline gene segments. Therefore, the 4 Vκ families defined by sequence homology and usage corresponded also to 4 types of canonical structures found in Vκ germline genes.

The 3 Vλ families defined above showed 3 types of CDR1 conformation, each family with one unique type. The Vλ1 family contained 2 different CDR1 lengths (13 and 14 amino acids), but identical canonical residues, and it is thought that both lengths adopt the same canonical conformation (Chothia & Lesk, 1987). In the CDR2 of the used Vλ germlines, only one canonical conformation exists, and the CDR3 conformation is not encoded in the germline gene segments. Therefore, the 3 Vλ families defined by sequence homology and usage corresponded also to 3 types of canonical structures.

The structural repertoire of the human VH sequences was analyzed in detail by Chothia et al., 1992. In total, 3 conformations of CDR1 (H1-1, H1-2 and H1-3) and 6 conformations of CDR2 (H2-1, H2-2, H2-3, H2-4, H2-5 and H2-x) could be defined. Since the CDR3 is encoded in the D- and J-minigene segments, no particular canonical residues are defined for this CDR.

All the members of the VH1 family defined above contained the CDR1 conformation H1-1, but differed in their CDR2 conformation: the H2-2 conformation was found in 6 germline genes, whereas the conformation H2-3 was found in 8 germline genes. Since the two types of CDR2 conformations are defined by different types of amino acid at the framework position 72, the VH1 family was divided into two subfamilies: VH1A with CDR2 conformation H2-2 and VH1B with the conformation H2-3. The members of the VH2 family all had the conformations H1-3 and H2-1 in CDR1 and CDR2, respectively. The CDR1 conformation of the VH3 members was found in all cases to be H1-1, but 4 different types were found in CDR2 (H2-1, H2-3, H2-4 and H2-x). In these CDR2 conformations, the canonical framework residue 71 is always defined by an arginine. Therefore, it was not necessary to divide the VH3 family into subfamilies, since the 4 types of CDR2 conformations were defined solely by the CDR2 itself. The same was true for the VH4 family. Here, all 3 types of CDR1 conformations were found, but since the CDR1 conformation was defined by the CDR itself (the canonical framework residue 26 was found to be glycine in all cases), no subdivisions were necessary. The CDR2 conformation of the VH4 members was found to be H2-1 in all cases. All members of the VH5 family were found to have the conformation H1-1 and H2-2, respectively. The single germline gene of the VH6 family had the conformations H1-3 and H2-5 in CDR1 and CDR2, respectively.

In summary, all possible CDR conformations of the Vκ and Vλ genes were present in the 7 families defined by sequence comparison. From the 12 different CDR conformations found in the used VH germline genes, 7 could be covered by dividing the family VH1 into two subfamilies, thereby creating 7 VH families. The remaining 5 CDR conformations (3 in the VH3 and 2 in the VH4 family) were defined by the CDRs themselves and could be created during the construction of CDR libraries. Therefore, the structural repertoire of the used human V genes could be covered by 49 (7×7) different frameworks.

1.2.3 Computation of Consensus Sequences

The 14 databases of rearranged sequences (4 Vκ, 3 Vλ, and 7 VH) were used to compute the HuCAL consensus sequences of each subgroup (4 HuCAL-Vκ, 3 HuCAL-Vλ, 7 HuCAL-VH, see Table 4, 5 and 5). This was done by counting the number of amino acid residues used at each position (position variability) and subsequently identifying the amino acid residue most frequently used at each position. By using the rearranged sequences instead of the used germline sequences for the calculation of the consensus, the consensus was weighted according to the frequency of usage. Additionally, frequently mutated and highly conserved positions could be identified. The consensus sequences were cross-checked with the consensus of the germline families to see whether the rearranged sequences were biased at certain positions towards amino acid residues which do not occur in the collected germline sequences, but this was found not to be the case. Subsequently, the number of differences of each of the 14 consensus sequences to each of the germline sequences found in each specific family was calculated. The overall deviation from the most homologous germline sequence was found to be 2.4 amino acid residues (s.d.=2.7), ensuring that the "artificial" consensus sequences can still be considered as truly human sequences as far as immunogenicity is concerned.

1.3 Structural Analysis

So far, only sequence information was used to design the consensus sequences. Since it was possible that during the calculation certain artificial combinations of amino acid residues have been created, which are located far away in the sequence but have contacts to each other in the three dimensional structure, leading to destabilized or even mistolded frameworks, the 14 consensus sequences were analyzed according to their structural properties.

It was rationalized that all rearranged sequences present in the database correspond to functional and therefore correctly folded antibody molecules. Hence, the most homologous rearranged sequence was calculated for each consensus sequence. The positions where the consensus differed from the rearranged sequence were identified as potential "artificial residues" and inspected.

The inspection itself was done in two directions. First, the local sequence stretch around each potentially "artificial residue" was compared with the corresponding stretch of all the rearranged sequences. If this stretch was found to be truly artificial, i.e. never occurred in any of the rearranged sequences, the critical residue was converted into the second most common amino acid found at this position and analyzed again. Second, the potentially "artificial residues" were analyzed for their long range interactions. This was done by collecting all available structures of human antibody variable domains from the corresponding PDB files and calculating for every structure the number and type of interactions each amino acid residue established to each side-chain. These "interaction maps" were used to analyze the probable side-chain/side-chain interactions of the potentially "artificial residues". As a result of this analysis, the following residues were exchanged (given is the name of the gene, the position according to Kabat's numbering scheme, the amino acid found at this position as the most abundant one and the amino acid which was used instead):

VH2: $S_{65}T$

Vκ1: $N_{34}A$,

Vκ3: $G_9A$, $D_{60}A$, $R_{77}S$

Vκ3: $V_{78}T$

1.4 Design of CDR Sequences

The process described above provided the complete consensus sequences derived solely from the databases of rearranged sequences. It was rationalized that the CDR1 and CDR2 regions should be taken from the databases of used germline sequences, since the CDRs of rearranged and mutated sequences, are biased towards their particular antigens. Moreover, the germline CDR sequences are known to allow binding to a variety of antigens in the primary immune response, where only CDR3 is varied. Therefore, the consensus CDRs obtained from the calculations described above were replaced by germline CDRs in the case of VH and Vκ. In the case of Vλ, a few amino acid exchanges were introduced in some of the chosen germline CDRs in order to avoid possible protease cleavage sites as well as possible structural constraints.

The CDRs of following germline genes have been chosen:

| HuCAL gene | CDR1 | CDR2 |
|---|---|---|
| HuCAL-VH1A | VH1-12-1 | VH1-12-1 |
| HuCAL-VH1B | VH1-13-16 | VH1-13-6,-7,-8,-9 |
| HuCAL-VH2 | VH2-31-10,-11,-12,-13 | VH2-31-3,-4 |
| HuCAL-VH3 | VH3-13-8,-9,-10 | VH3-13-8,-9,-10 |
| HuCAL-VH4 | VH4-11-7 to -14 | VH4-11-8,-9,-11,-12,-14,-16 VH4-31-17,-18,-19,-20 |
| HuCAL-VH5 | VH5-12-1,-2 | VH5-12-1,-2 |
| HuCAL-VH6 | VH6-35-1 | VH6-35-1 |
| HuCAL-Vκ1 | Vκ1-14,-15 | Vκ1-2,-3,-4,-5,-7,-8,-12,-13, -18,-19 |
| HuCAL-Vκ2 | Vκ2-6 | Vκ2-6 |
| HuCAL-Vκ3 | Vκ3-1,-4 | Vκ3-4 |
| HuCAL-Vκ4 | Vκ4-1 | Vκ4-1 |
| HuCAL-Vλ1 | HUMLV117,DPL5 | DPL5 |
| HuCAL-Vλ2 | DPL11,DPL12 | DPL12 |
| HuCAL-Vλ3 | DPL23 | HUMLV318 |

In the case of the-CDR3s, any sequence could be chosen since these CDRs were planned to be the first to be replaced by oligonucleotide libraries. In order to study the expression and folding behavior of the consensus sequences in *E. coli*, it would be useful to have all sequences with the same CDR3, since the influence of the CDR3s on the folding behavior would then be identical in all cases. The dummy sequences QQHYTTPP (see, for instance, positions 89–96 of SEQ ID NO: 28 and positions 88–95 of SEQ ID NO: 34) and ARWGGDGFYAMDY (positions 97–109 of SEQ ID NOS 35 & 36) were selected for the VL chains (kappa and lambda) and for the VH chains, respectively. These sequences are known to be compatible with antibody folding in *E. coli* (Carter et al., 1992).

1.5 Gene Design

The final outcome of the process described above was a collection of 14 HuCAL amino acid sequences, which represent the frequently used structural antibody repertoire of the human immune system (see FIG. 2). These sequences were back-translated into DNA sequences. In a first step, the back-translation was done using only codons which are known to be frequently used in *E. Coli*. These gene sequences were then used for creating a database of all possible restriction endonuclease sites, which could be introduced without changing the corresponding amino acid sequences. Using this database, cleavage sites were selected which were located at the flanking regions of all sub-elements of the genes (CDRs and framework regions) and which could be introduced in all HuCAL VH, Vκ or Vλ genes simultaneously at the same position. In a few cases it was not possible to find cleavage sites for all genes of a subgroup. When this happened, the amino acid sequence was changed, it this was possible according to the available sequence and structural information. This exchange was then analyzed again as described above. In total, the following 6 amino acid residues were exchanged during this design (given is the name of the gene, the position according to Kabat's numbering scheme, the amino acid found at this position as the most abundant one and the amino acid which was used instead):

VH2: $T_3Q$

VH6: $S_{42}G$

Vκ3: $E_1D$, $I_{58}V$

Vκ4: $K_{24}R$

Vλ3: $T_{22}S$

In one case (5'-end of VH framework 3) it was not possible to identify a single cleavage site for all 7 VH genes. Two different type of cleavage sites were used instead: BstEII for HuCAL VH1A, VH1B, VH4 and VH5, and NspV for HuCAL VH2, VH3, VH4 and VH6.

Several restriction endonuclease sites were identified, which were not located at the flanking regions of the sub-elements but which could be introduced in every gene of a given group without changing the amino acid sequence. These cleavage sites were also introduced in order to make the system more flexible for further improvements. Finally, all but one remaining restriction endonuclease sites were removed in every gene sequence. The single cleavage site, which was not removed was different in all genes of a subgroup and could be therefore used as a "fingerprint" site to ease the identification of the different genes by restriction digest. The designed genes, together with the corresponding amino acid sequences and the group-specific restriction endonuclease sites are shown in FIG. 3, 4 and 5, respectively.

1.6 Gene Synthesis and Cloning

The consensus genes were synthesized using the method described by Prodromou & Pearl, 1992, using the oligonucleotides shown in FIG. 6. Gene segments encoding the human constant domains Cκ, Cλ and CH1 were also synthesized, based on sequence information given by Kabat et al., 1991 (see FIG. 6 and FIG. 7). Since for both the CDR3 and the framework 4 gene segments identical sequences were chosen in all HuCAL Vκ, Vλ and VH genes, respectively, this part was constructed only once, together with the corresponding gene segments encoding the constant domains. The PCR products were cloned into pCR-Script KS(+) (Stratagene, Inc.) or pZErO-1 (Invitrogen, Inc.) and verified by sequencing.

Example 2

Cloning and Testing of a HuCAL-Based Antibody Library

A combination of two of the synthetic consensus genes was chosen after construction to test whether binding antibody fragments can be isolated from a library based on these two consensus frameworks. The two genes were cloned as a single-chain Fv (scFv) fragment, and a VH-CDR3 library was inserted. In order to test the library for the presence of functional antibody molecules, a selection procedure was carried out using the small hapten fluorescein bound to BSA (FITC-BSA) as antigen.

2.1 Cloning of the HuCAL VH3-Vκ2 scFv Fragment
2.1 Cloning of the HuCAL VH3-Vk2 scFv Fragment In order to test the design of the consensus genes, one randomly chosen combination of synthetic light and heavy gene (HuCAL-Vκ2 and HuCAL-VH3) was used for the construction of a single-chain antibody (scFv) fragment. Briefly, the gene segments encoding the VH3 consensus gene and the CH1 gene segment including the CDR3—framework 4 region, as well as the Vκ2 consensus gene and the Cκ gene segment including the CDR3—framework 4 region were assembled yielding the gene for the VH3-CH1 Fd fragment and the gene encoding the Vκ2-Cκ light chain, respectively. The CH1 gene segment was then replaced by an oligonucleotide (SEQ ID NOS 2 & 3, respectively) cassette encoding a 20-mer peptide linker (SEO ID NO: 1) with the sequence AGGGSGGGGSGGGGSGGGGS. The two oligonucleotides encoding this linker were 5'-TCAGCGGGTGGCGGTTCTGGCGGCGGTGGGAG CGGTGGCGGTGGTTCTGGCGGTGGTGGTTCCGAT ATCGGTCCACGTACGG-3' and 5'-MTTCCG TACGTG-GACCGATATCGGMCCACCACCGCCAGAA CCAC-CGCCACCGCTCCCACCGCCGCCAGAACCG CCACCCGC-3', respectively. Finally, the HuCAL-Vκ2 gene was inserted via EcoRV and BsiWI into the plasmid encoding the HuCAL-VH3-linker fusion, leading to the final gene HuCAL-VH3-Vκ2, which encoded the two consensus sequences in the single-chain format VH-linker-VL. The complete coding sequence is shown in FIG. 8.

2.2 Construction of a Monovalent Phage-display Phagemid Vector pIG10.3

Phagemid pIG10.3 (FIG. 9) was constructed in order to create a phage-display system (Winter et al., 1994) for the H3κ2 scFv gene. Briefly, the EcoRI/HindIII restriction fragment in the phagemid vector pIG10 (Ge et al., 1995) was replaced by the c-myc followed by an amber codon (which encodes an glutamate in the amber-suppresser strain XL1 Blue and a stop codon in the non-suppresser strain JM83) and a truncated version of the gene III (fusion junction at codon 249, see Lowman et al., 1991) through PCR mutagenesis.

2.3 Construction of H-CDR3 Libraries

Heavy chain CDR3 libraries of two lengths (10 and 15 amino acids) were constructed using trinucleotide codon containing oligonucleotides (Virnekäs et al., 1994) as templates and the oligonucleotides complementing the flanking regions as primers. To concentrate only on the CDR3 structures that appear most often in functional antibodies, we kept the salt-bridge of $R_{H94}$ and $D_{H101}$ in the CDR3 loop. For the 15-mer library, both phenylalanine and methionine were introduced at position 100 since these two residues were found to occur quite often in human CDR3s of this length (not shown). For the same reason, valine and tyrosine were introduced at position 102. All other randomized positions contained codons for all amino acids except cystein, which was not used in the trinucleotide mixture.

The CDR3 libraries of lengths 10 and 15 were generated from the PCR fragments using oligonucleotide templates (SEQ ID NOS 4 & 5, respectively) O3HCDR103T (5'-GATACGGCCGTGTATTATTGCGCGCGT (TRI)$_6$ GATTATTGGGGCCAAGGCACCCTG-3') and O3HCDR153T (5'-GATACGGCCGTGTATT ATTGCGCGCGT(TRI)$_{10}$ (TTT/ATG)GAT(GTT/TAT) TGGGGCCAAGGCACCCTG-3'), and primers (SEQ ID NOS 6 & 7, respectively) O3HCDR35 (5'-GATACGGCCGTGTATTATTGC-3') and O3HCDR33 (5'-CAGGGTGCCTTGGCCCC-3'), where TRI are trinucleotide mixtures representing all amino acids without cystein, (TTT/ATG) and (GTT/TAT) are trinucleotide mixtures encoding the amino acids phenylalanine/methionine and valine/tyrosine, respectively. The potential diversity of these libraries was $4.7 \times 10^7$ and $3.4 \times 10^{10}$ for 10-mer and 15-mer library, respectively. The library cassettes were first synthesized from PCR amplification of the oligo templates in the presence of both primers: 25 pmol of the oligo template O3HCDR103T or O3HCDR153T, 50 pmol each of the primers O3HCDR35 and O3HCDR33, 20 nmol of dNTP, 10x buffer and 2.5 units of Pfu DNA polymerase (Stratagene) in a total volume of 100 ml for 30 cycles (1 minute at 92° C., 1 minute at 62° C. and 1 minute at 72° C.). A hot-start procedure was used. The resulting mixtures were phenol-extracted, ethanol-precipitated and digested ovemight with EagI and StyI. The vector pIG10.3-scH3□2cat, where the EagI-StyI fragment in the vector pIG10.3-scH3κ2 encoding the H-CDR3 was replaced by the chloramphenicol acetyltransferase gene (cat) flanked with these two sites, was similarly digested. The digested vector (35 µg) was gel-purified and ligated with 100 µg of the library cassette overnight at 16° C. The ligation mixtures were isopropanol precipitated, air-dried and the pellets were redissolved in 100 ml of ddH20. The ligation was mixed with 1 ml of freshly prepared electrocompetent XL1 Blue on ice. 20 rounds of electroporation were performed and the transformants were diluted in SOC medium, shaken at 37° C. for 30 minutes and plated out on large LB plates (Amp/Tet/Glucose)

In order to test the quality of the initial library, phagemids from 24 independent colonies (12 from the 10-mer and 12 from the 15-mer library, respectively) were isolated and analyzed by restriction digestion and sequencing. The restriction analysis of the 24 phagemids indicated the presence of intact vector in all cases. Sequence analysis of these clones (see FIG. 10) indicated that 22 out of 24 contained a functional sequence in their heavy chain CDR3 regions. 1 out of 12 clones of the 10-mer library had a CDR3 of length 9 instead of 10, and 2 out of 12 clones of the 15-mer library had no open reading frame, thereby leading to a non-functional scFv; one of these two clones contained two consecutive inserts, but out of frame (data not shown). All codons introduced were presented in an even distribution.

Expression levels of individual library members were also measured. Briefly, 9 clones from each library were grown in 2xYT medium containing Amp/Tet/0.5% glucose at 37° C. overnight. Next day, the cultures were diluted into fresh medium with Amp/Tet. At an $OD_{600nm}$ of 0.4, the cultures were induced with 1 mM of IPTG and shaken at RT overnight. Then the cell pellets were suspended in 1 ml of PBS buffer+1 mM of EDTA. The suspensions were sonicated and the supernatants were separated on an SDS-PAGE under reducing conditions, blotted on nylon membrane and detected with anti-FLAG M1 antibody (see FIG. 11). From the nine clones of the 10-mer library, all express the scFv fragments. Moreover, the gene III/scFv fusion proteins were present in all cases. Among the nine clones from the 15-mer library analyzed, 6/9 (67%) led to the expression of both scFv and the gene III/scFv fusion proteins. More importantly, all clones expressing the scFvs and gene III/scFv fusions gave rise to about the same level of expression.

2.4 Biopanning

Phages displaying the antibody libraries were prepared using standard protocols. Phages derived from the 10-mer library were mixed with phages from the 15-mer library in a ratio of 20:1 ($1\times10^{10}$ cfu/well of the 10-mer and $5\times10^8$ cfu/well of the 15-mer phages, respectively). Subsequently, the phage solution was used for panning in ELISA plates (Maxisorp, Nunc) coated with FITC-BSA (Sigma) at concentration of 100 µg/ml in PBS at 4° C. overnight. The antigen-coated wells were blocked with 3% powder milk in PBS and the phage solutions in 1% powder milk were added to each well and the plate was shaken at RT for 1 hr. The wells were then washed with PBST and PBS (4 times each with shaking at RT for 5 minutes). The bound phages were eluted with 0.1 M triethylamine (TEA) at RT for 10 minutes. The eluted phage solutions were immediately neutralized with ½ the volume of 1 M Tris.Cl, pH 7.6. Eluted phage solutions (ca. 450 µl) were used to infect 5 ml of XL1 Blue cells at 37° C. for 30 min. The infected cultures were then plated out on large LB plates (Amp/Tet/Glucose) and allowed to grow at 37° C. until the colonies were visible. The colonies were suspended in 2xYT medium and the glycerol cultures were made as above described. This panning round was repeated twice, and In the third round elution was carried out with addition of fluorescein in a concentration of 100 µg/ml in PBS. The enrichment of specific phage antibodies was monitored by panning the initial as well as the subsequent fluorescein-specific sub-libraries against the blocking buffer (FIG. 12). Antibodies with specificity against fluorescein were isolated after 3 rounds of panning.

2.5 ELISA Measurements

One of the criteria for the successful biopanning is the isolation of individual phage clones that bind to the targeted antigen or hapten. We undertook the isolation of anti-FITC phage antibody clones and characterized them first in a phage ELISA format. After the 3rd round of biopanning (see above), 24 phagemid containing clones were used to inoculate 100 µl of 2xYT medium (Amp/Tet/Glucose) in an ELISA plate (Nunc), which was subsequently shaken at 37° C. for 5 hrs. 100 µl of 2xYT medium (Amp/Tet/1 mM IPTG) were added and shaking was continued for 30 minutes. A further 100 µl of 2xYT medium (Amp/Tet) containing the helper phage ($1\times10^9$ cfu/well) was added and shaking was done at RT for 3 hrs. After addition of kanamycin to select for successful helper phage infection, the shaking was continued overnight. The plates were then centrifuged and the supernatants were pipetted directly into ELISA wells coated with 100 µl FITC-BSA (100 µg/ml) and blocked with milk powder. Washing was performed similarly as during the panning procedure and the bound phages were detected with anti-M13 antibody-POD conjugate (Pharmacia) using soluble POD substrate (Boehringer-Mannheim). Of the 24 clones screened against FITC-BSA, 22 were active in the ELISA (FIG. 13). The initial libraries of similar liter gave rise to no detectable signal.

Specificity for fluorescein was measured in a competitive ELISA. Periplasmic fractions of live FITC specific scFvs were prepared as described above. Western blotting indicated that all clones expressed about the same amount of scFv fragment (data not shown). ELISA was performed as described above, but additionally, the periplasmic fractions were incubated 30 min at RT either with buffer (no inhibition), with 10 mg/ml BSA (inhibition with BSA) or with 10 mg/ml fluorescein (inhibition with fluorescein) before adding to the well. Binding scFv fragment was detected using the anti-FLAG antibody M1. The ELISA signal could only be inhibited, when soluble fluorescein was added, indicating binding of the scFvs was specific for fluorescein (FIG. 14).

2.6 Sequence Analysis

The heavy chain CDR3 region of 20 clones were sequenced in order to estimate the sequence diversity of fluorescein binding antibodies in the library (FIG. 15). In total, 16 of 20 sequences (80%) were different, showing that the constructed library contained a highly diverse repertoire of fluorescein binders. The CDR3s showed no particular sequence homology, but contained on average 4 arginine residues. This bias towards arginine in fluorescein binding antibodies had already been described by Barbas et al., 1992.

2.7 Production

E. coli JM83 was transformed with phagemid DNA of 3 selected clones and cultured in 0.5 L 2xYT medium. Induction was carried out with 1 mM IPTG at $OD_{600nm}=0.4$ and growth was continued with vigorous shaking at RT overnight. The cells were harvested and pellets were suspended in PBS buffer and sonicated. The supernatants were separated from the cell debris via centrifugation and purified via the BioLogic system (Bio-Rad) by with a POROS®MC 20 column (IMAC, PerSeptive Biosystems, Inc.) coupled with an ion-exchange chromatography column. The ion-exchange column was one of the POROS®HS, CM or HQ or PI 20 (PerSeptive Biosystems, Inc.) depended on the theoretical pI of the scFv being purified. The pH of all the buffers was adjusted to one unit lower or higher than the pI of the scFv being purified throughout. The sample was loaded onto the first IMAC column, washed with 7 column volumes of 20 mM sodium phosphate, 1 M NaCl and 10 mM imidazole. This washing was followed by 7 column volumes of 20 mM sodium phosphate and 10 mM imidazole. Then 3 column volumes of an imidazole gradient (10 to 250 mM) were applied and the eluent was connected directly to the ion-exchanger. Nine column volumes of isocratic washing with 250 mM imidazole was followed by 15 column volumes of 250 mM to 100 mM and 7 column volumes of an imidazole/NaCl gradient (100 to 10 mM imidazole, 0 to 1 M NaCl). The flow rate was 5 ml/min. The purity of scFv fragments was checked by SDS-PAGE Coomassie staining (FIG. 16). The concentration of the fragments was determined from the absorbance at 280 nm using the theoretically determined extinction coefficient (Gill & von Hippel, 1989). The scFv fragments could be purified to homogeneity (see FIG. 16). The yield of purified fragments ranged from 5 to 10 mg/L/OD.

Example 3

HuCAL H3κ2 Library Against a Collection of Antigens

In order to test the library used in Example 2 further, a new selection procedure was carried out using a variety of antigens comprising β-estradiol, testosterone, Lewis-Y epitope (LeY), interleukin-2 (IL-2), lymphotoxin-β (LT-β). E-selectin ligand-1 (ESL-1), and BSA.

3.1 Biopanning

The library and all procedures were identical to those described in Example 2. The ELISA plates were coated with β-estradiol-BSA (100 μg/ml), testosterone-BSA (100 μg/ml), LeY-BSA (20 μg/ml) IL-2 (20 μg/ml), ESL-1 (20 μg/ml) and BSA (100 μg/ml), LT-β (denatured protein, 20 μg/ml). In the first two rounds, bound phages were eluted with 0.1 M triethylamine (TEA) at RT for 10 minutes. In the case of BSA, elution after three rounds of panning was carried out with addition of BSA in a concentration of 100 μg/ml in PBS. In the case of the other antigens, third round elution was done with 0.1 M triethylamine. In all cases except LeY, enrichment of binding phages could be seen (FIG. 17). Moreover, a repetition of the biopanning experiment using only the 15-mer library resulted in the enrichment of LeY-binding phages as well (data not shown).

3.2. ELISA Measurements

Clones binding to β-estradiol, testosterone, LeY, LT-β, ESL-1 and BSA were further analyzed and characterized as described in Example 2 for FITC. ELISA data for anti-β-estradiol and anti-ESL-1 antibodies are shown in FIG. 18. In one experiment, selectivity and cross-reactivity of binding scFv fragments were tested. For this purpose, an ELISA plate was coated with FITC, testosterone, β-estradiol, BSA, and ESL-1, with 5 wells for each antigen arranged in 5 rows, and 5 antibodies, one against each of the antigens, were screened against each of the antigens. FIG. 19 shows the specific binding of the antibodies to the antigen it was selected for, and the low cross-reactivity with the other four antigens.

3.3 Sequence Analysis

The sequencing data of several clones against β-estradiol (34 clones), testosterone (12 clones), LT-β (23 clones), ESL-1 (34 clones), and BSA (10 clones) are given in FIGS. 20 to 24.

Example 4

Vector Construction

To be able to take advantage of the modularity of the consensus gene repertoire, a vector system had to be constructed which could be used in phage display screening of HuCAL libraries and subsequent optimization procedures. Therefore, all necessary vector elements such as origins of single-stranded or double-stranded replication, promotor/operator, repressor or terminator elements, resistance genes, potential recombination sites, gene III for display on filamentous phages, signal sequences, or detection tags had to be made compatible with the restriction site pattern of the modular consensus genes. FIG. 25 shows a schematic representation of the pCAL vector system and the arrangement of vector modules and restriction sites therein. FIG. 25a shows a list of all restriction sites which are already incorporated Into the consensus genes or the vector elements as part of the modular system or which are not yet present in the whole system. The latter could be used in a later stage for the introduction of or within new modules.

4.1 Vector Modules

A series of vector modules was constructed where the restriction sites flanking the gene sub-elements of the HuCAL genes were removed, the vector modules themselves being flanked by unique restriction sites. These modules were constructed either by gene synthesis or by mutagenesis of templates. Mutagenesis was done by add-on PCR, by site-directed mutagenesis (Kunkel et al., 1991) or multisite oligonucleotide-mediated mutagenesis (Sutherland et al., 1995; Perlak, 1990) using a PCR-based assembly method.

FIG. 26 contains a list of the modules constructed. Instead of the terminator module M9 (HindIII-Ipp-PacI), a larger cassette M9II was prepared to introduce FseI as additional restriction site. M9II can be cloned via HindIII/BsrGI.

All vector modules were characterized by restriction analysis and sequencing. In the case of module M11-II, sequencing of the module revealed a two-base difference in positions 164/65 compared to the sequence database of the template. These two different bases (CA→GC) created an additional BanII site. Since the same two-base difference occurs in the f1 origin of other bacteriophages, it can be assumed that the two-base difference was present in the template and not created by mutagenesis during cloning. This BanII site was removed by site-directed mutagenesis, leading to module M11-III. The BssSI site of nodule M14 could initially not be removed without impact on the function of the ColE1 origin, therefore M14-Ext2 was used for cloning of the first pCAL vector series. FIGS. 29 to 34 are showing the functional maps and sequences of the modules used for assembly of the modular vector pCAL4 (see below). The functional maps and sequences of additional modules can be found in FIG. 35a. FIG. 35b contains a list of oligonucleotides and primers used for the synthesis of the modules.

4.2 Cloning Vector pMCS

To be able to assemble the individual vector modules, a cloning vector pMCS containing a specific multi-cloning site (MCS) was constructed. First, an MCS cassette (FIG. 27) was made by gene synthesis. This cassette contains all those restriction sites in the order necessary for the sequential introduction of all vector modules and can be cloned via the 5'-HindIII site and a four base overhang at the 3'-end compatible with an AatII site. The vector pMCS (FIG. 28) was constructed by digesting pUC19 with AatII and HindIII, isolating the 2174 base pair fragment containing the bla gene and the ColE1 origin, and ligating the MCS cassette.

4.3 Cloning of Modular Vector pCAL4

This was cloned step by step by restriction digest of pMCS and subsequent ligation of the modules M1 (via AatII/XbaI), M7III (via EcoRI/HindIII), and M9II (via HindIII/BsrGI), and M11-II (via BsrGI/NheI). Finally, the bla gene was replaced by the cat gene module M17 (via AatII/BglII), and the wild type ColE1 origin by module M14-Ext2 (via BglII/NheI). FIG. 35 is showing the functional map and the sequence of pCAL4.

4.4 Cloning of Low-copy Number Plasmid Vectors pCALO

A series of low-copy number plasmid vectors was constructed in a similar way using the p15A module M12 instead of the ColE1 module M14-Ext2. FIG. 35a is showing the functional maps and sequences of the vectors pCALO1 to pCALO3.

Example 5

Construction of a HuCAL scFv Library 5.1. Cloning of All 49 HuCAL scFv Fragments All 49 combinations of the 7 HuCAL-VH and 7 HuCAL-VL consensus genes were assembled as described for the HuCAL VH3-Vκ2 scFv in Example 2 and inserted into the vector pBS12, a modified version of the pLisc series of antibody expression vectors (Skerra et al., 1991).

5.2 Construction of a CDR Cloning Cassette

For replacement of CDRs, a universal β-lactamase cloning cassette was constructed having a multi-cloning site at the 5'-end as well as at the 3'-end. The 5'-multi-cloning site comprises all restriction sites adjacent to the 5'-end of the HuCAL VH and VL CDRs, the 3'-multi-cloning site comprises all restriction sites adjacent to the 3' end of the HuCAL VH and VL CDRs. Both 5'- and 3'-multi-cloning site were prepared as cassettes via add-on PCR using synthetic oligonucleotides as 5'- and 3'-primers using wild type β-lactamase gene as template. FIG. 36 shows the functional map and the sequence of the cassette bla-MCS.

5.3. Preparation of VL-CDR3 Library Cassettes

The VL-CDR3 libraries comprising 7 random positions were generated from the PCR fragments using oligonucleotide templates Vκ1&Vκ3, Vκ2 and Vκ4 and primers O_K3L_5 and O_K3L_3 (FIG. 37) for the Vκ genes, and Vλ, and primers O_L3L_5 (5'-GCAGAAGGCGAACGTCC-3') and O_L3LA_3 (FIG. 38) for the Vλ genes. Construction of the cassettes was performed as described in Example 2.3.

5.4 Cloning of HuCAL scFv Genes with VL-CDR3 Libraries

Each of the 49 single-chains was subcloned into pCAL4 via XbaI/EcoRI and the VL-CDR3 replaced by the β-lactamase cloning cassette via BbsI/MscI, which was then replaced by the corresponding VL-CDR3 library cassette synthesized as described above. This CDR replacement is described in detail in Example 2.3 where the cat gene was used.

5.5 Preparation of VH-CDR3 Library Cassette

The VH-CDR3 libraries were designed and synthesized as described in Example 2.3.

5.6 Cloning of HuCAL scFv Genes with VL- and VH-CDR3 Libraries

Each of the 49 single-chain VL-CDR3 libraries was digested with BssHII/StyI to replace VH-CDR3. The "dummy" cassette digested with BssHII/StyI was inserted, and was then replaced by a corresponding VH-CDR3 library cassette synthesized as described above.

Example 6

Expression Tests

Expression and toxicity studies were performed using the scFv format VH-linker-VL. All 49 combinations of the 7 HuCAL-VH and 7 HuCAL-VL consensus genes assembled as described in Example 5 were inserted into the vector pBS13, a modified version of the pLisc series of antibody expression vectors (Skerra et al., 1991). A map of this vector is shown in FIG. 39.

E. coli JM83 was transformed 49 times with each of the vectors and stored as glycerol stock. Between 4 and 6 clones were tested simultaneously, always including the clone H3κ2, which was used as internal control throughout. As additional control, the McPC603 scFv fragment (Knappik & Plückthun, 1995) in pBS13 was expressed under identical conditions. Two days before the expression test was performed, the clones were cultivated on LB plates containing 30 µg/ml chloramphenicol and 60 mM glucose. Using this plates an 3 ml culture (LB medium containing 90 µg chloramphenicol and 60 mM glucose) was inoculated overnight at 37° C. Next day the overnight culture was used to inoculate 30 ml LB medium containing chloramphenicol (30 µg/ml). The starting $OD_{600nm}$ was adjusted to 0.2 and a growth temperature of 30° C. was used. The physiology of the cells was monitored by measuring every 30 minutes for 8 to 9 hours the optical density at 600 nm. After the culture reached an $OD_{600nm}$ of 0.5, antibody expression was induced by adding IPTG to a final concentration of 1 mM. A 5 ml aliquot of the culture was removed after 2 h of induction in order to analyze the antibody expression. The cells were lysed and the soluble and insoluble fractions of the crude extract were separated as described in Knappik & Plückthun, 1995. The fractions were assayed by reducing SDS-PAGE with the samples normalized to identical optical densities. After blotting and immunostaining using the α-FLAG antibody M1 as the first antibody (see Ge et al., 1994) and an Fc-specific anti-mouse antiserum conjugated to alkaline phosphatase as the second antibody, the lanes were scanned and the intensities of the bands of the expected size (appr. 30 kDa) were quantified densitometrically and tabulated relative to the control antibody (see FIG. 40).

Example 7

Optimization of Fluorescein Binders 7.1. Construction of L-CR3 and H-CDR2 Library Cassettes A L-CDR3 library cassette was prepared from the oligonucleotide (SEQ ID NO: 9) template CDR3L (5'-TGGAAGCTGAAGACGTGGGCGTGTATTATTGCCA GCAG(TR5)(TRI)$_4$CCG(TRI)TTTGGCCA GGGTACGAAAGTT-3') and primer (SEQ ID NO: 10) 5'-AATTTCGTACCCTGGCC-3' for synthesis of the complementary strand, where (TRI) was a trinucleotide mixture representing all amino acids except Cys, (TR5) comprised a trinucleotide mixture representing the 5 codons for Ala, Arg, His, Ser. and Tyr.

A H-CDR2 library cassette was prepared from the oligonucleotide template CDRsH (SEQ ID NOS 11 & 12, respectvely) (5'-AGGGTCTCGAGTGGGTGAGC(TRI) ATT(TRI)$_{2-3}$(6)$_2$(TRI)ACC(TRI)TATGCGG TAGCGT-GAAAGGCCGTTTTACCATTTCACGTGAT MTTCGAAAAACACCA-3'), and primer (SEQ ID NO: 13) 5'-TGGTGTTTTTCGMTTATCA-3' for synthesis of the complementary strand, where (TRI) was a trinucleotide mixture representing all amino acids except Cys, (6) comprised the incorporation of (ANG) (A/C/G) T, resulting in the formation of 6 codons for Ala, Asn, Asp, Gly, Ser, and Thr, and the length distribution being obtained by performing one substoichiometric coupling of the (TRI) mixture during synthesis, omitting the capping step normally used in DNA synthesis.

DNA synthesis was performed on a 40 nmole scale, oligos were dissolved in TE buffer, purified via gel filtration using spin columns (S-200), and the DNA concentration determined by OD measurement at 260 nm (OD 1.0=40 µg/ml). 10 nmole of the oligonucleotide templates and 12 nmole of the corresponding primers were mixed and annealed at 80° C. for 1 min, and slowly cooled down to 37° C. within 20 to 30 min. The fill-in reaction was performed for 2 h at 37° C. using Klenow polymerase (2.0 µl) and 250 nmole of each dNTP. The excess of dNTPs was removed by gel filtration using Nick-Spin columns (Pharmacia), and the double-stranded DNA digested with BbsI/MscI (L-CDR3), or XhoI/ SfuI (H-CDR2) over night at 37° C. The cassettes were purified via Nick-Spin columns (Pharmacia), the concentration determined by OD measurement, and the cassettes aliquoted (15 pmole) for being stored at −80° C.

7.2 Library Cloning:

DNA was prepared from the collection of FITC binding clones obtained in Example 2 (approx. $10^4$ to clones). The collection of scFv fragments was isolated via XbaI/EcoRI digest. The vector pCAL4 (100 fmole, 10 µg) described in Example 4.3 was similarly digested with XbaI/EcoRI, gel-purified and ligated with 300 fmole of the scFv fragment collection over night at 16° C. The ligation mixture was isopropanol precipitated, air-dried, and the pellets were redissolved in 100 µl of dd H$_2$O. The ligation mixture was mixed with 1 ml of freshly prepared electrocompetent SCS 101 cells (for optimization of L-CDR3), or XL1 Blue cells (for optimization of H-CDR2) on ice. One round of electroporation was performed and the transformants were eluted in SOC medium, shaken at 37° C. for 30 minutes, and an aliquot plated out on LB plates (Amp/Tet/Glucose) at 37° C. for 6–9 hrs. The number of transformants was 5×$10^4$.

Vector DNA (100 μg) was isolated and digested (sequence and restriction map of scH3κ2 see FIG. 8) with BbsI/MscI for optimization of L-CDR3, or XhoI/NspV for optimization of H-CDR2, 10 μg of purified vector fragments (5 pmole) were ligated with 15 pmole of the L-CDR3 or H-CDR2 library cassettes over night at 16° C. The ligation mixtures were isopropanol precipitated, air-dried, and the pellets were redissolved in 100 μl of dd H$_2$O. The ligation mixtures were mixed with 1 ml of freshly prepared electrocompetent XL1 Blue cells on ice. Electroporation was performed and the transformants were eluted in SOC medium and shaken at 37° C. for 30 minutes. An aliquot was plated out on LB plates (Amp/Tet/Glucose) al 37° C. for 6–9 hrs. The number of transformants (library size) was greater than $10^8$ for both libraries. The libraries were stored as glycerol cultures.

7.3. Biopanning

This was performed as described for the initial H3κ2 H-CDR3 library in Example 2.1. Optimized scFvs binding to FITC could be characterized and analyzed as described in Example 2.2 and 2.3, and further rounds of optimization could be made if necessary.

REFERENCES

Barbas III, C. F., Bain, J. D., Hoekstra, D. M. & Lerner, R. A., PNAS 89, 4457–4461 (1992).

Better, M., Chang, P., Robinson, R. & Horwitz, A. H., Science 240, 1041–1043 (1988).

Blake. M. S., Johnston, K. H., Russel-Jones, G. J. & Gotschlich, E. C., Anal. Biochem. 136, 175–179 (1984).

Carter, P., Kelly, R. F., Rodrigues, M. L., Snedecor, B., Covrrubias, M., Velligan, M. D., Wong, W. L. T., Rowland, A. M., Kotts. C. E., Carver, M. E., Yang, M., Bourell, J. H., Shepard, H. M. & Henner, D., Bio/Technology 10, 163–167 (1992).

Chothia, C. & Lesk, A. M., J. Biol. Chem. 196, 910–917 (1987).

Chothia, C., Lesk, A. M., Gherardi, E., Tomlinson, I. A., Walter, G., Marks, J. D., Liewelyn, M. B. & Winter, G., J. Mol. Biol. 227, 799–817 (1992).

Chothia, C., Lesk, A. M., Tramontano, A., Levitt, M., Smith-Gill, S. J., Air, G., Sheriff, S., Padlan, E. A., Davies, D., Tulip, W. R., Colman, P. M., Spinelli, S., Alzari, P. M. & Poljak, R. J., Nature 342, 877–883 (1989).

Chuchana, P., Blancher, A., Brockly, F., Alexandre, D., Lefranc, G & Lefranc, M.-P., Eur. J. Immunol. 20, 1317–1325 (1990).

Cox, J. P. L., Tomlinson, I. M. & Winier, G., Eur. J. Immunol. 24, 827–836 (1994).

Ge, L., Knappik, A., Pack, P., Freund, C. & Plückthun, A., In: Antibody Engineering. Borrebaeck, C. A. K. (Ed.). p.229–266 (1995), Oxford University Press, New York, Oxford.)

Gill, S. C. & von Hippel, P. H., Anal. Biochem. 182, 319.326 (1989).

Hochuli, E., Bannwarth, W., Döbeli, H., Gentz, R. & Stüber, D., Bio/Technology 6, 1321–1325 (1988).

Hopp, T. P., Prickett, K. S., Price, V. L., Libby, R. T., March. C. J., Cerretti, D. P., Urdal, D. L. & Conlon, P. J. Bio/Technology 6, 1204–1210 (1988).

Kabat, E. A., Wu, T. T., Perry, H. M., Gottesmann, K. S. & Foeller, C., Sequences of proteins of immunological interest, NIH publication 91-3242 (1991).

Knappik, A. & Plückthun, A., Biotechniques 17, 754–761 (1994).

Knappik, A. & Plückthun, A., Protein Engineering 8, 81–89 (1995).

Kunkel, T. A. Bebenek, K. & McClary, J., Methods in Enzymol. 204, 125–39 (1991).

Lindner, P., Guth, B., Wülfing, C., Krebber, C., Steipe, B., Müller, F. & Plückthun, A., Methods: A Companion to Methods Enzymol. 4, 41–56 (1992).

Lowman, H. B., Bass, S. H., Simpson, N. and Wells, J. A., Biochemistry 30, 10832–10838 (1991).

Pack, P. & Plückthun, A., Biochemistry 31, 1579–1584 (1992).

Pack, P., Kujau, M., Schroeckh, V., Knüpfer, U., Wenderoth, R., Riesenberg D. & Plückthun, A., Bio/Technology 11, 1271–1277 (1993).

Pack, P., Ph.D. thesis, Ludwig-Maximilians-Universität München (1994).

Perlak, F. J., Nuc. Acids Res. 18, 7457–7458 (1990).

Plückthun, A., Krebber, A., Krebber, C., Horn, U., Knüpfer, U., Wenderoth, R., Nieba, L., Proba, K. & Riesenberg, D., A practical approach. Antibody Engineering (Ed. J. McCafferty). IRL Press, Oxford, pp. 203–252 (1996).

Prodromou, C. & Pearl, L. H., Protein Engineering 5, 827–829 (1992).

Rosenberg, S. A. & Lotze, M. T., Ann. Rev. Immunol. 4, 681–709 (1986).

Skerra, A. & Plückthun, A., Science 240, 1038–1041 (1988).

Skerra, A., Pfitzinger, I. & Plückthun, A., Bio/Technology 9, 273–278 (1991).

Sutherland, L., Davidson, J., Glass, L. L., & Jacobs, H. T., BioTechniques 18, 458–464, 1995.

Tomlinson, I. M., Walter, G., Marks, J. D., Llewelyn, M. B. & Winter, G., J. Mol. Biol. 227, 776–798 (1992).

Ullrich, H. D., Patten, P. A., Yang, P. L., Romesberg, F. E. & Schultz, P. G., Proc. Natl. Acad. Sci. USA 92, 11907–11911 (1995).

Van Dijk, K. W., Mortari, F., Kirkham, P. M., Schroeder Jr., H. W. & Milner, E. C. B., Eur. J. Immunol. 23, 832–839 (1993).

Virnekäs, B., Ge, L., Plückthun, A., Schneider, K. C., Wellnhofer, G. & Moroney, S. E., Nucleic Acids Research 22, 5600–5607 (1994).

Vitetta, E. S., Thorpe. P. E. & Uhr, J., Immunol. Today 14, 253–259 (1993).

Williams, S. C. & Winter, G., Eur. J. Immunol. 23, 1456–1461 (1993).

Winter, G., Griffiths, A. D., Hawkins, R. E. & Hoogenboom, H. R., Ann. Rev. Immunol. 12, 433–455 (1994).

TABLE 1A

| Human kappa germline gene segments | | | |
|---|---|---|---|
| Used Name[1] | Reference[2] | Family[3] | Germline genes[4] |
| Vk1-1 | 9 | 1 | O8; O18; DPK1 |
| Vk1-2 | 1 | 1 | L14; DPK2 |
| Vk1-3 | 2 | 1 | L15(1); HK101; HK146; HK189 |
| Vk1-4 | 9 | 1 | L11 |
| Vk1-5 | 2 | 1 | A30 |
| Vk1-6 | 1 | 1 | LFVK5 |
| Vk1-7 | 1 | 1 | LFVK431 |
| Vk1-8 | 1 | 1 | L1; HK137 |
| Vk1-9 | 1 | 1 | A20; DPK4 |
| Vk1-10 | 1 | 1 | L18; Va" |
| Vk1-11 | 1 | 1 | L4; L18; Va'; V4a |
| Vk1-12 | 2 | 1 | L5; L19(1); Vb; Vb4; DPK5; L19(2); Vb"; DPK6 |
| Vk1-13 | 2 | 1 | L15(2); HK134; HK166; DPK7 |
| Vk1-14 | 8 | 1 | L8; Vd; DPK8 |
| Vk1-15 | 8 | 1 | L9; Ve |
| Vk1-16 | 1 | 1 | L12(1); HK102; V1 |
| Vk1-17 | 2 | 1 | L12(2) |
| Vk1-18 | 1 | 1 | O12a(V3b) |

TABLE 1A-continued

Human kappa germline gene segments

| Used Name[1] | Reference[2] | Family[3] | Germline genes[4] |
|---|---|---|---|
| Vk1-19 | 6 | 1 | O2; O12; DPK9 |
| Vk1-20 | 2 | 1 | L24; Ve"; V13; DPK10 |
| Vk1-21 | 1 | 1 | O4; O14 |
| Vk1-22 | 2 | 1 | L22 |
| Vk1-23 | 2 | 1 | L23 |
| Vk2-1 | 1 | 2 | A2; DPK12 |
| Vk2-2 | 6 | 2 | O1; O11(1); DPK13 |
| Vk2-3 | 6 | 2 | O12(2); V3a |
| Vk2-4 | 2 | 2 | L13 |
| Vk2-5 | 1 | 2 | DPK14 |
| Vk2-6 | 4 | 2 | A3; A19; DPK15 |
| Vk2-7 | 4 | 2 | A29; DPK27 |
| Vk2-8 | 4 | 2 | A13 |
| Vk2-9 | 1 | 2 | A23 |
| Vk2-10 | 4 | 2 | A7; DPK17 |
| Vk2-11 | 4 | 2 | A17; DPK18 |
| Vk2-12 | 4 | 2 | A1; DPK19 |
| Vk3-1 | 11 | 3 | A11; humkv305; DPK20 |
| Vk3-2 | 1 | 3 | L20; Vg" |
| Vk3-3 | 2 | 3 | L2; L16; humkv328; humkv328h2; humkv328h5; DPK21 |
| Vk3-4 | 11 | 3 | A27; humkv325; VkRF; DPK22 |
| Vk3-5 | 2 | 3 | L25; DPK23 |
| Vk3-6 | 2 | 3 | L10(1) |
| Vk3-7 | 7 | 3 | L10(2) |
| Vk3-8 | 7 | 3 | L6; Vg |
| Vk4-1 | 3 | 4 | B3; VkIV; DPK24 |
| Vk5-1 | 10 | 5 | B2; EV15 |
| Vk6-1 | 12 | 6 | A14; DPK25 |
| Vk6-2 | 12 | 6 | A10; A26; DPK26 |
| Vk7-1 | 5 | 7 | B1 |

TABLE 1B

Human lambda germline gene segments

| Used Name[1] | Reference[2] | Family[3] | Germline genes[4] |
|---|---|---|---|
| DPL1 | 1 | 1 | |
| DPL2 | 1 | 1 | |
| DPL3 | 1 | 1 | HUMLV1L1 |
| DPL4 | 1 | 1 | HUMLV122 |
| HUMLV117 | 2 | 1 | VLAMBDA 1.1 |
| DPL5 | 1 | 1 | HUMLV117D |
| DPL6 | 1 | 1 | |
| DPL7 | 1 | 1 | IGLV1S2 |
| DPL8 | 1 | 1 | HUMLV1042 |
| DPL9 | 1 | 1 | HUMLV101 |
| DPL10 | 1 | 2 | |
| VLAMBDA 2.1 | 3 | 2 | |
| DPL11 | 1 | 2 | |
| DPL12 | 1 | 2 | |
| DPL13 | 1 | 2 | |
| DPL14 | 1 | 2 | |
| DPL16 | 1 | 3 | Humlv418; IGLV351 |
| DPL23 | 1 | 3 | VI III.1 |
| Humlv318 | 4 | 3 | |
| DPL18 | 1 | 7 | 4A; HUMIGLVA |
| DPL19 | 1 | 7 | |
| DPL21 | 1 | 8 | VL8.1 |
| HUMLV801 | 5 | 8 | |
| DPL22 | 1 | 9 | |
| DPL24 | 1 | unassigned | VLAMBDA N.2 |
| gVLX-4.4 | 6 | 10 | |

TABLE 1C

Human heavy chain germline gene segments

| Used Name[1] | Reference[2] | Family[3] | Germline genes[4] |
|---|---|---|---|
| VH1-12-1 | 19 | 1 | DP10; DA-2; DA-6 |
| VH1-12-8 | 22 | 1 | RR.VH1:2 |
| VH1-12-2 | 6 | 1 | hv1263 |
| VH1-12-9 | 7 | 1 | YAC-7; RR.VH1.1; 1-69 |
| VH1-12-3 | 19 | 1 | DP3 |
| VH1-12-4 | 19 | 1 | DP21; 4d275a; VH7a |
| VH1-12-5 | 18 | 1 | I-4.1b; V1-4.1b |
| VH1-12-6 | 21 | 1 | 1D37; VH7b; 7-81; YAC-10 |
| VH1-12-7 | 19 | 1 | DP14; VH1GRR; V1-18 |
| VH1-13-1 | 10 | 1 | 71-5; DP2 |
| VH1-13-2 | 10 | 1 | E3-10 |
| VH1-13-3 | 19 | 1 | DP1 |
| VH1-13-4 | 12 | 1 | V35 |
| VH1-13-5 | 8 | 1 | V1-2b |
| VH1-13-6 | 18 | 1 | I-2; DP75 |
| VH1-13-7 | 21 | 1 | V1-2 |
| VH1-13-8 | 19 | 1 | DP8 |
| VH1-13-9 | 3 | 1 | 1-1 |
| VH1-13-10 | 19 | 1 | DP12 |
| VH1-13-11 | 15 | 1 | V13C |
| VH1-13-12 | 18 | 1 | I-3b; DP25; V1-3b |
| VH1-13-13 | 3 | 1 | 1-92 |
| VH1-13-14 | 18 | 1 | I-3; V1-3 |
| VH1-13-15 | 19 | 1 | DP15; V1-8 |
| VH1-13-16 | 3 | 1 | 21-2; 3-1; DP7; V1-46 |
| VH1-13-17 | 16 | 1 | HG3 |
| VH1-13-18 | 19 | 1 | DP4; 7-2; V1-45 |
| VH1-13-19 | 27 | 1 | COS 5 |
| VH1-1X-1 | 19 | 1 | DP5; 1-24P |
| VH2-21-1 | 18 | 2 | II-5b |
| VH2-31-1 | 2 | 2 | VH2S12-1 |
| VH2-31-2 | 2 | 2 | VH2S12-7 |
| VH2-31-3 | 2 | 2 | VH2S12-9; DP27 |
| VH2-31-4 | 2 | 2 | VH2S12-10 |
| VH2-31-5 | 14 | 2 | V2-26; DP26; 2-26 |
| VH2-31-6 | 15 | 2 | VF2-26 |
| VH2-31-7 | 19 | 2 | DP28; DA-7 |
| VH2-31-14 | 7 | 2 | YAC-3; 2-70 |
| VH2-31-8 | 2 | 2 | VH2S12-5 |
| VH2-31-9 | 2 | 2 | VH2S12-12 |
| VH2-31-10 | 18 | 2 | II-5; V2-5 |
| VH2-31-11 | 2 | 2 | VH2S12-2; VH2S12-8 |
| VH2-31-12 | 2 | 2 | VH2S12-4; VH2S12-6 |
| VH2-31-13 | 2 | 2 | VH2S12-14 |
| VH3-11-1 | 13 | 3 | v65-2; DP44 |
| VH3-11-2 | 19 | 3 | DP45 |
| VH3-11-3 | 3 | 3 | 13-2; DP48 |
| VH3-11-4 | 19 | 3 | DP52 |
| VH3-11-5 | 14 | 3 | v3-13 |
| VH3-11-6 | 19 | 3 | DP42 |
| VH3-11-7 | 3 | 3 | 8-1B; YAC-5; 3-66 |
| VH3-11-8 | 14 | 3 | V3-53 |
| VH3-13-1 | 3 | 3 | 22-2B; DP35; V3-11 |
| VH3-13-5 | 19 | 3 | DP59; VH19; V3-35 |
| VH3-13-6 | 25 | 3 | f1-p1; DP61 |
| VH3-13-7 | 19 | 3 | DP46; GL-SJ2; COS 8; hv3005; hv3005f3; 3d21b; 56p1 |
| VH3-13-8 | 24 | 3 | VH26 |
| VH3-13-9 | 5 | 3 | vh26c |
| VH3-13-10 | 19 | 3 | DP47; VH26; 3-23 |
| VH3-13-11 | 3 | 3 | 1-91 |
| VH3-13-12 | 19 | 3 | DP58 |
| VH3-13-13 | 3 | 3 | 1-9III; DP49; 3-30; 3d28.1 |
| VH3-13-14 | 24 | 3 | 3019B9; DP50; 3-33; 3d277 |
| VH3-13-15 | 27 | 3 | COS 3 |
| VH3-13-16 | 19 | 3 | DP51 |
| VH3-13-17 | 16 | 3 | H11 |
| VH3-13-18 | 19 | 3 | DP53; COS 6; 3-74; DA-8 |
| VH3-13-19 | 19 | 3 | DP54; VH3-11; V3-7 |
| VH3-13-20 | 14 | 3 | V3-64; YAC-6 |
| VH3-13-21 | 14 | 3 | V3-48 |
| VH3-13-22 | 14 | 3 | V3-43; DP33 |
| VH3-13-23 | 14 | 3 | V3-33 |
| VH3-13-24 | 14 | 3 | V3-21; DP77 |
| VH3-13-25 | 14 | 3 | V3-20; DP32 |

TABLE 1C-continued

Human heavy chain germline gene segments

| Used Name[1] | Reference[2] | Family[3] | Germline genes[4] |
|---|---|---|---|
| VH3-13-26 | 14 | 3 | V3-9; DP31 |
| VH3-14-1 | 3 | 3 | 12-2; DP29; 3-72; DA-3 |
| VH3-14-4 | 7 | 3 | YAC-9; 3-73; MTGL |
| VH3-14-2 | 4 | 3 | VHD26 |
| VH3-14-3 | 19 | 3 | DP30 |
| VH3-1X-1 | 1 | 3 | LSG8.1; LSG9.1; LSG10.1; HUM12IGVH; HUM13IGVH |
| VH3-1X-2 | 1 | 3 | LSG11.1; HUM4IGVH |
| VH3-1X-3 | 3 | 3 | 9-1; DP38; LSG7.1; RCG1.1; LSG1.1; LSG3.1; LSG5.1; HUM15IGVH; HUM2IGVH; HUM9IGVH |
| VH3-1X-4 | 1 | 3 | LSG4.1 |
| VH3-1X-5 | 1 | 3 | LSG2.1 |
| VH3-1X-6 | 1 | 3 | LSG6.1; HUM10IGVH |
| VH3-1X-7 | 18 | 3 | 3-15; V3-15 |
| VH3-1X-8 | 1 | 3 | LSG12.1; HUM5IGVH |
| VH3-1X-9 | 14 | 3 | V3-49 |
| VH4-11-1 | 22 | 4 | Tou-VH4.21 |
| VH4-11-2 | 17 | 4 | VH4.21; DP63; VH5; 4d76; V4-34 |
| VH4-11-3 | 23 | 4 | 4.44 |
| VH4-11-4 | 23 | 4 | 4.44.3 |
| VH4-11-5 | 23 | 4 | 4.36 |
| VH4-11-6 | 23 | 4 | 4.37 |
| VH4-11-7 | 18 | 4 | IV-4; 4.35; V4-4 |
| VH4-11-8 | 17 | 4 | VH4.11; 3d197d; DP71; 58p2 |
| VH4-11-9 | 20 | 4 | H7 |
| VH4-11-10 | 20 | 4 | H8 |
| VH4-11-11 | 20 | 4 | H9 |
| VH4-11-12 | 17 | 4 | VH4.16 |
| VH4-11-13 | 23 | 4 | 4.38 |
| VH4-11-14 | 17 | 4 | VH4.15 |
| VH4-11-15 | 11 | 4 | 58 |
| VH4-11-16 | 10 | 4 | 71-4; V4-59 |
| VH4-21-1 | 11 | 4 | 11 |
| VH4-21-2 | 17 | 4 | VH4.17; VH4.23; 4d255; 4.40; DP69 |
| VH4-21-3 | 17 | 4 | VH4.19; 79; V4-4b |
| VH4-21-4 | 19 | 4 | DP70; 4d68; 4.41 |
| VH4-21-5 | 19 | 4 | DP67; VH4-4B |
| VH4-21-6 | 17 | 4 | VH4.22; VHSP; VH-JA |
| VH4-21-7 | 17 | 4 | VH4.13; 1-9II; 12G-1; 3d28d; 4.42; DP68; 4-28 |
| VH4-21-8 | 26 | 4 | hv4005; 3d24d |
| VH4-21-9 | 17 | 4 | VH4.14 |
| VH4-31-1 | 23 | 4 | 4.34; 3d230d; DP78 |
| VH4-31-2 | 23 | 4 | 4.34.2 |
| VH4-31-3 | 19 | 4 | DP64; 3d216d |
| VH4-31-4 | 19 | 4 | DP65; 4-31; 3d277d |
| VH4-31-5 | 23 | 4 | 4.33; 3d75d |
| VH4-31-6 | 20 | 4 | H10 |
| VH4-31-7 | 20 | 4 | H11 |
| VH4-31-8 | 23 | 4 | 4.31 |
| VH4-31-9 | 23 | 4 | 4.32 |
| VH4-31-10 | 20 | 4 | 3d277d |
| VH4-31-11 | 20 | 4 | 3d216d |
| VH4-31-12 | 20 | 4 | 3d279d |
| VH4-31-13 | 17 | 4 | VH4.18; 4d154; DP79 |
| VH4-31-14 | 8 | 4 | V4-39 |
| VH4-31-15 | 11 | 4 | 2-1; DP79 |
| VH4-31-16 | 23 | 4 | 4.30 |
| VH4-31-17 | 17 | 4 | VH4.12 |
| VH4-31-18 | 10 | 4 | 71-2; DP66 |
| VH4-31-19 | 23 | 4 | 4.39 |
| VH4-31-20 | 8 | 4 | V4-61 |
| VH5-12-1 | 9 | 5 | VH251; DP73; VHVCW; 51-R1; VHVLB; VHVCH; VHVTT; VHVAU; VHVBLK; VhAU; V5-51 |
| VH5-12-2 | 17 | 5 | VHVJB |
| VH5-12-3 | 3 | 5 | 1-v; DP80; 5-78 |
| VH5-12-4 | 9 | 5 | VH32; VHVRG; VHVMW; 5-2R1 |
| VH6-35-1 | 4 | 6 | VHVI; VH6; VHVIIS; VHVITE; VHVIJB; VHVICH; VHVICW; VHVIBLK; VHVIMW; DP74; 6-1G1; V6-1 |

TABLE 2A rearranged human kappa sequences

| Name[1] | aa[2] | Computed family[3] | Germline gene[4] | Diff. to germline[5] | % diff. to germline[6] | Reference[7] |
|---|---|---|---|---|---|---|
| III-3R | 108 | 1 | O8 | 1 | 1.1% | 70 |
| No. 86 | 109 | 1 | O8 | 3 | 3.2% | 80 |
| AU | 108 | 1 | O8 | 6 | 6.3% | 103 |
| ROY | 108 | 1 | O8 | 6 | 6.3% | 43 |
| ICA | 108 | 1 | O8 | 6 | 6.3% | 70 |
| HIV-B26 | 106 | 1 | O8 | 3 | 3.2% | 8 |
| GRI | 108 | 1 | O8 | 8 | 8.4% | 30 |
| AG | 106 | 1 | O8 | 8 | 8.6% | 116 |
| REI | 108 | 1 | O8 | 9 | 9.5% | 86 |
| CLL PATIENT 16 | 88 | 1 | O8 | 2 | 2.3% | 122 |
| CLL PATIENT 14 | 87 | 1 | O8 | 2 | 2.3% | 122 |
| CLL PATIENT 15 | 88 | 1 | O8 | 2 | 2.3% | 122 |
| GM4672 | 108 | 1 | O8 | 11 | 11.6% | 24 |
| HUM. YFC51.1 | 108 | 1 | O8 | 12 | 12.6% | 110 |
| LAY | 108 | 1 | O8 | 12 | 12.6% | 48 |
| HIV-b13 | 106 | 1 | O8 | 9 | 9.7% | 8 |
| MAL-NaCl | 108 | 1 | O8 | 13 | 13.7% | 102 |
| STRAb SA-1A | 108 | 1 | O2 | 0 | 0.0% | 120 |
| HuVHCAMP | 108 | 1 | O8 | 13 | 13.7% | 100 |
| CRO | 108 | 1 | O2 | 10 | 10.5% | 30 |
| Am 107 | 108 | 1 | O2 | 12 | 12.6% | 108 |
| WALKER | 107 | 1 | O2 | 4 | 4.2% | 57 |
| III-2R | 109 | 1 | A20 | 0 | 0.0% | 70 |
| FOG1-A4 | 107 | 1 | A20 | 4 | 4.2% | 41 |
| HK137 | 95 | 1 | L1 | 0 | 0.0% | 10 |
| CEA4-8A | 107 | 1 | O2 | 7 | 7.4% | 41 |
| Va' | 95 | 1 | L4 | 0 | 0.0% | 90 |
| TR1.21 | 108 | 1 | O2 | 4 | 4.2% | 92 |
| HAU | 108 | 1 | O2 | 6 | 6.3% | 123 |
| HK102 | 95 | 1 | L12(1) | 0 | 0.0% | 9 |
| H20C3K | 108 | 1 | L12(2) | 3 | 3.2% | 125 |
| CHEB | 108 | 1 | O2 | 7 | 7.4% | 5 |
| HK134 | 95 | 1 | L15(2) | 0 | 0.0% | 10 |
| TEL9 | 108 | 1 | O2 | 9 | 9.5% | 73 |
| TR1.32 | 103 | 1 | O2 | 3 | 3.2% | 92 |
| RF-KES1 | 97 | 1 | A20 | 4 | 4.2% | 121 |
| WES | 108 | 1 | L5 | 10 | 10.5% | 61 |
| DILp1 | 95 | 1 | O4 | 1 | 1.1% | 70 |
| SA-4B | 107 | 1 | L12(2) | 8 | 8.4% | 120 |
| HK101 | 95 | 1 | L15(1) | 0 | 0.0% | 9 |
| TR1.23 | 108 | 1 | O2 | 5 | 5.3% | 92 |
| HF2-1/17 | 108 | 1 | A30 | 0 | 0.0% | 4 |
| 2E7 | 108 | 1 | A30 | 1 | 1.1% | 62 |
| 33.C9 | 107 | 1 | L12(2) | 7 | 7.4% | 126 |
| 3D6 | 105 | 1 | L12(2) | 2 | 2.1% | 34 |
| I-2a | 108 | 1 | L8 | 8 | 8.4% | 70 |
| RF-KL1 | 97 | 1 | L8 | 4 | 4.2% | 121 |
| TNF-E7 | 108 | 1 | A30 | 9 | 9.5% | 41 |
| TR1.22 | 108 | 1 | O2 | 7 | 7.4% | 92 |
| HIV-B35 | 106 | 1 | O2 | 2 | 2.2% | 8 |
| HIV-b22 | 106 | 1 | O2 | 2 | 2.2% | 8 |
| HIV-b27 | 106 | 1 | O2 | 2 | 2.2% | 8 |
| HIV-B8 | 107 | 1 | O2 | 10 | 10.8% | 8 |
| HIV-b8 | 107 | 1 | O2 | 10 | 10.8% | 8 |
| RF-SJ5 | 95 | 1 | A30 | 5 | 5.3% | 113 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| GAL(I) | 108 | 1 | A30 | 6 | 6.3% | 64 |
| R3.5H5G | 108 | 1 | O2 | 6 | 6.3% | 70 |
| HIV-b14 | 106 | 1 | A20 | 2 | 2.2% | 8 |
| TNF-E1 | 105 | 1 | L5 | 8 | 8.4% | 41 |
| WEA | 108 | 1 | A30 | 8 | 8.4% | 37 |
| EU | 108 | 1 | L12(2) | 5 | 5.3% | 40 |
| FOG1-G8 | 108 | 1 | L8 | 11 | 11.6% | 41 |
| 1X7RG1 | 108 | 1 | L1 | 8 | 8.4% | 70 |
| BLI | 108 | 1 | L8 | 3 | 3.2% | 72 |
| KUE | 108 | 1 | L12(2) | 11 | 11.6% | 32 |
| LUNm01 | 108 | 1 | L12(2) | 10 | 10.5% | 6 |
| HIV-b1 | 106 | 1 | A20 | 4 | 4.3% | 8 |
| HIV-s4 | 103 | 1 | O2 | 2 | 2.2% | 8 |
| CAR | 107 | 1 | L12(2) | 11 | 11.7% | 79 |
| BR | 107 | 1 | L12(2) | 11 | 11.6% | 50 |
| CLL PATIENT 10 | 88 | 1 | O2 | 0 | 0.0% | 122 |
| CLL PATIENT 12 | 88 | 1 | O2 | 0 | 0.0% | 122 |
| KING | 108 | 1 | L12(2) | 12 | 12.6% | 30 |
| V13 | 95 | 1 | L24 | 0 | 0.0% | 46 |
| CLL PATIENT 11 | 87 | 1 | O2 | 0 | 0.0% | 122 |
| CLL PATIENT 13 | 87 | 1 | O2 | 0 | 0.0% | 122 |
| CLL PATIENT 9 | 88 | 1 | O12 | 1 | 1.1% | 122 |
| HIV-B2 | 106 | 1 | A20 | 9 | 9.7% | 8 |
| HIV-b2 | 106 | 1 | A20 | 9 | 9.7% | 8 |
| CLL PATIENT 5 | 88 | 1 | A20 | 1 | 1.1% | 122 |
| CLL PATIENT 1 | 88 | 1 | L8 | 2 | 2.3% | 122 |
| CLL PATIENT 2 | 88 | 1 | L8 | 0 | 0.0% | 122 |
| CLL PATIENT 7 | 88 | 1 | L5 | 0 | 0.0% | 122 |
| CLL PATIENT 8 | 88 | 1 | L5 | 0 | 0.0% | 122 |
| HIV-b5 | 105 | 1 | L5 | 11 | 12.0% | 8 |
| CLL PATIENT 3 | 87 | 1 | L8 | 1 | 1.1% | 122 |
| CLL PATIENT 4 | 88 | 1 | L9 | 0 | 0.0% | 122 |
| CLL PATIENT 18 | 85 | 1 | L9 | 6 | 7.1% | 122 |
| CLL PATIENT 17 | 86 | 1 | L12(2) | 7 | 8.1% | 122 |
| HIV-b20 | 107 | 3 | A27 | 11 | 11.7% | 8 |
| 2C12 | 108 | 1 | L12(2) | 20 | 21.1% | 68 |
| 1B11 | 108 | 1 | L12(2) | 20 | 21.1% | 68 |
| 1H1 | 108 | 1 | L12(2) | 21 | 22.1% | 68 |
| 2A12 | 108 | 1 | L12(2) | 21 | 22.1% | 68 |
| CUR | 109 | 3 | A27 | 0 | 0.0% | 66 |
| GLO | 109 | 3 | A27 | 0 | 0.0% | 16 |
| RF-TS1 | 96 | 3 | A27 | 0 | 0.0% | 121 |
| GAR' | 109 | 3 | A27 | 0 | 0.0% | 67 |
| FLO | 109 | 3 | A27 | 0 | 0.0% | 66 |
| PIE | 109 | 3 | A27 | 0 | 0.0% | 91 |
| HAH 14.1 | 109 | 3 | A27 | 1 | 1.0% | 51 |
| HAH 14.2 | 109 | 3 | A27 | 1 | 1.0% | 51 |
| HAH 16.1 | 109 | 3 | A27 | 1 | 1.0% | 51 |
| NOV | 109 | 3 | A27 | 1 | 1.0% | 52 |
| 33.F12 | 108 | 3 | A27 | 1 | 1.0% | 126 |
| BE10 | 110 | 3 | A27 | 1 | 1.0% | 25 |
| TH3 | 109 | 3 | A27 | 1 | 1.0% | 25 |
| HIC(R) | 108 | 3 | A27 | 0 | 0.0% | 51 |
| SON | 110 | 3 | A27 | 1 | 1.0% | 67 |
| PAY | 109 | 3 | A27 | 1 | 1.0% | 66 |
| GOT | 109 | 3 | A27 | 1 | 1.0% | 67 |
| mAbA6H4C5 | 109 | 3 | A27 | 1 | 1.0% | 12 |
| BOR' | 109 | 3 | A27 | 2 | 2.1% | 84 |
| RF-SJ3 | 96 | 3 | A27 | 2 | 2.1% | 121 |
| SIE | 109 | 3 | A27 | 2 | 2.1% | 15 |
| ESC | 109 | 3 | A27 | 2 | 2.1% | 98 |
| HEW' | 110 | 3 | A27 | 2 | 2.1% | 98 |
| YES8c | 109 | 3 | A27 | 3 | 3.1% | 33 |
| TI | 109 | 3 | A27 | 3 | 3.1% | 114 |
| mAb113 | 109 | 3 | A27 | 3 | 3.1% | 71 |
| HEW | 107 | 3 | A27 | 0 | 0.0% | 94 |
| BRO | 106 | 3 | A27 | 0 | 0.0% | 94 |
| ROB | 106 | 3 | A27 | 0 | 0.0% | 94 |
| NG9 | 96 | 3 | A27 | 4 | 4.2% | 11 |
| NEU | 109 | 3 | A27 | 4 | 4.2% | 66 |
| WOL | 109 | 3 | A27 | 4 | 4.2% | 2 |
| 35G6 | 109 | 3 | A27 | 4 | 4.2% | 59 |
| RF-SJ4 | 109 | 3 | A11 | 0 | 0.0% | 88 |
| KAS | 109 | 3 | A27 | 4 | 4.2% | 84 |
| BRA | 106 | 3 | A27 | 1 | 1.1% | 94 |
| HAH | 106 | 3 | A27 | 1 | 1.1% | 94 |
| HIC | 105 | 3 | A27 | 0 | 0.0% | 94 |
| FS-2 | 109 | 3 | A27 | 6 | 6.3% | 87 |
| JH' | 107 | 3 | A27 | 6 | 6.3% | 38 |
| EV1-15 | 109 | 3 | A27 | 6 | 6.3% | 83 |
| SCA | 108 | 3 | A27 | 6 | 6.3% | 65 |
| mAb112 | 109 | 3 | A27 | 6 | 6.3% | 71 |
| SIC | 103 | 3 | A27 | 3 | 3.3% | 94 |
| 5A-4A | 109 | 3 | A27 | 6 | 6.3% | 120 |
| SER | 108 | 3 | A27 | 6 | 6.3% | 98 |
| GOL' | 109 | 3 | A27 | 7 | 7.3% | 82 |
| B5G10K | 105 | 3 | A27 | 9 | 9.7% | 125 |
| HG2B10K | 110 | 3 | A27 | 9 | 9.4% | 125 |
| Taykv322 | 105 | 3 | A27 | 5 | 5.4% | 52 |
| CLL PATIENT 24 | 89 | 3 | A27 | 1 | 1.1% | 122 |
| HIV-b24 | 107 | 3 | A27 | 7 | 7.4% | 8 |
| HIV-b6 | 107 | 3 | A27 | 7 | 7.4% | 8 |
| Taykv310 | 99 | 3 | A27 | 1 | 1.1% | 52 |
| KA3D1 | 108 | 3 | L6 | 0 | 0.0% | 85 |
| 19.E7 | 107 | 3 | L6 | 0 | 0.0% | 126 |
| rsv6L | 109 | 3 | A27 | 12 | 12.5% | 7 |
| Taykv320 | 98 | 3 | A27 | 1 | 1.2% | 52 |
| Vh | 96 | 3 | L10(2) | 0 | 0.0% | 89 |
| LS8 | 108 | 3 | L6 | 1 | 1.1% | 109 |
| LS1 | 108 | 3 | L6 | 1 | 1.1% | 109 |
| LS2S3-3 | 107 | 3 | L6 | 2 | 2.1% | 99 |
| LS2 | 108 | 3 | L6 | 1 | 1.1% | 109 |
| LS7 | 108 | 3 | L6 | 1 | 1.1% | 109 |
| LS2S3-4d | 107 | 3 | L6 | 2 | 2.1% | 99 |
| LS2S3-4a | 107 | 3 | L6 | 2 | 2.1% | 99 |
| LS4 | 108 | 3 | L6 | 1 | 1.1% | 109 |
| LS6 | 108 | 3 | L6 | 1 | 1.1% | 109 |
| LS2S3-10a | 107 | 3 | L6 | 2 | 2.1% | 99 |
| LS2S3-8c | 107 | 3 | L6 | 2 | 2.1% | 99 |
| LS5 | 108 | 3 | L6 | 1 | 1.1% | 109 |
| LS2S3-5 | 107 | 3 | L6 | 3 | 3.2% | 99 |
| LUNm03 | 109 | 3 | A27 | 13 | 13.5% | 6 |
| IARC/BL41 | 108 | 3 | A27 | 13 | 13.7% | 55 |
| slkv2Z | 99 | 3 | A27 | 3 | 3.5% | 13 |
| POP | 108 | 3 | L6 | 4 | 4.2% | 111 |
| LS2S3-10b | 107 | 3 | L6 | 3 | 3.2% | 99 |
| LS2S3-8f | 107 | 3 | L6 | 3 | 3.2% | 99 |
| LS2S3-12 | 107 | 3 | L6 | 3 | 3.2% | 99 |
| HIV-B30 | 107 | 3 | A27 | 11 | 11.7% | 8 |
| HIV-B20 | 107 | 3 | A27 | 11 | 11.7% | 8 |
| HIV-b3 | 108 | 3 | A27 | 11 | 11.7% | 8 |
| HIV-s6 | 104 | 3 | A27 | 9 | 9.9% | 8 |
| YSE | 107 | 3 | L2/L16 | 1 | 1.1% | 72 |
| POM | 109 | 3 | L2/L16 | 9 | 9.4% | 53 |
| Humkv328 | 95 | 3 | L2/L16 | 1 | 1.1% | 19 |
| CLL | 109 | 3 | L2/L16 | 3 | 3.2% | 47 |
| LES | 96 | 3 | L2/L16 | 3 | 3.2% | 38 |
| HIV-s5 | 104 | 3 | A27 | 11 | 12.1% | 8 |
| HIV-s7 | 104 | 3 | A27 | 11 | 12.1% | 8 |
| slkv1 | 99 | 3 | A27 | 7 | 8.1% | 13 |
| Humka31es | 95 | 3 | L2/L16 | 4 | 4.2% | 18 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| slkv12 | 101 | 3 | A27 | 8 | 9.2% | 13 |
| RF-TS2 | 95 | 3 | L2/L16 | 3 | 3.2% | 121 |
| II-1 | 109 | 3 | L2/L16 | 4 | 4.2% | 70 |
| HIV-s3 | 105 | 3 | A27 | 13 | 14.3% | 8 |
| RF-TMC1 | 96 | 3 | L6 | 10 | 10.5% | 121 |
| GER | 109 | 3 | L2/L16 | 7 | 7.4% | 75 |
| GF4/1.1 | 109 | 3 | L2/L16 | 8 | 8.4% | 36 |
| mAb114 | 109 | 3 | L2/L16 | 6 | 6.3% | 71 |
| HIV-loop13 | 109 | 3 | L2/L16 | 7 | 7.4% | 8 |
| bkv16 | 86 | 3 | L6 | 1 | 1.2% | 13 |
| CLL PATIENT 29 | 86 | 3 | L6 | 1 | 1.2% | 122 |
| slkv9 | 98 | 3 | L6 | 3 | 3.5% | 13 |
| bkv17 | 99 | 3 | L6 | 1 | 1.2% | 13 |
| slkv14 | 99 | 3 | L6 | 1 | 1.2% | 13 |
| slkv16 | 101 | 3 | L6 | 2 | 2.3% | 13 |
| bkv33 | 101 | 3 | L6 | 4 | 4.7% | 13 |
| slkv15 | 99 | 3 | L6 | 2 | 2.3% | 13 |
| bkv6 | 100 | 3 | L6 | 3 | 3.5% | 13 |
| R688K | 108 | 3 | L2/L16 | 12 | 12.6% | 125 |
| AL 700 | 107 | 3 | L2/L16 | 9 | 9.5% | 117 |
| slkv11 | 100 | 3 | L2/L16 | 3 | 3.5% | 13 |
| slkv4 | 97 | 3 | L6 | 4 | 4.8% | 13 |
| CLL PATIENT 26 | 87 | 3 | L2/L16 | 1 | 1.1% | 122 |
| AL Se124 | 103 | 3 | L2/L16 | 9 | 9.5% | 117 |
| slkv13 | 100 | 3 | L2/L16 | 6 | 7.0% | 13 |
| bkv7 | 100 | 3 | L2/L16 | 5 | 5.8% | 13 |
| bkv22 | 100 | 3 | L2/L16 | 6 | 7.0% | 13 |
| CLL PATIENT 27 | 84 | 3 | L2/L16 | 0 | 0.0% | 122 |
| bkv35 | 100 | 3 | L6 | 8 | 9.3% | 13 |
| CLL PATIENT 25 | 87 | 3 | L2/L16 | 4 | 4.6% | 122 |
| slkv3 | 86 | 3 | L2/L16 | 7 | 8.1% | 13 |
| slkv7 | 99 | 1 | O2 | 7 | 8.1% | 13 |
| HuFd79 | 111 | 3 | L2/L16 | 24 | 24.2% | 21 |
| RAD | 99 | 3 | A27 | 9 | 10.3% | 78 |
| CLL PATIENT 28 | 83 | 3 | L2/L16 | 4 | 4.8% | 122 |
| REE | 104 | 3 | L2/L16 | 25 | 27.2% | 95 |
| FR4 | 99 | 3 | A27 | 8 | 9.2% | 77 |
| MD3.3 | 92 | 3 | L6 | 1 | 1.3% | 54 |
| MD3.1 | 92 | 3 | L6 | 0 | 0.0% | 54 |
| GA3.6 | 92 | 3 | L6 | 2 | 2.6% | 54 |
| M3.5N | 92 | 3 | L6 | 3 | 3.8% | 54 |
| WEI' | 82 | 3 | A27 | 0 | 0.0% | 65 |
| MD3.4 | 92 | 3 | L2/L16 | 1 | 1.3% | 54 |
| MD3.2 | 91 | 3 | L6 | 3 | 3.8% | 54 |
| VER | 97 | 3 | A27 | 19 | 22.4% | 20 |
| CLL PATIENT 30 | 78 | 3 | L6 | 3 | 3.8% | 122 |
| M3.1N | 92 | 3 | L2/L16 | 1 | 1.3% | 54 |
| MD3.6 | 91 | 3 | L2/L16 | 0 | 0.0% | 54 |
| MD3.8 | 91 | 3 | L2/L16 | 0 | 0.0% | 54 |
| GA3.4 | 92 | 3 | L6 | 7 | 9.0% | 54 |
| M3.6N | 92 | 3 | A27 | 0 | 0.0% | 54 |
| MD3.10 | 92 | 3 | A27 | 0 | 0.0% | 54 |
| MD3.13 | 91 | 3 | A27 | 0 | 0.0% | 54 |
| MD3.7 | 93 | 3 | A27 | 0 | 0.0% | 54 |
| MD3.9 | 93 | 3 | A27 | 0 | 0.0% | 54 |
| GA3.1 | 93 | 3 | A27 | 6 | 7.6% | 54 |
| bkv32 | 101 | 3 | A27 | 5 | 5.7% | 13 |
| GA3.5 | 93 | 3 | A27 | 5 | 6.3% | 54 |
| GA3.7 | 92 | 3 | A27 | 7 | 8.9% | 54 |
| MD3.12 | 92 | 3 | A27 | 2 | 2.5% | 54 |
| M3.2N | 90 | 3 | L6 | 6 | 7.8% | 54 |
| MD3.5 | 92 | 3 | A27 | 1 | 1.3% | 54 |
| M3.4N | 91 | 3 | L2/L16 | 8 | 10.3% | 54 |
| M3.8N | 91 | 3 | L2/L16 | 7 | 9.0% | 54 |
| M3.7N | 92 | 3 | A27 | 3 | 3.8% | 54 |
| GA3.2 | 92 | 3 | A27 | 9 | 11.4% | 54 |
| GA3.8 | 93 | 3 | A27 | 4 | 5.1% | 54 |
| GA3.3 | 92 | 3 | A27 | 8 | 10.1% | 54 |
| M3.3N | 92 | 3 | A27 | 5 | 6.3% | 54 |
| B6 | 83 | 3 | A27 | 8 | 11.3% | 78 |
| E29.1 KAPPA | 78 | 3 | L2/L16 | 0 | 0.0% | 22 |
| SCW | 108 | 1 | O8 | 12 | 12.6% | 31 |
| REI-based CAMPATH-9 | 107 | 1 | O8 | 14 | 14.7% | 39 |
| RZ | 107 | 1 | O8 | 14 | 14.7% | 50 |
| BI | 108 | 1 | O8 | 14 | 14.7% | 14 |
| AND | 107 | 1 | O2 | 13 | 13.7% | 69 |
| 2A4 | 109 | 1 | O2 | 12 | 12.6% | 23 |
| KA | 108 | 1 | O8 | 19 | 20.0% | 107 |
| MEV | 109 | 1 | O2 | 14 | 14.7% | 29 |
| DEE | 106 | 1 | O2 | 13 | 14.0% | 76 |
| OU(IOC) | 108 | 1 | O2 | 18 | 18.9% | 60 |
| HuRSV19VK | 111 | 1 | O8 | 21 | 21.0% | 115 |
| SP2 | 108 | 1 | O2 | 17 | 17.9% | 93 |
| BJ26 | 99 | 1 | O8 | 21 | 24.1% | 1 |
| N1 | 112 | 1 | O8 | 24 | 24.2% | 106 |
| BMA 0310EUCIV2 | 106 | 1 | L12(1) | 21 | 22.3% | 105 |
| CLL PATIENT 6 | 71 | 1 | A20 | 0 | 0.0% | 122 |
| BJ19 | 85 | 1 | O8 | 16 | 21.9% | 1 |
| GM 607 | 113 | 2 | A3 | 0 | 0.0% | 58 |
| R5A3K | 114 | 2 | A3 | 1 | 1.0% | 125 |
| R1C8K | 114 | 2 | A3 | 1 | 1.0% | 125 |
| VK2.R149 | 113 | 2 | A3 | 2 | 2.0% | 118 |
| TR1.6 | 109 | 2 | A3 | 4 | 4.0% | 92 |
| TR1.37 | 104 | 2 | A3 | 5 | 5.0% | 92 |
| FS-1 | 113 | 2 | A3 | 6 | 6.0% | 87 |
| TR1.8 | 110 | 2 | A3 | 6 | 6.0% | 92 |
| NIM | 113 | 2 | A3 | 8 | 8.0% | 28 |
| Inc | 112 | 2 | A3 | 11 | 11.0% | 35 |
| TEW | 107 | 2 | A3 | 6 | 6.4% | 96 |
| CUM | 114 | 2 | O1 | 7 | 6.9% | 44 |
| HRF1 | 71 | 2 | A3 | 4 | 5.6% | 124 |
| CLL PATIENT 19 | 87 | 2 | A3 | 0 | 0.0% | 122 |
| CLL PATIENT 20 | 87 | 2 | A3 | 0 | 0.0% | 122 |
| MIL | 112 | 2 | A3 | 16 | 16.2% | 26 |
| FR | 113 | 2 | A3 | 20 | 20.0% | 101 |
| MAL-Urine | 83 | 1 | O2 | 6 | 8.6% | 102 |
| Taykv306 | 73 | 3 | A27 | 1 | 1.6% | 52 |
| Taykv312 | 75 | 3 | A27 | 1 | 1.6% | 52 |
| HIV-b29 | 93 | 3 | A27 | 14 | 17.5% | 8 |
| 1-185-37 | 110 | 3 | A27 | 0 | 0.0% | 119 |
| 1-187-29 | 110 | 3 | A27 | 0 | 0.0% | 119 |
| TT117 | 110 | 3 | A27 | 9 | 9.4% | 63 |
| HIV-loop8 | 108 | 3 | A27 | 16 | 16.8% | 8 |
| rsv23L | 108 | 3 | A27 | 16 | 16.8% | 7 |
| HIV-b7 | 107 | 3 | A27 | 14 | 14.9% | 8 |
| HIV-b11 | 107 | 3 | A27 | 15 | 16.0% | 8 |
| HIV-LC1 | 107 | 3 | A27 | 19 | 20.2% | 8 |
| HIV-LC7 | 107 | 3 | A27 | 20 | 21.3% | 8 |
| HIV-LC22 | 107 | 3 | A27 | 21 | 22.3% | 8 |
| HIV-LC13 | 107 | 3 | A27 | 21 | 22.3% | 8 |
| HIV-LC3 | 107 | 3 | A27 | 21 | 22.3% | 8 |
| HIV-LC5 | 107 | 3 | A27 | 21 | 22.3% | 8 |
| HIV-LC28 | 107 | 3 | A27 | 21 | 22.3% | 8 |
| HIV-b4 | 107 | 3 | A27 | 22 | 23.4% | 8 |
| CLL PATIENT 31 | 87 | 3 | A27 | 15 | 17.2% | 122 |
| HIV-loop2 | 108 | 3 | L2/L16 | 17 | 17.9% | 8 |
| HIV-loop35 | 108 | 3 | L2/L16 | 17 | 17.9% | 8 |
| HIV-LC11 | 107 | 3 | A27 | 23 | 24.5% | 8 |
| HIV-LC24 | 107 | 3 | A27 | 23 | 24.5% | 8 |
| HIV-b12 | 107 | 3 | A27 | 24 | 25.5% | 8 |
| HIV-LC25 | 107 | 3 | A27 | 24 | 25.5% | 8 |
| HIV-b21 | 107 | 3 | A27 | 24 | 25.5% | 8 |
| HIV-LC26 | 107 | 3 | A27 | 26 | 27.7% | 8 |
| G3D10k | 108 | 1 | L12(2) | 12 | 12.6% | 125 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| TT125 | 108 | 1 | L5 | 8 | 8.4% | 63 |
| HIV-s2 | 103 | 3 | A27 | 28 | 31.1% | 8 |
| 265-695 | 108 | 1 | L5 | 7 | 7.4% | 3 |
| 2-115-19 | 108 | 1 | A30 | 2 | 2.1% | 119 |
| rsv13L | 107 | 1 | O2 | 20 | 21.1% | 7 |
| HIV-b18 | 106 | 1 | O2 | 14 | 15.1% | 8 |
| RF-KL5 | 98 | 3 | L6 | 36 | 36.7% | 97 |
| ZM1-1 | 113 | 2 | A17 | 7 | 7.0% | 3 |
| HIV-s8 | 103 | 1 | O8 | 16 | 17.8% | 8 |
| K-EV15 | 95 | 5 | B2 | 0 | 0.0% | 112 |
| RF-TS3 | 100 | 2 | A23 | 0 | 0.0% | 121 |
| HF-21/28 | 111 | 2 | A17 | 1 | 1.0% | 17 |
| RPMI6410 | 113 | 2 | A17 | 1 | 1.0% | 42 |
| JC11 | 113 | 2 | A17 | 1 | 1.0% | 49 |
| O-81 | 114 | 2 | A17 | 5 | 5.0% | 45 |
| FK-001 | 113 | 4 | B3 | 0 | 0.0% | 81 |
| CD5+.28 | 101 | 4 | B3 | 1 | 1.0% | 27 |
| LEN | 114 | 4 | B3 | 1 | 1.0% | 104 |
| UC | 114 | 4 | B3 | 1 | 1.0% | 111 |
| CD5+.5 | 101 | 4 | B3 | 1 | 1.0% | 27 |
| CD5+.26 | 101 | 4 | B3 | 1 | 1.0% | 27 |
| CD5+.12 | 101 | 4 | B3 | 2 | 2.0% | 27 |
| CD5+.23 | 101 | 4 | B3 | 2 | 2.0% | 27 |
| CD5+.7 | 101 | 4 | B3 | 2 | 2.0% | 27 |
| VJI | 113 | 4 | B3 | 3 | 3.0% | 56 |
| LOC | 113 | 4 | B3 | 3 | 3.0% | 72 |
| MAL | 113 | 4 | B3 | 3 | 3.0% | 72 |
| CD5+.6 | 101 | 4 | B3 | 3 | 3.0% | 27 |
| H2F | 113 | 4 | B3 | 3 | 3.0% | 70 |
| PB17IV | 114 | 4 | B3 | 4 | 4.0% | 74 |
| CD5+.27 | 101 | 4 | B3 | 4 | 4.0% | 27 |
| CD5+.9 | 101 | 4 | B3 | 4 | 4.0% | 27 |
| CD5-.28 | 101 | 4 | B3 | 5 | 5.0% | 27 |
| CD5-.26 | 101 | 4 | B3 | 6 | 5.9% | 27 |
| CD5+.24 | 101 | 4 | B3 | 6 | 5.9% | 27 |
| CD5+.10 | 101 | 4 | B3 | 6 | 5.9% | 27 |
| CD5-.19 | 101 | 4 | B3 | 6 | 5.9% | 27 |
| CD5-.18 | 101 | 4 | B3 | 7 | 6.9% | 27 |
| CD5-.16 | 101 | 4 | B3 | 8 | 7.9% | 27 |
| CD5-.24 | 101 | 4 | B3 | 8 | 7.9% | 27 |
| CD5-.17 | 101 | 4 | B3 | 10 | 9.9% | 27 |
| MD4.1 | 92 | 4 | B3 | 0 | 0.0% | 54 |
| MD4.4 | 92 | 4 | B3 | 0 | 0.0% | 54 |
| MD4.5 | 92 | 4 | B3 | 0 | 0.0% | 54 |
| MD4.6 | 92 | 4 | B3 | 0 | 0.0% | 54 |
| MD4.7 | 92 | 4 | B3 | 0 | 0.0% | 54 |
| MD4.2 | 92 | 4 | B3 | 1 | 1.3% | 54 |
| MD4.3 | 92 | 4 | B3 | 5 | 6.3% | 54 |
| CLL PATIENT 22 | 87 | 2 | A17 | 2 | 2.3% | 122 |
| CLL PATIENT 23 | 84 | 2 | A17 | 2 | 2.4% | 122 |

TABLE 2B rearranged human lambda sequences

| Name[1] | aa[2] | Computed family[3] | Germline gene[4] | Diff. to germline[5] | % diff. to germline[6] | Reference[7] |
|---|---|---|---|---|---|---|
| WAH | 110 | 1 | DPL3 | 7 | 7% | 68 |
| 1B9/F2 | 112 | 1 | DPL3 | 7 | 7% | 9 |
| DIA | 112 | 1 | DPL2 | 7 | 7% | 36 |
| mAb67 | 89 | 1 | DPL3 | 0 | 0% | 29 |
| HiH2 | 110 | 1 | DPL3 | 12 | 11% | 3 |
| NIG-77 | 112 | 1 | DPL2 | 9 | 9% | 72 |
| OKA | 112 | 1 | DPL2 | 7 | 7% | 84 |
| KOL | 112 | 1 | DPL2 | 12 | 11% | 40 |
| T2:C5 | 111 | 1 | DPL5 | 0 | 0% | 6 |
| T2:C14 | 110 | 1 | DPL5 | 0 | 0% | 6 |
| PR-TS1 | 110 | 1 | DPL5 | 0 | 0% | 55 |
| 4G12 | 111 | 1 | DPL5 | 1 | 1% | 35 |
| KIM46L | 112 | 1 | HUMLV117 | 0 | 0% | 8 |
| Fog-B | 111 | 1 | DPL5 | 3 | 3% | 31 |
| 9F2L | 111 | 1 | DPL5 | 3 | 3% | 79 |
| mAb111 | 110 | 1 | DPL5 | 3 | 3% | 48 |
| PHOX15 | 111 | 1 | DPL5 | 4 | 4% | 49 |
| BL2 | 111 | 1 | DPL5 | 4 | 4% | 74 |
| NIG-64 | 111 | 1 | DPL5 | 4 | 4% | 72 |
| RF-SJ2 | 100 | 1 | DPL5 | 6 | 6% | 78 |
| AL EZI | 112 | 1 | DPL5 | 7 | 7% | 41 |
| ZIM | 112 | 1 | HUMLV117 | 7 | 7% | 18 |
| RF-SJ1 | 100 | 1 | DPL5 | 9 | 9% | 78 |
| IGLV1.1 | 98 | 1 | DPL4 | 0 | 0% | 1 |
| NEW | 112 | 1 | HUMLV117 | 11 | 10% | 42 |
| CB-201 | 87 | 1 | DPL2 | 1 | 1% | 62 |
| MEM | 109 | 1 | DPL2 | 6 | 6% | 50 |

TABLE 2B-continued rearranged human lambda sequences

| Name[1] | aa[2] | Computed family[3] | Germline gene[4] | Diff. to germline[5] | % diff. to germline[6] | Reference[7] |
|---|---|---|---|---|---|---|
| H210 | 111 | 2 | DPL10 | 4 | 4% | 45 |
| NOV | 110 | 2 | DPL10 | 8 | 8% | 25 |
| NEI | 111 | 2 | DPL10 | 8 | 8% | 24 |
| AL MC | 110 | 2 | DPL11 | 6 | 6% | 28 |
| MES | 112 | 2 | DPL11 | 8 | 8% | 84 |
| FOG1-A3 | 111 | 2 | DPL11 | 9 | 9% | 27 |
| AL NOV | 112 | 2 | DPL11 | 7 | 7% | 28 |
| HMST-1 | 110 | 2 | DPL11 | 4 | 4% | 82 |
| HBW4-1 | 108 | 2 | DPL12 | 9 | 9% | 52 |
| WH | 110 | 2 | DPL11 | 11 | 11% | 34 |
| 11-50 | 110 | 2 | DPL11 | 7 | 7% | 82 |
| HBp2 | 110 | 2 | DPL12 | 8 | 8% | 3 |
| NIG-84 | 113 | 2 | DPL11 | 12 | 11% | 73 |
| VIL | 112 | 2 | DPL11 | 9 | 9% | 58 |
| TRO | 111 | 2 | DPL12 | 10 | 10% | 61 |
| ES492 | 108 | 2 | DPL11 | 15 | 15% | 76 |
| mAb216 | 89 | 2 | DPL12 | 1 | 1% | 7 |
| BSA3 | 109 | 3 | DPL16 | 0 | 0% | 49 |
| THY-29 | 110 | 3 | DPL16 | 0 | 0% | 27 |
| PR-TS2 | 108 | 3 | DPL16 | 0 | 0% | 55 |
| E29.1 LAMBDA | 107 | 3 | DPL16 | 1 | 1% | 13 |
| mAb63 | 109 | 3 | DPL16 | 2 | 2% | 29 |
| TEL14 | 110 | 3 | DPL16 | 6 | 6% | 49 |
| 6H-3C4 | 108 | 3 | DPL16 | 7 | 7% | 39 |
| SH | 109 | 3 | DPL16 | 7 | 7% | 70 |
| AL GIL | 109 | 3 | DPL16 | 8 | 8% | 23 |
| H6-3C4 | 108 | 3 | DPL16 | 8 | 8% | 83 |
| V-lambda-2.DS | 111 | 2 | DPL11 | 3 | 3% | 15 |
| 8.12 ID | 110 | 2 | DPL11 | 3 | 3% | 81 |
| DSC | 111 | 2 | DPL11 | 3 | 3% | 56 |
| PV11 | 110 | 2 | DPL11 | 1 | 1% | 56 |
| 33.H11 | 110 | 2 | DPL11 | 4 | 4% | 81 |
| AS17 | 111 | 2 | DPL11 | 7 | 7% | 56 |
| SD6 | 110 | 2 | DPL11 | 7 | 7% | 56 |
| KS3 | 110 | 2 | DPL11 | 9 | 9% | 56 |
| PV6 | 110 | 2 | DPL12 | 5 | 5% | 56 |
| NGD9 | 110 | 2 | DPL11 | 7 | 7% | 56 |
| MUC1-1 | 111 | 2 | DPL11 | 11 | 10% | 27 |
| A30c | 111 | 2 | DPL10 | 6 | 6% | 56 |
| KS6 | 110 | 2 | DPL12 | 6 | 6% | 56 |
| TEL13 | 111 | 2 | DPL11 | 11 | 10 | 49 |
| AS7 | 110 | 2 | DPL12 | 6 | 6% | 56 |
| MCG | 112 | 2 | DPL12 | 12 | 11% | 20 |
| U266L | 110 | 2 | DPL12 | 13 | 12% | 77 |
| PR-SJ2 | 110 | 2 | DPL12 | 14 | 13% | 55 |
| BOH | 112 | 2 | DPL12 | 11 | 10% | 37 |
| TOG | 111 | 2 | DPL11 | 19 | 18% | 53 |
| TEL16 | 111 | 2 | DPL11 | 19 | 18% | 49 |
| No.13 | 110 | 2 | DPL10 | 14 | 13% | 52 |
| BO | 112 | 2 | DPL12 | 18 | 17% | 80 |
| WIN | 112 | 2 | DPL12 | 17 | 16% | 11 |
| BUR | 104 | 2 | DPL12 | 15 | 15% | 46 |
| NIG-58 | 110 | 2 | DPL12 | 20 | 19% | 69 |
| WEIR | 112 | 2 | DPL11 | 26 | 25% | 21 |
| THY-32 | 111 | 1 | DPL8 | 8 | 8% | 27 |
| TNF-H9G1 | 111 | 1 | DPL8 | 9 | 9% | 27 |
| mAb61 | 111 | 1 | DPL3 | 1 | 1% | 29 |
| LV1L1 | 98 | 1 | DPL2 | 0 | 0% | 54 |
| HA | 113 | 1 | DPL3 | 14 | 13% | 63 |
| LA1L1 | 111 | 1 | DPL2 | 3 | 3% | 54 |
| RHE | 112 | 1 | DPL1 | 17 | 16% | 22 |
| K1B12L | 113 | 1 | DPL8 | 17 | 16% | 79 |
| LOC | 113 | 1 | DPL2 | 15 | 14% | 84 |
| NIG-51 | 112 | 1 | DPL2 | 12 | 11% | 67 |
| NEWM | 104 | 1 | DPL8 | 23 | 22% | 10 |
| MD3-4 | 106 | 3 | DPL23 | 14 | 13% | 4 |
| COX | 112 | 1 | DPL2 | 13 | 12% | 84 |
| HiH10 | 106 | 3 | DPL23 | 13 | 12% | 3 |
| VOR | 112 | 1 | DPL2 | 16 | 15% | 16 |
| AL POL | 113 | 1 | DPL2 | 16 | 15% | 57 |
| CD4-74 | 111 | 1 | DPL2 | 19 | 18% | 27 |
| AMYLOID MOL | 102 | 3 | DPL23 | 15 | 15% | 30 |
| OST577 | 108 | 3 | Humlv318 | 10 | 10% | 4 |
| NIG-48 | 113 | 1 | DPL3 | 42 | 40% | 66 |

TABLE 2B-continued rearranged human lambda sequences

| Name[1] | aa[2] | Computed family[3] | Germline gene[4] | Diff. to germline[5] | % diff. to germline[6] | Reference[7] |
|---|---|---|---|---|---|---|
| CARR | 108 | 3 | DPL23 | 18 | 17% | 19 |
| mAb60 | 108 | 3 | DPL23 | 14 | 13% | 29 |
| NIG-68 | 99 | 3 | DPL23 | 25 | 26% | 32 |
| KERN | 107 | 3 | DPL23 | 26 | 25% | 59 |
| ANT | 106 | 3 | DPL23 | 17 | 16% | 19 |
| LEE | 110 | 3 | DPL23 | 18 | 17% | 85 |
| CLE | 94 | 3 | DPL23 | 17 | 17% | 19 |
| VL8 | 98 | 8 | DPL21 | 0 | 0% | 81 |
| MOT | 110 | 3 | Humlv318 | 23 | 22% | 38 |
| GAR | 108 | 3 | DPL23 | 26 | 25% | 33 |
| 32.89 | 98 | 8 | DPL21 | 5 | 5% | 81 |
| PUG | 108 | 3 | Humlv318 | 24 | 23% | 19 |
| T1 | 115 | 8 | HUMLV801 | 52 | 50% | 6 |
| RF-TS7 | 96 | 7 | DPL18 | 4 | 4% | 60 |
| YM-1 | 116 | 8 | HUMLV801 | 51 | 49% | 75 |
| K6H6 | 112 | 8 | HUMLV801 | 20 | 19% | 44 |
| K5C7 | 112 | 8 | HUMLV801 | 20 | 19% | 44 |
| K5B8 | 112 | 8 | HUMLV801 | 20 | 19% | 44 |
| K5G5 | 112 | 8 | HUMLV801 | 20 | 19% | 44 |
| K4B8 | 112 | 8 | HUMLV801 | 19 | 18% | 44 |
| K6F5 | 112 | 8 | HUMLV801 | 17 | 16% | 44 |
| HIL | 108 | 3 | DPL23 | 22 | 21% | 47 |
| KIR | 109 | 3 | DPL23 | 20 | 19% | 19 |
| CAP | 109 | 3 | DPL23 | 19 | 18% | 84 |
| 1B8 | 110 | 3 | DPL23 | 22 | 21% | 43 |
| SHO | 108 | 3 | DPL23 | 19 | 18% | 19 |
| HAN | 108 | 3 | DPL23 | 20 | 19% | 19 |
| cML23 | 96 | 3 | DPL23 | 3 | 3% | 12 |
| PR-SJ1 | 96 | 3 | DPL23 | 7 | 7% | 55 |
| BAU | 107 | 3 | DPL23 | 9 | 9% | 5 |
| TEX | 99 | 3 | DPL23 | 8 | 8% | 19 |
| X(PET) | 107 | 3 | DPL23 | 9 | 9% | 51 |
| DOY | 106 | 3 | DPL23 | 9 | 9% | 19 |
| COT | 106 | 3 | DPL23 | 13 | 12% | 19 |
| Pag-1 | 111 | 3 | Humlv318 | 5 | 5% | 31 |
| DIS | 107 | 3 | Humlv318 | 2 | 2% | 19 |
| WIT | 108 | 3 | Humlv318 | 7 | 7% | 19 |
| LRH | 108 | 3 | Humlv318 | 12 | 11% | 19 |
| S1-1 | 108 | 3 | Humlv318 | 12 | 11% | 52 |
| DEL | 108 | 3 | Humlv318 | 14 | 13% | 17 |
| TYR | 108 | 3 | Humlv318 | 11 | 10% | 19 |
| J.RH | 109 | 3 | Humlv318 | 13 | 12% | 19 |
| THO | 112 | 2 | DPL13 | 38 | 36% | 26 |
| LBV | 113 | 1 | DPL3 | 38 | 36% | 2 |
| WLT | 112 | 1 | DPL3 | 33 | 31% | 14 |
| SUT | 112 | 2 | DPL12 | 37 | 35% | 65 |

TABLE 2C rearranged human heavy chain sequences

| Name | aa[2] | Computed family[3] | Germline gene[4] | Diff. to germline[5] | % diff. to germline[6] | Reference[7] |
|---|---|---|---|---|---|---|
| 21/28 | 119 | 1 | VH1-13-12 | 0 | 0.0% | 31 |
| 8E10 | 123 | 1 | VH1-13-12 | 0 | 0.0% | 31 |
| MUC1-1 | 118 | 1 | VH1-13-12 | 4 | 4.1% | 42 |
| gF1 | 98 | 1 | VH1-13-12 | 10 | 10.2% | 75 |
| VHGL 1.2 | 98 | 1 | VH1-13-6 | 2 | 2.0% | 26 |
| HV1L1 | 98 | 1 | VH1-13-6 | 0 | 0.0% | 81 |
| RF-TS7 | 104 | 1 | VH1-13-6 | 3 | 3.1% | 96 |
| E55 1.A15 | 106 | 1 | VH1-13-15 | 1 | 1.0% | 26 |
| HA1L1 | 126 | 1 | VH1-13-6 | 7 | 7.1% | 81 |
| UC | 123 | 1 | VH1-13-6 | 5 | 5.1% | 115 |
| WIL2 | 123 | 1 | VH1-13-6 | 6 | 6.1% | 55 |
| R3.5H5G | 122 | 1 | VH1-13-6 | 10 | 10.2% | 70 |
| N89P2 | 123 | 1 | VH1-13-16 | 11 | 11.2% | 77 |
| mAb113 | 126 | 1 | VH1-13-6 | 10 | 10.2% | 71 |
| LS2S3-3 | 126 | 1 | VH1-12-7 | 5 | 5.1% | 98 |
| LS2S3-12a | 126 | 1 | VH1-12-7 | 5 | 5.1% | 98 |
| LS2S3-5 | 125 | 1 | VH1-12-7 | 5 | 5.1% | 98 |
| LS2S3-12e | 125 | 1 | VH1-12-7 | 5 | 5.1% | 98 |
| LS2S3-4 | 125 | 1 | VH1-12-7 | 5 | 5.1% | 98 |
| LS2S3-10 | 125 | 1 | VH1-12-7 | 5 | 5.1% | 98 |
| LS2S3-12d | 125 | 1 | VH1-12-7 | 6 | 6.1% | 98 |
| LS2S3-8 | 125 | 1 | VH1-12-7 | 5 | 5.1% | 98 |
| LS2 | 125 | 1 | VH1-12-7 | 6 | 6.1% | 113 |
| LS4 | 105 | 1 | VH1-12-7 | 6 | 6.1% | 113 |
| LS5 | 125 | 1 | VH1-12-7 | 6 | 6.1% | 113 |
| LS1 | 125 | 1 | VH1-12-7 | 6 | 6.1% | 113 |
| LS6 | 125 | 1 | VH1-12-7 | 6 | 6.1% | 113 |
| LS8 | 125 | 1 | VH1-12-7 | 7 | 7.1% | 113 |

TABLE 2C-continued rearranged human heavy chain sequences

| Name | aa[2] | Computed family[3] | Germline gene[4] | Diff. to germline[5] | % diff. to germline[6] | Reference[7] |
|---|---|---|---|---|---|---|
| THY-29 | 122 | 1 | VH1-12-7 | 0 | 0.0% | 42 |
| 1B9/F2 | 122 | 1 | VH1-12-7 | 10 | 10.2% | 21 |
| 51P1 | 122 | 1 | VH1-12-1 | 0 | 0.0% | 105 |
| NEI | 127 | 1 | VH1-12-1 | 0 | 0.0% | 55 |
| AND | 127 | 1 | VH1-12-1 | 0 | 0.0% | 55 |
| L7 | 127 | 1 | VH1-12-1 | 0 | 0.0% | 54 |
| L22 | 124 | 1 | VH1-12-1 | 0 | 0.0% | 54 |
| L24 | 127 | 1 | VH1-12-1 | 0 | 0.0% | 54 |
| L26 | 116 | 1 | VH1-12-1 | 0 | 0.0% | 54 |
| L33 | 119 | 1 | VH1-12-1 | 0 | 0.0% | 54 |
| L34 | 117 | 1 | VH1-12-1 | 0 | 0.0% | 54 |
| L36 | 118 | 1 | VH1-12-1 | 0 | 0.0% | 54 |
| L39 | 120 | 1 | VH1-12-1 | 0 | 0.0% | 54 |
| L41 | 120 | 1 | VH1-12-1 | 0 | 0.0% | 54 |
| L42 | 125 | 1 | VH1-12-1 | 0 | 0.0% | 54 |
| VHGL 1.8 | 101 | 1 | VH1-12-1 | 0 | 0.0% | 26 |
| 783c | 127 | 1 | VH1-12-1 | 0 | 0.0% | 22 |
| X17115 | 127 | 1 | VH1-12-1 | 0 | 0.0% | 37 |
| L25 | 124 | 1 | VH1-12-1 | 0 | 0.0% | 54 |
| L17 | 120 | 1 | VH1-12-1 | 1 | 1.0% | 54 |
| L30 | 127 | 1 | VH1-12-1 | 1 | 1.0% | 54 |
| L37 | 120 | 1 | VH1-12-1 | 1 | 1.0% | 54 |
| TNF-E7 | 116 | 1 | VH1-12-1 | 2 | 2.0% | 42 |
| mAb111 | 122 | 1 | VH1-12-1 | 7 | 7.1% | 71 |
| III-2R | 122 | 1 | VH1-12-9 | 3 | 3.1% | 70 |
| KAS | 121 | 1 | VH1-12-1 | 7 | 7.1% | 79 |
| YES8c | 122 | 1 | VH1-12-1 | 8 | 8.2% | 34 |
| RF-TS1 | 123 | 1 | VH1-12-1 | 8 | 8.2% | 82 |
| BOR' | 121 | 1 | VH1-12-8 | 7 | 7.1% | 79 |
| VHGL 1.9 | 101 | 1 | VH1-12-1 | 8 | 8.2% | 26 |
| mAb410.30F305 | 117 | 1 | VH1-12-9 | 5 | 5.1% | 52 |
| EV1-15 | 127 | 1 | VH1-12-8 | 10 | 10.2% | 78 |
| mAb112 | 122 | 1 | VH1-12-1 | 11 | 11.2% | 71 |
| EU | 117 | 1 | VH1-12-1 | 11 | 11.2% | 28 |
| H210 | 127 | 1 | VH1-12-1 | 12 | 12.2% | 66 |
| TRANSGENE | 104 | 1 | VH1-12-1 | 0 | 0.0% | 111 |
| CLL2-1 | 93 | 1 | VH1-12-1 | 0 | 0.0% | 30 |
| CLL10 13-3 | 97 | 1 | VH1-12-1 | 0 | 0.0% | 29 |
| LS7 | 99 | 1 | VH1-12-7 | 4 | 4.1% | 113 |
| ALL7-1 | 87 | 1 | VH1-12-7 | 0 | 0.0% | 30 |
| CLL3-1 | 91 | 1 | VH1-12-7 | 1 | 1.0% | 30 |
| ALL56-1 | 85 | 1 | VH1-13-8 | 0 | 0.0% | 30 |
| ALL1-1 | 87 | 1 | VH1-13-6 | 1 | 1.0% | 30 |
| ALL4-1 | 94 | 1 | VH1-13-8 | 0 | 0.0% | 30 |
| ALL56 15-4 | 85 | 1 | VH1-13-8 | 5 | 5.1% | 29 |
| CLL4-1 | 88 | 1 | VH1-13-1 | 1 | 1.0% | 30 |
| Au92.1 | 98 | 1 | VH1-12-5 | 0 | 0.0% | 49 |
| RF-TS3 | 120 | 1 | VH1-12-5 | 1 | 1.0% | 82 |
| Au4.1 | 98 | 1 | VH1-12-5 | 1 | 1.0% | 49 |
| HP1 | 121 | 1 | VH1-13-6 | 13 | 13.3% | 110 |
| BLI | 127 | 1 | VH1-13-15 | 5 | 5.1% | 72 |
| No.13 | 127 | 1 | VH1-12-2 | 19 | 19.4% | 76 |
| TR1.23 | 122 | 1 | VH1-13-2 | 23 | 23.5% | 88 |
| S1-1 | 125 | 1 | VH1-12-2 | 18 | 18.4% | 76 |
| TR1.10 | 119 | 1 | VH1-13-12 | 14 | 14.3% | 88 |
| E55 1.A2 | 102 | 1 | VH1-13-15 | 3 | 3.1% | 26 |
| SP2 | 119 | 1 | VH1-13-6 | 15 | 15.3% | 89 |
| TNF-H9G1 | 111 | 1 | VH1-13-18 | 2 | 2.0% | 42 |
| G3D10H | 127 | 1 | VH1-13-16 | 19 | 19.4% | 127 |
| TR1.9 | 118 | 1 | VH1-13-12 | 14 | 14.3% | 88 |
| TR1.8 | 121 | 1 | VH1-12-1 | 24 | 24.5% | 88 |
| LUNm01 | 127 | 1 | VH1-13-6 | 22 | 22.4% | 9 |
| K1B12H | 127 | 1 | VH1-12-7 | 23 | 23.5% | 127 |
| L3B2 | 99 | 1 | VH1-13-6 | 2 | 2.0% | 46 |
| ss2 | 100 | 1 | VH1-13-6 | 2 | 2.0% | 46 |
| No.86 | 124 | 1 | VH1-12-1 | 20 | 20.4% | 76 |
| TR1.6 | 124 | 1 | VH1-12-1 | 19 | 19.4% | 88 |
| ss7 | 99 | 1 | VH1-12-7 | 3 | 3.1% | 46 |
| s5B7 | 102 | 1 | VH1-12-1 | 0 | 0.0% | 46 |
| s6A3 | 97 | 1 | VH1-12-1 | 0 | 0.0% | 46 |
| ss6 | 99 | 1 | VH1-12-1 | 0 | 0.0% | 46 |
| L2H7 | 103 | 1 | VH1-13-12 | 0 | 0.0% | 46 |
| s6BG8 | 93 | 1 | VH1-13-12 | 0 | 0.0% | 46 |
| s6C9 | 107 | 1 | VH1-13-12 | 0 | 0.0% | 46 |
| HIV-b4 | 124 | 1 | VH1-13-12 | 21 | 21.4% | 12 |
| HIV-b12 | 124 | 1 | VH1-13-12 | 21 | 21.4% | 12 |
| L3G5 | 98 | 1 | VH1-13-6 | 1 | 1.0% | 46 |
| 22 | 115 | 1 | VH1-13-6 | 11 | 11.2% | 118 |
| L2A12 | 99 | 1 | VH1-13-15 | 3 | 3.1% | 46 |
| PHOX15 | 124 | 1 | VH1-12-7 | 20 | 20.4% | 73 |
| LUNm03 | 127 | 1 | VH1-1X-1 | 18 | 18.4% | 9 |
| CEA4-8A | 129 | 1 | VH1-12-7 | 1 | 1.0% | 42 |
| M60 | 121 | 2 | VH2-31-3 | 3 | 3.0% | 103 |
| HiH10 | 127 | 2 | VH2-31-5 | 9 | 9.0% | 4 |
| COR | 119 | 2 | VH2-31-2 | 11 | 11.0% | 91 |
| 2-115-19 | 124 | 2 | VH2-31-11 | 8 | 8.1% | 124 |
| OU | 125 | 2 | VH2-31-14 | 20 | 25.6% | 92 |
| HE | 120 | 2 | VH2-31-13 | 19 | 19.0% | 27 |
| CLL33 40-1 | 78 | 2 | VH2-31-5 | 2 | 2.0% | 29 |
| E55 3.9 | 88 | 3 | VH3-11-5 | 7 | 7.2% | 26 |
| MTFC3 | 125 | 3 | VH3-14-4 | 21 | 21.0% | 131 |
| MTFC11 | 125 | 3 | VH3-14-4 | 21 | 21.0% | 131 |
| MTFJ1 | 114 | 3 | VH3-14-4 | 21 | 21.0% | 131 |
| MTFJ2 | 114 | 3 | VH3-14-4 | 21 | 21.0% | 131 |
| MTFUJ4 | 100 | 3 | VH3-14-4 | 21 | 21.0% | 131 |
| MTFUJ5 | 100 | 3 | VH3-14-4 | 21 | 21.0% | 131 |
| MTFUJ2 | 100 | 3 | VH3-14-4 | 22 | 22.0% | 131 |
| MTFC8 | 125 | 3 | VH3-14-4 | 23 | 23.0% | 131 |
| TD e Vq | 113 | 3 | VH3-14-4 | 0 | 0.0% | 16 |
| rMTF | 114 | 3 | VH3-14-4 | 5 | 5.0% | 131 |
| MTFUJ6 | 100 | 3 | VH3-14-4 | 10 | 10.0% | 131 |
| RF-KES | 107 | 3 | VH3-14-4 | 9 | 9.0% | 85 |
| N51P8 | 126 | 3 | VH3-14-1 | 9 | 9.0% | 77 |
| TEI | 119 | 3 | VH3-13-8 | 21 | 21.4% | 20 |
| 33.H11 | 115 | 3 | VH3-13-19 | 10 | 10.2% | 129 |
| SB1/D8 | 101 | 3 | VH3-1X-8 | 14 | 14.0% | 2 |
| 38P1 | 119 | 3 | VH3-11-3 | 0 | 0.0% | 104 |
| BRO'IGM | 119 | 3 | VH3-11-3 | 13 | 13.4% | 19 |
| NIE | 119 | 3 | VH3-13-7 | 15 | 15.3% | 87 |
| 3D6 | 126 | 3 | VH3-13-26 | 5 | 5.1% | 35 |
| ZM1-1 | 112 | 3 | VH3-11-3 | 8 | 8.2% | 5 |
| E55 3.15 | 110 | 3 | VH3-13-26 | 0 | 0.0% | 26 |
| gF9 | 108 | 3 | VH3-13-8 | 15 | 15.3% | 75 |
| THY-32 | 120 | 3 | VH3-13-26 | 3 | 3.1% | 42 |
| RF-KLS | 100 | 3 | VH3-13-26 | 5 | 5.1% | 96 |
| OST577 | 122 | 3 | VH3-13-13 | 6 | 6.1% | 5 |
| BO | 113 | 3 | VH3-13-19 | 15 | 15.3% | 10 |
| TT125 | 121 | 3 | VH3-13-10 | 15 | 15.3% | 64 |
| 2-115-58 | 127 | 3 | VH3-13-10 | 11 | 11.2% | 124 |
| KOL | 126 | 3 | VH3-13-14 | 16 | 16.3% | 102 |
| mAb60 | 118 | 3 | VH3-13-17 | 14 | 14.3% | 45 |
| RF-AN | 106 | 3 | VH3-13-26 | 8 | 8.2% | 85 |
| BUT | 115 | 3 | VH3-11-6 | 13 | 13.4% | 119 |
| KOL-based CAMPATH-9 | 118 | 3 | VH3-13-13 | 16 | 16.3% | 41 |
| B1 | 119 | 3 | VH3-13-19 | 13 | 13.3% | 53 |
| N98P1 | 127 | 3 | VH3-13-1 | 13 | 13.3% | 77 |
| TT117 | 107 | 3 | VH3-13-10 | 12 | 12.2% | 64 |
| WEA | 114 | 3 | VH3-13-12 | 15 | 15.3% | 40 |
| HIL | 120 | 3 | VH3-13-14 | 14 | 14.3% | 23 |
| s5A10 | 97 | 3 | VH3-13-14 | 0 | 0.0% | 46 |
| s5D11 | 98 | 3 | VH3-13-7 | 0 | 0.0% | 46 |
| s6C8 | 100 | 3 | VH3-13-7 | 0 | 0.0% | 46 |
| s6H12 | 98 | 3 | VH3-13-7 | 0 | 0.0% | 46 |
| VH10.7 | 119 | 3 | VH3-13-14 | 16 | 16.3% | 128 |
| HIV-loop2 | 126 | 3 | VH3-13-7 | 16 | 16.3% | 12 |
| HIV-loop35 | 126 | 3 | VH3-13-7 | 16 | 16.3% | 12 |
| TRO | 122 | 3 | VH3-13-1 | 13 | 13.3% | 61 |
| SA-4B | 123 | 3 | VH3-13-1 | 15 | 15.3% | 125 |
| L2B5 | 98 | 3 | VH3-13-13 | 0 | 0.0% | 46 |
| s6E11 | 95 | 3 | VH3-13-13 | 0 | 0.0% | 46 |
| s6H7 | 100 | 3 | VH3-13-13 | 0 | 0.0% | 46 |
| ss1 | 102 | 3 | VH3-13-13 | 0 | 0.0% | 46 |
| ss8 | 94 | 3 | VH3-13-13 | 0 | 0.0% | 46 |

TABLE 2C-continued rearranged human heavy chain sequences

| Name | aa[2] | Computed family[3] | Germline gene[4] | Diff. to germline[5] | % diff. to germline[6] | Reference[7] |
|---|---|---|---|---|---|---|
| DOB | 120 | 3 | VH3-13-26 | 21 | 21.4% | 116 |
| THY-33 | 115 | 3 | VH3-13-15 | 20 | 20.4% | 42 |
| NOV | 118 | 3 | VH3-13-19 | 14 | 14.3% | 38 |
| rsv13H | 120 | 3 | VH3-13-24 | 20 | 20.4% | 11 |
| L3G11 | 98 | 3 | VH3-13-20 | 2 | 2.0% | 46 |
| L2E8 | 99 | 3 | VH3-13-19 | 0 | 0.0% | 46 |
| L2D10 | 101 | 3 | VH3-13-10 | 1 | 1.0% | 46 |
| L2E7 | 98 | 3 | VH3-13-10 | 1 | 1.0% | 46 |
| L3A10 | 100 | 3 | VH3-13-24 | 0 | 0.0% | 46 |
| L2E5 | 97 | 3 | VH3-13-2 | 1 | 1.0% | 46 |
| BUR | 119 | 3 | VH3-13-7 | 21 | 21.4% | 67 |
| s4D5 | 107 | 3 | VH3-11-3 | 1 | 1.0% | 46 |
| 19 | 116 | 3 | VH3-13-16 | 4 | 4.1% | 118 |
| s5D4 | 99 | 3 | VH3-13-1 | 0 | 0.0% | 46 |
| s6A8 | 100 | 3 | VH3-13-1 | 0 | 0.0% | 46 |
| HIV-loop13 | 123 | 3 | VH3-13-12 | 17 | 17.3% | 12 |
| TR1.32 | 112 | 3 | VH3-11-8 | 18 | 18.6% | 88 |
| L2B10 | 97 | 3 | VH3-11-3 | 1 | 1.0% | 46 |
| TR1.5 | 114 | 3 | VH3-11-8 | 21 | 21.6% | 88 |
| s6H9 | 101 | 3 | VH3-13-25 | 0 | 0.0% | 46 |
| 8 | 112 | 3 | VH3-13-1 | 6 | 6.1% | 118 |
| 23 | 115 | 3 | VH3-13-1 | 6 | 6.1% | 118 |
| 7 | 115 | 3 | VH3-13-1 | 4 | 4.1% | 118 |
| TR1.3 | 120 | 3 | VH3-11-8 | 20 | 20.6% | 88 |
| 18/2 | 125 | 3 | VH3-13-10 | 0 | 0.0% | 32 |
| 18/9 | 125 | 3 | VH3-13-10 | 0 | 0.0% | 31 |
| 3OP1 | 119 | 3 | VH3-13-10 | 0 | 0.0% | 106 |
| HF2-1/17 | 125 | 3 | VH3-13-10 | 0 | 0.0% | 8 |
| A77 | 109 | 3 | VH3-13-10 | 0 | 0.0% | 44 |
| B19.7 | 108 | 3 | VH3-13-10 | 0 | 0.0% | 44 |
| M43 | 119 | 3 | VH3-13-10 | 0 | 0.0% | 103 |
| 1/17 | 125 | 3 | VH3-13-10 | 0 | 0.0% | 31 |
| 18/17 | 125 | 3 | VH3-13-10 | 0 | 0.0% | 31 |
| E54 3.4 | 109 | 3 | VH3-13-10 | 0 | 0.0% | 26 |
| LAMBDA-VH26 | 98 | 3 | VH3-13-10 | 1 | 1.0% | 95 |
| E54 3.8 | 111 | 3 | VH3-13-10 | 1 | 1.0% | 26 |
| GL16 | 106 | 3 | VH3-13-10 | 1 | 1.0% | 44 |
| 4G12 | 125 | 3 | VH3-13-10 | 1 | 1.0% | 56 |
| A73 | 106 | 3 | VH3-13-10 | 2 | 2.0% | 44 |
| AL1.3 | 111 | 3 | VH3-13-10 | 3 | 3.1% | 117 |
| 3.A290 | 118 | 3 | VH3-13-10 | 2 | 2.0% | 108 |
| Ab18 | 127 | 3 | VH3-13-8 | 2 | 2.0% | 100 |
| E54 3.3 | 105 | 3 | VH3-13-10 | 3 | 3.1% | 26 |
| 35G6 | 121 | 3 | VH3-13-10 | 3 | 3.1% | 57 |
| A95 | 107 | 3 | VH3-13-10 | 5 | 5.1% | 44 |
| Ab25 | 128 | 3 | VH3-13-10 | 5 | 5.1% | 100 |
| N87 | 126 | 3 | VH3-13-10 | 4 | 4.1% | 77 |
| ED8.4 | 99 | 3 | VH3-13-10 | 6 | 6.1% | 2 |
| RF-KL1 | 122 | 3 | VH3-13-10 | 6 | 6.1% | 82 |
| AL1.1 | 112 | 3 | VH3-13-10 | 2 | 2.0% | 117 |
| AL3.11 | 102 | 3 | VH3-13-10 | 1 | 1.0% | 117 |
| 32.B9 | 127 | 3 | VH3-13-8 | 6 | 6.1% | 129 |
| TK1 | 109 | 3 | VH3-13-10 | 2 | 2.0% | 117 |
| POP | 123 | 3 | VH3-13-10 | 8 | 8.2% | 115 |
| gF2H | 127 | 3 | VH3-13-10 | 9 | 9.2% | 127 |
| VD | 115 | 3 | VH3-13-10 | 9 | 9.2% | 10 |
| Vh38Cl.10 | 121 | 3 | VH3-13-10 | 8 | 8.2% | 74 |
| Vh38Cl.9 | 121 | 3 | VH3-13-10 | 8 | 8.2% | 74 |
| Vh38Cl.8 | 121 | 3 | VH3-13-10 | 8 | 8.2% | 74 |
| 63P1 | 120 | 3 | VH3-11-8 | 0 | 0.0% | 104 |
| 60P2 | 117 | 3 | VH3-11-8 | 0 | 0.0% | 104 |
| AL3.5 | 90 | 3 | VH3-13-10 | 2 | 2.0% | 117 |
| GF4/L.1 | 123 | 3 | VH3-13-10 | 10 | 10.2% | 39 |
| Ab21 | 126 | 3 | VH3-13-10 | 12 | 12.2% | 100 |
| TD d Vp | 118 | 3 | VH3-13-17 | 2 | 2.0% | 16 |
| Vh38Cl.4 | 119 | 3 | VH3-13-10 | 8 | 8.2% | 74 |
| Vh38Cl.5 | 119 | 3 | VH3-13-10 | 8 | 8.2% | 74 |
| AL3.4 | 104 | 3 | VH3-13-10 | 1 | 1.0% | 117 |
| FOG1-A3 | 115 | 3 | VH3-13-19 | 2 | 2.0% | 42 |
| HA3D1 | 117 | 3 | VH3-13-21 | 1 | 1.0% | 81 |
| E54 3.2 | 112 | 3 | VH3-13-24 | 0 | 0.0% | 26 |
| mAb52 | 128 | 3 | VH3-13-12 | 2 | 2.0% | 51 |
| mAb53 | 128 | 3 | VH3-13-12 | 2 | 2.0% | 51 |
| mAb56 | 128 | 3 | VH3-13-12 | 2 | 2.0% | 51 |
| mAb57 | 128 | 3 | VH3-13-12 | 2 | 2.0% | 51 |
| mAb58 | 128 | 3 | VH3-13-12 | 2 | 2.0% | 51 |
| mAb59 | 128 | 3 | VH3-13-12 | 2 | 2.0% | 51 |
| mAb105 | 128 | 3 | VH3-13-12 | 2 | 2.0% | 51 |
| mAb107 | 128 | 3 | VH3-13-12 | 2 | 2.0% | 51 |
| E55 3.14 | 110 | 3 | VH3-13-19 | 0 | 0.0% | 26 |
| F13-28 | 106 | 3 | VH3-13-19 | 1 | 1.0% | 94 |
| mAb55 | 127 | 3 | VH3-13-18 | 4 | 4.1% | 51 |
| YSE | 117 | 3 | VH3-13-24 | 6 | 6.1% | 72 |
| E55 3.23 | 106 | 3 | VH3-13-19 | 2 | 2.0% | 26 |
| RF-TS5 | 101 | 3 | VH3-13-1 | 3 | 3.1% | 85 |
| N42P5 | 124 | 3 | VH3-13-2 | 7 | 7.1% | 77 |
| FOGI-H6 | 110 | 3 | VH3-13-16 | 7 | 7.1% | 42 |
| O-81 | 115 | 3 | VH3-13-19 | 11 | 11.2% | 47 |
| HIV-s8 | 122 | 3 | VH3-13-12 | 11 | 11.2% | 12 |
| mAb114 | 125 | 3 | VH3-13-19 | 12 | 12.2% | 71 |
| 33.F12 | 116 | 3 | VH3-13-2 | 4 | 4.1% | 129 |
| 4B4 | 119 | 3 | VH3-1X-3 | 0 | 0.0% | 101 |
| M26 | 123 | 3 | VH3-1X-3 | 0 | 0.0% | 103 |
| VHGL 3.1 | 100 | 3 | VH3-1X-3 | 0 | 0.0% | 26 |
| E55 3.13 | 113 | 3 | VH3-1X-3 | 1 | 1.0% | 26 |
| SB5/D6 | 101 | 3 | VH3-1X-6 | 3 | 3.0% | 2 |
| RAY4 | 101 | 3 | VH3-1X-6 | 3 | 3.0% | 2 |
| 82-D V-D | 106 | 3 | VH3-1X-3 | 5 | 5.0% | 112 |
| MAL | 129 | 3 | VH3-1X-3 | 5 | 5.0% | 72 |
| LOC | 123 | 3 | VH3-1X-6 | 5 | 5.0% | 72 |
| LSF2 | 101 | 3 | VH3-1X-6 | 11 | 11.0% | 2 |
| HIB RC3 | 100 | 3 | VH3-1X-6 | 11 | 11.0% | 1 |
| 56P1 | 119 | 3 | VH3-13-7 | 0 | 0.0% | 104 |
| M72 | 122 | 3 | VH3-13-7 | 0 | 0.0% | 103 |
| M74 | 121 | 3 | VH3-13-7 | 0 | 0.0% | 103 |
| E54 3.5 | 105 | 3 | VH3-13-7 | 0 | 0.0% | 26 |
| 2E7 | 123 | 3 | VH3-13-7 | 0 | 0.0% | 63 |
| 2P1 | 117 | 3 | VH3-13-7 | 0 | 0.0% | 104 |
| RF-SJ2 | 127 | 3 | VH3-13-7 | 1 | 1.0% | 83 |
| PP-TS1 | 114 | 3 | VH3-13-7 | 1 | 1.0% | 85 |
| KIM46H | 127 | 3 | VH3-13-13 | 0 | 0.0% | 18 |
| E55 3.6 | 108 | 3 | VH3-13-7 | 2 | 2.0% | 26 |
| E55 3.10 | 107 | 3 | VH3-13-13 | 1 | 1.0% | 26 |
| 3.86 | 114 | 3 | VH3-13-13 | 2 | 2.0% | 108 |
| E54 3.6 | 110 | 3 | VH3-13-13 | 1 | 1.0% | 26 |
| FL2-2 | 114 | 3 | VH3-13-13 | 1 | 1.0% | 80 |
| RF-SJ3 | 112 | 3 | VH3-13-7 | 2 | 2.0% | 85 |
| E55 3.5 | 105 | 3 | VH3-13-14 | 1 | 1.0% | 26 |
| BSA3 | 121 | 3 | VH3-13-13 | 1 | 1.0% | 73 |
| HMST-1 | 119 | 3 | VH3-13-7 | 3 | 3.1% | 130 |
| RF-TS2 | 126 | 3 | VH3-13-13 | 4 | 4.1% | 82 |
| E55 3.12 | 109 | 3 | VH3-13-15 | 0 | 0.0% | 26 |
| 19.E7 | 126 | 3 | VH3-13-14 | 3 | 3.1% | 129 |
| 11-50 | 119 | 3 | VH3-13-13 | 6 | 6.1% | 130 |
| E29.1 | 120 | 3 | VH3-13-15 | 2 | 2.0% | 25 |
| E55 3.16 | 108 | 3 | VH3-13-7 | 6 | 6.1% | 26 |
| TNF-E1 | 117 | 3 | VH3-13-7 | 7 | 7.1% | 42 |
| RF-SJ1 | 127 | 3 | VH3-13-13 | 6 | 6.1% | 83 |
| FOG1-A4 | 116 | 3 | VH3-13-7 | 8 | 8.2% | 42 |
| TNF-A1 | 117 | 3 | VH3-13-15 | 4 | 4.1% | 42 |
| PR-SJ2 | 107 | 3 | VH3-13-14 | 8 | 8.2% | 85 |
| HN.14 | 124 | 3 | VH3-13-13 | 10 | 10.2% | 33 |
| CAM' | 121 | 3 | VH3-13-7 | 12 | 12.2% | 65 |
| HIV-B8 | 125 | 3 | VH3-13-7 | 9 | 9.2% | 12 |
| HIV-b27 | 125 | 3 | VH3-13-7 | 9 | 9.2% | 12 |
| HIV-b8 | 125 | 3 | VH3-13-7 | 9 | 9.2% | 12 |
| HIV-s4 | 125 | 3 | VH3-13-7 | 9 | 9.2% | 12 |
| HIV-B26 | 125 | 3 | VH3-13-7 | 9 | 9.2% | 12 |
| HIV-B35 | 125 | 3 | VH3-13-7 | 10 | 10.2% | 12 |
| HIV-b18 | 125 | 3 | VH3-13-7 | 10 | 10.2% | 12 |
| HIV-b22 | 125 | 3 | VH3-13-7 | 11 | 11.2% | 12 |
| HIV-b13 | 125 | 3 | VH3-13-7 | 12 | 12.2% | 12 |
| 333 | 117 | 3 | VH3-14-4 | 24 | 24.0% | 24 |
| 1HI | 120 | 3 | VH3-14-4 | 24 | 24.0% | 24 |

TABLE 2C-continued rearranged human heavy chain sequences

| Name | aa[2] | Computed family[3] | Germline gene[4] | Diff. to germ-line[5] | % diff. to germ-line[6] | Reference[7] |
|---|---|---|---|---|---|---|
| 1B11 | 120 | 3 | VH3-14-4 | 23 | 23.0% | 24 |
| CLL30 2-3 | 86 | 3 | VH3-13-19 | 1 | 1.0% | 29 |
| GA | 110 | 3 | VH3-13-7 | 19 | 19.4% | 36 |
| JeB | 99 | 3 | VH3-13-14 | 3 | 3.1% | 7 |
| GAL | 110 | 3 | VH3-13-19 | 10 | 10.2% | 126 |
| K6H6 | 119 | 3 | VH3-1X-6 | 18 | 18.0% | 60 |
| K4B8 | 119 | 3 | VH3-1X-6 | 18 | 18.0% | 60 |
| K5B8 | 119 | 3 | VH3-1X-6 | 18 | 18.0% | 60 |
| K5C7 | 119 | 3 | VH3-1X-6 | 19 | 19.0% | 60 |
| K5G5 | 119 | 3 | VH3-1X-6 | 19 | 19.0% | 60 |
| K6F5 | 119 | 3 | VH3-1X-6 | 19 | 19.0% | 60 |
| AL3.16 | 98 | 3 | VH3-13-10 | 1 | 1.0% | 117 |
| N86P2 | 98 | 3 | VH3-13-10 | 3 | 3.1% | 77 |
| N54P6 | 95 | 3 | VH3-13-16 | 7 | 7.1% | 77 |
| LAMBDA HT112-1 | 126 | 4 | VH4-11-2 | 0 | 0.0% | 3 |
| HY18 | 121 | 4 | VH4-11-2 | 0 | 0.0% | 43 |
| mAb63 | 126 | 4 | VH4-11-2 | 0 | 0.0% | 45 |
| FS-3 | 105 | 4 | VH4-11-2 | 0 | 0.0% | 86 |
| FS-5 | 111 | 4 | VH4-11-2 | 0 | 0.0% | 86 |
| FS-7 | 107 | 4 | VH4-11-2 | 0 | 0.0% | 86 |
| FS-8 | 110 | 4 | VH4-11-2 | 0 | 0.0% | 86 |
| PR-TS2 | 105 | 4 | VH4-11-2 | 0 | 0.0% | 85 |
| RF-TMC | 102 | 4 | VH4-11-2 | 0 | 0.0% | 85 |
| mAb216 | 122 | 4 | VH4-11-2 | 1 | 1.0% | 15 |
| mAb410.7.F91 | 122 | 4 | VH4-11-2 | 1 | 1.0% | 52 |
| mAbA6H4C5 | 124 | 4 | VH4-11-2 | 1 | 1.0% | 15 |
| Ab44 | 127 | 4 | VH4-11-2 | 2 | 2.1% | 100 |
| 6H-3C4 | 124 | 4 | VH4-11-2 | 3 | 3.1% | 59 |
| FS-6 | 108 | 4 | VH4-11-2 | 6 | 6.2% | 86 |
| FS-2 | 114 | 4 | VH4-11-2 | 6 | 6.2% | 84 |
| HIG1 | 126 | 4 | VH4-11-2 | 7 | 7.2% | 62 |
| FS-4 | 105 | 4 | VH4-11-2 | 8 | 8.2% | 86 |
| SA-4A | 123 | 4 | VH4-11-2 | 9 | 9.3% | 125 |
| LES-C | 119 | 4 | VH4-11-2 | 10 | 10.3% | 99 |
| DI | 78 | 4 | VH4-11-9 | 16 | 16.5% | 58 |
| Ab26 | 126 | 4 | VH4-31-4 | 8 | 8.1% | 100 |
| TS2 | 124 | 4 | VH4-31-12 | 15 | 15.2% | 110 |
| 265-695 | 115 | 4 | VH4-11-7 | 16 | 16.5% | 5 |
| WAH | 129 | 4 | VH4-31-13 | 19 | 19.2% | 93 |
| 268-D | 122 | 4 | VH4-11-8 | 22 | 22.7% | 6 |
| 58P2 | 118 | 4 | VH4-11-8 | 0 | 0.0% | 104 |
| mAb67 | 128 | 4 | VH4-21-4 | 1 | 1.0% | 45 |
| 4.L39 | 115 | 4 | VH4-11-8 | 2 | 2.1% | 108 |
| mF7 | 111 | 4 | VH4-31-13 | 3 | 3.0% | 75 |
| 33.C9 | 122 | 4 | VH4-21-5 | 7 | 7.1% | 129 |
| Pag-1 | 124 | 4 | VH4-11-16 | 5 | 5.2% | 50 |
| B3 | 123 | 4 | VH4-21-3 | 8 | 8.2% | 53 |
| IC4 | 120 | 4 | VH4-11-8 | 6 | 6.2% | 70 |
| C6B2 | 127 | 4 | VH4-31-12 | 4 | 4.0% | 48 |
| N78 | 118 | 4 | VH4-11-9 | 11 | 11.3% | 77 |
| B2 | 109 | 4 | VH4-11-8 | 12 | 12.4% | 53 |
| WRD2 | 123 | 4 | VH4-11-12 | 6 | 6.2% | 90 |
| mAb426.4.2F20 | 126 | 4 | VH4-11-8 | 2 | 2.1% | 52 |
| E54 4.58 | 115 | 4 | VH4-11-8 | 1 | 1.0% | 26 |
| WRD6 | 123 | 4 | VH4-11-12 | 10 | 10.3% | 90 |
| mAb426.12.3F1.4 | 122 | 4 | VH4-11-9 | 4 | 4.1% | 52 |
| E54 4.2 | 108 | 4 | VH4-21-6 | 2 | 2.0% | 26 |
| WIL | 127 | 4 | VH4-31-13 | 0 | 0.0% | 90 |
| COF | 126 | 4 | VH4-31-13 | 0 | 0.0% | 90 |
| LAR | 122 | 4 | VH4-31-13 | 2 | 2.0% | 90 |
| WAT | 125 | 4 | VH4-31-13 | 4 | 4.0% | 90 |
| mAb61 | 123 | 4 | VH4-31-13 | 5 | 5.1% | 45 |
| WAG | 127 | 4 | VH4-31-4 | 0 | 0.0% | 90 |
| RF-SJ4 | 108 | 4 | VH4-31-12 | 2 | 2.0% | 85 |
| E54 4.4 | 110 | 4 | VH4-11-7 | 0 | 0.0% | 26 |
| E55 4.A1 | 108 | 4 | VH4-11-7 | 0 | 0.0% | 26 |
| PR-SJ1 | 103 | 4 | VH4-11-7 | 1 | 1.0% | 85 |
| E54 4.23 | 111 | 4 | VH4-11-7 | 1 | 1.0% | 26 |
| CLL7 7-2 | 97 | 4 | VH4-11-12 | 0 | 0.0% | 29 |
| 37P1 | 95 | 4 | VH4-11-12 | 0 | 0.0% | 104 |
| ALL52 30-2 | 91 | 4 | VH4-31-12 | 4 | 4.0% | 29 |
| EBV-21 | 98 | 5 | VH5-12-1 | 0 | 0.0% | 13 |
| CB-4 | 98 | 5 | VH5-12-1 | 0 | 0.0% | 13 |
| CLL-12 | 98 | 5 | VH5-12-1 | 0 | 0.0% | 13 |
| L3-4 | 98 | 5 | VH5-12-1 | 0 | 0.0% | 13 |
| CLL11 | 98 | 5 | VH5-12-1 | 0 | 0.0% | 17 |
| CORD3 | 98 | 5 | VH5-12-1 | 0 | 0.0% | 17 |
| CORD4 | 98 | 5 | VH5-12-1 | 0 | 0.0% | 17 |
| CORD8 | 98 | 5 | VH5-12-1 | 0 | 0.0% | 17 |
| CORD9 | 98 | 5 | VH5-12-1 | 0 | 0.0% | 17 |
| CD+1 | 98 | 5 | VH5-12-1 | 0 | 0.0% | 17 |
| CD+3 | 98 | 5 | VH5-12-1 | 0 | 0.0% | 17 |
| CD+4 | 98 | 5 | VH5-12-1 | 0 | 0.0% | 17 |
| CD-1 | 98 | 5 | VH5-12-1 | 0 | 0.0% | 17 |
| CD-5 | 98 | 5 | VH5-12-1 | 0 | 0.0% | 17 |
| VERG14 | 98 | 5 | VH5-12-1 | 0 | 0.0% | 17 |
| PBL1 | 98 | 5 | VH5-12-1 | 0 | 0.0% | 17 |
| PBL10 | 98 | 5 | VH5-12-1 | 0 | 0.0% | 17 |
| STRAb SA-1A | 127 | 5 | VH5-12-1 | 0 | 0.0% | 125 |
| DOB' | 122 | 5 | VH5-12-1 | 0 | 0.0% | 97 |
| VERG5 | 98 | 5 | VH5-12-1 | 0 | 0.0% | 17 |
| PBL2 | 98 | 5 | VH5-12-1 | 1 | 1.0% | 17 |
| Tu16 | 119 | 5 | VH5-12-1 | 1 | 1.0% | 49 |
| PBL12 | 98 | 5 | VH5-12-1 | 1 | 1.0% | 17 |
| CD+2 | 98 | 5 | VH5-12-1 | 1 | 1.0% | 11 |
| CORD10 | 98 | 5 | VH5-12-1 | 1 | 1.0% | 17 |
| PBL9 | 98 | 5 | VH5-12-1 | 1 | 1.0% | 17 |
| CORD2 | 98 | 5 | VH5-12-1 | 2 | 2.0% | 17 |
| PBL6 | 98 | 5 | VH5-12-1 | 2 | 2.0% | 17 |
| CORD5 | 98 | 5 | VH5-12-1 | 2 | 2.0% | 17 |
| CD-2 | 98 | 5 | VH5-12-1 | 2 | 2.0% | 17 |
| CORD1 | 98 | 5 | VH5-12-1 | 2 | 2.0% | 17 |
| CD-3 | 98 | 5 | VH5-12-1 | 3 | 3.1% | 17 |
| VERG4 | 98 | 5 | VH5-12-1 | 3 | 3.1% | 17 |
| PBL13 | 98 | 5 | VH5-12-1 | 3 | 3.1% | 17 |
| PBL7 | 98 | 5 | VH5-12-1 | 3 | 3.1% | 17 |
| HAN | 119 | 5 | VH5-12-1 | 3 | 3.1% | 97 |
| VERG3 | 98 | 5 | VH5-12-1 | 3 | 3.1% | 17 |
| PBL3 | 98 | 5 | VH5-12-1 | 3 | 3.1% | 17 |
| VERG7 | 98 | 5 | VH5-12-1 | 3 | 3.1% | 17 |
| PBL5 | 94 | 5 | VH5-12-1 | 0 | 0.0% | 17 |
| CD-4 | 98 | 5 | VH5-12-1 | 4 | 4.1% | 17 |
| CLL10 | 98 | 5 | VH5-12-1 | 4 | 4.1% | 17 |
| PBL11 | 98 | 5 | VH5-12-1 | 4 | 4.1% | 17 |
| CORD6 | 98 | 5 | VH5-12-1 | 4 | 4.1% | 17 |
| VERG2 | 98 | 5 | VH5-12-1 | 5 | 5.1% | 17 |
| 83P2 | 119 | 5 | VH5-12-1 | 0 | 0.0% | 103 |
| VERG9 | 98 | 5 | VH5-12-1 | 6 | 6.1% | 17 |
| CLL6 | 98 | 5 | VH5-12-1 | 6 | 6.1% | 17 |
| PBL8 | 98 | 5 | VH5-12-1 | 7 | 7.1% | 17 |
| Ab2022 | 120 | 5 | VH5-12-1 | 3 | 3.1% | 100 |
| CAV | 127 | 5 | VH5-12-4 | 0 | 0.0% | 97 |
| HOW' | 120 | 5 | VH5-12-4 | 0 | 0.0% | 97 |
| PET | 127 | 5 | VH5-12-4 | 0 | 0.0% | 97 |
| ANG | 121 | 5 | VH5-12-4 | 0 | 0.0% | 97 |
| KER | 121 | 5 | VH5-12-4 | 0 | 0.0% | 97 |
| 5.M13 | 118 | 5 | VH5-12-4 | 0 | 0.0% | 107 |
| Au2.1 | 118 | 5 | VH5-12-4 | 1 | 1.0% | 49 |
| WS1 | 126 | 5 | VH5-12-1 | 9 | 9.2% | 110 |
| TD Vn | 98 | 5 | VH5-12-4 | 1 | 1.0% | 16 |
| TEL13 | 116 | 5 | VH5-12-4 | 9 | 9.2% | 73 |
| E55 5.237 | 112 | 5 | VH5-12-4 | 2 | 2.0% | 26 |
| VERG1 | 98 | 5 | VH5-12-1 | 10 | 10.2% | 17 |
| CD4-74 | 117 | 5 | VH5-12-1 | 10 | 10.2% | 42 |
| 257-D | 125 | 5 | VH5-12-1 | 11 | 11.2% | 6 |
| CLL4 | 98 | 5 | VH5-12-1 | 11 | 11.2% | 17 |
| CLL8 | 98 | 5 | VH5-12-1 | 11 | 11.2% | 17 |
| Ab2 | 124 | 5 | VH5-12-1 | 12 | 12.2% | 120 |
| Vh363ex | 98 | 5 | VH5-12-1 | 12 | 12.2% | 120 |
| CLL3 | 98 | 5 | VH5-12-2 | 11 | 11.2% | 17 |
| Au59.1 | 122 | 5 | VH5-12-1 | 12 | 12.2% | 49 |
| TEL16 | 117 | 5 | VH5-12-1 | 12 | 12.2% | 73 |
| M61 | 104 | 5 | VH5-12-1 | 0 | 0.0% | 103 |

TABLE 2C-continued rearranged human heavy chain sequences

| Name | aa[2] | Computed family[3] | Germline gene[4] | Diff. to germline[5] | % diff. to germline[6] | Reference[7] |
|---|---|---|---|---|---|---|
| TuO | 99 | 5 | VH5-12-1 | 5 | 5.1% | 49 |
| P2-51 | 122 | 5 | VH5-12-1 | 13 | 13.3% | 121 |
| P2-54 | 122 | 5 | VH5-12-1 | 11 | 11.2% | 121 |
| P1-56 | 119 | 5 | VH5-12-1 | 9 | 9.2% | 121 |
| P2-53 | 122 | 5 | VH5-12-1 | 10 | 10.2% | 121 |
| P1-51 | 123 | 5 | VH5-12-1 | 19 | 19.4% | 121 |
| P1-54 | 123 | 5 | VH5-12-1 | 3 | 3.1% | 121 |
| P3-69 | 127 | 5 | VH5-12-1 | 4 | 4.1% | 121 |
| P3-9 | 119 | 5 | VH5-12-1 | 4 | 4.1% | 121 |
| 1-185-37 | 125 | 5 | VH5-12-4 | 0 | 0.0% | 124 |
| 1-187-29 | 125 | 5 | VH5-12-4 | 0 | 0.0% | 124 |
| P1-58 | 128 | 5 | VH5-12-4 | 10 | 10.2% | 121 |
| P2-57 | 118 | 5 | VH5-12-4 | 3 | 3.1% | 121 |
| P2-55 | 123 | 5 | VH5-12-1 | 5 | 5.1% | 121 |
| P2-56 | 123 | 5 | VH5-12-1 | 20 | 20.4% | 121 |
| P2-52 | 122 | 5 | VH5-12-1 | 11 | 11.2% | 121 |
| P3-60 | 122 | 5 | VH5-12-1 | 8 | 8.2% | 121 |
| P1-57 | 123 | 5 | VH5-12-1 | 4 | 4.1% | 121 |
| P1-55 | 122 | 5 | VH5-12-1 | 14 | 14.3% | 121 |
| MD3-4 | 128 | 5 | VH5-12-4 | 12 | 12.2% | 5 |
| P1-52 | 121 | 5 | VH5-12-1 | 11 | 11.2% | 121 |
| CLL5 | 98 | 5 | VH5-12-1 | 13 | 13.3% | 17 |
| CLL7 | 98 | 5 | VH5-12-1 | 14 | 14.3% | 17 |
| L2F10 | 100 | 5 | VH5-12-1 | 1 | 1.0% | 46 |
| L3B6 | 98 | 5 | VH5-12-1 | 1 | 1.0% | 46 |
| VH6A12 | 119 | 6 | VH6-35-1 | 13 | 12.9% | 122 |
| s5A9 | 102 | 6 | VH6-35-1 | 1 | 1.0% | 46 |
| s6G4 | 99 | 6 | VH6-35-1 | 1 | 1.0% | 46 |
| ss3 | 99 | 6 | VH6-35-1 | 1 | 1.0% | 46 |
| 6-1G1 | 101 | 6 | VH6-35-1 | 0 | 0.0% | 14 |
| F19L16 | 107 | 6 | VH6-35-1 | 0 | 0.0% | 68 |
| L16 | 120 | 6 | VH6-35-1 | 0 | 0.0% | 69 |
| M71 | 121 | 6 | VH6-35-1 | 0 | 0.0% | 103 |
| ML1 | 120 | 6 | VH6-35-1 | 0 | 0.0% | 69 |
| F19ML1 | 107 | 6 | VH6-35-1 | 0 | 0.0% | 68 |
| 15P1 | 127 | 6 | VH6-35-1 | 0 | 0.0% | 104 |
| VH6.N1 | 121 | 6 | VH6-35-1 | 0 | 0.0% | 122 |
| VH6.N11 | 123 | 6 | VH6-35-1 | 0 | 0.0% | 122 |
| VH6.N12 | 123 | 6 | VH6-35-1 | 0 | 0.0% | 122 |
| VH6.N2 | 125 | 6 | VH6-35-1 | 0 | 0.0% | 122 |
| VH6.N5 | 125 | 6 | VH6-35-1 | 0 | 0.0% | 122 |
| VH6.N6 | 127 | 6 | VH6-35-1 | 0 | 0.0% | 122 |
| VH6.N7 | 126 | 6 | VH6-35-1 | 0 | 0.0% | 122 |
| VH6.N8 | 123 | 6 | VH6-35-1 | 0 | 0.0% | 122 |
| VH6.N9 | 123 | 6 | VH6-35-1 | 0 | 0.0% | 122 |
| VH6.N10 | 123 | 6 | VH6-35-1 | 0 | 0.0% | 122 |
| VH6.A3 | 123 | 6 | VH6-35-1 | 0 | 0.0% | 122 |
| VH6.A1 | 124 | 6 | VH6-35-1 | 0 | 0.0% | 122 |
| VH6.A4 | 120 | 6 | VH6-35-1 | 0 | 0.0% | 122 |
| E55 6.16 | 116 | 6 | VH6-35-1 | 0 | 0.0% | 26 |
| E55 6.17 | 120 | 6 | VH6-35-1 | 0 | 0.0% | 26 |
| E55 6.6 | 120 | 6 | VH6-35-1 | 0 | 0.0% | 26 |
| VHGL 6.3 | 102 | 6 | VH6-35-1 | 0 | 0.0% | 26 |
| CB-201 | 118 | 6 | VH6-35-1 | 0 | 0.0% | 109 |
| VH6.N4 | 122 | 6 | VH6-35-1 | 0 | 0.0% | 122 |
| E54 6.4 | 109 | 6 | VH6-35-1 | 1 | 1.0% | 26 |
| VH6.A6 | 126 | 6 | VH6-35-1 | 1 | 1.0% | 122 |
| E55 6.14 | 120 | 6 | VH6-35-1 | 1 | 1.0% | 26 |
| E54 6.6 | 107 | 6 | VH6-35-1 | 1 | 1.0% | 26 |
| E55 6.10 | 112 | 6 | VH6-35-1 | 1 | 1.0% | 26 |
| E54 6.1 | 107 | 6 | VH6-35-1 | 2 | 2.0% | 26 |
| E55 6.13 | 120 | 6 | VH6-35-1 | 2 | 2.0% | 26 |
| E55 6.3 | 120 | 6 | VH6-35-1 | 2 | 2.0% | 26 |
| E55 6.7 | 116 | 6 | VH6-35-1 | 2 | 2.0% | 26 |
| E55 6.2 | 120 | 6 | VH6-35-1 | 2 | 2.0% | 26 |
| E55 6.X | 111 | 6 | VH6-35-1 | 2 | 2.0% | 26 |
| E55 6.11 | 111 | 6 | VH6-35-1 | 3 | 3.0% | 26 |
| VH6.A11 | 118 | 6 | VH6-35-1 | 3 | 3.0% | 122 |
| A10 | 107 | 6 | VH6-35-1 | 3 | 3.0% | 68 |
| E55 6.1 | 120 | 6 | VH6-35-1 | 4 | 4.0% | 26 |
| FK-001 | 124 | 6 | VH6-35-1 | 4 | 4.0% | 65 |
| VH6.A5 | 121 | 6 | VH6-35-1 | 4 | 4.0% | 122 |
| VH6.A7 | 123 | 6 | VH6-35-1 | 4 | 4.0% | 122 |
| HBp2 | 119 | 6 | VH6-35-1 | 4 | 4.0% | 4 |
| Au46.2 | 123 | 6 | VH6-35-1 | 5 | 5.0% | 49 |
| A431 | 106 | 6 | VH6-35-1 | 5 | 5.0% | 68 |
| VH6.A2 | 120 | 6 | VH6-35-1 | 5 | 5.0% | 122 |
| VH6.A9 | 125 | 6 | VH6-35-1 | 8 | 7.9% | 122 |
| VH6.A8 | 118 | 6 | VH6-35-1 | 10 | 9.9% | 122 |
| VH6-FF3 | 118 | 6 | VH6-35-1 | 2 | 2.0% | 123 |
| VH6.A10 | 126 | 6 | VH6-35-1 | 12 | 11.9% | 122 |
| VH6-EB10 | 117 | 6 | VH6-35-1 | 3 | 3.0% | 123 |
| VH6-E6 | 119 | 6 | VH6-35-1 | 6 | 5.9% | 123 |
| VH6-FE2 | 121 | 6 | VH6-35-1 | 6 | 5.9% | 123 |
| VH6-EE6 | 116 | 6 | VH6-35-1 | 6 | 5.9% | 123 |
| VH6-FD10 | 118 | 6 | VH6-35-1 | 6 | 5.9% | 123 |
| VH6-EX8 | 113 | 6 | VH6-35-1 | 6 | 5.9% | 123 |
| VH6-FG9 | 121 | 6 | VH6-35-1 | 8 | 7.9% | 123 |
| VH6-E5 | 116 | 6 | VH6-35-1 | 9 | 8.9% | 123 |
| VH6-EC8 | 122 | 6 | VH6-35-1 | 9 | 8.9% | 123 |
| VH6-E10 | 120 | 6 | VH6-35-1 | 10 | 9.9% | 123 |
| VH6-FF11 | 122 | 6 | VH6-35-1 | 11 | 10.9% | 123 |
| VH6-FD2 | 115 | 6 | VH6-35-1 | 11 | 10.9% | 123 |
| CLL10 17-2 | 86 | 6 | VH6-35-1 | 4 | 4.0% | 29 |
| VH6-BB11 | 94 | 6 | VH6-35-1 | 4 | 4.0% | 123 |
| VH6-B41 | 93 | 6 | VH6-35-1 | 7 | 6.9% | 123 |
| JU17 | 102 | 6 | VH6-35-1 | 3 | 3.0% | 114 |
| VH6-BD9 | 96 | 6 | VH6-35-1 | 11 | 10.9% | 123 |
| VH6-BB9 | 94 | 6 | VH6-35-1 | 12 | 11.9% | 123 |

TABLE 3A assignment of rearranged V kappa sequences to their germline counterparts

| Family[1] | Name | Rearranged[2] | Sum |
|---|---|---|---|
| 1 | Vk1-1 | 28 | |
| 1 | Vk1-2 | 0 | |
| 1 | Vk1-3 | 1 | |
| 1 | Vk1-4 | 0 | |
| 1 | Vk1-5 | 7 | |
| 1 | Vk1-6 | 0 | |
| 1 | Vk1-7 | 0 | |
| 1 | Vk1-8 | 2 | |
| 1 | Vk1-9 | 9 | |
| 1 | Vk1-10 | 0 | |
| 1 | Vk1-11 | 1 | |
| 1 | Vk1-12 | 7 | |
| 1 | Vk1-13 | 1 | |
| 1 | Vk1-14 | 7 | |
| 1 | Vk1-15 | 2 | |
| 1 | Vk1-16 | 2 | |
| 1 | Vk1-17 | 16 | |
| 1 | Vk1-18 | 1 | |
| 1 | Vk1-19 | 33 | |
| 1 | Vk1-20 | 1 | |
| 1 | Vk1-21 | 1 | |
| 1 | Vk1-22 | 0 | |
| 1 | Vk1-23 | 0 | 119 entries |
| 2 | Vk2-1 | 0 | |
| 2 | Vk2-2 | 1 | |
| 2 | Vk2-3 | 0 | |
| 2 | Vk2-4 | 0 | |
| 2 | Vk2-5 | 0 | |
| 2 | Vk2-6 | 16 | |
| 2 | Vk2-7 | 0 | |
| 2 | Vk2-8 | 0 | |
| 2 | Vk2-9 | 1 | |
| 2 | Vk2-10 | 0 | |
| 2 | Vk2-11 | 7 | |

TABLE 3A-continued assignment of rearranged V kappa sequences to their germline counterparts

| Family[1] | Name | Rearranged[2] | Sum |
|---|---|---|---|
| 2 | Vk2-12 | 0 | 25 entries |
| 3 | Vk3-1 | 1 | |
| 3 | Vk3-2 | 0 | |
| 3 | Vk3-3 | 35 | |
| 3 | Vk3-4 | 115 | |
| 3 | Vk3-5 | 0 | |
| 3 | Vk3-6 | 0 | |
| 3 | Vk3-7 | 1 | |
| 3 | Vk3-8 | 40 | 192 entries |
| 4 | Vk4-1 | 33 | 33 entries |
| 5 | Vk5-1 | 1 | 1 entry |
| 6 | Vk6-1 | 0 | |
| 6 | Vk6-2 | 0 | 0 entries |
| 7 | Vk7-1 | 0 | 0 entries |

TABLE 3B assignment of rearranged V lambda sequences to their germline counterparts

| Family[1] | Name | Rearranged[2] | Sum |
|---|---|---|---|
| 1 | DPL1 | 1 | |
| 1 | DPL2 | 14 | |
| 1 | DPL3 | 6 | |
| 1 | DPL4 | 1 | |
| 1 | HUMLV117 | 4 | |
| 1 | DPL5 | 13 | |
| 1 | DPL6 | 0 | |
| 1 | DPL7 | 0 | |
| 1 | DPL8 | 3 | |
| 1 | DPL9 | 0 | 42 entries |
| 2 | DPL10 | 5 | |
| 2 | VLAMBDA 2.1 | 0 | |
| 2 | DPL11 | 23 | |
| 2 | DPL12 | 15 | |
| 2 | DPL13 | 0 | |
| 2 | DPL14 | 0 | 43 entries |
| 3 | DPL16 | 10 | |
| 3 | DPL23 | 19 | |
| 3 | Humlv318 | 9 | 38 entries |
| 7 | DPL18 | 1 | |
| 7 | DPL19 | 0 | 1 entries |
| 8 | DPL21 | 2 | |
| 8 | HUMLV801 | 6 | 8 entries |
| 9 | DPL22 | 0 | 0 entries |
| unassigned | DPL24 | 0 | 0 entries |
| 10 | gVLX-4.4 | 0 | 0 entries |

TABLE 3C assignment of rearranged V heavy chain sequences to their germline counterparts

| Family[1] | Name | Rearranged[2] | Sum |
|---|---|---|---|
| 1 | VH1-12-1 | 38 | |
| 1 | VH1-12-8 | 2 | |
| 1 | VH1-12-2 | 2 | |
| 1 | VH1-12-9 | 2 | |
| 1 | VH1-12-3 | 0 | |
| 1 | VH1-12-4 | 0 | |
| 1 | VH1-12-5 | 3 | |
| 1 | VH1-12-6 | 0 | |
| 1 | VH1-12-7 | 23 | |
| 1 | VH1-13-1 | 1 | |
| 1 | VH1-13-2 | 1 | |
| 1 | VH1-13-3 | 0 | |
| 1 | VH1-13-4 | 0 | |

TABLE 3C-continued assignment of rearranged V heavy chain sequences to their germline counterparts

| Family[1] | Name | Rearranged[2] | Sum |
|---|---|---|---|
| 1 | VH1-13-5 | 0 | |
| 1 | VH1-13-6 | 17 | |
| 1 | VH1-13-7 | 0 | |
| 1 | VH1-13-8 | 3 | |
| 1 | VH1-13-9 | 0 | |
| 1 | VH1-13-10 | 0 | |
| 1 | VH1-13-11 | 0 | |
| 1 | VH1-13-12 | 10 | |
| 1 | VH1-13-13 | 0 | |
| 1 | VH1-13-14 | 0 | |
| 1 | VH1-13-15 | 4 | |
| 1 | VH1-13-16 | 2 | |
| 1 | VH1-13-17 | 0 | |
| 1 | VH1-13-18 | 1 | |
| 1 | VH1-13-19 | 0 | |
| 1 | VH1-1X-1 | 1 | 110 entries |
| 2 | VH2-21-1 | 0 | |
| 2 | VH2-31-1 | 0 | |
| 2 | VH2-31-2 | 1 | |
| 2 | VH2-31-3 | 1 | |
| 2 | VH2-31-4 | 0 | |
| 2 | VH2-31-5 | 2 | |
| 2 | VH2-31-6 | 0 | |
| 2 | VH2-31-7 | 0 | |
| 2 | VH2-31-14 | 1 | |
| 2 | VH2-31-8 | 0 | |
| 2 | VH2-31-9 | 0 | |
| 2 | VH2-31-10 | 0 | |
| 2 | VH2-31-11 | 1 | |
| 2 | VH2-31-12 | 0 | |
| 2 | VH2-31-13 | 1 | 7 entries |
| 3 | VH3-11-1 | 0 | |
| 3 | VH3-11-2 | 0 | |
| 3 | VH3-11-3 | 5 | |
| 3 | VH3-11-4 | 0 | |
| 3 | VH3-11-5 | 1 | |
| 3 | VH3-11-6 | 1 | |
| 3 | VH3-11-7 | 0 | |
| 3 | VH3-11-8 | 5 | |
| 3 | VH3-13-1 | 9 | |
| 3 | VH3-13-2 | 3 | |
| 3 | VH3-13-3 | 0 | |
| 3 | VH3-13-4 | 0 | |
| 3 | VH3-13-5 | 0 | |
| 3 | VH3-13-6 | 0 | |
| 3 | VH3-13-7 | 32 | |
| 3 | VH3-13-8 | 4 | |
| 3 | VH3-13-9 | 0 | |
| 3 | VH3-13-10 | 46 | |
| 3 | VH3-13-11 | 0 | |
| 3 | VH3-13-12 | 11 | |
| 3 | VH3-13-13 | 17 | |
| 3 | VH3-13-14 | 8 | |
| 3 | VH3-13-15 | 4 | |
| 3 | VH3-13-16 | 3 | |
| 3 | VH3-13-17 | 2 | |
| 3 | VH3-13-18 | 1 | |
| 3 | VH3-13-19 | 13 | |
| 3 | VH3-13-20 | 1 | |
| 3 | VH3-13-21 | 1 | |
| 3 | VH3-13-22 | 0 | |
| 3 | VH3-13-23 | 0 | |
| 3 | VH3-13-24 | 4 | |
| 3 | VH3-13-25 | 1 | |
| 3 | VH3-13-26 | 6 | |
| 3 | VH3-14-1 | 1 | |
| 3 | VH3-14-4 | 15 | |
| 3 | VH3-14-2 | 0 | |
| 3 | VH3-14-3 | 0 | |
| 3 | VH3-1X-1 | 0 | |
| 3 | VH3-1X-2 | 0 | |
| 3 | VH3-1X-3 | 6 | |
| 3 | VH3-1X-4 | 0 | |
| 3 | VH3-1X-5 | 0 | |

TABLE 3C-continued assignment of rearranged V heavy chain sequences to their germline counterparts

| Family[1] | Name | Rearranged[2] | Sum |
|---|---|---|---|
| 3 | VH3-1X-6 | 11 | |
| 3 | VH3-1X-7 | 0 | |
| 3 | VH3-1X-8 | 1 | |
| 3 | VH3-1X-9 | 0 | 212 entries |
| 4 | VH4-11-1 | 0 | |
| 4 | VH4-11-2 | 20 | |
| 4 | VH4-11-3 | 0 | |
| 4 | VH4-11-4 | 0 | |
| 4 | VH4-11-5 | 0 | |
| 4 | VH4-11-6 | 0 | |
| 4 | VH4-11-7 | 5 | |
| 4 | VH4-11-8 | 7 | |
| 4 | VH4-11-9 | 3 | |
| 4 | VH4-11-10 | 0 | |
| 4 | VH4-11-11 | 0 | |
| 4 | VH4-11-12 | 4 | |
| 4 | VH4-11-13 | 0 | |
| 4 | VH4-11-14 | 0 | |
| 4 | VH4-11-15 | 0 | |
| 4 | VH4-11-16 | 1 | |
| 4 | VH4-21-1 | 0 | |
| 4 | VH4-21-2 | 0 | |
| 4 | VH4-21-3 | 1 | |
| 4 | VH4-21-4 | 1 | |
| 4 | VH4-21-5 | 1 | |
| 4 | VH4-21-6 | 1 | |
| 4 | VH4-21-7 | 0 | |
| 4 | VH4-21-8 | 0 | |
| 4 | VH4-21-9 | 0 | |
| 4 | VH4-31-1 | 0 | |
| 4 | VH4-31-2 | 0 | |
| 4 | VH4-31-3 | 0 | |
| 4 | VH4-31-4 | 2 | |
| 4 | VH4-31-5 | 0 | |
| 4 | VH4-31-6 | 0 | |
| 4 | VH4-31-7 | 0 | |
| 4 | VH4-31-8 | 0 | |
| 4 | VH4-31-9 | 0 | |
| 4 | VH4-31-10 | 0 | |
| 4 | VH4-31-11 | 0 | |
| 4 | VH4-31-12 | 4 | |
| 4 | VH4-31-13 | 7 | |
| 4 | VH4-31-14 | 0 | |
| 4 | VH4-31-15 | 0 | |
| 4 | VH4-31-16 | 0 | |
| 4 | VH4-31-17 | 0 | |
| 4 | VH4-31-18 | 0 | |
| 4 | VH4-31-19 | 0 | |
| 4 | VH4-31-20 | 0 | 57 entries |
| 5 | VH5-12-1 | 82 | |
| 5 | VH5-12-2 | 1 | |
| 5 | VH5-12-3 | 0 | |
| 5 | VH5-12-4 | 14 | 97 entries |
| 6 | VH6-35-1 | 74 | 74 entries |

TABLE 4A

Analysis of V kappa subgroup 1

| amino acid[1] | Framework I | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| A | | 1 | | | | | | | 1 | | | | 102 | | 1 | | | |
| B | | | 1 | | | 1 | | | | | | | | | | | | |
| C | | | | | | | | | | | | | | | 1 | | | |
| D | 64 | | | | | | | | | | | | | | | | 101 | |
| E | 8 | | 14 | | | | | | | | | | | | 1 | | 2 | |
| F | | | | | | | | | 1 | 6 | | | | | 1 | | | |
| G | | | | | | | | | | | | | | | | 105 | | |
| H | | | | | | | | | | | | | | | | | | |
| I | | 65 | | | | | | | | | | | | | | 4 | | |
| K | | | 1 | | | | | | | | | | | | | | | |
| L | | | 6 | | 21 | | | | | | 96 | | 1 | | | | | |
| M | 1 | | | 66 | | | | | | | | | | | | | | |
| N | | | | | | | | | | | | | | | | | | |
| P | | | | | | | | 103 | | | 1 | | 2 | | 1 | | | |
| Q | | 62 | | | | 88 | | | | | 1 | | | | | | | |
| R | | | | | | | | | | | | | | | | | | 94 |
| S | | | | | | 89 | | 102 | 80 | | 103 | | 103 | | | | | 5 |
| T | 1 | | 88 | | | | | | 18 | | | | | | | | | 6 |
| V | 1 | 9 | | | | | | | | | 8 | | 2 | | 98 | | | |
| W | | | | | | | | | | | | | | | | | | |

TABLE 4A-continued

Analysis of V kappa subgroup 1

| | | | | | | | | | | | | | | | | | | |
|---|---|---|---|---|---|---|---|---|---|---|---|---|---|---|---|---|---|---|
| X | 1 | | | | | | | | | | | | | | | | 1 | |
| Y | | | | | | | | | | | | | | | | | 1 | |
| — | | | | | | | | | | | | | | | | | | |
| unknown (?) | | | | | | | | | | | | | | | | | | |
| not sequenced | 31 | 31 | 18 | 18 | 17 | 16 | 16 | 2 | 1 | | | | | | | | | |
| sum of seq[2] | 74 | 74 | 87 | 87 | 88 | 89 | 89 | 103 | 104 | 105 | 105 | 105 | 105 | 105 | 105 | 105 | 105 | 105 |
| oomcaa[3] | 64 | 65 | 62 | 66 | 88 | 88 | 89 | 103 | 102 | 80 | 96 | 103 | 102 | 103 | 98 | 105 | 101 | 94 |
| mcaa[4] | D | I | Q | M | T | Q | S | P | S | S | L | S | A | S | V | G | D | R |
| rel. oomcaa[5] | 86% | 88% | 71% | 76% | 100% | 99% | 100% | 100% | 98% | 76% | 91% | 98% | 97% | 98% | 93% | 100% | 96% | 90% |
| pos occupied[6] | 4 | 5 | 5 | 2 | 1 | 2 | 1 | 1 | 3 | 4 | 3 | 2 | 3 | 3 | 5 | 1 | 4 | 3 |

| | Framework I | | | | | CDRI | | | | | | | | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | A | B | C | D | E | F | 28 | 29 | 30 |
| A | 1 | 1 | | 1 | | | 103 | | | | | | | | | | | 1 |
| B | | | | | | | | | 1 | | | | | | | | | |
| C | | | | | 105 | | | | | | | | | | | | | |
| D | | | | | | | | | | | | | | | | 25 | | 1 |
| E | | | | | | 1 | 1 | | 2 | | | | | | | | | |
| F | | | 2 | | | | | | | | | | | | | | 1 | 1 |
| G | | | | | | | | 1 | | | | | | | | 25 | | 7 |
| H | | | | | | | | | 1 | | | | | | | | | 1 |
| I | 6 | 4 | 101 | 1 | | | | | | | | | | | | | 98 | 1 |
| K | | | | | | 2 | | | 1 | | | | | | | | | |
| L | | | | | | 1 | | | | | | | | | | | | 2 |
| M | | | | | | | | | | | | | | | | | | |
| N | | | | | | | | | 1 | | | | | | | 6 | | 16 |
| P | | | | | | | | | | | | | | | | | | |
| Q | | | | | | 20 | | | 100 | | | | | | | | | |
| R | | | | | | 81 | | | | | | | | | | | | 16 |
| S | | 1 | | | | | | 102 | | | | | | | | 41 | 2 | 57 |
| T | | 99 | | 103 | | | 1 | 1 | | | | | | | | 7 | | |
| V | 98 | | 2 | | | | | | | | | | | | | 1 | 4 | 1 |
| W | | | | | | | | | | | | | | | | | | |
| X | | | | | | | | | | | | | | | | | | |
| Y | | | | | | | | | | | | | | | | | | 1 |
| — | | | | | | | | | | 105 | 105 | 105 | 105 | 105 | 105 | | | |
| unknown (?) | | | | | | | | | | | | | | | | | | |
| not sequenced | | | | | | | | | | | | | | | | | | |
| sum of seq[2] | 105 | 105 | 105 | 105 | 105 | 105 | 105 | 105 | 105 | 105 | 105 | 105 | 105 | 105 | 105 | 105 | 105 | 105 |
| oomcaa[3] | 98 | 99 | 101 | 103 | 105 | 81 | 103 | 102 | 100 | 105 | 105 | 105 | 105 | 105 | 105 | 41 | 98 | 57 |
| mcaa[4] | V | T | I | T | C | R | A | S | Q | — | — | — | — | — | — | S | I | S |
| rel. oomcaa[5] | 93% | 94% | 96% | 98% | 100% | 77% | 98% | 97% | 95% | 100% | 100% | 100% | 100% | 100% | 100% | 39% | 93% | 54% |
| pos occupied[6] | 3 | 4 | 3 | 3 | 1 | 5 | 3 | 4 | 5 | 1 | 1 | 1 | 1 | 1 | 1 | 6 | 4 | 12 |

| | CDRI | | | | | | | | | Framework II | | | | | | | | |
|---|---|---|---|---|---|---|---|---|---|---|---|---|---|---|---|---|---|---|
| amino acid[1] | 31 | 32 | 33 | 34 | 35 | 36 | 37 | 38 | 39 | 40 | 41 | 42 | 43 | 44 | 45 | 46 | 47 | 48 |
| A | 1 | | 1 | 42 | | | | | | | | | 94 | | | | | |
| B | | | | | | | 1 | 1 | | | | | | | | | | |
| C | | 1 | | | | | | | | | | | | | | | | |
| D | 5 | 7 | | | | | 1 | | | | | | | | | | | |
| E | | 1 | | | | | 2 | | | | 1 | 3 | | | 1 | 1 | | |
| F | | 7 | | | | 6 | | | | | | | | | | 1 | | |
| G | 3 | | | 4 | | | | | | | 100 | | 1 | | | | | |
| H | 2 | 2 | | 1 | | | 2 | | | | | | | | | | | |
| I | 4 | | | 1 | | | | | | | | 1 | | | | 1 | | 100 |
| K | 7 | | | | | | | | 95 | | | 95 | | | 86 | | | |
| L | 1 | | 101 | | | | | | | | | 1 | | | 89 | 103 | | |
| M | | | | | | | | | | | | | | | | | | 2 |
| N | 42 | | | 50 | | | | | | | | | | | 10 | | | |
| P | | | | | | | | | | 102 | | | | 104 | | 1 | | |
| Q | | | | | | | 98 | 103 | 2 | | | 1 | | | 1 | | | |
| R | 3 | 2 | | | | | | | 3 | 1 | | | | | 3 | 3 | | |
| S | 32 | 3 | 1 | 1 | | | | | | 1 | | | | | 1 | | | |
| T | 4 | | | 4 | | | | | 1 | | | 3 | | | 1 | | | |
| V | | | 1 | | | | | | | | | | 9 | | | 9 | | |
| W | | 21 | | | 104 | | | | | | | | | | | | | |
| X | | | | 1 | | | | | | | | | | | 1 | | | |
| Y | | 60 | | | | 98 | | | | | | | | | | | | |
| unknown (?) | | | | | | | | | 3 | | 3 | | | | | | | |
| not sequenced | 1 | 1 | 1 | 1 | 1 | 1 | 1 | 1 | 1 | 1 | 1 | 1 | 1 | 1 | 1 | 1 | 2 | 3 |
| sum of seq[2] | 104 | 104 | 104 | 104 | 104 | 104 | 104 | 104 | 104 | 104 | 104 | 104 | 104 | 104 | 104 | 104 | 103 | 102 |
| oomcaa[3] | 42 | 60 | 101 | 50 | 104 | 98 | 98 | 103 | 95 | 102 | 100 | 95 | 94 | 104 | 86 | 89 | 103 | 100 |

TABLE 4A-continued

Analysis of V kappa subgroup 1

| | | | | | | | | | | | | | | | | | | |
|---|---|---|---|---|---|---|---|---|---|---|---|---|---|---|---|---|---|---|
| mcaa[4] | N | Y | L | N | W | Y | Q | Q | K | P | G | K | A | P | K | L | L | I |
| rel. oomcaa[5] | 40% | 58% | 97% | 48% | 100% | 94% | 94% | 99% | 91% | 98% | 96% | 91% | 90% | 100% | 83% | 86% | 100% | 98% |
| pos occupied[6] | 11 | 9 | 4 | 8 | 1 | 2 | 5 | 2 | 4 | 3 | 2 | 6 | 3 | 1 | 8 | 6 | 1 | 2 |

| | Framework II | CDR II | | | | | | | Framework III | | | | | | | | |
|---|---|---|---|---|---|---|---|---|---|---|---|---|---|---|---|---|---|
| amino acid[1] | 49 | 50 | 51 | 52 | 53 | 54 | 55 | 56 | 57 | 58 | 59 | 60 | 61 | 62 | 63 | 64 | 65 | 66 |
| A | | 50 | 95 | | | | | 3 | | | | | | | | | | 2 |
| B | | | | | | | | | | | 1 | | | | | | | |
| C | | | | | | | | | | | | | | | | | | |
| D | | 21 | 1 | 1 | 1 | | | 1 | | | | | | | | | | |
| E | | 1 | | 1 | | | 33 | | | | | | | | | | | |
| F | 3 | | | 1 | | | | | | 1 | | | | 103 | | | | |
| G | | 9 | 2 | | | | | 2 | 105 | | | | | | | 105 | 4 | 101 |
| H | 2 | | | | | | 1 | | | | | | | | | | | |
| I | | | | | 1 | | | 3 | | 4 | | | | 1 | 3 | | | |
| K | | 16 | | | 2 | | 5 | 1 | | | | | 1 | | | | | |
| L | | | | | | 101 | | | | | | | | | 1 | | | |
| M | | | | | | | | | | | | | | | | | | |
| N | | 2 | | 1 | 25 | | | 6 | | | | | | | | | | |
| P | | 1 | | | | | 1 | 1 | | | | 101 | 2 | | | | | |
| Q | | | | | | | 62 | | | | | | | | | | 1 | |
| R | | | | | 1 | 1 | 2 | 1 | | | | | 103 | | 1 | | 1 | 1 |
| S | 5 | 1 | 1 | 99 | 41 | 2 | | 68 | | 2 | 103 | | 1 | | 98 | | 96 | |
| T | | 1 | 4 | 1 | 31 | | | 19 | | | 1 | | 1 | | 2 | | 3 | |
| V | | | 1 | | 1 | | | | | 99 | | | | 1 | | | | |
| W | | | | | | | | | | | | | | | | | | |
| X | | | | | 1 | | | | | 1 | | | | | | | | 1 |
| Y | 92 | 1 | | | | | | | | | | | | | | | | |
| — | | | | | | | | | | | | | | | | | | |
| unknown (?) | | | | | | | | | | | | | | | | | | |
| not sequenced | 3 | 2 | 1 | 1 | 1 | 1 | 1 | | | | | | | | | | | |
| sum of seq[2] | 102 | 103 | 104 | 104 | 104 | 104 | 104 | 104 | 105 | 105 | 105 | 105 | 105 | 105 | 105 | 105 | 105 | 105 |
| oomcaa[3] | 92 | 50 | 95 | 99 | 41 | 101 | 62 | 68 | 105 | 99 | 101 | 103 | 103 | 103 | 98 | 105 | 96 | 101 |
| mcaa[4] | Y | A | A | S | S | L | Q | S | G | V | P | S | R | F | S | G | S | G |
| rel. oomcaa[5] | 90% | 49% | 91% | 95% | 39% | 97% | 60% | 65% | 100% | 94% | 96% | 98% | 98% | 98% | 93% | 100% | 91% | 96% |
| pos occupied[6] | 4 | 10 | 6 | 6 | 9 | 3 | 6 | 10 | 1 | 4 | 4 | 2 | 3 | 3 | 5 | 1 | 5 | 4 |

| | Framework III | | | | | | | | | | | | | | | | | |
|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 |
| A | 1 | 1 | 1 | | | 3 | | | | 1 | | | | 2 | | | | 101 |
| B | | | | | | | | | | | | | 3 | | 2 | | | |
| C | | | | | | | | | | | | | | | | | | |
| D | | | | 67 | | | | | | 1 | | | | | 16 | 101 | | |
| E | | 1 | | 30 | | | | | | | | | | | 83 | | | |
| F | 3 | | | | 102 | 1 | 21 | | | | | | | | | | 73 | |
| G | | 102 | | | | | | | | | 4 | | | | 1 | | | 2 |
| H | | | | 3 | | | | | | | | | | | | | | |
| I | | | | | | | | | 99 | 5 | | | | | | | 17 | |
| K | | | | | 1 | | | | | | | | | | | | | |
| L | | | | | | | 81 | | | | | 103 | 1 | | | | 1 | |
| M | | | 1 | | | | | | | | | | | | | | | |
| N | | | | | | | | | | 7 | 4 | | | | | | | |
| P | | | | | | | | | | | | | | 97 | | | | |
| Q | | | | | | | | | | | | | 97 | | | | | |
| R | | | 2 | | | | | | | 2 | 1 | | 2 | | | | | |
| S | 100 | | | | | 2 | | 1 | | 86 | 94 | | | | 4 | | | 1 |
| T | | | 101 | | | 98 | | 102 | | 2 | 1 | | | | | | | |
| V | | | | 1 | 1 | | 2 | | 4 | | | 1 | | | | | 11 | |
| W | | | | | | | | | | | | | | | | | | |
| X | | 1 | | 2 | | | 1 | | | | | | | 1 | 2 | | | |
| Y | 1 | | | 1 | 1 | | | | | | | | | | | | | |
| — | | | | | | | | | | | | | | | | | | |
| unknown (?) | | | | | | | | | | | | | | | | | | |
| not sequenced | | | | 1 | 1 | 1 | 1 | 1 | 1 | 1 | 1 | 1 | 2 | 2 | 2 | 2 | 2 | 2 |
| sum of seq[2] | 105 | 105 | 105 | 105 | 104 | 104 | 104 | 104 | 104 | 104 | 104 | 104 | 103 | 103 | 103 | 103 | 103 | 103 |
| oomcaa[3] | 100 | 102 | 101 | 67 | 102 | 98 | 81 | 102 | 99 | 86 | 94 | 103 | 97 | 97 | 83 | 101 | 73 | 101 |
| mcaa[4] | S | G | T | D | F | T | L | T | I | S | S | L | Q | P | E | D | F | A |
| rel. oomcaa[5] | 95% | 97% | 96% | 64% | 98% | 94% | 78% | 98% | 95% | 83% | 90% | 99% | 94% | 94% | 81% | 98% | 71% | 98% |
| pos occupied[6] | 4 | 4 | 4 | 7 | 3 | 4 | 3 | 3 | 3 | 7 | 5 | 2 | 4 | 3 | 5 | 2 | 5 | 2 |

TABLE 4A-continued

Analysis of V kappa subgroup 1

| | Framework III | | | | CDR III | | | | | | | | | | | | |
|---|---|---|---|---|---|---|---|---|---|---|---|---|---|---|---|---|---|
| amino acid[1] | 85 | 86 | 87 | 88 | 89 | 90 | 91 | 92 | 93 | 94 | 95 | A | B | C | D | E | F | 96 |
| A | 1 | | | | | 1 | 7 | 1 | | 5 | 1 | | | | | | | 1 |
| B | | | | | 2 | 3 | | | | | | | | | | | | |
| C | | | | 102 | | | | | | | | | | | | | | |
| D | | | | | | | | 23 | 5 | 1 | | | | | | | | 1 |
| E | | | | | | | 1 | | 1 | | 1 | 1 | | | | | | |
| F | | | 7 | | | | 3 | | | 13 | | | | | | | | 6 |
| G | | | | | | | 1 | | 1 | 2 | 1 | | 1 | | | | | |
| H | | | 1 | | 4 | 6 | 7 | 3 | 1 | | | | | | | | | 2 |
| I | | | | | | | | 4 | 1 | 2 | 1 | | | | | | | 5 |
| K | | 1 | | | | 7 | | 1 | | | | | | | | | | 1 |
| L | | | | | 7 | | 6 | 2 | | 18 | 2 | | | | | | | 18 |
| M | 1 | | | | | | | | | | | | | | | | | |
| N | 1 | | | | | | 6 | 31 | 19 | 1 | | | | | | | | 1 |
| P | 1 | | | | | | | | | 1 | 82 | 6 | | | | | | 6 |
| Q | | | | | 90 | 86 | 1 | 2 | | | | | | | | | | 1 |
| R | | | | | | | 1 | | 2 | 2 | | | | | | | | 6 |
| S | | 1 | | | | | 27 | 3 | 58 | 5 | 10 | | | | | | | 2 |
| T | 97 | | | | | | 3 | 1 | 15 | 25 | | | | | | | | 2 |
| V | 1 | | | | | | | | | 5 | | | | | | | | 2 |
| W | | | | | | | | | | 1 | | | | | | | | 15 |
| X | | | | | | | | | | | | | | | | | | |
| Y | | 101 | 93 | | | | 42 | 32 | 1 | 23 | | | | | | | | 16 |
| — | | | | | | | | | | | 3 | 82 | 88 | 89 | 89 | 89 | 89 | 4 |
| unknown (?) | | | 1 | | | | | | | | | | | | | | | |
| not sequenced | 3 | 2 | 3 | 3 | 2 | 2 | 1 | 1 | 1 | 1 | 4 | 16 | 16 | 16 | 16 | 16 | 16 | 16 |
| sum of seq[2] | 102 | 103 | 102 | 102 | 103 | 103 | 104 | 104 | 104 | 104 | 101 | 89 | 89 | 89 | 89 | 89 | 89 | 89 |
| oomcaa[3] | 97 | 101 | 93 | 102 | 90 | 86 | 42 | 32 | 58 | 25 | 82 | 82 | 88 | 89 | 89 | 89 | 89 | 18 |
| mcaa[4] | T | Y | Y | C | Q | Q | Y | Y | S | T | P | — | — | — | — | — | — | L |
| rel. oomcaa[5] | 95% | 98% | 91% | 100% | 87% | 83% | 40% | 31% | 56% | 24% | 81% | 92% | 99% | 100% | 100% | 100% | 100% | 20% |
| pos occupied[6] | 6 | 3 | 3 | 1 | 4 | 5 | 11 | 12 | 10 | 14 | 8 | 3 | 2 | 1 | 1 | 1 | 1 | 17 |

| | CDR III | Framework IV | | | | | | | | | | | |
|---|---|---|---|---|---|---|---|---|---|---|---|---|---|
| amino acid[1] | 97 | 98 | 99 | 100 | 101 | 102 | 103 | 104 | 105 | 106 | A | 107 | 108 | sum |
| A | | | | | | | | | | | | | | 627 |
| B | | | | | 1 | | | | | 1 | | | | 19 |
| C | | | | | | | | | | | | | | 209 |
| D | | | | | | | | | | 15 | | | | 459 |
| E | | | | | 2 | | | | | 65 | | | | 258 |
| F | | 86 | | | | | | | | | 2 | | | 451 |
| G | | | 87 | 29 | 87 | | | | | | | | 2 | 894 |
| H | 1 | | | | | | | | | | | | | 40 |
| I | | | | | | | | 1 | | 72 | | | | 606 |
| K | 1 | | | | | | 77 | | | | | 79 | | 480 |
| L | 1 | 1 | | | | | | | 22 | 4 | 2 | | | 793 |
| M | 1 | | | | | | | | | 5 | | | | 77 |
| N | | | | | | | | | | 1 | | 2 | | 232 |
| P | | | | | 7 | | | | | | | | 1 | 620 |
| Q | | | | | 48 | | | | | 1 | | | | 865 |
| R | | | | | | | 6 | | | | | 2 | 70 | 413 |
| S | 2 | | | | | | | | | | | | | 1636 |
| T | 82 | | | | | 87 | 3 | | | | | 2 | | 1021 |
| V | | | | | | | 1 | 63 | | 3 | | | | 440 |
| W | | | | | | | | | | | | | | 141 |
| X | | | | | | | | | | | | | | 14 |
| Y | | | | | | | | | | | | | | 564 |
| — | | 1 | | | | | | | | | 85 | | 1 | 1250 |
| unknown (?) | | | | | | | | | | | | | | 7 |
| not sequenced | 16 | 18 | 18 | 18 | 18 | 18 | 18 | 19 | 19 | 20 | 20 | 20 | 31 | 589 |
| sum of seq[2] | 89 | 87 | 87 | 87 | 87 | 87 | 87 | 86 | 86 | 85 | 85 | 85 | 74 | |
| oomcaa[3] | 82 | 86 | 87 | 48 | 87 | 87 | 77 | 63 | 65 | 72 | 85 | 79 | 70 | |
| mcaa[4] | T | F | G | G | G | T | K | V | E | I | — | K | R | |
| rel. oomcaa[5] | 92% | 99% | 100% | 55% | 100% | 100% | 89% | 73% | 76% | 85% | 100% | 93% | 95% | |
| pos occupied[6] | 7 | 2 | 1 | 5 | 1 | 1 | 4 | 3 | 5 | 6 | 1 | 4 | 4 | |

TABLE 4B

Analysis of V kappa subgroup 2

| | Framework I | | | | | | | | | | | | | | | | | |
|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 |
| A | | | | | | | | | | | | | | | | | | |
| B | | | | | | | | | | | | | | | | | | |
| C | | | | | | | | | | | | | | | | | | |
| D | 14 | | | | | | | | | | | | | | | | | |
| E | 3 | | | | | | | | | | | | | | | | 15 | |
| F | | | | | | | | | 1 | 1 | | | | | | | | |
| G | | | | | | | | | | | | | | | | 22 | | |
| H | | | | | | | | | | | | | | | | | | |
| I | | 8 | | | | | | | | | | | | | | | | |
| K | | | | | | | | | | | | | | | | | | |
| L | | 3 | | 1 | | | | | | 17 | | 18 | | | 6 | | | |
| M | | | | 15 | | | | | | | | | | | | | | |
| N | | | | | | | | | | | | | | | | | | |
| P | | | | | | | | | 18 | | | 18 | | | 15 | | | 22 |
| Q | | | | | | 18 | | | | | | | | | | | 7 | |
| R | | | | | | | | | | | | | | | | | | |
| S | | | | | | | | 18 | | | 17 | | | | | | | |
| T | | | | | 17 | | | | | | | | | 21 | | | | |
| V | | 6 | 17 | 1 | | | | | | | | | 18 | | | | | |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | 1 | | | | | | | | | | | | | |
| not sequenced | 5 | 5 | 5 | 5 | 4 | 4 | 4 | 4 | 4 | 4 | 4 | 4 | 4 | 1 | 1 | | | |
| sum of seq[2] | 17 | 17 | 17 | 17 | 18 | 18 | 18 | 18 | 18 | 18 | 18 | 18 | 18 | 21 | 21 | 22 | 22 | 22 |
| oomcaa[3] | 14 | 8 | 17 | 15 | 17 | 18 | 18 | 18 | 17 | 17 | 17 | 18 | 18 | 18 | 21 | 15 | 22 | 22 |
| mcaa[4] | D | I | V | M | T | Q | S | P | L | S | L | P | V | T | P | G | E | P |
| rel. oomcaa[5] | 82% | 47% | 100% | 88% | 94% | 100% | 100% | 100% | 94% | 94% | 100% | 100% | 100% | 100% | 71% | 100% | 68% | 100% |
| pos occupied[6] | 2 | 3 | 1 | 3 | 1 | 1 | 1 | 1 | 2 | 2 | 1 | 1 | 1 | 1 | 2 | 1 | 2 | 1 |

| | Framework I | | | | | CDRI | | | | | | | | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | A | B | C | D | E | F | 28 | 29 | 30 |
| A | 22 | | | | | | | | | | | | | | | | | |
| B | | | | | | | | | | | | | | | | | | |
| C | | | | | | 22 | | | | | | | | | | | | |
| D | | | | | | | | | | | | | 1 | | | | 9 | 1 |
| E | | | | | | | | | | | | | | | | | | |
| F | | | | | | | | | | | | | | | | | | 2 |
| G | | | | | | | | | | | | | | 1 | | | 22 | |
| H | | | | | | | | | | | | | 16 | | | | | |
| I | | | | 22 | | | | | | | | | | | | | | |
| K | | | | | | | 1 | | | | | | | | | | | |
| L | | | | | | | | | 1 | | 22 | 13 | | | | | | |
| M | | | | | | | | | | | | 1 | | | | | | |
| N | | | | | | | | | | | | | | | | | 10 | 7 |
| P | | | | | | | | | | | | | | | | | | |
| Q | | | 1 | | | | | | 21 | | | | | | | | | |
| R | | | | | | 21 | | | | | | | | 2 | | | | |
| S | | 22 | | | 21 | | 22 | 22 | | 22 | | | | 19 | | 1 | | |
| T | | | | | | | | | | | | | | | | | | |
| V | | | | | | | | | | | | 8 | | | | | | |
| W | | | | | | | | | | | | | 1 | | | | | |
| X | | | | | | | | | | | | | | | | | 1 | 1 |
| Y | | | | | | | | | | | | | | 4 | | | 1 | 11 |
| — | | | | | | | | | | | | | | | 22 | | | |
| unknown (?) | | | | | | | | | | | | | | | | | | |
| not sequenced | | | | | | | | | | | | | | | | | | |
| sum of seq[2] | 22 | 22 | 22 | 22 | 22 | 22 | 22 | 22 | 22 | 22 | 22 | 22 | 22 | 22 | 22 | 22 | 22 | 22 |
| oomcaa[3] | 22 | 22 | 22 | 21 | 22 | 21 | 22 | 22 | 21 | 22 | 22 | 13 | 16 | 19 | 22 | 10 | 22 | 11 |
| mcaa[4] | A | S | I | S | C | R | S | S | Q | S | L | L | H | S | — | N | G | Y |
| rel. oomcaa[5] | 100% | 100% | 100% | 95% | 100% | 95% | 100% | 100% | 95% | 100% | 100% | 59% | 73% | 86% | 100% | 45% | 100% | 50% |
| pos occupied[6] | 1 | 1 | 1 | 2 | 1 | 2 | 1 | 1 | 2 | 1 | 1 | 3 | 4 | 3 | 1 | 5 | 1 | 5 |

| | CDRI | | | | Framework II | | | | | | | | | | | | | |
|---|---|---|---|---|---|---|---|---|---|---|---|---|---|---|---|---|---|---|
| amino acid[1] | 31 | 32 | 33 | 34 | 35 | 36 | 37 | 38 | 39 | 40 | 41 | 42 | 43 | 44 | 45 | 46 | 47 | 48 |
| A | | | | | | | | | | | | | | | | | | |
| B | | | | | | | | | | | | | | | | | | |
| C | | | | | | | | | | | | | | | | | | |

TABLE 4B-continued

Analysis of V kappa subgroup 2

| amino acid[1] | | | | | | | | | | | | | | | | | | |
|---|---|---|---|---|---|---|---|---|---|---|---|---|---|---|---|---|---|---|
| D | 1 | | | 11 | | | | | | | | | | | | | | |
| E | | | | | | | | | | | | | | | 1 | | | |
| F | | | | | 7 | | | | | | | | | | | | | |
| G | | | | | | | | | | | 22 | | | | | | | |
| H | | 1 | | 1 | | | | | | | | | | | | | | |
| I | | | | | | | | | | | | | | | | 1 | | 22 |
| K | 1 | | | | | | | | 15 | | | | | | | | | |
| L | | | 22 | | | 16 | | | | | | | | | | 14 | 21 | |
| M | | | | | | | | | | | | | | | | | | |
| N | 12 | | | 9 | | | | | | | | | | | | | | |
| P | | | | | | | | | 22 | | | | 21 | | | | | |
| Q | | | | | 6 | 22 | | | | 22 | | | 12 | | | | | |
| R | | | | | | | 7 | | | | | 21 | 8 | 7 | | | | |
| S | | | | | | | | | | | | | | | | | | |
| T | 8 | | | | | | | | | | | | | | | 1 | | |
| V | | | | | | | | | | | | | | | | | | |
| W | | | | | 22 | | | | | | | | | | | | | |
| X | | | 1 | | | | | | | | | | | | | | | |
| Y | | 21 | | | 15 | | | | | | | | | | | | | |
| — | | | | | | | | | | | | | | | | | | |
| unknown (?) | | | | | | | | | | | | | | | | | | |
| not sequenced | | | | | | | | | | | | | 1 | 1 | 1 | | | |
| sum of seq[2] | 22 | 22 | 22 | 22 | 22 | 22 | 22 | 22 | 22 | 22 | 22 | 22 | 21 | 21 | 21 | 22 | 22 | 22 |
| oomcaa[3] | 12 | 21 | 22 | 11 | 22 | 15 | 16 | 22 | 15 | 22 | 22 | 22 | 21 | 21 | 12 | 14 | 21 | 22 |
| mcaa[4] | N | Y | L | D | W | Y | L | Q | K | P | G | Q | S | P | Q | L | L | I |
| rel. oomcaa[5] | 55% | 95% | 100% | 50% | 100% | 68% | 73% | 100% | 68% | 100% | 100% | 100% | 100% | 100% | 57% | 64% | 95% | 100% |
| pos occupied[6] | 4 | 2 | 1 | 4 | 1 | 2 | 2 | 1 | 2 | 1 | 1 | 1 | 1 | 1 | 3 | 3 | 2 | 1 |

| | Framework II | CDR II | | | | | | | Framework III | | | | | | | | | |
|---|---|---|---|---|---|---|---|---|---|---|---|---|---|---|---|---|---|---|
| amino acid[1] | 49 | 50 | 51 | 52 | 53 | 54 | 55 | 56 | 57 | 58 | 59 | 60 | 61 | 62 | 63 | 64 | 65 | 66 |
| A | | | | | | | | 14 | | | | | | | | | | |
| B | | | | | | | | | | | | | | | | | | |
| C | | | | | | | | | | | | | | | | | | |
| D | | | | | | | 7 | | | | | 22 | | | | 1 | | |
| E | | | | | | | | | | | | | | | | | | |
| F | | | | | | | | | | | | | 21 | | | | | |
| G | | | 12 | | | 1 | | | 22 | | | | | | | 21 | | 22 |
| H | | | | | | | | | | | | | | | | | | |
| I | | | | | | | | | | | | | | | | | | |
| K | | 5 | | | | | | | | | | | | | | | | |
| L | | 14 | 1 | | | | | | | | | | | | | | | |
| M | | | | | | | | | | | | | | | | | | |
| N | | | | | 18 | | | | | | | | | | | | | |
| P | | | | | | | | | | | | | 22 | | | | | |
| Q | | 1 | | | | | | | | | | | | | | | | |
| R | | 1 | | | | 22 | | | | | | | 20 | | | | 1 | |
| S | | | 2 | 22 | 2 | | | 22 | | | | | 1 | | 22 | | 21 | |
| T | | | | | 1 | | | | | | | | 1 | | | | | |
| V | | | 6 | | | | | | | 22 | | | | 1 | | | | |
| W | | | | | | | | | | | | | | | | | | |
| X | | | | | | | | | | | | | | | | | | |
| Y | 21 | | | | 1 | | | | | | | | | | | | | |
| — | | | | | | | | | | | | | | | | | | |
| unknown (?) | | | | | | | | | | | | | | | | | | |
| not sequenced | 1 | 1 | 1 | | | | | | | | | | | | | | | |
| sum of seq[2] | 21 | 21 | 21 | 22 | 22 | 22 | 22 | 22 | 22 | 22 | 22 | 22 | 22 | 22 | 22 | 22 | 22 | 22 |
| oomcaa[3] | 21 | 14 | 12 | 22 | 18 | 22 | 14 | 22 | 22 | 22 | 22 | 22 | 20 | 21 | 22 | 21 | 21 | 22 |
| mcaa[4] | Y | L | G | S | N | R | A | S | G | V | P | D | R | F | S | G | S | G |
| rel. oomcaa[5] | 100% | 67% | 57% | 100% | 82% | 100% | 64% | 100% | 100% | 100% | 100% | 100% | 91% | 95% | 100% | 95% | 95% | 100% |
| pos occupied[6] | 1 | 4 | 4 | 1 | 4 | 1 | 3 | 1 | 1 | 1 | 1 | 1 | 3 | 2 | 1 | 2 | 2 | 1 |

| | Framework III | | | | | | | | | | | | | | | | | |
|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 |
| A | | | | | | | | | | | | | | 20 | | | | |
| B | | | | | | | | | | | | | | | | | | |
| C | | | | | | | | | | | | | | | | | | |
| D | | 1 | | 22 | | | | | | | | | | | 1 | 21 | | |
| E | | | | | | | | | | | | | 19 | 20 | | | | |
| F | | | | | 22 | | | | | | | | | | | | | |
| G | | 21 | | | | | | | | | | | | | 1 | | | 21 |
| H | | | | | | | | | | | | | | | | | | |
| I | | | | | | | 1 | 21 | | | | | | | | | | |

TABLE 4B-continued

Analysis of V kappa subgroup 2

| | | | | | | | | | | | | | | | | | | |
|---|---|---|---|---|---|---|---|---|---|---|---|---|---|---|---|---|---|---|
| K | | | | | | | | | 19 | | | | | | | | | |
| L | | | | | | | | 21 | 1 | | | | | | | | | |
| M | | | | | | | | | | | | | | | | | | |
| N | | | | | | | | | | | | | | | | | | |
| P | | | | | | | | | | | | | | | 1 | | | |
| Q | | | | | | | | | | | | | | 1 | | | | |
| R | | | | | | | | | | | 20 | | | | | | | |
| S | 22 | | | | | | | | | 20 | 1 | | | | | | | |
| T | | 22 | | 21 | | | | | | 1 | | | | | | | | |
| V | | | | | | | | | | | | 21 | | | | | | 21 |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | 1 | | | | | | | | | | | | | |
| not sequenced | | | | | | | 1 | 1 | 1 | 1 | 1 | 1 | 1 | 1 | 1 | 1 | 1 | 1 |
| sum of seq[2] | 22 | 22 | 22 | 22 | 22 | 22 | 21 | 21 | 21 | 21 | 21 | 21 | 21 | 21 | 21 | 21 | 21 | 21 |
| oomcaa[3] | 22 | 21 | 22 | 22 | 22 | 21 | 21 | 19 | 21 | 20 | 20 | 21 | 19 | 20 | 20 | 21 | 21 | 21 |
| mcaa[4] | S | G | T | D | F | T | L | K | I | S | R | V | E | A | E | D | V | G |
| rel. oomcaa[5] | 100% | 95% | 100% | 100% | 100% | 95% | 100% | 90% | 100% | 95% | 95% | 100% | 90% | 95% | 95% | 100% | 100% | 100% |
| pos occupied[6] | 1 | 2 | 1 | 1 | 1 | 1 | 1 | 3 | 1 | 2 | 2 | 1 | 3 | 2 | 2 | 1 | 1 | 1 |

| | Framework III | | | | CDR III | | | | | | | | | | | | |
|---|---|---|---|---|---|---|---|---|---|---|---|---|---|---|---|---|---|
| amino acid[1] | 85 | 86 | 87 | 88 | 89 | 90 | 91 | 92 | 93 | 94 | 95 | A | B | C | D | E | F | 96 |
| A | | | | | | | 14 | | | 1 | | | | | | | | |
| B | | | | | | 1 | | | 1 | | | | | | | | | |
| C | | | | 21 | | | | | | | | | | | | | | |
| D | | | | | | | | | | | | | | | | | | |
| E | | | | | | | | | | | | | | | | | | |
| F | | | | | | | | | | | | | | | | | | 1 |
| G | | | | | | | 6 | | | 1 | | 2 | | | | | | |
| H | | | | | | | 1 | | 7 | | | | | | | | | |
| I | 1 | | | | | | | | | 1 | | | | | | | | 3 |
| K | | | | | | | | | | | | | | | | | | |
| L | 1 | | | | | | | 12 | | | 2 | | | | | | | 2 |
| M | | | | | 21 | | | | | | | | | | | | | |
| N | | | | | | | | | | | | | | | | | | |
| P | | | | | | | | | | 2 | 16 | 1 | | | | | | 1 |
| Q | | | | | | 20 | | | 13 | | | | | | | | | 1 |
| R | | | | | | | | 1 | | | | | | | | | | |
| S | | | | | | | | | | 3 | 2 | | | | | | | |
| T | | | | | | | | 8 | | 7 | | | | | | | | |
| V | 19 | | | | | | | | | | | | | | | | | |
| W | | | | | | | | | | | 6 | | | | | | | 2 |
| X | | | | | | | | | | | | | | | | | | |
| Y | | 21 | 21 | | | | | | | | | | | | | | | 7 |
| — | | | | | | | | | | | | 14 | 17 | 17 | 17 | 17 | 17 | |
| unknown (?) | | | | | | | | | | | | | | | | | | |
| not sequenced | 1 | 1 | 1 | 1 | 1 | 1 | 1 | 1 | 1 | 1 | 2 | 5 | 5 | 5 | 5 | 5 | 5 | 5 |
| sum of seq[2] | 21 | 21 | 21 | 21 | 21 | 21 | 21 | 21 | 21 | 21 | 20 | 17 | 17 | 17 | 17 | 17 | 17 | 17 |
| oomcaa[3] | 19 | 21 | 21 | 21 | 21 | 20 | 14 | 12 | 13 | 7 | 16 | 14 | 17 | 17 | 17 | 17 | 17 | 7 |
| mcaa[4] | V | Y | Y | C | M | Q | A | L | Q | T | P | — | — | — | — | — | — | Y |
| rel. oomcaa[5] | 90% | 100% | 100% | 100% | 100% | 95% | 67% | 57% | 62% | 33% | 80% | 82% | 100% | 100% | 100% | 100% | 100% | 41% |
| pos occupied[6] | 3 | 1 | 1 | 1 | 1 | 2 | 3 | 3 | 3 | 7 | 3 | 3 | 1 | 1 | 1 | 1 | 1 | 7 |

| | CDR III | | | | | | Framework IV | | | | | |
|---|---|---|---|---|---|---|---|---|---|---|---|---|
| amino acid[1] | 97 | 98 | 99 | 100 | 101 | 102 | 103 | 104 | 105 | 106 | A | 107 | 108 | sum |
| A | | | | | | | | | | | | | | 71 |
| B | | | | | | | | | | 1 | | | | 3 |
| C | | | | | | | | | | | | | | 43 |
| D | | | | | | | | | | | | | | 112 |
| E | | | | | | | | | 13 | | | | | 71 |
| F | 17 | | | | | | | | | | | | | 72 |
| G | | 17 | 2 | 16 | | | | | 1 | | | | | 233 |
| H | | | | | | | | | | | | | | 26 |
| I | | | | | | | | | | 14 | | | | 94 |
| K | | | | | | | 12 | | | | | 13 | | 66 |
| L | | | | | | | | 11 | | | | | | 219 |
| M | | | | | | | | | | | | | | 37 |
| N | | | | | | | | | | | | | | 56 |
| P | | | | | | | | | | | | | | 159 |
| Q | | | | | 14 | | | | | | | | | 159 |
| R | | | | | | | | 4 | | | | | 12 | 126 |

TABLE 4B-continued

Analysis of V kappa subgroup 2

|  |  |  |  |  |  |  |  |  |  |  |  |  |  |
|---|---|---|---|---|---|---|---|---|---|---|---|---|---|
| S |  |  |  |  |  |  |  |  |  |  |  |  | 325 |
| T | 17 |  |  |  | 16 |  |  |  |  |  |  |  | 140 |
| V |  |  |  |  |  |  |  | 5 |  |  |  |  | 146 |
| W |  |  |  |  |  |  |  |  |  |  |  |  | 31 |
| X |  |  |  |  |  |  |  |  |  |  |  |  | 3 |
| Y |  |  |  |  |  |  |  |  |  |  |  |  | 123 |
| — |  |  |  |  |  |  |  |  |  |  | 13 |  | 134 |
| unknown (?) |  |  |  |  |  |  |  |  |  |  |  |  | 2 |
| not sequenced | 5 | 5 | 5 | 6 | 6 | 6 | 6 | 6 | 7 | 8 | 9 | 9 | 10 | 211 |
| sum of seq[2] | 17 | 17 | 17 | 16 | 16 | 16 | 16 | 16 | 15 | 14 | 13 | 13 | 12 |
| oomcaa[3] | 17 | 17 | 17 | 14 | 16 | 16 | 12 | 11 | 13 | 14 | 13 | 13 | 12 |
| mcaa[4] | T | F | G | Q | G | T | K | L | I | — | K | R |
| rel. oomcaa[5] | 100% | 100% | 100% | 88% | 100% | 100% | 75% | 69% | 87% | 100% | 100% | 100% | 100% |
| pos occupied[6] | 1 | 1 | 1 | 2 | 1 | 1 | 2 | 2 | 3 | 1 | 1 | 1 | 1 |

TABLE 4C

Analysis of V kappa subgroup 3

Framework I

| amino acid[1] | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| A |  | 5 |  |  |  |  |  | 2 |  | 27 |  |  |  |  | 1 |  |  |  |
| B | 1 |  |  |  |  |  |  |  |  |  |  |  |  |  |  |  |  |  |
| C |  |  |  |  |  |  |  |  |  |  |  | 2 |  |  |  |  |  |  |
| D | 2 |  |  |  |  |  |  |  | 14 |  |  |  |  |  |  |  | 6 |  |
| E | 76 |  | 27 |  |  |  |  |  |  |  |  |  |  |  |  |  | 146 | 1 |
| F |  | 1 |  |  |  |  |  |  |  |  |  |  |  | 1 |  |  |  |  |
| G | 1 |  |  |  |  |  |  |  | 82 |  |  |  |  |  | 1 | 152 | 1 | 1 |
| H |  |  |  |  |  |  |  |  |  | 1 |  |  |  |  |  |  |  |  |
| I |  | 75 |  |  |  |  |  |  |  |  |  |  |  |  |  |  |  | 1 |
| K | 3 |  |  |  |  |  |  |  |  |  |  |  |  |  |  |  |  | 1 |
| L |  | 4 | 1 | 104 |  |  | 1 |  |  |  |  | 150 |  | 129 |  | 1 |  |  |
| M | 5 |  |  |  | 13 |  |  |  |  |  |  |  |  |  |  |  |  |  |
| N |  |  |  |  |  |  |  |  |  |  |  |  |  |  | 5 |  |  |  |
| P |  |  |  |  |  |  |  |  | 124 |  |  |  |  |  | 147 |  |  |  |
| Q |  |  |  |  |  | 123 |  |  |  |  |  |  |  |  |  |  |  |  |
| R |  |  |  |  |  |  | 1 |  |  |  |  |  |  |  |  |  |  | 175 |
| S |  |  |  |  |  |  | 119 |  | 3 | 1 |  | 150 | 1 | 141 |  | 1 |  |  |
| T |  | 2 |  |  | 117 |  |  |  |  | 147 |  |  |  | 5 | 1 |  |  | 1 |
| V |  | 1 | 89 | 1 |  |  | 1 |  |  |  | 1 |  | 22 |  | 1 |  |  | 1 |
| W |  |  |  |  |  |  | 1 |  |  |  | 1 |  | 22 |  | 1 |  |  |  |
| X |  |  |  |  |  |  |  |  |  |  |  |  |  |  |  |  |  |  |
| Y |  |  |  |  |  |  |  |  |  |  |  |  |  |  |  |  |  |  |
| — |  |  |  |  |  |  |  |  |  |  |  |  |  |  |  |  |  |  |
| unknown (?) |  |  |  |  |  |  |  |  |  |  |  |  |  |  |  |  |  |  |
| not sequenced |  |  |  |  |  |  |  |  |  |  |  |  |  |  |  |  |  |  |
| sum of seq[2] | 88 | 88 | 117 | 118 | 118 | 123 | 123 | 124 | 126 | 149 | 151 | 152 | 152 | 152 | 152 | 152 | 153 | 181 |
| oomcaa[3] | 76 | 75 | 89 | 104 | 117 | 123 | 119 | 124 | 82 | 147 | 150 | 150 | 129 | 141 | 147 | 152 | 146 | 175 |
| mcaa[4] | E | I | V | L | T | Q | S | P | G | T | L | S | L | S | P | G | E | R |
| rel. oomcaa[5] | 86% | 85% | 76% | 88% | 99% | 100% | 97% | 100% | 65% | 99% | 99% | 99% | 85% | 93% | 97% | 100% | 95% | 97% |
| pos occupied[6] | 6 | 6 | 3 | 3 | 2 | 1 | 4 | 1 | 4 | 3 | 2 | 2 | 3 | 4 | 6 | 1 | 3 | 7 |

| | Framework I | | | | | CDRI | | | | | | | | | | | |
|---|---|---|---|---|---|---|---|---|---|---|---|---|---|---|---|---|---|
| amino acid[1] | 19 | 20 | 21 | 22 | 23 | 24 | 25 | 26 | 27 | A | B | C | D | E | F | 28 | 29 | 30 |
| A | 178 | 2 |  |  |  | 166 | 1 |  |  |  |  |  |  |  |  |  |  | 1 |
| B |  |  |  |  |  |  |  |  |  |  |  |  |  |  |  |  |  |  |
| C |  |  |  |  | 181 |  | 1 |  |  |  |  |  |  |  |  |  |  |  |
| D |  |  |  |  |  |  |  |  |  |  |  |  |  |  |  |  | 1 | 1 |
| E |  |  |  |  |  |  |  | 1 |  |  |  |  |  |  |  |  |  |  |
| F |  |  | 7 | 1 |  |  |  |  |  |  |  |  |  |  |  | 1 |  |  |
| G |  |  |  |  |  | 1 | 1 |  | 1 |  |  |  |  |  |  |  | 2 | 7 |
| H |  |  |  |  |  |  |  |  | 17 |  |  |  |  |  |  |  |  | 1 |
| I |  | 5 | 2 |  |  |  |  |  |  |  |  |  |  |  |  | 24 | 4 | 1 |
| K |  |  |  |  |  | 5 |  |  |  |  |  |  |  |  |  |  |  | 1 |
| L |  |  | 173 |  |  |  |  |  | 1 | 1 |  |  |  |  |  | 8 | 1 |  |
| M |  |  |  |  |  |  |  |  |  |  |  |  |  |  |  |  |  |  |
| N |  |  |  |  |  |  |  |  | 9 |  |  |  |  |  |  |  | 3 | 12 |
| P |  |  |  |  |  |  |  |  |  |  |  |  |  |  |  |  |  |  |
| Q |  |  |  |  |  |  |  |  | 159 |  |  |  |  |  |  |  |  |  |
| R |  |  |  |  |  | 176 |  | 1 | 1 | 10 |  |  |  |  |  |  | 10 | 3 |
| S |  |  |  |  | 180 |  | 7 | 175 |  | 87 |  |  |  |  |  | 72 | 86 | 151 |

TABLE 4C-continued

Analysis of V kappa subgroup 3

| | | | | | | | | | | | | | | | | | | |
|---|---|---|---|---|---|---|---|---|---|---|---|---|---|---|---|---|---|---|
| T | | 174 | | | | | 7 | 2 | | 1 | | | | | | 1 | 1 | 3 |
| V | 4 | 1 | | | | | 1 | | | 1 | | | | | | 76 | 68 | |
| W | | | | | 1 | | | | | | | | | | | | 5 | |
| X | | | | | | | | | | | | | | | | | | |
| Y | | | | 1 | | | | | | 1 | | | | | | | | 1 |
| — | | | | | | | | | | | 72 | 182 | 182 | 182 | 182 | 182 | | |
| unknown (?) | | | | | | | | | | 1 | | | | | | | | |
| not sequenced | | | | | | | | | | | | | | | | | | |
| sum of seq[2] | 182 | 182 | 182 | 182 | 181 | 182 | 182 | 181 | 181 | 182 | 182 | 182 | 182 | 182 | 182 | 182 | 182 | 181 |
| oomcaa[3] | 178 | 174 | 173 | 180 | 181 | 176 | 166 | 175 | 159 | 87 | 182 | 182 | 182 | 182 | 182 | 76 | 86 | 151 |
| mcaa[4] | A | T | L | S | C | R | A | S | Q | S | — | — | — | — | — | V | S | S |
| rel. oomcaa[5] | 98% | 96% | 95% | 99% | 100% | 97% | 91% | 97% | 88% | 48% | 100% | 100% | 100% | 100% | 100% | 42% | 47% | 83% |
| pos occupied[6] | 2 | 4 | 3 | 3 | 1 | 3 | 5 | 6 | 6 | 8 | 1 | 1 | 1 | 1 | 1 | 6 | 11 | 10 |

| | CDRI | | | | Framework II | | | | | | | | | | | | | |
|---|---|---|---|---|---|---|---|---|---|---|---|---|---|---|---|---|---|---|
| amino acid[1] | 31 | 32 | 33 | 34 | 35 | 36 | 37 | 38 | 39 | 40 | 41 | 42 | 43 | 44 | 45 | 46 | 47 | 48 |
| A | 1 | | | 181 | | | | | | | | | 176 | | | | | |
| B | | | | | | | | | | | | | | | | | | |
| C | | | | | | | | | | | | | | | | | | |
| D | 2 | 1 | | | | | | | | | | | | | | | | |
| E | | 1 | | | | | | | 1 | | | 1 | | | | | | |
| F | | 7 | | | | 1 | | | | | | | | | | 1 | | 1 |
| G | 3 | 1 | | 2 | | | | | | 1 | 184 | | | | | | | |
| H | | 2 | | | | 1 | | 12 | 1 | 1 | | | | | | | | |
| I | 1 | | | | | | | | | | | | | | | | | 178 |
| K | 1 | | | | | | | | 153 | | | | | | 1 | | | |
| L | | 1 | 176 | | | | | 3 | | | | 2 | | 1 | | 179 | 174 | 1 |
| M | | | | | | | | | | | | | | | | | | 3 |
| N | 25 | 32 | | | | | | | | 170 | | | 5 | 184 | 1 | | | |
| P | 1 | | | | | | | | | | | 181 | | | | | | |
| Q | 1 | 1 | | | | | 183 | 167 | 1 | | | | | | | | | |
| R | 18 | 16 | | 1 | | | 1 | | 27 | 5 | | | | | 182 | | | |
| S | 118 | 4 | | | | | | | | 5 | | | | | | | | |
| T | 8 | 1 | | | | | | | 1 | | | | 3 | | | | | |
| V | 1 | | 7 | | | | | 3 | | 2 | | | | | | 3 | 9 | |
| W | | | | | 185 | | | | | | | | | | | | | |
| X | | | | | | | | | | | | | | | | | | |
| Y | 1 | 115 | | | | 183 | | | | | | | | | | | | |
| — | | | | | | | | | | | | | | | | | | |
| unknown (?) | | | | | | | | 1 | | | | | | | 1 | | | |
| not sequenced | | | | | | | | | | | | | | | | | | |
| sum of seq[2] | 181 | 182 | 183 | 184 | 185 | 185 | 185 | 185 | 184 | 184 | 184 | 184 | 184 | 185 | 185 | 183 | 183 | 183 |
| oomcaa[3] | 118 | 115 | 176 | 181 | 185 | 183 | 183 | 167 | 153 | 170 | 184 | 181 | 176 | 184 | 182 | 179 | 174 | 178 |
| mcaa[4] | S | Y | L | A | W | Y | Q | Q | K | P | G | Q | A | P | R | L | L | I |
| rel. oomcaa[5] | 65% | 63% | 96% | 98% | 100% | 99% | 99% | 90% | 83% | 92% | 100% | 98% | 96% | 99% | 98% | 98% | 95% | 97% |
| pos occupied[6] | 13 | 12 | 2 | 3 | 1 | 3 | 2 | 4 | 6 | 6 | 1 | 3 | 3 | 2 | 3 | 3 | 2 | 4 |

| | Framework II | CRD II | | | | | | | Framework III | | | | | | | | | |
|---|---|---|---|---|---|---|---|---|---|---|---|---|---|---|---|---|---|---|
| amino acid[1] | 49 | 50 | 51 | 52 | 53 | 54 | 55 | 56 | 57 | 58 | 59 | 60 | 61 | 62 | 63 | 64 | 65 | 66 |
| A | | 4 | 147 | | | 176 | 1 | | | | | 68 | | | | | | 3 |
| B | | | | | | | | | | | | | | | | | | |
| C | | | 1 | | | | | | | | | | | | | | | |
| D | | 43 | | | | | 2 | | 4 | | | 112 | | | | 1 | | |
| E | | | | | | | | | | | | | | | | | | 1 |
| F | 4 | | | | | | | | | | | | | 183 | | | | |
| G | | 125 | | | | 2 | 10 | 179 | | | | | 1 | | 184 | 3 | 178 | |
| H | 9 | | 1 | | | | | | | | | | | | | | | |
| I | | | | | | | | 1 | | 168 | | | | 1 | | | | |
| K | | | | | 7 | 1 | | | | | | | 1 | | | | | |
| L | | | | | | | | | | | | | | | 1 | | | |
| M | | | | | 1 | | | | | | | | | | | | | 1 |
| N | | 1 | | | 53 | | | 2 | | | | 1 | | | | | | |
| P | | | | 2 | | | 2 | 2 | | | | 177 | | | | | | |
| Q | 1 | | | | | | | | | | | | | | | | | |
| R | | 1 | | | 4 | 180 | | | | | | | 182 | 2 | | | 1 | |
| S | 3 | 6 | 4 | 179 | 74 | 1 | | 5 | | | 7 | | | 180 | | 179 | | |
| T | | | 11 | 2 | 44 | | | 164 | | 2 | 1 | | 2 | | 3 | | 2 | |
| V | | 3 | 19 | | | | 3 | | | 15 | 3 | | | | | | | 1 |
| W | 1 | | | | | 1 | | | | | | | | | | | | |
| X | | | | | | | | | | | | | | | | | | |
| Y | 165 | | | | | | | | | 2 | | | | | | | | |
| — | | | | | | | | | | | | | | | | | | |

TABLE 4C-continued

Analysis of V kappa subgroup 3

| unknown (?) | | | | | | | | | | | | | | | | | | 1 |
|---|---|---|---|---|---|---|---|---|---|---|---|---|---|---|---|---|---|---|
| not sequenced | | | | | | | | | | | | | | | | | | |
| sum of seq[2] | 183 | 183 | 183 | 183 | 183 | 183 | 185 | 185 | 185 | 185 | 185 | 185 | 185 | 185 | 185 | 185 | 185 | 185 |
| oomcaa[3] | 165 | 125 | 147 | 179 | 74 | 180 | 176 | 164 | 179 | 168 | 177 | 112 | 182 | 183 | 180 | 184 | 179 | 178 |
| mcaa[4] | Y | G | A | S | S | R | A | T | G | I | P | D | R | F | S | G | S | G |
| rel. oomcaa[5] | 90% | 68% | 80% | 98% | 40% | 98% | 95% | 89% | 97% | 91% | 96% | 61% | 98% | 99% | 97% | 99% | 97% | 96% |
| pos occupied[6] | 6 | 7 | 6 | 3 | 6 | 4 | 5 | 7 | 3 | 3 | 3 | 5 | 3 | 3 | 3 | 2 | 4 | 5 |

| | Framework III |
|---|---|

| amino acid[1] | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|
| A | | 5 | 3 | 1 | | 3 | | | | | | | | | 3 | | | 174 |
| B | | | | | | | | | | | | | | 1 | | | | |
| C | | | | | | | | | | | | | | | | | 2 | |
| D | | | | 152 | | | | | | | 1 | | | | 3 | 182 | | |
| E | | 1 | | 30 | | | | | | | | 149 | | 175 | | | | |
| F | | | | | 183 | | 2 | | | | 1 | | | | | | 178 | |
| G | | 177 | | | | | | | | | 3 | | | | 1 | | | 2 |
| H | | | | | | | | | | | | | | | | | | |
| I | | | | | | | 1 | | 3 | 178 | | | | | | 1 | 1 | |
| K | | | | | | | | | | | | | | 1 | | | | |
| L | | | | | | | | 182 | | | | 178 | | 1 | | | 1 | |
| M | | | | | | | | | | | | | | | | | | 1 |
| N | | | | | | | 1 | | | 1 | 5 | | | | | | | |
| P | | | | | | | | | | | | | | 149 | | | | |
| Q | | | | 1 | | | | | | | | | 34 | | | | | |
| R | | | 2 | | | | | | | | 1 | 111 | | | | | | 3 |
| S | 185 | | 3 | | | 7 | | 2 | | 169 | 65 | | | 34 | | | 1 | |
| T | | | 177 | | | 172 | | 179 | | 8 | 4 | | | | | | | 1 |
| V | | 1 | | | | | | | 4 | | | 6 | | | | | 1 | 3 |
| W | | 1 | | | | | | | | | | | | | | | | |
| X | | | | | | | | | | | | | | | | | | |
| Y | | | | | 1 | | | | 1 | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 185 | 185 | 185 | 184 | 184 | 184 | 184 | 184 | 184 | 184 | 184 | 184 | 184 | 184 | 182 | 184 | 184 | 184 |
| oomcaa[3] | 185 | 177 | 177 | 152 | 183 | 172 | 182 | 179 | 178 | 169 | 111 | 178 | 149 | 149 | 175 | 182 | 178 | 174 |
| mcaa[4] | S | G | T | D | F | T | L | T | I | S | R | L | E | P | E | D | F | A |
| rel. oomcaa[5] | 100% | 96% | 96% | 83% | 99% | 93% | 99% | 97% | 97% | 92% | 60% | 97% | 81% | 81% | 96% | 99% | 97% | 95% |
| pos occupied[6] | 1 | 5 | 4 | 4 | 2 | 5 | 2 | 3 | 4 | 5 | 7 | 2 | 3 | 3 | 4 | 3 | 6 | 6 |

| | Framework III | | | | CDR III | | | | | | | | | | | | |
|---|---|---|---|---|---|---|---|---|---|---|---|---|---|---|---|---|---|

| amino acid[1] | 85 | 86 | 87 | 88 | 89 | 90 | 91 | 92 | 93 | 94 | 95 | A | B | C | D | E | F | 96 |
|---|---|---|---|---|---|---|---|---|---|---|---|---|---|---|---|---|---|---|
| A | | | | | | | | 1 | 8 | 3 | 3 | | | | | | | |
| B | | | | | | | | | | | | | | | | | | |
| C | | | 1 | 182 | | | 2 | | | 1 | | | | | | | | 2 |
| D | | | | | | | | 8 | 5 | | | | | | | | | |
| E | | | | | | 2 | | 2 | | | | | | | | | | 1 |
| F | 2 | 1 | 4 | | | | 5 | | 2 | | | | | | | | | 7 |
| G | | | | | | | 1 | 104 | 15 | | 1 | 1 | 2 | | | | | 1 |
| H | 1 | | | | 1 | 7 | 4 | 1 | | | | | | | | | | 2 |
| I | 9 | | | | | | | | 1 | | 1 | | | | | | | 4 |
| K | | | | | | | | | 2 | | 1 | | | | | | | 1 |
| L | 7 | | 1 | | | 1 | | | | 2 | 7 | 5 | | | | | | 42 |
| M | 5 | | | | | | | 1 | | | 1 | 2 | | | | | | |
| N | | | | | | | | 28 | 71 | | | | | | | | | 1 |
| P | | | | | | | | | | 1 | 139 | 24 | | | | | | 7 |
| Q | | | | 1 | 181 | 155 | 1 | | 1 | | 3 | 1 | | | | | | 3 |
| R | | | | | | 1 | 34 | 2 | 3 | | 2 | 2 | | | | | | 19 |
| S | | | 2 | | | | 2 | 33 | 58 | 102 | 15 | 2 | | | | | | 1 |
| T | | | | | | 8 | | 2 | 13 | 1 | 1 | 2 | | | | | | 1 |
| V | 159 | | | | | 7 | | | | 3 | 1 | | | | | | | 2 |
| W | | | | | | | | | | 69 | | | | | | | | 24 |
| X | | | | | | | | | | | | | | | | | | |
| Y | 1 | 183 | 176 | | 1 | 2 | 134 | 1 | 1 | | | | | | | | | 43 |
| — | | | | | | | | | 3 | 3 | 7 | 127 | 167 | 169 | 169 | 169 | 169 | 8 |
| unknown (?) | | | | | | | | | | | | | | | | | | |
| not sequenced | | | | | | | | | | | | 14 | 14 | 14 | 14 | 14 | 14 | 14 |
| sum of seq[2] | 184 | 184 | 184 | 183 | 183 | 183 | 183 | 183 | 183 | 182 | 182 | 169 | 169 | 169 | 169 | 169 | 169 | 169 |
| oomcaa[3] | 159 | 183 | 176 | 182 | 181 | 155 | 134 | 104 | 71 | 102 | 139 | 127 | 167 | 169 | 169 | 169 | 169 | 43 |
| mcaa[4] | V | Y | Y | C | Q | Q | Y | G | N | S | P | — | — | — | — | — | — | Y |
| rel. oomcaa[5] | 86% | 99% | 96% | 99% | 99% | 85% | 73% | 57% | 39% | 56% | 76% | 75% | 99% | 100% | 100% | 100% | 100% | 25% |
| pos occupied[6] | 7 | 2 | 5 | 2 | 3 | 8 | 8 | 11 | 13 | 8 | 11 | 12 | 2 | 1 | 1 | 1 | 1 | 18 |

TABLE 4C-continued

Analysis of V kappa subgroup 3

| amino acid[1] | CDR III | Framework IV | | | | | | | | | | | | sum |
|---|---|---|---|---|---|---|---|---|---|---|---|---|---|---|
| | 97 | 98 | 99 | 100 | 101 | 102 | 103 | 104 | 105 | 106 | A | 107 | 108 | |
| A | | | | | 1 | | | | | | | | | 1345 |
| B | | | | | | | | | | | | | | 2 |
| C | | | | | | | | | | | | | | 375 |
| D | 1 | | | | | | | | | 23 | | | | 564 |
| E | | | | | | | 3 | | 141 | | | | | 759 |
| F | | 166 | | | | | | | | 6 | | | | 765 |
| G | | | 166 | 41 | 166 | | | | | | | | 1 | 1804 |
| H | | | | | | | | | | 1 | | | | 64 |
| I | | | | | | | | | | 143 | | | | 803 |
| K | | | | | 1 | | 152 | | | | | 157 | | 489 |
| L | | | | | | | | 54 | | 1 | | | 2 | 1596 |
| M | | | | | | | | | | 3 | | | | 36 |
| N | | | | | | 1 | | | | | | 3 | | 255 |
| P | 2 | | | | 9 | 1 | | 1 | | | | | | 1147 |
| Q | | | | 114 | | | 1 | | 1 | | | | | 1314 |
| R | | | | | | | 9 | | | 2 | | 4 | 134 | 1326 |
| S | 8 | | | | | 2 | | | | | | | | 2629 |
| T | 154 | | | | | 162 | 1 | | | | | 1 | | 1593 |
| V | | | | | | | | 111 | | 11 | | | | 646 |
| W | | | | | | | | | | | | | | 287 |
| X | | | | | | | | | | | | | | |
| Y | | | | | | | 1 | | | | | | | 1014 |
| — | | 1 | 1 | 1 | 1 | 1 | 1 | 1 | 1 | 1 | 166 | 1 | 1 | 2151 |
| unknown (?) | | | | | | | | | | | | | | 4 |
| not sequenced | 17 | 16 | 16 | 16 | 16 | 16 | 15 | 16 | 16 | 16 | 17 | 17 | 45 | 337 |
| sum of seq[2] | 166 | 167 | 167 | 167 | 167 | 167 | 168 | 167 | 167 | 167 | 166 | 166 | 138 | |
| oomcaa[3] | 154 | 166 | 166 | 114 | 166 | 162 | 152 | 111 | 141 | 143 | 166 | 157 | 134 | |
| mcaa[4] | T | F | G | Q | G | T | K | V | E | I | — | K | R | |
| rel. oomcaa[5] | 93% | 99% | 99% | 68% | 99% | 97% | 90% | 66% | 84% | 86% | 100% | 95% | 97% | |
| pos occupied[6] | 5 | 2 | 2 | 6 | 2 | 5 | 7 | 4 | 5 | 7 | 1 | 5 | 4 | |

TABLE 4D

Analysis of V kappa subgroup 4

| amino acid[1] | Framework I | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| A | | | | | | | | | | | | 24 | | | | | 1 | |
| B | | | | | | | | | | | | | | | | | | |
| C | | | | | | | | | 1 | | | | | | | 1 | | |
| D | 25 | | | | | | | 26 | | | | | | | | | | |
| E | | | | | | | | | | | | | | | | | 25 | |
| F | | | | | | | | | | | | | | | | | | |
| G | | | | | | | | | | | | 1 | | | | 24 | | |
| H | | | | | | | | | | | | | | | | | | |
| I | | 26 | | | | | | | | | | | | | | | | |
| K | | | | | | | | 1 | | | | | | | | | | |
| L | | | | 1 | | | | | | | | 26 | | | 26 | | | |
| M | | | | 24 | | | | | | | | | | | | | | |
| N | 1 | | | | | | | | | | | | | | | | | |
| P | | | | | | | | | 26 | | | 1 | | | | | | |
| Q | | | 1 | | 25 | | | | | | | | | | | | | |
| R | | | | | | | | | | | | | | | | | | 26 |
| S | | | | | | 26 | | | 25 | | | | 26 | | 1 | | | |
| T | | | | | 26 | | | | | | | | | | | | | |
| V | | | 25 | 1 | | | | | | | | | 26 | | | | | |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | | | | | | | | | | | | | | |
| not sequenced | 7 | 7 | 7 | 7 | 7 | 7 | 7 | 7 | 7 | 7 | 7 | 7 | 7 | 7 | 7 | 7 | 7 | 7 |
| sum of seq[2] | 26 | 26 | 26 | 26 | 26 | 26 | 26 | 26 | 26 | 26 | 26 | 26 | 26 | 26 | 26 | 26 | 26 | 26 |
| oomcaa[3] | 25 | 26 | 25 | 24 | 26 | 25 | 26 | 26 | 26 | 25 | 26 | 24 | 26 | 26 | 26 | 24 | 25 | 26 |
| mcaa[4] | D | I | V | M | T | Q | S | P | D | S | L | A | V | S | L | G | E | R |
| rel. oomcaa[5] | 96% | 100% | 96% | 92% | 100% | 96% | 100% | 100% | 100% | 96% | 100% | 92% | 100% | 100% | 100% | 92% | 96% | 100% |
| pos occupied[6] | 2 | 1 | 2 | 3 | 1 | 2 | 1 | 1 | 1 | 2 | 1 | 3 | 1 | 1 | 1 | 3 | 2 | 1 |

TABLE 4D-continued

Analysis of V kappa subgroup 4

| | Framework I | | | | | CDRI | | | | | | | | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | A | B | C | D | E | F | 28 | 29 | 30 |
| A | 26 | | | | | | 1 | | | | 1 | | | | | | | |
| B | | | | | | | | | | | | | | | | | | |
| C | | | | | 33 | | | | | | | | | | | | | |
| D | | | | | | | | | | | | | 1 | | 1 | 1 | | |
| E | | | | | | | | | | | | | | | | | | |
| F | | | | | | | | | | | | | | | | | | |
| G | | | | | | | | | | | | | | | | | | |
| H | | | | | | | | | | | | | | | | | | |
| I | | | 26 | | | | | | | | 1 | | | | | | | |
| K | | | | | | 33 | | | | | | | | | | 2 | | 30 |
| L | | | | | | | | | | | 2 | 31 | | | | | | |
| M | | | | | | | | | | | | | | | | | | |
| N | | | | 26 | | | | | | | | | | | | 30 | 31 | 1 |
| P | | | | | | | 1 | | | | | | | | 1 | | | |
| Q | | | | | | | | | 32 | | | | | | | | | 1 |
| R | | | | | | | | | 1 | | | | | | | | 1 | 1 |
| S | | | | | | | 31 | 33 | | 33 | | | | 32 | 32 | 1 | | |
| T | | 26 | | | | | | | | | | | | 1 | | | | |
| V | | | | | | | | | | | 28 | 2 | | | | | | |
| W | | | | | | | | | | | | | | | | | | |
| X | | | | | | | | | | | | | | | | | | |
| Y | | | | | | | | | | | | | | 32 | | | | |
| — | | | | | | | | | | | | | | | | | | |
| unknown (?) | | | | | | | | | | | | | | | | | | |
| not sequenced | 7 | 7 | 7 | 7 | | | | | | | | | | | | | | |
| sum of seq[2] | 26 | 26 | 26 | 26 | 33 | 33 | 33 | 33 | 33 | 33 | 33 | 33 | 33 | 33 | 33 | 33 | 33 | 33 |
| oomcaa[3] | 26 | 26 | 26 | 26 | 33 | 33 | 31 | 33 | 32 | 33 | 28 | 31 | 32 | 32 | 32 | 30 | 31 | 30 |
| mcaa[4] | A | T | I | N | C | K | S | S | Q | S | V | L | Y | S | S | N | N | K |
| rel. oomcaa[5] | 100% | 100% | 100% | 100% | 100% | 100% | 94% | 100% | 97% | 100% | 85% | 94% | 97% | 97% | 97% | 91% | 94% | 91% |
| pos occupied[6] | 1 | 1 | 1 | 1 | 1 | 1 | 3 | 1 | 2 | 1 | 5 | 2 | 2 | 2 | 2 | 3 | 3 | 4 |

| | CDRI | | | | Framework II | | | | | | | | | | | | |
|---|---|---|---|---|---|---|---|---|---|---|---|---|---|---|---|---|---|
| amino acid[31] | 31 | 32 | 33 | 34 | 35 | 36 | 37 | 38 | 39 | 40 | 41 | 42 | 43 | 44 | 45 | 46 | 47 | 48 |
| A | | | | 32 | | | | | | | 2 | | | | | | | |
| B | | | | | | | | | | | | | | | | | | |
| C | | | | | | | | | | | | | | | | | | |
| D | | | | | | | | | | | | | | | | | | |
| E | | | | | | | | | | | | 1 | | | | | | |
| F | | | | | | | | | | | | 32 | | | | | | |
| G | | | | | | | | | | | | 32 | | | | | | |
| H | | | | | | 2 | | | | | | | | | | | | |
| I | | | | | | | | | | | | | | | | | | 32 |
| K | | | | | | | | | 33 | | | | | | 32 | | | |
| L | | | 33 | | | | | | | | | | | | | 29 | 33 | |
| M | | | | | | | | | | | | | | | | | | 1 |
| N | 33 | | | | | | | | | | | | | | | | | |
| P | | | | | | | | | | | 31 | | | 31 | 33 | | | |
| Q | | | | | | 32 | 33 | | | | | | 32 | | | | | |
| R | | | | | | | 1 | | | | | | 1 | | | 1 | | |
| S | | | | | | | | | | | | | | 2 | | | | |
| T | | | | 1 | | | | | | | | | | | | | | |
| V | | | | | | | | | | | | | | | | 4 | | |
| W | | | | | | | 33 | | | | | | | | | | | |
| X | | | | | | | | | | | | | | | | | | |
| Y | | 33 | | | 31 | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 | 33 |
| oomcaa[3] | 33 | 33 | 33 | 32 | 33 | 31 | 32 | 33 | 33 | 31 | 32 | 32 | 31 | 33 | 32 | 29 | 33 | 32 |
| mcaa[4] | N | Y | L | A | W | Y | Q | Q | K | P | G | Q | P | P | K | L | L | I |
| rel. oomcaa[5] | 100% | 100% | 100% | 97% | 100% | 94% | 97% | 100% | 100% | 94% | 97% | 97% | 94% | 100% | 97% | 88% | 100% | 97% |
| pos occupied[6] | 1 | 1 | 1 | 2 | 1 | 2 | 2 | 1 | 1 | 2 | 2 | 2 | 2 | 1 | 2 | 2 | 1 | 2 |

TABLE 4D-continued

Analysis of V kappa subgroup 4

| | Framework II | CDR II | | | | | | | | Framework III | | | | | | | |
|---|---|---|---|---|---|---|---|---|---|---|---|---|---|---|---|---|---|
| amino acid[1] | 49 | 50 | 51 | 52 | 53 | 54 | 55 | 56 | 57 | 58 | 59 | 60 | 61 | 62 | 63 | 64 | 65 | 66 |
| A | | | 30 | | | | | | | | | | | | | | | |
| B | | | | | | | | | | | | | | | | | | |
| C | | | | | | | | | | | | | | | | | | |
| D | | | | | | | | | | | | 33 | | | | | | |
| E | | | | | | | 32 | | | | | | | | | | | |
| F | | | | | | | | | | | | | | 33 | | | | |
| G | | | | | | | | | | 33 | | | | | 1 | 33 | | 33 |
| H | | | | | | | | | | | | | | | | | | |
| I | | | | | 1 | | | | | | | | | | | | | |
| K | | | | | | | | | | | | | | | | | | |
| L | | | | | | | | | | | | | | | | | | |
| M | | | | | | | | | | | | | | | | | | |
| N | | | | | | 2 | | | | | | | | | | | | |
| P | | | | 1 | | | | | | | 33 | | 1 | | | | | |
| Q | | | | | | | | | | | | | | | | | | |
| R | | | | | | | 33 | | | | | | 32 | | | | | |
| S | | | 1 | 31 | 1 | | | 33 | | | | | | | 32 | | 33 | |
| T | | | 2 | 1 | 29 | | | | | | | | | | | | | |
| V | | | | | | | | | 1 | | 33 | | | | | | | |
| W | | 33 | | | | | | | | | | | | | | | | |
| X | | | | | | | | | | | | | | | | | | |
| Y | 33 | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 | 33 |
| oomcaa[3] | 33 | 33 | 30 | 31 | 29 | 33 | 32 | 33 | 33 | 33 | 33 | 33 | 32 | 33 | 32 | 33 | 33 | 33 |
| mcaa[4] | Y | W | A | S | T | R | E | S | G | V | P | D | R | F | S | G | S | G |
| rel. oomcaa[5] | 100% | 100% | 91% | 94% | 88% | 100% | 97% | 100% | 100% | 100% | 100% | 100% | 97% | 100% | 97% | 100% | 100% | 100% |
| pos occupied[6] | 1 | 1 | 3 | 3 | 4 | 1 | 2 | 1 | 1 | 1 | 1 | 1 | 2 | 1 | 2 | 1 | 1 | 1 |

| | Framework III | | | | | | | | | | | | | | | | | |
|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 |
| A | | | | | | | | | | | | | | 33 | | | | 32 |
| B | | | | | | | | | | | | | | | | | | |
| C | | | | | | | | | | | | | | | | | | |
| D | | | | 32 | | | | | | | | | | | | 33 | | |
| E | | | | | | | | | | | | | | | 33 | | | |
| F | | | | | 32 | | | | | | | | | | | | | |
| G | | 33 | | 1 | | | | | | | | | | | | | | |
| H | | | | | | | | | | | | | | | | | | |
| I | | | | | | | | | 33 | | | | | | | | | |
| K | | | | | | | | | | | | | | | | | | |
| L | | | | | | | 33 | | | | | | | 32 | | | | |
| M | | | | | | | | | | | | | | 1 | | | | |
| N | | | | | | | | | | 2 | 1 | | | | | | | |
| P | | | | | | | | | | | | | | | | | | |
| Q | | | | | | | | | | | | | | | 32 | | | |
| R | | | | | | | | | | | | | | | 1 | | | |
| S | 33 | | | | | | | | | 30 | 32 | | | | | | | |
| T | | | 33 | | | 33 | | 33 | | 1 | | | | | | | | |
| V | | | | | 1 | | | | | | | | | | | | 33 | |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 | 33 |
| oomcaa[3] | 33 | 33 | 33 | 32 | 32 | 33 | 33 | 33 | 33 | 30 | 32 | 32 | 32 | 33 | 33 | 33 | 33 | 32 |
| mcaa[4] | S | G | T | D | F | T | L | T | I | S | S | L | Q | A | E | D | V | A |
| rel. oomcaa[5] | 100% | 100% | 100% | 97% | 97% | 100% | 100% | 100% | 100% | 91% | 97% | 97% | 97% | 100% | 100% | 100% | 100% | 97% |
| pos occupied[6] | 1 | 1 | 1 | 2 | 2 | 1 | 1 | 1 | 1 | 3 | 2 | 2 | 2 | 1 | 1 | 1 | 1 | 2 |

| | Framework III | | | CDR III | | | | | | | | | | | |
|---|---|---|---|---|---|---|---|---|---|---|---|---|---|---|---|
| amino acid[1] | 85 | 86 | 87 | 88 | 89 | 90 | 91 | 92 | 93 | 94 | 95 | A | B | C | D | E | F | 96 |
| A | | | | | | | | | | | 1 | | | | | | | |
| B | | | | | | | | | | | | | | | | | | |

TABLE 4D-continued

Analysis of V kappa subgroup 4

| amino acid | | | | | | | | | | | | | | | | | | | |
|---|---|---|---|---|---|---|---|---|---|---|---|---|---|---|---|---|---|---|---|
| C | | | | | 33 | | | | | | | | | | | | | | |
| D | | | | | | | | | 1 | 1 | | | | | | | | | |
| E | | | | | | | | | | | | | | | | | | | |
| F | | | 1 | | | | | | 1 | | | | | | | | | | |
| G | | | | | | | | | | 2 | | | | | | | | | |
| H | | | 1 | | 3 | | | | | | | | | | | | | | |
| I | | | | | | | | | | | 2 | | | | | | | | |
| K | | | | | | | | | | | | | | | | | | | |
| L | | | | | | | 1 | | | 2 | | 1 | 3 | | | | | | 1 |
| M | | | | | | | | | | | | | | | | | | | |
| N | | | | | | | | | | 4 | 4 | | | | | | | | |
| P | | | | | | | | | | | | 1 | 29 | 1 | | | | | 4 |
| Q | | | | | | 30 | 32 | | | | | | 1 | | | | | | 1 |
| R | | | | | | | | | | | 1 | | | 1 | | | | | 2 |
| S | | | | | | | | 2 | | | 23 | 2 | | | | | | | 1 |
| T | | | | | | | | | | | 2 | 22 | | | | | | | |
| V | 33 | | | | | | | | | | | | | | | | | | |
| W | | | | | | | | | | | | | | | | | | | 2 |
| X | | | | | | | | | | | | | | | | | | | |
| Y | | 33 | 31 | | | | | 31 | 29 | | | | | | | | | | 1 |
| — | | | | | | | | | | | | | | 13 | 15 | 15 | 15 | 15 | 15 | 3 |
| unknown (?) | | | | | | | | | | | | | | | | | | | |
| not sequenced | | | | | | | | | | | | | | 18 | 18 | 18 | 18 | 18 | 18 | 18 |
| sum of seq[2] | 33 | 33 | 33 | 33 | 33 | 33 | 33 | 33 | 33 | 33 | 33 | 33 | 33 | 15 | 15 | 15 | 15 | 15 | 15 | 15 |
| oomcaa[3] | 33 | 33 | 31 | 33 | 30 | 32 | 31 | 29 | 23 | 22 | 29 | 13 | 15 | 15 | 15 | 15 | 15 | 4 |
| mcaa[4] | V | Y | Y | C | Q | Q | Y | Y | S | T | P | — | — | — | — | — | — | P |
| rel. oomcaa[5] | 100% | 100% | 94% | 100% | 91% | 97% | 94% | 88% | 70% | 67% | 88% | 87% | 100% | 100% | 100% | 100% | 100% | 27% |
| pos occupied[6] | 1 | 1 | 3 | 1 | 2 | 2 | 4 | 6 | 7 | 3 | 3 | 1 | 1 | 1 | 1 | 1 | 8 |

| | CDR III | | | | Framework IV | | | | | | | | |
|---|---|---|---|---|---|---|---|---|---|---|---|---|---|
| amino acid[1] | 97 | 98 | 99 | 100 | 101 | 102 | 103 | 104 | 105 | 106 | A | 107 | 108 | sum |
| A | | | | | | | | | | | | | | 183 |
| B | | | | | | | | | | | | | | |
| C | | | | | | | | | | | | | | 68 |
| D | | | | | | | | | | | | | | 154 |
| E | | | | | | | | | | 14 | | | | 105 |
| F | | 15 | | | | | | | | | | | | 82 |
| G | | | 15 | 4 | 15 | | | | | | | | | 228 |
| H | | | | | | | | | | | | | | 6 |
| I | | | | | | | | | | 14 | | | | 135 |
| K | | | | | | | | 14 | | | | 13 | | 158 |
| L | | | | | | | | | 4 | | | | | 258 |
| M | 1 | | | | | | | | | | | | | 27 |
| N | | | | | | | | | | | | 1 | | 136 |
| P | | | | | | 1 | | | | | | | | 195 |
| Q | | | | | 11 | | | | 1 | | | | | 264 |
| R | | | | | | | 1 | | 1 | | 1 | 11 | | 116 |
| S | 2 | | | | | | | | | 1 | | | | 499 |
| T | 12 | | | | | | 14 | | | | | | | 236 |
| V | | | | | | | | 9 | | | | | | 196 |
| W | | | | | | | | 1 | | | | | | 69 |
| X | | | | | | | | | | | | | | |
| Y | | | | | | | | | | | | | | 254 |
| — | | | | | | | | | | 15 | | | | 106 |
| unknown (?) | | | | | | | | | | | | | | |
| not sequenced | 18 | 18 | 18 | 18 | 18 | 18 | 18 | 18 | 18 | 18 | 18 | 18 | 22 | 518 |
| sum of seq[2] | 15 | 15 | 15 | 15 | 15 | 15 | 15 | 15 | 15 | 15 | 15 | 15 | 11 | |
| oomcaa[3] | 12 | 15 | 15 | 11 | 15 | 14 | 14 | 9 | 14 | 14 | 15 | 13 | 11 | |
| mcaa[4] | T | F | G | Q | G | T | K | V | E | I | — | K | R | |
| rel. oomcaa[5] | 80% | 100% | 100% | 73% | 100% | 93% | 93% | 60% | 93% | 93% | 100% | 87% | 100% | |
| pos occupied[6] | 3 | 1 | 1 | 2 | 1 | 2 | 2 | 4 | 2 | 2 | 1 | 3 | 1 | |

TABLE 5A

Analysis of V lambda subgroup 1

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | | | | | | | | 19 | | 18 | 20 | | | | |
| B | | | | | | | | | | | | | | | | | | | |

TABLE 5A-continued

Analysis of V lambda subgroup 1

| | | | | | | | | | | | | | | | | | | |
|---|---|---|---|---|---|---|---|---|---|---|---|---|---|---|---|---|---|---|
| C | | | | | | | | | | | | | | | | | | |
| D | | | | | | | | | | | | | | | | | | |
| E | | | | | | | | | | | | | | | | | 1 | |
| F | | | | | | | | | | | | | | | | | | |
| G | | | | | | | | | | | | 22 | | | 42 | | | |
| H | 2 | | | | | | | | | | | | | | | | | |
| I | | | 1 | | | | | | | 1 | | | | | | | | |
| K | | | | | | | | | | | | | | | | | 14 | |
| L | | | 1 | 41 | | | | | | 1 | | | | | | | | |
| M | | | | | | | | | | | | | | | | | | |
| N | | | | | | | | | | | | | | | | | | |
| P | | | | | | 41 | 41 | | | | | | 1 | 41 | | | | |
| Q | 22 | | 1 | | | 41 | | | | | | | | | 42 | | | |
| R | | | | | | | | | | | | | | | | | 25 | |
| S | | 39 | | | | | | 41 | | | 41 | | 1 | | | | 1 | |
| T | | | | | 41 | | | | | | | 19 | | | | | 1 | |
| V | | 1 | 38 | | | | | | | 20 | | 1 | 1 | | | | | 42 |
| W | | | | | | | | | | | | | | | | | | |
| X | | | | | | | | | | | | | | | | | | |
| Y | | | | | | | | | | | | | | | | | | |
| Z | 16 | | | | | | | | | | | | | | | | | |
| — | | | | | | | | | 41 | | | | | | | | | |
| unknown (?) | | | | | | | | | | | | | | | | | | |
| not sequenced | 2 | 2 | 1 | 1 | 1 | 1 | 1 | 1 | 1 | 1 | 1 | 1 | 1 | 1 | | | | |
| sum of seq[2] | 40 | 40 | 41 | 41 | 41 | 41 | 41 | 41 | 41 | 41 | 41 | 41 | 41 | 41 | 42 | 42 | 42 | 42 | 42 |
| oomcaa[3] | 22 | 39 | 38 | 41 | 41 | 41 | 41 | 41 | 41 | 20 | 41 | 22 | 20 | 41 | 42 | 42 | 25 | 42 |
| mcaa[4] | Q | S | V | L | T | Q | P | P | S | — | V | S | G | A | P | G | Q | R | V |
| rel. oomcaa[5] | 55% | 98% | 93% | 100% | 100% | 100% | 100% | 100% | 100% | 100% | 49% | 100% | 54% | 49% | 98% | 100% | 100% | 60% | 100% |
| pos occupied[6] | 3 | 2 | 4 | 1 | 1 | 1 | 1 | 1 | 1 | 1 | 4 | 1 | 3 | 4 | 2 | 1 | 1 | 5 | 1 |

| | CDR I | | | | | | | | | | | | | | | | | |
|---|---|---|---|---|---|---|---|---|---|---|---|---|---|---|---|---|---|---|
| amino acid[1] | 20 | 21 | 22 | 23 | 24 | 25 | 26 | 27 | D | E | 28 | 29 | 30 | 31 | A | 32 | 33 | 34 | 35 |
| A | 2 | | | | | | | 1 | | | | 2 | 2 | | | 1 | | | |
| B | | | | | | | | | | | | | | | | | | | |
| C | | | 42 | | | | | | | | | | | | | | | | |
| D | | | | | | | | | 3 | | | | 3 | 1 | | 3 | | 1 | |
| E | | | | | | | | | | | | | 1 | | | | | | |
| F | | | | | 1 | | | | 1 | | | | 4 | 2 | | 1 | 1 | | |
| G | | | | | | 42 | 3 | 1 | | | 2 | 39 | | | | 2 | | 2 | |
| H | | | | | | | | | | | | | | 2 | | 2 | | 2 | |
| I | 1 | 41 | | | | | | | 1 | 37 | | | 1 | | | | | 1 | |
| K | | | | | | | | | 1 | | | 1 | | | | | | | |
| L | | 1 | | | | | | | | | 1 | | | | | | | | |
| M | | | | | | | | | | | 1 | | | | | | | | |
| N | | | | | | | 2 | 1 | 37 | | | 13 | 31 | 2 | | 1 | 9 | | |
| P | | | | | | | | | | | | | 1 | | | | | | |
| Q | | | | | | | | | | | | | | | | 1 | | | |
| R | | | | | | | 1 | 1 | | | | 5 | | | | | | | |
| S | 1 | | 42 | | 38 | | 34 | 34 | 38 | | | 13 | 1 | 1 | | 3 | 19 | | |
| T | 38 | | | | 3 | | 4 | 3 | 2 | | 1 | | 1 | | | 7 | 2 | | |
| V | | | | | | | | | | | | 1 | | | | 2 | 40 | | |
| W | | | | | | | | | | | | | | | | | | | 42 |
| X | | | | | | | | | | | | | | | | | | | |
| Y | | | | | | | | | | | | | 4 | 1 | 20 | | 7 | | |
| Z | | | | | | | | | | | | | | 36 | | | | | |
| — | | | | | | | | | | | | | | | | | | | |
| unknown (?) | | | | | | | | | | | | | | | | | | | |
| not sequenced | | | | | | | | | | | | | | 1 | 1 | 1 | 1 | | |
| sum of seq[2] | 42 | 42 | 42 | 42 | 42 | 42 | 42 | 42 | 42 | 42 | 42 | 42 | 42 | 42 | 41 | 41 | 41 | 41 | 42 |
| oomcaa[3] | 38 | 41 | 42 | 42 | 38 | 42 | 34 | 34 | 38 | 37 | 37 | 39 | 13 | 31 | 36 | 20 | 40 | 19 | 42 |
| mcaa[4] | T | I | S | C | S | G | S | S | S | N | I | G | N | N | — | Y | V | S | W |
| rel. oomcaa[5] | 90% | 98% | 100% | 100% | 90% | 100% | 81% | 81% | 90% | 88% | 88% | 93% | 31% | 74% | 88% | 49% | 98% | 46% | 100% |
| pos occupied[6] | 4 | 2 | 1 | 1 | 3 | 1 | 4 | 6 | 4 | 4 | 5 | 3 | 8 | 7 | 5 | 10 | 2 | 7 | 1 |

| | Framework II | | | | | | | | | | | | | | | | | |
|---|---|---|---|---|---|---|---|---|---|---|---|---|---|---|---|---|---|---|
| amino acid[1] | 36 | 37 | 38 | 39 | 40 | 41 | 42 | 43 | 44 | 45 | 46 | 47 | 48 | 49 | 50 | 51 | 52 | 53 | 54 |
| A | | | | | | | 4 | 40 | | | | | | | | 1 | | | |
| B | | | | | | | | | | | | | | | | | | | |
| C | | | | | | | | | | | | | | | | | | | |

TABLE 5A-continued

Analysis of V lambda subgroup 1

| amino acid[1] | | | | | | | | | | | | | | | | | | | |
|---|---|---|---|---|---|---|---|---|---|---|---|---|---|---|---|---|---|---|---|
| D | | | | | | 1 | | | | | | | | | 13 | 10 | 8 | 1 | |
| E | | | | | | | | | 2 | | | | | | 5 | | | 1 | |
| F | 1 | | | 4 | | | | | | | | | | 1 | | | | | |
| G | | | | | | 39 | | | | | | | | | 1 | | | | |
| H | 1 | 1 | 6 | 1 | | | | | | | | | | 1 | 1 | | | 1 | |
| I | | | | | | | | | | | | | 40 | | 1 | | | | |
| K | | | | | | | 1 | | 35 | | | | | | 1 | 1 | | 18 | |
| L | | | 1 | 31 | | | | | | 41 | 40 | | | | | | | 1 | 1 |
| M | | | | | | | 1 | | | | | 1 | | | | | | 1 | |
| N | | | | | | | | | 1 | | | | | | 3 | 28 | 30 | 2 | |
| P | | | | | 42 | 1 | | | 42 | | | | | | | | | | |
| Q | | 39 | 34 | | | | | | | | | | | | | | | 15 | |
| R | | 2 | | 1 | | 1 | | | 4 | | | | | | 7 | | | 2 | 40 |
| S | | | | | | | 1 | | | | | | | | 9 | 2 | 3 | 1 | |
| T | | | | | | 36 | 1 | | | | | | | | 1 | | | | |
| V | | | 1 | 5 | | | | | | 1 | 2 | 1 | | | | | | | |
| W | | | | | | | | | | | | | | | | | | | 1 |
| X | | | | | | | | | | | | | | | | | | | |
| Y | 40 | | | | | | | | | | | | | 40 | 1 | 1 | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 42 | 42 | 42 | 42 | 42 | 42 | 42 | 42 | 42 | 42 | 42 | 42 | 42 | 42 | 42 | 42 | 42 | 42 | 42 |
| oomcaa[3] | 40 | 39 | 34 | 31 | 42 | 39 | 36 | 40 | 42 | 35 | 41 | 40 | 40 | 40 | 13 | 28 | 30 | 18 | 40 |
| mcaa[4] | Y | Q | Q | L | P | G | T | A | P | K | L | L | I | Y | D | N | N | K | R |
| rel. oomcaa[5] | 95% | 93% | 81% | 74% | 100% | 93% | 86% | 95% | 100% | 83% | 98% | 95% | 95% | 95% | 31% | 67% | 71% | 43% | 95% |
| pos occupied[6] | 3 | 3 | 4 | 5 | 1 | 4 | 4 | 3 | 1 | 4 | 2 | 3 | 3 | 3 | 10 | 5 | 4 | 9 | 3 |

| | CDR II | | | | | | | | | | | | | | | | | |
|---|---|---|---|---|---|---|---|---|---|---|---|---|---|---|---|---|---|---|
| amino acid[1] | 55 | 56 | A | B | C | D | E | 57 | 58 | 59 | 60 | 61 | 62 | 63 | 64 | 65 | 66 | A | B |
| A | 1 | | | | | | | | | | | | | | | 5 | | | | |
| B | | | | | | | | | | | | | | | | | | | | |
| C | | | | | | | | | | | | | | | | | | | | |
| D | | | | | | | | | | | | | 38 | | | | | | | |
| E | | | | | | | | | | | | | | | | | | | | |
| F | | | | | | | | | | | | | | | 38 | | | | | |
| G | | | | | | | | | 41 | | | 2 | | | | 36 | | | | |
| H | | | | | | | | | | | | | 1 | | | | | | | |
| I | | | | | | | | | | 17 | | | | 3 | | | | | | |
| K | | | | | | | | | | | | | | | | | | | 38 | |
| L | | 1 | | | | | | | | | 1 | | | | | | | | | |
| M | | | | | | | | | | | | | | | | | | | | |
| N | | | | | | | | | | | | | | | | | | | | |
| P | 38 | | | | | | | | | | | 38 | | | | | | | | |
| Q | | | | | | | | | | | | | | | | | | | | |
| R | | | | | | | | | | | | | 42 | | | | 4 | | | |
| S | 2 | 40 | | | | | | | | | 2 | | | 42 | | 42 | | | | |
| T | | | | | | | | | | | | | | | 1 | | | | | |
| V | | | | | | | | | 24 | | | | | 1 | | | | | | |
| W | | | | | | | | | | | | | | | | | | | | |
| X | | | | | | | | | | | | | | | | | | | | |
| Y | | | | | | | | | | | | | | | | | | | | |
| Z | | | | | | | | | | | | | | | | | | | | |
| — | | | 41 | 41 | 41 | 41 | 42 | | | | | | | | | | | 42 | 42 |
| unknown (?) | | | | | | | | | | | | | | | | | | | | |
| not sequenced | 1 | 1 | | | | | | 1 | 1 | 1 | 1 | | | | | | | | | |
| sum of seq[2] | 41 | 41 | 41 | 41 | 41 | 41 | 42 | 41 | 41 | 41 | 41 | 42 | 42 | 42 | 42 | 42 | 42 | 42 | 42 |
| oomcaa[3] | 38 | 40 | 41 | 41 | 41 | 41 | 42 | 41 | 24 | 38 | 38 | 42 | 42 | 38 | 36 | 42 | 38 | 42 | 42 |
| mcaa[4] | P | S | — | — | — | — | — | G | V | P | D | R | F | S | G | S | K | — | — |
| rel. oomcaa[5] | 93% | 98% | 100% | 100% | 100% | 100% | 100% | 100% | 59% | 93% | 93% | 100% | 90% | 100% | 86% | 100% | 90% | 100% | 100% |
| pos occupied[6] | 3 | 2 | 1 | 1 | 1 | 1 | 1 | 1 | 2 | 3 | 3 | 1 | 3 | 1 | 3 | 1 | 2 | 1 | 1 |

| | Framework III | | | | | | | | | | | | | | | | | |
|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 | 85 |
| A | | 1 | 3 | | 41 | | | 24 | | | | | | | 2 | | | 38 | 1 |
| B | | | | | | | | | | | | | | | | | | | |
| C | | | | | | | | | | | | | | | | | | | |
| D | | 1 | | | | | | | | | | | | | | 1 | 41 | | 37 |

TABLE 5A-continued

Analysis of V lambda subgroup 1

| amino acid | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| E | | | | | | | | | | | | | 1 | | 24 | | 42 | | 1 |
| F | | | | | | | | | | | | | | | | | | | |
| G | | 40 | | | | | 17 | | 1 | | 42 | | | 15 | | | | | |
| H | | | | | | | | | | | | | 1 | | | | | | 2 |
| I | | | | | | | | | 41 | | | | | | | | | | 1 |
| K | | | | | | | | | | | | | | | | | | | |
| L | | | | | | | 42 | | | | | 41 | | | | | | | |
| M | | | | | | | | | | | | | | | | | | | |
| N | | | | | | | | | | | | | | | | | 1 | | |
| P | | | | | | | | | | | | | | 2 | | | | | |
| Q | | | | | | | | | | | | | 31 | | | | | | |
| R | | | | | | | | | | | | | 8 | | | | | | |
| S | 42 | | 1 | 42 | | 24 | | | | | 20 | | | 20 | | | | 1 | |
| T | | | 38 | | 18 | | | | | 21 | | | | 17 | | | | | 3 |
| V | | | | | 1 | | | 1 | 1 | | | 1 | | 1 | | | | | |
| W | | | | | | | | | | | | | 1 | | | 2 | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 42 | 42 | 42 | 42 | 42 | 42 | 42 | 42 | 42 | 42 | 42 | 42 | 42 | 42 | 42 | 42 | 42 | 42 | 42 |
| oomcaa[3] | 42 | 40 | 38 | 42 | 41 | 24 | 42 | 24 | 41 | 21 | 42 | 41 | 31 | 20 | 24 | 41 | 42 | 38 | 37 |
| mcaa[4] | S | G | T | S | A | S | L | A | I | T | G | L | Q | S | E | D | E | A | D |
| rel. oomcaa[5] | 100% | 95% | 90% | 100% | 98% | 57% | 100% | 57% | 98% | 50% | 100% | 98% | 74% | 48% | 57% | 98% | 100% | 90% | 88% |
| pos occupied[6] | 1 | 3 | 3 | 1 | 2 | 2 | 1 | 3 | 2 | 3 | 1 | 2 | 5 | 5 | 4 | 2 | 1 | 3 | 5 |

| | CDR III | | | | | | | | | | | | | | | | | |
|---|---|---|---|---|---|---|---|---|---|---|---|---|---|---|---|---|---|---|
| amino acid[1] | 86 | 87 | 88 | 89 | 90 | 91 | 92 | 93 | 94 | 95 | A | B | C | D | E | F | 96 | 97 | 98 |
| A | | | | 22 | 15 | | | 1 | | | | 16 | | | | | 4 | 1 | |
| B | | | | | | | | | | | | | | | | | | | |
| C | | | 42 | | | | | | | | | | | | | | | | |
| D | | | | | | | | 39 | 17 | | | 7 | | | | | | | |
| E | | | | | | | | | | | | 1 | | | | | 1 | | |
| F | | 2 | | | | | | | | 1 | | | | | | | | | 36 |
| G | | | | 14 | | | | | 1 | | | 17 | 1 | | | | 5 | 1 | |
| H | | 1 | | | | | | | | | | | 1 | | | | | | |
| I | | | | | | | | | | | 1 | | | | | | | 1 | |
| K | | | | | | | | | | | 1 | | | | | | | | |
| L | | | | 1 | | | | | | 37 | | | 1 | | | | | 1 | |
| M | | | | | | | | | | | | | | | | | | | 1 |
| N | | | | | | | 2 | 2 | | | 9 | 1 | | | | | | | |
| P | | | | | | | | | | | 1 | | | | | | 6 | | |
| Q | | | | 3 | | | | | | | | | | | | | | | |
| R | | | | | | | | | 5 | 1 | 2 | | | | | | 2 | | |
| S | | | | | 4 | | | 17 | 35 | | 18 | | 1 | | | | 1 | | |
| T | | | | | 22 | | | 1 | 1 | | 1 | | | | | | | | |
| V | | | | 1 | | | | 1 | | 1 | | 2 | | | | | 9 | 34 | |
| W | | | | | | 38 | | | | | | | | | | | 7 | | |
| X | | | | | | | | | | | | | | | | | | | |
| Y | 42 | 39 | | | | | 3 | | 1 | | | | | | | | 3 | | |
| Z | | | | | | | | | | | | | | | | | | | |
| — | | | | | | | | | | | 2 | 4 | 35 | 39 | 38 | 38 | 1 | | |
| unknown (?) | | | | | | | | | | | | | | | | | | | |
| not sequenced | | | | 1 | 1 | 1 | 1 | 1 | 1 | 1 | 1 | 1 | 3 | 3 | 3 | 3 | 3 | 3 | 4 |
| sum of seq[2] | 42 | 42 | 42 | 41 | 41 | 41 | 41 | 41 | 41 | 41 | 41 | 41 | 39 | 39 | 38 | 38 | 39 | 39 | 36 |
| oomcaa[3] | 42 | 39 | 42 | 22 | 22 | 38 | 39 | 17 | 35 | 37 | 18 | 17 | 35 | 39 | 38 | 38 | 9 | 34 | 36 |
| mcaa[4] | Y | Y | C | A | T | W | D | D | S | L | S | G | S | D | E | F | V | V | F |
| rel. oomcaa[5] | 100% | 93% | 100% | 54% | 54% | 93% | 95% | 41% | 85% | 90% | 44% | 41% | 90% | 100% | 100% | 100% | 23% | 87% | 100% |
| pos occupied[6] | 1 | 3 | 1 | 5 | 3 | 2 | 2 | 8 | 3 | 5 | 8 | 6 | 5 | 1 | 1 | 1 | 10 | 6 | 1 |

| | Framework IV | | | | | | | | | |
|---|---|---|---|---|---|---|---|---|---|---|
| amino acid[1] | 99 | 100 | 101 | 102 | 103 | 104 | 105 | 106 | A | 107 | 108 | sum |
| A | | | | | | | | | | | | 285 |
| B | | | | | | | | | | | | 84 |
| C | | | | | | | | | | | | 224 |
| D | | | | | | | | | | | | 81 |
| E | | | | | 1 | | | | | | | |

TABLE 5A-continued

Analysis of V lambda subgroup 1

| amino acid[1] | | | | | | | | | | | | total |
|---|---|---|---|---|---|---|---|---|---|---|---|---|
| F | | | | | | | | | | | | 87 |
| G | 36 | 31 | 36 | | | | | | | 26 | | 559 |
| H | | | | | | | | | | | | 25 |
| I | | | | | | | | | | | | 188 |
| K | | | | | 30 | | | | | | | 141 |
| L | | | | | | 25 | | | 34 | | | 344 |
| M | | | | | | | | | | | | 5 |
| N | | | | | 1 | | | | | | | 176 |
| P | | | | | | | | | | | 1 | 296 |
| Q | | | | | 3 | | | | 1 | | 18 | 251 |
| R | | | | | 1 | | | | | 2 | | 156 |
| S | | 1 | | | | | | | | 2 | | 720 |
| T | | 3 | | 36 | 1 | | 36 | | | | | 359 |
| V | | 1 | | | | 11 | | 36 | | | | 282 |
| W | | | | | | | | | | 1 | | 92 |
| X | | | | | | | | | | | | |
| Y | | | | | | | | | | | | 202 |
| Z | | | | | | | | | | | | 16 |
| — | | | | | | | | | | | | 524 |
| unknown (?) | | | | | | | | | | | | |
| not sequenced | 4 | 6 | 6 | 6 | 6 | 6 | 6 | 6 | 6 | 10 | 22 | 141 |
| sum of seq[2] | 36 | 36 | 36 | 36 | 36 | 36 | 36 | 36 | 36 | 31 | 19 | |
| oomcaa[3] | 36 | 31 | 36 | 36 | 30 | 25 | 36 | 36 | 34 | 26 | 18 | |
| mcaa[4] | G | G | G | T | K | L | T | V | L | G | Q | |
| rel. oomcaa[5] | 100% | 86% | 100% | 100% | 83% | 69% | 100% | 100% | 94% | 84% | 95% | |
| pos occupied[6] | 1 | 4 | 1 | 1 | 5 | 2 | 1 | 1 | 3 | 4 | 2 | |

TABLE 5B

Analysis of V lambda subgroup 2

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | 35 | | | | | 30 | | | 6 | | 1 | 1 | | | | | |
| B | | | | | | | | | | | | | | | | | | | |
| C | | | | | | | | | | | | | | | | | | | |
| D | | | | | | | | | | | | | | | | 1 | | | |
| E | | | | | | | | | | | | | | | | | | | |
| F | | | | | | | | | | | | | | | | | | | |
| G | | | | | | | | | | | | | 42 | | 42 | | | 1 | |
| H | 2 | | | | | | | | | | | | | | | 1 | | | |
| I | | | 1 | | | | | | | | | | | | | | | | 28 |
| K | | | | | | | | | | | | | | | | | | | |
| L | | | | 40 | | | | | | | | | | | 3 | | | | 1 |
| M | | | | | | | | | | | | | | | | | | | |
| N | | | | | | | | | | | | | | | | | | | |
| P | | | | | | | 42 | 6 | | | | | | | 40 | | 42 | | |
| Q | 22 | | 4 | | | 41 | | | | | | | | | | | 42 | | |
| R | | | | | | | | 6 | 1 | | | | | | | | | | |
| S | | 41 | | | | | | | 40 | | | 42 | | 42 | | | | 43 | |
| T | | | | | 42 | | | | 1 | | | | | | | | | | |
| V | | 1 | 2 | | | | | | | | 36 | | | | | | | | 14 |
| W | | | | | | | | | | | | | | | | | | | |
| X | | | | | | | | | | | | | | | | | | | |
| Y | | | | | | | | | | | | | | | | | | | |
| Z | 16 | | | | | | | | | | | | | | | | | | |
| — | | | | | | | | | | 42 | | | | | | | | | |
| unknown (?) | | | | | | 1 | | | | | | | | | | | | | |
| not sequenced | 3 | 1 | 1 | 3 | 1 | 1 | 1 | 1 | 1 | 1 | 1 | 1 | | | | | | | |
| sum of seq[2] | 40 | 42 | 42 | 40 | 42 | 42 | 42 | 42 | 42 | 42 | 42 | 42 | 43 | 43 | 43 | 43 | 43 | 43 | 43 |
| oomcaa[3] | 22 | 41 | 35 | 40 | 42 | 41 | 42 | 30 | 40 | 42 | 36 | 42 | 42 | 42 | 40 | 42 | 42 | 43 | 28 |
| mcaa[4] | Q | S | A | L | T | Q | P | A | S | — | V | S | G | S | P | G | Q | S | I |
| rel. oomcaa[5] | 55% | 98% | 83% | 100% | 100% | 98% | 100% | 71% | 95% | 100% | 86% | 100% | 98% | 98% | 93% | 98% | 98% | 100% | 65% |
| pos occupied[6] | 3 | 2 | 4 | 1 | 1 | 1 | 1 | 3 | 3 | 1 | 2 | 1 | 2 | 2 | 2 | 2 | 2 | 1 | 3 |

TABLE 5B-continued

Analysis of V lambda subgroup 2

CDR I

| amino acid[1] | 20 | 21 | 22 | 23 | 24 | 25 | 26 | 27 | D | E | 28 | 29 | 30 | 31 | A | 32 | 33 | 34 | 35 |
|---|---|---|---|---|---|---|---|---|---|---|---|---|---|---|---|---|---|---|---|
| A |  |  |  |  | 3 |  | 1 |  |  |  |  |  | 1 |  |  | 1 |  |  |  |
| B |  |  |  |  |  |  |  |  |  |  |  |  |  |  |  |  |  |  |  |
| C |  |  |  | 42 |  |  |  |  | 1 |  |  |  |  | 1 |  |  |  |  |  |
| D |  |  |  |  |  |  |  |  |  |  | 39 |  | 1 | 4 |  | 5 |  |  |  |
| E |  |  |  |  |  |  |  |  |  |  |  |  |  |  |  | 1 |  |  |  |
| F |  | 1 |  |  |  |  |  |  |  |  |  |  | 1 |  |  |  | 4 |  |  |
| G |  |  |  |  |  |  | 43 |  | 1 |  |  |  | 39 | 26 |  |  |  |  |  |
| H |  |  |  |  |  |  |  | 1 |  |  |  |  |  |  |  | 1 | 1 |  |  |
| I |  | 41 |  |  | 1 |  |  |  |  |  | 6 |  |  |  |  | 4 |  |  |  |
| K |  |  |  |  |  |  |  |  |  |  |  |  |  |  |  | 4 |  |  |  |
| L |  | 1 |  |  |  |  |  |  |  |  |  |  |  |  |  |  | 4 |  |  |
| M |  |  |  |  |  |  |  |  |  |  |  |  |  |  |  |  |  |  |  |
| N |  |  |  |  |  |  |  | 1 | 3 | 4 |  | 1 | 4 | 3 | 28 |  |  |  |  |
| P |  |  |  |  |  |  |  | 1 |  |  |  |  |  |  |  |  |  |  |  |
| Q |  |  |  |  |  |  |  |  |  |  |  |  |  |  |  |  |  |  |  |
| R |  |  |  |  |  |  |  |  | 1 |  |  |  | 2 |  |  |  |  |  |  |
| S |  |  | 42 |  | 3 |  | 3 | 35 | 38 |  |  |  | 5 | 1 | 2 | 4 | 1 | 42 |  |
| T | 43 |  |  |  | 36 |  | 39 | 3 |  |  |  | 1 |  | 1 |  |  | 41 |  |  |
| V |  |  |  |  |  |  |  |  |  |  |  | 37 |  |  |  |  |  |  |  |
| W |  |  |  |  |  |  |  |  |  |  |  |  |  |  |  |  |  |  | 43 |
| X |  |  |  |  |  |  |  |  |  |  |  |  |  |  |  |  |  |  |  |
| Y |  |  |  |  |  |  |  | 1 |  |  |  | 1 |  | 37 |  | 29 |  |  |  |
| Z |  |  |  |  |  |  |  |  |  |  |  |  |  |  |  |  |  |  |  |
| — |  |  |  |  |  |  |  |  |  |  |  |  |  |  | 1 |  |  |  |  |
| unknown (?) |  |  |  |  |  |  |  |  |  |  |  |  |  |  | 1 |  |  |  |  |
| not sequenced |  |  | 1 | 1 |  |  |  |  |  |  |  |  |  |  |  |  |  | 1 | 1 |
| sum of seq[2] | 43 | 43 | 42 | 42 | 43 | 43 | 43 | 43 | 43 | 43 | 43 | 43 | 43 | 43 | 43 | 43 | 42 | 42 | 43 |
| oomcaa[3] | 43 | 41 | 42 | 42 | 36 | 43 | 39 | 35 | 38 | 39 | 37 | 39 | 26 | 37 | 28 | 29 | 41 | 42 | 43 |
| mcaa[4] | T | I | S | C | T | G | T | S | S | D | V | G | G | Y | N | Y | V | S | W |
| rel. oomcaa[5] | 100% | 95% | 100% | 100% | 84% | 100% | 91% | 81% | 88% | 91% | 86% | 91% | 60% | 86% | 65% | 67% | 98% | 100% | 100% |
| pos occupied[6] | 1 | 3 | 1 | 1 | 4 | 1 | 3 | 7 | 4 | 2 | 2 | 5 | 7 | 5 | 7 | 6 | 2 | 1 | 1 |

Framework II

| amino acid[1] | 36 | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|---|
| A |  |  |  |  | 1 | 4 |  | 40 |  |  |  |  |  |  |  |  |  |  |  |
| B |  |  |  |  |  |  |  |  |  |  |  |  |  |  |  |  |  |  |  |
| C |  |  |  |  |  |  |  |  |  |  |  |  |  |  |  |  |  |  |  |
| D |  |  |  | 1 |  | 2 |  |  |  |  |  |  |  |  | 20 | 1 | 2 | 1 |  |
| E |  |  |  |  |  |  |  |  |  |  |  |  |  |  | 20 |  |  | 2 |  |
| F | 2 |  |  |  |  |  |  |  |  |  |  |  |  | 7 |  | 1 |  |  |  |
| G |  |  |  |  |  | 36 |  |  |  |  |  |  |  |  | 2 | 2 |  | 1 |  |
| H |  |  | 2 | 34 |  |  |  |  |  |  |  |  |  |  |  |  |  | 1 |  |
| I |  |  |  |  |  |  | 1 |  |  |  | 1 | 9 | 43 |  |  |  | 1 |  |  |
| K |  |  |  |  |  |  | 40 |  |  | 41 |  |  |  |  |  |  | 1 | 21 |  |
| L |  |  | 1 | 1 |  |  |  |  |  |  | 38 | 6 |  |  |  |  |  |  |  |
| M |  |  |  |  |  |  |  |  |  |  |  | 26 |  |  |  |  | 1 |  |  |
| N |  |  |  | 2 |  |  |  |  |  |  |  |  |  |  | 1 |  | 8 | 12 |  |
| P |  |  |  |  | 41 |  |  | 43 |  |  |  |  |  |  |  |  |  |  |  |
| Q |  | 41 | 39 |  |  |  |  |  |  | 2 |  |  |  |  |  |  |  |  |  |
| R |  | 1 |  |  |  | 1 |  |  |  |  |  |  |  |  |  | 2 |  |  | 43 |
| S |  |  |  |  | 1 |  |  |  |  |  |  |  | 2 |  |  | 21 | 3 |  |  |
| T |  |  |  |  |  | 1 |  |  |  |  |  |  |  |  |  | 7 |  |  |  |
| V |  |  |  |  |  | 1 |  | 3 |  |  | 4 | 2 |  |  |  | 39 |  |  |  |
| W |  |  |  |  |  |  |  |  |  |  |  |  |  |  |  |  |  |  |  |
| X |  |  |  |  |  |  |  |  |  |  |  |  |  |  |  |  |  |  |  |
| Y | 41 |  |  |  |  | 5 |  |  |  |  |  |  |  | 34 |  |  |  | 2 |  |
| Z |  |  |  |  |  |  |  |  |  |  |  |  |  |  |  |  |  |  |  |
| — |  |  |  |  |  |  |  |  |  |  |  |  |  |  |  |  |  |  |  |
| unknown (?) |  |  | 1 | 1 |  |  |  |  |  |  |  |  |  |  |  |  |  |  |  |
| not sequenced |  |  |  |  |  |  |  |  |  |  |  |  |  |  |  |  |  |  |  |
| sum of seq[2] | 43 | 43 | 43 | 43 | 43 | 43 | 43 | 43 | 43 | 43 | 43 | 43 | 43 | 43 | 43 | 43 | 43 | 43 | 43 |
| oomcaa[3] | 41 | 41 | 39 | 34 | 41 | 36 | 40 | 40 | 43 | 41 | 38 | 26 | 43 | 34 | 20 | 39 | 21 | 21 | 43 |
| mcaa[4] | Y | Q | Q | H | P | G | K | A | P | K | L | M | I | Y | D | V | S | K | R |
| rel. oomcaa[5] | 95% | 95% | 91% | 79% | 95% | 84% | 93% | 93% | 100% | 95% | 88% | 60% | 100% | 79% | 47% | 91% | 49% | 49% | 100% |
| pos occupied[6] | 2 | 2 | 3 | 5 | 3 | 4 | 4 | 2 | 1 | 2 | 3 | 4 | 1 | 3 | 4 | 4 | 8 | 8 | 1 |

TABLE 5B-continued

Analysis of V lambda subgroup 2

| | CDR II | | | | | | | | | | | | | | | | | |
|---|---|---|---|---|---|---|---|---|---|---|---|---|---|---|---|---|---|---|
| amino acid[1] | 55 | 56 | A | B | C | D | E | 57 | 58 | 59 | 60 | 61 | 62 | 63 | 64 | 65 | 66 | A | B |
| A | | | | | | | | | | | | | | | 2 | | | | |
| B | | | | | | | | | | | | | | | | | | | |
| C | | | | | | | | | | | | | | | | 1 | | | |
| D | | | | | | | | | | | 17 | | | | | | | | |
| E | | | | | | | | | | | | | | | | | | | |
| F | | | | | | | | | | | | | 42 | | | | | | |
| G | | | | | | | | 43 | 1 | | | | | | 41 | | | | |
| H | | | | | | | | | | | 2 | | | | | | | | |
| I | | | | | | | | | 3 | | | | | | | | | | |
| K | | | | | | | | | | | | | | | | | 42 | | |
| L | | | | | | | | | | | 1 | | 1 | | | | | | |
| M | | | | | | | | | | | | | | | | | | | |
| N | | | | | | | | | | | 19 | | | | | | | | |
| P | 43 | | | | | | | | | | | | | | | | | | |
| Q | | | | | | | | | 15 | | | | | | | | | | |
| R | | | | | | | | | | | | | | 43 | | | 1 | | |
| S | | 43 | | | | | | | 28 | 2 | | | | | 43 | 42 | | | |
| T | | | | | | | | | | | | | | | | | | | |
| V | | | | | | | | | 39 | | | | | | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | 2 | | | | | | | | |
| — | | | 43 | 43 | 43 | 43 | 43 | | | | | | | | | | | 43 | 43 |
| unknown (?) | | | | | | | | | | | | | | | | | | | |
| not sequenced | | | | | | | | | | | | | | | | | | | |
| sum of seq[2] | 43 | 43 | 43 | 43 | 43 | 43 | 43 | 43 | 43 | 43 | 43 | 43 | 43 | 43 | 43 | 43 | 43 | 43 | 43 |
| oomcaa[3] | 43 | 43 | 43 | 43 | 43 | 43 | 43 | 43 | 39 | 28 | 19 | 43 | 42 | 43 | 41 | 42 | 42 | 43 | 43 |
| mcaa[4] | P | S | — | — | — | — | — | G | V | S | N | R | F | S | G | S | K | — | — |
| rel. oomcaa[5] | 100% | 100% | 100% | 100% | 100% | 100% | 100% | 100% | 91% | 65% | 44% | 100% | 98% | 100% | 95% | 98% | 98% | 100% | 100% |
| pos occupied[6] | 1 | 1 | 1 | 1 | 1 | 1 | 1 | 1 | 3 | 2 | 6 | 1 | 2 | 1 | 2 | 2 | 2 | 1 | 1 |

| | Framework III | | | | | | | | | | | | | | | | | | |
|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 | 85 |
| A | | 3 | | 1 | 43 | | | | | | | | | 36 | | | | 43 | |
| B | | | | | | | | | | | | | | | | | | | |
| C | | | | | | | | | | | | | | | | | | | |
| D | | 1 | 2 | | | | | | | | 1 | | | | 3 | 42 | | | 39 |
| E | | | | | | | | | | | | | | | 38 | | 43 | | |
| F | | | | | | | | | | | | | | | | | | | |
| G | | 39 | | | | | | | | | 42 | | | | 1 | | | | |
| H | | | | | | | | | | | | | | | | | | | 2 |
| I | | | | | | | | | 35 | | | | | | | | | | |
| K | | | 1 | | | | | | | | | | | | | | | | |
| L | | | | | | | 43 | | | | | 43 | | | | | | | |
| M | | | | | | | | | | | | | | | | | | | |
| N | | | 38 | | | | | | | | | | | | 1 | 1 | | | 1 |
| P | | | | | | | | | | | | | | 2 | | | | | |
| Q | | | | | | | | | | | | | 41 | | | | | | |
| R | | | | | | | | | | | | | 2 | | | | | | |
| S | 42 | | | 1 | | 43 | | | | | 42 | | | | | | | | |
| T | | | 1 | 41 | | | | 43 | | 1 | | | | 2 | | | | | |
| V | | | | | | | | | 8 | | | | | 3 | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | 1 | | | | | | | | | | | | | | | | 1 |
| not sequenced | 1 | | | | | | | | | | | | | | | | | | |
| sum of seq[2] | 42 | 43 | 43 | 43 | 43 | 43 | 43 | 43 | 43 | 43 | 43 | 43 | 43 | 43 | 43 | 43 | 43 | 43 | 43 |
| oomcaa[3] | 42 | 39 | 38 | 41 | 43 | 43 | 43 | 43 | 35 | 42 | 42 | 43 | 41 | 36 | 38 | 42 | 43 | 43 | 39 |
| mcaa[4] | S | G | N | T | A | S | L | T | I | S | G | L | Q | A | E | D | E | A | D |
| rel. oomcaa[5] | 100% | 91% | 88% | 95% | 100% | 100% | 100% | 100% | 81% | 98% | 98% | 100% | 95% | 84% | 88% | 98% | 100% | 100% | 91% |
| pos occupied[6] | 1 | 3 | 4 | 3 | 1 | 1 | 1 | 1 | 2 | 2 | 2 | 1 | 2 | 4 | 4 | 2 | 1 | 1 | 3 |

TABLE 5B-continued

Analysis of V lambda subgroup 2

| amino acid[1] | CDR III | | | | | | | | | | | | | | | | | | |
|---|---|---|---|---|---|---|---|---|---|---|---|---|---|---|---|---|---|---|---|
| | 86 | 87 | 88 | 89 | 90 | 91 | 92 | 93 | 94 | 95 | A | B | C | D | E | F | 96 | 97 | 98 |
| A | | | | 2 | 1 | | 21 | | 1 | | | | | | | | 1 | 1 | |
| B | | | | | | | | | | | | | | | | | | | |
| C | | | 43 | 11 | | | | | | | | | | | | | | | |
| D | | | | | | | | 3 | 1 | 2 | | | | | | | 1 | | |
| E | | | | | | | 1 | 1 | | | | | | | | | | | |
| F | | 3 | | | | 3 | | | | 1 | | 1 | | | | | 5 | | 42 |
| G | | | | | | | 1 | 21 | 3 | 4 | | | | | | | 1 | | |
| H | | | | | | 1 | | | | | | | | | | | | | |
| I | | | | | | | 1 | 1 | | 1 | 2 | | | | | | 1 | 7 | |
| K | | | | | | | | | 3 | | | | | | | | | | |
| L | | | | | | | | | | | | 1 | 1 | | | | 6 | 5 | |
| M | | | | | | | | | | | | | | | | | 1 | 1 | |
| N | | | | | | | | | 5 | 7 | 5 | | | | | | 1 | | |
| P | | | | | | | 1 | | | | | 4 | | | | | | | |
| Q | | | | | | | | | 1 | 2 | | | | | | | | | |
| R | | | | | | | 2 | | 3 | | | 1 | | | | | 5 | | |
| S | | 1 | | 30 | 41 | | | 12 | 23 | 14 | 9 | | | | | | 1 | | |
| T | | | | | | | 16 | 4 | 4 | 3 | 21 | | | | | | | | |
| V | | | | | | | 1 | | | | | | | | | | 11 | 28 | |
| W | | | | | | | | | | | | | | | | | 5 | | |
| X | | | | | | | | | | | | | | | | | | | |
| Y | 43 | 39 | | | | 39 | | | 1 | 6 | | | | | | | 4 | | |
| Z | | | | | | | | | | | | | | | | | | | |
| — | | | | | | | | | | 1 | 3 | 36 | 42 | 43 | 43 | 43 | | | |
| unknown (?) | | | | | | | | | 2 | | | | | | | | | | |
| not sequenced | | | | | 1 | | | | | 1 | | | | | | | | 1 | 1 |
| sum of seq[2] | 43 | 43 | 43 | 43 | 42 | 43 | 43 | 43 | 43 | 43 | 42 | 43 | 43 | 43 | 43 | 43 | 43 | 42 | 42 |
| oomcaa[3] | 43 | 39 | 43 | 30 | 41 | 39 | 21 | 21 | 23 | 14 | 21 | 36 | 42 | 43 | 43 | 43 | 11 | 28 | 42 |
| mcaa[4] | Y | Y | C | S | S | Y | A | G | S | S | T | — | — | — | — | — | V | V | F |
| rel. oomcaa[5] | 100% | 91% | 100% | 70% | 98% | 91% | 49% | 49% | 53% | 33% | 50% | 84% | 98% | 100% | 100% | 100% | 26% | 67% | 100% |
| pos occupied[6] | 1 | 3 | 1 | 3 | 2 | 3 | 7 | 7 | 8 | 11 | 6 | 5 | 2 | 1 | 1 | 1 | 13 | 5 | 1 |

| amino acid[1] | Framework IV | | | | | | | | | | | sum |
|---|---|---|---|---|---|---|---|---|---|---|---|---|
| | 99 | 100 | 101 | 102 | 103 | 104 | 105 | 106 | A | 107 | 108 | |
| A | | 1 | | | | | | | | | | 280 |
| B | | | | | | | | | | | | |
| C | | | | | | | | | | | | 99 |
| D | | | | | | | | | | | | 188 |
| E | | | | | | | | | | | | 107 |
| F | | | | | | | | | | | | 113 |
| G | 42 | 33 | 42 | | | | | | | 19 | | 567 |
| H | | | | | | | | | | | | 48 |
| I | | | | | | | 1 | | | | | 184 |
| K | | | | | | 36 | | | | | | 189 |
| L | | | | | | | 28 | | | 40 | | 264 |
| M | | | | | | | | | | | | 29 |
| N | | | | | 1 | | | | | | | 146 |
| P | | | | | | | | | | | | 238 |
| Q | | | | | 1 | | | | | | 14 | 250 |
| R | | 1 | | | 2 | | | | | 4 | | 121 |
| S | | | | | | | 1 | | | 2 | | 831 |
| T | | 7 | | 41 | | | 40 | | | | | 398 |
| V | | | | | | 14 | | 42 | 1 | | | 327 |
| W | | | | | | | | | | | | 48 |
| X | | | | | | | | | | | | |
| Y | | | | | | | 1 | | | | | 285 |
| Z | | | | | | | | | | | | 16 |
| — | | | | | | | | | | | | 555 |
| unknown (?) | | | | | | | | | | | | 8 |
| not sequenced | 1 | 1 | 1 | 2 | 2 | 1 | 1 | 1 | 2 | 15 | 28 | 80 |
| sum of seq[2] | 42 | 42 | 42 | 41 | 41 | 42 | 42 | 42 | 41 | 25 | 14 | |
| oomcaa[3] | 42 | 33 | 42 | 41 | 36 | 28 | 40 | 42 | 40 | 19 | 14 | |
| mcaa[4] | G | G | G | T | K | L | T | V | L | G | Q | |
| rel. oomcaa[5] | 100% | 79% | 100% | 100% | 88% | 67% | 95% | 100% | 98% | 76% | 100% | |
| pos occupied[6] | 1 | 4 | 1 | 1 | 5 | 2 | 3 | 1 | 2 | 3 | 1 | |

TABLE 5C

Analysis of V lambda subgroup 3

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | 1 | | 1 | 2 | 7 | | | | | 20 | 1 | | | | 27 |
| B | | | | | | | | | | | | | | | | | | | |
| C | | | | | | | | | | | | | | | | | | | |
| D | | | 5 | | | | 10 | | | | | | | | | | | | |
| E | | | 20 | | | | | | | | | | 1 | | | 1 | | | |
| F | 1 | 1 | | | | | | | | | | 1 | | | 1 | | | | |
| G | | | 1 | | | | | | | | | | | | | 37 | | | |
| H | | | | | | | | | | | | | | | | | | | |
| I | | | | | | | | | | | | | | | | | | | |
| K | | | | | | | | | | | | | | | | | 2 | | |
| L | | | | 37 | | | | | | | | 4 | | 1 | 9 | | | | |
| M | | | | | | | | | | | | | | | | | | | |
| N | | | | | | | | | | | | | | | | | | | |
| P | | | | | | | 26 | 35 | 1 | | | | | | 27 | | | | 1 |
| Q | 4 | | 4 | | | 38 | | | | | | | | | | | 36 | | |
| R | | | | | | | | | | | | | | | | | | | |
| S | 13 | 14 | | | 1 | | 1 | | 28 | | | 37 | | 18 | | | | | |
| T | | | | | 36 | | | 1 | | | | | | | | | | 38 | |
| V | | | 8 | 1 | | | | | 2 | | 34 | | 36 | | | | | | 10 |
| W | | | | | | | | | | | | | | | | | | | |
| X | | | | | | | | | | | | | | | | | | | |
| Y | | 23 | | | | | | | | | | | | | | | | | |
| Z | | | | | | | | | | | | | | | | | | | |
| — | 20 | | | | | | | | | | 38 | | | | | | | | |
| unknown (?) | | | | | | | | | | | | | | | | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 20 | 23 | 20 | 37 | 36 | 38 | 26 | 35 | 28 | 38 | 34 | 37 | 36 | 20 | 27 | 37 | 36 | 38 | 27 |
| mcaa[4] | — | Y | E | L | T | Q | P | P | S | — | V | S | V | A | P | G | Q | T | A |
| rel. oomcaa[5] | 53% | 61% | 53% | 97% | 95% | 100% | 68% | 92% | 74% | 100% | 89% | 97% | 95% | 53% | 71% | 97% | 95% | 100% | 71% |
| pos occupied[6] | 4 | 3 | 5 | 2 | 3 | 1 | 4 | 3 | 4 | 1 | 2 | 2 | 3 | 2 | 4 | 2 | 2 | 1 | 3 |

| | CDR I | | | | | | | | | | | | | | | | |
|---|---|---|---|---|---|---|---|---|---|---|---|---|---|---|---|---|---|
| amino acid[1] | 20 | 21 | 22 | 23 | 24 | 25 | 26 | 27 | D | E | 28 | 29 | 30 | 31 | A | 32 | 33 | 34 | 35 |
| A | | | 1 | | | | | 5 | | | | | 1 | 1 | | | 21 | 3 | |
| B | | | | | | | | | | | | | | | | | | | |
| C | | | | 38 | | | | | | | | | | | | | | 5 | |
| D | | | | | | | 30 | 1 | | | | | 10 | | | 3 | | 1 | |
| E | | | | | | | 2 | 2 | | | | 1 | 3 | 6 | | | 2 | | |
| F | | | | | | | | | | | | | | | 1 | | 2 | | |
| G | | | | | 9 | 38 | | 1 | | | | 23 | 4 | | | | | | |
| H | | | | | | | 1 | | | | | | | 1 | | | 2 | 9 | |
| I | | 38 | | | | | | | | | 9 | | | 1 | | | | | |
| K | | | | | | | | 7 | | | | | 2 | 13 | | | | | |
| L | | | | | | | | | | | 28 | | | | | | | | |
| M | 1 | | | | | | | | | | | | 1 | | | | | | |
| N | | | 2 | | | | 4 | 9 | | | 1 | | 2 | | | 1 | | 2 | |
| P | | | 1 | | | | | | | | | 3 | | | | | | | |
| Q | | | | | 10 | | | | | | | | | 4 | | | | | |
| R | 25 | | | | | | | 2 | | | | 10 | 1 | | | | 1 | | |
| S | 9 | | 1 | | 19 | | | 10 | | | | | 11 | 2 | | 8 | | 14 | |
| T | 3 | | 33 | | | | | 1 | | | | 1 | 4 | | | | | | |
| V | | | | | | | | | | | | | | | | 1 | 15 | | |
| W | | | | | | | | | | | | | | | | | | | 38 |
| X | | | | | | | | | | | | | | | | | | | |
| Y | | | | | | | | 1 | | | | | 8 | | | 20 | 1 | 4 | |
| Z | | | | | | | | | | | | | | | | | | | |
| — | | | | | | | | | 38 | 38 | | | | 37 | | | | | |
| unknown (?) | | | | | | | | | | | | | | 1 | 1 | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 37 | 37 | 37 | 38 | 38 | 38 |
| oomcaa[3] | 25 | 38 | 33 | 38 | 19 | 38 | 30 | 10 | 38 | 38 | 28 | 23 | 11 | 13 | 37 | 20 | 21 | 14 | 38 |
| mcaa[4] | R | I | T | C | S | G | D | S | — | — | L | G | S | K | — | Y | A | S | W |
| rel. oomcaa[5] | 66% | 100% | 87% | 100% | 50% | 100% | 79% | 26% | 100% | 100% | 74% | 61% | 29% | 35% | 100% | 54% | 55% | 37% | 100% |
| pos occupied[6] | 4 | 1 | 5 | 1 | 3 | 1 | 5 | 9 | 1 | 1 | 3 | 5 | 9 | 9 | 1 | 7 | 4 | 7 | 1 |

TABLE 5C-continued

Analysis of V lambda subgroup 3

| | Framework II | | | | | | | | | | | | | | | | | | |
|---|---|---|---|---|---|---|---|---|---|---|---|---|---|---|---|---|---|---|---|
| amino acid[1] | 36 | 37 | 38 | 39 | 40 | 41 | 42 | 43 | 44 | 45 | 46 | 47 | 48 | 49 | 50 | 51 | 52 | 53 | 54 |
| A | | | | | | | | 23 | | | | | | | | 1 | | 1 | |
| B | | | | | | | | | | | | | | | | | | | |
| C | | | | | | | | | | | | | | | | | | | |
| D | | | | | | | | | | | | | | | 9 | 22 | 2 | 8 | |
| E | | | 1 | | | | | | | | | | | | 5 | 3 | | 3 | |
| F | 3 | | | | | | | | | | | | 2 | | | | 1 | | |
| G | | | | | | 36 | | | | | | | | | 9 | 2 | | | |
| H | | | | | | | | 1 | | | | | | 1 | 3 | | | 1 | |
| I | | | | | | | | | | 1 | | | 28 | | | | 1 | | |
| K | | | | 32 | | | | | | | | | | | 2 | 6 | 1 | 13 | |
| L | | | 2 | | | | | | | 6 | 33 | 1 | | | | | | | |
| M | | | | | | | | | | | 1 | | 1 | | | | | | |
| N | | | | | | | | | | | | | | | 1 | 19 | 9 | | |
| P | | | | | 36 | | 1 | | 38 | | | | | | | | | | |
| Q | | 37 | 35 | 1 | | | 36 | | | | | | | | 9 | | | 1 | |
| R | | 1 | | 4 | | 2 | | | | | | | | | 1 | 1 | | 1 | 38 |
| S | | | | 1 | 2 | | | 14 | | | | | | | | | 10 | 1 | |
| T | | | | | | | | | | | | | | | 2 | 4 | | | |
| V | | | | | | | | 1 | | 31 | 4 | 37 | 9 | | | | | | |
| W | | | | | | | | | | | | | | | | | | | |
| X | | | | | | | | | | | | | | | | | | | |
| Y | 35 | | | | | | | | | | | | | 35 | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 35 | 37 | 35 | 32 | 36 | 36 | 36 | 23 | 38 | 31 | 33 | 37 | 28 | 35 | 9 | 22 | 19 | 13 | 38 |
| mcaa[4] | Y | Q | Q | K | P | G | Q | A | P | V | L | V | I | Y | D | D | N | K | R |
| rel. oomcaa[5] | 92% | 97% | 92% | 84% | 95% | 95% | 95% | 61% | 100% | 82% | 87% | 97% | 74% | 92% | 24% | 58% | 50% | 34% | 100% |
| pos occupied[6] | 2 | 2 | 3 | 4 | 2 | 2 | 3 | 3 | 1 | 3 | 3 | 2 | 3 | 3 | 7 | 8 | 7 | 9 | 1 |

| | CDR II | | | | | | | | | | | | | | | | | |
|---|---|---|---|---|---|---|---|---|---|---|---|---|---|---|---|---|---|---|
| amino acid[1] | 55 | 56 | A | B | C | D | E | 57 | 58 | 59 | 60 | 61 | 62 | 63 | 64 | 65 | 66 | A | B |
| A | | 1 | | | | | | | | | | | | | | | | | |
| B | | | | | | | | | | | | | | | | | | | |
| C | | | | | | | | | | | | | | | | | | | |
| D | | | | | | | | | | | | 9 | | | | | | | |
| E | | | | | | | | | | | | 27 | | | | | | | |
| F | | | | | | | | | | | | | | 38 | | | | | |
| G | | | | | | | | 38 | | | | | | | 38 | | | | |
| H | | | | | | | | | | | | | | | | | | | |
| I | | | | | | | | | 37 | | | | | | | | | | |
| K | | | | | | | | | | | | | | | | | | | |
| L | | | | | | | | | | | | | | | | | | | |
| M | | | | | | | | | | | | | | | | | | | |
| N | | | | | | | | | | | | | | | | | 21 | | |
| P | 37 | 1 | | | | | | | | | 36 | | | | | | | | |
| Q | | | | | | | | | | | | | | | | | | | |
| R | | | | | | | | | | | | | 38 | | | | | | |
| S | 1 | 36 | | | | | | | | 1 | | | | | 38 | | 38 | 12 | |
| T | | | | | | | | | | | | | | | | | | 5 | |
| V | | | | | | | | | | | | | | | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | 38 | 38 | 38 | 38 | 38 | | | | | | | | | | | 38 | 38 |
| unknown (?) | | | | | | | | | | | 1 | | | | | | | | |
| not sequenced | | | | | | | | | 1 | 1 | 1 | | | | | | | | |
| sum of seq[2] | 38 | 38 | 38 | 38 | 38 | 38 | 38 | 38 | 37 | 37 | 37 | 38 | 38 | 38 | 38 | 38 | 38 | 38 | 38 |
| oomcaa[3] | 37 | 36 | 38 | 38 | 38 | 38 | 38 | 38 | 37 | 36 | 27 | 38 | 38 | 38 | 38 | 38 | 21 | 38 | 38 |
| mcaa[4] | P | S | — | — | — | — | — | G | I | P | E | R | F | S | G | S | N | — | — |
| rel. oomcaa[5] | 97% | 95% | 100% | 100% | 100% | 100% | 100% | 100% | 100% | 97% | 73% | 100% | 100% | 100% | 100% | 100% | 55% | 100% | 100% |
| pos occupied[6] | 2 | 3 | 1 | 1 | 1 | 1 | 1 | 1 | 1 | 1 | 2 | 2 | 1 | 1 | 1 | 1 | 3 | 1 | 1 |

TABLE 5C-continued

Analysis of V lambda subgroup 3

Framework III

| amino acid[1] | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|
| A |  |  |  | 1 | 36 | 1 |  | 1 |  |  |  | 11 | 1 | 34 |  |  |  | 38 |  |
| B |  |  |  |  |  |  |  |  |  |  |  |  |  |  |  |  |  |  |  |
| C |  |  |  |  |  |  |  |  |  |  |  |  |  |  |  |  |  |  |  |
| D |  |  |  |  |  |  |  |  |  |  |  |  |  |  |  | 38 |  |  | 37 |
| E |  |  |  |  |  |  |  |  |  |  |  |  | 10 |  | 14 |  | 38 |  | 1 |
| F |  |  |  |  |  |  |  |  |  |  |  |  |  |  |  |  |  |  |  |
| G |  | 37 |  |  |  |  |  |  |  |  | 28 |  |  |  | 10 |  |  |  |  |
| H |  |  | 1 |  |  |  |  |  |  |  |  |  |  |  |  |  |  |  |  |
| I |  |  |  |  |  | 1 |  |  | 1 | 37 | 1 |  |  |  | 1 |  |  |  |  |
| K |  |  | 1 |  |  |  |  |  |  |  |  |  |  |  |  |  |  |  |  |
| L |  |  |  |  |  |  |  | 38 |  |  |  |  |  |  | 2 |  |  |  |  |
| M |  |  |  |  |  |  |  |  |  |  |  |  |  |  | 10 |  |  |  |  |
| N |  |  | 28 |  |  |  |  |  |  | 1 |  |  |  |  |  |  |  |  |  |
| P |  |  |  |  |  |  |  |  |  |  |  |  |  |  |  |  |  |  |  |
| Q |  | 1 |  |  |  |  |  |  |  |  |  |  | 25 |  |  |  |  |  |  |
| R |  |  |  |  |  |  |  |  |  | 1 | 10 |  | 1 |  |  |  |  |  |  |
| S | 37 |  | 2 |  |  | 11 |  |  |  | 23 |  |  |  |  | 1 |  |  |  |  |
| T | 1 |  | 6 | 37 |  | 25 |  | 36 |  | 12 |  | 13 |  | 2 | 1 |  |  |  |  |
| V |  |  |  |  | 2 |  |  |  | 1 |  |  | 14 | 1 | 1 | 1 |  |  |  |  |
| W |  |  |  |  |  |  |  |  |  |  |  |  |  |  |  |  |  |  |  |
| X |  |  |  |  |  |  |  |  |  |  |  |  |  |  |  |  |  |  |  |
| Y |  |  |  |  |  |  |  |  |  |  |  |  |  |  |  |  |  |  |  |
| Z |  |  |  |  |  |  |  |  |  |  |  |  |  |  |  |  |  |  |  |
| — |  |  |  |  |  |  |  |  |  |  |  |  |  |  |  |  |  |  |  |
| unknown (?) |  |  |  |  |  |  |  |  |  |  |  |  |  |  |  |  |  |  |  |
| not sequenced |  |  |  |  |  |  |  |  |  |  |  |  |  |  |  |  |  |  |  |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 37 | 37 | 28 | 37 | 36 | 25 | 38 | 36 | 37 | 23 | 28 | 14 | 25 | 34 | 14 | 38 | 38 | 38 | 37 |
| mcaa[4] | S | G | N | T | A | T | L | T | I | S | G | V | Q | A | E | D | E | A | D |
| rel. oomcaa[5] | 97% | 97% | 74% | 97% | 95% | 66% | 100% | 95% | 97% | 61% | 74% | 37% | 66% | 89% | 37% | 100% | 100% | 100% | 97% |
| pos occupied[6] | 2 | 2 | 5 | 2 | 2 | 4 | 1 | 3 | 2 | 5 | 2 | 3 | 5 | 4 | 6 | 1 | 1 | 1 | 2 |

CDR III

| amino acid[1] | 86 | 87 | 88 | 89 | 90 | 91 | 92 | 93 | 94 | 95 | A | B | C | D | E | F | 96 | 97 | 98 |
|---|---|---|---|---|---|---|---|---|---|---|---|---|---|---|---|---|---|---|---|
| A |  |  |  |  | 13 | 3 | 2 |  |  | 1 | 2 |  |  |  |  |  | 4 |  |  |
| B |  |  |  |  |  |  |  |  |  |  |  |  |  |  |  |  |  |  |  |
| C |  |  | 38 |  |  |  |  |  |  |  |  |  |  |  |  |  |  |  |  |
| D |  |  |  | 1 |  |  | 32 | 1 | 1 |  | 6 |  |  |  |  |  |  |  |  |
| E |  |  |  |  | 1 |  |  |  |  |  |  | 2 |  |  |  |  | 2 |  |  |
| F |  | 2 |  |  |  |  |  | 2 |  |  |  |  |  |  |  |  |  |  | 35 |
| G |  |  |  |  |  |  |  | 3 | 14 | 3 |  | 12 |  |  | 1 |  | 3 | 1 |  |
| H |  |  |  |  |  |  |  |  |  |  |  | 12 | 1 |  |  |  |  | 4 |  |
| I |  |  |  |  |  |  |  |  |  |  |  |  |  |  |  |  |  | 4 |  |
| K |  |  |  |  |  |  |  |  |  | 1 |  |  |  |  |  |  |  |  |  |
| L |  |  |  | 1 |  |  |  | 1 |  | 1 |  | 1 | 1 |  |  |  | 4 | 2 |  |
| M |  |  |  |  |  |  |  |  | 1 |  |  |  |  |  |  |  | 1 | 1 |  |
| N |  |  |  | 10 |  |  | 2 | 1 | 2 |  | 10 | 1 |  |  |  |  | 1 |  |  |
| P |  |  |  |  |  |  |  |  | 1 |  |  |  |  | 3 |  |  | 1 |  |  |
| Q |  |  |  | 25 |  |  |  |  |  | 1 | 1 |  |  |  |  |  |  |  |  |
| R |  |  |  |  |  | 10 |  | 1 | 2 |  |  | 2 |  |  |  |  |  |  |  |
| S |  |  |  | 1 | 14 | 1 |  | 28 | 26 | 13 |  | 1 |  |  |  |  | 1 |  |  |
| T |  |  |  |  |  | 1 |  | 3 |  | 7 | 2 |  |  |  |  |  |  |  |  |
| V |  |  |  |  | 11 |  |  |  |  |  |  |  |  |  |  |  | 18 | 28 |  |
| W |  |  |  |  |  | 23 |  |  |  |  |  |  |  |  |  |  | 1 |  |  |
| X |  |  |  |  |  |  |  |  |  |  |  |  |  |  |  |  |  |  |  |
| Y | 38 | 36 |  |  |  |  | 1 |  | 1 |  | 1 | 3 | 1 |  |  |  | 3 |  |  |
| Z |  |  |  |  |  |  |  |  |  |  |  |  |  |  |  |  |  |  |  |
| — |  |  |  |  |  |  |  |  |  |  | 10 | 15 | 31 | 36 | 37 | 36 |  | 1 |  |
| unknown (?) |  |  |  |  |  |  |  |  |  |  |  |  |  |  |  |  |  |  |  |
| not sequenced |  |  |  |  |  |  | 1 | 1 | 1 | 1 | 2 | 1 | 1 | 1 | 1 | 1 | 1 | 1 | 3 |
| sum of seq[2] | 38 | 38 | 38 | 38 | 38 | 38 | 37 | 37 | 37 | 37 | 36 | 37 | 37 | 37 | 37 | 37 | 37 | 37 | 35 |
| oomcaa[3] | 38 | 36 | 38 | 25 | 14 | 23 | 32 | 28 | 26 | 14 | 10 | 15 | 31 | 36 | 37 | 36 | 18 | 28 | 35 |
| mcaa[4] | Y | Y | C | Q | S | W | D | S | S | G | N | — | — | — | — | — | V | V | F |
| rel. oomcaa[5] | 100% | 95% | 100% | 66% | 37% | 61% | 86% | 76% | 70% | 38% | 28% | 41% | 84% | 97% | 100% | 97% | 49% | 76% | 100% |
| pos occupied[6] | 1 | 2 | 1 | 5 | 3 | 5 | 4 | 7 | 8 | 6 | 9 | 8 | 5 | 2 | 1 | 2 | 9 | 6 | 1 |

TABLE 5C-continued

Analysis of V lambda subgroup 3

| | | Framework IV | | | | | | | | | | |
|---|---|---|---|---|---|---|---|---|---|---|---|---|
| amino acid[1] | 99 | 100 | 101 | 102 | 103 | 104 | 105 | 106 | A | 107 | 108 | sum |
| A | | | | | | | | | | | | 265 |
| B | | | | | | | | | | | | |
| C | | | | | | | | | | 1 | | 82 |
| D | | | | | | | | | | | | 225 |
| E | | | | | | 2 | | | | | | 145 |
| F | | | | | | | | | | | | 90 |
| G | 35 | 31 | 35 | | | | | | | 24 | | 461 |
| H | | | | | | | | | | | | 32 |
| I | | | | | | | | | | | | 160 |
| K | | | | | 30 | | | | | | | 110 |
| L | | | | | | | 28 | | 33 | | | 233 |
| M | | | | | | | | | | | | 17 |
| N | | | | | | | | | | | | 126 |
| P | | | | | | | | | 1 | | | 249 |
| Q | | | | | | | | | | | 7 | 275 |
| R | | | | | | 2 | | | | | | 154 |
| S | | | | | | | | | | 2 | | 501 |
| T | | 4 | | 35 | | | 35 | | | | | 347 |
| V | | | | | | | 7 | 35 | | | | 308 |
| W | | | | | | | | | | | | 62 |
| X | | | | | | | | | | | | |
| Y | | | | | | | | | | | | 211 |
| Z | | | | | | | | | | | | |
| — | | | | | | | | | | | | 603 |
| unknown (?) | | | | | | | | | | | | 1 |
| not sequenced | 3 | 3 | 3 | 3 | 4 | 3 | 3 | 3 | 4 | 11 | 28 | 89 |
| sum of seq[2] | 35 | 35 | 35 | 35 | 34 | 35 | 35 | 35 | 34 | 27 | 7 | |
| oomcaa[3] | 35 | 31 | 35 | 35 | 30 | 28 | 35 | 35 | 33 | 24 | 7 | |
| mcaa[4] | G | G | G | T | K | L | T | V | L | G | Q | |
| rel. oomcaa[5] | 100% | 89% | 100% | 100% | 88% | 80% | 100% | 100% | 97% | 89% | 100% | |
| pos occupied[6] | 1 | 2 | 1 | 1 | 3 | 2 | 1 | 1 | 2 | 3 | 1 | |

TABLE 6A

Analysis of V heavy chain subgroup 1A

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | 1 | 14 | | | 60 | | | | | | | 24 | 1 | | |
| B | | | | | | | | | | | | | | | | | | | |
| C | | | | | | | | | | | | | | | | | | | |
| D | | | | | | | | | | | | | | | | | | | |
| E | 1 | | | | 2 | 1 | | 2 | | 64 | | | | | | | | | |
| F | | | | | | | | | | | | | | | | | | | |
| G | | | | | | | | 58 | 1 | | | | | | 64 | | | | |
| H | | | 2 | | | | | | | | | | | | | | | | |
| I | | 2 | | | | | | | | | | | | | | | | | |
| K | | 2 | | | | | | | | | | 57 | 64 | | | | | | 60 |
| L | | | 2 | 59 | | | | | | | 3 | | | | | | | | |
| M | | 1 | | | | | | | | | | | | | | | | | |
| N | | | | | | | | | | | | | 6 | | | | | | |
| P | | | | | | | | | | | | | | 63 | | | | | |
| Q | 53 | | 56 | | 2 | 45 | | | | | | | | | | | | | |
| R | | | | | | | | | | | | 1 | | | | | | | 3 |
| S | | | | | | 60 | | 3 | | | | | | 1 | | 40 | 63 | | |
| T | | | | | | | | | | | | | | | | | | | 1 |
| V | 2 | 55 | | 1 | 55 | | | | | | 61 | | | | | | | 64 | |
| W | | | | | | | | | | | | | | | | | | | |
| X | | | | | | | | | | | | | | | | | | | |

TABLE 6A-continued

Analysis of V heavy chain subgroup 1A

| amino acid[1] | | | | | | | | | | | | | | | | | | | |
|---|---|---|---|---|---|---|---|---|---|---|---|---|---|---|---|---|---|---|---|
| Y | | | | | | | | | | | | | | | | | | | |
| Z | 3 | | | | | | | | | | | | | | | | | | |
| — | | | | | | | | | | | | | | | | | | | |
| unknown (?) | | | | | | | | | | | | | | | | | | | |
| not sequenced | 11 | 10 | 10 | 10 | 10 | 10 | 10 | 10 | 6 | 6 | 6 | 6 | 6 | 6 | 6 | 6 | 6 | 6 | 6 |
| sum of seq[2] | 59 | 60 | 60 | 60 | 60 | 60 | 60 | 60 | 64 | 64 | 64 | 64 | 64 | 64 | 64 | 64 | 64 | 64 | 64 |
| oomcaa[3] | 53 | 55 | 56 | 59 | 55 | 45 | 60 | 58 | 60 | 64 | 61 | 57 | 64 | 63 | 64 | 40 | 63 | 64 | 60 |
| mcaa[4] | Q | V | Q | L | V | Q | S | G | A | E | V | K | K | P | G | S | S | V | K |
| rel. oomcaa[5] | 90% | 92% | 93% | 98% | 92% | 75% | 100% | 97% | 94% | 100% | 95% | 89% | 100% | 98% | 100% | 63% | 98% | 100% | 94% |
| pos occupied[6] | 4 | 4 | 3 | 2 | 4 | 3 | 1 | 2 | 3 | 1 | 2 | 3 | 1 | 2 | 1 | 2 | 2 | 1 | 3 |

| amino acid[1] | 20 | 21 | 22 | 23 | 24 | 25 | 26 | 27 | 28 | 29 | 30 | 31 | A | B | 32 | 33 | 34 | 35 | 36 |
|---|---|---|---|---|---|---|---|---|---|---|---|---|---|---|---|---|---|---|---|
| | | | | | | | | | | | | | | CDR I | | | | | |
| A | | | | | 62 | | | | 1 | | | | | | | 41 | | | |
| B | | | | | | | | | | | | | | | | | | | |
| C | | | 63 | | | | | | | | | | | | | | | | |
| D | | | | | | | | 1 | | | | | | | | | | | |
| E | | | | | | | | | | | | | | | | | | | |
| F | | | | | | | | | | 69 | | | | | 3 | | 3 | | |
| G | | | | | | 1 | | 69 | 41 | | 1 | | | | | 23 | | | |
| H | | | | | | | | | | | | 1 | | | 1 | | | 1 | |
| I | | | | | | | | | 1 | | | | | | | | 61 | 1 | |
| K | | | | 63 | | | | | | | | 1 | 1 | | | | | | |
| L | | | | | | | | | | | | | | | | 1 | 2 | | |
| M | | | | | | | | | | | | | | | | | 4 | | |
| N | | | | | | | | | | | 2 | 5 | | | | | | 4 | |
| P | | | | | | | | | | | | | | | | 1 | | | |
| Q | | | | | | | | | | | | | | | | | | | |
| R | | | 1 | 1 | | | | | | | | 1 | 1 | | | | | | |
| S | | 63 | | | | | 68 | | 1 | | | 40 | 60 | | 2 | | | 60 | |
| T | | 1 | | | 2 | | | | 68 | | 25 | 3 | | | | 3 | | 4 | |
| V | 64 | | | | | | | | | | | | | | | 1 | | | |
| W | | | | | | | | | | | | | | | | | | | 70 |
| X | | | | | | | | | | | | | | | | | | | |
| Y | | | | | | | | 27 | | | | | | | 64 | | | | |
| Z | | | | | | | | | | | | | | | | | | | |
| — | | | | | | | | | | | | 70 | 70 | | | | | | |
| unknown (?) | | | | | | | | | | | | | | | | | | | |
| not sequenced | 6 | 6 | 6 | 6 | 5 | 2 | 1 | | | | | | | | | | | | |
| sum of seq[2] | 64 | 64 | 64 | 64 | 65 | 68 | 69 | 70 | 70 | 70 | 70 | 70 | 70 | 70 | 70 | 70 | 70 | 70 | 70 |
| oomcaa[3] | 64 | 63 | 63 | 63 | 62 | 68 | 69 | 41 | 68 | 69 | 40 | 60 | 70 | 70 | 64 | 41 | 61 | 60 | 70 |
| mcaa[4] | V | S | C | K | A | S | G | G | T | F | S | S | — | — | Y | A | I | S | W |
| rel. oomcaa[5] | 100% | 98% | 98% | 98% | 95% | 100% | 100% | 59% | 97% | 99% | 57% | 86% | 100% | 100% | 91% | 59% | 87% | 86% | 100% |
| pos occupied[6] | 1 | 2 | 2 | 2 | 3 | 1 | 1 | 4 | 3 | 2 | 6 | 5 | 1 | 1 | 4 | 6 | 4 | 5 | 1 |

| amino acid[1] | 37 | 38 | 39 | 40 | 41 | 42 | 43 | 44 | 45 | 46 | 47 | 48 | 49 | 50 | 51 | 52 | A | B | C |
|---|---|---|---|---|---|---|---|---|---|---|---|---|---|---|---|---|---|---|---|
| | Framework II | | | | | | | | | | | | | | | | | | |
| A | | | | 70 | | | | | | | | | 1 | | | 5 | | | |
| B | | | | | | | | | | | | | | | | | | | |
| C | | | | | | | | | | | | | | | | | | | |
| D | | | | | | | | | | 1 | | | | | | | | | |
| E | | | | | | | | | | 69 | | | | | | | | | |
| F | | | | | | | | | | | | | | | 2 | | | | |
| G | | | | | 1 | 68 | | 69 | | | 1 | | 69 | 39 | | | 1 | | |
| H | | | | | | 1 | | | | | | | | | | | | | |
| I | | 1 | | | | | | | | | | | | | 65 | 38 | | | |
| K | | | | | | | | | | | | | | | | | | | |
| L | | | | | 1 | | | | 68 | | | 1 | | 1 | | | | | |
| M | | | | | | | | | | | | 67 | | | | 2 | | | |
| N | | | | | | | | | | | | | | | | 4 | | | |
| P | | | | | | 68 | | | | 1 | | | | | | | 44 | | |
| Q | | | 69 | | | | 69 | | | | | | | | | | | | |
| R | | 70 | 1 | | | 1 | | 1 | | | | | | 4 | | | | | |
| S | | | | | | | 1 | | | | | 1 | 1 | | 1 | 22 | 4 | | |
| T | 69 | | | | | | | | | | | | | | 2 | 2 | 16 | | |
| V | | | | | | | | | | | 1 | | | | | | | | |
| W | | | | | | | | | | 1 | | 67 | | 26 | | | | | |
| X | | | | | | | | | | | | | | | | | | | |
| Y | | | | | | | | | | | | | 1 | | | | | | |

TABLE 6A-continued

Analysis of V heavy chain subgroup 1A

| | | | | | | | | | | | | | | | | | | | |
|---|---|---|---|---|---|---|---|---|---|---|---|---|---|---|---|---|---|---|---|
| Z | | | | | | | | | | | | | | | | | | | |
| — | | | | | | | | | | | | | | | | | | 70 | 70 |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 69 | 70 | 69 | 70 | 68 | 68 | 69 | 69 | 68 | 69 | 67 | 67 | 69 | 39 | 65 | 38 | 44 | 70 | 70 |
| mcaa[4] | V | R | Q | A | P | G | Q | G | L | E | W | M | G | G | I | I | P | — | — |
| rel. oomcaa[5] | 99% | 100% | 99% | 100% | 97% | 97% | 99% | 99% | 97% | 99% | 96% | 96% | 99% | 56% | 93% | 54% | 63% | 100% | 100% |
| pos occupied[6] | 2 | 1 | 2 | 1 | 3 | 3 | 2 | 2 | 3 | 2 | 4 | 4 | 2 | 4 | 4 | 6 | 5 | 1 | 1 |

| | CDR II | | | | | | | | | | | | | | | | | |
|---|---|---|---|---|---|---|---|---|---|---|---|---|---|---|---|---|---|---|
| amino acid[1] | 53 | 54 | 55 | 56 | 57 | 58 | 59 | 60 | 61 | 62 | 63 | 64 | 65 | 66 | 67 | 68 | 69 | 70 | 71 |
| A | | | | 1 | 34 | | | 69 | | | | | | | | | | | 43 |
| B | | | | | | | | | | | | | | | | | | | |
| C | | | | | | | | | | | | | | | | | | | |
| D | | | | 15 | | 1 | | | | | | | 2 | | | | | | |
| E | | | | | | | | | | | | 1 | | | | | | | |
| F | 3 | 39 | | | | | 1 | | | | 48 | | | | 3 | | 4 | | |
| G | | | 68 | 1 | | | | | | 3 | | | 67 | | | | | | |
| H | | | | | | 1 | | | | | | | | | | | | | |
| I | 34 | | | 4 | | | | | | | | | | | | 1 | 44 | | |
| K | | | | 1 | | 2 | 1 | | | 47 | | 1 | | 1 | | | | | |
| L | 2 | 4 | | 1 | 1 | | | | | | | 22 | | | 2 | | 1 | | 3 |
| M | 4 | | | | | | | | | | | | | | | | 21 | | |
| N | 3 | 22 | | 9 | | 59 | | | | 18 | | | | | | | | | |
| P | | | | 1 | 7 | | | | | | | | | | | | | | |
| Q | 1 | 1 | 1 | 1 | 1 | | | | 70 | | | 64 | | | | | | | |
| R | 1 | | | 2 | | | | | | 2 | | 1 | | 69 | | | | | |
| S | | 1 | 1 | | 1 | 2 | | 1 | | | | | | | | | | 5 | |
| T | 1 | 3 | | 34 | 26 | 4 | | | | | | 3 | | | | 66 | | 65 | 24 |
| V | 1 | | | | | | | | | | | | 1 | | 65 | 3 | | | |
| W | | | | | | | | | | | | | | | | | | | |
| X | | | | | | | | | | | | | | | | | | | |
| Y | 20 | | | | | 1 | 68 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 34 | 39 | 68 | 34 | 34 | 59 | 68 | 69 | 70 | 47 | 48 | 64 | 67 | 69 | 65 | 66 | 44 | 65 | 43 |
| mcaa[4] | I | F | G | T | A | N | Y | A | Q | K | F | Q | G | R | V | T | I | T | A |
| rel. oomcaa[5] | 49% | 56% | 97% | 49% | 49% | 84% | 97% | 99% | 100% | 67% | 69% | 91% | 96% | 99% | 93% | 94% | 63% | 93% | 61% |
| pos occupied[6] | 10 | 6 | 3 | 11 | 6 | 7 | 3 | 2 | 1 | 4 | 2 | 5 | 3 | 2 | 3 | 3 | 4 | 2 | 3 |

| | Framework III | | | | | | | | | | | | | | | | | |
|---|---|---|---|---|---|---|---|---|---|---|---|---|---|---|---|---|---|---|
| amino acid[1] | 72 | 73 | 74 | 75 | 76 | 77 | 78 | 79 | 80 | 81 | 82 | A | B | C | 83 | 84 | 85 | 86 | 87 |
| A | | | | | | | 64 | | | 1 | | | | | | 3 | | | 1 |
| B | | | | | | | | | | | | | | | | | | | |
| C | | | | | | | | | | | | | | | | | | | |
| D | 70 | | | | | | | | 2 | | | | | | | 26 | 70 | | |
| E | | 33 | | | | | | | | 64 | | | | | | 44 | | | |
| F | | | | | | | | | | | | | | | | | | | |
| G | | | | | | | | | | | | | 1 | | | | | | |
| H | | | | | | | | 1 | | | | 1 | | | | | | | |
| I | | 1 | | | | 1 | | | | | 3 | 1 | 1 | | | | | | |
| K | | 8 | | | | | | | | | | | | | 3 | | | | |
| L | | | | | | | | | 3 | | 63 | | | 70 | | | | | |
| M | | | | | | | | | | 67 | | | | | | | | | 1 |
| N | | | | | 4 | | | | | | | 1 | 16 | | | | | | |
| P | | | | | | | | | | | | | | | | | | | |
| Q | | | | | | | | | 1 | | 3 | | | | | | | | |
| R | | 1 | | | 3 | | | | | | | 23 | 1 | | 62 | | | | |
| S | | | 70 | | 62 | | 1 | | | | | 41 | 49 | | | 67 | | | 1 |
| T | | 27 | | 67 | 1 | 69 | 2 | | | | | 3 | 2 | | 4 | | | | 67 |
| V | | | | 3 | | | 3 | | | 4 | | | | | 1 | | | | |
| W | | | | | | | | | | | | | | | | | | | |
| X | | | | | | | | | | | | | | | | | | | |
| Y | | | | | | | | 68 | | | | | | | | | | | |
| Z | | | | | | | | | | | | | | | | | | | |

TABLE 6A-continued

Analysis of V heavy chain subgroup 1A

| | | | | | | | | | | | | | | | | | | | |
|---|---|---|---|---|---|---|---|---|---|---|---|---|---|---|---|---|---|---|---|
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 70 | 33 | 70 | 67 | 62 | 69 | 64 | 68 | 67 | 64 | 63 | 41 | 49 | 70 | 62 | 67 | 44 | 70 | 67 |
| mcaa[4] | D | E | S | T | S | T | A | Y | M | E | L | S | S | L | R | S | E | D | T |
| rel. oomcaa[5] | 100% | 47% | 100% | 96% | 89% | 99% | 91% | 97% | 96% | 91% | 90% | 59% | 70% | 100% | 89% | 96% | 63% | 100% | 96% |
| pos occupied[6] | 1 | 5 | 1 | 2 | 4 | 2 | 4 | 3 | 2 | 4 | 3 | 6 | 6 | 1 | 4 | 2 | 2 | 1 | 4 |

| | | | | | | CDR III | | | | | | | | | | | | |
|---|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 70 | | | | | 66 | 2 | 16 | | 1 | 1 | 1 | 4 | 1 | 2 | 2 | 1 | 1 | |
| B | | | | | | | | | | | | | | | | | | | |
| C | | | | | 70 | | | | | 1 | 1 | 16 | 2 | | 1 | 1 | 7 | 2 | 1 |
| D | | | | | | | | 16 | 5 | 3 | | 3 | 5 | 4 | 3 | 4 | | | 1 |
| E | | | | | | | | 9 | | | | 2 | | | 1 | | | 1 | |
| F | | 1 | 1 | 2 | | | | | | 1 | 3 | | 2 | | 3 | 1 | 2 | | 2 |
| G | | | | | | | 2 | 14 | 13 | 20 | 10 | 14 | 5 | 20 | 15 | 16 | 3 | 3 | 4 |
| H | | | | | | | | | | | | | | | 1 | 1 | 1 | | 1 |
| I | | 2 | | | | | | 2 | 5 | 2 | 2 | | 2 | 2 | 2 | 1 | 1 | | |
| K | | | | | | | 5 | | | 2 | 1 | | | 1 | | | | | |
| L | | 2 | | | | | 1 | 4 | 4 | 2 | 5 | 2 | 1 | 1 | | 4 | 2 | | 1 |
| M | | 1 | | | | | | 1 | | 2 | | 1 | | 1 | | | 1 | 1 | |
| N | | | | | | | | 2 | 2 | 1 | 2 | 1 | 2 | 2 | 2 | 2 | 2 | | |
| P | | | | | | | | 20 | 3 | | | 1 | 3 | 2 | 2 | 2 | 4 | 2 | 1 |
| Q | | | | | | | | 1 | | | | 1 | | 1 | 1 | 1 | 1 | | |
| R | | | | | | | 55 | 1 | 5 | 7 | 8 | 1 | 4 | | 2 | | 1 | | 16 |
| S | | | | | | | 1 | 1 | 5 | 5 | 5 | 5 | 21 | 5 | 11 | 8 | 4 | 3 | |
| T | | | | | | 1 | 3 | 3 | 5 | 4 | 1 | 3 | 4 | 2 | 5 | 2 | | 1 | |
| V | | 64 | | | | 3 | | 3 | 2 | 4 | 3 | 3 | 3 | 4 | 2 | 2 | 2 | 1 | 2 |
| W | | | | | | | | 1 | 1 | 3 | 1 | 1 | | | | 2 | | 3 | |
| X | | | | | | | | | | | | | | | | | | | |
| Y | | | 69 | 68 | | | 1 | | 2 | 3 | 20 | 5 | 4 | 9 | 1 | 2 | 11 | 20 | 10 |
| Z | | | | | | | | | | | | | | | | | | | |
| — | | | | | | | 1 | 2 | 2 | 3 | 6 | 11 | 11 | 14 | 23 | 26 | 26 | | |
| unknown (?) | | | | | | | | | | | | | | | | | 1 | | |
| not sequenced | | | | | | | 2 | 2 | 2 | 4 | 4 | 4 | 4 | 5 | 5 | 5 | 5 | 5 | 5 |
| sum of seq[2] | 70 | 70 | 70 | 70 | 70 | 70 | 70 | 68 | 68 | 68 | 66 | 66 | 66 | 66 | 65 | 65 | 65 | 65 | 65 |
| oomcaa[3] | 70 | 64 | 69 | 68 | 70 | 66 | 55 | 16 | 20 | 20 | 20 | 16 | 21 | 20 | 15 | 16 | 23 | 26 | 26 |
| mcaa[4] | A | V | Y | Y | C | A | R | A | P | G | Y | C | S | G | — | — | — | — | — |
| rel. oomcaa[5] | 100% | 91% | 99% | 97% | 100% | 94% | 79% | 24% | 29% | 29% | 30% | 24% | 32% | 30% | 23% | 25% | 35% | 40% | 40% |
| pos occupied[6] | 1 | 5 | 2 | 2 | 1 | 3 | 8 | 10 | 14 | 18 | 15 | 18 | 15 | 15 | 17 | 17 | 15 | 12 | 11 |

| | | | | | | | | Framework IV | | | | | | | | | | |
|---|---|---|---|---|---|---|---|---|---|---|---|---|---|---|---|---|---|---|
| amino acid[1] | G | H | I | J | K | 101 | 102 | 103 | 104 | 105 | 106 | 107 | 108 | 109 | 110 | 111 | 112 | 113 | sum |
| A | 1 | 1 | 1 | 2 | | 1 | | | | | | | | | | | | | 670 |
| B | | | | | | | | | | | | | | | | | | | |
| C | | | | | | | | | | | | | | | | | | | 165 |
| D | 1 | 14 | | | 59 | | 1 | 1 | | | | | | | | | | | 308 |
| E | | 1 | | | | | 1 | 1 | | | | | | | | | | | 297 |
| F | 1 | | | | 28 | 2 | 2 | | | | | | | | | | | | 226 |
| G | 15 | 1 | 1 | 7 | | | | | | 58 | | 59 | 1 | 1 | | | | | 928 |
| H | | | | | | | | | | | 1 | | | | | | | | 14 |
| I | 1 | | | | | | 3 | | | | | | | | 4 | | | | 286 |
| K | | | | | | | | | | 3 | | 1 | | | | | | | 325 |
| L | | | 1 | | 1 | | 3 | | | 1 | | | 40 | 1 | | | | | 386 |
| M | | | | | 10 | | 1 | | | | | | 3 | | | | | | 189 |
| N | 1 | 1 | 4 | | | | 1 | | | 1 | | | | | | | | | 176 |
| P | 4 | 1 | | 1 | | 1 | 5 | | | | | | | | | | | 1 | 238 |
| Q | | | | | | | | | | 52 | | | | | | | | | 494 |
| R | | | | | | | | | | 1 | | | | | | | | | 351 |
| S | 2 | 1 | | 2 | | 1 | | | | | | | | | | | 53 | 51 | 972 |
| T | | 1 | 1 | | | | | | | | | 54 | 11 | 1 | 51 | | 1 | | 736 |
| V | 1 | | | | | | 15 | | 1 | | | | 1 | 54 | | 54 | | 1 | 699 |
| W | | | 1 | 5 | 1 | | | 59 | | 1 | | | | | | | | | 243 |
| X | | | | | | | | | | | | | | | | | | | |
| Y | 6 | 9 | 10 | 7 | 1 | | 34 | | 1 | | | | | | | | | | 542 |
| Z | | | | | | | | | | | | | | | | | | | 3 |
| — | 31 | 34 | 46 | 39 | 21 | 1 | 1 | | | | | | | | | | | | 578 |

TABLE 6A-continued

Analysis of V heavy chain subgroup 1A

| unknown (?) | 1 | 1 | | 2 | 3 | | | | | | | | | | | | | | 8 |
|---|---|---|---|---|---|---|---|---|---|---|---|---|---|---|---|---|---|---|---|
| not sequenced | 5 | 5 | 5 | 5 | 5 | 5 | 5 | 9 | 9 | 10 | 11 | 14 | 14 | 14 | 15 | 16 | 16 | 17 | 406 |
| sum of seq[2] | 65 | 65 | 65 | 65 | 65 | 65 | 65 | 61 | 61 | 60 | 59 | 56 | 56 | 56 | 55 | 54 | 54 | 53 | |
| oomcaa[3] | 31 | 34 | 46 | 39 | 28 | 59 | 34 | 59 | 58 | 52 | 59 | 54 | 40 | 54 | 51 | 54 | 53 | 51 | |
| mcaa[4] | — | — | — | — | F | D | Y | W | G | Q | G | T | L | V | T | V | S | S | |
| rel. oomcaa[5] | 48% | 52% | 71% | 60% | 43% | 91% | 52% | 97% | 95% | 87% | 100% | 96% | 71% | 96% | 93% | 100% | 98% | 96% | |
| pos occupied[6] | 11 | 10 | 8 | 7 | 6 | 6 | 9 | 3 | 4 | 7 | 1 | 3 | 5 | 3 | 2 | 1 | 2 | 3 | |

TABLE 6B

Analysis of V heavy chain subgroup 18

| | Framework I | | | | | | | | | | | | | | | | | |
|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 |
| A | | | | | | | | | 32 | | | | | | | 34 | | |
| B | | | | | | | | | | | | | | | | | | |
| C | | | | | | | | | | | | | | | | | | |
| D | | | | | | | | | | | | | | | | | | |
| E | | 1 | | | 5 | 1 | | | | 35 | | | | | | | | |
| F | | | | | | | | | | | | | | | | | | |
| G | | | | | | | 27 | | | | | | | | 35 | | | |
| H | | | 1 | | | | | | | | | | | 1 | | | | |
| I | | | | | | | | | | | | | | | | | | |
| K | | 3 | 1 | | | | | | | | | 34 | 33 | | | | | |
| L | | | 3 | 26 | 1 | | | | | | | | | | | | | |
| M | | | | | 1 | 1 | | | | | | | | | | | | |
| N | | | | | | | | | | | | | | | | | | |
| P | | | | | | | | | 1 | | | | | 33 | | | 1 | |
| Q | 21 | | 20 | | | 26 | | | | | | | | | | | | |
| R | 1 | | | | | | | | | | | 1 | 2 | | | | | |
| S | | | | | | | 27 | | | | 1 | | | | | 1 | 34 | |
| T | | | | | | | | | 1 | | | | | 1 | | | | |
| V | 3 | 21 | | | 20 | | | | | | 35 | | | | | | | 35 |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | | | | | | | | | | | | | | | | |
| unknown (?) | | | | | | | | | | | | | | | | | | |
| not sequenced | 15 | 15 | 15 | 13 | 13 | 13 | 13 | 13 | 6 | 5 | 5 | 5 | 5 | 5 | 5 | 5 | 5 | 5 |
| sum of seq[2] | 25 | 25 | 25 | 27 | 27 | 27 | 27 | 27 | 34 | 35 | 35 | 35 | 35 | 35 | 35 | 35 | 35 | 35 |
| oomcaa[3] | 21 | 21 | 20 | 26 | 20 | 26 | 27 | 27 | 32 | 35 | 35 | 34 | 33 | 33 | 35 | 34 | 34 | 35 |
| mcaa[4] | Q | V | Q | L | V | Q | S | G | A | E | V | K | K | P | G | A | S | V |
| rel. oomcaa[5] | 84% | 84% | 80% | 96% | 74% | 96% | 100% | 100% | 94% | 100% | 100% | 97% | 94% | 94% | 100% | 97% | 97% | 100% |
| pos occupied[6] | 3 | 3 | 4 | 2 | 4 | 2 | 1 | 1 | 3 | 1 | 1 | 2 | 2 | 3 | 1 | 2 | 2 | 1 |

| | Framework I | | | | | | | | | | | | CDR I | | | | |
|---|---|---|---|---|---|---|---|---|---|---|---|---|---|---|---|---|---|
| amino acid[1] | 19 | 20 | 21 | 22 | 23 | 24 | 25 | 26 | 27 | 28 | 29 | 30 | 31 | A | B | 32 | 33 | 34 |
| A | | | | | | 30 | | | | | | | 2 | | | | 6 | |
| B | | | | | | | | | | | | | | | | | | |
| C | | | | | 35 | | | | | | | | | | | | | |
| D | | | | | | | | | | | | | 1 | | | | 5 | |
| E | | | | | 3 | | | | | | | | 1 | | | | | |
| F | | | | | | | | | 2 | | 39 | | | | | 2 | 2 | |
| G | | | | | | | 1 | | 40 | | | | 1 | 14 | | | 1 | |
| H | | | | | | | | | | | | | | | | 3 | 1 | |
| I | | 1 | | | | | | | 1 | | 1 | | | | | | | 9 |
| K | 33 | | | 28 | | | | | | | | | | | | | | |
| L | | | | | | | | | | | | 1 | | 1 | | | | 5 |
| M | | | | | | | | | | | | | | | | | | 23 |
| N | | | | | | | | | | 1 | | | 1 | 3 | | | | 1 |
| P | | | | | | | | | | | | | | | | | 1 | |
| Q | | | | | | 2 | | | | | | | 1 | | | | 1 | |
| R | | | | | | 2 | | | | | 2 | | | | | 1 | | |
| S | | | 35 | | | | 40 | | | 5 | | 2 | 15 | | | 2 | 1 | |
| T | 2 | | | | 3 | | | | | 32 | | 34 | | | | | 1 | |
| V | | 34 | | | 1 | | | 1 | | | | 1 | 1 | | | | 2 | 2 |
| W | | | | | | | | | | | | | | | | | | |

TABLE 6B-continued

Analysis of V heavy chain subgroup 18

| amino acid[1] | | | | | | | | | | | | | | | | | | |
|---|---|---|---|---|---|---|---|---|---|---|---|---|---|---|---|---|---|---|
| X | | | | | | | | | | | | | | | | | | |
| Y | | | | | | | | 36 | | | | 1 | | | 32 | 19 | |
| Z | | | | | | | | | | | | | | | | | | |
| — | | | | | | | | | | | | | 40 | 40 | | | |
| unknown (?) | | | | | | | | | | | | | | | | | | |
| not sequenced | 5 | 5 | 5 | 5 | 5 | 5 | | | | | | | | | | | | |
| sum of seq[2] | 35 | 35 | 35 | 35 | 35 | 35 | 40 | 40 | 40 | 40 | 40 | 40 | 40 | 40 | 40 | 40 | 40 | 40 |
| oomcaa[3] | 33 | 34 | 35 | 35 | 28 | 30 | 40 | 40 | 36 | 32 | 39 | 34 | 15 | 40 | 40 | 32 | 19 | 23 |
| mcaa[4] | K | V | S | C | K | A | S | G | Y | T | F | T | S | — | — | Y | Y | M |
| rel. oomcaa[5] | 94% | 97% | 100% | 100% | 80% | 86% | 100% | 100% | 90% | 80% | 98% | 85% | 38% | 100% | 100% | 80% | 48% | 58% |
| pos occupied[6] | 2 | 2 | 1 | 1 | 4 | 4 | 1 | 1 | 4 | 4 | 2 | 6 | 10 | 1 | 1 | 5 | 11 | 5 |

| | CDR I | | Framework II | | | | | | | | | | | | | CDR II | | |
|---|---|---|---|---|---|---|---|---|---|---|---|---|---|---|---|---|---|---|
| amino acid[1] | 35 | 36 | 37 | 38 | 39 | 40 | 41 | 42 | 43 | 44 | 45 | 46 | 47 | 48 | 49 | 50 | 51 | 52 |
| A | | | | | | 39 | | | | 1 | | | | | 1 | | | |
| B | | | | | | | | | | | | | | | | | | |
| C | | | | | | | | | | | | | | | | | | |
| D | 1 | | | 1 | | | | | | | | | | | | | | 1 |
| E | | | | | | | 1 | | | | | 39 | | | | | | |
| F | | | | | | | | | | | 2 | | | | | | 1 | |
| G | | | 1 | | | | | 39 | | 28 | | | | | 39 | 1 | | |
| H | 34 | | | | | | | | | | | | | | | | | |
| I | | | | | | | | | | | | | | 3 | | | | 34 |
| K | | | | | | | | | 1 | | | | | | | | | |
| L | | | 2 | | | | 1 | | | | 37 | | | | | | 1 | |
| M | | | | | | | | | | | | | | 37 | | | 2 | 4 |
| N | 3 | | | | | | | | | | | | | | | | | 35 |
| P | | | | | | 1 | 34 | | | | | 1 | | | | | | |
| Q | 1 | | | 1 | 39 | | | | 39 | | | | 1 | | | | | |
| R | | | 37 | | 1 | | | | | 10 | | | | | | | 4 | |
| S | | | | | | | | 1 | | | 1 | | | | | | | 2 |
| T | | | | | | | | 4 | | | | | | | | | | 1 |
| V | | | | 38 | | | | | | | | | | | | | | 1 |
| W | | 40 | | | | | | | | | | | 40 | | | 33 | | |
| X | | | | | | | | | | | | | | | | | | |
| Y | 1 | | | | | | | | | | | | | | | | | |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 |
| oomcaa[3] | 34 | 40 | 38 | 37 | 39 | 39 | 34 | 39 | 39 | 28 | 37 | 39 | 40 | 37 | 39 | 33 | 34 | 35 |
| mcaa[4] | H | W | V | R | Q | A | P | G | Q | G | L | E | W | M | G | W | I | N |
| rel. oomcaa[5] | 85% | 100% | 95% | 93% | 98% | 98% | 85% | 98% | 98% | 70% | 93% | 98% | 100% | 93% | 98% | 83% | 85% | 88% |
| pos occupied[6] | 5 | 1 | 2 | 4 | 2 | 2 | 4 | 2 | 2 | 4 | 3 | 2 | 1 | 2 | 2 | 4 | 4 | 5 |

| | CDR II | | | | | | | | | | | | | | |
|---|---|---|---|---|---|---|---|---|---|---|---|---|---|---|---|
| amino acid[1] | A | B | C | 53 | 54 | 55 | 56 | 57 | 58 | 59 | 60 | 61 | 62 | 63 | 64 | 65 | 66 |
| A | 7 | | | 1 | | | 1 | 2 | | | 27 | 2 | | | | 1 | |
| B | | | | | | | | | | | | | | | | | |
| C | | | | | | | | | | | | | | | | | |
| D | | | | | 1 | | 1 | | | | | | | | | 4 | |
| E | | | | 1 | 1 | | 2 | | 2 | | | 1 | | | | 1 | |
| F | | | | 1 | | | | | | 4 | | | | 39 | | | |
| G | 1 | | | 9 | 1 | 39 | 15 | | 6 | | | 1 | | | | 34 | |
| H | | | | 2 | | | | | 1 | 1 | | | | | | | |
| I | | | | | | | | 1 | 1 | | | | | | | | |
| K | | | | | 1 | | 2 | 2 | 8 | | | | 36 | | 1 | | |
| L | | | | | | | | | | | | 1 | | 1 | | | |
| M | | | | | | | | | | | | | | | | | |
| N | | | | 20 | 12 | 1 | 17 | | 18 | | | | 1 | | | | |
| P | 31 | | | | | | | | | | | | | | | | |
| Q | | | | | | | | | | | | 36 | | | 37 | | |
| R | | | | 3 | 1 | | | | 2 | | | | | 1 | 2 | | 37 |
| S | | | | 1 | 20 | | 1 | | 2 | | 11 | | 1 | | | | |
| T | | | | | 3 | | | 35 | 2 | | 1 | | 1 | | | | |
| V | 1 | | | | | | 1 | | | | | | | | | | |
| W | | | | | | | | | | | | | | | | | 3 |
| X | | | | | | | | | | | | | | | | | |

TABLE 6B-continued

Analysis of V heavy chain subgroup 18

| amino acid[1] | | | | | | | | | | | | | | | | | |
|---|---|---|---|---|---|---|---|---|---|---|---|---|---|---|---|---|---|
| Y | | | | 2 | | | | | | 33 | | | | | | | |
| Z | | | | | | | | | | | | | | | | | |
| — | | 40 | 40 | | | | | | | | | | | | | | |
| unknown (?) | | | | | | | | | | | | | | | | | |
| not sequenced | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 |
| oomcaa[3] | 31 | 40 | 40 | 20 | 20 | 39 | 17 | 35 | 18 | 33 | 27 | 36 | 36 | 39 | 37 | 34 | 37 |
| mcaa[4] | P | — | — | N | S | G | N | T | N | Y | A | Q | K | F | Q | G | R |
| rel. oomcaa[5] | 78% | 100% | 100% | 50% | 50% | 98% | 43% | 88% | 45% | 83% | 68% | 90% | 90% | 98% | 93% | 85% | 93% |
| pos occupied[6] | 4 | 1 | 1 | 9 | 8 | 2 | 8 | 4 | 8 | 4 | 4 | 4 | 5 | 2 | 3 | 4 | 2 |

Framework III

| amino acid[1] | 67 | 68 | 69 | 70 | 71 | 72 | 73 | 74 | 75 | 76 | 77 | 78 | 79 | 80 | 81 | 82 | A | B |
|---|---|---|---|---|---|---|---|---|---|---|---|---|---|---|---|---|---|---|
| A | 1 | | | | 2 | | | | 12 | | | 35 | | | | | | |
| B | | | | | | | | | | | | | | | | | | |
| C | | | | | | | | | | | | | | | | | | |
| D | | | | | | 35 | | | | 1 | | | | | 4 | | | |
| E | | | | | 1 | | | | | | | | | | 35 | | | |
| F | | | 3 | | | | | | | | | 1 | | | | | | |
| G | | | | | | | | | | | | | | | 1 | | 1 | 2 |
| H | | | | | | 1 | | | | | | | | | | | | |
| I | 1 | 1 | 13 | | | | | | 22 | | 1 | | | | | | | |
| K | | | | | 1 | | | | | | | | | | | | | |
| L | | | 1 | | | | | | | | | | | 2 | | 39 | | |
| M | | | 23 | | | | 1 | | 1 | | | | | 37 | | 1 | | |
| N | | | | | | 4 | | | | 7 | | | | | | | 1 | 2 |
| P | | | | | | | | 3 | | | | | | | | | | |
| Q | | | | | | | | | | | | | | | | | | |
| R | | | | | 34 | | 1 | | | 4 | | | | | | | 2 | 16 |
| S | | | | | 1 | | | 37 | | 27 | | | 1 | | | | 35 | 20 |
| T | | 39 | | 40 | 1 | | 38 | | 5 | 1 | 39 | | | | | | 1 | |
| V | 38 | | | | | | | | | | | 4 | 1 | | | | | |
| W | | | | | | | | | | | | | | | | | | |
| X | | | | | | | | | | | | | | | | | | |
| Y | | | | | | | | | | | | | 39 | | | | | |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 |
| oomcaa[3] | 38 | 39 | 23 | 40 | 34 | 35 | 38 | 37 | 22 | 27 | 39 | 35 | 39 | 37 | 35 | 39 | 35 | 20 |
| mcaa[4] | V | T | M | T | R | D | T | S | I | S | T | A | Y | M | E | L | S | S |
| rel. oomcaa[5] | 95% | 98% | 58% | 100% | 85% | 88% | 95% | 93% | 55% | 68% | 98% | 88% | 98% | 93% | 88% | 98% | 88% | 50% |
| pos occupied[6] | 3 | 2 | 4 | 1 | 6 | 3 | 3 | 2 | 4 | 5 | 2 | 3 | 2 | 3 | 3 | 2 | 5 | 4 |

Framework III / CDR III

| | Framework III | | | | | | | | | | | CDR III | | | | | | |
|---|---|---|---|---|---|---|---|---|---|---|---|---|---|---|---|---|---|---|
| amino acid[1] | C | 83 | 84 | 85 | 86 | 87 | 88 | 89 | 90 | 91 | 92 | 93 | 94 | 95 | 96 | 97 | 98 | 99 |
| A | | | 1 | 2 | | | 40 | | | | | 37 | 1 | 6 | | | 1 | 1 |
| B | | | | | | | | | | | | | | | | | | |
| C | | | | | | | | | | | 37 | | 1 | | | | 3 | |
| D | | | | 19 | 40 | | | 1 | | | | | | 7 | | 5 | 2 | 3 |
| E | | | | 19 | | | | | | | | | | 2 | | 1 | | |
| F | | | 2 | | | | | | | 2 | 1 | | | | 1 | 1 | 3 | |
| G | | | | | | | | | | | | 1 | | 7 | 7 | 5 | 5 | 9 |
| H | | | | | | | | | | | | | | 1 | | | | 2 |
| I | | | | | | | | 1 | | | | 1 | | 1 | | 1 | 3 | 1 |
| K | | | 1 | | | | | | | | | | 1 | | | 1 | | |
| L | 39 | | | | | | | 2 | | | 1 | | 2 | 4 | | 4 | 4 | 3 |
| M | | | | | | | | 2 | | | | | | | 2 | | 1 | 1 |
| N | | | | | | | | | | | | | | | | 1 | | |
| P | | | | 1 | | | | | | 1 | | | | | 6 | 4 | | |
| Q | | | | | | | | | | | | | | | | | 1 | |
| R | | 37 | | | | | | | | | | 1 | 31 | 5 | 1 | 1 | 1 | 3 |
| S | | 1 | 36 | | | | | | 1 | 1 | | 1 | 3 | 3 | 1 | | 4 | 3 |
| T | | | 1 | | | 40 | | | | | | | 2 | 1 | 1 | 2 | 2 | 1 |
| V | 1 | | | | | | | | 33 | | | 1 | | 7 | 1 | 1 | 1 | 1 |
| W | | | | | | | | | | | | | | 1 | | 1 | | 2 |
| X | | | | | | | | | | | | | | | | | | |

TABLE 6B-continued

Analysis of V heavy chain subgroup 18

| | | | | | | | | | | | | | | | | | | |
|---|---|---|---|---|---|---|---|---|---|---|---|---|---|---|---|---|---|---|
| Y | | | | | | | | 38 | 35 | | | | | 5 | 5 | 4 | 2 |
| Z | | | | | | | | | | | | | | | | | | |
| — | | | | | | | | | | | | | | 1 | 1 | 4 | 6 |
| unknown (?) | | | | | | | | | | | | | | | | | | |
| not sequenced | | | | | | | | 1 | 1 | 1 | 1 | 1 | 1 | 3 | 3 | 3 | 3 | 3 |
| sum of seq[2] | 40 | 40 | 40 | 40 | 40 | 40 | 40 | 39 | 39 | 39 | 39 | 39 | 39 | 37 | 37 | 37 | 37 | 37 |
| oomcaa[3] | 39 | 37 | 36 | 19 | 40 | 40 | 40 | 33 | 38 | 35 | 37 | 37 | 31 | 7 | 7 | 5 | 5 | 9 |
| mcaa[4] | L | R | S | D | D | T | A | V | Y | Y | C | A | R | D | G | D | G | G |
| rel. oomcaa[5] | 98% | 93% | 90% | 48% | 100% | 100% | 100% | 85% | 97% | 90% | 95% | 95% | 79% | 19% | 19% | 14% | 14% | 24% |
| pos occupied[6] | 2 | 4 | 4 | 3 | 1 | 1 | 1 | 5 | 2 | 4 | 3 | 3 | 8 | 10 | 12 | 18 | 13 | 13 |

| | CDR III | | | | | | | | | | | | Framework IV | | | | | |
|---|---|---|---|---|---|---|---|---|---|---|---|---|---|---|---|---|---|---|
| amino acid[1] | 100 | A | B | C | D | E | F | G | H | I | J | K | 101 | 102 | 103 | 104 | 105 | 106 |
| A | 2 | 3 | 1 | 3 | | 1 | | | | | 5 | | | | | | | |
| B | | | | | | | | | | | | | | | | | | |
| C | | | 2 | 1 | | | | | | | | | | | | | | |
| D | 1 | 5 | 4 | | 1 | | 2 | 2 | 1 | 2 | | | 27 | 2 | | | | |
| E | 1 | 1 | | 2 | | 1 | | 1 | | | | | | | | | 1 | |
| F | | 2 | 1 | 1 | 1 | 1 | | | | | 2 | 15 | | 1 | | | | |
| G | 4 | 7 | 1 | 3 | | 2 | 2 | 1 | | 1 | 3 | | 1 | | | 27 | | 26 |
| H | | | 1 | 1 | | | | | | | | | | 1 | | | | |
| I | 1 | 1 | 1 | 1 | 1 | | | | | | | 1 | | 7 | | | | |
| K | | 1 | 1 | | 1 | | 1 | | | 1 | | | | | | | 2 | |
| L | | 1 | 2 | 1 | 1 | 2 | | 1 | | | 2 | | | | | | | |
| M | | | | | | | | 1 | | | 4 | | | | | | | |
| N | 1 | | 1 | 1 | 1 | | 3 | | 1 | | | | 1 | 1 | | | | |
| P | | 1 | 1 | | 3 | 2 | | | 1 | | | | 1 | | | | 1 | |
| Q | | | | | 1 | 2 | 1 | | | | | | | | | | 23 | |
| R | | | | | 1 | | 1 | | | | 1 | | | | | | | |
| S | 6 | 3 | 2 | 2 | 1 | | 1 | | | | | | 3 | | | | | |
| T | 5 | 1 | 1 | 1 | | 1 | | | 1 | | 1 | | | | | | | |
| V | 3 | 1 | 2 | | 1 | | | 1 | 2 | 1 | | | 1 | 6 | | | | |
| W | 2 | | 1 | 1 | | | | | 1 | | 4 | | | | 29 | | | |
| X | | | | | | | | | | | | | | | | | | |
| Y | 3 | | 4 | 3 | 3 | 2 | 1 | 2 | 5 | 6 | 2 | | | 11 | | | | |
| Z | | | | | | | | | | | | | | | | | | |
| — | 8 | 10 | 11 | 14 | 20 | 23 | 25 | 25 | 25 | 23 | 18 | 11 | 6 | 3 | | | | |
| unknown (?) | | | | | | | | | | | | 3 | | | | | | |
| not sequenced | 3 | 4 | 4 | 4 | 4 | 4 | 4 | 4 | 4 | 4 | 4 | 4 | 4 | 4 | 11 | 13 | 13 | 14 |
| sum of seq[2] | 37 | 36 | 36 | 36 | 36 | 36 | 36 | 36 | 36 | 36 | 36 | 36 | 36 | 36 | 29 | 27 | 27 | 26 |
| oomcaa[3] | 8 | 10 | 11 | 14 | 20 | 23 | 25 | 25 | 25 | 23 | 18 | 15 | 27 | 11 | 29 | 27 | 23 | 26 |
| mcaa[4] | — | — | — | — | — | — | — | — | — | — | — | F | D | Y | W | G | Q | G |
| rel. oomcaa[5] | 22% | 28% | 31% | 39% | 56% | 64% | 69% | 69% | 69% | 64% | 50% | 42% | 75% | 31% | 100% | 100% | 85% | 100% |
| pos occupied[6] | 12 | 12 | 17 | 14 | 13 | 10 | 9 | 8 | 7 | 8 | 8 | 5 | 5 | 10 | 1 | 1 | 4 | 1 |

| | Framework IV | | | | | | | |
|---|---|---|---|---|---|---|---|---|
| amino acid[1] | 107 | 108 | 109 | 110 | 111 | 112 | 113 | sum |
| A | | | | | | | | 340 |
| B | | | | | | | | |
| C | | | | | | | | 79 |
| D | | | | | | | | 179 |
| E | | | | | | | | 159 |
| F | | | | | | | | 130 |
| G | | | | | 1 | | | 450 |
| H | | | | | | | | 51 |
| I | | | | 3 | | | | 113 |
| K | | | | | | | | 194 |
| L | | 12 | | | 1 | | | 204 |
| M | | 2 | | | | | | 144 |
| N | | | | | | | | 138 |
| P | | | | | | | | 128 |
| Q | | | | | | | | 253 |
| R | | | 1 | | | | | 247 |
| S | | | | 1 | | 18 | 18 | 432 |
| T | 21 | 6 | | 16 | | 1 | | 390 |
| V | | | 21 | | 18 | | | 342 |
| W | | | | | | | | 158 |
| X | | | | | | | | |

TABLE 6B-continued

Analysis of V heavy chain subgroup 18

|  |  |  |  |  |  |  |  |
|---|---|---|---|---|---|---|---|
| Y |  |  |  |  |  |  | 294 |
| Z |  |  |  |  |  |  |  |
| — |  |  |  |  |  |  | 394 |
| unknown (?) |  |  |  |  |  |  | 3 |
| not sequenced | 19 | 19 | 19 | 20 | 20 | 21 | 22 | 458 |
| sum of seq[2] | 21 | 21 | 21 | 20 | 20 | 19 | 18 |
| oomcaa[3] | 21 | 12 | 21 | 16 | 18 | 18 | 18 |
| mcaa[4] | T | L | V | T | V | S | S |
| rel. oomcaa[5] | 100% | 57% | 100% | 80% | 90% | 95% | 100% |
| pos occupied[6] | 1 | 4 | 1 | 3 | 3 | 2 | 1 |

TABLE 6C

Analysis of V heavy chain subgroup 2

| amino acid[1] | Framework I | | | | | | | | | | | | | | | | | |
|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 | 17 | 18 |
| A |  |  |  |  |  |  |  |  |  | 3 |  |  |  |  |  |  |  |  |
| B |  |  |  |  |  |  |  |  |  |  |  |  |  |  |  |  |  |  |
| C |  |  |  |  |  |  |  |  |  |  |  |  |  |  |  |  |  |  |
| D |  |  |  |  |  |  |  |  |  |  |  |  |  |  |  |  |  |  |
| E | 1 |  |  |  |  | 6 |  |  |  |  |  |  |  |  |  | 2 |  |  |
| F |  |  |  |  |  |  |  |  |  |  |  |  |  |  |  |  |  |  |
| G |  |  |  |  |  |  |  |  | 6 |  |  |  |  |  |  |  |  |  |
| H |  |  |  |  |  |  |  |  |  |  |  |  |  |  |  |  |  |  |
| I |  | 1 |  |  |  |  |  |  |  |  |  |  |  |  |  |  |  |  |
| K |  |  |  |  | 3 |  |  |  |  |  |  |  |  | 6 |  | 1 |  |  |
| L |  |  |  | 6 |  |  |  |  |  |  | 6 |  |  |  |  |  |  | 6 |
| M |  |  |  |  |  |  |  |  |  |  |  |  |  |  |  |  |  |  |
| N |  |  |  |  |  |  |  | 1 |  |  |  |  |  |  |  |  |  |  |
| P |  |  |  |  |  |  |  | 1 |  | 6 |  |  |  |  | 6 |  | 1 |  |
| Q | 2 |  |  |  |  |  |  |  |  |  |  |  |  |  |  | 4 |  |  |
| R |  |  |  |  | 2 |  |  |  |  |  |  |  |  |  |  |  |  |  |
| S |  |  |  |  |  |  | 4 |  |  |  |  |  |  |  |  |  |  |  |
| T |  |  | 6 |  | 1 |  |  |  |  | 2 |  |  |  |  | 5 |  | 5 |  |
| V |  | 5 |  |  |  |  |  |  |  | 1 |  | 6 |  |  |  |  |  |  |
| W |  |  |  |  |  |  |  |  |  |  |  |  |  |  |  |  |  |  |
| X |  |  |  |  |  |  |  |  |  |  |  |  |  |  |  |  |  |  |
| Y |  |  |  |  |  |  |  |  |  |  |  |  |  |  |  |  |  |  |
| Z | 3 |  |  |  |  |  |  |  |  |  |  |  |  |  |  |  |  |  |
| — |  |  |  |  |  |  |  |  |  |  |  |  |  |  |  |  |  |  |
| unknown (?) |  |  |  |  |  |  |  |  |  |  |  |  |  |  |  |  |  |  |
| not sequenced | 1 | 1 | 1 | 1 | 1 | 1 | 1 | 1 | 1 | 1 | 1 | 1 | 1 | 1 | 1 | 1 | 1 | 1 |
| sum of seq[2] | 6 | 6 | 6 | 6 | 6 | 6 | 6 | 6 | 6 | 6 | 6 | 6 | 6 | 6 | 6 | 6 | 6 | 6 |
| oomcaa[3] | 3 | 5 | 6 | 6 | 3 | 6 | 4 | 6 | 6 | 3 | 6 | 6 | 6 | 6 | 5 | 4 | 5 | 6 |
| mcaa[4] | Z | V | T | L | K | E | S | G | P | A | L | V | K | P | T | Q | T | L |
| rel. oomcaa[5] | 50% | 83% | 100% | 100% | 50% | 100% | 67% | 100% | 100% | 50% | 100% | 100% | 100% | 100% | 83% | 67% | 83% | 100% |
| pos occupied[6] | 3 | 2 | 1 | 1 | 3 | 1 | 3 | 1 | 1 | 3 | 1 | 1 | 1 | 2 | 2 | 2 | 1 |

| amino acid[1] | Framework I | | | | | | | | | | | | CDR I | | | | |
|---|---|---|---|---|---|---|---|---|---|---|---|---|---|---|---|---|---|
|  | 19 | 20 | 21 | 22 | 23 | 24 | 25 | 26 | 27 | 28 | 29 | 30 | 31 | A | B | 32 | 33 | 34 |
| A |  |  |  |  |  |  |  |  |  | 1 |  |  | 1 |  |  | 1 |  |  |
| B |  |  |  |  |  |  |  |  |  |  |  |  |  |  |  |  |  |  |
| C |  |  |  | 7 |  |  |  |  |  |  |  |  |  |  |  | 2 |  |  |
| D |  |  |  |  |  |  |  |  |  |  |  |  | 1 |  |  |  |  |  |
| E |  |  |  |  |  |  |  |  |  |  |  |  |  |  |  |  |  |  |
| F |  |  |  |  |  | 3 |  |  | 6 | 1 |  |  |  |  |  |  |  |  |
| G |  |  |  |  |  |  |  | 7 |  |  |  |  |  |  |  | 4 | 3 |  |
| H |  |  |  |  |  |  |  |  |  |  |  |  |  |  |  |  |  |  |
| I |  |  |  |  |  |  |  |  |  |  |  |  |  |  |  | 1 |  |  |
| K |  |  |  |  |  |  |  |  |  |  |  |  |  |  |  |  |  |  |
| L |  | 6 |  |  |  | 2 |  |  | 1 |  | 6 |  |  |  |  |  |  |  |
| M |  |  |  |  |  |  |  |  |  |  |  |  |  |  |  | 5 |  |  |
| N |  |  |  |  |  |  |  |  |  |  |  |  | 2 |  |  |  |  |  |
| P |  |  |  |  |  |  |  |  |  |  |  |  |  |  |  |  |  |  |
| Q |  |  |  |  |  |  |  |  |  |  |  |  |  |  |  |  |  |  |
| R |  |  |  |  |  |  |  |  |  |  |  |  |  |  |  | 2 | 1 |  |
| S |  |  |  |  | 1 |  | 6 |  |  | 6 |  |  | 6 | 2 | 4 |  |  |  |
| T | 6 |  | 6 |  |  | 6 |  |  |  |  |  |  | 1 | 3 | 1 |  |  |  |
| V |  |  |  |  |  | 2 |  |  |  |  |  |  |  |  |  | 2 |  | 7 |

TABLE 6C-continued

Analysis of V heavy chain subgroup 2

| amino acid | | | | | | | | | | | | | | | | | | |
|---|---|---|---|---|---|---|---|---|---|---|---|---|---|---|---|---|---|---|
| W | | | | | | | | | | | | | | | | | | |
| X | | | | | | | | | | | | | | | | | | |
| Y | | | | | | 1 | | | | | | | | | | | | |
| Z | | | | | | | | | | | | | | | | | | |
| — | | | | | | | | | | | | | | | | | | |
| unknown (?) | | | | | | | | | | | | | | | | | | |
| not sequenced | 1 | 1 | 1 | | | | | | | | | | | | | | | |
| sum of seq[2] | 6 | 6 | 6 | 7 | 7 | 7 | 7 | 7 | 7 | 7 | 7 | 7 | 7 | 7 | 7 | 7 | 7 | 7 |
| oomcaa[3] | 6 | 6 | 6 | 7 | 6 | 3 | 6 | 7 | 6 | 6 | 6 | 6 | 3 | 4 | 4 | 5 | 3 | 7 |
| mcaa[4] | T | L | T | C | T | F | S | G | F | S | L | S | T | S | G | M | G | V |
| rel. oomcaa[5] | 100% | 100% | 100% | 100% | 86% | 43% | 86% | 100% | 86% | 86% | 86% | 86% | 43% | 57% | 57% | 71% | 43% | 100% |
| pos occupied[6] | 1 | 1 | 1 | 1 | 2 | 3 | 2 | 1 | 2 | 2 | 2 | 2 | 3 | 4 | 3 | 2 | 4 | 1 |

| | CDR I | | | Framework II | | | | | | | | | | | | CDR II | | |
|---|---|---|---|---|---|---|---|---|---|---|---|---|---|---|---|---|---|---|
| amino acid[1] | 35 | 36 | 37 | 38 | 39 | 40 | 41 | 42 | 43 | 44 | 45 | 46 | 47 | 48 | 49 | 50 | 51 | 52 |
| A | | | | | | | | | | 6 | | | | | 7 | | | |
| B | | | | | | | | | | | | | | | | | | |
| C | | | | | | | | | | | | | | | | | | |
| D | | | | | | | | | | | | | | | | | | 2 |
| E | | | | | | | | | | | | 7 | | | | | | |
| F | | | | | | | | | | | | | | | | | | 2 |
| G | 3 | | | | 1 | | 7 | | 1 | | | | | | | | | |
| H | | | | | | | | | | | | | | | | 2 | | |
| I | | | 7 | | | | | | | | | | | | | | 6 | |
| K | | | | | | | | | | 6 | | | | | | | | |
| L | | | | | | | | | | | 7 | | | 7 | | 2 | 1 | 1 |
| M | | | | | | | | | | | | | | | | | | |
| N | | | | | | | | | | | | | | | | | | |
| P | | | | | | 5 | 7 | | | | | | | | | | | |
| Q | | | | | | 6 | | | | | | | | | | | | |
| R | | | | 7 | 1 | | | | 1 | | | | | | | 2 | | |
| S | 4 | | | | 1 | | | | | | | | | | | | | |
| T | | | | | | | | | | | | | | | | | | |
| V | | | | | | | | | | | | | | | | | | |
| W | | 7 | | | | | | | | | | | 7 | | 1 | | | |
| X | | | | | | | | | | | | | | | | | | 1 |
| Y | | | | | | | | | | | | | | | | | | |
| Z | | | | | | | | | | | | | | | | | | 1 |
| — | | | | | | | | | | | | | | | | | | |
| unknown (?) | | | | | | | | | | | | | | | | | | |
| not sequenced | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 |
| oomcaa[3] | 4 | 7 | 7 | 7 | 6 | 5 | 7 | 7 | 6 | 6 | 7 | 7 | 7 | 7 | 7 | 2 | 6 | 2 |
| mcaa[4] | S | W | I | R | Q | P | P | G | K | A | L | E | W | L | A | H | I | D |
| rel. oomcaa[5] | 57% | 100% | 100% | 100% | 86% | 71% | 100% | 100% | 86% | 86% | 100% | 100% | 100% | 100% | 100% | 29% | 86% | 29% |
| pos occupied[6] | 2 | 1 | 1 | 1 | 2 | 3 | 1 | 1 | 2 | 2 | 1 | 1 | 1 | 1 | 1 | 4 | 2 | 5 |

| | CDR II | | | | | | | | | | | | | | | |
|---|---|---|---|---|---|---|---|---|---|---|---|---|---|---|---|---|
| amino acid[1] | A | B | C | 53 | 54 | 55 | 56 | 57 | 58 | 59 | 60 | 61 | 62 | 63 | 64 | 65 | 66 |
| A | | | | | | | | | | | | | | | | | |
| B | | | | | | | | | | | | | | | | | |
| C | | | | | | | | | | | | | | | | | |
| D | | | | 3 | 6 | 5 | | | | | | | | | | | |
| E | | | | | | 1 | | | | | | | | | 1 | | |
| F | | | | | | | 1 | | 1 | | | | | | | | |
| G | | | | | | | | | | | | | | | | | |
| H | | | | | | 1 | | | 1 | | | | | | | | |
| I | | | | | | | | | | | | | | | | | |
| K | | | | | | | 1 | 6 | | | | | | | 4 | | |
| L | | | | | | | | | | | | | | 7 | | | |
| M | | | | | | | | | | | | | | | | | |
| N | | | | | 3 | | | | | | | | | | | | |
| P | | | | | | | | | | | | 2 | | | | | |
| Q | | | | | | | | | | | | | | | | | |
| R | | | | | | | | | | | 2 | | 1 | | 2 | | 7 |
| S | | | | 2 | | | | | 2 | | | 6 | | 7 | | 4 | |
| T | | | | | | | | | | | | | 4 | | | 3 | |
| V | | | | | | | | | | | | | | | | | |
| W | | | | | 4 | | | | | 1 | | | | | | | |
| X | | | | | 1 | 1 | | | | | | 1 | | | | | |
| Y | 1 | | | | | | | | 3 | 4 | | | | | | | |
| Z | | | | | | | | | | | | | | | | | |
| — | 6 | 7 | 7 | | | | | | | | | | | | | | |

TABLE 6C-continued

Analysis of V heavy chain subgroup 2

| | | | | | | | | | | | | | | | | | |
|---|---|---|---|---|---|---|---|---|---|---|---|---|---|---|---|---|---|
| unknown (?) | | | | | | | | | | | | | | | | | |
| not sequenced | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 |
| oomcaa[3] | 6 | 7 | 7 | 4 | 3 | 6 | 5 | 6 | 3 | 4 | 6 | 4 | 7 | 7 | 4 | 4 | 7 |
| mcaa[4] | — | — | — | W | D | D | D | K | Y | Y | S | T | S | L | K | S | R |
| rel. oomcaa[5] | 86% | 100% | 100% | 57% | 43% | 86% | 71% | 86% | 43% | 57% | 86% | 57% | 100% | 100% | 57% | 57% | 100% |
| pos occupied[6] | 2 | 1 | 1 | 3 | 3 | 2 | 3 | 2 | 3 | 4 | 2 | 3 | 1 | 1 | 3 | 2 | 1 |

Framework III

| amino acid[1] | 67 | 68 | 69 | 70 | 71 | 72 | 73 | 74 | 75 | 76 | 77 | 78 | 79 | 80 | 81 | 82 | A | B |
|---|---|---|---|---|---|---|---|---|---|---|---|---|---|---|---|---|---|---|
| A | | | | | | | | | | | | | | | | | | |
| B | | | | | | | | | | | | | | | | | | |
| C | | | | | | | | | | | | | | | | | | |
| D | | | | | | 6 | 1 | | | | | | | | | | | |
| E | | | | | | | | | | | | | | | | | | |
| F | | | | | | | | | | | | | | 1 | | | | |
| G | | | | | | | | | | | | | | | | | | |
| H | | | | | | | | | | | | | | | | | | |
| I | | | 6 | | | | | | | | | | | | 2 | | 1 | |
| K | | | | | | 6 | | | | 6 | | | | | | | | |
| L | 7 | | | | | | | | | | | | | 6 | | | | |
| M | | | | | | | | | | | | | | | 7 | | | |
| N | | | | | | 1 | | | | 5 | | | | | | | | 6 |
| P | | | | | | | | | | | | | | | | | | |
| Q | | | | | | | | | | | | 7 | | | | | | |
| R | | | | | | 1 | | | | 1 | | | | | | | | |
| S | | 1 | | 5 | | | | 7 | | 2 | | | | | | | | |
| T | | 6 | | 2 | | | 6 | | | | | | | | 5 | | 5 | |
| V | | | 1 | | | | | | | | | 7 | 7 | | | | | |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | | | | | | | | | | | | | | 1 | | 1 |
| unknown (?) | | | | | | | | | | | | | | | | | | |
| not sequenced | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 |
| oomcaa[3] | 7 | 6 | 6 | 5 | 6 | 6 | 6 | 7 | 6 | 5 | 7 | 7 | 7 | 6 | 5 | 7 | 5 | 6 |
| mcaa[4] | L | T | I | S | K | D | T | S | K | N | Q | V | V | L | T | M | T | N |
| rel. oomcaa[5] | 100% | 86% | 86% | 71% | 86% | 86% | 86% | 100% | 86% | 71% | 100% | 100% | 100% | 86% | 71% | 100% | 71% | 86% |
| pos occupied[6] | 1 | 2 | 2 | 2 | 2 | 2 | 2 | 1 | 2 | 2 | 1 | 1 | 1 | 2 | 2 | 1 | 3 | 2 |

| | Framework III | | | | | | | | | | | CDR III | | | | | | |
|---|---|---|---|---|---|---|---|---|---|---|---|---|---|---|---|---|---|---|
| amino acid[1] | C | 83 | 84 | 85 | 86 | 87 | 88 | 89 | 90 | 91 | 92 | 93 | 94 | 95 | 96 | 97 | 98 | 99 |
| A | | | | 1 | | 5 | | | | | | 5 | | | | | | |
| B | | | | | | | | | | | | | | | | | | |
| C | | | | | | | | | | | | 7 | | | | | | |
| D | | 6 | | | 7 | | | | | | | | | | | | | |
| E | | | | | | | | | | | | | | | | | | |
| F | | | | | | | | | | | | | | | | | | |
| G | | | | | | | 2 | | | | | | | | | | 1 | 1 |
| H | | | | | | | | | | | | | 1 | | 1 | | | |
| I | | | | | | | | | | | | | | 3 | | | 2 | |
| K | | | | | | | | | | | | | | | | | | 1 |
| L | | | | | | | | | | | | | | | | | | |
| M | 5 | | | | | | | | | | | | | | | | | |
| N | | 1 | | | | | | | | | | | | | 1 | 2 | | |
| P | | | 7 | | | | | | | | | | | | 1 | 1 | | 1 |
| Q | | | | | | | | | | | | | | | 1 | | | |
| R | | | | | | | | | | | | 6 | 1 | | | | 1 | |
| S | | | | | | | | | | | | | | | 1 | | 1 | 1 |
| T | | | | | | | 7 | | 7 | | | | | | 1 | | 1 | 1 |
| V | 1 | | | 6 | | | | | | | | 2 | | 1 | 1 | 1 | | 1 |
| W | | | | | | | | | | | | | | | | 1 | | |
| X | | | | | | | | | | | | | | | | | | |
| Y | | | | | | | | | 7 | 7 | | | | | | | 2 | |
| Z | | | | | | | | | | | | | | | | | | |
| — | 1 | | | | | | | | | | | | | | | | | |
| unknown (?) | | | | | | | | | | | | | | | | | | |
| not sequenced | | | | | | | | | | | | | | 1 | 1 | 1 | 1 | 1 |
| sum of seq[2] | 7 | 7 | 7 | 7 | 7 | 7 | 7 | 7 | 7 | 7 | 7 | 7 | 7 | 6 | 6 | 6 | 6 | 6 |
| oomcaa[3] | 5 | 6 | 7 | 6 | 7 | 7 | 5 | 7 | 7 | 7 | 7 | 5 | 6 | 3 | 1 | 2 | 2 | 1 |
| mcaa[4] | M | D | P | V | D | T | A | T | Y | Y | C | A | R | I | H | N | I | G |

TABLE 6C-continued

Analysis of V heavy chain subgroup 2

| | | | | | | | | | | | | | | | | | | |
|---|---|---|---|---|---|---|---|---|---|---|---|---|---|---|---|---|---|---|
| rel. oomcaa[5] | 71% | 86% | 100% | 86% | 100% | 100% | 71% | 100% | 100% | 100% | 100% | 71% | 86% | 50% | 17% | 33% | 33% | 17% |
| pos occupied[6] | 3 | 2 | 1 | 2 | 1 | 1 | 2 | 1 | 1 | 1 | 1 | 2 | 2 | 4 | 6 | 4 | 5 | 6 |

| | CDR III | | | | | | | | | | | Framework IV | | | | | | |
|---|---|---|---|---|---|---|---|---|---|---|---|---|---|---|---|---|---|---|
| amino acid[1] | 100 | A | B | C | D | E | F | G | H | I | J | K | 101 | 102 | 103 | 104 | 105 | 106 |
| A | 1 | 2 | 1 | | | | | | | | | | | | | | | |
| B | | | | | | | | | | | | | | | | | | |
| C | | | | | | | | | | | | | | | | | | |
| D | | | | | | | | | | | | | | 6 | | | | |
| E | 2 | | | 1 | | | | | | | | | | | | | | |
| F | | | | | | | | | | | | | 3 | | | | | |
| G | | 1 | 2 | 1 | 1 | 1 | 1 | | | | | | | | | 6 | | 6 |
| H | | | | | | | | | | | | | | | | | | |
| I | | | | | | | | | | | | | | | | | | |
| K | | | | | | | | | | | | | | | | | 1 | |
| L | 1 | | 1 | | | | | | | | | 1 | | 1 | | | | |
| M | 1 | | | | | | | | | | | 2 | | | | | | |
| N | | | | | | | | 1 | | | | | | | | | | |
| P | | 1 | | | | | | | | | | | | 1 | | | | |
| Q | | | | | | | | | | | | | | | | | 3 | |
| R | | 1 | | | | | | | | | | | | | | | 2 | |
| S | | | | | | | | | | | | | | | | | | |
| T | | 1 | | | | | | | | | | | | | | | | |
| V | 1 | | 1 | | | | | | | | | | 3 | | | | | |
| W | | | | | | | 1 | | 1 | | | | | 6 | | | | |
| X | | | | | | | | | | | | | | | | | | |
| Y | | 1 | 2 | 1 | 1 | 1 | | | | 2 | | | 1 | | | | | |
| Z | | | | | | | | | | | | | | | | | | |
| — | | 2 | 2 | 3 | 4 | 4 | 4 | 6 | 5 | 3 | | | | | | | | |
| unknown (?) | | | | | | | | | | | | | | | | | | |
| not sequenced | 1 | 1 | 1 | 1 | 1 | 1 | 1 | 1 | 1 | 1 | 1 | 1 | 1 | 1 | 1 | 1 | 1 | 1 |
| sum of seq[2] | 6 | 6 | 6 | 6 | 6 | 6 | 6 | 6 | 6 | 6 | 6 | 6 | 6 | 6 | 6 | 6 | 6 | 6 |
| oomcaa[3] | 2 | 2 | 2 | 2 | 3 | 4 | 4 | 4 | 6 | 5 | 3 | 3 | 6 | 3 | 6 | 6 | 3 | 6 |
| mcaa[4] | E | A | — | — | — | — | — | — | — | — | — | F | D | V | W | G | Q | G |
| rel. oomcaa[5] | 33% | 33% | 33% | 33% | 50% | 67% | 67% | 67% | 100% | 83% | 50% | 50% | 100% | 50% | 100% | 100% | 50% | 100% |
| pos occupied[6] | 5 | 5 | 4 | 5 | 3 | 3 | 3 | 3 | 1 | 2 | 3 | 3 | 1 | 4 | 1 | 1 | 3 | 1 |

| | Framework IV | | | | | | | |
|---|---|---|---|---|---|---|---|---|
| amino acid[1] | 107 | 108 | 109 | 110 | 111 | 112 | 113 | sum |
| A | | | | 1 | | | | 35 |
| B | | | | | | | | |
| C | | | | | | | | 16 |
| D | | | | | | | | 43 |
| E | | | | | | | | 21 |
| F | | | | | | | | 18 |
| G | | | | | | | | 55 |
| H | | | | | | | | 6 |
| I | | | | | | | | 29 |
| K | | 1 | | | | | | 42 |
| L | | 3 | | | | | | 78 |
| M | | | | | | | | 20 |
| N | | | | | | | | 23 |
| P | | 1 | | | | | | 41 |
| Q | | | | | | | | 23 |
| R | | | | | | | | 41 |
| S | | | | | | 6 | 3 | 82 |
| T | 6 | 1 | | 5 | | | | 102 |
| V | | | 6 | | 6 | | | 68 |
| W | | | | | | | | 29 |
| X | | | | | | | | 4 |
| Y | | | | | | | | 35 |
| Z | | | | | | | | 3 |
| — | | | | | | | | 56 |
| unknown (?) | | | | | | | | |
| not sequenced | 1 | 1 | 1 | 1 | 1 | 1 | 4 | 54 |
| sum of seq[2] | 6 | 6 | 6 | 6 | 6 | 6 | 3 | |
| oomcaa[3] | 6 | 3 | 6 | 5 | 6 | 6 | 3 | |
| mcaa[4] | T | L | V | T | V | S | S | |
| rel. oomcaa[5] | 100% | 50% | 100% | 83% | 100% | 100% | 100% | |
| pos occupied[6] | 1 | 4 | 1 | 2 | 1 | 1 | 1 | |

TABLE 6D

Analysis of V heavy chain subgroup 3

Framework I

| amino acid[1] | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| A |  |  |  |  | 1 |  | 1 |  |  | 12 |  | 1 |  | 3 | 1 |  |  |  |
| B |  |  | 1 |  |  | 1 |  |  |  |  |  |  |  |  |  |  |  |  |
| C |  |  |  |  |  |  |  |  |  |  |  |  |  |  |  |  |  |  |
| D | 1 |  |  |  |  | 1 |  |  |  | 16 |  |  |  |  |  |  |  |  |
| E | 110 |  | 9 |  | 15 | 166 |  |  | 9 |  |  |  |  | 8 | 2 | 8 |  |  |
| F |  |  |  |  |  |  |  |  |  |  | 4 |  |  |  |  |  | 1 | 1 |
| G |  |  |  |  |  |  |  | 181 | 193 | 174 |  | 1 | 4 |  | 202 | 134 |  |  |
| H |  |  | 5 |  |  |  |  |  |  |  |  |  |  |  |  |  |  |  |
| I |  |  |  |  |  |  |  |  |  |  |  | 9 |  |  |  |  |  |  |
| K |  | 5 | 3 |  |  |  |  |  |  |  |  |  | 26 |  |  |  |  |  |
| L |  | 1 | 5 | 176 | 43 |  |  |  |  |  | 140 |  |  |  | 1 |  |  | 205 |
| M |  | 12 |  | 1 |  |  |  |  |  |  |  |  |  |  |  |  |  | 1 |
| N |  |  |  |  |  |  |  |  |  | 1 |  |  |  |  |  |  |  |  |
| P |  |  |  |  |  |  |  |  |  |  |  |  | 1 | 194 |  |  |  |  |
| Q | 41 |  | 138 | 1 | 3 | 12 |  |  |  |  |  |  | 162 |  |  |  |  | 1 |
| R |  |  | 6 |  |  |  |  |  |  |  |  |  | 4 |  |  | 62 |  |  |
| S |  |  |  |  |  |  | 178 |  |  | 2 |  |  | 8 |  |  |  | 206 |  |
| T |  |  |  |  |  |  | 1 |  |  |  |  |  |  |  |  | 4 | 1 |  |
| V | 5 | 147 |  | 1 | 118 |  |  |  |  |  | 62 | 195 |  |  |  |  |  |  |
| W |  |  |  |  |  |  |  |  |  |  |  |  |  | 1 |  |  |  |  |
| X |  |  |  |  |  |  |  |  |  |  |  |  |  |  |  |  |  |  |
| Y |  |  |  |  |  |  |  |  |  |  |  |  |  |  |  |  |  |  |
| Z | 8 |  |  |  |  |  |  |  |  |  |  |  |  |  |  |  |  |  |
| — |  |  |  |  |  |  |  |  |  |  |  |  |  |  |  |  |  |  |
| unknown (?) |  |  |  |  |  |  |  |  |  |  |  |  |  |  |  |  |  |  |
| not sequenced | 47 | 47 | 45 | 33 | 32 | 32 | 32 | 31 | 10 | 7 | 6 | 6 | 6 | 6 | 6 | 4 | 4 | 4 |
| sum of seq[2] | 165 | 165 | 167 | 179 | 180 | 180 | 180 | 181 | 202 | 205 | 206 | 206 | 206 | 206 | 206 | 208 | 208 | 208 |
| oomcaa[3] | 110 | 147 | 138 | 176 | 118 | 166 | 178 | 181 | 193 | 174 | 140 | 195 | 162 | 194 | 202 | 134 | 206 | 205 |
| mcaa[4] | E | V | Q | L | V | E | S | G | G | G | L | V | Q | P | G | G | S | L |
| rel. oomcaa[5] | 67% | 89% | 83% | 98% | 66% | 92% | 99% | 100% | 96% | 85% | 68% | 95% | 79% | 94% | 98% | 64% | 99% | 99% |
| pos occupied[6] | 5 | 4 | 7 | 4 | 5 | 4 | 3 | 1 | 2 | 5 | 3 | 4 | 7 | 4 | 4 | 4 | 3 | 4 |

Framework I / CDR I

| amino acid[1] | 19 | 20 | 21 | 22 | 23 | 24 | 25 | 26 | 27 | 28 | 29 | 30 | 31 | A | B | 32 | 33 | 34 |
|---|---|---|---|---|---|---|---|---|---|---|---|---|---|---|---|---|---|---|
| A |  |  |  |  | 183 | 192 |  | 1 |  |  |  |  | 1 |  |  | 17 | 80 |  |
| B |  |  |  |  |  |  |  |  |  |  |  |  |  |  |  |  |  |  |
| C |  |  | 1 | 209 |  |  |  |  |  |  |  |  |  |  |  |  |  |  |
| D |  |  |  |  |  |  |  |  |  |  |  | 7 | 26 |  |  | 3 | 7 |  |
| E |  |  |  |  | 8 |  |  | 3 |  | 1 |  |  | 1 |  |  | 5 | 10 |  |
| F |  |  | 1 |  |  |  |  |  | 201 |  | 201 |  |  |  |  | 5 | 31 |  |
| G |  |  |  |  | 2 |  |  | 207 |  |  |  | 3 | 13 |  |  |  | 4 |  |
| H |  |  |  |  |  |  |  |  |  |  |  | 1 |  |  |  | 4 |  |  |
| I |  |  |  |  |  | 2 |  |  | 3 | 17 | 1 |  | 1 | 1 |  |  |  | 15 |
| K | 15 |  |  |  |  |  |  |  |  |  |  | 4 | 7 |  |  |  |  |  |
| L |  | 201 |  |  |  |  |  |  | 6 |  | 3 |  | 3 |  |  |  |  | 3 |
| M |  |  |  |  |  |  |  |  |  | 1 |  |  |  |  |  |  |  | 193 |
| N |  |  |  |  |  |  |  |  |  | 10 |  | 10 | 35 |  |  | 8 | 3 |  |
| P |  |  |  |  | 1 |  |  |  |  | 2 |  |  | 1 |  |  |  |  |  |
| Q |  |  |  |  |  |  |  |  |  |  |  |  |  |  |  |  |  |  |
| R | 191 |  |  |  |  |  |  |  |  |  |  | 11 | 7 |  |  |  |  |  |
| S |  |  | 207 |  | 4 | 2 | 209 |  |  | 15 |  | 174 | 103 |  |  | 17 | 8 |  |
| T | 2 |  |  |  | 4 | 4 |  |  | 1 | 163 |  |  | 9 |  |  |  | 15 |  |
| V |  | 8 |  |  | 7 | 9 |  |  |  | 1 | 6 |  | 2 |  |  |  | 7 | 1 |
| W |  |  |  |  |  |  |  |  |  |  |  |  |  |  |  |  | 30 |  |
| X |  |  |  |  |  |  |  |  |  |  |  |  | 1 |  |  |  |  |  |
| Y |  |  |  |  |  |  |  |  |  |  |  |  | 1 |  |  | 154 | 19 |  |
| Z |  |  |  |  |  |  |  |  |  |  |  |  |  |  |  |  |  |  |
| — |  |  |  |  |  |  |  |  |  |  |  |  |  | 210 | 210 |  |  |  |
| unknown (?) |  |  |  |  |  |  |  |  |  |  |  |  |  |  |  |  |  |  |
| not sequenced | 4 | 3 | 3 | 3 | 3 | 3 | 3 | 1 | 1 | 2 | 1 | 2 | 2 |  |  | 2 | 2 |  |
| sum of seq[2] | 208 | 209 | 209 | 209 | 209 | 209 | 209 | 211 | 211 | 210 | 211 | 210 | 210 | 210 | 210 | 210 | 210 | 212 |
| oomcaa[3] | 191 | 201 | 207 | 209 | 183 | 192 | 209 | 207 | 201 | 163 | 201 | 174 | 103 | 210 | 210 | 154 | 80 | 193 |
| mcaa[4] | R | L | S | C | A | A | S | G | F | T | F | S | S | — | — | Y | A | M |
| rel. oomcaa[5] | 92% | 96% | 99% | 100% | 88% | 92% | 100% | 98% | 95% | 78% | 95% | 83% | 49% | 100% | 100% | 73% | 38% | 91% |
| pos occupied[6] | 3 | 2 | 3 | 1 | 7 | 5 | 1 | 3 | 4 | 8 | 4 | 7 | 14 | 1 | 1 | 9 | 10 | 4 |

TABLE 6D-continued

Analysis of V heavy chain subgroup 3

| | CDR I | | Framework II | | | | | | | | | | | | | CDR II | | |
|---|---|---|---|---|---|---|---|---|---|---|---|---|---|---|---|---|---|---|
| amino acid[1] | 35 | 36 | 37 | 38 | 39 | 40 | 41 | 42 | 43 | 44 | 45 | 46 | 47 | 48 | 49 | 50 | 51 | 52 |
| A | 1 | | | 1 | | 187 | | 1 | | 1 | | | | | 77 | 42 | | 1 |
| B | | | | | | | | | | | | | 3 | | | | | |
| C | | | | | | 1 | | 1 | | | | | | | | | | |
| D | 2 | | | | | | | | | | | 1 | | | | | | |
| E | | | | | | | 1 | 1 | | | | 198 | | | | | | 3 |
| F | | | | | | | | | | | | | | | | 7 | 1 | 2 |
| G | 1 | | | | | 2 | | 209 | | 207 | | | | | 33 | 11 | | 10 |
| H | 88 | | | | | | | | | | | | | | | 6 | | |
| I | | | | 12 | | | | | | | | | | 3 | | 3 | 191 | |
| K | | | | | 1 | | | | 202 | | | | | | | | 1 | 37 |
| L | | | 2 | 3 | 1 | 2 | 1 | | | | 211 | | | 5 | | 12 | 1 | |
| M | | | | | | | | | | | | | | | | 1 | 1 | |
| N | 34 | | | | | | | | | | | | | | | 13 | | 7 |
| P | 1 | | | | | 4 | 191 | | | | | 1 | | | | | | |
| Q | | | | | 209 | | 1 | | 1 | | | | 7 | | | 7 | | |
| R | | | 207 | | | 7 | | 8 | | 1 | | | | | | 24 | 1 | 17 |
| S | 72 | | | | | 3 | 14 | | | 3 | | | 1 | | 102 | 11 | 9 | 118 |
| T | 10 | | | | | 4 | 5 | | | | | | | 204 | | 3 | 5 | 4 |
| V | | | 197 | | | 2 | | | | | | | 3 | | | 49 | 2 | |
| W | | 212 | | | | | | | | | | | 210 | | | 1 | | 8 |
| X | | | | | | | | | | | | | | | | | | |
| Y | 3 | | | | | | | | | | | | | | 1 | 22 | | 5 |
| Z | | | | | | | | | | | | | | | | | | |
| — | | | | | | | | | | | | | | | | | | |
| unknown (?) | | | | | | | | | | | | | | | | | | |
| not sequenced | | | 1 | 1 | 1 | | | | | | | | | | | | | |
| sum of seq[2] | 212 | 212 | 211 | 211 | 211 | 212 | 212 | 212 | 212 | 212 | 212 | 212 | 212 | 212 | 212 | 212 | 212 | 212 |
| oomcaa[3] | 88 | 212 | 197 | 207 | 209 | 187 | 191 | 209 | 202 | 207 | 211 | 198 | 210 | 204 | 102 | 49 | 191 | 118 |
| mcaa[4] | H | W | V | R | Q | A | P | G | K | G | L | E | W | V | S | V | I | S |
| rel. oomcaa[5] | 42% | 100% | 93% | 98% | 99% | 88% | 90% | 99% | 95% | 98% | 100% | 93% | 99% | 96% | 48% | 23% | 90% | 56% |
| pos occupied[6] | 9 | 1 | 3 | 3 | 3 | 9 | 5 | 4 | 4 | 4 | 2 | 5 | 3 | 3 | 3 | 15 | 9 | 11 |

| | CDR II | | | | | | | | | | | | | | | | |
|---|---|---|---|---|---|---|---|---|---|---|---|---|---|---|---|---|---|
| amino acid[1] | A | B | C | 53 | 54 | 55 | 56 | 57 | 58 | 59 | 60 | 61 | 62 | 63 | 64 | 65 | 66 |
| A | 2 | | 14 | | 7 | | 9 | 1 | 2 | | 174 | 33 | | | | | |
| B | 1 | | | | | | 1 | 2 | | | | | | | | | |
| C | | | | 1 | | | | | | | | | | | | | |
| D | 7 | | | 94 | 8 | 3 | 11 | | 17 | | | 160 | | | | | |
| E | 2 | 1 | | 2 | | 1 | 8 | 3 | 2 | | | 1 | | | 2 | | |
| F | 1 | | | | 1 | 8 | 1 | | 3 | 2 | | | | | | | |
| G | 46 | | | 4 | 163 | 85 | 5 | 1 | 5 | | 4 | 5 | | | | 212 | 1 |
| H | 1 | | | | | | 1 | | 4 | | | | | | | | |
| I | 1 | | | | | 1 | 3 | 37 | 2 | | | | | 8 | | | |
| K | 2 | 30 | | 3 | 1 | | 1 | 61 | | | | | | | 199 | | 8 |
| L | | | | | | | 1 | 1 | 1 | | 1 | | | | | | |
| M | | | | | | | 8 | | 2 | | 1 | | | | | | |
| N | 9 | 2 | | 13 | 11 | 1 | 51 | | 4 | | | 2 | | | 2 | | |
| P | 1 | | | 1 | | | 1 | 1 | | | 6 | 8 | 18 | | 1 | | |
| Q | 10 | | | | | | 3 | 2 | | | | | | | 2 | | 2 |
| R | 5 | 1 | | 2 | | 16 | 5 | 4 | | | 5 | | | | 6 | | 201 |
| S | 43 | | 1 | 74 | 17 | 82 | 48 | | 11 | | 4 | | 193 | | | | |
| T | 2 | | 13 | 12 | 3 | 3 | 42 | 97 | 5 | | 7 | | | 204 | | | |
| V | 1 | | 6 | | | | | | 2 | | 10 | 2 | | 204 | | | |
| W | 6 | | | | | | | | 2 | | | | | | | | |
| X | | | | | 4 | | 3 | 4 | | | | 1 | | | | | |
| Y | 58 | | | | | | 8 | 9 | 151 | 210 | | | 1 | | | | |
| Z | | | | | | | | | | | | | | | | | |
| — | | 14 | 178 | 178 | 2 | 1 | 1 | | | | | | | | | | |
| unknown (?) | | | | | | | | | | | | | | | | | |
| not sequenced | | | | | | | | | | | | | | | | | |
| sum of seq[2] | 212 | 212 | 212 | 212 | 212 | 212 | 212 | 212 | 212 | 212 | 212 | 212 | 212 | 212 | 212 | 212 | 212 |
| oomcaa[3] | 58 | 178 | 178 | 94 | 163 | 85 | 51 | 97 | 151 | 210 | 174 | 160 | 193 | 204 | 199 | 212 | 201 |
| mcaa[4] | Y | — | — | D | G | G | N | T | Y | Y | A | D | S | V | K | G | R |
| rel. oomcaa[5] | 27% | 84% | 84% | 44% | 77% | 40% | 24% | 46% | 71% | 99% | 82% | 75% | 91% | 96% | 94% | 100% | 95% |
| pos occupied[6] | 19 | 5 | 5 | 12 | 9 | 12 | 19 | 12 | 15 | 2 | 9 | 8 | 3 | 2 | 6 | 1 | 4 |

TABLE 6D-continued

Analysis of V heavy chain subgroup 3

| | Framework III | | | | | | | | | | | | | | | | | |
|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | A | B |
| A | | 1 | | | | | | 57 | | | 1 | 8 | | | | | | 1 |
| B | | | | | | | | | | | | | | | 2 | | | |
| C | | | | | | | | | | | | | | | | | | |
| D | | | | | | 199 | 38 | | 2 | 2 | | | 1 | | | | 10 | |
| E | | | | | | 6 | | | 4 | | | | | | 5 | | | |
| F | 207 | | | | | | | | | | | | 13 | | | | | |
| G | | | | | | | | | | | | | | | | | 1 | 4 |
| H | | | | | | | | | 1 | | | | 1 | | 2 | | 2 | |
| I | | 14 | 208 | | | | 1 | | | | 2 | 2 | | | | 3 | 1 | 1 |
| K | | | | | | | | | 186 | 6 | | | | | | | 3 | |
| L | 1 | | 1 | | | | | | | | | 188 | | 209 | | | 3 | 1 |
| M | | | | | 1 | | | | 2 | | 10 | 3 | | 2 | | 205 | | |
| N | | | | | | 5 | 170 | | 2 | 188 | | | | | 3 | | 181 | 10 |
| P | | | | | | | | | | | 1 | | | | | | | |
| Q | | | | | | | | | 7 | | | | | | 199 | | | |
| R | | | | | | | 211 | | 1 | 1 | | | | | | | 2 | 8 |
| S | 2 | 7 | | 211 | | | | 153 | 8 | 10 | 56 | | 3 | | 1 | | 6 | 186 |
| T | | 189 | | 1 | | | | | | | 142 | | | | 1 | | 4 | 2 |
| V | 1 | | 3 | | | | | 1 | | | | 11 | | 1 | | 1 | | |
| W | | | | | | | | | | | | | | | | | | |
| X | | | | | | 2 | 2 | | | 4 | | | | | | | 1 | |
| Y | 1 | 1 | | | | | | | | | | | 194 | | | | | |
| Z | | | | | | | | | | | | | | | | | | |
| — | | | | | | | | | | | | | | | | | | |
| unknown (?) | | | | | | | | | | | | | | | | | | |
| not sequenced | | | | | | | 1 | 1 | | | | | | | | | | |
| sum of seq[2] | 212 | 212 | 212 | 212 | 212 | 212 | 212 | 212 | 212 | 212 | 212 | 212 | 212 | 212 | 212 | 212 | 212 | 212 |
| oomcaa[3] | 207 | 189 | 208 | 211 | 211 | 199 | 170 | 153 | 186 | 188 | 142 | 188 | 194 | 209 | 199 | 205 | 181 | 186 |
| mcaa[4] | F | T | I | S | R | D | N | S | K | N | T | L | Y | L | Q | M | N | S |
| rel. oomcaa[5] | 98% | 89% | 98% | 100% | 100% | 94% | 81% | 73% | 88% | 89% | 67% | 89% | 92% | 99% | 94% | 97% | 85% | 88% |
| pos occupied[6] | 5 | 5 | 3 | 2 | 2 | 4 | 4 | 3 | 8 | 7 | 6 | 5 | 5 | 3 | 6 | 4 | 11 | 7 |

| | Framework III | | | | | | | | | | CDR III | | | | | | | |
|---|---|---|---|---|---|---|---|---|---|---|---|---|---|---|---|---|---|---|
| amino acid[1] | C | 83 | 84 | 85 | 86 | 87 | 88 | 89 | 90 | 91 | 92 | 93 | 94 | 95 | 96 | 97 | 98 | 99 |
| A | | | 149 | 1 | | 1 | 207 | | | | | 173 | 2 | 15 | 9 | 11 | 7 | 13 |
| B | | | | | | | | | | | | | | | | | | |
| C | | | | | | | | | | 1 | 210 | | 5 | 2 | | 1 | 13 | 5 |
| D | | | 5 | 15 | 209 | | | | | | | 2 | 54 | 7 | 6 | 11 | 7 |
| E | | 1 | | 190 | | | | | | | | | 11 | 2 | 11 | 6 | 3 |
| F | | | | | | | | 1 | | 15 | | 1 | | 9 | 6 | 3 | 5 |
| G | | 1 | 1 | 6 | | | 4 | 1 | | | | 2 | 8 | 34 | 26 | 35 | 34 | 17 |
| H | | | 1 | | | | | | | 1 | | | | 3 | 11 | 3 | 4 |
| I | | | 8 | | | | | 2 | | | | | 4 | 15 | 10 | 6 | 11 |
| K | | 30 | | | | | | | | | | 60 | 4 | 3 | 5 | 2 | 11 |
| L | 212 | | | | | | | 18 | | | | 1 | 6 | 11 | 7 | 26 | 13 |
| M | | | | | | | 2 | 1 | | | | | | 6 | 1 | | 1 |
| N | | | 1 | | 1 | | | | | | | 2 | 20 | 4 | 3 | 4 | 6 |
| P | | | 9 | | | | | | | | | 1 | 3 | 4 | 29 | 10 | 6 | 5 |
| Q | | | | | 1 | | | | | | | | 5 | 3 | 9 | 2 | 4 |
| R | | 177 | | | | | | | | | | 103 | 9 | 30 | 19 | 4 | 10 |
| S | | | 1 | | 1 | | | | | | | 3 | 9 | 8 | 11 | 16 | 28 |
| T | | 3 | 28 | | | 207 | | 1 | | | | 25 | 15 | 7 | 6 | 20 | 6 | 12 |
| V | | | 9 | | | | | 187 | | | | 10 | 1 | 7 | 7 | 15 | 13 | 7 |
| W | | | | | | | | | | | 1 | | 3 | 4 | 3 | 6 | 5 |
| X | | | | | 1 | | | | | | | | | | | | |
| Y | | | | | | | | | 211 | 194 | | | 12 | 9 | 8 | 16 | 14 |
| Z | | | | | | | | | | | | | | | | | | |
| — | | | | | | | | | | | | | 1 | 3 | 4 | 12 | 21 |
| unknown (?) | | | | | | | | | | | | | | | | | | |
| not sequenced | | | | | | 1 | 1 | 1 | 1 | 1 | 1 | 1 | 1 | 7 | 12 | 13 | 14 | 14 |
| sum of seq[2] | 212 | 212 | 211 | 211 | 211 | 211 | 211 | 211 | 211 | 211 | 211 | 211 | 211 | 205 | 200 | 199 | 198 | 198 |
| oomcaa[3] | 212 | 177 | 149 | 190 | 209 | 207 | 207 | 187 | 211 | 194 | 210 | 173 | 103 | 54 | 30 | 35 | 34 | 28 |
| mcaa[4] | L | R | A | E | D | T | A | V | Y | Y | C | A | R | D | R | G | G | S |
| rel. oomcaa[5] | 100% | 83% | 70% | 90% | 99% | 98% | 98% | 89% | 100% | 92% | 100% | 82% | 49% | 26% | 15% | 18% | 17% | 14% |
| pos occupied[6] | 1 | 5 | 10 | 4 | 4 | 4 | 2 | 7 | 1 | 4 | 2 | 5 | 14 | 18 | 20 | 21 | 20 | 20 |

TABLE 6D-continued

Analysis of V heavy chain subgroup 3

| | CDR III | | | | | | | | | | | | Framework IV | | | | | |
|---|---|---|---|---|---|---|---|---|---|---|---|---|---|---|---|---|---|---|
| amino acid[1] | 100 | A | B | C | D | E | F | G | H | I | J | K | 101 | 102 | 103 | 104 | 105 | 106 |
| A | 7 | 9 | 6 | 2 | 3 | 5 | 5 | | 9 | | 13 | | 2 | 1 | | 1 | | |
| B | | | | | | | | | | | | | | | | | 1 | |
| C | | 1 | 2 | 11 | 3 | | 2 | | | | | 1 | | | | | | |
| D | 10 | 4 | 2 | 3 | 10 | 3 | 3 | 1 | | 3 | 2 | | 146 | 2 | | | | |
| E | 1 | 13 | | 1 | 1 | | | | | | | | 1 | | | | | 1 |
| F | 4 | 5 | 5 | 6 | 3 | 5 | 7 | 2 | | 1 | 1 | 65 | 1 | 2 | | | | |
| G | 35 | 17 | 14 | 23 | 10 | 5 | 1 | 5 | 3 | 2 | 32 | | 6 | | | 140 | | 130 |
| H | 3 | 2 | 9 | 2 | | 1 | 3 | 1 | 2 | 8 | 1 | | | 4 | | | | |
| I | 4 | 4 | 3 | 1 | 3 | 10 | 3 | 3 | 2 | | 1 | 2 | | 15 | | | | |
| K | | | 3 | 1 | | | | | | | | | | | | | 13 | |
| L | 4 | 12 | 8 | 2 | 6 | 3 | 10 | 3 | | | | 2 | 1 | 10 | | | 1 | |
| M | 2 | | | | | | | | 1 | | | 32 | | | | | | |
| N | 4 | 3 | 2 | 2 | 6 | | | | 2 | 5 | | | 2 | 1 | | | | |
| P | 5 | 6 | 9 | 8 | 2 | 3 | 2 | 1 | | 3 | | 9 | | 17 | | | | |
| Q | 1 | 1 | 1 | 1 | 1 | | | | | 1 | | | | | | | 111 | |
| R | 9 | 7 | 5 | 5 | 2 | 3 | 1 | | 1 | | 2 | | 4 | | | | 8 | |
| S | 27 | 25 | 24 | 8 | 11 | 9 | 3 | | 2 | 3 | 1 | 1 | 1 | 7 | 1 | | | |
| T | 9 | 17 | 17 | 1 | 2 | 5 | 1 | 9 | 3 | 1 | | | | | | | | |
| V | 15 | 4 | 3 | 6 | 2 | 12 | | | 1 | 1 | 1 | | | 34 | | 1 | | |
| W | 6 | 7 | 2 | 4 | | | | 1 | | 6 | 10 | | | | 158 | | | |
| X | | 1 | | | | | | | | | | | 1 | | | | | |
| Y | 17 | 5 | 8 | 18 | 20 | 13 | 20 | 25 | 28 | 32 | 28 | | | 82 | | | | |
| Z | | | | | | | | | | | | | | | | | | |
| — | 35 | 54 | 73 | 87 | 102 | 110 | 126 | 135 | 134 | 120 | 91 | 71 | 21 | 9 | 2 | 2 | 2 | 2 |
| unknown (?) | | | | | 3 | 2 | 1 | 1 | | | 3 | 2 | | | | | | |
| not sequenced | 14 | 14 | 15 | 19 | 21 | 22 | 23 | 23 | 23 | 25 | 25 | 26 | 25 | 27 | 50 | 67 | 75 | 78 |
| sum of seq[2] | 198 | 197 | 196 | 192 | 190 | 189 | 188 | 188 | 188 | 186 | 186 | 185 | 186 | 184 | 161 | 144 | 136 | 133 |
| oomcaa[3] | 35 | 54 | 73 | 87 | 102 | 110 | 126 | 135 | 134 | 120 | 91 | 71 | 146 | 82 | 158 | 140 | 111 | 130 |
| mcaa[4] | G | — | — | — | — | — | — | — | — | — | — | — | D | Y | W | G | Q | G |
| rel. oomcaa[5] | 18% | 27% | 37% | 45% | 54% | 58% | 67% | 72% | 71% | 65% | 49% | 38% | 78% | 45% | 98% | 97% | 82% | 98% |
| pos occupied[6] | 19 | 20 | 19 | 20 | 17 | 14 | 14 | 12 | 12 | 13 | 12 | 8 | 11 | 12 | 3 | 4 | 6 | 3 |

| | Framework IV | | | | | | | |
|---|---|---|---|---|---|---|---|---|
| amino acid[1] | 107 | 108 | 109 | 110 | 111 | 112 | 113 | sum |
| A | 2 | | | | | | | 1767 |
| B | | | | | | | | 13 |
| C | | | | | | | | 470 |
| D | | | | | | | | 1121 |
| E | | | | | | | | 832 |
| F | | | | | | | | 807 |
| G | | | 1 | | | | | 2743 |
| H | | | | | | | | 179 |
| I | | | | | 1 | 1 | | 651 |
| K | | | | | | | | 933 |
| L | | 91 | | | | | 2 | 1881 |
| M | | 6 | | | | | | 496 |
| N | 1 | | | | | | | 844 |
| P | 1 | 1 | | | | | | 568 |
| Q | | | | | | | | 949 |
| R | | | | | | | | 1413 |
| S | | | | | | 118 | 110 | 3009 |
| T | 123 | 27 | | 122 | | | 1 | 1426 |
| V | 1 | | 125 | | 119 | | | 1851 |
| W | | | | | | | | 686 |
| X | | | | | | | | 26 |
| Y | | | | | | | | 1598 |
| Z | | | | | | | | 8 |
| — | 2 | 2 | 2 | 2 | 2 | 1 | 1 | 2023 |
| unknown (?) | | | | | | | | 12 |
| not sequenced | 81 | 83 | 84 | 86 | 89 | 92 | 97 | 1650 |
| sum of seq[2] | 130 | 128 | 127 | 125 | 122 | 119 | 114 | |
| oomcaa[3] | 123 | 91 | 125 | 122 | 119 | 118 | 110 | |
| mcaa[4] | T | L | V | T | V | S | S | |
| rel. oomcaa[5] | 95% | 71% | 98% | 98% | 98% | 99% | 96% | |
| pos occupied[6] | 6 | 6 | 2 | 3 | 3 | 2 | 4 | |

TABLE 6E

Analysis of V heavy chain subgroup 4

Framework I

| amino acid[1] | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| A | | | | | | | | | 19 | | | | | 1 | | | 1 | |
| B | | | | | | | | | | | | | | | | | | |
| C | | | | | | | | | | | | | | | | | | |
| D | | | | | | | | | | | | | | | | | | |
| E | | | | | | 32 | | | | | | | | | | 44 | | |
| F | | | | | | | | | | | | | | | | | | |
| G | | | | | | | | | 54 | 1 | 53 | | | | | 2 | | |
| H | | | | 4 | | 2 | | | | | | | | | | | | |
| I | | | | | | | | | | | | | | | | | | |
| K | | | | | | | | | | | | | 1 | 54 | | | | |
| L | | 7 | | 54 | | | | | | | | 53 | 19 | | 1 | | | 53 |
| M | | | | | | | | | | | | | | | | | | |
| N | | | | | | | | | | | | | | | | | | |
| P | | | | | | | | | 33 | | | | | 51 | 1 | | | |
| Q | 52 | | 50 | | 51 | 20 | | | | | | | | | | 7 | | |
| R | 1 | | | | | | | | | | | | | | | | | |
| S | | | | | | | 33 | | | | | | | | 52 | | | |
| T | | | | | | | | | 1 | | | | | | | | 52 | |
| V | | 47 | | | 1 | | | | | | | 34 | | | | | | |
| W | | | | | | 20 | | | | | | | | | | | | |
| X | | | | | | | | | | | | | | | | | | |
| Y | | | | | | | | | | | | | | | | | | |
| Z | 1 | | | | | | | | | | | | | | | | | |
| — | | | | | | | | | | | | | | | | | | |
| unknown (?) | | | | | | | | | | | | | | | | | | |
| not sequenced | 3 | 3 | 3 | 3 | 4 | 4 | 4 | 3 | 3 | 4 | 4 | 3 | 3 | 4 | 4 | 4 | 4 | 4 |
| sum of seq[2] | 54 | 54 | 54 | 54 | 53 | 53 | 53 | 54 | 54 | 53 | 53 | 54 | 54 | 53 | 53 | 53 | 53 | 53 |
| oomcaa[3] | 52 | 47 | 50 | 54 | 51 | 32 | 33 | 54 | 33 | 53 | 53 | 34 | 54 | 51 | 52 | 44 | 52 | 53 |
| mcaa[4] | Q | V | Q | L | Q | E | S | G | P | G | L | V | K | P | S | E | T | L |
| rel. oomcaa[5] | 96% | 87% | 93% | 100% | 96% | 60% | 62% | 100% | 61% | 100% | 100% | 63% | 100% | 96% | 98% | 83% | 98% | 100% |
| pos occupied[6] | 3 | 2 | 2 | 1 | 2 | 3 | 2 | 1 | 4 | 1 | 1 | 3 | 1 | 3 | 2 | 3 | 2 | 1 |

| | Framework I | | | | | | | | | | | | CDR I | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | 28 | 29 | 30 | 31 | A | B | 32 | 33 | 34 |
| A | 1 | | | 22 | | | | | | | | | | | | 1 | | |
| B | | | | | | | | | | | | | | | | | | |
| C | | | 53 | | | | | | | | | | | | | | 1 | |
| D | | | | 1 | | | | | | | | | 4 | 1 | 1 | 1 | | |
| E | | | | | | | | | | | | | | | | | | |
| F | | | | | 1 | | | | | 22 | | | | | | 1 | 1 | |
| G | | | | | | | 53 | 53 | | | | | 21 | 3 | 4 | | | |
| H | | | | | | | | 1 | | | | | | | | 2 | | |
| I | | | | 1 | | | | | 1 | 32 | | | | | | | | |
| K | 1 | | | | | | | | | | | | | | | | | |
| L | | 50 | | | | | | | | | | | | | | | | |
| M | | | | | | | | | | | | | | | | | | |
| N | | | | | | | | | | | 3 | | 1 | 1 | | 2 | 2 | |
| P | | 2 | | | | | | | | 3 | | | | 1 | | | | |
| Q | | | | | | | | | | | | | | | | | | |
| R | | | | | | | 1 | | | | | 3 | 2 | | 1 | | | |
| S | 52 | | | | 2 | | 35 | | | 51 | 1 | 52 | 25 | 5 | 9 | 1 | | |
| T | | | 53 | | 29 | | | | | | | | 2 | 1 | | | | |
| V | | 1 | | | | 55 | | 1 | | | 1 | | | | | | | |
| W | | | | | | | | | | | | | 1 | | | | 2 | 56 |
| X | | | | | | | | | | | | | | | | | | |
| Y | | | | | | | 19 | | 1 | | | | | | | 48 | 52 | |
| Z | | | | | | | | | | | | | | | | | | |
| — | | | | | | | | | | | | | 45 | 39 | | | | |
| unknown (?) | | | | | | | | | | | | | | | | | | |
| not sequenced | 3 | 4 | 4 | 4 | 2 | 2 | 2 | 2 | 2 | 2 | 1 | 1 | 1 | | | 1 | 1 | 1 |
| sum of seq[2] | 54 | 53 | 53 | 53 | 55 | 55 | 55 | 55 | 55 | 55 | 56 | 56 | 56 | 56 | 56 | 56 | 56 | 56 |
| oomcaa[3] | 52 | 50 | 53 | 53 | 29 | 55 | 35 | 53 | 53 | 51 | 32 | 52 | 25 | 45 | 39 | 48 | 52 | 56 |
| mcaa[4] | S | L | T | C | T | V | S | G | G | S | I | S | S | — | — | Y | Y | W |
| rel. oomcaa[5] | 96% | 94% | 100% | 100% | 53% | 100% | 64% | 96% | 96% | 93% | 57% | 93% | 45% | 80% | 70% | 86% | 93% | 100% |
| pos occupied[6] | 3 | 3 | 1 | 1 | 5 | 1 | 3 | 3 | 3 | 3 | 4 | 3 | 7 | 6 | 6 | 7 | 4 | 1 |

TABLE 6E-continued

Analysis of V heavy chain subgroup 4

| | CDR I | | Framework II | | | | | | | | | | | | | | CDR II | |
|---|---|---|---|---|---|---|---|---|---|---|---|---|---|---|---|---|---|---|
| amino acid[1] | 35 | 36 | 37 | 38 | 39 | 40 | 41 | 42 | 43 | 44 | 45 | 46 | 47 | 48 | 49 | 50 | 51 | 52 |
| A | | | | | | | 8 | 1 | | | | | | | | 1 | | |
| B | | | | | | | | | | | | | | | | | | |
| C | | | | | | | | | | | | | | | | | | |
| D | 1 | | | | | | | | | | | | | | | | | 1 |
| E | | | | | | | | 1 | | | | 56 | | | | 22 | | |
| F | | | 1 | | | | | | | | | | | | | 1 | | 1 |
| G | 8 | | | | | | | 55 | | 55 | | | | | 56 | 1 | | |
| H | | | | | | 2 | | | | | | | | | | | | |
| I | | | | 51 | | | | | | | | | | 54 | | | 1 | 54 |
| K | | | | | | | | | 54 | | | | | | | | | |
| L | | | | 1 | | 1 | | | | | 55 | | | 2 | | | | |
| M | | | | | | | | | | | | | | | | | | |
| N | 1 | | | | | | | | | | | | | | | | | 21 |
| P | | | | | | 50 | 49 | | | | | 2 | | | | | | |
| Q | | | | | 56 | | | | | | | | 1 | | | 1 | | |
| R | | | | 57 | | | | | 3 | 2 | | | | | | 9 | | 1 |
| S | 44 | | 1 | | | 3 | | | | | | | | | | 7 | | 1 |
| T | 3 | | | | 1 | 1 | | | | | | | | | | | | |
| V | | | 3 | | | | | | | | | | | 1 | | | 3 | |
| W | | 57 | | | | | | | | | | | 56 | | | | | |
| X | | | | | | | | | | | | | | | | | | |
| Y | | | | | | | | | | | | | | 1 | | 15 | | 32 |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 57 | 57 | 57 | 57 | 57 | 57 | 57 | 57 | 57 | 57 | 57 | 57 | 57 | 57 | 57 | 57 | 57 | 57 |
| oomcaa[3] | 44 | 57 | 51 | 57 | 56 | 50 | 49 | 55 | 54 | 55 | 55 | 56 | 56 | 54 | 56 | 22 | 54 | 32 |
| mcaa[4] | S | W | I | R | Q | P | P | G | K | G | L | E | W | I | G | E | I | Y |
| rel. oomcaa[5] | 77% | 100% | 89% | 100% | 98% | 88% | 86% | 96% | 95% | 96% | 96% | 98% | 98% | 95% | 98% | 39% | 95% | 56% |
| pos occupied[6] | 5 | 1 | 5 | 1 | 2 | 5 | 2 | 3 | 2 | 2 | 2 | 2 | 2 | 3 | 2 | 8 | 2 | 6 |

| | CDR II | | | | | | | | | | | | | | | | |
|---|---|---|---|---|---|---|---|---|---|---|---|---|---|---|---|---|---|
| amino acid[1] | A | B | C | 53 | 54 | 55 | 56 | 57 | 58 | 59 | 60 | 61 | 62 | 63 | 64 | 65 | 66 |
| A | | | | | | | | | 1 | | | | | | | | 1 |
| B | | | | | | | | | | | | | | | | | |
| C | | | | | | | | | | | | | | | | | |
| D | | | | 1 | | | | | 2 | | | | | | | | |
| E | | | | | | | | | | | | | | | | | |
| F | | | | | | | | | | | 3 | | | | | | |
| G | | | | 1 | | 57 | 1 | | | | | | | | | 1 | |
| H | | | | 24 | | | | | 2 | | | | | | | | |
| I | | | | | | | 1 | 1 | | | | | | | | | |
| K | | | | | | | | | | | | 1 | | | 53 | | |
| L | | | | | | | | | | | | | 1 | 55 | | | |
| M | | | | | | | | | | | | | | | | | |
| N | | | | | | | 2 | | 40 | | 53 | | | | | | |
| P | | | | | | | | | | | | | 54 | 1 | | | |
| Q | | | | | | | | | | | | | | | | | |
| R | | | | | | | 2 | | | | | | | | 3 | | 56 |
| S | | | | | 52 | | 49 | | 1 | | 2 | | 56 | | 1 | 56 | |
| T | | | | 8 | 5 | | 1 | 54 | 1 | | | 1 | | | 1 | | |
| V | | | | | | | 1 | 1 | | | | | | | | | |
| W | | | | | | | | | | | | | | | | | |
| X | | | | | | | | | | | | | | | | | |
| Y | | | | 23 | | | | | 11 | 54 | | | | | | | |
| Z | | | | | | | | | | | | | | | | | |
| — | 57 | 57 | 57 | | | | | | | | | | | | | | |
| unknown (?) | | | | | | | | | | | | | | | | | |
| not sequenced | | | | | | | | | | | 1 | 1 | 1 | 1 | | | |
| sum of seq[2] | 57 | 57 | 57 | 57 | 57 | 57 | 57 | 57 | 57 | 57 | 56 | 56 | 56 | 56 | 57 | 57 | 57 |
| oomcaa[3] | 57 | 57 | 57 | 24 | 52 | 57 | 49 | 54 | 40 | 54 | 53 | 54 | 56 | 55 | 53 | 56 | 56 |
| mcaa[4] | — | — | — | H | S | G | S | T | N | Y | N | P | S | L | K | S | R |
| rel. oomcaa[5] | 100% | 100% | 100% | 42% | 91% | 100% | 86% | 95% | 70% | 95% | 95% | 96% | 100% | 98% | 93% | 98% | 98% |
| pos occupied[6] | 1 | 1 | 1 | 5 | 2 | 1 | 7 | 4 | 6 | 2 | 3 | 3 | 1 | 2 | 3 | 2 | 2 |

TABLE 6E-continued

Analysis of V heavy chain subgroup 4

Framework III

| amino acid[1] | 67 | 68 | 69 | 70 | 71 | 72 | 73 | 74 | 75 | 76 | 77 | 78 | 79 | 80 | 81 | 82 | A | B |
|---|---|---|---|---|---|---|---|---|---|---|---|---|---|---|---|---|---|---|
| A | | 1 | | | 1 | | | | 1 | | | | | | | | | |
| B | | | | | | | | | | | | | | | | | | |
| C | | | | | | | | | | | | | | | | | | |
| D | 1 | | | | | 55 | | | | | | | | | 1 | | | |
| E | | | | | | 1 | | | | | | | | | | 1 | | |
| F | | | | | | | | 1 | | | | | 54 | | | | | 1 |
| G | | | | | | | | | | | | | | | | | 1 | |
| H | | | | | | | | | | | | | | | | | | |
| I | 1 | 1 | 48 | | 3 | | | | | | | 1 | | | | | 1 | |
| K | | | | | | | 1 | | 51 | 3 | | | | | 46 | | 2 | |
| L | 1 | | | | 3 | | | | 1 | | 3 | 1 | | 55 | | 53 | | |
| M | | | 7 | | | | 2 | | | | | | | | 1 | 1 | | |
| N | | 2 | | | | | | | 1 | 54 | | | | | 3 | | 3 | 1 |
| P | | | | | | | | | | | | | | | | | | |
| Q | | | | | | 1 | | | | | 54 | | | 1 | 1 | | | |
| R | | | | | | | | | 2 | | | | | | 2 | | 2 | |
| S | | 1 | | 56 | | | 1 | 57 | | | | 1 | 57 | | 2 | 1 | 44 | 55 |
| T | | 51 | | 1 | | 52 | | | | | | | | | 1 | 4 | | |
| V | 53 | | 2 | | 50 | | | | 1 | | | | | | 2 | | | |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | | | | | | | | | | | | | | | | |
| unknown (?) | | | | | | | | | | | | | | | | | | |
| not sequenced | 1 | 1 | | | | | | | | | | | | | | | | |
| sum of seq[2] | 56 | 56 | 57 | 57 | 57 | 57 | 57 | 57 | 57 | 57 | 57 | 57 | 57 | 57 | 57 | 57 | 57 | 57 |
| oomcaa[3] | 53 | 51 | 48 | 56 | 50 | 55 | 52 | 57 | 51 | 54 | 54 | 54 | 57 | 55 | 46 | 53 | 44 | 55 |
| mcaa[4] | V | T | I | S | V | D | T | S | K | N | Q | F | S | L | K | L | S | S |
| rel. oomcaa[5] | 95% | 91% | 84% | 98% | 88% | 96% | 91% | 100% | 89% | 95% | 95% | 95% | 100% | 96% | 81% | 93% | 77% | 96% |
| pos occupied[6] | 4 | 5 | 3 | 2 | 4 | 3 | 5 | 1 | 6 | 2 | 2 | 4 | 1 | 3 | 8 | 4 | 7 | 3 |

| | Framework III | | | | | | | | | | CDR III | | | | | | |
|---|---|---|---|---|---|---|---|---|---|---|---|---|---|---|---|---|---|
| amino acid[1] | C | 83 | 84 | 85 | 86 | 87 | 88 | 89 | 90 | 91 | 92 | 93 | 94 | 95 | 96 | 97 | 98 | 99 |
| A | | | 55 | 57 | | | 57 | | | | | 56 | | 3 | 3 | 3 | 2 | 5 |
| B | | | | | | | | | | | | | | | | | | |
| C | | | | | | | | | | | 57 | | | | | 1 | | |
| D | | | | | 57 | | | | | | | | | 6 | 5 | 5 | 5 | 5 |
| E | | | | | | | | | | | | | | 6 | 1 | 1 | 2 | 1 |
| F | | | | | | | | | | | | | | | 4 | 1 | 1 | |
| G | | | | | | | | | | | | | | 25 | 9 | 10 | 8 | 10 |
| H | | | | | | | | | | | | | | 1 | | | | 1 |
| I | | 3 | | | | | | | | | | | | | 1 | | 2 | 4 |
| K | | | | | | | | | | | | | | 2 | 1 | | | |
| L | 2 | | | | | | | 1 | | | | | | 2 | 6 | 7 | 3 | 5 |
| M | 1 | | | | | | | 1 | | | | | | | 1 | 4 | | 3 |
| N | | | | | | | | | | | | | | | 3 | | | |
| P | | | | | | | | | | | | | | | 4 | 5 | 3 | 1 |
| Q | | | | | | | | | | | | | | | 1 | 1 | | |
| R | | | 1 | | | | | | | | | | 54 | 4 | 12 | 2 | 5 | 5 |
| S | | 1 | | | | 2 | | | | 1 | | | 1 | 1 | 4 | 8 | 8 | 1 |
| T | | 53 | | | | 55 | | | | | | | 1 | 1 | 2 | 1 | 3 | 4 |
| V | 54 | | 1 | | | | | 55 | | | | 1 | 1 | 4 | 2 | 2 | 5 | 4 |
| W | | | | | | | | | | | | | | 1 | 2 | 1 | 2 | 2 |
| X | | | | | | | | | | | | | | | | | | |
| Y | | | | | | | | | 57 | 56 | | | | | 1 | 4 | 5 | 3 |
| Z | | | | | | | | | | | | | | | | | | |
| — | | | | | | | | | | | | | | | | | 1 | 2 |
| unknown (?) | | | | | | | | | | | | | | | | | | |
| not sequenced | | | | | | | | | | | | | | 1 | 1 | 1 | 1 | 1 |
| sum of seq[2] | 57 | 57 | 57 | 57 | 57 | 57 | 57 | 57 | 57 | 57 | 57 | 57 | 57 | 56 | 56 | 56 | 56 | 56 |
| oomcaa[3] | 54 | 53 | 55 | 57 | 57 | 55 | 57 | 55 | 57 | 56 | 57 | 56 | 54 | 25 | 12 | 10 | 8 | 10 |
| mcaa[4] | V | T | A | A | D | T | A | V | Y | Y | C | A | R | G | R | G | G | G |
| rel. oomcaa[5] | 95% | 93% | 96% | 100% | 100% | 96% | 100% | 96% | 100% | 98% | 100% | 98% | 95% | 45% | 21% | 18% | 14% | 18% |
| pos occupied[6] | 3 | 3 | 3 | 1 | 1 | 2 | 1 | 3 | 1 | 2 | 1 | 2 | 4 | 12 | 16 | 16 | 16 | 16 |

TABLE 6E-continued

Analysis of V heavy chain subgroup 4

| | CDR III | | | | | | | | | | | | Framework IV | | | | | |
|---|---|---|---|---|---|---|---|---|---|---|---|---|---|---|---|---|---|---|
| amino acid[1] | 100 | A | B | C | D | E | F | G | H | I | J | K | 101 | 102 | 103 | 104 | 105 | 106 |
| A | 4 | 2 | 2 | 4 | | 2 | 1 | | 1 | 1 | 12 | | | | | | | |
| B | | | | | | | | | | | | | | | | | | |
| C | | 1 | | | | | | | | | | | | | | | | |
| D | 4 | 3 | 2 | 4 | 3 | 1 | | | 1 | 2 | 1 | | | 41 | | | | |
| E | | | 1 | 3 | 1 | 2 | 1 | | | | | | | | | | | |
| F | 2 | 3 | 2 | 2 | | 1 | 1 | | | | | | 31 | | | | | |
| G | 11 | 4 | 7 | 7 | 6 | 1 | 1 | 1 | 2 | 1 | 9 | | | 2 | 1 | | 41 | 40 |
| H | | | | | | 1 | | | 1 | | | | | 2 | 1 | | | |
| I | 1 | 3 | 2 | 3 | | 1 | | | | | | | 1 | | 9 | | | |
| K | | | 2 | 2 | | | 1 | | | | | | | | | | 3 | |
| L | 3 | 2 | 4 | 1 | 5 | 3 | 3 | | 1 | | | | | 4 | | | | |
| M | 1 | | 2 | 1 | | | | | | | 9 | | | | | | | |
| N | | 2 | 1 | 1 | 5 | 1 | 1 | | | 2 | | | | | | | | |
| P | 1 | 2 | 1 | 1 | 1 | 2 | 3 | | 2 | 1 | | | | 3 | | | 2 | |
| Q | 1 | | | 1 | 1 | | | 3 | | | | | 1 | | | | 29 | |
| R | 3 | 2 | 3 | 1 | 2 | | | 2 | 1 | | | | | 1 | | | 4 | |
| S | 2 | 5 | 7 | 4 | 2 | 1 | 1 | 1 | | | | | | 1 | | | 1 | |
| T | 4 | 3 | 3 | | | 1 | 1 | 1 | | | | | | | | | 1 | |
| V | 4 | 7 | 3 | 1 | 2 | 1 | | | | | | | | 12 | | | | |
| W | 4 | 5 | 1 | 1 | 2 | | 2 | 1 | | 3 | 2 | | | | 46 | | | |
| X | | | | | | | | | | | | | | | | | | |
| Y | 6 | 4 | 2 | 3 | 4 | 8 | 4 | 8 | 3 | 5 | 8 | | | 2 | 16 | | | |
| Z | | | | | | | | | | | | | | | | | | |
| — | 4 | 6 | 9 | 11 | 16 | 23 | 27 | 29 | 34 | 31 | 14 | 4 | | | | | | |
| unknown (?) | | | | | | | 1 | | | | 1 | 1 | 1 | | | | | |
| not sequenced | 2 | 3 | 3 | 6 | 7 | 8 | 9 | 9 | 10 | 11 | 11 | 11 | 11 | 10 | 11 | 16 | 17 | 17 |
| sum of seq[2] | 55 | 54 | 54 | 51 | 50 | 49 | 48 | 48 | 47 | 46 | 46 | 46 | 46 | 47 | 46 | 41 | 40 | 40 |
| oomcaa[3] | 11 | 7 | 9 | 11 | 16 | 23 | 27 | 29 | 34 | 31 | 14 | 31 | 41 | 16 | 46 | 41 | 29 | 40 |
| mcaa[4] | G | V | — | — | — | — | — | — | — | — | — | F | D | Y | W | G | Q | G |
| rel. oomcaa[5] | 20% | 13% | 17% | 22% | 32% | 47% | 56% | 60% | 72% | 67% | 30% | 67% | 89% | 34% | 100% | 100% | 73% | 100% |
| pos occupied[6] | 16 | 16 | 18 | 18 | 13 | 15 | 13 | 10 | 9 | 8 | 5 | 4 | 4 | 8 | 1 | 1 | 6 | 1 |

| | Framework IV | | | | | | | |
|---|---|---|---|---|---|---|---|---|
| amino acid[1] | 107 | 108 | 109 | 110 | 111 | 112 | 113 | sum |
| A | 1 | | | 1 | | | | 332 |
| B | | | | | | | | |
| C | | | | | | | | 113 |
| D | | | | | | | | 210 |
| E | | | | | | | | 176 |
| F | | | | | | | | 135 |
| G | 1 | | | | | | | 674 |
| H | | | | | 1 | | | 45 |
| I | 1 | | | | | | | 282 |
| K | | | | | | | | 278 |
| L | | 19 | | | | | | 540 |
| M | | 9 | | | | | | 43 |
| N | 1 | | | | | | | 204 |
| P | | | | | | | 2 | 281 |
| Q | | | | | | | | 334 |
| R | | | | 1 | | | | 250 |
| S | | | | | | 36 | 33 | 986 |
| T | 33 | 8 | | 34 | | | | 532 |
| V | | | 36 | | 36 | | | 488 |
| W | | | | | | | | 267 |
| X | | | | | | | | |
| Y | | | | | | | | 455 |
| Z | | | | | | | | 1 |
| — | | | | | | | | 466 |
| unknown (?) | | | | | | | | 4 |
| not sequenced | 20 | 20 | 21 | 21 | 21 | 21 | 22 | 426 |
| sum of seq[2] | 37 | 37 | 36 | 36 | 36 | 36 | 35 | |
| oomcaa[3] | 33 | 19 | 36 | 34 | 36 | 36 | 33 | |
| mcaa[4] | T | L | V | T | V | S | S | |
| rel. oomcaa[5] | 89% | 51% | 100% | 94% | 100% | 100% | 94% | |
| pos occupied[6] | 5 | 4 | 1 | 3 | 1 | 1 | 2 | |

TABLE 6F

Analysis of V heavy chain subgroup 5

| | Framework I | | | | | | | | | | | | | | | | | |
|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 |
| A | | | | | 1 | | | 1 | 89 | | 1 | | | 1 | | | | |
| B | | | | | | | | | | | | | | | | | | |
| C | | | | | | | 1 | | | | | | | | | | | |
| D | | | | | | | | | | 2 | | | | | | | | |
| E | 88 | 1 | | | 2 | | | | 4 | 93 | | | | | | 92 | | |
| F | | | | | | | | | | | | | | | | | 1 | |
| G | 1 | | | | | | | 92 | | | | | | | 94 | | | |
| H | | | | | | | | | | | | | | | | | | |
| I | | | | | | | | | | | | | | | | | | |
| K | | | | | | | | | | | | | 94 | 94 | | | | |
| L | | 1 | | 91 | | 2 | | | | | | | | | | | | 95 |
| M | | | | | | | | | | | | 3 | | | | | | |
| N | | | | | | | | | | | | | | | | | | |
| P | | | | | 1 | | | | 1 | | | | | | 94 | | | |
| Q | 3 | | 92 | | | 1 | 90 | | | | | | | | | 3 | | |
| R | | | | | | | 1 | | | | | 1 | 1 | | 1 | | | |
| S | | | | | | | | 92 | | | | | | | | | 94 | |
| T | | | | | | | | | | | | | | | | | | |
| V | | 90 | | | 89 | | | | 1 | | 91 | | | | | | | |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | | | | | | | | | | | | | | | | |
| unknown (?) | | | | | | | | | | | | | | | | | | |
| not sequenced | 5 | 5 | 5 | 5 | 4 | 4 | 4 | 4 | 2 | 2 | 2 | 2 | 2 | 2 | 2 | 2 | 2 | 2 |
| sum of seq[2] | 92 | 92 | 92 | 92 | 93 | 93 | 93 | 93 | 95 | 95 | 95 | 95 | 95 | 95 | 95 | 95 | 95 | 95 |
| oomcaa[3] | 88 | 90 | 92 | 91 | 89 | 90 | 92 | 92 | 89 | 93 | 91 | 94 | 94 | 94 | 94 | 92 | 94 | 95 |
| mcaa[4] | E | V | Q | L | V | Q | S | G | A | E | V | K | K | P | G | E | S | L |
| rel. oomcaa[5] | 96% | 98% | 100% | 99% | 96% | 97% | 99% | 99% | 94% | 98% | 96% | 99% | 99% | 99% | 99% | 97% | 99% | 100% |
| pos occupied[6] | 3 | 3 | 1 | 2 | 4 | 3 | 2 | 2 | 4 | 2 | 3 | 2 | 2 | 2 | 2 | 2 | 2 | 1 |

| | Framework I | | | | | | | | | | | | CDR I | | | | |
|---|---|---|---|---|---|---|---|---|---|---|---|---|---|---|---|---|---|
| amino acid[1] | 19 | 20 | 21 | 22 | 23 | 24 | 25 | 26 | 27 | 28 | 29 | 30 | 31 | A | B | 32 | 33 | 34 |
| A | | | | | | 3 | 2 | | | | | 4 | | | | | | |
| B | | | | | | | | | | | | | | | | | | |
| C | | | | 96 | | | | | 1 | | | 1 | | | | | | |
| D | | | | | | | | | 2 | | | 2 | | | | | | |
| E | | | | | | 2 | | | | | | 1 | | | | | | |
| F | | | | | | 3 | | 6 | | | 97 | | | | | 2 | | |
| G | | | | | 92 | | 93 | | | | | 1 | | | | | | |
| H | | | | | | | | | | | | 1 | | | | 4 | | |
| I | | 96 | | | | | | | | | | 4 | | | | | | 93 |
| K | 77 | | | | 89 | | | | 1 | | | | | | | | | |
| L | | | | | | | | | | | | | | | | 1 | | |
| M | 1 | | | 1 | | | | | | | | | | | | 2 | | 1 |
| N | | | | 1 | | | 1 | | | 2 | | 4 | 14 | | | 2 | | |
| P | | | | | | | | | | | | | | | | | | |
| Q | 1 | | | 4 | | | | | 1 | | | | | | | | | |
| R | 17 | | | 1 | | | | 1 | | | | 2 | | | | | 1 | |
| S | | | 94 | | 1 | 90 | | | | 84 | | 10 | 61 | | | 2 | 2 | |
| T | | | 2 | | | | | | | 5 | | 75 | 16 | | | | | 2 |
| V | | | | | | | | | | | | | | | | | | 1 |
| W | | | | | | | | | | | | | | | | 93 | | |
| X | | | | | | | | | | | | | | | | | | |
| Y | | | | | | | 90 | | | | | | | | | 87 | | |
| Z | | | | | | | | | | | | | | | | | | |
| — | | | | | | | | | | | | | 97 | 97 | | | | |
| unknown (?) | | | | | | | | | | | | | | | | | | |
| not sequenced | 1 | 1 | 1 | 1 | 1 | 1 | 1 | 1 | 1 | | | | | | | | | |
| sum of seq[2] | 96 | 96 | 96 | 96 | 96 | 96 | 96 | 96 | 96 | 97 | 97 | 97 | 97 | 97 | 97 | 97 | 97 | 97 |
| oomcaa[3] | 77 | 96 | 94 | 96 | 89 | 92 | 90 | 93 | 90 | 84 | 97 | 75 | 61 | 97 | 97 | 87 | 93 | 93 |
| mcaa[4] | K | I | S | C | K | G | S | G | Y | S | F | T | S | — | — | Y | W | I |
| rel. oomcaa[5] | 80% | 100% | 98% | 100% | 93% | 96% | 94% | 97% | 94% | 87% | 100% | 77% | 63% | 100% | 100% | 90% | 96% | 96% |
| pos occupied[6] | 4 | 1 | 2 | 1 | 5 | 3 | 4 | 3 | 2 | 7 | 1 | 5 | 8 | 1 | 1 | 5 | 4 | 4 |

TABLE 6F-continued

| | Analysis of V heavy chain subgroup 5 | | | | | | | | | | | | | | | | | |
|---|---|---|---|---|---|---|---|---|---|---|---|---|---|---|---|---|---|---|
| | CDR I | | Framework II | | | | | | | | | | | | | | CDR II | |
| amino acid[1] | 35 | 36 | 37 | 38 | 39 | 40 | 41 | 42 | 43 | 44 | 45 | 46 | 47 | 48 | 49 | 50 | 51 | 52 |
| A | 8 | | 1 | | | | 1 | | | 1 | | | | | | | | |
| B | | | | | | | | | | | | | | | | | | |
| C | | | | | | | | | | | | | | | | | | 1 |
| D | 1 | | | | | | | | | | | | | | | | | 14 |
| E | | | | | | | | | 3 | | | 97 | | | | | | |
| F | | | | | | | | | | | | | | | | 1 | | 2 |
| G | 72 | | | | | | 97 | | 96 | | | | | | 95 | | | |
| H | | | | 1 | | | | | | | | | | | | | | 3 |
| I | | | | | | | | | | | | | 1 | | | 75 | 92 | |
| K | | | | | | 1 | | | 94 | | | | | | | | | |
| L | | 2 | | | | | | | | | 94 | | | 2 | | 2 | | 1 |
| M | | 1 | | | 92 | | | | | | | | 89 | | | | 1 | |
| N | | | | | | | | | | | | | | | | | | |
| P | | | 1 | | | 96 | | | | | 2 | | | | | | | 1 |
| Q | | | | 97 | | | | | | 1 | | | | | | | | |
| R | | 95 | | | | 1 | | | | | | | | | 1 | 14 | | |
| S | 15 | | | | | | | | | | | | | | | 1 | | |
| T | 1 | | | | | 1 | | | | | | | | | | 3 | 1 | |
| V | | | 93 | | | 2 | | | | | | | 5 | 1 | | 1 | | 2 |
| W | | 97 | | | | | | | | | | | 94 | | | | | |
| X | | | | | | | | | | | | | | | | | | |
| Y | | | | | | | | | | | | | 3 | | | | | 76 |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | 97 |
| oomcaa[3] | 72 | 97 | 93 | 95 | 97 | 92 | 96 | 97 | 94 | 96 | 94 | 97 | 94 | 89 | 95 | 75 | 92 | 76 |
| mcaa[4] | G | W | V | R | Q | M | P | G | K | G | L | E | W | M | G | I | I | Y |
| rel. oomcaa[5] | 74% | 100% | 96% | 98% | 100% | 95% | 99% | 100% | 97% | 99% | 97% | 100% | 97% | 92% | 98% | 77% | 95% | 78% |
| pos occupied[6] | 5 | 1 | 4 | 3 | 1 | 5 | 2 | 1 | 2 | 2 | 3 | 1 | 2 | 4 | 3 | 7 | 5 | 6 |

| | CDR II | | | | | | | | | | | | | | | | | |
|---|---|---|---|---|---|---|---|---|---|---|---|---|---|---|---|---|---|---|
| amino acid[1] | A | B | C | 53 | 54 | 55 | 56 | 57 | 58 | 59 | 60 | 61 | 62 | 63 | 64 | 65 | 66 | |
| A | 1 | | | 2 | 1 | | | 6 | | | | | | 1 | | | | |
| B | | | | | | | | | | | | | | | | | | |
| C | | | | 1 | | | | | | | 1 | | | | | 1 | | |
| D | | | | 8 | 93 | | 77 | | | | | | | | | | 2 | |
| E | | | | | 2 | | 3 | | | | | | | | 2 | | | |
| F | | | | | | | | | | 2 | | | | 91 | | | | |
| G | | | | 69 | 1 | | 1 | | | | | | | | | 94 | | |
| H | 1 | | | | | | | | | | | | | | | | 15 | |
| I | | | | | | | | 4 | 1 | | | | | 1 | | | | |
| K | | | | | | | | | 2 | | | | | | | | | |
| L | | | | | | | | | | | | 1 | | | 4 | | | |
| M | | | | | | | | | | | | | | | | | | |
| N | | | | | | | 2 | | 14 | 2 | | | | | | | | |
| P | 93 | | | | | 1 | | | | | | 95 | 1 | | 1 | | | |
| Q | | | | | | | | | | | | | | | 91 | | 81 | |
| R | | | | | | | | | 78 | | | | | | 3 | | 1 | |
| S | 1 | | | 16 | | 96 | 2 | 2 | | | 95 | 1 | 95 | 1 | | | | |
| T | 1 | | | | | | | 85 | 2 | | 1 | | | | | | | |
| V | | | | | | | | | | 1 | | | | | | | | |
| W | | | | | | | | | | | | | | | | | | |
| X | | | | | | | | | | | | | | | | | | |
| Y | | | | | | | 12 | | | 92 | | | | | | | | |
| Z | | | | | | | | | | | | | | | | | | |
| — | | 97 | 97 | | | | | | | | | | | | | | | |
| unknown (?) | | | | | | | | | | | | | | | | | | |
| not sequenced | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | |
| oomcaa[3] | 93 | 97 | 97 | 69 | 93 | 96 | 77 | 85 | 78 | 92 | 95 | 95 | 95 | 91 | 91 | 94 | 81 | |
| mcaa[4] | P | — | — | G | D | S | D | T | R | Y | S | P | S | F | Q | G | Q | |
| rel. oomcaa[5] | 96% | 100% | 100% | 71% | 96% | 99% | 79% | 88% | 80% | 95% | 98% | 98% | 98% | 94% | 94% | 97% | 84% | |
| pos occupied[6] | 5 | 1 | 1 | 6 | 4 | 2 | 6 | 4 | 5 | 4 | 3 | 3 | 3 | 4 | 4 | 3 | 3 | |

TABLE 6F-continued

Analysis of V heavy chain subgroup 5

| | Framework III | | | | | | | | | | | | | | | | | |
|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | A | B |
| A | | | | | | 88 | | | | | | 1 | 91 | | | | | |
| B | | | | | | | | | | | | | | | | | | |
| C | | | | | | | | | | | | | | | | 1 | | |
| D | | | | | 97 | | | | | | | | | 1 | | | | |
| E | | | | | | 2 | | | | | | | | | 1 | | | |
| F | 1 | | 3 | | | | | | | | | | 1 | | | | | |
| G | | | | | | | | | | | | | | | 3 | | 3 | 1 |
| H | | | | | | | | | | | | | | 3 | | | | |
| I | 3 | | 88 | | | | | | 91 | | | | | | | | | |
| K | | | | | | | 93 | | | | | | | | | | | |
| L | | | | 2 | | | | | | | | | | 96 | | | | |
| M | | 3 | | | | | | 1 | | | | | | | | | | |
| N | | | | | | | | | | | 7 | | | | | | 2 | 2 |
| P | | | | | | | 1 | | | | | 1 | | | | | | |
| Q | | | | | | 1 | | | | | | | | | 93 | | | |
| R | | | 1 | | | | 1 | | | | 1 | | | | | 1 | 1 | 3 |
| S | | 1 | | 95 | | | | 96 | 1 | 87 | 2 | 1 | 1 | | | | 90 | 91 |
| T | | 96 | | | | | | | 4 | 2 | 94 | 2 | | | | | 1 | |
| V | 93 | | 2 | | 9 | | | | | | | 2 | | 1 | | | | |
| W | | | | | | | | | | | | | | | | 95 | | |
| X | | | | | | | | | | | | | | | | | | |
| Y | | | | | | | | | | | | | 94 | | | | | |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | 97 |
| oomcaa[3] | 93 | 96 | 88 | 95 | 88 | 97 | 93 | 96 | 91 | 87 | 94 | 91 | 94 | 96 | 93 | 95 | 90 | 91 |
| mcaa[4] | V | T | I | S | A | D | K | S | I | S | T | A | Y | L | Q | W | S | S |
| rel. oomcaa[5] | 96% | 99% | 91% | 98% | 91% | 100% | 96% | 99% | 94% | 90% | 97% | 94% | 97% | 99% | 96% | 98% | 93% | 94% |
| pos occupied[6] | 3 | 2 | 5 | 2 | 2 | 1 | 4 | 2 | 4 | 4 | 3 | 5 | 4 | 2 | 3 | 3 | 5 | 4 |

| | Framework III | | | | | | | | | | | CDR III | | | | | |
|---|---|---|---|---|---|---|---|---|---|---|---|---|---|---|---|---|---|
| amino acid[1] | C | 83 | 84 | 85 | 86 | 87 | 88 | 89 | 90 | 91 | 92 | 93 | 94 | 95 | 96 | 97 | 98 | 99 |
| A | | 1 | 96 | | | | 93 | | | | | 92 | | 1 | 1 | 2 | | 3 |
| B | | | | | | | | | | | | | | | | | | |
| C | | | | | | | | | | | 95 | | | | | | 1 | 1 |
| D | | | | | 96 | | | | | | | | | 3 | 3 | 3 | 3 | 3 |
| E | | 1 | | | | | | | | | | | | 1 | 1 | 1 | 2 | |
| F | | | | | | | | | 2 | 6 | | | | | | 1 | | 3 |
| G | | | | | | | 4 | | | | | | | 1 | 9 | 11 | 12 | 12 |
| H | | | | | | | | | | | | | | 10 | 1 | | 2 | |
| I | | | | | | 2 | | 9 | | | | | | | 3 | | 2 | 2 |
| K | | 91 | | | | | | 1 | | | | 1 | 1 | 1 | | | 1 | 3 |
| L | 97 | | | | | | | 2 | | | | | | 11 | 2 | 3 | 1 | 1 |
| M | | | | | | | | 84 | | | | | | | | 2 | 1 | 1 |
| N | | | | | | 2 | | | | | | | | | 1 | | 2 | |
| P | | | | | | | | | | | | | | 5 | 1 | 4 | 3 | 1 |
| Q | | | | | | | | | | | | 1 | 3 | 2 | | | 1 | 1 |
| R | | 3 | | | | | | | | | | 92 | 7 | 9 | 2 | | 2 | |
| S | | | | 96 | | 5 | | | | | | | 1 | 1 | 3 | 2 | 6 | 4 |
| T | | 1 | 1 | 1 | | 88 | | 1 | | | 1 | | 1 | 3 | 2 | 1 | | 2 |
| V | | | | | 1 | | | | | | | | 2 | 2 | 4 | 4 | | 1 |
| W | | | | | | | | | | | | | | 1 | | 2 | 1 | |
| X | | | | | | | | | | | | | | | | | | |
| Y | | | | | | | | | 94 | 89 | | | | | 1 | 6 | 3 | 6 |
| Z | | | | | | | | | | | | | | | | | | |
| — | | | | | | | | | | | | | | | | | 1 | 1 |
| unknown (?) | | | | | | | | | | | | | | | | | | |
| not sequenced | | | | | | | | | 1 | 2 | 2 | 2 | 2 | 52 | 52 | 52 | 52 | 52 |
| sum of seq[2] | 97 | 97 | 97 | 97 | 97 | 97 | 97 | 97 | 96 | 95 | 95 | 95 | 95 | 45 | 45 | 45 | 45 | 45 |
| oomcaa[3] | 97 | 91 | 96 | 96 | 96 | 88 | 93 | 84 | 94 | 89 | 95 | 92 | 92 | 11 | 9 | 11 | 12 | 12 |
| mcaa[4] | L | K | A | S | D | T | A | M | Y | Y | C | A | R | L | G | G | G | G |
| rel. oomcaa[5] | 100% | 94% | 99% | 99% | 99% | 91% | 96% | 87% | 98% | 94% | 100% | 97% | 97% | 24% | 20% | 24% | 27% | 27% |
| pos occupied[6] | 1 | 5 | 2 | 2 | 2 | 4 | 2 | 5 | 2 | 2 | 1 | 3 | 4 | 13 | 16 | 14 | 18 | 16 |

TABLE 6F-continued

Analysis of V heavy chain subgroup 5

| amino acid[1] | CDR III | | | | | | | | | | | | Framework IV | | | | | |
|---|---|---|---|---|---|---|---|---|---|---|---|---|---|---|---|---|---|---|
| | 100 | A | B | C | D | E | F | G | H | I | J | K | 101 | 102 | 103 | 104 | 105 | 106 |
| A | 4 | 3 | 2 | | 1 | | | 1 | | | 4 | | 2 | | | | | |
| B | | | | | | | | | | | | | | | | | | |
| C | 1 | | | 2 | | 1 | | | | | | | | | | | | |
| D | 1 | 2 | 1 | 1 | 2 | | 2 | 1 | 1 | 2 | | | 37 | 1 | | | | |
| E | | 1 | 1 | | | | 1 | | | 1 | | | | | | | 1 | |
| F | | | 3 | 2 | | 1 | | | | | | | 26 | | 2 | | | |
| G | 5 | 2 | 4 | 3 | 10 | 2 | 1 | | | | 5 | | | | | 41 | | 41 |
| H | | 1 | 1 | | 1 | | | | | | | | | | | | | |
| I | 1 | 1 | 4 | 1 | 1 | | 1 | 1 | | | | | | 9 | | | | |
| K | 1 | | | | | | | | 2 | | | | | | | | 3 | |
| L | 2 | 5 | | 1 | | 1 | | 1 | | | | | | 2 | | | | |
| M | | 1 | 1 | 1 | 1 | | | | | | 10 | | | | | | | |
| N | 1 | 1 | 2 | | | 1 | | | | | 2 | | | | | | | |
| P | 2 | | | | 1 | 1 | 1 | 1 | | | | | | 2 | | | | |
| Q | 4 | 2 | 1 | 2 | | | | | | | | | 3 | | | | 34 | |
| R | 2 | 1 | | 2 | | | | | | | | | | | | | 3 | |
| S | 4 | 5 | 3 | 5 | 3 | 2 | 2 | | | 1 | | 1 | | 2 | | | | |
| T | 6 | 3 | 3 | 6 | 1 | | 1 | | | | | | | 1 | | | | |
| V | | 1 | 2 | | | 1 | | | | | | | | 11 | | | | |
| W | | | | 1 | | 2 | | 1 | | 1 | 1 | | | | 43 | | | |
| X | | | | | | | | | | | | | | | | | | |
| Y | 9 | 8 | 7 | 2 | 1 | 2 | 6 | 8 | 9 | 9 | 10 | | 1 | 13 | | | | |
| Z | | | | | | | | | | | | | | | | | | |
| — | 2 | 8 | 10 | 16 | 23 | 30 | 30 | 31 | 32 | 30 | 22 | 7 | 2 | 2 | | | | |
| unknown (?) | | | | | | 1 | | | 1 | 1 | 1 | | | | | | | |
| not sequenced | 52 | 52 | 52 | 52 | 52 | 52 | 52 | 52 | 52 | 52 | 52 | 53 | 52 | 52 | 54 | 56 | 56 | 56 |
| sum of seq[2] | 45 | 45 | 45 | 45 | 45 | 45 | 45 | 45 | 45 | 45 | 45 | 44 | 45 | 45 | 43 | 41 | 41 | 41 |
| oomcaa[3] | 9 | 8 | 10 | 16 | 23 | 30 | 30 | 31 | 32 | 30 | 22 | 26 | 37 | 13 | 43 | 41 | 34 | 41 |
| mcaa[4] | Y | Y | — | — | — | — | — | — | — | — | — | F | D | Y | W | G | Q | G |
| rel. oomcaa[5] | 20% | 18% | 22% | 36% | 51% | 67% | 67% | 69% | 71% | 67% | 49% | 59% | 82% | 29% | 100% | 100% | 83% | 100% |
| pos occupied[6] | 15 | 16 | 15 | 14 | 11 | 11 | 9 | 8 | 4 | 6 | 6 | 4 | 5 | 10 | 1 | 1 | 4 | 1 |

| amino acid[1] | Framework IV | | | | | | | sum |
|---|---|---|---|---|---|---|---|---|
| | 107 | 108 | 109 | 110 | 111 | 112 | 113 | |
| A | | | | | | | 1 | 611 |
| B | | | | | | | | |
| C | | | | | | | | 205 |
| D | | | | | | | | 458 |
| E | | | | | | | | 404 |
| F | | | | | | | | 256 |
| G | | | | | | | | 1065 |
| H | | | | | | | | 44 |
| I | | | | 2 | | | | 588 |
| K | | | | | | | | 650 |
| L | | 25 | 1 | | | | | 549 |
| M | | 8 | | | | | | 303 |
| N | | | | | | | | 64 |
| P | 1 | | | | | 1 | | 414 |
| Q | | | | | | | | 612 |
| R | | | | | | | | 351 |
| S | | | | | | 40 | 39 | 1545 |
| T | 40 | 8 | | 39 | | | | 604 |
| V | | | 40 | | 41 | | | 594 |
| W | | | | | | | | 432 |
| X | | | | | | | | |
| Y | | | | | | | | 738 |
| Z | | | | | | | | |
| — | | | | | | | | 635 |
| unknown (?) | | | | | | | | 4 |
| not sequenced | 56 | 56 | 56 | 56 | 56 | 56 | 57 | 1678 |
| sum of seq[2] | 41 | 41 | 41 | 41 | 41 | 41 | 40 | |
| oomcaa[3] | 40 | 25 | 40 | 39 | 41 | 40 | 39 | |
| mcaa[4] | T | L | V | T | V | S | S | |
| rel. oomcaa[5] | 98% | 61% | 98% | 95% | 100% | 98% | 98% | |
| pos occupied[6] | 2 | 3 | 2 | 2 | 1 | 2 | 2 | |

TABLE 6G

Analysis of V heavy chain subgroup 6

Framework I

| amino acid[1] | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| A | | | | | | | | | | | | 1 | | | | | | |
| B | | | | | | | | | | | | | | | | | | |
| C | | | | | | | | | | | | | | | | | | |
| D | | | | | | | | | | | | | | | | | | |
| E | | | | | | | | | | | | | | | | | | |
| F | | | | | | | | | | | | | | | | | | |
| G | | | | | | | | | 52 | | 67 | | | | | | | |
| H | | | | | | | | | | | | | | | | | | |
| I | | | | | | | | | | | | | | | | | | |
| K | | | | | | | | | | | | | | 68 | | | | |
| L | | | | 52 | | | | | | | | 68 | 1 | | | | | 67 |
| M | | | | | | | | | | | | | | | | | | |
| N | | | | | | | | | | | | | | | | | | |
| P | | | | | | | | | 68 | | | | | 67 | | | | |
| Q | 52 | | 52 | | 51 | 52 | | | | | | | | | | 68 | | |
| R | | | | | | 1 | | | | | 1 | | | | | | | |
| S | | | | | | | 52 | | | | | | | | 1 | 68 | | |
| T | | | | | | | | | | | | | | | | | 68 | |
| V | | 52 | | | | | | | | | | | 66 | | | | | 1 |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | | | | | | | | | | | | | | | | |
| unknown (?) | | | | | | | | | | | | | | | | | | |
| not sequenced | 22 | 22 | 22 | 22 | 22 | 22 | 22 | 22 | 6 | 6 | 6 | 6 | 6 | 6 | 6 | 6 | 6 | 6 |
| sum of seq[2] | 52 | 52 | 52 | 52 | 52 | 52 | 52 | 52 | 68 | 68 | 68 | 66 | 68 | 68 | 68 | 68 | 68 | 68 |
| oomcaa[3] | 52 | 52 | 52 | 52 | 51 | 52 | 52 | 52 | 68 | 67 | 68 | 66 | 68 | 67 | 68 | 68 | 68 | 67 |
| mcaa[4] | Q | V | Q | L | Q | Q | S | G | P | G | L | V | K | P | S | Q | T | L |
| rel. oomcaa[5] | 100% | 100% | 100% | 100% | 98% | 100% | 100% | 100% | 100% | 99% | 100% | 97% | 100% | 99% | 100% | 100% | 100% | 99% |
| pos occupied[6] | 1 | 1 | 1 | 1 | 2 | 1 | 1 | 1 | 1 | 2 | 1 | 3 | 1 | 2 | 1 | 1 | 1 | 2 |

| | Framework I | | | | | | | | | | | | CDR I | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | 28 | 29 | 30 | 31 | A | B | 32 | 33 | 34 |
| A | | | 1 | | 67 | | | | | | | | | | | 66 | 67 | |
| B | | | | | | | | | | | | | | | | | | |
| C | | | | 68 | | | | | | | | | | | | | | |
| D | | | | | | | | | 68 | | | | 1 | | | | | |
| E | | | | | | | | | | | | | | | | | | |
| F | | | | | | | | | | | | 2 | | | | 1 | 1 | |
| G | | | | | 1 | | 69 | | | | | | | | 3 | 1 | 2 | |
| H | | | | | | | | | | | | | | | | | | |
| I | | | | | | 64 | | | | | | | 2 | | | | | |
| K | | | | | | | | | | | | | 3 | | | | | |
| L | 1 | 68 | | | | | | | | | | | | | | | | |
| M | | | | | | | | | | | | | | | | | | |
| N | | | | | | | | 1 | | | | | 2 | 66 | | | | |
| P | 1 | | | | | | | | | | | | | | | | | |
| Q | | | | | | | | | | | | | | | | | | |
| R | | | | | | | | | | | | | 2 | 1 | | | | |
| S | 66 | | 1 | | | 1 | 69 | | | 69 | | 68 | 66 | | 67 | | 3 | |
| T | | | 67 | | | | | | | | | | 2 | 1 | 4 | | 1 | |
| V | | | | | 1 | 4 | | | | | 70 | | | | | 6 | | |
| W | | | | 1 | | | | | | | | | | | | | | 74 |
| X | | | | | | | | | | | | | | | | | | |
| Y | | | | | | | | | | | | | 1 | | | | | |
| Z | | | | | | | | | | | | | | | | | | |
| — | | | | | | | | | | | | | | | | | | |
| unknown (?) | | | | | | | | | | | | | 1 | | | | | |
| not sequenced | 6 | 6 | 5 | 5 | 5 | 5 | 5 | 5 | 5 | 5 | 4 | 4 | | | | | | |
| sum of seq[2] | 68 | 68 | 69 | 69 | 69 | 69 | 69 | 69 | 69 | 69 | 70 | 70 | 74 | 74 | 74 | 74 | 74 | 74 |
| oomcaa[3] | 66 | 68 | 67 | 68 | 67 | 64 | 69 | 69 | 68 | 69 | 70 | 68 | 66 | 66 | 67 | 66 | 67 | 74 |
| mcaa[4] | S | L | T | C | A | I | S | G | D | S | V | S | S | N | S | A | A | W |
| rel. oomcaa[5] | 97% | 100% | 97% | 99% | 97% | 93% | 100% | 100% | 99% | 100% | 100% | 97% | 89% | 89% | 91% | 89% | 91% | 100% |
| pos occupied[6] | 3 | 1 | 3 | 2 | 3 | 3 | 1 | 1 | 2 | 1 | 1 | 2 | 5 | 6 | 3 | 4 | 5 | 1 |

TABLE 6G-continued

Analysis of V heavy chain subgroup 6

| amino acid[1] | CDR I | | Framework II | | | | | | | | | | | | | CDR II | | |
|---|---|---|---|---|---|---|---|---|---|---|---|---|---|---|---|---|---|---|
| | 35 | 36 | 37 | 38 | 39 | 40 | 41 | 42 | 43 | 44 | 45 | 46 | 47 | 48 | 49 | 50 | 51 | 52 |
| A | | | | | | | | 1 | | | | | | | | | 1 | |
| B | | | | | | | | | | | | | | | | | | |
| C | | | | | | | | | | | | | | | | | | |
| D | 1 | | | | | | | | | | | | | | | | | |
| E | | | | | | | | | | | | 74 | | | | | | |
| F | | | 1 | | | | | | | | | | | | | | | 2 |
| G | | | | | | | | | | 74 | | | | | 74 | 1 | | |
| H | 1 | | | | | | | | | | | | | | | | | |
| I | 1 | | | 70 | | | | | | | | | | | | | | |
| K | | | | | | 1 | | | 1 | | | | | | | | | |
| L | | | | | | 1 | | | | | 74 | | | 74 | | | | |
| M | | | | | | | | | | | | | | | | | | |
| N | 70 | | | | | | | | | | | | | | | | | |
| P | | | | | | | | 73 | | | | | | | | | | |
| Q | | | | | 72 | | | | | | | | | | | | | |
| R | | | | 74 | | | | | 73 | | | | | | | 73 | | |
| S | 1 | | | | | | 74 | 1 | 73 | | | | | | | | | |
| T | | | | | | | | | | | | | | | | | 73 | |
| V | | | 2 | | | | | | | | | | | | | | | |
| W | | 74 | | | | | | | | | | | 74 | | | | | |
| X | | | | | | | | | | | | | | | | | | |
| Y | | | 1 | | | | | | | | | | | | | | | 72 |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 74 | 74 | 74 | 74 | 74 | 74 | 74 | 74 | 74 | 74 | 74 | 74 | 74 | 74 | 74 | 74 | 74 | 74 |
| oomcaa[3] | 70 | 74 | 70 | 74 | 72 | 74 | 73 | 73 | 73 | 74 | 74 | 74 | 74 | 74 | 74 | 73 | 73 | 72 |
| mcaa[4] | N | W | I | R | Q | S | P | S | R | G | L | E | W | L | G | R | T | Y |
| rel. oomcaa[5] | 95% | 100% | 95% | 100% | 97% | 100% | 99% | 99% | 99% | 100% | 100% | 100% | 100% | 100% | 100% | 99% | 99% | 97% |
| pos occupied[6] | 5 | 1 | 4 | 1 | 3 | 1 | 2 | 2 | 2 | 1 | 1 | 1 | 1 | 1 | 1 | 2 | 2 | 2 |

| amino acid[1] | CDR II | | | | | | | | | | | | | | | | |
|---|---|---|---|---|---|---|---|---|---|---|---|---|---|---|---|---|---|
| | A | B | C | 53 | 54 | 55 | 56 | 57 | 58 | 59 | 60 | 61 | 62 | 63 | 64 | 65 | 66 |
| A | | | | 1 | | | | | | | 73 | 1 | | | | | |
| B | | | | | | | | | | | | | | | | | |
| C | | | | | | | | | | 1 | | | | | | | |
| D | | | | | | | | | 68 | | | 1 | | | | | |
| E | | | | | | | 1 | | 3 | | | 7 | | | 1 | | |
| F | 1 | | | 1 | | | 7 | | | | | | | | | | |
| G | | | | | 1 | | | | 1 | | | | 1 | | | 8 | |
| H | 1 | | | | | | 1 | | | | | | | | | | |
| I | | | | | | | | | | | | 1 | | | | | |
| K | | 1 | | | 66 | | | 1 | | | | | | | 67 | | |
| L | | | | | | | | 1 | | | | 5 | | 2 | | | |
| M | | | | | | | | | | | | | | | | | |
| N | | | | | 1 | | 2 | 65 | 1 | | | | | | 1 | | |
| P | | | | | | | | | | | 1 | 1 | | | | | |
| Q | | | | | | | | | | | | | | | 2 | | 1 |
| R | | 72 | | | | 1 | 1 | | 1 | | | | | | 3 | | 73 |
| S | | 1 | | 72 | | | 2 | 2 | 1 | 1 | | | 73 | | | 66 | |
| T | | | | | 5 | | | | 4 | | | | | | | | |
| V | | | | | | | | | | | | 58 | 72 | | | | |
| W | | | | | | 73 | | | | | | | | | | | |
| X | | | | | | | | | | | | | | | | | |
| Y | 72 | | | | | | | 60 | 1 | 72 | | | | | | | |
| Z | | | | | | | | | | | | | | | | | |
| — | | | 74 | | | | | | | | | | | | | | |
| unknown (?) | | | | | | | | | | | | | | | | | |
| not sequenced | | | | | | | | | | | | | | | | | |
| sum of seq[2] | 74 | 74 | 74 | 74 | 74 | 74 | 74 | 74 | 74 | 74 | 74 | 74 | 74 | 74 | 74 | 74 | 74 |
| oomcaa[3] | 72 | 72 | 74 | 72 | 66 | 73 | 60 | 65 | 68 | 72 | 73 | 58 | 73 | 72 | 67 | 66 | 73 |
| mcaa[4] | Y | R | — | S | K | W | Y | N | D | Y | A | V | S | V | K | S | R |
| rel. oomcaa[5] | 97% | 97% | 100% | 97% | 89% | 99% | 81% | 88% | 92% | 97% | 99% | 78% | 99% | 97% | 91% | 89% | 99% |
| pos occupied[6] | 3 | 3 | 1 | 3 | 5 | 2 | 7 | 6 | 5 | 3 | 2 | 7 | 2 | 2 | 5 | 2 | 2 |

TABLE 6G-continued

Analysis of V heavy chain subgroup 6

Framework III

| amino acid[1] | 67 | 68 | 69 | 70 | 71 | 72 | 73 | 74 | 75 | 76 | 77 | 78 | 79 | 80 | 81 | 82 | A | B |
|---|---|---|---|---|---|---|---|---|---|---|---|---|---|---|---|---|---|---|
| A | | 2 | | | 6 | | 1 | | | | | | | | | | | |
| B | | | | | | | | | | | | | | | | | | |
| C | | | | | | | | | | | | | | | | | | |
| D | | | | 2 | | 73 | | | | | | | | | | | 3 | |
| E | | | | | | | | | 2 | | | | | | | | | |
| F | | | | | | | | | | | | | 71 | | | | | 1 |
| G | | | | | | | | | | | | | | | | | | |
| H | | | | | | 1 | | | | | | | | | 2 | | 1 | |
| I | 65 | 2 | 71 | | | | 1 | | | | | 1 | | | | | | |
| K | | | | 1 | | | | | 70 | | | | | | | | 4 | |
| L | 4 | | | | | | 1 | | | | 1 | | | 74 | | 72 | | |
| M | 1 | | | | | | | | | | | | | | | 1 | | |
| N | | | | 69 | | | | 74 | | | | | | | | | 63 | |
| P | | | | | | 66 | | | | | | | | | | | | |
| Q | | | | | | | | | | | 72 | | | | 71 | | | |
| R | | | | | | | | | | | 1 | | | | 1 | | 1 | |
| S | | 1 | | 2 | 1 | | 73 | | | | | | 74 | | | | 1 | 73 |
| T | | 69 | 1 | | | | 71 | 1 | 2 | | | | | | | | 1 | |
| V | 4 | | 2 | | 1 | | | | | | | 2 | | | | 1 | | |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 74 | 74 | 74 | 74 | 74 | 74 | 74 | 74 | 74 | 74 | 74 | 74 | 74 | 74 | 74 | 74 | 74 | 74 |
| oomcaa[3] | 65 | 69 | 71 | 69 | 66 | 73 | 71 | 73 | 70 | 74 | 72 | 71 | 74 | 74 | 71 | 72 | 63 | 73 |
| mcaa[4] | I | T | I | N | P | D | T | S | K | N | Q | F | S | L | Q | L | N | S |
| rel. oomcaa[5] | 88% | 93% | 96% | 93% | 89% | 99% | 96% | 99% | 95% | 100% | 97% | 96% | 100% | 100% | 96% | 97% | 85% | 99% |
| pos occupied[6] | 4 | 4 | 3 | 4 | 4 | 2 | 4 | 2 | 3 | 1 | 3 | 3 | 1 | 1 | 3 | 3 | 7 | 2 |

Framework III / CDR III

| amino acid[1] | C | 83 | 84 | 85 | 86 | 87 | 88 | 89 | 90 | 91 | 92 | 93 | 94 | 95 | 96 | 97 | 98 | 99 |
|---|---|---|---|---|---|---|---|---|---|---|---|---|---|---|---|---|---|---|
| A | | | | 1 | | | 74 | | | | | 69 | | 11 | 1 | 3 | 12 | 4 |
| B | | | | | | | | | | | | | | | | | | |
| C | | | | | | | | | | | 73 | | | | 1 | | | 1 |
| D | | | | | 73 | | | | | | | | | 19 | 4 | 3 | 7 | 4 |
| E | | | | 73 | | | | | | | | | | 10 | 4 | 2 | 1 | 2 |
| F | | | | | | | | | | 3 | | 1 | | 1 | 1 | 1 | | 1 |
| G | | | | | 1 | | | | | | | 1 | | 16 | 4 | 15 | 15 | 11 |
| H | | | | | | | | | | | | | | 1 | | | 1 | |
| I | | | | | | | | 2 | | | | | | 1 | 2 | | | 2 |
| K | | | | | | | | | | | | | 1 | 1 | 1 | 1 | 1 | 1 |
| L | | | | | | | | | | | | | 1 | 8 | 4 | 2 | | 3 |
| M | 1 | | | | | | | 2 | | | | | | 1 | | | | |
| N | | | | | | | | | | 1 | | | | 1 | 3 | 1 | 2 | 1 |
| P | | | 70 | | | | | | | | | | | | 10 | 4 | 1 | 5 |
| Q | | | | | | | | | | | | | | 1 | 1 | 1 | | 1 |
| R | | | | | | | | | | | 1 | | 69 | 1 | 7 | 8 | 1 | 8 |
| S | | 1 | 3 | | | | | | | | | | 3 | 5 | 5 | 5 | 7 | 6 |
| T | | 73 | | | | 74 | | | 1 | | | | | 1 | 1 | 4 | 3 | 4 |
| V | 73 | | | | | | | 70 | | | | 3 | 1 | 4 | 5 | 1 | 9 | |
| W | | | | | | | | | | | | | | 1 | 6 | 8 | | 3 |
| X | | | | | | | | | | | | | | | | | | |
| Y | | | | | | | | | 73 | 70 | | | | 6 | 4 | 2 | 2 | |
| Z | | | | | | | | | | | | | | | | | | |
| — | | | | | | | | | | | | | | 2 | 3 | 7 | | 14 |
| unknown (?) | | | | | | | | | | | | | | | | | | |
| not sequenced | | | 1 | | | | | | | | | | | 1 | 2 | 2 | | 1 |
| sum of seq[2] | 74 | 74 | 73 | 74 | 74 | 74 | 74 | 74 | 74 | 74 | 74 | 74 | 74 | 73 | 72 | 71 | 71 | 72 |
| oomcaa[3] | 73 | 73 | 70 | 73 | 73 | 74 | 74 | 70 | 73 | 70 | 73 | 69 | 69 | 19 | 10 | 15 | 15 | 14 |
| mcaa[4] | V | T | P | E | D | T | A | V | Y | Y | C | A | R | D | P | G | G | — |
| rel. oomcaa[5] | 99% | 99% | 96% | 99% | 99% | 100% | 100% | 95% | 99% | 95% | 99% | 93% | 93% | 26% | 14% | 21% | 21% | 19% |
| pos occupied[6] | 2 | 2 | 2 | 2 | 2 | 1 | 1 | 3 | 2 | 3 | 2 | 4 | 4 | 14 | 20 | 19 | 15 | 17 |

TABLE 6G-continued

Analysis of V heavy chain subgroup 6

| amino acid[1] | CDR III | | | | | | | | | | | | Framework IV | | | | | |
|---|---|---|---|---|---|---|---|---|---|---|---|---|---|---|---|---|---|---|
| | 100 | A | B | C | D | E | F | G | H | I | J | K | 101 | 102 | 103 | 104 | 105 | 106 |
| A | 3 | 2 | 5 | | 8 | | | | | | 10 | 1 | | | | | | |
| B | | | | | | | | | | | | | | | | | | |
| C | | | 1 | | 1 | 1 | | | | | | | | | | | | |
| D | 3 | 1 | 6 | 1 | 1 | 1 | | | | | | | | 62 | | | | |
| E | 2 | 1 | 2 | | | | | | | 1 | | | | | | | | |
| F | 2 | 3 | | 2 | | | 1 | | | | | | 38 | 4 | 2 | | | |
| G | 8 | 6 | 2 | 5 | 1 | 8 | 6 | 1 | | | 17 | | | | | 49 | | 50 |
| H | | 1 | 1 | 1 | 1 | | | | 1 | 1 | 1 | | | 2 | | | | |
| I | | | 5 | 1 | | | | | | | | | | 9 | | | | |
| K | 1 | | | | 1 | | | | | | | | | | | | 1 | |
| L | 2 | 1 | | | | | 1 | 5 | | | | 8 | | 5 | | | | |
| M | 1 | | | 5 | | | | | | | | 11 | | | | | | |
| N | 1 | 1 | 3 | | 2 | | 1 | | 1 | 3 | | | | | | | | |
| P | 3 | | 5 | 1 | | 1 | | | | | | | | 4 | | | 6 | |
| Q | | | | 1 | | | | | | | | | 1 | | | | 40 | |
| R | 8 | 3 | | 1 | 1 | 5 | | | | | | | 1 | | | | 2 | |
| S | 7 | 3 | 4 | 2 | | | | | 1 | 1 | | | | 4 | | 1 | | |
| T | 4 | 6 | 3 | 1 | | | 1 | | | | | | | | | | | |
| V | | 4 | | 9 | 5 | 1 | 1 | | | | | 2 | | 21 | | | | |
| W | 2 | 4 | | | | | | | 4 | 4 | | | | | 65 | | | |
| X | | | | | | | | | | | | | | | | | | |
| Y | 2 | 6 | 6 | 2 | 4 | 2 | 1 | 8 | 8 | 12 | 12 | | | 19 | | | | |
| Z | | | | | | | | | | | | | | | | | | |
| — | 23 | 25 | 33 | 41 | 47 | 53 | 54 | 57 | 56 | 50 | 28 | 12 | 4 | 2 | | | | |
| unknown (?) | | | | | | | 6 | 1 | 5 | | | | | | | | | |
| not sequenced | 1 | 1 | 1 | 1 | 1 | 1 | 1 | 1 | 1 | 1 | 1 | 1 | 1 | 5 | 8 | 23 | 24 | 23 |
| sum of seq[2] | 72 | 72 | 72 | 72 | 72 | 72 | 72 | 72 | 72 | 72 | 72 | 72 | 72 | 68 | 65 | 50 | 49 | 50 |
| oomcaa[3] | 23 | 25 | 33 | 41 | 47 | 53 | 54 | 57 | 56 | 50 | 28 | 38 | 62 | 21 | 65 | 49 | 40 | 50 |
| mcaa[4] | — | — | — | — | — | — | — | — | — | — | — | F | D | V | W | G | Q | G |
| rel. oomcaa[5] | 32% | 35% | 46% | 57% | 65% | 74% | 75% | 79% | 78% | 69% | 39% | 53% | 86% | 31% | 100% | 98% | 82% | 100% |
| pos occupied[6] | 16 | 16 | 13 | 13 | 11 | 8 | 8 | 4 | 5 | 7 | 6 | 6 | 5 | 9 | 1 | 2 | 4 | 1 |

| amino acid[1] | Framework IV | | | | | | | sum |
|---|---|---|---|---|---|---|---|---|
| | 107 | 108 | 109 | 110 | 111 | 112 | 113 | |
| A | | 2 | | | | | | 494 |
| B | | | | | | | | |
| C | | | | | | | | 147 |
| D | | | 1 | | | | | 403 |
| E | | | | | | | | 186 |
| F | | | | | | | 2 | 150 |
| G | | | | | | | | 571 |
| H | | | | | | | | 18 |
| I | 3 | | 1 | | | | | 304 |
| K | | 1 | | | | | | 293 |
| L | | 26 | | | | | | 632 |
| M | | 8 | | | | | | 31 |
| N | | | | | | | | 436 |
| P | | | | | | | 1 | 387 |
| Q | | | | | | | | 539 |
| R | | | | | | | | 495 |
| S | 1 | | | | | 43 | 46 | 1271 |
| T | 45 | 4 | | 45 | | | | 640 |
| V | | 2 | 46 | | 48 | | | 647 |
| W | | 5 | | | | | | 398 |
| X | | | | | | | | |
| Y | | | | | | | | 518 |
| Z | | | | | | | | |
| — | | | | | | | | 585 |
| unknown (?) | | | | | | | | 13 |
| not sequenced | 24 | 25 | 25 | 28 | 25 | 28 | 26 | 580 |
| sum of seq[2] | 49 | 48 | 48 | 45 | 48 | 45 | 47 | |
| oomcaa[3] | 45 | 26 | 46 | 45 | 48 | 43 | 46 | |
| mcaa[4] | T | L | V | T | V | S | S | |
| rel. oomcaa[5] | 92% | 54% | 96% | 100% | 100% | 96% | 98% | |
| pos occupied[6] | 3 | 7 | 3 | 1 | 1 | 2 | 2 | |

Appendix to Tables 1A–C
A. References of Rearranged Sequences
References of Rearranged Human Kappa Sequences Used for Alignment 1. Alescio-Zonta, L. & Baglioni, C (1970) Eur. J. Biochem., 15, 450–463.
2. Andrews, D. W. & Capra, J. D. (1981) Biochemistry, 20, 5816–5822.
3. Andris, J. S., Ehrlich, P. H., Ostberg, L. & Capra. J. D. (1992) J. Immunol., 149, 4053–4059.
4. Atkinson, P. M., Lampman, G. W., Furie, B. C., Naparstek, Y., Schwartz, R. S., Stollar, B. D. & Furie, B. (1985) J. Clin. Invest., 75. 1138–1143.
5. Aucouturier, P., Bauwens, M., Khamlichi, A. A., Denoroy, L. Spinelli, S., Touchard, G., Preud'homme, J.-L. & Cogne, M. (1993) J. Immunol., 150, 03561–3568.
6. Avila, M. A., Vazques, J., Danielsson, L., Fernandez De Cossio, M. E. & Borrebaeck, C. A. K. (1993) Gene, 127, 273–274.
7. Barbas Iil, C. F., Crowe, Jr., J. E., Cababa, D., Jones, T. M., Zebedee, S. L., Murphy, B. R., Chanock, R. M. & Burton, D. R. (1992) Proc. Natl. Acad. Sci. Usa, 89, 10164–10168.
8. Barbas, C. F., Iii, et al. (1993) J-Mol-Biol., 230, 812–23.
9. Bentley, D. L. & Rabbitts, T. H. (1980) Nature, 288, 730–733.
10. Bentley, D. L. & Rabbitts, T. H. (1983) Cell, 32, 181–189.
11. Bentley, D. L. (1984) Nature, 307, 77–80.
12. Bhat, N. M., Bieber, M. M., Chapman, C. J., Stevenson, F. K. & Teng, N. N. H. (1993) J. Immunol., 151, 5011–5021.
13. Blaison, G., Kuntz, J.-L. & Pasquali, J.-L. (1991) Eur. J. Immunol., 21, 1221–1227.
14. Braun, H., Leibold, W., Barnikol, H. U. & Hilschmann, N. (1971) Z. Physiol. Chem., 352, 647–651; (1972) Z. Physiol. Chem., 353, 1284–1306.
15. Capra, J. D. & Kehoe, J. M. (1975) Adv. Immunology, 20, 1–40.; Andrews, D. W. & Capra, J. D. (1981) Proc. Nat. Acad. Sci. Usa, 78, 3799–3803.
16. Capra, J. D. & Kehoe, J. M. (1975) Adv. Immunology, 20, 1–40.; Ledford, D. K., Goni, F., Pizzolato, M., Franklin, E. C. Solomon, A. & Frangione, B. (1983) J. Immunol., 131, 1322–1325.
17. Chastagner, P., Theze, J. & Zouali, M. (1991) Gene, 101, 305–306.
18. Chen, P. P., Robbins, D. L., Jirik, F. R. Kipps, T. J. & Carson, D. A. (1987) J. Exp. Med, 166, 1900–1905.
19. Chen, P. P., Robbins, D. L., Jirik, F. R., Kipps, T. J. & Carson, D. A. (1987) J. Exp. Med. 166, 1900–1905; Liu, M.-F., Robbins, D. L., Crowley, J. J., Sinha, S., Kozin, F., Kipps, T. J., Carson, D. A. & Chen. P. P. (1989) J. Immunol., 142, 688–694.
20. Chersi, A. & Natali, P. G. (1978) Immunochemistry, 15, 585–589.
21. Co, M. S., Deschamps, M., Whitley, R. J. & Queen, C. (1991) Proc. Natl. Acad. Sci. Usa, 88. 2869–2873.
22. Cuisinier, A.-M., Fumoux. F., Fougereau, M. & Tonnelle, C. (1992) Mol. Immunol., 29, 1363–1373.
23. Davidson, A., Manheimer-Lory, A., Aranow, C., Peterson, R., Hannigan, N. & Diamond, B. (1990) J. Clin. Invest., 85, 1401–1409.
24. Denomme, G. A., Mahmoudi, M., Edwards, J. Y., Massicotte, H., Cairns, E. & Bell, D. A. (1993) Hum. Antibod. Hybridomas, 4, 98–103.
25. Dersimonian, H., Mcadam, K. P. W. J., Mackworth-Young, C. & Stollar, B. D. (1989) J. Immunol., 142, 4027–4033.
26. Dreyer, W. J., Gray, W. R. & Hood, L. (1967) Cold Spring Harbor Symp. Quantitative Biol., 32, 353–367.
27. Ebeling, S. B., Schutte, M. E. M. & Logtenberg, T. (1993) Eur. J. Immunol., 23, 1405–1408.
28. Eulitz, M. & Kley, H.-P. (1977) Immunochem., 14, 289–297.
29. Eulitz, M. & Linke. R. P. (1982) Z. Physiol. Chem., 363, 1347–1358.
30. Eulitz, M., Breuer, M., Eblen, A., Weiss, D. T. & Solomon, A. (1990) In Amyloid And Amyloidosis, Eds J. B. Natvig, O. Forre, G. Husby, A. Husebekk, B. Skogen, K. Sletten & P. Westermark, Kluwer Academic
31. Eulitz, M., Gotze, D. & Hilschmann, N. (1972) Z. Physiol. Chem., 353, 487–491; Eulitz, M. & Hilschmann, N. (1974) Z. Physiol. Chem., 355, 842–866.
32. Eulitz, M., Kley, H. P. & Zeitler, H. J. (1979) Z. Physiol. Chem., 360, 725–734.
33. Ezaki, I., Kanda, H., Sakai, K., Fukui, N., Shingu, M., Nobunaga, M. & Watanabe, T. (1991) Arthritis And Rheumatism, 34, 343–350.
34. Felgenhauer, M., Kohl, J. & Ruker, F. (1990) Nucl. Acids Res., 18, 4927.
35. Ferri, G., Stoppini, M., Iadarola, P., Bellotti, V. & Merlini, G. (1989) Biochim. Biophys. Acta, 995, 103–108.
36. Gillies, S. D., Dorai, H., Wesolowski, J., Majeau, G., Young, D., Boyd, J., Gardner, J. & James, K. (1989) Bio/Tech., 7, 799–804.
37. Goni, F. & Frangione, B. (1983) Proc. Nat. Acad. Sci. Usa, 80, 4837–4841.
38. Goni, F. R., Chen, P. P., Mcginnis, D., Arjonilla, M. L., Fernandez. J., Carson, D., Solomon, A., Mendez, E. & Frangione, B. (1989) J. Immunol., 142, 3158–3163.
39. Gorman, S. D., Clark, M. R., Routledge, E. G., Cobbold, S. P. & Waldmann, H. (1991) Proc. Natl. Acad. Sci. Usa, 88, 4181–4185.
40. Gottlieb, P. D., Cunningham, B. A., Rutishauser, U. & Edelman, G. M. (1970) Biochemistry, 9, 3155–3161.
41. Griffiths, A. D., Malmqvist, M., Marks, J. D., Bye, J. M., Embleton, M. J., Mccafferty, J., Baier, M., Holliger, K. P., Gorick, B. D., Hughes-Jones, N. C., Hoogenboom, H. R. & Winter, G. (1993) Embo J., 12, 725–734.
42. Hieter, P. A., Max, E. E., Seidman, J. G., Maizel. J. V., Jr. & Leder, P. (1980) Cell, 22, 197–207; Klobeck, H. G., Meindl, A., Combriato, G., Solomon. A. & Zachau, H. G. (1985) Nucl. Acids Res., 13, 6499–6513; Weir, L. & Leder, P. (1986)
43. Hilschmann, N. & Craig, L. C. (1965) Proc. Nat. Acad. Sci. Usa, 53, 1403–1409; Hilschmann, N. (1967) Z. Physiol. Chem., 348, 1077–1080.
44. Hilschmann, N. & Craig, L. C. (1965) Proc. Nat. Acad. Sci. Usa, 53, 1403–1409; Hilschmann, N. (1967) Z. Physiol. Chem., 348, 1718–1722; Hilschmann, N. (1969) Naturwissenschaften, 56, 195–205.
45. Hirabayashi, Y., Munakata, Y., Sasaki, T. & Sano, H. (1992) Nucl. Acids Res., 20, 2601.
46. Jaenichen, H.-R., Pech, M., Lindenmaier, W., Wildgruber, N. & Zachau, H. G. (1984) Nuc. Acids Res., 12, 5249–5263.
47. Jirik, F. R., Sorge, J., Fong, S., Heitzmann, J. G., Curd, J. G., Chen, P. P., Goldfien, R. & Carson, D. A. (1986) Proc. Nat. Acad. Sci. Usa, 83, 2195–2199.
48. Kaplan, A. P. & Metzger, H. (1969) Biochemistry, 8, 3944–3951.; Klapper, D. G. & Capra, J. D. (1976) Ann. Immunol. (Inst. Pasteur). 127c, 261–271.
49. Kennedy, M. A. (1991) J. Exp. Med., 173, 1033–1036.
50. Kim, H. S. & Deutsch, H. F. (1988) Immunol., 64, 573–579.

51 Kipps, T. J., Tomhave, E., Chen, P. P. & Carson, D. A. (1988) J. Exp. Med., 167, 840–852.
52 Kipps, T. J., Tomhave, E., Chen, P. P. & Fox, R. I. (1989) J. Immunol., 142, 4261–4268.
53 Klapper, D. G. & Capra, J. D. (1976) Ann. Immunol. (Inst. Pasteur), 127c. 261–271.
54 Klein, U., Kuppers, R. & Rajewsky, K. (1993) Eur. J. Immunol., 23, 3272–3277.
55 Klobeck, H. G. Mcindl, A., Combriato, G., Solomon., A. & Zachau, H. G. (1985) Nucl. Acids Res., 13, 6499–6513.
56 Klobeck, H. G., Bornkammm, G. W., Combriato, G., Mocikat, R., Pohlenz, H. D. & Zachau, H. G. (1985) Nucl. Acids Res., 13, 6515–6529.
57 Klobeck, H. G., Combriato, G. & Zachau, H. G. (1984) Nuc. Acids Res., 12, 6995–7006.
58 Klobeck, H. G., Solomon, A. & Zachau, H. G. (1984) Nature, 309, 73–76.
59 Knight, G. B., Agnello, V., Bonagura, V., Barnes, J. L., Panka. D. J. & Zhang, O.-X. (1993) J. Exp. Med., 178, 1903–1911.
60 Kohler, H., Shimizu, A., Paul, C. & Putnam, F. W. (1970) Science, 169, 56–59. (Kaplan, A. P. & Metzger, H. (1969) Biochemistry, 8, 3944–3951.)
61 Kratzin, H., Yang, C. Y., Krusche, J. U. & Hilschmann, N. (1980) Z. Physiol. Chem., 361, 1591–1598.
62 Kunicki, T. J., Annis, D. S., Gorski, J. & Nugent, D. J. (1991) J. Autoimmunity, 4, 433–446.
63 Larrick, J. W., Wallace, E. F., Coloma, M. J., Bruderer, U., Lang, A. B. & Fry, K. E. (1992) Immunological Reviews, 130, 69–85.
64 Laure, C. J., Watanabe, S. & Hilschmann, N. (1973) Z. Physiol. Chem., 354, 1503–1504.
65 Ledford, D. K., Goni, F., Pizzolato, M., Franklin, E. C., Solomon, A. & Frangione, B. (1983) J. Immunol., 131, 1322–1325.
66 Ledford, D. K., Goni, F., Pizzolato, M., Franklin, E. C., Solomon, A. & Frangione, B. (1983) J. Immunol., 131, 1322–1325.
67 Ledford, D. K., Goni, F., Pizzolato, M., Franklin, E. C., Solomon, A. & Frangione, B. (1983) J. Immunol., 131, 1322–1325. Pons-Estel, B., Goni, F., Solomon, A. & Frangione, B. (1984) J. Exp. Med., 160, 893.
68 Levy, S., Mendel, E., Kon, S., Avnur, Z. & Levy, R. (1988) J. Exp. Med., 168, 475–489.
69 Liepnieks, J. J., Dwulet, F. E. & Benson, M. D. (1990) Mol. Immunol., 27, 481–485.
70 Manheimer-Lory, A., Katz, J. B., Pillinger, M., Ghossein, C., Smith, A. & Diamond, B. (1991) J. Exp. Med., 174, 1639–1652.
71 Mantovani, L., Wilder, R. L. & Casali, P. (1993) J. Immunol., 151, 473–488.
72 Mariette, X., Tsapis, A. & Brouet, J.-C. (1993) Eur. J. Immunol., 23, 846–851.
73 Marks, J. D., Hoogenboom, H. R., Bonnert, T. P., Mccafferty, J., Grifriths, A. D. & Winter, G. (1991) J. Mol. Biol, 222, 581–597.
74 Marsh, P., Mills, F. & Gould, H. (1985) Nuc. Acids Res., 13, 6531–6544.
75 Middaugh, C. R. & Litman, G. W. (1987) J. Biol. Chem., 262, 3671–3673.
76 Milstein, C. & Deverson, E. V. (1971) Biochem. J., 123, 945–958.
77 Milstein, C. (1969) Febs Letters, 2, 301–304.
78 Milstein, C. (1969) Febs Letters, 2, 301–304.
79 Milstein, C. P. & Deverson, E. V. (1974) Eur. J. Biochem., 49, 377–391.
80 Moran, M. J., Andris, J. S., Matsumato, Y.-I., Capra, J. D. & Hersh, E. M. (1993) Mol. Immunol., 30, 1543–1551.
81 Nakatani, T., Nomura, N., Horigome, K., Ohtsuka, H. & Noguchi, H. (1989) Bio/Tech., 7, 805–810.
82 Newkirk, M., Chen, P. P., Carson, D., Posnett, D. & Capra, J. D. (1986) Mol. Immunol., 23, 239–244.
83 Newkirk, M. M., Gram, H., Heinrich, G. F., Ostberg, L. Capra, J. D. & Wasserman, R. L. (1988) J. Clin. Invest., 81, 1511–1518.
84 Newkirk, M. M., Mageed, R. A., Jefferis, R., Chen, P. P. & Capra, J. D. (1987) J. Exp. Med., 166, 550–564.
85 Olee, B. T., Lu, E. W., Huang, D.-F., Soto-Gil, R. W., Deftos, M., Kozin, F., Carson, D. A. & Chen, P. P. (1992) J. Exp. Med., 175, 831–842.
86 Palm, W. & Hilschmann, N. (1973) Z. Physiol. Chem., 354, 1651–1654; (1975) Z. Physiol. Chem., 356, 167–191.
87 Pascual, V., Victor, K., Lelsz, D., Spellerberg, M. B., Hamblin, T. J., Thompson, K. M., Randen, I., Natvig, J., Capra, J. D. & Stevenson, F. K. (1991) J. Immunol., 146, 4385–4391.
88 Pascual, V., Victor, K., Randen, I., Thompson, K., Steinitz, M., Forre, O., Fu, S.-M., Natvig, J. B. & Capra, J. D. (1992) Scand. J. Immunol., 36, 349–362.
89 Pech, M. & Zachau, H. G. (1984) Nuc. Acids Res., 12, 9229–9236.
90 Pech, M., Jaenichen, H.-R., Pohlenz, H.-D., Neumaier, P. S., Klobeck, H.-G. & Zachau, H. G. (1984) J. Mol. Biol., 176, 189–204.
91 Pons-Estel, B., Goni, F., Solomon, A. & Frangione, B. (1984) J. Exp. Med., 160, 893–904.
92 Portolano, S., Mclachlan, S. M. & Rapoport, B. (1993) J. Immunol., 151, 2839–2851.
93 Portolano, S., Seto, P., Chazenbalk, G. D., Nagayama, Y., Mclachlan, S. M. & Rapoport, B. (1991) Biochem. Biophys. Res. Commun., 179, 372–377.
94 Pratt, L. F., Rassenti, L., Larrick, J., Robbins, B., Banks, P. M. & Kipps, T. J. (1989) J. Immunol., 143, 699–705.
95 Prelli, F., Tummolo, D., Solomon, A. & Frangione, B. (1986) J. Immunol., 136, 4169–4173.
96 Putnam, F. W., Whitley, E. J., Jr., Paul, C. & Davidson, J. N. (1973) Biochemistry, 12, 3763–3780.
97 Randen, I., Pascual, V., Victor, K., Thompson, K. M., Forre, O., Capra, J. D. & Natvig, J. B. (1993) Eur. J. Immunol., 23, 1220–1225.
98 Rassenti, L. Z., Pratt, L. F., Chen, P. P., Carson, D. A. & Kipps, T. J. (1991) J. Immunol., 147, 1060–1066.
99 Reidl, L. S., Friedman, D. F., Goldman, J., Hardy, R. R., Jefferies, L. C. & Silberstein, L. E. (1991) J. Immunol., 147, 3623–3631.
100 Riechmann, L., Clark, M., Waldmann, H. & Winter, G. (1988) Nature, 332, 323–327.
101 Riesen, W., Rudikoff, S., Oriol, R. & Potter, M. (1975) Biochemistry, 14, 1052–1057; Riesen, W. F., Braun, D. G. & Jaton, J. C. (1976) Proc. Nat. Acad. Sci. Usa, 73, 2096–2100; Riesen, W. F. & Jaton, J. C. (1976) Biochemistry, 15, 3829.
102 Rodilla Sala, E., Kratzin, D. H., Pick, A. I. & Hilschmann, N. (1990) In Amyloid And Arnyloidosis, Eds. J. B. Natvig, O. Forre, G. Husby, A. Husebekk, B. Skogen, K. Sletten & P. Westermark, Kluwer Academic
103 Schiechl, H. & Hilschmann, N. (1971) Z. Physiol. Chem., 352, 111–115; (1972) Z. Physiol. Chem., 353, 345–370.
104 Schneider, M. & Hilschmann, N. (1974) Z. Physiol. Chem., 355, 1164–1168.
105 Shearman, C. W., Pollock, D., White, G., Hehir, K., Moore, G. P., Kanzy, E. J. & Kurrle, R. (1991) J. Immunol., 147, 4366–4373.

106 Shinoda, T. (1973) J. Biochem., 73, 433–446.

107 Shinoda, T. (1975) J. Biochem., 77, 1277–1296.

108 Shinoda, T., Takenawa, T., Hoshi, A. & Isobe, T. (1990) In Amyloid And Amyloidosis, Eds. J. B. Natvig, O. Forre, G. Husby, A. Husebekk, B. Skogen, K. Sletten & P. Westermark, Kluwer Academic Publishers, Dordrecht/Boston/London, Pp.157

109 Silberstein, L. E., Litwin, S. & Carmack, C. E. (1989) J. Exp. Med., 169, 1631–1643.

110 Sims, M. J., Hassal, D. G. Brett, S., Rowan. W., Lockyer, M. J., Angel, A., Lewis, A. P., Hale, G., Waldmann, H. & Crowe, J. S. (1993) J. Immunol., 151, 2296–2308.

111 Spatz, L. A., Wong, K. K., Williams, M., Desai, R., Golier, J., Berman, J. E., Alt, F. W. & Latov, N. (1990) J. Immunol., 144, 2821–2828.

112 Stavnezer, J., Kekish, O., Batter, D., Grenier, J., Balazs, I., Henderson, E. & Zegers, B. J. M. (1985) Nucl. Acids Res., 13, 3495–3514.

113 Straubinger, B., Thiebe, R., Pech, M. & Zachau, H. G. (1988) Gene. 69.209–214.

114 Suter, L., Barnikol, H. U., Watanabe, S. & Hilschmann, N. (1969) Z. Physiol. Chem, 350, 275–278; (1972) Z. Physiol. Chem., 353, 189–208.

115 Tempest, P. R., Bremner, P., Lambert, M., Taylor, G., Furze, J. M., Carr, F. J. & Harris, W. J. (1991) Bio/Tech., 9, 266–271.

116 Titani, K., Shinoda, T. & Putnam, F. W. (1969) J. Biol. Chem., 244, 3550–3560.

117 Toft, K. G., Olstad, O. K., Sletten, K. & Westermark, P. (1990) In Amyloid And Amyloidosis, Eds. J. B. Natvig, O. Forre. G. Husby, A. Husebekk, B. Skogen, K. Sletten & P. Westermark, Kluwer Academic 118 Van Es, J. H., Aanstoot, H., Gmelig-Meyling, F. H. J., Derksen, R. H. W. M. & Logtenberg, T. (1992) J. Immunol., 149, 2234–2240.

119 Victor, K. D., Pascual, V., Lefvert, A. K. & Capra, J. D. (1992) Mol. Immunol., 29, 1501–1506.

120 Victor, K. D., Pascual, V., Williams, C. L., Lennon, V. A. & Capra, J. D. (1992) Eur. J. Immunol., 22, 2231–2236.

121 Victor, K. D., Randen, I., Thompson, K., Forre, O., Natvig, J. B., Fu, S. M. & Capra, J. D. (1991) J. Clin. Invest., 87, 1603–1613.

122 Wagner, S. D. & Luzzatto, L. (1993) Eur. J. Immunol., 23, 391–397.

123 Watanabe, S. & Hilschmann, N. (1970) Z. Physiol. Chem., 351, 1291–1295.

124 Weisbart, R. H., Wong, A. L., Noritake, D., Kacena, A., Chan, G., Ruland, C., Chin, E., Chen, I. S. Y. & Rosenblatt, J. D. (1991) J. Immunol., 147, 2795–2801.

125 Weng, N.-P., Yu-Lee, L.-Y., Sanz, I., Patten, B. M. & Marcus, D. M. (1992) J. Immunol., 149, 2518–2529.

126 Winkler, T. H., Fehr, H. & Kalden, J. R. (1992) Eur. J. Immunol., 22, 1719–1728.

References of Rearranged Human Lambdo Sequences Used for Alignment

1 Alexandre, D., Chuchana, P., Brockly, F., Blancher, A., Lefranc, G. & Lefrane, M.-P. (1989) Nuc. Acids Res., 17, 3975.

2 Anderson, M. L. M., Brown, L., Mckenzie, E., Kellow, J. E. & Young, B. D. (1985) Nuc.Acids Res., 13, 2931–2941.

3 Andris, J. S., Brodeur, B. R. & Capra. J. D. (1993, Mol.Immunol., 30, 1601–1616.

4 Andris, J. S., Ehrlich, P. H., Ostberg, L & Capra, J. D. (1992) J.Immunol., 149, 4053–4069.

5 Baczko, K., Braun, D. G., Hess, M. & Hilschmann, N. (1970) Z.Physiol.Chem., 351, 763–767; Baczko, K., Braun, D. G. & Hilschmann, N. (1974) Z.Physiol.Chem., 355,131–154.

6 Berinstein, N., Levy. S. & Levy, R. (1989) Science, 244, 337–339.

7 Bhat, N. M., Bieber, M. M., Chapman, C. J., Stevenson, F. K. & Teng, N. N. H. (1993) J.Immunol., 151, 5011–5021.

8 Cairns, E., Kwong, P. C., Misener, V., Ip, P., Bell, D. A. & Siminovitch, K. A. (1989) J.Immunol., 143, 685–691.

9 Carroll, W. L., Yu, M., Link, M. P. & Korsmeyer, S. J. (1989) J.Immunol., 143, 692–698.

10 Chen, B. L. & Poljak, R. J. (1974) Biochemistry, 13, 1295–1302.

11 Chen, B. L, Chiu, Y. Y. H., Humphrey, R. L. & Poljak, R. J. (1978) Biochim.Biophys.Acta, 537, 9–21.

12 Combriato, G. & Klobeck. H. G. (1991) Eur.J.Immunol., 21, 1513–1522.

13 Cuisinier, A.-M., Fumoux. F., Fougereau, M. & Tonnelle. C. (1992) Mol.Immunol., 29, 1363–1373.

14 Dwulet, F. E., Strako, K. & Benson. M. D. (1985) ScandJ.Immunol., 22, 653–660.

15 Elahna, P., Livneh, A, Manheimer-Lory, A. J. & Diamond, B. (1991) J.Immunol., 147, 2771–2776.

16 Engelhard, M., Hess, M. & Hilschmann, N. (1974) Z.Physiol.Chem., 355, 85–88; Engelhard, M. & Hilschmann, N. (1975) Z.Physiol.Chem., 356, 1413–1444.

17 Eulitz, M. (1974) Eur.J.Biochem., 50, 49–69.

18 Eulitz, M., Breuer, M. & Linke, R. P. (1987) Biol.Che.Hoppe-Seyler, 368, 863–870.

19 Eulitz, M., Murphy, C., Weiss, D. T. & Solomon, A. (1991) J.Immunol., 146. 3091–3096.

20 Fett, J. W. & Deutsch, H. F. (1974) Biochemistry, 13, 4102–4114.

21 Fett. J. W. & Deutsch, H. F. (1976) Immunochem., 13, 149–155.; Jabusch, J. R. & Deutsch, H. F. (1982) Mol.Immunol., 19, 901–906.

22 Furey, W. Jr., Wang, B. C., Yoo, CS. & Sax. M. (1983) J.Mol.Biol., 167, 661–692.

23 Fykse, E. -M., Sletten. K., Husby. G. & Cornwell, G. G., Iii (1988) Biochem.J., 256, 973–980.

24 Garver, F. A. & Hilschmann, N. (1971) Febs Letters, 16, 128–132; (1972) EurJ.Biochem., 26, 10–32.

25 Gawinowicz, M. A, Merlini, G., Birken, S., Osserman, E. F. & Kabat, E. A (1991) J.Immunol., 147, 915–920.

26 Ghiso, J., Solomon. A. & Frangione, B. (1986) J.Immunol., 136, 716–719.

27 Griffiths, A. D., Malmqvist, M., Marks, J. D., Bye. J. M., Embleton, M. J., Mccafferty, J., Baier, M., Holliger, K. P., Gorick, B. D., Hughes-Jones N. C., Hoogenboom, H. R. & Winter, G. (1993) Embo J., 12, 725–734.

28 Gullasken, N., Idso, H., Nilsen, R., Sletten, K., Husby, G. & Cornwell, G. G. (1990) in Amyloid And Amyloidosis, Eds. J. B. Natvig, O. Forre, G. Husby, A. Husebekk, B. Skogen, K.Sletten & P. Westermark. Kluwer Academic 29 Harindranath, N., Goldfarb, I. S., Ikematsu, H., Burastero, S. E., Wilder. R. L., Notkins, A. L. & Casali, P. (1991) Int.Immunol., 3.865–875.

30 Holm, E., Sletten, K. & Husby, G. (1986) Biochem.J., 239, 545–551.

31 Hughes-Jones, N. C., Bye, J. M., Beale, D. & Coadwell, J. (1990) Biochem.J., 268, 135–140.

32 Kametani, F., Yoshimura, K., Tonoike, H., Hoshi, A., Shinoda, T. & Isobe, T. (1985) Biochem.Biophys.Res.Commun., 126, 848–852.

33 Kiefer, C. R., Mcguire, B. S., Jr., Osserman, E. F. & Garver, F. A. (1983) J.Immunol., 131, 1871–1875.

34 Kiefer, C. R., Patton, H. M., Jr., Mcquire, B. S., Jr. & Garver, F. A. (1980) J.Immunol., 124, 301–306.

35 Kishimoto, T., Okajima, H., Okumoto, T. & Taniguchi, M. (1989) Nucl.Acids Res., 17, 4385.

36 Klafki, H.-W., Kratzin, H. D., Pick. A. I., Eckart, K. & Hilschmann. N. (1990) In Amyloid And Amyloidosis, Eds. J. B. Natvig, O. Forre, G. Husby, A. Husebekk, B. Skogen, K. Sletten & P. Westermark, Kluwer Academic 37 Kohler, H., Rudofsky, S. & Kluskens, L. (1975) J.Immunology, 114, 415–421.

38 Kojima, M., Odani, S. & Ikenaka, T. (1980) Mol.Immunol., 17, 1407–1414.

39 Komori, S., Yamasaki, N., Shigeta, M., Isojima, S. & Watanabe, T. (1988) Clin.Exp.Immunol., 71, 508–516.

40 Kratzin, H. D., Palm, W., Stangel. M., Schmidt, W. E., Friedrich. J. & Hilschmann, N. (1989) Biol.Chem.Hoppe-Seyler, 370 263–272.

41 Kratzin, H. D., Pick, A. I., Stangel, M. & Hilschmann, N. (1990) In Amyloid And Amyloidosis, Eds. J. B. Natvig, O. Forre. G. Husby, A. Husebekk, B. Skogen, K. Sletten & P. Westermark, Kluwer Academic Publishers, Dordrecht/Boston/London, Pp. 181.

42 Langer, B., Steinmetz-Kayne, M. & Hilschmann, N. (1968) Z. Physiol.Chem., 349, 945–951.

43 Larrick, J. W., Danielsson, L. Brenner, C. A., Wallace, E. F., Abrahamson, M., Fry, K. E. & Borrebaeck, C. A. K. (1989) Bio/Tech., 7. 934–938.

44 Levy, S., Mendel, E., Kon. S., Avnur, Z. & Levy, R. (1988) J.Exp.Med., 168, 475–489.

45 Lewis, A. P., Lemon, S. M., Barber, K. A., Murphy, P., Parry, N. R., Peakman, T. C., Sims, M. J., Worden, J. & Crowe, J. S. (1993) J.Immunol., 151, 2829–2838.

46 Liu, V. Y. S., Low, T. L. K., Infante, A. & Putnam, F. W. (1976) Science, 193, 1017–1020; Infante, A. & Putnam, F. W. (1979) J.Biol.Chem., 254, 9006–9016.

47 Lopez De Castro, J. A., Chiu, Y. Y. H. & Poljak, R. J. (1978) Biochemistry, 17, 1718–1723.

48 Mantovani, L., Wilder, R. L. & Casali, P. (1993) J.Immunol., 151, 473–488.

49 Marks, J. D., Hoogenboom, H. R., Bonnert, T. P., Mccafferty, J., Griffiths. A. D. & Winter, G. (1991) J.Mol.Biol., 222, 581–597.

50 Mihaesco, E., Roy, J.-P., Congy, N., Peran-Rivat, L. & Mihaesco, C. (1985) EurJ.Biochem., 150, 349–357.

51 Milstein. C., Clegg, J. B. & Jarvis, J. M. (1968) BiochemJ., 110, 631–652.

52 Moran, M. J., Andris, J. S., Matsumato, Y.-I., Capra, J. D. & Hersh, E. M. (1993) Mol.Immunol., 30,1543–1551.

53 Nabeshima, Y. & Ikenaka, T. (1979) Mol.Immunol, 16, 439–444.

54 Olee, B. T., Lu, E. W., Huang, D.-F., Soto-Gil, R. W., Deftos, M., Kozin, F., Carson, D. A. & Chen, P. P. (1992) J.Exp.Med., 175, 831–842.

55 Pascual, V., Victor, K., Randen, I., Thompson, K., Steinitz, M., Forre, O., Fu, S.-M., Natvig. J. B. & Capra, J. D. (1992) Scand.J.Immunol., 36, 349–362.

56 Paul, E., Iliev, A. A., Livneh, A. & Diamond, B. (1992) J.Immunol., 149, 3588–3595.

57 Pick, A. I., Kratzin, H. D., Barnikol-Watanabe, S. & Hilschmann, N. (1990) In Amyloid And Amyloidosis. Eds. J. B. Natvig. O. Forre, G. Husby, A. Husebekk, B. Skogen, K. Sletten & P. Westermark, Kluwer Academic 58 Ponstingl, H. & Hilschmann, N. (1969) Z.Physiol.Chem., 350, 1148–1152; (1971) Z.Physiol.Chem, 352, 859–877.

59 Ponstingl, H., Hess, M. & Hilschmann, N. (1968) Z.Physiol.Chem., 349, 867–871; (1971) Z.Physiol.Chem., 352, 247–266.

60 Randen, I., Pascual, V., Victor, K., Thompson, K. M., Forre, O., Capra, J. D. & Natvig, J. B. (1993) EurJ.Immunol., 23, 1220–1225.

61 Scholz, R. & Hilschmann, N. (1975) Z.Physiol.Chem., 356, 1333–1335.

62 Settmacher, U., Jahn, S., Siegel, P., Von Baehr, R. & Hansen, A. (1993) Mol.Immunol, 30, 953–954.

63 Shinoda, T., Titani, K. & Putnam, F. W. (1970) J.Biol.Chem., 245, 4475–4487.

64 Sletten, K., Husby, G. & Natvig, J. B. (1974) Scand.J.Immunol., 3, 833–836.; Sletten. K., Natvig, J. B., Husby, G. & Juul, J. (1981) BiochemJ., 195, 561–572.

65 Solomon, A, Frangione. B. & Franklin, E. C. (1982) J.Clin.Invest, 70, 453–460.; Frangione, B., Moloshok, T. & Solomon, A. (1983) J.Immunol., 131, 2490–2493.

66 Takahashi, N., Takayasu, T., Isobe, T., Shinoda, T., Okuyama, T. & Shimizu, A. (1979) J.Biochem., 86, 1523–1535.

67 Takahashi, N., Takayasu, T., Shinoda, T., Ito, S., Okuyama, T. & Shimizu. A. (1980) Biomed.Res., 1, 321–333.

68 Takahashi, Y., Takahashi, N., Tetaert, D. & Putnam, F. W. (1983) Proc.Nat.Acad.Sci.Usa, 80, 3686–3690.

69 Takayasu, T., Takahashi, N., Shinoda, T., Okuyama, T. & Tomioka, H. (1980) J.Biochem., 89, 421–436.

70 Titani, K., Wikier, M., Shinoda, T. & Putnam, F. W. (1970) J.Biol.Chem., 245, 2171–2176.

71 Toft, K. G., Sletten, K. & Husby, G. (1985) Biol.Chem.Hoppe-Seyler, 366, 617–625.

72 Tonoike. H., Kametani, F., Hoshi, A., Shinoda, T. & Isobe, T. (1985) Biochem.Biophys.Res.Commun., 126, 1228–1234.

73 Tonoike, H., Kametani, F., Hoshi, A., Shinoda, T. & Isobe, T. (1985) Febs Letters, 185, 139–141.

74 Tsujimoto, Y. & Croce, C. M. (1984) Nucl.Acids Res., 12, 8407–8414.

75 Tsunetsugu-Yokota. Y., Minekawa, T., Shigemoto, K., Shirasawa. T. & Takemori, T. (1992) Mol.Immunol., 29, 723–728.

76 Tveteraas, T., Sletten. K. & Westermark, P. (1985) Biochem.J., 232, 183–190.

77 Vasicek, T. J. & Leder, P. (1990) J.Exp.Med., 172, 609–620.

78 Victor, K. D., Randen, I., Thompson, K., Forre, O., Natvig. J. B., Fu, S. M. & Capra, J. D. (1991) J.Clin.Invest., 87, 1603–1613.

79 Weng, N.-P., Yu-Lee, L.-Y., Sanz, I., Patten, B. M. & Marcus, D. M. (1992) J.Immunol., 149, 2518–2529.

80 Wikler, M. & Putnam, F. W. (1970) J.Biol.Chem., 245, 4488–4507.

81 Winkler, T. H., Fehr, H. & Kalden, J. R. (1992) EurJ.Immunol., 22, 1719–1728.

82 Yago, K., Zenita, K., Ohwaki, I., Harada, Y., Nozawa, S., Tsukazaki, K., Iwamori, M., Endo. N., Yasuda, N., Okuma, M. & Kannagi, R. (1993) Mol.Immunol., 30, 1481–1489.

83 Yamasaki, N., Komori, S. & Watanabe, T. (1987) Mol.Immunol., 24, 981–985.

84 Zhu, D., Kim. H. S. & Deutsch, H. F. (1983) Mol.Immunol., 20, 1107–1116.

85 Zhu, D., Zhang, H., Zhu. N. & Luo, X. (1986) Scientia Sinica, 29, 746–755.

References of Rearranged Human Heavy Chain Sequences Used for Alignment

1 Adderson, E. E., Azmi. F. H., Wilson. P. M., Shackelford, P. G. & Carroll, W. L. (1993) J.Immunol., 151, 800–809.

2 Adderson, E. E., Shackelford, P. G., Quinn, A. & Carroll, W. L. (1991) J.Immunol. 147, 1667–1674.

3 Akahori, Y., Kurosawa, Y., Kamachi, Y., Torii, S. & Matsuoka, H. (1990) J.Clin.Invest, 85, 1722–1727.
4 Andris, J. S., Brodeur, B. R. & Capra, J. D. (1993) Mol.Immunol., 30, 1601–1616.
5 Andris, J. S., Ehrlich, P. H., Ostberg, L. & Capra, J. D. (1992) J.Immunol., 149, 4053–4059.
6 Andris. J. S., Johnson, S., Zolla-Pazner, S. & Capra, J. D. (1991) Proc.NatlAcad.Sci.Usa, 88, 7783–7787.
7 Anker, R., Conley, M. E. & Pollok, B. A. (1989) J.Exp.Med., 169, 2109–2119.
8 Atkinson. P. M., Lampman, G. W., Furie, B. C., Naparstek, Y., Schwartz, R. S., Stollar, B. D. & Furie. B. (1985) J.Clin.Invest., 75, 1138–1143.; Lampman, G. W., Furie, B., Schwartz, R. S., Stollar, B. D. & Furie, B. C. (1989)
9 Avila, M. A., Vazques, J., Danielsson, L., Fernandez De Cossio, M. E. & Borrebaeck, C. A. K. (1993) Gene, 127, 273–274.
10 Bakkus, M. H. C., Heirman, C., Van Riet, I., Van Camp. B. & Thielemans, K. (1992) Blood, 80, 2326–2335.
11 Barbas Iii, C. F., Crowe, Jr., J. E., Cababa, D., Jones, T. M., Zebedee, S. L., Murphy, B. R., Chanock. R. M. & Burton. D. R. (1992) Proc.Natl.Acad.Sci.Usa, 89, 10164–10168.
12 Barbas, C. F., Iii, Collet, T. A., Amberg, W. Roben, P., Binley, J. M., Hoekstra, D., Cababa, D., Jones, T. M., Williamson, R. A., Pilkington. G. R., Haigwood, N. L., Cabezas, E., Satterthwait, A. C., Sanz, I. & Burton, D. R. (1993) J.Mol.Biol., 230, 812–823.
13 Berman, J. E., Humphries, C. G., Barth, J., Alt, F. W. & Tucker, P. W. (1991) J.Exp.Med., 173, 1529–1535.
14 Berman. J. E., Mellis, S. J., Pollock, R., Smith. C. L., Suh, H., Heinke, B., Kowal, C., Surti, U., Chess, L, Cantor, C. R & Alt, F. W. (1988) Embo J., 7, 727–738.
15 Bhat, N. M., Bieber, M. M., Chapman, C. J., Stevenson, F. K. & Teng, N. N. H. (1993) J.Immunol., 151, 5011–5021.
16 Bird, J., Galili, N., Link, M., Stites, D. & Sklar, J. (1988) J.Exp.Med., 168, 229–245.
17 Cai, J., Humphries, C., Richardson, A. & Tucker, P. W. (1992) J.Exp.Med., 176, 1073–1081.
18 Cairns, E., Kwong, P. C., Misener, V., Ip, P., Bell, D. A. & Siminovitch, K. A (1989) J.Immunol., 143, 685–691.
19 Capra, J. D. & Hopper, J. E. (1976) Immunochemistry, 13, 995–999; Hopper, J. E., Noyes, C., Heinrikson, R. & Kessel, J. W. (1976) J.Immunol., 116, 743–746.
20 Capra, J. D. & Kehoe. J. M. (1974) Proc.Nat.Acad.Sci.Usa, 71, 845–848.
21 Carroll, W. L., Yu, M., Link, M. P. & Korsmeyer, S. J. (1989) J.Immunol., 143, 692–698.
22 Chen, P. P., Liu. M.-F., Glass, C. A., Sinha, S., Kipps, T. J. & Carson, D. A. (1989) Arthritis & Rheumatism, 32, 72–76; Kipps, T. J., Tomhave, E., Pratt, L. F., Duffy, S., Chen, P. P. & Carson, D. A. (1989) Proc.Natl.Acad.Sci.Usa, 86, 5913–5917.
23 Chiu, Y. Y. H., Lopez De Castro, J. A. & Poljak. R. J. (1979) Biochemistry, 18, 553–560.
24 Cleary, M. L., Meeker, T. C., Levy, S., Lee, E., Trela, M., Sklar, J. & Levy, R. (1986) Cell, 44, 97–106.
25 Cuisinier, A.-M., Fumoux. F., Fougereau, M. & Tonnelle, C. (1992) Mol.Immunol., 29, 1363–1373.
26 Cuisinier, A.-M., Gauthier, L., Boubli, L., Fougereau, M. & Tonnelle, C. (1993) EurJ.Immunol., 23, 110–118.
27 Cunningham, B. A., Gottlieb. P. D., Pflumm, M. N. & Edelman, G. M. (1971) Progress In Immunology (B. Amos, Ed.), Academic Press, N.Y., Pp.3–24.
28 Cunningham, B. A., Rutishauser, U., Gall, W. E., Gottlieb, P. D., Waxdal, M. J. & Edelman, G. M. (1970) Biochemistry, 9, 3161–3170.
29 Deane, M. & Norton, J. D. (1990) EurJ.Immunol., 20, 2209–2217.
30 Deane, M. & Norton, J. D. (l991) Leukemia, 5, 646–650.
31 Dersimonian, H., Schwartz, R. S., Barrett. K. J. & Stollar, B. D. (1987) J.Immunol., 139, 2496–2501.
32 Dersimonian, H., Schwartz, R. S., Barrett, K. J. & Stollar, B. D. (1987) J.Immunol, 139, 2496–2501; Chen, P. P., Liu, M.-F., Sinha, S. & Carson, D. A. (1988) Arth.Rheum., 31, 1429–1431.
33 Desai, R., Spatz, L., Matsuda, T., Ilyas, A. A., Berman, J. E., Alt, F. W., Kabat, E. A. & Latov, N. (1990) J.Neuroimmunol., 26, 35–41.
34 Ezaki, I., Kanda, H., Sakai, K., Fukui, N., Shingu, M., Nobunaga, M. & Watanabe, T. (1991) Arthritis And Rheumatism, 34, 343–350.
35 Felgenhauer, M., Kohl, J. & Ruker, F. (1990) Nucl.Acids Res., 18, 4927.
36 Florent, G., Lehman, D. & Putnam, F. W. (1974) Biochemistry, 13, 2482–2498.
37 Friedlander, R. M., Nussenzweig, M. C. & Leder, P. (1990) Nucl.Acids Res., 18, 4278.
38 Gawinowicz, M. A., Merlini, G., Birken. S., Osserman, E. F. & Kabat, E. A. (1991) J.Immunol., 147, 915–920.
39 Gillies, S. D., Dorai, H., Wesolowski, J., Majeau, G., Young, D., Boyd, J., Gardner, J. & James, K. (1989) Bio/Tech., 7, 799–804.
40 Goni, F. & Frangione, B. (1983) Proc.Nat.Acad.Sci.Usa, 80, 4837–4841.
41 Gorman, S. D., Clark, M. R., Routledge, E. G., Cobbold, S. P. & Waldmann, H. (1991) Proc.Natl.Acad.Sci.Usa, 88, 4181–4185.
42 Griffiths, A. D., Malmqist, M., Marks, J. D., Bye, J. M., Embleton, M. J., Mccafferty, J., Baier, M., Holliger, K. P., Gorick, B. D., Hughes-Jones, N. C., Hoogenboom, H. R. & Winter, G. (1993) Embo J., 12, 725–734.
43 Grillot-Courvalin, C., Brouet, J.-C., Piller, F., Rassenti, L. Z., Labaume, S., Silverman, G. J., Silberstein, L. & Kipps, T. J. (1992) EurJ.Immunol., 22, 1781–1788.
44 Guillaume, T., Rubinstein, D. B., Young, F., Tucker, L., Logtenberg, T., Schwartz, R. S. & Barrett. K. L. (1990) J.Immunol., 145, 1934–1945; Young, F., Tucker. L., Rubinstein, D., Guillaume, T., Andre-Schwartz, J., Barrett, K. J., Schwartz, R. S. & Logtenberg, T. (1990)
45 Harindranath, N., Goldfarb, I. S., Ikematsu, H., Burastero, S. E., Wilder, R. L. Notkins, A. L. & Casali, P. (1991) Int.Immunol., 3, 865–875.
46 Hilison, J. L., Oppliger, I. R., Sasso, E. H., Milner, E. C. B. & Wener, M. H. (1992) J.Immunol., 149, 3741–3752.
47 Hirabayashi, Y., Munakata, Y., Sasaki, T. & Sano, H. (1992) Nucl.Acids Res., 20, 2601.
48 Hoch, S. & Schwaber, J. (1987) J.Immunol., 139, 1689–1693.
49 Huang, C., Stewarl A. K., Schwartz, R. S., & Stollar, B. D. (1992) J.Clin.Invest., 89, 1331–1343.
50 Hughes-Jones, N. C., Bye, J. M., Beale, D. & Coadwell, J. (1990) Biochem.J., 268, 135–140.
51 Ikematsu, H., Harindranath, N., Ueki, Y., Notkins, A. L. & Casali, P. (1993) J.Immunol., 150, 1325–1337.
52 Ikematsu, H., Kasaian, M. T., Schettino, E. W. & Casali, P. (1993) J.Immunol., 151, 3604–3616.
53 Kelly, P. J., Pascual, V., Capra, J. D. & Lipsky, P. E. (1992) J.Immunol., 148, 1294–1301.
54 Kipps, T. J. & Duffy, S. F. (1991) J.Clin.Invest., 87, 2087–2096.
55 Kipps, T. J., Tomhave, E., Pratt, L. F., Duffy, S., Chen, P. P. & Carson, D. A. (1989) Proc.Natl.Acad.Sci.Usa, 86, 5913–5917.

56 Kishimoto, T., Okajima, H., Okumoto, T. & Taniguchi, M. (1989) Nucl.Acids Res., 17, 4385.

57 Knight, G. B., Agnello, V., Bonagura, V., Barnes, J. L., Panka, D. J. & Zhang, Q.-X (1993) J.Exp.Med., 178, 1903–1911.

58 Kohler, H., Shimizu, A., Paul, C., Moore, V. & Putnam, F. W. (1970) Nature, 227, 1318–1320; Florent, G., Lehman, D. & Putnam, F. W. (1974) Biochemistry, 13, 2482–2498

59 Komori, S., Yamasaki, N., Shigeta, M., Isojima, S. & Watanabe, T. (1988) Clin.Exp.Immunol., 71, 508–516.

60 Kon, S., Levy, S. & Levy, R. (1987) Proc.Natl.Acad.Sci.Usa, 84, 5053–5057.

61 Kratzin, H., Altevogt P., Ruban, E., Kortt, A., Staroscik, K. & Hilschmann, N. (1975) Z.Physiol.Chem., 356, 1337–1342; Kratzin, H., Altevogt, P., Kortt, A., Ruban, E. & Hilschmann, N. (1978) Z.Physiol.Chem., 359, 1717–1745.

62 Kudo, A., Ishihara, T., Nishimura, Y. & Watanabe, T. (1985) Gene, 33, 181–189.

63 Kunicki, T. J., Annis, D. S., Gorski, J. & Nugent, D. J. (1991) J.Autoimmunity, 4, 433–446.

64 Larrick, J. W., Wallace, E. F., Coloma, M. J., Bruderer, U., Lang, A. B. & Fry, K. E. (1992) Immunological Reviews, 130, 69–85.

65 Lehman, D. W. & Putnam, F. W. (1980) Proc.Nat.Acad.Sci.Usa, 77, 3239–3243.

66 Lewis, A. P., Lemon, S. M., Barber, K. A., Murphy, P., Parry, N. R., Peakman, T. C, Sims, M. J., Worden, J. & Crowe, J. S. (1993) J.Immunol., 151, 2829–2838.

67 Liu, V. Y. S., Low, T. L. K., Infante, A. & Putnam, F. W. (1976) Science, 193, 1017–1020.

68 Logtenberg, T., Young, F. M., Van Es, J., Gmelig-Meyling, F. H. J., Berman, J. E. & Alt, F. W. (1989) J.Autoimmunity, 2, 203–213.

69 Logtenberg, T., Young, F. M., Van Es, J. H., Gmelig-Meyling, F. H. J. & Alt, F. W. (1989) J.Exp.Med., 170, 1347–1355.

70 Manheimer-Lory, A., Katz, J. B., Pillinger, M., Ghossein, C., Smith, A. & Diamond, B. (1991) J.Exp.Med., 174, 1639–1652.

71 Mantovani, L, Wilder, R. L. & Casali, P. (1993) J.Immunol., 151, 473–488.

72 Mariette, X., Tsapis, A. & Brouet, J.-C. (1993) EurJ.Immunol., 23, 846–851.

73 Marks, J. D., Hoogenboom, H. R., Bonnert T. P., Mccafferty, J., Griffiths, A. D. & Winter, G. (1991) J.Mol.Biol., 222, 581–597.

74 Meeker, T. C., Grimaldi, J., O'rourke, R., Loeb, J. Juliusson, G. & Einhorn, S. (1988) J.Immol., 141, 3994–3998.

75 Mililli, M., Fougereau, M., Guglielmi, P. & Schiff, C. (1991) Mol.Immunol., 28, 753–761.

76 Moran, M. J., Andris, J. S., Matsumato, Y.-I., Capra, J. D. & Hersh, E. M. (1993) Mol.Immunol., 30, 1543–1551.

77 Mortari, F., Wang, J.-Y. & Schroeder, Jr., H. W. (1993) J.Immunol., 150, 1348–1357.

78 Newkirk, M. M., Gram, H., Heinrich, G. F., Ostberg, L., Capra, J. D. & Wasserman, R. L. (1988) J.Clin.Invest., 81, 1511–1518.

79 Newkirk, M. M., Mageed, R. A., Jefferis, R., Chen, P. P. & Capra, J. D. (1987) J.Exp.Med., 166, 550–564.

80 Nickerson, K. G., Berman, J., Glickman, E., Chess, L & Alt, F. W. (1989) J.Exp.Med., 169, 1391–1403.

81 Olee, B. T., Lu, E. W, Huang, D.-F., Soto-Gil, R. W., Deftos, M., Kozin, F., Carson, D. A. & Chen, P. P. (1992) J.Exp.Med., 175, 831–842.

82 Pascual, V., Randen, I., Thompson, K., Sioud, M. Forre, O., Natvig, J. & Capra, J. D. (1990) J.Clin.Invest., 86, 1320–1328.

83 Pascual, V., Randen, I., Thompson. K., Sioud, M. Forre, O., Natvig, J. & Capra, J. D. (1990) J.Clin.Invest., 86, 1320–1328; Randen, I., Brown, D., Thompson, K. M., Hughes-Jones. N., Pascual, V., Victor, K., Capra, J. D., Forre, O. & Natvig, J. B. (1992)

84 Pascual. V., Victor, K., Lelsz, D., Spellerberg. M. B., Hamblin, T. J., Thompson, K. M., Randen, I., Natvig. J., Capra, J. D. & Stevenson, F. K. (1991) J.Immunol., 146, 4385–4391.

85 Pascual, V., Victor., K, Randen, I., Thompson, K., Steinitz, M., Forre, O., Fu, S.-M., Natvig, J. B. & Capra. J. D. (1992) Scand.J.Immunol., 36, 349–362.

86 Pascual, V., Victor, K., Spellerberg. M., Hamblin, T. J., Stevenson, F. K. & Capra. J. D. (1992) J.Immunol., 149, 2337–2344.

87 Ponstingl, H., Schwarz, J., Reichel, W. & Hilschmann, N. (1970) Z.Physiol.Chem., 351, 1591–1594.; Ponstingl, H. & Hilschmann, N. (1976) Z.Physiol.Chem., 357, 1571–1604.

88 Portolano, S., Mclachlan, S. M. & Rapoport, B. (1993) J.Immunol., 151, 2839–2851.

89 Portolano, S., Seto, P., Chazenbalk. G. D., Nagayama, Y., Mclachlan, S. M. & Rapoport, B. (1991) Biochem.Biophys.Res.Commun., 179, 372–377.

90 Pratt, L. F., Szubin, R., Carson, D. A. & Kipps. T. J. (1991) J.Immunol., 147, 2041–2046.

91 Press, E. M. & Hogg, N. M. (1970) Biochem.J., 117, 641–660.

92 Putnam, F. W., Shimizu, A., Paul., C., Shinoda, T. & Kohler, H. (1971) Ann.N.Y.Acad.Sci., 190, 83–103.

93 Putnam, F. W., Takahashi, N., Tetaert, D., Debuire, B. & Lin, L. C. (1981) Proc.Nat.Acad.Sci.Usa; 78, 6168–6172.; Tabhashi, N., Tetaert. D., Debuire, B., Lin, L. & Putnam, F. W. (1982) Proc.Nat.Acad.Sci.Usa, 79, 2850–2854.

94 Raaphorst, F. M., Timmers, E., Kenter, M. J. H., Van Tol. M. J. D., Vossen, J. M. & Schuurman, R. K. B. (1992) EurJ.Immunol., 22, 247–251.

95 Rabbitts. T. H., Bentley, D. L., Dunnicik; W., Forster. A., Matthyssens, G. & Milstein, C. (1980) Cold Spring Harb.Symp.Quanti.Biol., 45, 867–878; Matthyssens, G. & Rabbitts, T. H. (1980) Proc.Nat.Acad.Sci.Usa, 77, 6561–6565.

96 Randen, I., Pascual, V., Victor, K., Thompson, K. M., Forre, O., Capra, J. D. & Natvig, J. B. (1993) EurJ.Immunol., 23, 1220–1225.

97 Rassenti, L. Z. & Kipps. T. J. (1993) J.Exp.Med., 177, 1039–1046.

98 Reidl, L. S., Friedman, D. F., Goldman, J., Hardy. R. R., Jefferies, L. C. & Silberstein, L. E. (1991) J.Immunol., 147, 3623–3631.

99 Roudier, J., Silverman, G. J., Chen, P. P., Carson, D. A & Kipps, T. J. (1990) J.Immunol., 144, 1526–1530.

100 Sanz, I., Casali, P., Thomas, J. W., Notkins, A. L. & Capra, J. D. (1989) J.Immunol., 142, 4054–4061.

101 Sanz, I., Dang. H., Takei, M., Talal, N. & Capra, J. D. (1989) J.Immunol., 142, 883–887.

102 Schmidt, W. E, Jung, H-. D., Palm, W. & Hilschmann, N. (1983) Z.Physiol.Chem., 364, 713–747.

103 Schroeder, H. W., Jr. & Wang, J. Y. (1990) Proc.NatlAcad.Sci.Usa, 87, 6146–6150.

104 Schroeder, H. W., Jr., Hillson, J. L. & Perlmutter, R. M. (1987) Science, 238, 791–793.

105 Schroeder, H. W., Jr., Hillson, J. L. & Perlmutter, R. M. (1987) Science, 238, 791–793; Chen, P. P., Liu, M.-F., Glass, C. A., Sinha. S., Kipps, T. J. & Carson, D. A. (1989) Arthritis & Rheumatism, 32, 72–76.
106 Schroeder, H. W., Jr., Hillson, J. L. & Perlmutter, R. M. (1987) Science, 238, 791–793; Chen, P. P., Liu, M.-F., Sinha, S. & Carson, D. A. (1988) Arth.Rheum., 31, 1429–1431.
107 Schutte, M. E., Ebeling, S. B., Akkermans, K. E., Gmelig-Meyling, F. H. & Logtenberg, T. (1991) EurJ.Immunol., 21, 1115–1121.
108 Schutte, M. E., Ebeling, S. B., Akkermans, K. E., Gmelig-Meyling, F. H. J. & Logtenberg, T. (1991) EurJ.Immunol., 21, 1115–1121.
109 Settmacher, U., Jahn, S., Siegel, P., Von Baehr, R. & Hansen, A. (1993) Mol.Immunol., 30, 953–954.
110 Shen, A., Humphries, C., Tucker, P. & Blattner, F. (1987) Proc.Natl.Acad.Sci.Usa, 84, 8563–8567.
111 Shimizu, A., Nussenzweig, M. C., Mizuta, T.-R., Leder. P. & Honjo, T. (1989) Proc.Natl.Acad.Sci.Usa, 86, 8020–8023.
112 Shin, E. K., Matsuda, F., Fujikura, J., Akamizu, T., Sugawa, H., Mori, T. & Honjo, T. (1993) EurJ.Immunol., 23, 2365–2367.
113 Silberstein, L. E., Litwin, S. & Carmack, C. E. (1989) J.Exp.Med., 169, 1631–1643.
114 Singal, D. P., Frame, B., Joseph, S., Blajchman, M. A. & Leber, B. F. (1993) Immunogenet., 38, 242.
115 Spatz, L. A., Wong, K. K., Williams, M., Desai, R., Golier, J., Berman, J. E, Alt, F. W. & Latov, N. (1990) J.Immunol., 144, 2821–2828.
116 Steiner, L. A., Garcia-Pardo, A. & Margolies, M. N. (1979) Biochemistry, 18, 4068–4080.
117 Stewart, A. K., Huang, C., Stollar, B. D. & Schwartz, R. S. (1993) J.Exp.Med., 177, 409–418.
118 Thomas. J. W. (1993) J.Immunol., 150, 1375–1382.
119 Torano, A. & Putnam, F. W. (1978) Proc.Nat.Acad.Sci.Usa, 75, 966–969.
120 Van Der Heijden, R. W. J., Bunschoten, H., Pascual, V., Uytdehaag, F. G. C. M., Osterhaus, A. D. M. E. & Capra, J. D. (1990) J.Immunol., 144, 2835–2839.
121 Van Der Stoep. N., Van Der Linden, J. & Logtenberg, T. (1993) J.Exp.Med., 177, 99–107.
122 Van Es, J. H., Gmelig-Meyling, F. H. J. & Logtenberg, T. (1992) Eur.J.Immunol., 22, 2761–2764.
123 Varade, W. S., Marin, E., Kittelberger, A. M. & Insel, R. A. (1993) J.Immunol., 150, 4985–4995.
124 Victor, K. D., Pascual, V., Lefvert, A. K. & Capra, J. D. (1992) Mol.Immunol., 29, 1501–1506.
125 Victor, K. D, Pascual, V., Williams, C. L., Lennon, V. A. & Capra, J. D. (1992) Eur.J.Immunol., 22, 2231–2236.
126 Watanabe, S., Barnikol, H. U., Horn, J., Bertram, J. & Hilschmann, N. (1973) Z.Physiol.Chem, 354, 1505–1509.
127 Weng, N.-P., Yu-Lee, L.-Y., Sanz, I., Patten, B. M. & Marcus, D. M. (1992) J.Immunol., 149, 2518–2529.
128 White, M. B., Word, C. J., Humphries, C. G., Blattner, F. R. & Tucker, P. W. (1990) Mol.Cell.Biol., 10, 3690–3699.
129 Winkler, T. H., Fehr, H. & Kalden, J. R. (1992) Eur.J.Immunol., 22, 1719–1728.
130 Yago, K., Zenita, K., Ohwaki, I., Harada, Y., Nozawa, S., Tsukazaki, K., Iwamori, M., Endo, N., Yasuda, N., Okuma, M. & Kannagi, R. (1993) Mol.Immunol., 30, 1481–1489.
131 Zelenetz, A. D., Chen, T. T. & Levy, R. (1992) J.Exp.Med., 176, 1137–1148.

B. References of Germline Sequences

References of Human Germline Kappa Sequences

1 Cox. J. P. L., Tomlinson, I. M. & Winter, G. (1994) Eur.J.Immunol., 24, 827–836.

2 Huber, C., & Al. (1993) Eur.J.Immunol., 23, 2868.
3 Klobeck. H. G., Bornkammm, G. W., Combriato, G., Mocikat, R., Pohlenz, H. D. & Zachau, H. G. (1985) Nucl.Acids Res., 13, 6515–6529.
4 Lautner-Rieske, A., Huber, C., Meindi, A., Pargent, W., Schäble, K. F., Thiebe. R., Zocher. I. & Zachau, H. G. (1992) Eur.J.Immunol. 22, 1023.
5 Lorenz, W., Schäble, K. F., Thiebe, R., Stavnezer, J. & Zachau, H. G. (1988) Mol.Immunol., 25, 479.
6 Pargent, W., Meindl, A., Thiebe, R., Mitzel, S. & Zachau, H. G. (1991) Eur.J.Immunol., 21, 1821–1827.
7 Pech, M. & Zachau, H. G. (1984) Nuc.Acids Res., 12, 9229–9236.
8 Pech, M., Jaenichen, H.-R., Pohlenz, H.-D., Neumaier, P. S., Klobeck, H.-G. & Zachau, H. G. (1984) J.Mol.Biol., 176, 189–204.
9 Scott, M. G., Crimmins, D. L., Mccourt, D. W., Chung, G., Schable, K. F., Thiebe, R., Quenzel, E.-M., Zachau, H. G. & Nahm, M. H. (1991) J.Immunol., 147, 4007–4013.
10 Stavnezer, J., Kekish, O., Batter, D., Grenier, J., Balazs, I., Henderson, E. & Zegers, B. J. M. (1985) Nucl.Acids Res., 13, 3495–3514.
11 Straubinger, B., Huber, E., Lorenz. W., Osterholzer, E., Pargent, W., Pech, M., Pohlenz, H.-D., Zimmer, F.-J. & Zachau. H. G. (1988) J.Mol.Biol., 199, 23–34.
12 Straubinger, B., Thiebe, R., Huber, C., Osterholzer, E. & Zachau, H. G. (1988) Biol.Chem.Hoppe-Seyer, 369, 601–607.

References of Human Germline Lambda Sequences

1 Williams, S. C. & Winter, G. (1993) Eur.J.Immunol., 23, 1456–1461.
2 Siminovitch, K. A., Misener, V., Kwong, P. C., Song, Q.-L. & Chen, P. P. (1989) J.Clin.Invest., 84, 1675–1678.
3 Brockly, F., Alexandre, D., Chuchana, P., Huck. S., Lefranc, G. & Lefranc, M.-P. (1989) Nuc.Acids.Res., 17, 3976.
4 Daley, M. D., Peng, H.-O., Misener, V., Liu, X.-Y., Chen, P. P. & Siminovitch, K. A. (1992) Mol.Immunol., 29, 1515–1518.
5 Deftos, M., Soto-Gil, R., Quan, M., Olee, T. & Chen, P. P. (1994) Scand. J. Immunol., 39, 95.
6 Stiernholm, N. B. J., Kuzniar, B. & Berinstein, N. L. (1994) J. Immunol., 152, 4969–4975.
7 Combriato. G. & Klobeck H. G. (1991) Eur.J.Immunol., 21, 1513–1522.
8 Anderson. M. L. M., Szajnert M. F., Kaplan, J. C., Mccoll, L. & Young, B. D. (1984) Nuc.Acids Res., 12, 6647–6661.

References of Human Germline Heavy Chain Sequences

1 Adderson, E. E., Azmi, F. H., Wilson, P. M., Shackelford, P. G. & Carroll, W. L (1993) J.Immunol., 151, 800–809.
2 Andris, J. S., Brodeur, B. R. & Capra, J. D. (1993) Mol.Immunol., 30, 1601–1616.
3 Berman, J. E., Mellis, S. J., Pollock, R., Smith, C. L., Suh, H., Heinke, B., Kowal, C., Surti, U., Chess, L., Cantor, C. R & Alt, F. W. (1988) Embo J., 7,727–738.
4 Buluwela, L. & Rabbitts, T. H. (1988) Eur.J.Immunol., 18, 1843–1845.; Buluwela. L., Albertson, D. G., Sherrington, P., Rabbitts, P. H., Spurr, N. & Rabbitts, T. H. (1988) Embo J., 7, 2003–2010.
5 Chen, P. P, Liu, M.-F., Sinha, S. & Carson, D. A. (1988) Arth.Rheum., 31, 1429–1431.
6 Chen, P. P., Liu, M.-F., Glass, C. A., Sinha, S., Kipps, T. J. & Carson, D. A. (1989) Arthritis & Rheumatism, 32, 72–76.
7 Cook. G. P. et al. (1994) Nature Genetics 7, 162–168.
8 Haino, M. et al., (1994). J. Biol. Chem. 269, 2619–2626

9 Humphries, C. G., Shen, A., Kuziel, W. A., Capra, J. D., Blattner, F. R. & Tucker, P. W. (1988) Nature, 331, 446–449.
10 Kodaira, M., Kinashi, T., Umemura, I., Matsuda, F., Noma, T., Ono, Y. & Honjo, T. (1986) J.Mol.Biol., 190, 529–541.
11 Lee, K. H., Matsuda, F., Kinashi, T., Kodaira, M. & Honjo, T. (1987) J.Mol.Biol., 195, 761–768.
12 Matsuda, F., Lee, K. H., Nakai, S., Sato, T., Kodaira, M., Zong, S. Q., Ohno, H., Fukuhara, S. & Honjo. T. (1988) Embo J., 7, 1047–1051.
13 Matsuda. F., Shin. E. K., Hirabayashi, Y., Nagaoka. H., Yoshida, M. C., Zong, S. O., & Honjo, T. (1990) Embo J., 9, 2501–2506.
14 Matsuda, F., Shin, E. K, Nagaoka. H., Matsumura, R., Haino, M., Fukita. Y., Taka-Ishi, S., Imai, T., Riley, J. H., Anand, R. &, Al. (1993) Nature Genet. 3,88–94
15 Nagaoka, H., Ozawa, K., Matsuda, F., Hayashida. H., Matsumura, R., Haino, M., Shin, E. K., Fukita, Y., Imai, T., Anand, R., Yokoyama, K., Eki, T., Soeda, E. & Honjo, T. (1993). (Temporal)
16 Rechavi, G., Bienz, B., Ram, D., Ben-Neriah, Y., Cohen, J. B., Zakut, R. & Givol, D. (1982) Proc.Nat.Acad.Sci.Usa, 79, 4405–4409.
17 Sanz, I., Kelly, P., Williams, C., Scholl, S., Tucker, P. & Capra. J. D. (1989) Embo J., 8, 3741–3748.
18 Shin, E. K., Matsuda, F., Fujikura, J., Akamizu, T., Sugawa, H., Mori, T. & Honjo, T. (1993) Eur.J.Immnunol., 23, 2365–2367.
19 Tomlinson, Im., Walter, G., Marks, Jd., Llewelyn, Mb. & Winter. G. (1992) J.Mol.Biol. 227, 776–798.
20 Van Der Maarel, S., Van Dijk, K. W., Alexander, C. M., Sasso, E. H., Bull, A. & Milner, E. C. B. (1993) J.Immunol., 150, 2858–2868.
21 Van Dijk, K. W., Mortari, F., Kirkham, P. M., Schroeder, Jr., H. W. & Milner, E. C. B. (1993) Eur.J.Immunol., 23, 832–839.
22 Van Es, J. H., Aanstoot, H., Gmelig-Meyiing, F. H. J., Derksen, R. H. W. M. & Logtenberg, T. (1992) J.Immunol., 149, 2234–2240.
23 Weng, N.-P., Snyder, J. G., Yu-Lee, L.-Y. & Marcus, D. M. (1992) Eur.J.Immunol., 22, 1075–1082.
24 Winkler, T. H., Fehr, H. & Kalden, J. R. (1992) Eur.J.Immunol., 22, 1719–1728.
25 Olee, T., Yang, P. M., Siminovitch, K. A., Olsen, N. J., Hillson, J. L., Wu, J., Kozin, F., Carson, D. A. et Chen, P. P. (1991) J. Clin.Invest. 88, 193–203.
26 Chen, P. P. & Yang, P. M. (1990) Scand. J. Immunol. 31, 593–599.
27 Tomlinson, M., Walter, G., Cook&Winter, G. (Unpublished)

---

SEQUENCE LISTING (1) GENERAL INFORMATION:

(iii) NUMBER OF SEQUENCES: 373

(2) INFORMATION FOR SEQ ID NO: 1:

(i) SEQUENCE CHARACTERISTICS:
      (A) LENGTH: 20 amino acids
      (B) TYPE: amino acid
      (C) STRANDEDNESS: <Unknown>
      (D) TOPOLOGY: linear (ii) MOLECULE TYPE: protein (xi) SEQUENCE DESCRIPTION: SEQ ID NO: 1:

```
Ala Gly Gly Gly Ser Gly Gly Gly Gly Ser Gly Gly Gly Gly Ser Gly
1               5                   10                  15

Gly Gly Gly Ser
            20
```

(2) INFORMATION FOR SEQ ID NO: 2:

(i) SEQUENCE CHARACTERISTICS:
      (A) LENGTH: 82 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO: 2:

```
TCAGCGGGTG GCGGTTCTGG CGGCGGTGGG AGCGGTGGCG GTGGTTCTGG CGGTGGTGGT      60

TCCGATATCG GTCCACGTAC GG                                              82
```

(2) INFORMATION FOR SEQ ID NO: 3:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 3:

```
AATTCCGTAC GTGGACCGAT ATCGGAACCA CCACCGCCAG AACCACCGCC ACCGCTCCCA    60

CCGCCGCCAG AACCGCCACC CGC                                            83
```

(2) INFORMATION FOR SEQ ID NO: 4:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
        (A) NAME/KEY: misc_feature
        (B) LOCATION:28..45
        (D) OTHER INFORMATION:/product= "6 random codons by
            trinucleotide mutagenesis (19aa, no Cys)"

(xi) SEQUENCE DESCRIPTION: SEQ ID NO: 4:

```
GATACGGCCG TGTATTATTG CGCGCGTNNK NNKNNKNNKN NKNNKGATTA TTGGGGCCAA    60

GGCACCCTG                                                            69
```

(2) INFORMATION FOR SEQ ID NO: 5:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
        (A) NAME/KEY: misc_feature
        (B) LOCATION:28..57
        (D) OTHER INFORMATION:/product= "10 random codons by
            trinucleotide mutagenesis (19aa, no Cys)"

(ix) FEATURE:
        (A) NAME/KEY: misc_feature
        (B) LOCATION:58..60
        (D) OTHER INFORMATION:/product= "random codon by
            trinucleotide mutagenesis (TTT/ATG)"

(ix) FEATURE:
        (A) NAME/KEY: misc_feature
        (B) LOCATION:64..66
        (D) OTHER INFORMATION:/product= "random codon by
            trinucleotide mutagenesis (GTT/TAT)"

(xi) SEQUENCE DESCRIPTION: SEQ ID NO: 5:

```
GATACGGCCG TGTATTATTG CGCGCGTNNK NNKNNKNNKN NKNNKNNKNN KNNKNNKWTK    60

GATKWTTGGG GCCAAGGCAC CCTG                                           84
```

(2) INFORMATION FOR SEQ ID NO: 6:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 6:

GATACGGCCG TGTATTATTG C                                              21

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 7:

CAGGGTGCCT TGGCCCC                                                   17

(2) INFORMATION FOR SEQ ID NO: 8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 8:

GCAGAAGGCG AACGTCC                                                   17

(2) INFORMATION FOR SEQ ID NO: 9:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
        (A) NAME/KEY: misc_feature
        (B) LOCATION:39..41
        (D) OTHER INFORMATION:/product= "random codon (mixture of
            GCT, CGT, CAT, TCT, TAT)"

(ix) FEATURE:
        (A) NAME/KEY: misc_feature
        (B) LOCATION:42..53
        (D) OTHER INFORMATION:/product= "random codons by
            trinucleotide mutagenesis (19 aa, no Cys)"

(ix) FEATURE:
        (A) NAME/KEY: misc_feature
        (B) LOCATION:57..59
        (D) OTHER INFORMATION:/product= "random codon by
            trinucleotide mutagenesis (19 aa, no Cys)"

(xi) SEQUENCE DESCRIPTION: SEQ ID NO: 9:

TGGAAGCTGA AGACGTGGGC GTGTATTATT GCCAGCAGBV TNNKNNKNNK NNKCCGNNKT    60
```

TTGGCCAGGG TACGAAAGTT                                              80

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 10:

AACTTTCGTA CCCTGGCC                                                18

(2) INFORMATION FOR SEQ ID NO: 11:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
        (A) NAME/KEY: misc_feature
        (B) LOCATION:21..23
        (D) OTHER INFORMATION:/product= "random codon by
            trinucleotide mutagenesis (19aa, no Cys)"

(ix) FEATURE:
        (A) NAME/KEY: misc_feature
        (B) LOCATION:27..35
        (D) OTHER INFORMATION:/product= "random codons by
            trinucleotide mutagenesis (19 aa, no Cys)"

(ix) FEATURE:
        (A) NAME/KEY: misc_feature
        (B) LOCATION:36..41
        (D) OTHER INFORMATION:/product= "random codons by mixed
            monomers (A/G A/C/G T)"

(ix) FEATURE:
        (A) NAME/KEY: misc_feature
        (B) LOCATION:42..44
        (D) OTHER INFORMATION:/product= "random codon by
            trinucleotide mutagenesis (19aa, no Cys)"

(ix) FEATURE:
        (A) NAME/KEY: misc_feature
        (B) LOCATION:48..50
        (D) OTHER INFORMATION:/product= "random codon by
            trinucleotide mutagenesis (19aa, no Cys)"

(xi) SEQUENCE DESCRIPTION: SEQ ID NO: 11:

AGGGTCTCGA GTGGGTGAGC NNKATTNNKN NKNNKRVTRV TNNKACCNNK TATGCGGATA     60

GCGTGAAAGG CCGTTTTACC ATTTCACGTG ATAATTCGAA AAACACCA                108

(2) INFORMATION FOR SEQ ID NO: 12:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
            (A) NAME/KEY: misc_feature
            (B) LOCATION:21..23
            (D) OTHER INFORMATION:/product= "random codon by
                trinucleotide mutagenesis (19aa, no Cys)"

(ix) FEATURE:
            (A) NAME/KEY: misc_feature
            (B) LOCATION:27..32
            (D) OTHER INFORMATION:/product= "random codons by
                trinucleotide mutagenesis (19aa, no Cys)"

(ix) FEATURE:
            (A) NAME/KEY: misc_feature
            (B) LOCATION:33..38
            (D) OTHER INFORMATION:/product= "random codons by mixed
                monomers (A/G A/C/G T)"

(ix) FEATURE:
            (A) NAME/KEY: misc_feature
            (B) LOCATION:39..41
            (D) OTHER INFORMATION:/product= "random codon by
                trinucleotide mutagenesis (19aa, no Cys)"

(ix) FEATURE:
            (A) NAME/KEY: misc_feature
            (B) LOCATION:45..47
            (D) OTHER INFORMATION:/product= "random codon by
                trinucleotide mutagenesis (19aa, no Cys)"

(xi) SEQUENCE DESCRIPTION: SEQ ID NO: 12:

AGGGTCTCGA GTGGGTGAGC NNKATTNNKN NKRVTRVTNN KACCNNKTAT GCGGATAGCG        60

TGAAAGGCCG TTTTACCATT TCACGTGATA ATTCGAAAAA CACCA                      105

(2) INFORMATION FOR SEQ ID NO: 13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 13:

TGGTGTTTTT CGAATTATCA                                                   20

(2) INFORMATION FOR SEQ ID NO: 14:

(i) SEQUENCE CHARACTERISTICS:
            (A) LENGTH: 108 amino acids
            (B) TYPE: amino acid
            (C) STRANDEDNESS: <Unknown>
            (D) TOPOLOGY: linear (ii) MOLECULE TYPE: protein (xi) SEQUENCE DESCRIPTION: SEQ ID NO: 14:

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys Arg
            100                 105
```

(2) INFORMATION FOR SEQ ID NO: 15:

(i) SEQUENCE CHARACTERISTICS:
        (A) LENGTH: 113 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 15:

```
Asp Ile Val Met Thr Gln Ser Pro Leu Ser Leu Pro Val Thr Pro Gly
1                5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg
```

(2) INFORMATION FOR SEQ ID NO: 16:

(i) SEQUENCE CHARACTERISTICS:
        (A) LENGTH: 109 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 16:

```
Glu Ile Val Leu Thr Gln Ser Pro Gly Thr Leu Ser Leu Ser Pro Gly
1                5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Tyr Thr Phe Gly Gln Gly Thr Lys Val Glu Ile Lys Arg
            100                 105
```

(2) INFORMATION FOR SEQ ID NO: 17:

(i) SEQUENCE CHARACTERISTICS:
    (A) LENGTH: 114 amino acids
    (B) TYPE: amino acid
    (C) STRANDEDNESS: <Unknown>
    (D) TOPOLOGY: linear (ii) MOLECULE TYPE: protein (xi) SEQUENCE DESCRIPTION: SEQ ID NO: 17:

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys Arg
```

(2) INFORMATION FOR SEQ ID NO: 18:

(i) SEQUENCE CHARACTERISTICS:
    (A) LENGTH: 112 amino acids
    (B) TYPE: amino acid
    (C) STRANDEDNESS: <Unknown>
    (D) TOPOLOGY: linear (ii) MOLECULE TYPE: protein (xi) SEQUENCE DESCRIPTION: SEQ ID NO: 18:

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ala Thr Trp Asp Asp Ser Leu
                85                  90                  95

Ser Gly Val Val Phe Gly Gly Gly Thr Lys Leu Thr Val Leu Gly Gln
            100                 105                 110
```

(2) INFORMATION FOR SEQ ID NO: 19:

(i) SEQUENCE CHARACTERISTICS:
    (A) LENGTH: 112 amino acids
    (B) TYPE: amino acid
    (C) STRANDEDNESS: <Unknown>
    (D) TOPOLOGY: linear (ii) MOLECULE TYPE: protein (xi) SEQUENCE DESCRIPTION: SEQ ID NO: 19:

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Ser Thr Val Val Phe Gly Gly Gly Thr Lys Leu Thr Val Leu Gly Gln
                100                 105                 110

(2) INFORMATION FOR SEQ ID NO: 20:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 20:

Tyr Glu Leu Thr Gln Pro Pro Ser Val Ser Val Ala Pro Gly Gln Thr
1               5                   10                  15

Ala Arg Ile Thr Cys Ser Gly Asp Ser Leu Gly Ser Lys Tyr Ala Ser
                20                  25                  30

Trp Tyr Gln Gln Lys Pro Gly Gln Ala Pro Val Leu Val Ile Tyr Asp
            35                  40                  45

Asp Asn Lys Arg Pro Ser Gly Ile Pro Glu Arg Phe Ser Gly Ser Asn
    50                  55                  60

Ser Gly Asn Thr Ala Thr Leu Thr Ile Ser Gly Val Gln Ala Glu Asp
65                  70                  75                  80

Glu Ala Asp Tyr Tyr Cys Gln Ser Trp Asp Ser Ser Gly Asn Val Val
                85                  90                  95

Phe Gly Gly Gly Thr Lys Leu Thr Val Leu Gly Gln
                100                 105

(2) INFORMATION FOR SEQ ID NO: 21:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 21:

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

```
Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Gly Tyr Cys Ser Gly Phe Asp Tyr Trp Gly Gln Gly
            100                 105                 110

Thr Leu Val Thr Val Ser Ser
            115

(2) INFORMATION FOR SEQ ID NO: 22:

(i) SEQUENCE CHARACTERISTICS:
        (A) LENGTH: 117 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 22:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
                35                  40                  45

Gly Trp Ile Asn Pro Asn Ser Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Asp Gly Gly Phe Asp Tyr Trp Gly Gln Gly Thr Leu
            100                 105                 110

Val Thr Val Ser Ser
            115

(2) INFORMATION FOR SEQ ID NO: 23:

(i) SEQUENCE CHARACTERISTICS:
        (A) LENGTH: 120 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 23:

Glx Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Ala Leu Glu
                35                  40                  45

Trp Leu Ala His Ile Asp Trp Asp Asp Lys Tyr Tyr Ser Thr Ser
    50                  55                  60

Leu Lys Ser Arg Leu Thr Ile Ser Lys Asp Thr Ser Lys Asn Gln Val
65                  70                  75                  80
```

Val Leu Thr Met Thr Asn Met Asp Pro Val Asp Thr Ala Thr Tyr Tyr
            85                  90                  95

Cys Ala Arg Ile His Asn Ile Gly Glu Ala Phe Asp Val Trp Gly Gln
            100                 105                 110

Gly Thr Leu Val Thr Val Ser Ser
            115                 120

(2) INFORMATION FOR SEQ ID NO: 24:

(i) SEQUENCE CHARACTERISTICS:
        (A) LENGTH: 117 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 24:

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ser Val Ile Ser Tyr Asp Gly Gly Asn Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Gly Ser Gly Asp Tyr Trp Gly Gln Gly Thr Leu
            100                 105                 110

Val Thr Val Ser Ser
            115

(2) INFORMATION FOR SEQ ID NO: 25:

(i) SEQUENCE CHARACTERISTICS:
        (A) LENGTH: 118 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 25:

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Glu Ile Tyr His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Gly Arg Gly Gly Gly Gly Val Phe Asp Tyr Trp Gly Gln Gly Thr

```
                 100                 105                 110
Leu Val Thr Val Ser Ser
        115

(2) INFORMATION FOR SEQ ID NO: 26:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 26:

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Gly Gly Tyr Tyr Phe Asp Tyr Trp Gly Gln Gly
            100                 105                 110

Thr Leu Val Thr Val Ser Ser
        115

(2) INFORMATION FOR SEQ ID NO: 27:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 27:

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Phe Asp Val Trp Gly Gln Gly
            100                 105                 110

Thr Leu Val Thr Val Ser Ser
        115
```

(2) INFORMATION FOR SEQ ID NO: 28:

(i) SEQUENCE CHARACTERISTICS:
        (A) LENGTH: 109 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 28:

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
                100                 105
```

(2) INFORMATION FOR SEQ ID NO: 29:

(i) SEQUENCE CHARACTERISTICS:
        (A) LENGTH: 114 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 29:

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln His
                85                  90                  95

Tyr Thr Thr Pro Pro Thr Phe Gly Gln Gly Thr Lys Val Glu Ile Lys
                100                 105                 110

Arg Thr
```

(2) INFORMATION FOR SEQ ID NO: 30:

(i) SEQUENCE CHARACTERISTICS:
        (A) LENGTH: 110 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 30:

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln His Tyr Thr Thr Pro
                85                  90                  95

Pro Thr Phe Gly Gln Gly Thr Lys Val Glu Ile Lys Arg Thr
                100                 105                 110
```

(2) INFORMATION FOR SEQ ID NO: 31:

(i) SEQUENCE CHARACTERISTICS:
        (A) LENGTH: 115 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 31:

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Thr Thr Pro Pro Thr Phe Gly Gln Gly Thr Lys Val Glu Ile
                100                 105                 110

Lys Arg Thr
        115
```

(2) INFORMATION FOR SEQ ID NO: 32:

(i) SEQUENCE CHARACTERISTICS:
        (A) LENGTH: 109 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 32:

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
```

```
                    20                  25                  30
Tyr Val Ser Trp Tyr Gln Gln Leu Pro Gly Thr Ala Pro Lys Leu Leu
            35                  40                  45

Ile Tyr Asp Asn Gln Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Gln His Tyr Thr Thr Pro
                85                  90                  95

Pro Val Phe Gly Gly Gly Thr Lys Leu Thr Val Leu Gly
            100                 105
```

(2) INFORMATION FOR SEQ ID NO: 33:

(i) SEQUENCE CHARACTERISTICS:
        (A) LENGTH: 110 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 33:

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Gln His Tyr Thr Thr
                85                  90                  95

Pro Pro Val Phe Gly Gly Gly Thr Lys Leu Thr Val Leu Gly
            100                 105                 110
```

(2) INFORMATION FOR SEQ ID NO: 34:

(i) SEQUENCE CHARACTERISTICS:
        (A) LENGTH: 107 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 34:

```
Ser Tyr Glu Leu Thr Gln Pro Pro Ser Val Ser Val Ala Pro Gly Gln
 1               5                  10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80
```

```
Asp Glu Ala Asp Tyr Tyr Cys Gln Gln His Tyr Thr Thr Pro Pro Val
                85                  90                  95

Phe Gly Gly Gly Thr Lys Leu Thr Val Leu Gly
            100                 105
```

(2) INFORMATION FOR SEQ ID NO: 35:

(i) SEQUENCE CHARACTERISTICS:
        (A) LENGTH: 120 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 35:

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
            115                 120
```

(2) INFORMATION FOR SEQ ID NO: 36:

(i) SEQUENCE CHARACTERISTICS:
        (A) LENGTH: 120 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 36:

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
            115                 120
```

(2) INFORMATION FOR SEQ ID NO: 37:

(i) SEQUENCE CHARACTERISTICS:
        (A) LENGTH: 121 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 37:

```
Gln Val Gln Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Glu
         35                  40                  45

Trp Leu Ala Leu Ile Asp Trp Asp Asp Lys Tyr Tyr Ser Thr Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
             85                  90                  95

Cys Ala Arg Trp Gly Asp Gly Phe Tyr Ala Met Asp Tyr Trp Gly
            100                 105                 110

Gln Gly Thr Leu Val Thr Val Ser Ser
            115                 120
```

(2) INFORMATION FOR SEQ ID NO: 38:

(i) SEQUENCE CHARACTERISTICS:
        (A) LENGTH: 120 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 38:

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
            115                 120
```

(2) INFORMATION FOR SEQ ID NO: 39:

(i) SEQUENCE CHARACTERISTICS:

(A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 39:

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
50                      55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Gly Asp Gly Phe Tyr Ala Met Asp Tyr Trp Gly Gln Gly
            100                 105                 110

Thr Leu Val Thr Val Ser Ser
        115

(2) INFORMATION FOR SEQ ID NO: 40:

(i) SEQUENCE CHARACTERISTICS:
        (A) LENGTH: 120 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 40:

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
50                      55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120

(2) INFORMATION FOR SEQ ID NO: 41:

(i) SEQUENCE CHARACTERISTICS:
        (A) LENGTH: 123 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 41:

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser
        115                 120
```

(2) INFORMATION FOR SEQ ID NO: 42:

(i) SEQUENCE CHARACTERISTICS:
        (A) LENGTH: 327 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..327
        (D) OTHER INFORMATION:/product= "V kappa 1"

(xi) SEQUENCE DESCRIPTION: SEQ ID NO: 42:

```
GAT ATC CAG ATG ACC CAG AGC CCG TCT AGC CTG AGC GCG AGC GTG GGT     48
Asp Ile Gln Met Thr Gln Ser Pro Ser Ser Leu Ser Ala Ser Val Gly
1               5                   10                  15

GAT CGT GTG ACC ATT ACC TGC AGA GCG AGC CAG GGC ATT AGC AGC TAT     96
Asp Arg Val Thr Ile Thr Cys Arg Ala Ser Gln Gly Ile Ser Ser Tyr
            20                  25                  30

CTG GCG TGG TAC CAG CAG AAA CCA GGT AAA GCA CCG AAA CTA TTA ATT    144
Leu Ala Trp Tyr Gln Gln Lys Pro Gly Lys Ala Pro Lys Leu Leu Ile
        35                  40                  45

TAT GCA GCC AGC AGC TTG CAA AGC GGG GTC CCG TCC CGT TTT AGC GGC    192
Tyr Ala Ala Ser Ser Leu Gln Ser Gly Val Pro Ser Arg Phe Ser Gly
    50                  55                  60

TCT GGA TCC GGC ACT GAT TTT ACC CTG ACC ATT AGC AGC CTG CAA CCT    240
Ser Gly Ser Gly Thr Asp Phe Thr Leu Thr Ile Ser Ser Leu Gln Pro
65                  70                  75                  80

GAA GAC TTT GCG ACC TAT TAT TGC CAG CAG CAT TAT ACC ACC CCG CCG    288
Glu Asp Phe Ala Thr Tyr Tyr Cys Gln Gln His Tyr Thr Thr Pro Pro
            85                  90                  95

ACC TTT GGC CAG GGT ACG AAA GTT GAA ATT AAA CGT ACG                327
Thr Phe Gly Gln Gly Thr Lys Val Glu Ile Lys Arg Thr
            100                 105
```

(2) INFORMATION FOR SEQ ID NO: 43:

(i) SEQUENCE CHARACTERISTICS:

(A) LENGTH: 109 amino acids
            (B) TYPE: amino acid
            (D) TOPOLOGY: linear (ii) MOLECULE TYPE: protein (xi) SEQUENCE DESCRIPTION: SEQ ID NO: 43:

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

(2) INFORMATION FOR SEQ ID NO: 44:

(i) SEQUENCE CHARACTERISTICS:
        (A) LENGTH: 342 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..342
        (D) OTHER INFORMATION:/product= "V kappa 2"

(xi) SEQUENCE DESCRIPTION: SEQ ID NO: 44:

GAT ATC GTG ATG ACC CAG AGC CCA CTG AGC CTG CCA GTG ACT CCG GGC        48
Asp Ile Val Met Thr Gln Ser Pro Leu Ser Leu Pro Val Thr Pro Gly
110             115                 120                 125

GAG CCT GCG AGC ATT AGC TGC AGA AGC AGC CAA AGC CTG CTG CAT AGC        96
Glu Pro Ala Ser Ile Ser Cys Arg Ser Ser Gln Ser Leu Leu His Ser
                130                 135                 140

AAC GGC TAT AAC TAT CTG GAT TGG TAC CTT CAA AAA CCA GGT CAA AGC       144
Asn Gly Tyr Asn Tyr Leu Asp Trp Tyr Leu Gln Lys Pro Gly Gln Ser
            145                 150                 155

CCG CAG CTA TTA ATT TAT CTG GGC AGC AAC CGT GCC AGT GGG GTC CCG       192
Pro Gln Leu Leu Ile Tyr Leu Gly Ser Asn Arg Ala Ser Gly Val Pro
        160                 165                 170

GAT CGT TTT AGC GGC TCT GGA TCC GGC ACC GAT TTT ACC CTG AAA ATT       240
Asp Arg Phe Ser Gly Ser Gly Ser Gly Thr Asp Phe Thr Leu Lys Ile
175                 180                 185

AGC CGT GTG GAA GCT GAA GAC GTG GGC GTG TAT TAT TGC CAG CAG CAT       288
Ser Arg Val Glu Ala Glu Asp Val Gly Val Tyr Tyr Cys Gln Gln His
190                 195                 200                 205

TAT ACC ACC CCG CCG ACC TTT GGC CAG GGT ACG AAA GTT GAA ATT AAA       336
Tyr Thr Thr Pro Pro Thr Phe Gly Gln Gly Thr Lys Val Glu Ile Lys
                210                 215                 220

CGT ACG                                                                342
Arg Thr (2) INFORMATION FOR SEQ ID NO: 45:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO: 45:

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln His
                 85                  90                  95

Tyr Thr Thr Pro Pro Thr Phe Gly Gln Gly Thr Lys Val Glu Ile Lys
            100                 105                 110

Arg Thr
```

(2) INFORMATION FOR SEQ ID NO: 46:

(i) SEQUENCE CHARACTERISTICS:
        (A) LENGTH: 330 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..330
        (D) OTHER INFORMATION:/product= "V kappa 3"

(xi) SEQUENCE DESCRIPTION: SEQ ID NO: 46:

```
GAT ATC GTG CTG ACC CAG AGC CCG GCG ACC CTG AGC CTG TCT CCG GGC      48
Asp Ile Val Leu Thr Gln Ser Pro Ala Thr Leu Ser Leu Ser Pro Gly
115                 120                 125                 130

GAA CGT GCG ACC CTG AGC TGC AGA GCG AGC CAG AGC GTG AGC AGC AGC      96
Glu Arg Ala Thr Leu Ser Cys Arg Ala Ser Gln Ser Val Ser Ser Ser
            135                 140                 145

TAT CTG GCG TGG TAC CAG CAG AAA CCA GGT CAA GCA CCG CGT CTA TTA     144
Tyr Leu Ala Trp Tyr Gln Gln Lys Pro Gly Gln Ala Pro Arg Leu Leu
        150                 155                 160

ATT TAT GGC GCG AGC AGC CGT GCA ACT GGG GTC CCG GCG CGT TTT AGC     192
Ile Tyr Gly Ala Ser Ser Arg Ala Thr Gly Val Pro Ala Arg Phe Ser
    165                 170                 175

GGC TCT GGA TCC GGC ACG GAT TTT ACC CTG ACC ATT AGC AGC CTG GAA     240
Gly Ser Gly Ser Gly Thr Asp Phe Thr Leu Thr Ile Ser Ser Leu Glu
180                 185                 190

CCT GAA GAC TTT GCG GTG TAT TAT TGC CAG CAG CAT TAT ACC ACC CCG     288
Pro Glu Asp Phe Ala Val Tyr Tyr Cys Gln Gln His Tyr Thr Thr Pro
195                 200                 205                 210

CCG ACC TTT GGC CAG GGT ACG AAA GTT GAA ATT AAA CGT ACG             330
Pro Thr Phe Gly Gln Gly Thr Lys Val Glu Ile Lys Arg Thr
```

```
Pro Thr Phe Gly Gln Gly Thr Lys Val Glu Ile Lys Arg Thr
            215                 220
```

(2) INFORMATION FOR SEQ ID NO: 47:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO: 47:

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln His Tyr Thr Thr Pro
                85                  90                  95

Pro Thr Phe Gly Gln Gly Thr Lys Val Glu Ile Lys Arg Thr
            100                 105                 110
```

(2) INFORMATION FOR SEQ ID NO: 48:

(i) SEQUENCE CHARACTERISTICS:
        (A) LENGTH: 345 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..345
        (D) OTHER INFORMATION:/product= "V kappa 4"

(xi) SEQUENCE DESCRIPTION: SEQ ID NO: 48:

```
GAT ATC GTG ATG ACC CAG AGC CCG GAT AGC CTG GCG GTG AGC CTG GGC      48
Asp Ile Val Met Thr Gln Ser Pro Asp Ser Leu Ala Val Ser Leu Gly
            115                 120                 125

GAA CGT GCG ACC ATT AAC TGC AGA AGC AGC CAG AGC GTG CTG TAT AGC      96
Glu Arg Ala Thr Ile Asn Cys Arg Ser Ser Gln Ser Val Leu Tyr Ser
            130                 135                 140

AGC AAC AAC AAA AAC TAT CTG GCG TGG TAC CAG CAG AAA CCA GGT CAG     144
Ser Asn Asn Lys Asn Tyr Leu Ala Trp Tyr Gln Gln Lys Pro Gly Gln
        145                 150                 155

CCG CCG AAA CTA TTA ATT TAT TGG GCA TCC ACC CGT GAA AGC GGG GTC     192
Pro Pro Lys Leu Leu Ile Tyr Trp Ala Ser Thr Arg Glu Ser Gly Val
160                 165                 170

CCG GAT CGT TTT AGC GGC TCT GGA TCC GGC ACT GAT TTT ACC CTG ACC     240
Pro Asp Arg Phe Ser Gly Ser Gly Ser Gly Thr Asp Phe Thr Leu Thr
175                 180                 185                 190

ATT TCG TCC CTG CAA GCT GAA GAC GTG GCG GTG TAT TAT TGC CAG CAG     288
Ile Ser Ser Leu Gln Ala Glu Asp Val Ala Val Tyr Tyr Cys Gln Gln
                195                 200                 205
```

-continued

```
CAT TAT ACC ACC CCG CCG ACC TTT GGC CAG GGT ACG AAA GTT GAA ATT         336
His Tyr Thr Thr Pro Pro Thr Phe Gly Gln Gly Thr Lys Val Glu Ile
            210                 215                 220

AAA CGT ACG                                                             345
Lys Arg Thr
        225
```

(2) INFORMATION FOR SEQ ID NO: 49:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO: 49:

```
Asp Ile Val Met Thr Gln Ser Pro Asp Ser Leu Ala Val Ser Leu Gly
  1               5                  10                  15

Glu Arg Ala Thr Ile Asn Cys Arg Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Thr Thr Pro Pro Thr Phe Gly Gln Gly Thr Lys Val Glu Ile
            100                 105                 110

Lys Arg Thr
        115
```

(2) INFORMATION FOR SEQ ID NO: 50:

(i) SEQUENCE CHARACTERISTICS:
        (A) LENGTH: 327 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..327
        (D) OTHER INFORMATION:/product= "V lambda 1"

(xi) SEQUENCE DESCRIPTION: SEQ ID NO: 50:

```
CAG AGC GTG CTG ACC CAG CCG CCT TCA GTG AGT GGC GCA CCA GGT CAG          48
Gln Ser Val Leu Thr Gln Pro Pro Ser Val Ser Gly Ala Pro Gly Gln
                120                 125                 130

CGT GTG ACC ATC TCG TGT AGC GGC AGC AGC AGC AAC ATT GGC AGC AAC          96
Arg Val Thr Ile Ser Cys Ser Gly Ser Ser Ser Asn Ile Gly Ser Asn
            135                 140                 145

TAT GTG AGC TGG TAC CAG CAG TTG CCC GGG ACG GCG CCG AAA CTG CTG         144
Tyr Val Ser Trp Tyr Gln Gln Leu Pro Gly Thr Ala Pro Lys Leu Leu
        150                 155                 160

ATT TAT GAT AAC AAC CAG CGT CCC TCA GGC GTG CCG GAT CGT TTT AGC         192
Ile Tyr Asp Asn Asn Gln Arg Pro Ser Gly Val Pro Asp Arg Phe Ser
    165                 170                 175
```

```
GGA TCC AAA AGC GGC ACC AGC GCG AGC CTT GCG ATT ACG GGC CTG CAA        240
Gly Ser Lys Ser Gly Thr Ser Ala Ser Leu Ala Ile Thr Gly Leu Gln
180             185                 190                 195

AGC GAA GAC GAA GCG GAT TAT TAT TGC CAG CAG CAT TAT ACC ACC CCG        288
Ser Glu Asp Glu Ala Asp Tyr Tyr Cys Gln Gln His Tyr Thr Thr Pro
                200                 205                 210

CCT GTG TTT GGC GGC GGC ACG AAG TTA ACC GTT CTT GGC                    327
Pro Val Phe Gly Gly Gly Thr Lys Leu Thr Val Leu Gly
                215                 220
```

(2) INFORMATION FOR SEQ ID NO: 51:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO: 51:

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
                20                  25                  30

Tyr Val Ser Trp Tyr Gln Gln Leu Pro Gly Thr Ala Pro Lys Leu Leu
                35                  40                  45

Ile Tyr Asp Asn Asn Gln Arg Pro Ser Gly Val Pro Asp Arg Phe Ser
                50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Gln His Tyr Thr Thr Pro
                85                  90                  95

Pro Val Phe Gly Gly Gly Thr Lys Leu Thr Val Leu Gly
                100                 105
```

(2) INFORMATION FOR SEQ ID NO: 52:

(i) SEQUENCE CHARACTERISTICS:
        (A) LENGTH: 330 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..330
        (D) OTHER INFORMATION:/product= "V lambda 2"

(xi) SEQUENCE DESCRIPTION: SEQ ID NO: 52:

```
CAG AGC GCA CTG ACC CAG CCA GCT TCA GTG AGC GGC TCA CCA GGT CAG        48
Gln Ser Ala Leu Thr Gln Pro Ala Ser Val Ser Gly Ser Pro Gly Gln
110             115                 120                 125

AGC ATT ACC ATC TCG TGT ACG GGT ACT AGC AGC GAT GTG GGC GGC TAT        96
Ser Ile Thr Ile Ser Cys Thr Gly Thr Ser Ser Asp Val Gly Gly Tyr
                130                 135                 140

AAC TAT GTG AGC TGG TAC CAG CAG CAT CCC GGG AAG GCG CCG AAA CTG        144
Asn Tyr Val Ser Trp Tyr Gln Gln His Pro Gly Lys Ala Pro Lys Leu
                145                 150                 155

ATG ATT TAT GAT GTG AGC AAC CGT CCC TCA GGC GTG AGC AAC CGT TTT        192
Met Ile Tyr Asp Val Ser Asn Arg Pro Ser Gly Val Ser Asn Arg Phe
                160                 165                 170
```

```
AGC GGA TCC AAA AGC GGC AAC ACC GCG AGC CTG ACC ATT AGC GGC CTG         240
Ser Gly Ser Lys Ser Gly Asn Thr Ala Ser Leu Thr Ile Ser Gly Leu
        175                 180                 185

CAA GCG GAA GAC GAA GCG GAT TAT TAT TGC CAG CAG CAT TAT ACC ACC         288
Gln Ala Glu Asp Glu Ala Asp Tyr Tyr Cys Gln Gln His Tyr Thr Thr
190                 195                 200                 205

CCG CCT GTG TTT GGC GGC GGC ACG AAG TTA ACC GTT CTT GGC                 330
Pro Pro Val Phe Gly Gly Gly Thr Lys Leu Thr Val Leu Gly
                210                 215
```

(2) INFORMATION FOR SEQ ID NO: 53:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO: 53:

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gln Gln His Tyr Thr Thr
                85                  90                  95

Pro Pro Val Phe Gly Gly Gly Thr Lys Leu Thr Val Leu Gly
            100                 105                 110
```

(2) INFORMATION FOR SEQ ID NO: 54:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..321
        (D) OTHER INFORMATION:/product= "V lambda 3"

(xi) SEQUENCE DESCRIPTION: SEQ ID NO: 54:

```
AGC TAT GAA CTG ACC CAG CCG CCT TCA GTG AGC GTT GCA CCA GGT CAG         48
Ser Tyr Glu Leu Thr Gln Pro Pro Ser Val Ser Val Ala Pro Gly Gln
            115                 120                 125

ACC GCG CGT ATC TCG TGT AGC GGC GAT GCG CTG GGC GAT AAA TAC GCG         96
Thr Ala Arg Ile Ser Cys Ser Gly Asp Ala Leu Gly Asp Lys Tyr Ala
        130                 135                 140

AGC TGG TAC CAG CAG AAA CCC GGG CAG GCG CCA GTT CTG GTG ATT TAT        144
Ser Trp Tyr Gln Gln Lys Pro Gly Gln Ala Pro Val Leu Val Ile Tyr
    145                 150                 155

GAT GAT TCT GAC CGT CCC TCA GGC ATC CCG GAA CGC TTT AGC GGA TCC        192
Asp Asp Ser Asp Arg Pro Ser Gly Ile Pro Glu Arg Phe Ser Gly Ser
```

```
                      160                 165                 170
AAC AGC GGC AAC ACC GCG ACC CTG ACC ATT AGC GGC ACT CAG GCG GAA         240
Asn Ser Gly Asn Thr Ala Thr Leu Thr Ile Ser Gly Thr Gln Ala Glu
175                 180                 185                 190

GAC GAA GCG GAT TAT TAT TGC CAG CAG CAT TAT ACC ACC CCG CCT GTG         288
Asp Glu Ala Asp Tyr Tyr Cys Gln Gln His Tyr Thr Thr Pro Pro Val
                        195                 200                 205

TTT GGC GGC GGC ACG AAG TTA ACC GTT CTT GGC                             321
Phe Gly Gly Gly Thr Lys Leu Thr Val Leu Gly
            210                 215

(2) INFORMATION FOR SEQ ID NO: 55:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO: 55:

Ser Tyr Glu Leu Thr Gln Pro Pro Ser Val Ser Val Ala Pro Gly Gln
 1               5                  10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Gln His Tyr Thr Thr Pro Pro Val
                85                  90                  95

Phe Gly Gly Gly Thr Lys Leu Thr Val Leu Gly
            100                 105

(2) INFORMATION FOR SEQ ID NO: 56:

(i) SEQUENCE CHARACTERISTICS:
        (A) LENGTH: 361 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..360
        (D) OTHER INFORMATION:/product= "VH1A"

(xi) SEQUENCE DESCRIPTION: SEQ ID NO: 56:

CAG GTG CAA TTG GTT CAG TCT GGC GCG GAA GTG AAA AAA CCG GGC AGC          48
Gln Val Gln Leu Val Gln Ser Gly Ala Glu Val Lys Lys Pro Gly Ser
            110                 115                 120

AGC GTG AAA GTG AGC TGC AAA GCC TCC GGA GGC ACT TTT AGC AGC TAT          96
Ser Val Lys Val Ser Cys Lys Ala Ser Gly Gly Thr Phe Ser Ser Tyr
        125                 130                 135

GCG ATT AGC TGG GTG CGC CAA GCC CCT GGG CAG GGT CTC GAG TGG ATG         144
Ala Ile Ser Trp Val Arg Gln Ala Pro Gly Gln Gly Leu Glu Trp Met
140                 145                 150                 155

GGC GGC ATT ATT CCG ATT TTT GGC ACG GCG AAC TAC GCG CAG AAG TTT         192
```

-continued

```
                Gly Gly Ile Ile Pro Ile Phe Gly Thr Ala Asn Tyr Ala Gln Lys Phe
                                160                 165                 170

CAG GGC CGG GTG ACC ATT ACC GCG GAT GAA AGC ACC AGC ACC GCG TAT        240
Gln Gly Arg Val Thr Ile Thr Ala Asp Glu Ser Thr Ser Thr Ala Tyr
            175                 180                 185

ATG GAA CTG AGC AGC CTG CGT AGC GAA GAT ACG GCC GTG TAT TAT TGC        288
Met Glu Leu Ser Ser Leu Arg Ser Glu Asp Thr Ala Val Tyr Tyr Cys
            190                 195                 200

GCG CGT TGG GGC GGC GAT GGC TTT TAT GCG ATG GAT TAT TGG GGC CAA        336
Ala Arg Trp Gly Gly Asp Gly Phe Tyr Ala Met Asp Tyr Trp Gly Gln
            205                 210                 215

GGC ACC CTG GTG ACG GTT AGC TCA G                                      361
Gly Thr Leu Val Thr Val Ser Ser
220                 225
```

(2) INFORMATION FOR SEQ ID NO: 57:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 57:

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 58:

(i) SEQUENCE CHARACTERISTICS:
        (A) LENGTH: 361 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..360
        (D) OTHER INFORMATION:/product= "VH1B"

(xi) SEQUENCE DESCRIPTION: SEQ ID NO: 58:

```
CAG GTG CAA TTG GTT CAG AGC GGC GCG GAA GTG AAA AAA CCG GGC GCG        48
Gln Val Gln Leu Val Gln Ser Gly Ala Glu Val Lys Lys Pro Gly Ala
            125                 130                 135

AGC GTG AAA GTG AGC TGC AAA GCC TCC GGA TAT ACC TTT ACC AGC TAT        96
```

```
Ser Val Lys Val Ser Cys Lys Ala Ser Gly Tyr Thr Phe Thr Ser Tyr
        140                 145                 150

TAT ATG CAC TGG GTC CGC CAA GCC CCT GGG CAG GGT CTC GAG TGG ATG     144
Tyr Met His Trp Val Arg Gln Ala Pro Gly Gln Gly Leu Glu Trp Met
        155                 160                 165

GGC TGG ATT AAC CCG AAT AGC GGC GGC ACG AAC TAC GCG CAG AAG TTT     192
Gly Trp Ile Asn Pro Asn Ser Gly Gly Thr Asn Tyr Ala Gln Lys Phe
        170                 175                 180

CAG GGC CGG GTG ACC ATG ACC CGT GAT ACC AGC ATT AGC ACC GCG TAT     240
Gln Gly Arg Val Thr Met Thr Arg Asp Thr Ser Ile Ser Thr Ala Tyr
185                 190                 195                 200

ATG GAA CTG AGC AGC CTG CGT AGC GAA GAT ACG GCC GTG TAT TAT TGC     288
Met Glu Leu Ser Ser Leu Arg Ser Glu Asp Thr Ala Val Tyr Tyr Cys
                205                 210                 215

GCG CGT TGG GGC GGC GAT GGC TTT TAT GCG ATG GAT TAT TGG GGC CAA     336
Ala Arg Trp Gly Gly Asp Gly Phe Tyr Ala Met Asp Tyr Trp Gly Gln
            220                 225                 230

GGC ACC CTG GTG ACG GTT AGC TCA G                                   361
Gly Thr Leu Val Thr Val Ser Ser
        235                 240

(2) INFORMATION FOR SEQ ID NO: 59:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 59:

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120

(2) INFORMATION FOR SEQ ID NO: 60:

(i) SEQUENCE CHARACTERISTICS:
        (A) LENGTH: 364 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..363
        (D) OTHER INFORMATION:/product= "VH2"
```

(xi) SEQUENCE DESCRIPTION: SEQ ID NO: 60:

```
CAG GTG CAA TTG AAA GAA AGC GGC CCG GCC CTG GTA AAA CCG ACC CAA        48
Gln Val Gln Leu Lys Glu Ser Gly Pro Ala Leu Val Lys Pro Thr Gln
                125                 130                 135

ACC CTG ACC CTG ACC TGT ACC TTT TCC GGA TTT AGC CTG TCC ACG TCT        96
Thr Leu Thr Leu Thr Cys Thr Phe Ser Gly Phe Ser Leu Ser Thr Ser
            140                 145                 150

GGC GTT GGC GTG GGC TGG ATT CGC CAG CCG CCT GGG AAA GCC CTC GAG       144
Gly Val Gly Val Gly Trp Ile Arg Gln Pro Pro Gly Lys Ala Leu Glu
        155                 160                 165

TGG CTG GCT CTG ATT GAT TGG GAT GAT GAT AAG TAT TAT AGC ACC AGC       192
Trp Leu Ala Leu Ile Asp Trp Asp Asp Asp Lys Tyr Tyr Ser Thr Ser
    170                 175                 180

CTG AAA ACG CGT CTG ACC ATT AGC AAA GAT ACT TCG AAA AAT CAG GTG       240
Leu Lys Thr Arg Leu Thr Ile Ser Lys Asp Thr Ser Lys Asn Gln Val
185                 190                 195                 200

GTG CTG ACT ATG ACC AAC ATG GAC CCG GTG GAT ACG GCC ACC TAT TAT       288
Val Leu Thr Met Thr Asn Met Asp Pro Val Asp Thr Ala Thr Tyr Tyr
                205                 210                 215

TGC GCG CGT TGG GGC GGC GAT GGC TTT TAT GCG ATG GAT TAT TGG GGC       336
Cys Ala Arg Trp Gly Gly Asp Gly Phe Tyr Ala Met Asp Tyr Trp Gly
            220                 225                 230

CAA GGC ACC CTG GTG ACG GTT AGC TCA G                                 364
Gln Gly Thr Leu Val Thr Val Ser Ser
        235                 240
```

(2) INFORMATION FOR SEQ ID NO: 61:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO: 61:

```
Gln Val Gln Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Glu
         35                  40                  45

Trp Leu Ala Leu Ile Asp Trp Asp Asp Asp Lys Tyr Tyr Ser Thr Ser
     50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Trp Gly Gly Asp Gly Phe Tyr Ala Met Asp Tyr Trp Gly
            100                 105                 110

Gln Gly Thr Leu Val Thr Val Ser Ser
        115                 120
```

(2) INFORMATION FOR SEQ ID NO: 62:

(i) SEQUENCE CHARACTERISTICS:
        (A) LENGTH: 361 base pairs
        (B) TYPE: nucleic acid
        (C) STRANDEDNESS: double
        (D) TOPOLOGY: linear (ii) MOLECULE TYPE: other nucleic acid
    (A) DESCRIPTION: /desc = "synthetic gene"

(ix) FEATURE:
    (A) NAME/KEY: CDS
    (B) LOCATION:1..360
    (D) OTHER INFORMATION:/product= "VH3"

(xi) SEQUENCE DESCRIPTION: SEQ ID NO: 62:

| GAA | GTG | CAA | TTG | GTG | GAA | AGC | GGC | GGC | GGC | CTG | GTG | CAA | CCG | GGC | GGC | 48 |
| Glu | Val | Gln | Leu | Val | Glu | Ser | Gly | Gly | Gly | Leu | Val | Gln | Pro | Gly | Gly | |
| | | | 125 | | | | | 130 | | | | | 135 | | | |

| AGC | CTG | CGT | CTG | AGC | TGC | GCG | GCC | TCC | GGA | TTT | ACC | TTT | AGC | AGC | TAT | 96 |
| Ser | Leu | Arg | Leu | Ser | Cys | Ala | Ala | Ser | Gly | Phe | Thr | Phe | Ser | Ser | Tyr | |
| | | 140 | | | | | 145 | | | | | 150 | | | | |

| GCG | ATG | AGC | TGG | GTG | CGC | CAA | GCC | CCT | GGG | AAG | GGT | CTC | GAG | TGG | GTG | 144 |
| Ala | Met | Ser | Trp | Val | Arg | Gln | Ala | Pro | Gly | Lys | Gly | Leu | Glu | Trp | Val | |
| | 155 | | | | | 160 | | | | | 165 | | | | | |

| AGC | GCG | ATT | AGC | GGT | AGC | GGC | GGC | AGC | ACC | TAT | TAT | GCG | GAT | AGC | GTG | 192 |
| Ser | Ala | Ile | Ser | Gly | Ser | Gly | Gly | Ser | Thr | Tyr | Tyr | Ala | Asp | Ser | Val | |
| 170 | | | | | 175 | | | | | 180 | | | | | 185 | |

| AAA | GGC | CGT | TTT | ACC | ATT | TCA | CGT | GAT | AAT | TCG | AAA | AAC | ACC | CTG | TAT | 240 |
| Lys | Gly | Arg | Phe | Thr | Ile | Ser | Arg | Asp | Asn | Ser | Lys | Asn | Thr | Leu | Tyr | |
| | | | | 190 | | | | | 195 | | | | | 200 | | |

| CTG | CAA | ATG | AAC | AGC | CTG | CGT | GCG | GAA | GAT | ACG | GCC | GTG | TAT | TAT | TGC | 288 |
| Leu | Gln | Met | Asn | Ser | Leu | Arg | Ala | Glu | Asp | Thr | Ala | Val | Tyr | Tyr | Cys | |
| | | | 205 | | | | | 210 | | | | | 215 | | | |

| GCG | CGT | TGG | GGC | GGC | GAT | GGC | TTT | TAT | GCG | ATG | GAT | TAT | TGG | GGC | CAA | 336 |
| Ala | Arg | Trp | Gly | Gly | Asp | Gly | Phe | Tyr | Ala | Met | Asp | Tyr | Trp | Gly | Gln | |
| | | 220 | | | | | 225 | | | | | 230 | | | | |

| GGC | ACC | CTG | GTG | ACG | GTT | AGC | TCA | G | | | | | | | | 361 |
| Gly | Thr | Leu | Val | Thr | Val | Ser | Ser | | | | | | | | | |
| | | 235 | | | | | 240 | | | | | | | | | |

(2) INFORMATION FOR SEQ ID NO: 63:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 63:

| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
| | | 35 | | | | | 40 | | | | | 45 | | | |

| Ser | Ala | Ile | Ser | Gly | Ser | Gly | Gly | Ser | Thr | Tyr | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Arg | Trp | Gly | Gly | Asp | Gly | Phe | Tyr | Ala | Met | Asp | Tyr | Trp | Gly | Gln |
| | | | 100 | | | | | 105 | | | | | 110 | | |

| Gly | Thr | Leu | Val | Thr | Val | Ser | Ser |
| | | 115 | | | | | 120 |

(2) INFORMATION FOR SEQ ID NO: 64:

(i) SEQUENCE CHARACTERISTICS:
        (A) LENGTH: 358 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..357
        (D) OTHER INFORMATION:/product= "VH4"

(xi) SEQUENCE DESCRIPTION: SEQ ID NO: 64:

```
CAG GTG CAA TTG CAA GAA AGT GGT CCG GGC CTG GTA AAA CCG AGC GAA        48
Gln Val Gln Leu Gln Glu Ser Gly Pro Gly Leu Val Lys Pro Ser Glu
            125                 130                 135

ACC CTG AGC CTG ACC TGC ACC GTT TCC GGA GGC AGC ATT AGC AGC TAT        96
Thr Leu Ser Leu Thr Cys Thr Val Ser Gly Gly Ser Ile Ser Ser Tyr
            140                 145                 150

TAT TGG AGC TGG ATT CGC CAG CCG CCT GGG AAG GGT CTC GAG TGG ATT       144
Tyr Trp Ser Trp Ile Arg Gln Pro Pro Gly Lys Gly Leu Glu Trp Ile
            155                 160                 165

GGC TAT ATT TAT TAT AGC GGC AGC ACC AAC TAT AAT CCG AGC CTG AAA       192
Gly Tyr Ile Tyr Tyr Ser Gly Ser Thr Asn Tyr Asn Pro Ser Leu Lys
            170                 175                 180

AGC CGG GTG ACC ATT AGC GTT GAT ACT TCG AAA AAC CAG TTT AGC CTG       240
Ser Arg Val Thr Ile Ser Val Asp Thr Ser Lys Asn Gln Phe Ser Leu
185                 190                 195                 200

AAA CTG AGC AGC GTG ACG GCG GCG GAT ACG GCC GTG TAT TAT TGC GCG       288
Lys Leu Ser Ser Val Thr Ala Ala Asp Thr Ala Val Tyr Tyr Cys Ala
                    205                 210                 215

CGT TGG GGC GGC GAT GGC TTT TAT GCG ATG GAT TAT TGG GGC CAA GGC       336
Arg Trp Gly Gly Asp Gly Phe Tyr Ala Met Asp Tyr Trp Gly Gln Gly
                220                 225                 230

ACC CTG GTG ACG GTT AGC TCA G                                         358
Thr Leu Val Thr Val Ser Ser
            235
```

(2) INFORMATION FOR SEQ ID NO: 65:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 65:

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

-continued

```
                          85                  90                  95
Arg Trp Gly Gly Asp Gly Phe Tyr Ala Met Asp Tyr Trp Gly Gln Gly
            100                 105                 110
Thr Leu Val Thr Val Ser Ser
        115
```

(2) INFORMATION FOR SEQ ID NO: 66:

(i) SEQUENCE CHARACTERISTICS:
        (A) LENGTH: 361 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..360
        (D) OTHER INFORMATION:/product= "VH5"

(xi) SEQUENCE DESCRIPTION: SEQ ID NO: 66:

```
GAA GTG CAA TTG GTT CAG AGC GGC GCG GAA GTG AAA AAA CCG GGC GAA        48
Glu Val Gln Leu Val Gln Ser Gly Ala Glu Val Lys Lys Pro Gly Glu
120                 125                 130                 135

AGC CTG AAA ATT AGC TGC AAA GGT TCC GGA TAT TCC TTT ACG AGC TAT        96
Ser Leu Lys Ile Ser Cys Lys Gly Ser Gly Tyr Ser Phe Thr Ser Tyr
            140                 145                 150

TGG ATT GGC TGG GTG CGC CAG ATG CCT GGG AAG GGT CTC GAG TGG ATG       144
Trp Ile Gly Trp Val Arg Gln Met Pro Gly Lys Gly Leu Glu Trp Met
        155                 160                 165

GGC ATT ATT TAT CCG GGC GAT AGC GAT ACC CGT TAT TCT CCG AGC TTT       192
Gly Ile Ile Tyr Pro Gly Asp Ser Asp Thr Arg Tyr Ser Pro Ser Phe
        170                 175                 180

CAG GGC CAG GTG ACC ATT AGC GCG GAT AAA AGC ATT AGC ACC GCG TAT       240
Gln Gly Gln Val Thr Ile Ser Ala Asp Lys Ser Ile Ser Thr Ala Tyr
    185                 190                 195

CTT CAA TGG AGC AGC CTG AAA GCG AGC GAT ACG GCC ATG TAT TAT TGC       288
Leu Gln Trp Ser Ser Leu Lys Ala Ser Asp Thr Ala Met Tyr Tyr Cys
200                 205                 210                 215

GCG CGT TGG GGC GGC GAT GGC TTT TAT GCG ATG GAT TAT TGG GGC CAA       336
Ala Arg Trp Gly Gly Asp Gly Phe Tyr Ala Met Asp Tyr Trp Gly Gln
                220                 225                 230

GGC ACC CTG GTG ACG GTT AGC TCA G                                     361
Gly Thr Leu Val Thr Val Ser Ser
        235
```

(2) INFORMATION FOR SEQ ID NO: 67:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 67:

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45
```

```
Gly Ile Ile Tyr Pro Gly Asp Ser Asp Thr Arg Tyr Ser Pro Ser Phe
          50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 68:

(i) SEQUENCE CHARACTERISTICS:
        (A) LENGTH: 370 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..369
        (D) OTHER INFORMATION:/product= "VH6"

(xi) SEQUENCE DESCRIPTION: SEQ ID NO: 68:

```
CAG GTG CAA TTG CAA CAG TCT GGT CCG GGC CTG GTG AAA CCG AGC CAA      48
Gln Val Gln Leu Gln Gln Ser Gly Pro Gly Leu Val Lys Pro Ser Gln
                125                 130                 135

ACC CTG AGC CTG ACC TGT GCG ATT TCC GGA GAT AGC GTG AGC AGC AAC      96
Thr Leu Ser Leu Thr Cys Ala Ile Ser Gly Asp Ser Val Ser Ser Asn
            140                 145                 150

AGC GCG GCG TGG AAC TGG ATT CGC CAG TCT CCT GGG CGT GGC CTC GAG     144
Ser Ala Ala Trp Asn Trp Ile Arg Gln Ser Pro Gly Arg Gly Leu Glu
        155                 160                 165

TGG CTG GGC CGT ACC TAT TAT CGT AGC AAA TGG TAT AAC GAT TAT GCG     192
Trp Leu Gly Arg Thr Tyr Tyr Arg Ser Lys Trp Tyr Asn Asp Tyr Ala
    170                 175                 180

GTG AGC GTG AAA AGC CGG ATT ACC ATC AAC CCG GAT ACT TCG AAA AAC     240
Val Ser Val Lys Ser Arg Ile Thr Ile Asn Pro Asp Thr Ser Lys Asn
185                 190                 195                 200

CAG TTT AGC CTG CAA CTG AAC AGC GTG ACC CCG GAA GAT ACG GCC GTG     288
Gln Phe Ser Leu Gln Leu Asn Ser Val Thr Pro Glu Asp Thr Ala Val
                205                 210                 215

TAT TAT TGC GCG CGT TGG GGC GGC GAT GGC TTT TAT GCG ATG GAT TAT     336
Tyr Tyr Cys Ala Arg Trp Gly Gly Asp Gly Phe Tyr Ala Met Asp Tyr
            220                 225                 230

TGG GGC CAA GGC ACC CTG GTG ACG GTT AGC TCA G                       370
Trp Gly Gln Gly Thr Leu Val Thr Val Ser Ser
        235                 240
```

(2) INFORMATION FOR SEQ ID NO: 69:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO: 69:

-continued

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Gly Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
             85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser
            115                 120
```

(2) INFORMATION FOR SEQ ID NO: 70:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 70:

```
GAATGCATAC GCTGATATCC AGATGACCCA GAGCCCGTCT AGCCTGAGC         49
```

(2) INFORMATION FOR SEQ ID NO: 71:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 71:

```
CGCTCTGCAG GTAATGGTCA CACGATCACC CACGCTCGCG CTCAGGCTAG ACGGGC    56
```

(2) INFORMATION FOR SEQ ID NO: 72:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 72:

```
GACCATTACC TGCAGAGCGA GCCAGGGCAT TAGCAGCTAT CTGGCGTGGT ACCAGCAG    58
```

(2) INFORMATION FOR SEQ ID NO: 73:

(i) SEQUENCE CHARACTERISTICS:
        (A) LENGTH: 71 base pairs
        (B) TYPE: nucleic acid
        (C) STRANDEDNESS: single (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 73:

CTTTGCAAGC TGCTGGCTGC ATAAATTAAT AGTTTCGGTG CTTTACCTGG TTTCTGCTGG        60

TACCACGCCA G                                                             71

(2) INFORMATION FOR SEQ ID NO: 74:

(i) SEQUENCE CHARACTERISTICS:
            (A) LENGTH: 67 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 74:

CAGCCAGCAG CTTGCAAAGC GGGGTCCCGT CCCGTTTTAG CGGCTCTGGA TCCGGCACTG        60

ATTTTAC                                                                  67

(2) INFORMATION FOR SEQ ID NO: 75:

(i) SEQUENCE CHARACTERISTICS:
            (A) LENGTH: 67 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 75:

GATAATAGGT CGCAAAGTCT TCAGGTTGCA GGCTGCTAAT GGTCAGGGTA AAATCAGTGC        60

CGGATCC                                                                  67

(2) INFORMATION FOR SEQ ID NO: 76:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 76:

CGATATCGTG ATGACCCAGA GCCCACTGAG CCTGCCAGTG ACTCCGGGCG AGCC              54

(2) INFORMATION FOR SEQ ID NO: 77:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 77:

GCCGTTGCTA TGCAGCAGGC TTTGGCTGCT TCTGCAGCTA ATGCTCGCAG GCTCGCCCGG        60

```
AGTCAC                                                               66

(2) INFORMATION FOR SEQ ID NO: 78:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 78:

CTGCTGCATA GCAACGGCTA TAACTATCTG GATTGGTACC TTCAAAAACC AGGTCAAAGC     60

CC                                                                   62

(2) INFORMATION FOR SEQ ID NO: 79:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 79:

CGATCCGGGA CCCCACTGGC ACGGTTGCTG CCCAGATAAA TTAATAGCTG CGGGCTTTGA     60

CCTGGTTTTT G                                                         71

(2) INFORMATION FOR SEQ ID NO: 80:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 80:

AGTGGGGTCC CGGATCGTTT TAGCGGCTCT GGATCCGGCA CCGATTTTAC CCTGAAAATT     60

AGCCGTGTG                                                            69

(2) INFORMATION FOR SEQ ID NO: 81:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 81:

CCATGCAATA ATACACGCCC ACGTCTTCAG CTTCCACACG GCTAATTTTC AGGG           54

(2) INFORMATION FOR SEQ ID NO: 82:

(i) SEQUENCE CHARACTERISTICS:
        (A) LENGTH: 38 base pairs
        (B) TYPE: nucleic acid
        (C) STRANDEDNESS: single
```

(D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 82:

GAATGCATAC GCTGATATCG TGCTGACCCA GAGCCCGG                                    38

(2) INFORMATION FOR SEQ ID NO: 83:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 83:

CGCTCTGCAG CTCAGGGTCG CACGTTCGCC CGGAGACAGG CTCAGGGTCG CCGGGCTCTG            60

GGTCAGC                                                                     67

(2) INFORMATION FOR SEQ ID NO: 84:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 84:

CCCTGAGCTG CAGAGCGAGC CAGAGCGTGA GCAGCAGCTA TCTGGCGTGG TACCAG               56

(2) INFORMATION FOR SEQ ID NO: 85:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 85:

GCACGGCTGC TCGCGCCATA AATTAATAGA CGCGGTGCTT GACCTGGTTT CTGCTGGTAC            60

CACGCCAGAT AG                                                               72

(2) INFORMATION FOR SEQ ID NO: 86:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 86:

GCGCGAGCAG CCGTGCAACT GGGGTCCCGG CGCGTTTTAG CGGCTCTGGA TCCGGCACGG            60

ATTTTAC                                                                     67

(2) INFORMATION FOR SEQ ID NO: 87:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 87:

```
GATAATACAC CGCAAAGTCT TCAGGTTCCA GGCTGCTAAT GGTCAGGGTA AAATCCGTGC    60

CGGATC                                                               66
```

(2) INFORMATION FOR SEQ ID NO: 88:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 88:

```
GAATGCATAC GCTGATATCG TGATGACCCA GAGCCCGGAT AGCCTGGCG               49
```

(2) INFORMATION FOR SEQ ID NO: 89:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 89:

```
GCTTCTGCAG TTAATGGTCG CACGTTCGCC CAGGCTCACC GCCAGGCTAT CCGGGC        56
```

(2) INFORMATION FOR SEQ ID NO: 90:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 90:

```
CGACCATTAA CTGCAGAAGC AGCCAGAGCG TGCTGTATAG CAGCAACAAC AAAAACTATC    60

TGGCGTGGTA CCAG                                                      74
```

(2) INFORMATION FOR SEQ ID NO: 91:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 91:

GATGCCCAAT AAATTAATAG TTTCGGCGGC TGACCTGGTT TCTGCTGGTA CCACGCCAGA    60

TAG    63

(2) INFORMATION FOR SEQ ID NO: 92:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 92:

AAACTATTAA TTTATTGGGC ATCCACCCGT GAAAGCGGGG TCCCGGATCG TTTTAGCGGC    60

TCTGGATCCG GCAC    74

(2) INFORMATION FOR SEQ ID NO: 93:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 93:

GATAATACAC CGCCACGTCT TCAGCTTGCA GGGACGAAAT GGTCAGGGTA AAATCAGTGC    60

CGGATCCAGA GCC    73

(2) INFORMATION FOR SEQ ID NO: 94:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 94:

GAATGCATAC GCTCAGAGCG TGCTGACCCA GCCGCCTTCA GTGAGTGG    48

(2) INFORMATION FOR SEQ ID NO: 95:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 95:

CAATGTTGCT GCTGCTGCCG CTACACGAGA TGGTCACACG CTGACCTGGT GCGCCACTCA    60

CTGAAGGCGG C    71

(2) INFORMATION FOR SEQ ID NO: 96:

```
    (i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 96:

GGCAGCAGCA GCAACATTGG CAGCAACTAT GTGAGCTGGT ACCAGCAGTT GCCCGGGAC         59

(2) INFORMATION FOR SEQ ID NO: 97:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 97:

CCGGCACGCC TGAGGGACGC TGGTTGTTAT CATAAATCAG CAGTTTCGGC GCCGTCCCGG        60

GCAACTGC                                                                68

(2) INFORMATION FOR SEQ ID NO: 98:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 98:

CCCTCAGGCG TGCCGGATCG TTTTAGCGGA TCCAAAAGCG GCACCAGCGC GAGCCTTGCG        60

(2) INFORMATION FOR SEQ ID NO: 99:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 99:

CCGCTTCGTC TTCGCTTTGC AGGCCCGTAA TCGCAAGGCT CGCGCTGG                     48

(2) INFORMATION FOR SEQ ID NO: 100:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 100:

GAATGCATAC GCTCAGAGCG CACTGACCCA GCCAGCTTCA GTGAGCGGC                    49
```

(2) INFORMATION FOR SEQ ID NO: 101:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 101:

```
CGCTGCTAGT ACCCGTACAC GAGATGGTAA TGCTCTGACC TGGTGAGCCG CTCACTGAAG    60

CTGG                                                                 64
```

(2) INFORMATION FOR SEQ ID NO: 102:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 102:

```
GTACGGGTAC TAGCAGCGAT GTGGGCGGCT ATAACTATGT GAGCTGGTAC CAGCAGCATC    60

CCGG                                                                 64
```

(2) INFORMATION FOR SEQ ID NO: 103:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 103:

```
CGCCTGAGGG ACGGTTGCTC ACATCATAAA TCATCAGTTT CGGCGCCTTC CCGGGATGCT    60

GCTGGTAC                                                             68
```

(2) INFORMATION FOR SEQ ID NO: 104:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 104:

```
CAACCGTCCC TCAGGCGTGA GCAACCGTTT TAGCGGATCC AAAAGCGGCA ACACCGCGAG    60

CC                                                                   62
```

(2) INFORMATION FOR SEQ ID NO: 105:

(i) SEQUENCE CHARACTERISTICS:
        (A) LENGTH: 53 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 105:

CCGCTTCGTC TTCCGCTTGC AGGCCGCTAA TGGTCAGGCT CGCGGTGTTG CCG           53

(2) INFORMATION FOR SEQ ID NO: 106:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 106:

GAATGCATAC GCTAGCTATG AACTGACCCA GCCGCCTTCA GTGAGCG                  47

(2) INFORMATION FOR SEQ ID NO: 107:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 107:

CGCCCAGCGC ATCGCCGCTA CACGAGATAC GCGCGGTCTG ACCTGGTGCA ACGCTCACTG    60

AAGGCGGC                                                            68

(2) INFORMATION FOR SEQ ID NO: 108:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 108:

GGCGATGCGC TGGGCGATAA ATACGCGAGC TGGTACCAGC AGAAACCCGG GCAGGCGC      58

(2) INFORMATION FOR SEQ ID NO: 109:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 109:

GCGTTCCGGG ATGCCTGAGG GACGGTCAGA ATCATCATAA ATCACCAGAA CTGGCGCCTG    60

CCCGGGTTTC                                                          70
```

(2) INFORMATION FOR SEQ ID NO: 110:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 110:

```
CAGGCATCCC GGAACGCTTT AGCGGATCCA ACAGCGGCAA CACCGCGACC CTGACCATTA      60

GCGG                                                                  64
```

(2) INFORMATION FOR SEQ ID NO: 111:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 111:

```
CCGCTTCGTC TTCCGCCTGA GTGCCGCTAA TGGTCAGGGT C                         41
```

(2) INFORMATION FOR SEQ ID NO: 112:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 112:

```
GCTCTTCACC CCTGTTACCA AAGCCCAGGT GCAATTG                              37
```

(2) INFORMATION FOR SEQ ID NO: 113:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 113:

```
GGCTTTGCAG CTCACTTTCA CGCTGCTGCC CGGTTTTTTC ACTTCCGCGC CAGACTGAAC      60

CAATTGCACC TGGGCTTTG                                                  79
```

(2) INFORMATION FOR SEQ ID NO: 114:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

-continued

```
    (xi) SEQUENCE DESCRIPTION: SEQ ID NO: 114:

GAAAGTGAGC TGCAAAGCCT CCGGAGGCAC TTTTAGCAGC TATGCGATTA GCTGGGTGCG      60

CCAAGCCCCT GGGCAGGGTC                                                 80

(2) INFORMATION FOR SEQ ID NO: 115:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 115:

GCCCTGAAAC TTCTGCGCGT AGTTCGCCGT GCCAAAAATC GGAATAATGC CGCCCATCCA      60

CTCGAGACCC TGCCCAGGGG C                                               81

(2) INFORMATION FOR SEQ ID NO: 116:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 116:

GCGCAGAAGT TTCAGGGCCG GGTGACCATT ACCGCGGATG AAAGCACCAG CACCGCGTAT      60

ATGGAACTGA GCAGCCTGCG                                                 80

(2) INFORMATION FOR SEQ ID NO: 117:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 117:

GCGCGCAATA ATACACGGCC GTATCTTCGC TACGCAGGCT GCTCAGTTCC                 50

(2) INFORMATION FOR SEQ ID NO: 118:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 118:

GGCTTTGCAG CTCACTTTCA CGCTCGCGCC CGGTTTTTTC ACTTCCGCGC CGCTCTGAAC      60

CAATTGCACC TGGGCTTTG                                                  79

(2) INFORMATION FOR SEQ ID NO: 119:
```

```
    (i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 119:

GAAAGTGAGC TGCAAAGCCT CCGGATATAC CTTTACCAGC TATTATATGC ACTGGGTCCG     60

CCAAGCCCCT GGGCAGGGTC                                                 80

(2) INFORMATION FOR SEQ ID NO: 120:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 120:

GCCCTGAAAC TTCTGCGCGT AGTTCGTGCC GCCGCTATTC GGGTTAATCC AGCCCATCCA     60

CTCGAGACCC TGCCCAGGGG C                                               81

(2) INFORMATION FOR SEQ ID NO: 121:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 121:

GCGCAGAAGT TCAGGGCCG GGTGACCATG ACCCGTGATA CCAGCATTAG CACCGCGTAT      60

ATGGAACTGA GCAGCCTGCG                                                 80

(2) INFORMATION FOR SEQ ID NO: 122:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 122:

GGTACAGGTC AGGGTCAGGG TTTGGGTCGG TTTCACCAGG GCCGGCCGC TTTCTTTCAA      60

TTGCACCTGG GCTTTG                                                     76

(2) INFORMATION FOR SEQ ID NO: 123:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid
```

(A) DESCRIPTION: /desc = "synthetic oligonucleotide"

(xi) SEQUENCE DESCRIPTION: SEQ ID NO: 123:

CTGACCCTGA CCTGTACCTT TTCCGGATTT AGCCTGTCCA CGTCTGGCGT TGGCGTGGGC      60

TGGATTCGCC AGCCGCCTGG GAAAG      85

(2) INFORMATION FOR SEQ ID NO: 124:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 124:

GCGTTTTCAG GCTGGTGCTA TAATACTTAT CATCATCCCA ATCAATCAGA GCCAGCCACT      60

CGAGGGCTTT CCCAGGCGGC TGG      83

(2) INFORMATION FOR SEQ ID NO: 125:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 125:

GCACCAGCCT GAAAACGCGT CTGACCATTA GCAAAGATAC TTCGAAAAAT CAGGTGGTGC      60

TGACTATGAC CAACATGG      78

(2) INFORMATION FOR SEQ ID NO: 126:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 126:

GCGCGCAATA ATAGGTGGCC GTATCCACCG GGTCCATGTT GGTCATAGTC AGC      53

(2) INFORMATION FOR SEQ ID NO: 127:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 127:

CGAAGTGCAA TTGGTGGAAA GCGGCGGCGG CCTGGTGCAA CCGGGCGGCA G      51

(2) INFORMATION FOR SEQ ID NO: 128:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 128:

CATAGCTGCT AAAGGTAAAT CCGGAGGCCG CGCAGCTCAG ACGCAGGCTG CCGCCCGGTT      60

GCAC                                                                   64

(2) INFORMATION FOR SEQ ID NO: 129:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 129:

GATTTACCTT TAGCAGCTAT GCGATGAGCT GGGTGCGCCA AGCCCCTGGG AAGGGTCTCG      60

AGTGGGTGAG                                                             70

(2) INFORMATION FOR SEQ ID NO: 130:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 130:

GGCCTTTCAC GCTATCCGCA TAATAGGTGC TGCCGCCGCT ACCGCTAATC GCGCTCACCC      60

ACTCGAGACC C                                                           71

(2) INFORMATION FOR SEQ ID NO: 131:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 131:

CGGATAGCGT GAAAGGCCGT TTTACCATTT CACGTGATAA TTCGAAAAAC ACCCTGTATC      60

TGCAAATGAA CAG                                                         73

(2) INFORMATION FOR SEQ ID NO: 132:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "synthetic oligonucleotide"

(xi) SEQUENCE DESCRIPTION: SEQ ID NO: 132:

CACGCGCGCA ATAATACACG GCCGTATCTT CCGCACGCAG GCTGTTCATT TGCAGATACA        60

GG                                                                      62

(2) INFORMATION FOR SEQ ID NO: 133:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 133:

GGTCAGGCTC AGGGTTTCGC TCGGTTTCAC CAGGCCCGGA CCACTTTCTT GCAATTGCAC        60

CTGGGCTTTG                                                              70

(2) INFORMATION FOR SEQ ID NO: 134:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 134:

GAAACCCTGA GCCTGACCTG CACCGTTTCC GGAGGCAGCA TTAGCAGCTA TTATTGGAGC        60

TGGATTCGCC AGCCGC                                                       76

(2) INFORMATION FOR SEQ ID NO: 135:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 135:

GATTATAGTT GGTGCTGCCG CTATAATAAA TATAGCCAAT CCACTCGAGA CCCTTCCCAG        60

GCGGCTGGCG AATCCAG                                                      77

(2) INFORMATION FOR SEQ ID NO: 136:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 136:

CGGCAGCACC AACTATAATC CGAGCCTGAA AAGCCGGGTG ACCATTAGCG TTGATACTTC        60

GAAAAACCAG TTTAGCCTG                                                    79

(2) INFORMATION FOR SEQ ID NO: 137:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 137:

```
GCGCGCAATA ATACACGGCC GTATCCGCCG CCGTCACGCT GCTCAGTTTC AGGCTAAACT      60

GGTTTTTCG                                                              69
```

(2) INFORMATION FOR SEQ ID NO: 138:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 138:

```
GCTCTTCACC CCTGTTACCA AAGCCGAAGT GCAATTG                               37
```

(2) INFORMATION FOR SEQ ID NO: 139:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 139:

```
CCTTTGCAGC TAATTTTCAG GCTTTCGCCC GGTTTTTTCA CTTCCGCGCC GCTCTGAACC      60

AATTGCACTT CGGCTTTGG                                                   79
```

(2) INFORMATION FOR SEQ ID NO: 140:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 140:

```
CCTGAAAATT AGCTGCAAAG GTTCCGGATA TTCCTTTACG AGCTATTGGA TTGGCTGGGT      60

GCGCCAGATG CCTGG                                                       75
```

(2) INFORMATION FOR SEQ ID NO: 141:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 141:

CGGAGAATAA CGGGTATCGC TATCGCCCGG ATAAATAATG CCCATCCACT CGAGACCCTT    60

CCCAGGCATC TGGCGCAC    78

(2) INFORMATION FOR SEQ ID NO: 142:

(i) SEQUENCE CHARACTERISTICS:
            (A) LENGTH: 77 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 142:

CGATACCCGT TATTCTCCGA GCTTTCAGGG CCAGGTGACC ATTAGCGCGG ATAAAAGCAT    60

TAGCACCGCG TATCTTC    77

(2) INFORMATION FOR SEQ ID NO: 143:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 143:

GCGCGCAATA ATACATGGCC GTATCGCTCG CTTTCAGGCT GCTCCATTGA AGATACGCGG    60

TGCTAATG    68

(2) INFORMATION FOR SEQ ID NO: 144:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 144:

GAAATCGCAC AGGTCAGGCT CAGGGTTTGG CTCGGTTTCA CCAGGCCCGG ACCAGACTGT    60

TGCAATTGCA CCTGGGCTTT G    81

(2) INFORMATION FOR SEQ ID NO: 145:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO: 145:

GCCTGACCTG TGCGATTTCC GGAGATAGCG TGAGCAGCAA CAGCGCGGCG TGGAACTGGA    60

```
TTCGCCAGTC TCCTGGGCG                                                  79

(2) INFORMATION FOR SEQ ID NO: 146:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 146:

CACCGCATAA TCGTTATACC ATTTGCTACG ATAATAGGTA CGGCCCAGCC ACTCGAGGCC    60

ACGCCCAGGA GACTGGCG                                                  78

(2) INFORMATION FOR SEQ ID NO: 147:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 147:

GGTATAACGA TTATGCGGTG AGCGTGAAAA GCCGGATTAC CATCAACCCG GATACTTCGA    60

AAAACCAGTT TAGCCTGC                                                  78

(2) INFORMATION FOR SEQ ID NO: 148:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 148:

GCGCGCAATA ATACACGGCC GTATCTTCCG GGGTCACGCT GTTCAGTTGC AGGCTAAACT    60

GGTTTTTC                                                             68

(2) INFORMATION FOR SEQ ID NO: 149:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 149:

GGCTGAAGAC GTGGGCGTGT ATTATTGCCA GCAGCATTAT ACCACCCCGC CGACCTTTGG    60

CCAGGGTAC                                                            69

(2) INFORMATION FOR SEQ ID NO: 150:

(i) SEQUENCE CHARACTERISTICS:
```

(A) LENGTH: 71 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 150:

GCGGAAAAAT AAACACGCTC GGAGCAGCCA CCGTACGTTT AATTTCAACT TTCGTACCCT    60

GGCCAAAGGT C    71

(2) INFORMATION FOR SEQ ID NO: 151:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 151:

GAGCGTGTTT ATTTTTCCGC CGAGCGATGA ACAACTGAAA AGCGGCACGG CGAGCGTGGT    60

GTGCCTGCTG    70

(2) INFORMATION FOR SEQ ID NO: 152:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 152:

CAGCGCGTTG TCTACTTTCC ACTGAACTTT CGCTTCACGC GGATAAAAGT TGTTCAGCAG    60

GCACACCACG C    71

(2) INFORMATION FOR SEQ ID NO: 153:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 153:

GAAAGTAGAC AACGCGCTGC AAAGCGGCAA CAGCCAGGAA AGCGTGACCG AACAGGATAG    60

CAAAGATAG    69

(2) INFORMATION FOR SEQ ID NO: 154:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 154:

GTTTTTCATA ATCCGCTTTG CTCAGGGTCA GGGTGCTGCT CAGAGAATAG GTGCTATCTT    60

TGCTATCCTG TTCG    74

(2) INFORMATION FOR SEQ ID NO: 155:

(i) SEQUENCE CHARACTERISTICS:
      (A) LENGTH: 71 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO: 155:

GCAAAGCGGA TTATGAAAAA CATAAAGTGT ATGCGTGCGA AGTGACCCAT CAAGGTCTGA    60

GCAGCCCGGT G    71

(2) INFORMATION FOR SEQ ID NO: 156:

(i) SEQUENCE CHARACTERISTICS:
      (A) LENGTH: 57 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO: 156:

GGCATGCTTA TCAGGCCTCG CCACGATTAA AAGATTTAGT CACCGGGCTG CTCAGAC    57

(2) INFORMATION FOR SEQ ID NO: 157:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO: 157:

GGCGTCTAGA GGCCAAGGCA CCCTGGTGAC GGTTAGCTCA GCGTCGAC    48

(2) INFORMATION FOR SEQ ID NO: 158:

(i) SEQUENCE CHARACTERISTICS:
      (A) LENGTH: 63 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO: 158:

GTGCTTTTGC TGCTCGGAGC CAGCGGAAAC ACGCTTGGAC CTTTGGTCGA CGCTGAGCTA    60

ACC    63

(2) INFORMATION FOR SEQ ID NO: 159:

(i) SEQUENCE CHARACTERISTICS:

-continued

```
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 159:

CTCCGAGCAG CAAAAGCACC AGCGGCGGCA CGGCTGCCCT GGGCTGCCTG GTTAAAGATT       60

ATTTCC                                                                 66

(2) INFORMATION FOR SEQ ID NO: 160:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 160:

CTGGTCAGCG CCCCGCTGTT CCAGCTCACG GTGACTGGTT CCGGGAAATA ATCTTTAACC       60

AGGCA                                                                  65

(2) INFORMATION FOR SEQ ID NO: 161:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 161:

AGCGGGGCGC TGACCAGCGG CGTGCATACC TTTCCGGCGG TGCTGCAAAG CAGCGGCCTG       60

(2) INFORMATION FOR SEQ ID NO: 162:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 162:

GTGCCTAAGC TGCTGCTCGG CACGGTCACA ACGCTGCTCA GGCTATACAG GCCGCTGCTT       60

TGCAG                                                                  65

(2) INFORMATION FOR SEQ ID NO: 163:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 163:
```

GAGCAGCAGC TTAGGCACTC AGACCTATAT TTGCAACGTG AACCATAAAC CGAGCAACAC    60

C                                                                   61

(2) INFORMATION FOR SEQ ID NO: 164:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 164:

GCGCGAATTC GCTTTTCGGT TCCACTTTTT TATCCACTTT GGTGTTGCTC GGTTTATGG    59

(2) INFORMATION FOR SEQ ID NO: 165:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:7..321
        (D) OTHER INFORMATION:/product= "C kappa"

(xi) SEQUENCE DESCRIPTION: SEQ ID NO: 165:

CGTACG GTG GCT GCT CCG AGC GTG TTT ATT TTT CCG CCG AGC GAT GAA      48
       Val Ala Ala Pro Ser Val Phe Ile Phe Pro Pro Ser Asp Glu
            125             130             135

CAA CTG AAA AGC GGC ACG GCG AGC GTG GTG TGC CTG CTG AAC AAC TTT     96
Gln Leu Lys Ser Gly Thr Ala Ser Val Val Cys Leu Leu Asn Asn Phe
        140             145             150

TAT CCG CGT GAA GCG AAA GTT CAG TGG AAA GTA GAC AAC GCG CTG CAA    144
Tyr Pro Arg Glu Ala Lys Val Gln Trp Lys Val Asp Asn Ala Leu Gln
    155             160             165

AGC GGC AAC AGC CAG GAA AGC GTG ACC GAA CAG GAT AGC AAA GAT AGC    192
Ser Gly Asn Ser Gln Glu Ser Val Thr Glu Gln Asp Ser Lys Asp Ser
170             175             180             185

ACC TAT TCT CTG AGC AGC ACC CTG ACC CTG AGC AAA GCG GAT TAT GAA    240
Thr Tyr Ser Leu Ser Ser Thr Leu Thr Leu Ser Lys Ala Asp Tyr Glu
            190             195             200

AAA CAT AAA GTG TAT GCG TGC GAA GTG ACC CAT CAA GGT CTG AGC AGC    288
Lys His Lys Val Tyr Ala Cys Glu Val Thr His Gln Gly Leu Ser Ser
            205             210             215

CCG GTG ACT AAA TCT TTT AAT CGT GGC GAG GCC TGATAAGCAT GC          333
Pro Val Thr Lys Ser Phe Asn Arg Gly Glu Ala
            220             225

(2) INFORMATION FOR SEQ ID NO: 166:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO: 166:

```
Val Ala Ala Pro Ser Val Phe Ile Phe Pro Ser Asp Glu Gln Leu
 1               5                  10                  15

Lys Ser Gly Thr Ala Ser Val Val Cys Leu Leu Asn Asn Phe Tyr Pro
                20                  25                  30

Arg Glu Ala Lys Val Gln Trp Lys Val Asp Asn Ala Leu Gln Ser Gly
            35                  40                  45

Asn Ser Gln Glu Ser Val Thr Glu Gln Asp Ser Lys Asp Ser Thr Tyr
         50                  55                  60

Ser Leu Ser Ser Thr Leu Thr Leu Ser Lys Ala Asp Tyr Glu Lys His
 65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Ala
            100                 105
```

(2) INFORMATION FOR SEQ ID NO: 167:

(i) SEQUENCE CHARACTERISTICS:
        (A) LENGTH: 327 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:6..317
        (D) OTHER INFORMATION:/product= "CH1"

(xi) SEQUENCE DESCRIPTION: SEQ ID NO: 167:

```
GCTCA GCG TCG ACC AAA GGT CCA AGC GTG TTT CCG CTG GCT CCG AGC           47
      Ala Ser Thr Lys Gly Pro Ser Val Phe Pro Leu Ala Pro Ser
                     110                 115

AGC AAA AGC ACC AGC GGC GGC ACG GCT GCC CTG GGC TGC CTG GTT AAA         95
Ser Lys Ser Thr Ser Gly Gly Thr Ala Ala Leu Gly Cys Leu Val Lys
120                 125                 130                 135

GAT TAT TTC CCG GAA CCA GTC ACC GTG AGC TGG AAC AGC GGG GCG CTG         143
Asp Tyr Phe Pro Glu Pro Val Thr Val Ser Trp Asn Ser Gly Ala Leu
                140                 145                 150

ACC AGC GGC GTG CAT ACC TTT CCG GCG GTG CTG CAA AGC AGC GGC CTG         191
Thr Ser Gly Val His Thr Phe Pro Ala Val Leu Gln Ser Ser Gly Leu
                155                 160                 165

TAT AGC CTG AGC AGC GTT GTG ACC GTG CCG AGC AGC AGC TTA GGC ACT         239
Tyr Ser Leu Ser Ser Val Val Thr Val Pro Ser Ser Ser Leu Gly Thr
            170                 175                 180

CAG ACC TAT ATT TGC AAC GTG AAC CAT AAA CCG AGC AAC ACC AAA GTG         287
Gln Thr Tyr Ile Cys Asn Val Asn His Lys Pro Ser Asn Thr Lys Val
        185                 190                 195

GAT AAA AAA GTG GAA CCG AAA AGC GAA TTC TGATAAGCTT                      327
Asp Lys Lys Val Glu Pro Lys Ser Glu Phe
200                 205
```

(2) INFORMATION FOR SEQ ID NO: 168:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO: 168:

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Glu Phe
            100
```

(2) INFORMATION FOR SEQ ID NO: 169:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:85..396
        (D) OTHER INFORMATION:/product= "C lambda"

(xi) SEQUENCE DESCRIPTION: SEQ ID NO: 169:

```
GAAGACGAAG CGGATTATTA TTGCCAGCAG CATTATACCA CCCCGCCTGT GTTTGGCGGC     60

GGCACGAAGT TAACCGTTCT TGGC CAG CCG AAA GCC GCA CCG AGT GTG ACG       111
                           Gln Pro Lys Ala Ala Pro Ser Val Thr
                           105                 110

CTG TTT CCG CCG AGC AGC GAA GAA TTG CAG GCG AAC AAA GCG ACC CTG     159
Leu Phe Pro Pro Ser Ser Glu Glu Leu Gln Ala Asn Lys Ala Thr Leu
    115                 120                 125

GTG TGC CTG ATT AGC GAC TTT TAT CCG GGA GCC GTG ACA GTG GCC TGG     207
Val Cys Leu Ile Ser Asp Phe Tyr Pro Gly Ala Val Thr Val Ala Trp
130                 135                 140                 145

AAG GCA GAT AGC AGC CCC GTC AAG GCG GGA GTG GAG ACC ACC ACA CCC     255
Lys Ala Asp Ser Ser Pro Val Lys Ala Gly Val Glu Thr Thr Thr Pro
                150                 155                 160

TCC AAA CAA AGC AAC AAC AAG TAC GCG GCC AGC AGC TAT CTG AGC CTG     303
Ser Lys Gln Ser Asn Asn Lys Tyr Ala Ala Ser Ser Tyr Leu Ser Leu
            165                 170                 175

ACG CCT GAG CAG TGG AAG TCC CAC AGA AGC TAC AGC TGC CAG GTC ACG     351
Thr Pro Glu Gln Trp Lys Ser His Arg Ser Tyr Ser Cys Gln Val Thr
        180                 185                 190

CAT GAG GGG AGC ACC GTG GAA AAA ACC GTT GCG CCG ACT GAG GCC         396
His Glu Gly Ser Thr Val Glu Lys Thr Val Ala Pro Thr Glu Ala
    195                 200                 205

TGATAAGCAT GC                                                       408
```

(2) INFORMATION FOR SEQ ID NO: 170:

(i) SEQUENCE CHARACTERISTICS:
        (A) LENGTH: 104 amino acids

```
          (B) TYPE: amino acid
          (D) TOPOLOGY: linear (ii) MOLECULE TYPE: protein (xi) SEQUENCE DESCRIPTION: SEQ ID NO: 170:

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Ala
            100

(2) INFORMATION FOR SEQ ID NO: 171:

(i) SEQUENCE CHARACTERISTICS:
          (A) LENGTH: 78 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic oligonucleotide"

(xi) SEQUENCE DESCRIPTION: SEQ ID NO: 171:

GAAGACAAGC GGATTATTAT TGCCAGCAGC ATTATACCAC CCCGCCTGTG TTTGGCGGCG      60

GCACGAAGTT AACCGTTC                                                   78

(2) INFORMATION FOR SEQ ID NO: 172:

(i) SEQUENCE CHARACTERISTICS:
          (A) LENGTH: 80 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic oligonucleotide"

(xi) SEQUENCE DESCRIPTION: SEQ ID NO: 172:

CAATTCTTCG CTGCTCGGCG GAAACAGCGT CACACTCGGT GCGGCTTTCG GCTGGCCAAG      60

AACGGTTAAC TTCGTGCCGC                                                 80

(2) INFORMATION FOR SEQ ID NO: 173:

(i) SEQUENCE CHARACTERISTICS:
          (A) LENGTH: 80 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic oligonucleotide"

(xi) SEQUENCE DESCRIPTION: SEQ ID NO: 173:

CGCCGAGCAG CGAAGAATTG CAGGCGAACA AGCGACCCT GGTGTGCCTG ATTAGCGACT       60
```

```
TTTATCCGGG AGCCGTGACA                                              80

(2) INFORMATION FOR SEQ ID NO: 174:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 174:

TGTTTGGAGG GTGTGGTGGT CTCCACTCCC GCCTTGACGG GGCTGCTATC TGCCTTCCAG   60

GCCACTGTCA CGGCTCCCGG                                              80

(2) INFORMATION FOR SEQ ID NO: 175:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 175:

CCACACCCTC CAAACAAAGC AACAACAAGT ACGCGGCCAG CAGCTATCTG AGCCTGACGC   60

CTGAGCAGTG GAAGTCCCAC AGAAGCTACA GCTG                              94

(2) INFORMATION FOR SEQ ID NO: 176:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 176:

GCATGCTTAT CAGGCCTCAG TCGGCGCAAC GGTTTTTTCC ACGGTGCTCC CCTCATGCGT   60

GACCTGGCAG CTGTAGCTTC                                              80

(2) INFORMATION FOR SEQ ID NO: 177:

(i) SEQUENCE CHARACTERISTICS:
        (A) LENGTH: 843 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION:1..843
        (D) OTHER INFORMATION:/product= "VH3-Vk2"

(xi) SEQUENCE DESCRIPTION: SEQ ID NO: 177:

ATG AAA CAA AGC ACT ATT GCA CTG GCA CTC TTA CCG TTG CTC TTC ACC    48
Met Lys Gln Ser Thr Ile Ala Leu Ala Leu Leu Pro Leu Leu Phe Thr
105             110                 115                 120
```

```
CCT GTT ACC AAA GCC GAC TAC AAA GAT GAA GTG CAA TTG GTG GAA AGC      96
Pro Val Thr Lys Ala Asp Tyr Lys Asp Glu Val Gln Leu Val Glu Ser
            125                 130                 135

GGC GGC GGC CTG GTG CAA CCG GGC GGC AGC CTG CGT CTG AGC TGC GCG     144
Gly Gly Gly Leu Val Gln Pro Gly Gly Ser Leu Arg Leu Ser Cys Ala
        140                 145                 150

GCC TCC GGA TTT ACC TTT AGC AGC TAT GCG ATG AGC TGG GTG CGC CAA     192
Ala Ser Gly Phe Thr Phe Ser Ser Tyr Ala Met Ser Trp Val Arg Gln
        155                 160                 165

GCC CCT GGG AAG GGT CTC GAG TGG GTG AGC GCG ATT AGC GGT AGC GGC     240
Ala Pro Gly Lys Gly Leu Glu Trp Val Ser Ala Ile Ser Gly Ser Gly
        170                 175                 180

GGC AGC ACC TAT TAT GCG GAT AGC GTG AAA GGC CGT TTT ACC ATT TCA     288
Gly Ser Thr Tyr Tyr Ala Asp Ser Val Lys Gly Arg Phe Thr Ile Ser
185                 190                 195                 200

CGT GAT AAT TCG AAA AAC ACC CTG TAT CTG CAA ATG AAC AGC CTG CGT     336
Arg Asp Asn Ser Lys Asn Thr Leu Tyr Leu Gln Met Asn Ser Leu Arg
                205                 210                 215

GCG GAA GAT ACG GCC GTG TAT TAT TGC GCG CGT TGG GGC GGC GAT GGC     384
Ala Glu Asp Thr Ala Val Tyr Tyr Cys Ala Arg Trp Gly Gly Asp Gly
                220                 225                 230

TTT TAT GCG ATG GAT TAT TGG GGC CAA GGC ACC CTG GTG ACG GTT AGC     432
Phe Tyr Ala Met Asp Tyr Trp Gly Gln Gly Thr Leu Val Thr Val Ser
                235                 240                 245

TCA GCG GGT GGC GGT TCT GGC GGC GGT GGG AGC GGT GGC GGT GGT TCT     480
Ser Ala Gly Gly Gly Ser Gly Gly Gly Gly Ser Gly Gly Gly Gly Ser
            250                 255                 260

GGC GGT GGT GGT TCC GAT ATC GTG ATG ACC CAG AGC CCA CTG AGC CTG     528
Gly Gly Gly Gly Ser Asp Ile Val Met Thr Gln Ser Pro Leu Ser Leu
265                 270                 275                 280

CCA GTG ACT CCG GGC GAG CCT GCG AGC ATT AGC TGC AGA AGC AGC CAA     576
Pro Val Thr Pro Gly Glu Pro Ala Ser Ile Ser Cys Arg Ser Ser Gln
                285                 290                 295

AGC CTG CTG CAT AGC AAC GGC TAT AAC TAT CTG GAT TGG TAC CTT CAA     624
Ser Leu Leu His Ser Asn Gly Tyr Asn Tyr Leu Asp Trp Tyr Leu Gln
                300                 305                 310

AAA CCA GGT CAA AGC CCG CAG CTA TTA ATT TAT CTG GGC AGC AAC CGT     672
Lys Pro Gly Gln Ser Pro Gln Leu Leu Ile Tyr Leu Gly Ser Asn Arg
            315                 320                 325

GCC AGT GGG GTC CCG GAT CGT TTT AGC GGC TCT GGA TCC GGC ACC GAT     720
Ala Ser Gly Val Pro Asp Arg Phe Ser Gly Ser Gly Ser Gly Thr Asp
        330                 335                 340

TTT ACC CTG AAA ATT AGC CGT GTG GAA GCT GAA GAC GTG GGC GTG TAT     768
Phe Thr Leu Lys Ile Ser Arg Val Glu Ala Glu Asp Val Gly Val Tyr
345                 350                 355                 360

TAT TGC CAG CAG CAT TAT ACC ACC CCG CCG ACC TTT GGC CAG GGT ACG     816
Tyr Cys Gln Gln His Tyr Thr Thr Pro Pro Thr Phe Gly Gln Gly Thr
                365                 370                 375

AAA GTT GAA ATT AAA CGT ACG GAA TTC                                 843
Lys Val Glu Ile Lys Arg Thr Glu Phe
                380                 385

(2) INFORMATION FOR SEQ ID NO: 178:

(i) SEQUENCE CHARACTERISTICS:
        (A) LENGTH: 281 amino acids
        (B) TYPE: amino acid
        (D) TOPOLOGY: linear (ii) MOLECULE TYPE: protein
```

(xi) SEQUENCE DESCRIPTION: SEQ ID NO: 178:

```
Met Lys Gln Ser Thr Ile Ala Leu Ala Leu Leu Pro Leu Leu Phe Thr
 1               5                  10                  15

Pro Val Thr Lys Ala Asp Tyr Lys Asp Glu Val Gln Leu Val Glu Ser
                20                  25                  30

Gly Gly Gly Leu Val Gln Pro Gly Gly Ser Leu Arg Leu Ser Cys Ala
            35                  40                  45

Ala Ser Gly Phe Thr Phe Ser Ser Tyr Ala Met Ser Trp Val Arg Gln
        50                  55                  60

Ala Pro Gly Lys Gly Leu Glu Trp Val Ser Ala Ile Ser Gly Ser Gly
 65                  70                  75                  80

Gly Ser Thr Tyr Tyr Ala Asp Ser Val Lys Gly Arg Phe Thr Ile Ser
                85                  90                  95

Arg Asp Asn Ser Lys Asn Thr Leu Tyr Leu Gln Met Asn Ser Leu Arg
                100                 105                 110

Ala Glu Asp Thr Ala Val Tyr Tyr Cys Ala Arg Trp Gly Gly Asp Gly
            115                 120                 125

Phe Tyr Ala Met Asp Tyr Trp Gly Gln Gly Thr Leu Val Thr Val Ser
        130                 135                 140

Ser Ala Gly Gly Gly Ser Gly Gly Gly Ser Gly Gly Gly Gly Gly Ser
145                 150                 155                 160

Gly Gly Gly Gly Ser Asp Ile Val Met Thr Gln Ser Pro Leu Ser Leu
                165                 170                 175

Pro Val Thr Pro Gly Glu Pro Ala Ser Ile Ser Cys Arg Ser Ser Gln
                180                 185                 190

Ser Leu Leu His Ser Asn Gly Tyr Asn Tyr Leu Asp Trp Tyr Leu Gln
            195                 200                 205

Lys Pro Gly Gln Ser Pro Gln Leu Leu Ile Tyr Leu Gly Ser Asn Arg
        210                 215                 220

Ala Ser Gly Val Pro Asp Arg Phe Ser Gly Ser Gly Ser Gly Thr Asp
225                 230                 235                 240

Phe Thr Leu Lys Ile Ser Arg Val Glu Ala Glu Asp Val Gly Val Tyr
                245                 250                 255

Tyr Cys Gln Gln His Tyr Thr Thr Pro Pro Thr Phe Gly Gln Gly Thr
                260                 265                 270

Lys Val Glu Ile Lys Arg Thr Glu Phe
            275                 280
```

(2) INFORMATION FOR SEQ ID NO: 179:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 179:

```
Cys Ala Arg Trp Gly Gly Asp Gly Phe Tyr Ala Met Asp Tyr Trp
 1               5                  10                  15
```

(2) INFORMATION FOR SEQ ID NO: 180:

(i) SEQUENCE CHARACTERISTICS:
        (A) LENGTH: 12 amino acids

```
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 180:

Cys Ala Arg Phe Gly Lys Met Asn Tyr Asp Tyr Trp
1               5                   10

(2) INFORMATION FOR SEQ ID NO: 181:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 181:

Cys Ala Arg His Arg Thr Glu Trp His Asp Tyr Trp
1               5                   10

(2) INFORMATION FOR SEQ ID NO: 182:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 182:

Cys Ala Arg Val Arg Glu Leu Tyr His Asp Tyr Trp
1               5                   10

(2) INFORMATION FOR SEQ ID NO: 183:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 183:

Cys Ala Arg Lys Phe Leu Lys Ala Arg Asp Tyr Trp
1               5                   10

(2) INFORMATION FOR SEQ ID NO: 184:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal
```

(xi) SEQUENCE DESCRIPTION: SEQ ID NO: 184:

Cys Ala Arg Trp Asn Thr Thr Gly Tyr Asp Tyr Trp
1               5                   10

(2) INFORMATION FOR SEQ ID NO: 185:

(i) SEQUENCE CHARACTERISTICS:
      (A) LENGTH: 12 amino acids
      (B) TYPE: amino acid
      (C) STRANDEDNESS: <Unknown>
      (D) TOPOLOGY: linear (ii) MOLECULE TYPE: protein (v) FRAGMENT TYPE: internal (xi) SEQUENCE DESCRIPTION: SEQ ID NO: 185:

Cys Ala Arg Ile Asn Glu Ala Gln Pro Asp Tyr Trp
1               5                   10

(2) INFORMATION FOR SEQ ID NO: 186:

(i) SEQUENCE CHARACTERISTICS:
      (A) LENGTH: 11 amino acids
      (B) TYPE: amino acid
      (C) STRANDEDNESS: <Unknown>
      (D) TOPOLOGY: linear (ii) MOLECULE TYPE: protein (v) FRAGMENT TYPE: internal (xi) SEQUENCE DESCRIPTION: SEQ ID NO: 186:

Cys Ala Arg Thr Ala Ile Thr Arg Asp Tyr Trp
1               5                   10

(2) INFORMATION FOR SEQ ID NO: 187:

(i) SEQUENCE CHARACTERISTICS:
      (A) LENGTH: 12 amino acids
      (B) TYPE: amino acid
      (C) STRANDEDNESS: <Unknown>
      (D) TOPOLOGY: linear (ii) MOLECULE TYPE: protein (v) FRAGMENT TYPE: internal (xi) SEQUENCE DESCRIPTION: SEQ ID NO: 187:

Cys Ala Arg Trp Tyr Asn Arg Asn Ser Asp Tyr Trp
1               5                   10

(2) INFORMATION FOR SEQ ID NO: 188:

(i) SEQUENCE CHARACTERISTICS:
      (A) LENGTH: 12 amino acids
      (B) TYPE: amino acid
      (C) STRANDEDNESS: <Unknown>
      (D) TOPOLOGY: linear (ii) MOLECULE TYPE: protein (v) FRAGMENT TYPE: internal (xi) SEQUENCE DESCRIPTION: SEQ ID NO: 188:

Cys Ala Arg Ser Val Gly Asp Ser Lys Asp Tyr Trp
1               5                   10

(2) INFORMATION FOR SEQ ID NO: 189:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 189:

```
Cys Ala Arg Ser Lys Thr Phe Ala Ala Asp Tyr Trp
1               5                   10
```

(2) INFORMATION FOR SEQ ID NO: 190:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 190:

```
Cys Ala Arg Val Ala Pro Gln Tyr Asp Asp Tyr Trp
1               5                   10
```

(2) INFORMATION FOR SEQ ID NO: 191:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 191:

```
Cys Ala Arg Met Gln Ser Glu Trp Met Asp Tyr Trp
1               5                   10
```

(2) INFORMATION FOR SEQ ID NO: 192:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 192:

```
Cys Ala Arg Tyr Phe Val His Phe Leu Tyr Thr Met Val Met Asp Val
1               5                   10                  15

Trp
```

(2) INFORMATION FOR SEQ ID NO: 193:

(i) SEQUENCE CHARACTERISTICS:
        (A) LENGTH: 17 amino acids
        (B) TYPE: amino acid (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 193:

Cys Ala Arg Met Ala Leu Arg Ala Ser Gly Lys Tyr Ile Met Asp Val
1               5                   10                  15

Trp (2) INFORMATION FOR SEQ ID NO: 194:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 194:

Cys Ala Arg Lys Asn Gln Met Val Phe His Ala Arg Lys Phe Asp Val
1               5                   10                  15

Trp (2) INFORMATION FOR SEQ ID NO: 195:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 195:

Cys Ala Arg Thr Gln Ser Phe Trp Glu Gln Gln Lys Val Met Asp Tyr
1               5                   10                  15

Trp (2) INFORMATION FOR SEQ ID NO: 196:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 196:

Cys Ala Arg Tyr Pro Tyr Arg Ser Asn Phe Phe Met Pro Met Asp Val
1               5                   10                  15

Trp (2) INFORMATION FOR SEQ ID NO: 197:

(i) SEQUENCE CHARACTERISTICS:
        (A) LENGTH: 16 amino acids (B) TYPE: amino acid
            (C) STRANDEDNESS: <Unknown>
            (D) TOPOLOGY: linear (ii) MOLECULE TYPE: protein (v) FRAGMENT TYPE: internal (ix) FEATURE:
            (A) NAME/KEY: Modified-site
            (B) LOCATION:3..4
            (D) OTHER INFORMATION:/product= "see Figure 10C"
                /label= R*G
                /note= "* denotes codon with one-base deletion, causes
                 shift of reading fr..."

(xi) SEQUENCE DESCRIPTION: SEQ ID NO: 197:

Cys Ala Arg Gly Ser Gly Ser Glu His Trp Ser Ile Phe Asp Val Trp
1               5                  10                  15

(2) INFORMATION FOR SEQ ID NO: 198:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 198:

Cys Ala Arg Arg Asn Pro Trp Asn Val Asn Tyr Leu His Phe Asp Val
1               5                  10                  15

Trp (2) INFORMATION FOR SEQ ID NO: 199:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 199:

Cys Ala Arg Met Lys Pro Met Leu Asn Arg Asp Gly Thr Met Asp Val
1               5                  10                  15

Trp (2) INFORMATION FOR SEQ ID NO: 200:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 200:

Cys Ala Arg Lys Gly Ser Glu Phe Leu Glu Thr Asp Val Met Asp Tyr
1               5                  10                  15

-continued

Trp (2) INFORMATION FOR SEQ ID NO: 201:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 201:

Cys Ala Arg Ser Trp Thr Asn Asp Lys Pro Asn Phe Ile Met Asp Val
1               5                   10                  15
Trp (2) INFORMATION FOR SEQ ID NO: 202:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 202:

Cys Ala Arg Tyr Ala Gly Thr Thr Phe Lys Gln Gly Pro Met Asp Tyr
1               5                   10                  15
Trp (2) INFORMATION FOR SEQ ID NO: 203:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 203:

Cys Ala Arg Lys Arg Met Met Gln Asn Pro Arg Phe Arg Phe Asp Val
1               5                   10                  15
Trp (2) INFORMATION FOR SEQ ID NO: 204:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 204:

Cys Ala Arg Arg Ser Lys Gln Lys Arg Lys Met Arg Arg Phe Asp Val
1               5                   10                  15

Trp (2) INFORMATION FOR SEQ ID NO: 205:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 205:

Cys Ala Arg Arg Asn Gly Lys Arg His Leu Arg His Arg Phe Asp Val
1               5                   10                  15

Trp (2) INFORMATION FOR SEQ ID NO: 206:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 206:

Cys Ala Arg Arg Lys Met Arg Lys Arg Ile Lys Arg Arg Phe Asp Val
1               5                   10                  15

Trp (2) INFORMATION FOR SEQ ID NO: 207:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 207:

Cys Ala Arg Tyr Arg Lys Ile Met Lys Trp Lys Asn Ser Phe Asp Val
1               5                   10                  15

Trp (2) INFORMATION FOR SEQ ID NO: 208:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 208:

Cys Ala Arg Leu Ile Glu Val His Pro Ser Phe Asp Gln Met Asp Val

```
            1               5              10              15
Trp (2) INFORMATION FOR SEQ ID NO: 209:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 209:

Cys Ala Arg Arg Lys Pro Met Phe Leu Lys Lys Ala Val Phe Asp Val
1               5                  10                  15
Trp (2) INFORMATION FOR SEQ ID NO: 210:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 210:

Cys Ala Arg Arg Lys Phe His Arg Tyr Ser Thr Val Lys Phe Asp Tyr
1               5                  10                  15
Trp (2) INFORMATION FOR SEQ ID NO: 211:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 211:

Cys Ala Arg Arg Lys Thr Met Arg Ser Arg Val Lys Tyr Phe Asp Tyr
1               5                  10                  15
Trp (2) INFORMATION FOR SEQ ID NO: 212:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 212:
```

```
Cys Ala Arg Lys Lys Arg Ser Trp Arg Arg Met Asp Arg Phe Asp Val
1               5                   10                  15
Trp (2) INFORMATION FOR SEQ ID NO: 213:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 213:

Cys Ala Arg Arg Asn Pro Arg Arg Gly Arg Met Asn Arg Phe Asp Val
1               5                   10                  15
Trp (2) INFORMATION FOR SEQ ID NO: 214:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 214:

Cys Ala Arg Lys Gly Lys Lys Lys Phe Ala Arg Pro Arg Phe Asp Val
1               5                   10                  15
Trp (2) INFORMATION FOR SEQ ID NO: 215:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 215:

Cys Ala Arg Arg Met Val His Lys Gly Lys Arg Lys Ile Phe Asp Val
1               5                   10                  15
Trp (2) INFORMATION FOR SEQ ID NO: 216:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 216:
```

Cys Ala Arg Arg Lys His Ile Thr Tyr Pro Arg Lys Gln Phe Asp Val
1               5                   10                  15

Trp (2) INFORMATION FOR SEQ ID NO: 217:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 217:

Cys Ala Arg Arg Trp Thr Lys Arg Arg Ser Phe Ala Arg Phe Asp Val
1               5                   10                  15

Trp (2) INFORMATION FOR SEQ ID NO: 218:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 218:

Cys Ala Arg Lys Lys Leu Lys Gln Tyr Thr Phe Ser Arg Phe Asp Tyr
1               5                   10                  15

Trp (2) INFORMATION FOR SEQ ID NO: 219:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 219:

Cys Ala Arg Thr Arg Pro Trp Gln Ala Thr Arg Lys Gly Phe Asp Val
1               5                   10                  15

Trp (2) INFORMATION FOR SEQ ID NO: 220:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal -continued (xi) SEQUENCE DESCRIPTION: SEQ ID NO: 220:

Cys Ala Arg Asn Gln Trp Glu Phe Lys Asn Arg Arg Lys Met Asp Tyr
1               5                   10                  15
Trp (2) INFORMATION FOR SEQ ID NO: 221:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 221:

Cys Ala Arg Lys Arg Trp Met Trp Pro Ile Gly Lys Arg Phe Asp Tyr
1               5                   10                  15
Trp (2) INFORMATION FOR SEQ ID NO: 222:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 222:

Cys Ala Arg Tyr Ser Leu Trp Arg Leu Asp Glu Tyr Phe Phe Asp Tyr
1               5                   10                  15
Trp (2) INFORMATION FOR SEQ ID NO: 223:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 223:

Cys Ala Arg Val Pro Trp Gly Asp Phe Trp Ser Trp His Met Asp Val
1               5                   10                  15
Trp (2) INFORMATION FOR SEQ ID NO: 224:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 224:

Cys Ala Arg Asn Gly Leu Glu Pro Arg His Arg Lys Met Met Asp Tyr
1               5                   10                  15
Trp (2) INFORMATION FOR SEQ ID NO: 225:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 225:

Cys Ala Arg Ile Met Lys Ala Pro Pro Asp Tyr Trp
1               5                   10

(2) INFORMATION FOR SEQ ID NO: 226:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 226:

Cys Ala Arg Arg Lys Thr Trp His Trp Phe Tyr Lys Arg Met Asp Tyr
1               5                   10                  15
Trp (2) INFORMATION FOR SEQ ID NO: 227:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 227:

Cys Ala Arg Trp Lys Asp Met Trp Ser Gln Val Tyr Val Met Asp Tyr
1               5                   10                  15
Trp (2) INFORMATION FOR SEQ ID NO: 228:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal -continued (xi) SEQUENCE DESCRIPTION: SEQ ID NO: 228:

Cys Ala Arg Asn Lys Gln Gln Met Arg Phe Arg Arg Phe Met Asp Tyr
1               5                   10                  15
Trp (2) INFORMATION FOR SEQ ID NO: 229:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 229:

Cys Ala Arg Asn Met Leu Ala Leu Ser Arg Gly Lys Glu Met Asp Val
1               5                   10                  15
Trp (2) INFORMATION FOR SEQ ID NO: 230:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 230:

Cys Ala Arg Asn Met Arg Leu Met Arg Met Arg Lys Asn Phe Asp Val
1               5                   10                  15
Trp (2) INFORMATION FOR SEQ ID NO: 231:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 231:

Cys Ala Arg Tyr Ile Lys Gln Ala Lys Arg Lys Leu Ala Phe Asp Tyr
1               5                   10                  15
Trp (2) INFORMATION FOR SEQ ID NO: 232:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 232:

Cys Ala Arg Tyr Asn Arg His Ala Trp Gln Lys Met Gln Phe Asp Tyr
1               5                   10                  15
Trp (2) INFORMATION FOR SEQ ID NO: 233:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 233:

Cys Ala Arg Tyr Val Lys Tyr Ala Arg Asn Lys Met Gln Phe Asp Tyr
1               5                   10                  15
Trp (2) INFORMATION FOR SEQ ID NO: 234:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 234:

Cys Ala Arg Tyr Lys Arg Gly Ala Trp Met Lys Thr Met Phe Asp Val
1               5                   10                  15
Trp (2) INFORMATION FOR SEQ ID NO: 235:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 235:

Cys Ala Arg Arg Lys Pro Leu Arg Arg Ile Met Lys Trp Phe Asp Tyr
1               5                   10                  15
Trp (2) INFORMATION FOR SEQ ID NO: 236:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 236:

Cys Ala Arg Tyr Arg Lys Arg Ala Ser Arg Gln Met Gln Phe Asp Tyr
1               5                   10                  15
Trp (2) INFORMATION FOR SEQ ID NO: 237:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 237:

Cys Ala Arg Gln Arg Tyr Arg Ser Lys Ile Lys Gly His Phe Asp Val
1               5                   10                  15
Trp (2) INFORMATION FOR SEQ ID NO: 238:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 238:

Cys Ala Arg Trp Arg Asp Phe Asn Ser Tyr Asp Pro Met Asp Tyr Trp
1               5                   10                  15

(2) INFORMATION FOR SEQ ID NO: 239:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 239:

Cys Ala Arg Met Ala Asp Leu Asp Asn Tyr Trp Val Gln Phe Asp Tyr
1               5                   10                  15
Trp (2) INFORMATION FOR SEQ ID NO: 240:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal -continued (xi) SEQUENCE DESCRIPTION: SEQ ID NO: 240:

Cys Ala Arg Leu Gln Ala Tyr Leu Lys Pro His His Trp Met Asp Tyr
1               5                   10                  15
Trp (2) INFORMATION FOR SEQ ID NO: 241:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 241:

Cys Ala Arg Arg Leu Ile Glu Gln Ala Arg Asp His Val Met Asp Tyr
1               5                   10                  15
Trp (2) INFORMATION FOR SEQ ID NO: 242:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 242:

Cys Ala Arg Ser Trp His Asn Ser Gln Phe Thr Gln Ser Phe Asp Val
1               5                   10                  15
Trp (2) INFORMATION FOR SEQ ID NO: 243:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 243:

Cys Ala Arg Val Asp His Phe Gln Thr Glu Asn Glu Trp Met Asp Tyr
1               5                   10                  15
Trp (2) INFORMATION FOR SEQ ID NO: 244:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 244:

Cys Ala Arg Asp Trp Pro Thr Leu Ile Phe Trp Tyr Trp Phe Asp Tyr
1               5                   10                  15

Trp (2) INFORMATION FOR SEQ ID NO: 245:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 245:

Cys Ala Arg Gly Phe Gly Phe Thr Glu Asp Tyr Trp
1               5                   10

(2) INFORMATION FOR SEQ ID NO: 246:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 246:

Cys Ala Arg Gln Phe Asp Glu Asp Ser Phe Val Arg Arg Phe Asp Val
1               5                   10                  15

Trp (2) INFORMATION FOR SEQ ID NO: 247:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 247:

Cys Ala Arg Ile Leu Lys Glu Ser Ser Lys Ser Arg Gln Met Asp Val
1               5                   10                  15

Trp (2) INFORMATION FOR SEQ ID NO: 248:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 248:

Cys Ala Arg Glu Gln Asp Glu Tyr Gly Ala Ile Arg Ile Met Asp Tyr
1               5                   10                  15

Trp (2) INFORMATION FOR SEQ ID NO: 249:

(i) SEQUENCE CHARACTERISTICS:
            (A) LENGTH: 18 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 249:

Cys Ala Arg Asn His Phe Glu Ala Ser Trp Pro Arg Arg Gln Met Asp
1               5                   10                  15

Val Trp (2) INFORMATION FOR SEQ ID NO: 250:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 250:

Cys Ala Arg Glu Asn Glu Trp Val Asp Met Ile Leu Asp Met Asp Tyr
1               5                   10                  15

Trp (2) INFORMATION FOR SEQ ID NO: 251:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 251:

Cys Ala Arg Gln Tyr Ser Glu Thr Arg Trp Val Arg Lys Phe Asp Tyr
1               5                   10                  15

Trp (2) INFORMATION FOR SEQ ID NO: 252:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 252:

Cys Ala Arg Gln Phe Lys Glu Ser Lys Thr Arg Arg Lys Phe Asp Val
1               5                   10                  15
Trp (2) INFORMATION FOR SEQ ID NO: 253:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 253:

Cys Ala Arg Lys Lys Thr Gln Tyr Val His Asp Trp Arg Met Asp Val
1               5                   10                  15
Trp (2) INFORMATION FOR SEQ ID NO: 254:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 254:

Cys Ala Arg Arg Trp Arg Glu Thr Lys Ser Lys Arg Phe Phe Asp Val
1               5                   10                  15
Trp (2) INFORMATION FOR SEQ ID NO: 255:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 255:

Cys Ala Arg Asp Tyr Ile Met Glu Phe Asp Tyr Trp
1               5                   10

(2) INFORMATION FOR SEQ ID NO: 256:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 256:

Cys Ala Arg Gln Phe Glu Glu Thr Lys Gln Arg Arg Leu Met Asp Tyr
1               5                   10                  15
Trp (2) INFORMATION FOR SEQ ID NO: 257:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 257:

Cys Ala Arg Asp Gln Gly Phe Tyr Ala Ile Asp Tyr Val Met Asp Tyr
1               5                   10                  15
Trp (2) INFORMATION FOR SEQ ID NO: 258:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 258:

Cys Ala Arg Val Phe Thr Tyr Met Tyr Asn Tyr Phe Arg Phe Asp Val
    1               5                   10                  15
    Trp (2) INFORMATION FOR SEQ ID NO: 259:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 259:

Cys Ala Arg Val Phe Phe Glu Gln Met Glu Val Val Arg Met Asp Val
    1               5                   10                  15
    Trp (2) INFORMATION FOR SEQ ID NO: 260:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 260:

Cys Ala Arg Glu Lys Glu Tyr Arg Leu Ser Trp Ser Gln Met Asp Tyr
        1               5                   10                  15

Trp (2) INFORMATION FOR SEQ ID NO: 261:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 261:

Cys Ala Arg Tyr Pro Ser Arg Trp Ala Pro Asn Trp Tyr Met Asp Tyr
        1               5                   10                  15

Trp (2) INFORMATION FOR SEQ ID NO: 262:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: protein (v) FRAGMENT TYPE: internal (xi) SEQUENCE DESCRIPTION: SEQ ID NO: 262:

Cys Ala Arg Asp Gly Gly Phe Lys Pro Leu Thr His Phe Phe Asp Val
        1               5                   10                  15

Trp (2) INFORMATION FOR SEQ ID NO: 263:

(i) SEQUENCE CHARACTERISTICS:
            (A) LENGTH: 143 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "synthetic DNA cassette"

(xi) SEQUENCE DESCRIPTION: SEQ ID NO: 263:

ACATGTAAGC TTCCCCCCCC CCTTAATTAA CCCCCCCCCC TGTACACCCC CCCCCCGCTA        60

GCCCCCCCCC CCAGATCTCC CCCCCCCCGA CGTCCCCCCT CTAGACCCCC CCCCCGCATG       120

CCCCCCCCCC CGAATTCGAC GTC                                              143

(2) INFORMATION FOR SEQ ID NO: 264:

(i) SEQUENCE CHARACTERISTICS:
            (A) LENGTH: 1947 base pairs
            (B) TYPE: nucleic acid
            (C) STRANDEDNESS: double
            (D) TOPOLOGY: circular (ii) MOLECULE TYPE: other nucleic acid (A) DESCRIPTION: /desc = "synthetic vector"

(ix) FEATURE:
        (A) NAME/KEY: CDS
        (B) LOCATION:132..989
        (D) OTHER INFORMATION:/product= "Amp resistance"

(xi) SEQUENCE DESCRIPTION: SEQ ID NO: 264:

CAGGTGGCAC TTTTCGGGGA AATGTGCGCG GAACCCCTAT TTGTTTATTT TTCTAAATAC      60

ATTCAAATAT GTATCCGCTC ATGAGACAAT AACCCTGATA AATGCTTCAA TAATATTGAA     120

AAAGGAAGAG T ATG AGT ATT CAA CAT TTC CGT GTC GCC CTT ATT CCC TTT     170
             Met Ser Ile Gln His Phe Arg Val Ala Leu Ile Pro Phe
                 285                 290

TTT GCG GCA TTT TGC CTT CCT GTT TTT GCT CAC CCA GAA ACG CTG GTG      218
Phe Ala Ala Phe Cys Leu Pro Val Phe Ala His Pro Glu Thr Leu Val
295                 300                 305                 310

AAA GTA AAA GAT GCT GAA GAT CAG TTG GGT GCA CGA GTG GGT TAC ATC      266
Lys Val Lys Asp Ala Glu Asp Gln Leu Gly Ala Arg Val Gly Tyr Ile
                315                 320                 325

GAA CTG GAT CTC AAC AGC GGT AAG ATC CTT GAG AGT TTT CGC CCC GAA      314
Glu Leu Asp Leu Asn Ser Gly Lys Ile Leu Glu Ser Phe Arg Pro Glu
            330                 335                 340

GAA CGT TTT CCA ATG ATG AGC ACT TTT AAA GTT CTG CTA TGT GGC GCG      362
Glu Arg Phe Pro Met Met Ser Thr Phe Lys Val Leu Leu Cys Gly Ala
        345                 350                 355

GTA TTA TCC CGT ATT GAC GCC GGG CAA GAG CAA CTC GGT CGC CGC ATA      410
Val Leu Ser Arg Ile Asp Ala Gly Gln Glu Gln Leu Gly Arg Arg Ile
    360                 365                 370

CAC TAT TCT CAG AAT GAC TTG GTT GAG TAC TCA CCA GTC ACA GAA AAG      458
His Tyr Ser Gln Asn Asp Leu Val Glu Tyr Ser Pro Val Thr Glu Lys
375                 380                 385                 390

CAT CTT ACG GAT GGC ATG ACA GTA AGA GAA TTA TGC AGT GCT GCC ATA      506
His Leu Thr Asp Gly Met Thr Val Arg Glu Leu Cys Ser Ala Ala Ile
                395                 400                 405

ACC ATG AGT GAT AAC ACT GCG GCC AAC TTA CTT CTG ACA ACG ATC GGA      554
Thr Met Ser Asp Asn Thr Ala Ala Asn Leu Leu Leu Thr Thr Ile Gly
            410                 415                 420

GGA CCG AAG GAG CTA ACC GCT TTT TTG CAC AAC ATG GGG GAT CAT GTA      602
Gly Pro Lys Glu Leu Thr Ala Phe Leu His Asn Met Gly Asp His Val
        425                 430                 435

ACT CGC CTT GAT CGT TGG GAA CCG GAG CTG AAT GAA GCC ATA CCA AAC      650
Thr Arg Leu Asp Arg Trp Glu Pro Glu Leu Asn Glu Ala Ile Pro Asn
    440                 445                 450

GAC GAG CGT GAC ACC ACG ATG CCT GTA GCA ATG GCA ACA ACG TTG CGC      698
Asp Glu Arg Asp Thr Thr Met Pro Val Ala Met Ala Thr Thr Leu Arg
455                 460                 465                 470

AAA CTA TTA ACT GGC GAA CTA CTT ACT CTA GCT TCC CGG CAA CAA TTA      746
Lys Leu Leu Thr Gly Glu Leu Leu Thr Leu Ala Ser Arg Gln Gln Leu
                475                 480                 485

ATA GAC TGG ATG GAG GCG GAT AAA GTT GCA GGA CCA CTT CTG CGC TCG      794
Ile Asp Trp Met Glu Ala Asp Lys Val Ala Gly Pro Leu Leu Arg Ser
            490                 495                 500

GCC CTT CCG GCT GGC TGG TTT ATT GCT GAT AAA TCT GGA GCC GGT GAG      842
Ala Leu Pro Ala Gly Trp Phe Ile Ala Asp Lys Ser Gly Ala Gly Glu
        505                 510                 515

CGT GGG TCT CGC GGT ATC ATT GCA GCA CTG GGG CCA GAT GGT AAG CCC      890
Arg Gly Ser Arg Gly Ile Ile Ala Ala Leu Gly Pro Asp Gly Lys Pro
    520                 525                 530

TCC CGT ATC GTA GTT ATC TAC ACG ACG GGG AGT CAG GCA ACT ATG GAT      938

-continued

```
Ser Arg Ile Val Val Ile Tyr Thr Thr Gly Ser Gln Ala Thr Met Asp
535                 540                 545                 550

GAA CGA AAT AGA CAG ATC GCT GAG ATA GGT GCC TCA CTG ATT AAG CAT       986
Glu Arg Asn Arg Gln Ile Ala Glu Ile Gly Ala Ser Leu Ile Lys His
                    555                 560                 565

TGG TAACTGTCAG ACCAAGTTTA CTCATATATA CTTTAGATTG ATTTAAAACT           1039
Trp

TCATTTTTAA TTTAAAAGGA TCTAGGTGAA GATCCTTTTT GATAATCTCA TGACCAAAAT    1099

CCCTTAACGT GAGTTTTCGT TCCACTGAGC GTCAGACCCC GTAGAAAAGA TCAAAGGATC    1159

TTCTTGAGAT CCTTTTTTTC TGCGCGTAAT CTGCTGCTTG CAAACAAAAA AACCACCGCT    1219

ACCAGCGGTG GTTTGTTTGC CGGATCAAGA GCTACCAACT CTTTTTCCGA AGGTAACTGG    1279

CTTCAGCAGA GCGCAGATAC CAAATACTGT CCTTCTAGTG TAGCCGTAGT TAGGCCACCA    1339

CTTCAAGAAC TCTGTAGCAC CGCCTACATA CCTCGCTCTG CTAATCCTGT TACCAGTGGC    1399

TGCTGCCAGT GGCGATAAGT CGTGTCTTAC CGGGTTGGAC TCAAGACGAT AGTTACCGGA    1459

TAAGGCGCAG CGGTCGGGCT GAACGGGGGG TTCGTGCACA CAGCCCAGCT TGGAGCGAAC    1519

GACCTACACC GAACTGAGAT ACCTACAGCG TGAGCTATGA GAAAGCGCCA CGCTTCCCGA    1579

AGGGAGAAAG GCGGACAGGT ATCCGGTAAG CGGCAGGGTC GGAACAGGAG AGCGCACGAG    1639

GGAGCTTCCA GGGGGAAACG CCTGGTATCT TTATAGTCCT GTCGGGTTTC GCCACCTCTG    1699

ACTTGAGCGT CGATTTTTGT GATGCTCGTC AGGGGGGCGG AGCCTATGGA AAAACGCCAG    1759

CAACGCGGCC TTTTTACGGT TCCTGGCCTT TTGCTGGCCT TTTGCTCACA TGTAAGCTTC    1819

CCCCCCCCCT TAATTAACCC CCCCCCCTGT ACACCCCCCC CCCGCTAGCC CCCCCCCCCA    1879

GATCTCCCCC CCCCCGACGT CCCCCCTCTA GACCCCCCCC CCGCATGCCC CCCCCCCGA    1939

ATTCACGT                                                             1947

(2) INFORMATION FOR SEQ ID NO: 265:

(i) SEQUENCE CHARACTERISTICS:
        (A) LENGTH: 286 amino acids
        (B) TYPE: amino acid
        (D) TOPOLOGY: linear (ii) MOLECULE TYPE: protein (xi) SEQUENCE DESCRIPTION: SEQ ID NO: 265:

Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
                 20                  25                  30

Asp Ala Glu Asp Gln Leu Gly Ala Arg Val Gly Tyr Ile Glu Leu Asp
             35                  40                  45

Leu Asn Ser Gly Lys Ile Leu Glu Ser Phe Arg Pro Glu Glu Arg Phe
         50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
```

```
               130                 135                 140
Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
                180                 185                 190

Thr Gly Glu Leu Leu Thr Leu Ala Ser Arg Gln Gln Leu Ile Asp Trp
                195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
                275                 280                 285
```

(2) INFORMATION FOR SEQ ID NO: 266:

(i) SEQUENCE CHARACTERISTICS:
        (A) LENGTH: 142 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 266:

```
GACGTCTTAA TGTGAGTTAG CTCACTCATT AGGCACCCCA GGCTTTACAC TTTATGCTTC      60

CGGCTCGTAT GTTGTGTGGA ATTGTGAGCG GATAACAATT TCACACAGGA AACAGCTATG     120

ACCATGATTA CGAATTTCTA GA                                              142
```

(2) INFORMATION FOR SEQ ID NO: 267:

(i) SEQUENCE CHARACTERISTICS:
        (A) LENGTH: 520 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene cassette"

(ix) FEATURE:
        (A) NAME/KEY: CDS
        (B) LOCATION: 1..510
        (D) OTHER INFORMATION:/product= "gIIIp ss with myc-tag,
            amber codon"

(xi) SEQUENCE DESCRIPTION: SEQ ID NO: 267:

```
GAA TTC GAG CAG AAG CTG ATC TCT GAG GAG GAT CTG TAG GGT GGT GGC       48
Glu Phe Glu Gln Lys Leu Ile Ser Glu Glu Asp Leu  *  Gly Gly Gly
            290                 295                 300

TCT GGT TCC GGT GAT TTT GAT TAT GAA AAG ATG GCA AAC GCT AAT AAG       96
Ser Gly Ser Gly Asp Phe Asp Tyr Glu Lys Met Ala Asn Ala Asn Lys
            305                 310                 315

GGG GCT ATG ACC GAA AAT GCC GAT GAA AAC GCG CTA CAG TCT GAC GCT      144
Gly Ala Met Thr Glu Asn Ala Asp Glu Asn Ala Leu Gln Ser Asp Ala
```

-continued

```
                320                 325                 330
AAA GGC AAA CTT GAT TCT GTC GCT ACT GAT TAC GGT GCT GCT ATC GAT         192
Lys Gly Lys Leu Asp Ser Val Ala Thr Asp Tyr Gly Ala Ala Ile Asp
335                 340                 345                 350

GGT TTC ATT GGT GAC GTT TCC GGC CTT GCT AAT GGT AAT GGT GCT ACT         240
Gly Phe Ile Gly Asp Val Ser Gly Leu Ala Asn Gly Asn Gly Ala Thr
                355                 360                 365

GGT GAT TTT GCT GGC TCT AAT TCC CAA ATG GCT CAA GTC GGT GAC GGT         288
Gly Asp Phe Ala Gly Ser Asn Ser Gln Met Ala Gln Val Gly Asp Gly
            370                 375                 380

GAT AAT TCA CCT TTA ATG AAT AAT TTC CGT CAA TAT TTA CCT TCC CTC         336
Asp Asn Ser Pro Leu Met Asn Asn Phe Arg Gln Tyr Leu Pro Ser Leu
        385                 390                 395

CCT CAA TCG GTT GAA TGT CGC CCT TTT GTC TTT GGC GCT GGT AAA CCA         384
Pro Gln Ser Val Glu Cys Arg Pro Phe Val Phe Gly Ala Gly Lys Pro
    400                 405                 410

TAT GAA TTT TCT ATT GAT TGT GAC AAA ATA AAC TTA TTC CGT GGT GTC         432
Tyr Glu Phe Ser Ile Asp Cys Asp Lys Ile Asn Leu Phe Arg Gly Val
415                 420                 425                 430

TTT GCG TTT CTT TTA TAT GTT GCC ACC TTT ATG TAT GTA TTT TCT ACG         480
Phe Ala Phe Leu Leu Tyr Val Ala Thr Phe Met Tyr Val Phe Ser Thr
                435                 440                 445

TTT GCT AAC ATA CTG CGT AAT AAG GAG TCT TGATAAGCTT                      520
Phe Ala Asn Ile Leu Arg Asn Lys Glu Ser
            450                 455
```

(2) INFORMATION FOR SEQ ID NO: 268:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 268:

```
Glu Phe Glu Gln Lys Leu Ile Ser Glu Glu Asp Leu
 1               5                  10
```

(2) INFORMATION FOR SEQ ID NO: 269:

(i) SEQUENCE CHARACTERISTICS:
        (A) LENGTH: 123 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 269:

```
GGGGGGGGGG AAGCTTGACC TGTGAAGTGA AAAATGGCGC AGATTGTGCG ACATTTTTTT      60

TGTCTGCCGT TAATTAAAG GGGGGGGGGG GCCGGCCTGG GGGGGGGTGT ACAGGGGGGG      120

GGG                                                                    123
```

(2) INFORMATION FOR SEQ ID NO: 270:

(i) SEQUENCE CHARACTERISTICS:
        (A) LENGTH: 470 base pairs
        (B) TYPE: nucleic acid
        (C) STRANDEDNESS: double
        (D) TOPOLOGY: linear (ii) MOLECULE TYPE: other nucleic acid (A) DESCRIPTION: /desc = "synthetic DNA cassette"

(xi) SEQUENCE DESCRIPTION: SEQ ID NO: 270:

| | | | | | |
|---|---|---|---|---|---|
| GCTAGCACGC | GCCCTGTAGC | GGCGCATTAA | GCGCGGCGGG | TGTGGTGGTT | ACGCGCAGCG | 60 |
| TGACCGCTAC | ACTTGCCAGC | GCCCTAGCGC | CCGCTCCTTT | CGCTTTCTTC | CCTTCCTTTC | 120 |
| TCGCCACGTT | CGCCGGCTTT | CCCCGTCAAG | CTCTAAATCG | GGGCATCCCT | TTAGGGTTCC | 180 |
| GATTTAGTGC | TTTACGGCAC | CTCGACCCCA | AAAAACTTGA | TTAGGGTGAT | GGTTCTCGTA | 240 |
| GTGGGCCATC | GCCCTGATAG | ACGGTTTTTC | GCCCTTTGAC | GTTGGAGTCC | ACGTTCTTTA | 300 |
| ATAGTGGACT | CTTGTTCCAA | ACTGGAACAA | CACTCAACCC | TATCTCGGTC | TATTCTTTTG | 360 |
| ATTTATAAGG | GATTTTGCCG | ATTTCGGCCT | ATTGGTTAAA | AAATGAGCTG | ATTTAACAAA | 420 |
| AATTTAACGC | GAATTTTAAC | AAAATATTAA | CGTTTACAAT | TTCATGTACA | | 470 |

(2) INFORMATION FOR SEQ ID NO: 271:

(i) SEQUENCE CHARACTERISTICS:
    (A) LENGTH: 733 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc = "synthetic DNA cassette"

(xi) SEQUENCE DESCRIPTION: SEQ ID NO: 271:

| | | | | | |
|---|---|---|---|---|---|
| AGATCTGACC | AAAATCCCTT | AACGTGAGTT | TTCGTTCCAC | TGAGCGTCAG | ACCCCGTAGA | 60 |
| AAAGATCAAA | GGATCTTCTT | GAGATCCTTT | TTTTCTGCGC | GTAATCTGCT | GCTTGCAAAC | 120 |
| AAAAAAACCA | CCGCTACCAG | CGGTGGTTTG | TTTGCCGGAT | CAAGAGCTAC | CAACTCTTTT | 180 |
| TCCGAAGGTA | ACTGGCTACA | GCAGAGCGCA | GATACCAAAT | ACTGTTCTTC | TAGTGTAGCC | 240 |
| GTAGTTAGGC | CACCACTTCA | AGAACTCTGT | AGCACCGCCT | ACATACCTCG | CTCTGCTAAT | 300 |
| CCTGTTACCA | GTGGCTGCTG | CCAGTGGCGA | TAAGTCGTGT | CTTACCGGGT | TGGACTCAAG | 360 |
| ACGATAGTTA | CCGGATAAGG | CGCAGCGGTC | GGGCTGAACG | GGGGGTTCGT | GCACACAGCC | 420 |
| CAGCTTGGAG | CGAACGACCT | ACACCGAACT | GAGATACCTA | CAGCGTGAGC | TATGAGAAAG | 480 |
| CGCCACGCTT | CCCGAAGGGA | GAAAGGCGGA | CAGGTATCCG | GTAAGCGGCA | GGGTCGGAAC | 540 |
| AGGAGAGCGC | ACGAGGGAGC | TTCCAGGGGG | AAACGCCTGG | TATCTTTATA | GTCCTGTCGG | 600 |
| GTTTCGCCAC | CTCTGACTTG | AGCGTCGATT | TTTGTGATGC | TCGTCAGGGG | GGCGGAGCCT | 660 |
| ATGGAAAAAC | GCCAGCAACG | CGGCCTTTTT | ACGGTTCCTG | GCCTTTTGCT | GGCCTTTTGC | 720 |
| TCACATGGCT | AGC | | | | | 733 |

(2) INFORMATION FOR SEQ ID NO: 272:

(i) SEQUENCE CHARACTERISTICS:
    (A) LENGTH: 813 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc = "synthetic gene cassette"

(ix) FEATURE:
    (A) NAME/KEY: CDS
    (B) LOCATION: 102..758
    (D) OTHER INFORMATION:/product= "cat resistance"

(xi) SEQUENCE DESCRIPTION: SEQ ID NO: 272:

-continued

```
GGGACGTCGG GTGAGGTTCC AACTTTCACC ATAATGAAAT AAGATCACTA CCGGGCGTAT      60

TTTTTGAGTT ATCGAGATTT TCAGGAGCTA AGGAAGCTAA A ATG GAG AAA AAA        113
                                              Met Glu Lys Lys

ATC ACT GGA TAT ACC ACC GTT GAT ATA TCC CAA TGG CAT CGT AAA GAA      161
Ile Thr Gly Tyr Thr Thr Val Asp Ile Ser Gln Trp His Arg Lys Glu
175             180                 185                 190

CAT TTT GAG GCA TTT CAG TCA GTT GCT CAA TGT ACC TAT AAC CAG ACC      209
His Phe Glu Ala Phe Gln Ser Val Ala Gln Cys Thr Tyr Asn Gln Thr
                195                 200                 205

GTT CAG CTG GAT ATT ACG GCC TTT TTA AAG ACC GTA AAG AAA AAT AAG      257
Val Gln Leu Asp Ile Thr Ala Phe Leu Lys Thr Val Lys Lys Asn Lys
            210                 215                 220

CAC AAG TTT TAT CCG GCC TTT ATT CAC ATT CTT GCC CGC CTG ATG AAT      305
His Lys Phe Tyr Pro Ala Phe Ile His Ile Leu Ala Arg Leu Met Asn
                225                 230                 235

GCT CAC CCG GAG TTC CGT ATG GCA ATG AAA GAC GGT GAG CTG GTG ATA      353
Ala His Pro Glu Phe Arg Met Ala Met Lys Asp Gly Glu Leu Val Ile
    240                 245                 250

TGG GAT AGT GTT CAC CCT TGT TAC ACC GTT TTC CAT GAG CAA ACT GAA      401
Trp Asp Ser Val His Pro Cys Tyr Thr Val Phe His Glu Gln Thr Glu
255             260                 265                 270

ACG TTT TCA TCG CTC TGG AGT GAA TAC CAC GAC GAT TTC CGG CAG TTT      449
Thr Phe Ser Ser Leu Trp Ser Glu Tyr His Asp Asp Phe Arg Gln Phe
                275                 280                 285

CTA CAC ATA TAT TCG CAA GAT GTG GCG TGT TAC GGT GAA AAC CTG GCC      497
Leu His Ile Tyr Ser Gln Asp Val Ala Cys Tyr Gly Glu Asn Leu Ala
                290                 295                 300

TAT TTC CCT AAA GGG TTT ATT GAG AAT ATG TTT TTC GTC TCA GCC AAT      545
Tyr Phe Pro Lys Gly Phe Ile Glu Asn Met Phe Phe Val Ser Ala Asn
                305                 310                 315

CCC TGG GTG AGT TTC ACC AGT TTT GAT TTA AAC GTA GCC AAT ATG GAC      593
Pro Trp Val Ser Phe Thr Ser Phe Asp Leu Asn Val Ala Asn Met Asp
320             325                 330

AAC TTC TTC GCC CCC GTT TTC ACT ATG GGC AAA TAT TAT ACG CAA GGC      641
Asn Phe Phe Ala Pro Val Phe Thr Met Gly Lys Tyr Tyr Thr Gln Gly
335             340                 345                 350

GAC AAG GTG CTG ATG CCG CTG GCG ATT CAG GTT CAT CAT GCC GTT TGT      689
Asp Lys Val Leu Met Pro Leu Ala Ile Gln Val His His Ala Val Cys
                355                 360                 365

GAT GGC TTC CAT GTC GGC AGA ATG CTT AAT GAA TTA CAA CAG TAC TGC      737
Asp Gly Phe His Val Gly Arg Met Leu Asn Glu Leu Gln Gln Tyr Cys
                370                 375                 380

GAT GAG TGG CAG GGC GGG GCG TAATTTTTTT AAGGCAGTTA TTGGGTGCCC         788
Asp Glu Trp Gln Gly Gly Ala
            385

TTAAACGCCT GGTGCTAGAT CTTCC                                          813
```

(2) INFORMATION FOR SEQ ID NO: 273:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO: 273:

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
```

```
                         20                  25                  30
Tyr Asn Gln Thr Val Gln Leu Asp Ile Thr Ala Phe Leu Lys Thr Val
         35                  40                  45
Lys Lys Asn Lys His Lys Phe Tyr Pro Ala Phe Ile His Ile Leu Ala
         50                  55                  60
Arg Leu Met Asn Ala His Pro Glu Phe Arg Met Ala Met Lys Asp Gly
 65                  70                  75                  80
Glu Leu Val Ile Trp Asp Ser Val His Pro Cys Tyr Thr Val Phe His
                 85                  90                  95
Glu Gln Thr Glu Thr Phe Ser Ser Leu Trp Ser Glu Tyr His Asp Asp
                100                 105                 110
Phe Arg Gln Phe Leu His Ile Tyr Ser Gln Asp Val Ala Cys Tyr Gly
            115                 120                 125
Glu Asn Leu Ala Tyr Phe Pro Lys Gly Phe Ile Glu Asn Met Phe Phe
        130                 135                 140
Val Ser Ala Asn Pro Trp Val Ser Phe Thr Ser Phe Asp Leu Asn Val
145                 150                 155                 160
Ala Asn Met Asp Asn Phe Phe Ala Pro Val Phe Thr Met Gly Lys Tyr
                165                 170                 175
Tyr Thr Gln Gly Asp Lys Val Leu Met Pro Leu Ala Ile Gln Val His
                180                 185                 190
His Ala Val Cys Asp Gly Phe His Val Gly Arg Met Leu Asn Glu Leu
            195                 200                 205
Gln Gln Tyr Cys Asp Glu Trp Gln Gly Gly Ala
        210                 215

(2) INFORMATION FOR SEQ ID NO: 274:

(i) SEQUENCE CHARACTERISTICS:
        (A) LENGTH: 2755 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "synthetic vector"

(ix) FEATURE:
        (A) NAME/KEY: CDS
        (B) LOCATION:3..509
        (D) OTHER INFORMATION:/product= "gIIIp ss, myc tag, amber
            codon"

(ix) FEATURE:
        (A) NAME/KEY: CDS
        (B) LOCATION:complement (1853..2509)
        (D) OTHER INFORMATION:/product= "cat resistance"

(xi) SEQUENCE DESCRIPTION: SEQ ID NO: 274:

AA TTC GAG CAG AAG CTG ATC TCT GAG GAG GAT CTG TAG GGT GGT GGC          47
   Phe Glu Gln Lys Leu Ile Ser Glu Glu Asp Leu  *  Gly Gly Gly
       220                 225                 230

TCT GGT TCC GGT GAT TTT GAT TAT GAA AAG ATG GCA AAC GCT AAT AAG         95
Ser Gly Ser Gly Asp Phe Asp Tyr Glu Lys Met Ala Asn Ala Asn Lys
235                 240                 245                 250

GGG GCT ATG ACC GAA AAT GCC GAT GAA AAC GCG CTA CAG TCT GAC GCT        143
Gly Ala Met Thr Glu Asn Ala Asp Glu Asn Ala Leu Gln Ser Asp Ala
                255                 260                 265

AAA GGC AAA CTT GAT TCT GTC GCT ACT GAT TAC GGT GCT GCT ATC GAT        191
Lys Gly Lys Leu Asp Ser Val Ala Thr Asp Tyr Gly Ala Ala Ile Asp
            270                 275                 280
```

-continued

```
GGT TTC ATT GGT GAC GTT TCC GGC CTT GCT AAT GGT AAT GGT GCT ACT        239
Gly Phe Ile Gly Asp Val Ser Gly Leu Ala Asn Gly Asn Gly Ala Thr
            285                 290                 295

GGT GAT TTT GCT GGC TCT AAT TCC CAA ATG GCT CAA GTC GGT GAC GGT        287
Gly Asp Phe Ala Gly Ser Asn Ser Gln Met Ala Gln Val Gly Asp Gly
        300                 305                 310

GAT AAT TCA CCT TTA ATG AAT AAT TTC CGT CAA TAT TTA CCT TCC CTC        335
Asp Asn Ser Pro Leu Met Asn Asn Phe Arg Gln Tyr Leu Pro Ser Leu
315                 320                 325                 330

CCT CAA TCG GTT GAA TGT CGC CCT TTT GTC TTT GGC GCT GGT AAA CCA        383
Pro Gln Ser Val Glu Cys Arg Pro Phe Val Phe Gly Ala Gly Lys Pro
                335                 340                 345

TAT GAA TTT TCT ATT GAT TGT GAC AAA ATA AAC TTA TTC CGT GGT GTC        431
Tyr Glu Phe Ser Ile Asp Cys Asp Lys Ile Asn Leu Phe Arg Gly Val
            350                 355                 360

TTT GCG TTT CTT TTA TAT GTT GCC ACC TTT ATG TAT GTA TTT TCT ACG        479
Phe Ala Phe Leu Leu Tyr Val Ala Thr Phe Met Tyr Val Phe Ser Thr
        365                 370                 375

TTT GCT AAC ATA CTG CGT AAT AAG GAG TCT TGATAAGCTT GACCTGTGAA          529
Phe Ala Asn Ile Leu Arg Asn Lys Glu Ser
380                 385

GTGAAAAATG GCGCAGATTG TGCGACATTT TTTTTGTCTG CCGTTTAATT AAAGGGGGGG      589

GGGGGCCGGC CTGGGGGGGG GTGTACATGA AATTGTAAAC GTTAATATTT TGTTAAAATT      649

CGCGTTAAAT TTTTGTTAAA TCAGCTCATT TTTTAACCAA TAGGCCGAAA TCGGCAAAAT      709

CCCTTATAAA TCAAAAGAAT AGACCGAGAT AGGGTTGAGT GTTGTTCCAG TTTGGAACAA      769

GAGTCCACTA TTAAAGAACG TGGACTCCAA CGTCAAAGGG CGAAAAACCG TCTATCAGGG      829

CGATGGCCCA CTACGAGAAC CATCACCCTA ATCAAGTTTT TGGGGTCGA GGTGCCGTAA       889

AGCACTAAAT CGGAACCCTA AAGGGAGCCC CCGATTTAGA GCTTGACGGG GAAAGCCGGC      949

GAACGTGGCG AGAAAGGAAG GGAAGAAAGC GAAAGGAGCG GGCGCTAGGG CGCTGGCAAG     1009

TGTAGCGGTC ACGCTGCGCG TAACCACCAC ACCCGCCGCG CTTAATGCGC CGCTACAGGG     1069

CGCGTGCTAG CCATGTGAGC AAAAGGCCAG CAAAAGGCCA GGAACCGTAA AAAGGCCGCG     1129

TTGCTGGCGT TTTTCCATAG GCTCCGCCCC CCTGACGAGC ATCACAAAAA TCGACGCTCA     1189

AGTCAGAGGT GGCGAAACCC GACAGGACTA TAAAGATACC AGGCGTTTCC CCCTGGAAGC     1249

TCCCTCGTGC GCTCTCCTGT TCCGACCCTG CCGCTTACCG GATACCTGTC CGCCTTTCTC     1309

CCTTCGGGAA GCGTGGCGCT TTCTCATAGC TCACGCTGTA GGTATCTCAG TTCGGTGTAG     1369

GTCGTTCGCT CCAAGCTGGG CTGTGTGCAC GAACCCCCCG TTCAGCCCGA CCGCTGCGCC     1429

TTATCCGGTA ACTATCGTCT TGAGTCCAAC CCGGTAAGAC ACGACTTATC GCCACTGGCA     1489

GCAGCCACTG GTAACAGGAT TAGCAGAGCG AGGTATGTAG GCGGTGCTAC AGAGTTCTTG     1549

AAGTGGTGGC CTAACTACGG CTACACTAGA AGAACAGTAT TTGGTATCTG CGCTCTGCTG     1609

TAGCCAGTTA CCTTCGGAAA AAGAGTTGGT AGCTCTTGAT CCGGCAAACA AACCACCGCT     1669

GGTAGCGGTG GTTTTTTTGT TTGCAAGCAG CAGATTACGC GCAGAAAAAA AGGATCTCAA     1729

GAAGATCCTT TGATCTTTTC TACGGGTCT GACGCTCAGT GGAACGAAAA CTCACGTTAA      1789

GGGATTTTGG TCAGATCTAG CACCAGGCGT TTAAGGCAC CAATAACTGC CTTAAAAAAA      1849

TTACGCCCCG CCCTGCCACT CATCGCAGTA CTGTTGTAAT TCATTAAGCA TTCTGCCGAC     1909

ATGGAAGCCA TCACAAACGG CATGATGAAC CTGAATCGCC AGCGGCATCA GCACCTTGTC     1969

GCCTTGCGTA TAATATTTGC CCATAGTGAA AACGGGGGCG AAGAAGTTGT CCATATTGGC     2029
```

-continued

```
TACGTTTAAA TCAAAACTGG TGAAACTCAC CCAGGGATTG GCTGAGACGA AAAACATATT    2089

CTCAATAAAC CCTTTAGGGA AATAGGCCAG GTTTTCACCG TAACACGCCA CATCTTGCGA    2149

ATATATGTGT AGAAACTGCC GGAAATCGTC GTGGTATTCA CTCCAGAGCG ATGAAAACGT    2209

TTCAGTTTGC TCATGGAAAA CGGTGTAACA AGGGTGAACA CTATCCCATA TCACCAGCTC    2269

ACCGTCTTTC ATTGCCATAC GGAACTCCGG GTGAGCATTC ATCAGGCGGG CAAGAATGTG    2329

AATAAAGGCC GGATAAAACT TGTGCTTATT TTTCTTTACG GTCTTTAAAA AGGCCGTAAT    2389

ATCCAGCTGA ACGGTCTGGT TATAGGTACA TTGAGCAACT GACTGAAATG CCTCAAAATG    2449

TTCTTTACGA TGCCATTGGG ATATATCAAC GGTGGTATAT CCAGTGATTT TTTTCTCCAT    2509

TTTAGCTTCC TTAGCTCCTG AAAATCTCGA TAACTCAAAA AATACGCCCG GTAGTGATCT    2569

TATTTCATTA TGGTGAAAGT TGGAACCTCA CCCGACGTCT AATGTGAGTT AGCTCACTCA    2629

TTAGGCACCC CAGGCTTTAC ACTTTATGCT TCCGGCTCGT ATGTTGTGTG GAATTGTGAG    2689

CGGATAACAA TTTCACACAG GAAACAGCTA TGACCATGAT TACGAATTTC TAGAGCATGC    2749

GGGGGG                                                               2755
```

(2) INFORMATION FOR SEQ ID NO: 275:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 275:

```
Phe Glu Gln Lys Leu Ile Ser Glu Glu Asp Leu
 1               5                  10
```

(2) INFORMATION FOR SEQ ID NO: 276:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO: 276:

```
Met Glu Lys Lys Ile Thr Gly Tyr Thr Thr Val Asp Ile Ser Gln Trp
 1               5                  10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
            35                  40                  45

Lys Lys Asn Lys His Lys Phe Tyr Pro Ala Phe Ile His Ile Leu Ala
        50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140
```

```
Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

(2) INFORMATION FOR SEQ ID NO: 277:

(i) SEQUENCE CHARACTERISTICS:
        (A) LENGTH: 173 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 277:

```
GACGTCTTAA TGTGAGTTAG CTCACTCATT AGGCACCCCA GGCTTTACAC TTTATGCTTC    60

CGGCTCGTAT GTTGTGTGGA ATTGTGAGCG GATAACAATT TCACACAGGA AACAGCTATG   120

ACCATGTCTA GAATAACTTC GTATAATGTA CGCTATACGA AGTTATCGCA TGC          173
```

(2) INFORMATION FOR SEQ ID NO: 278:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 278:

```
AGATCTCATA ACTTCGTATA ATGTATGCTA TACGAAGTTA TGACGTC                   47
```

(2) INFORMATION FOR SEQ ID NO: 279:

(i) SEQUENCE CHARACTERISTICS:
        (A) LENGTH: 1255 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene cassette"

(ix) FEATURE:
        (A) NAME/KEY: CDS
        (B) LOCATION:1..1245
        (D) OTHER INFORMATION:/product= "gIIIp, GGGGS linker"

(xi) SEQUENCE DESCRIPTION: SEQ ID NO: 279:

```
GAA TTC GGT GGT GGT GGA TCT GCG TGC GCT GAA ACG GTT GAA AGT TGT    48
Glu Phe Gly Gly Gly Gly Ser Ala Cys Ala Glu Thr Val Glu Ser Cys
220                 225                 230                 235

TTA GCA AAA TCC CAT ACA GAA AAT TCA TTT ACT AAC GTC TGG AAA GAC    96
Leu Ala Lys Ser His Thr Glu Asn Ser Phe Thr Asn Val Trp Lys Asp
            240                 245                 250
```

```
GAC AAA ACT TTA GAT CGT TAC GCT AAC TAT GAG GGC TGT CTG TGG AAT      144
Asp Lys Thr Leu Asp Arg Tyr Ala Asn Tyr Glu Gly Cys Leu Trp Asn
            255                 260                 265

GCT ACA GGC GTT GTA GTT TGT ACT GGT GAC GAA ACT CAG TGT TAC GGT      192
Ala Thr Gly Val Val Val Cys Thr Gly Asp Glu Thr Gln Cys Tyr Gly
            270                 275                 280

ACA TGG GTT CCT ATT GGG CTT GCT ATC CCT GAA AAT GAG GGT GGT GGC      240
Thr Trp Val Pro Ile Gly Leu Ala Ile Pro Glu Asn Glu Gly Gly Gly
        285                 290                 295

TCT GAG GGT GGC GGT TCT GAG GGT GGC GGT TCT GAG GGT GGC GGT ACT      288
Ser Glu Gly Gly Gly Ser Glu Gly Gly Gly Ser Glu Gly Gly Gly Thr
300                 305                 310                 315

AAA CCT CCT GAG TAC GGT GAT ACA CCT ATT CCG GGC TAT ACT TAT ATC      336
Lys Pro Pro Glu Tyr Gly Asp Thr Pro Ile Pro Gly Tyr Thr Tyr Ile
                320                 325                 330

AAC CCT CTC GAC GGC ACT TAT CCG CCT GGT ACT GAG CAA AAC CCC GCT      384
Asn Pro Leu Asp Gly Thr Tyr Pro Pro Gly Thr Glu Gln Asn Pro Ala
            335                 340                 345

AAT CCT AAT CCT TCT CTT GAG GAG TCT CAG CCT CTT AAT ACT TTC ATG      432
Asn Pro Asn Pro Ser Leu Glu Glu Ser Gln Pro Leu Asn Thr Phe Met
        350                 355                 360

TTT CAG AAT AAT AGG TTC CGA AAT AGG CAG GGG GCA TTA ACT GTT TAT      480
Phe Gln Asn Asn Arg Phe Arg Asn Arg Gln Gly Ala Leu Thr Val Tyr
    365                 370                 375

ACG GGC ACT GTT ACT CAA GGC ACT GAC CCC GTT AAA ACT TAT TAC CAG      528
Thr Gly Thr Val Thr Gln Gly Thr Asp Pro Val Lys Thr Tyr Tyr Gln
380                 385                 390                 395

TAC ACT CCT GTA TCA TCA AAA GCC ATG TAT GAC GCT TAC TGG AAC GGT      576
Tyr Thr Pro Val Ser Ser Lys Ala Met Tyr Asp Ala Tyr Trp Asn Gly
                400                 405                 410

AAA TTC AGA GAC TGC GCT TTC CAT TCT GGC TTT AAT GAG GAT TTA TTT      624
Lys Phe Arg Asp Cys Ala Phe His Ser Gly Phe Asn Glu Asp Leu Phe
            415                 420                 425

GTT TGT GAA TAT CAA GGC CAA TCG TCT GAC CTG CCT CAA CCT CCT GTC      672
Val Cys Glu Tyr Gln Gly Gln Ser Ser Asp Leu Pro Gln Pro Pro Val
        430                 435                 440

AAT GCT GGC GGC GGC TCT GGT GGT GGT TCT GGT GGC GGC TCT GAG GGT      720
Asn Ala Gly Gly Gly Ser Gly Gly Gly Ser Gly Gly Gly Ser Glu Gly
    445                 450                 455

GGT GGC TCT GAG GGT GGC GGT TCT GAG GGT GGC GGC TCT GAG GGA GGC      768
Gly Gly Ser Glu Gly Gly Gly Ser Glu Gly Gly Gly Ser Glu Gly Gly
460                 465                 470                 475

GGT TCC GGT GGT GGC TCT GGT TCC GGT GAT TTT GAT TAT GAA AAG ATG      816
Gly Ser Gly Gly Gly Ser Gly Ser Gly Asp Phe Asp Tyr Glu Lys Met
                480                 485                 490

GCA AAC GCT AAT AAG GGG GCT ATG ACC GAA AAT GCC GAT GAA AAC GCG      864
Ala Asn Ala Asn Lys Gly Ala Met Thr Glu Asn Ala Asp Glu Asn Ala
            495                 500                 505

CTA CAG TCT GAC GCT AAA GGC AAA CTT GAT TCT GTC GCT ACT GAT TAC      912
Leu Gln Ser Asp Ala Lys Gly Lys Leu Asp Ser Val Ala Thr Asp Tyr
        510                 515                 520

GGT GCT GCT ATC GAT GGT TTC ATT GGT GAC GTT TCC GGC CTT GCT AAT      960
Gly Ala Ala Ile Asp Gly Phe Ile Gly Asp Val Ser Gly Leu Ala Asn
    525                 530                 535

GGT AAT GGT GCT ACT GGT GAT TTT GCT GGC TCT AAT TCC CAA ATG GCT     1008
Gly Asn Gly Ala Thr Gly Asp Phe Ala Gly Ser Asn Ser Gln Met Ala
540                 545                 550                 555

CAA GTC GGT GAA GGT GAT AAT TCA CCT TTA ATG AAT AAT TTC CGT CAA     1056
Gln Val Gly Glu Gly Asp Asn Ser Pro Leu Met Asn Asn Phe Arg Gln
                560                 565                 570
```

-continued

```
TAT TTA CCT TCC ATC CCT CAA TCG GTT GAA TGT CGC CCT TTT GTC TTT          1104
Tyr Leu Pro Ser Ile Pro Gln Ser Val Glu Cys Arg Pro Phe Val Phe
            575                 580                 585

GGC GCT GGT AAA CCC TAT GAA TTT TCT ATT GAT TGT GAC AAA ATA AAC          1152
Gly Ala Gly Lys Pro Tyr Glu Phe Ser Ile Asp Cys Asp Lys Ile Asn
            590                 595                 600

TTA TTC CGT GGT GTC TTT GCG TTT CTT TTA TAT GTT GCC ACC TTT ATG          1200
Leu Phe Arg Gly Val Phe Ala Phe Leu Leu Tyr Val Ala Thr Phe Met
            605                 610                 615

TAT GTA TTT TCT ACG TTT GCT AAC ATA CTG CGT AAT AAG GAG TCT              1245
Tyr Val Phe Ser Thr Phe Ala Asn Ile Leu Arg Asn Lys Glu Ser
620                 625                 630

TGATAAGCTT                                                               1255

(2) INFORMATION FOR SEQ ID NO: 280:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO: 280:

Glu Phe Gly Gly Gly Gly Ser Ala Cys Ala Glu Thr Val Glu Ser Cys
 1               5                  10                  15

Leu Ala Lys Ser His Thr Glu Asn Ser Phe Thr Asn Val Trp Lys Asp
                20                  25                  30

Asp Lys Thr Leu Asp Arg Tyr Ala Asn Tyr Glu Gly Cys Leu Trp Asn
            35                  40                  45

Ala Thr Gly Val Val Val Cys Thr Gly Asp Glu Thr Gln Cys Tyr Gly
        50                  55                  60

Thr Trp Val Pro Ile Gly Leu Ala Ile Pro Glu Asn Glu Gly Gly Gly
65                  70                  75                  80

Ser Glu Gly Gly Gly Ser Glu Gly Gly Ser Glu Gly Gly Gly Thr
                85                  90                  95

Lys Pro Pro Glu Tyr Gly Asp Thr Pro Ile Pro Gly Tyr Thr Tyr Ile
                100                 105                 110

Asn Pro Leu Asp Gly Thr Tyr Pro Pro Gly Thr Glu Gln Asn Pro Ala
            115                 120                 125

Asn Pro Asn Pro Ser Leu Glu Glu Ser Gln Pro Leu Asn Thr Phe Met
        130                 135                 140

Phe Gln Asn Asn Arg Phe Arg Asn Arg Gln Gly Ala Leu Thr Val Tyr
145                 150                 155                 160

Thr Gly Thr Val Thr Gln Gly Thr Asp Pro Val Lys Thr Tyr Tyr Gln
                165                 170                 175

Tyr Thr Pro Val Ser Ser Lys Ala Met Tyr Asp Ala Tyr Trp Asn Gly
            180                 185                 190

Lys Phe Arg Asp Cys Ala Phe His Ser Gly Phe Asn Glu Asp Leu Phe
        195                 200                 205

Val Cys Glu Tyr Gln Gly Gln Ser Ser Asp Leu Pro Gln Pro Pro Val
    210                 215                 220

Asn Ala Gly Gly Gly Ser Gly Gly Gly Ser Gly Gly Ser Glu Gly
225                 230                 235                 240

Gly Gly Ser Glu Gly Gly Gly Ser Glu Gly Gly Gly Ser Glu Gly Gly
                245                 250                 255
```

```
Gly Ser Gly Gly Gly Ser Gly Ser Gly Asp Phe Asp Tyr Glu Lys Met
            260                 265                 270

Ala Asn Ala Asn Lys Gly Ala Met Thr Glu Asn Ala Asp Glu Asn Ala
            275                 280                 285

Leu Gln Ser Asp Ala Lys Gly Lys Leu Asp Ser Val Ala Thr Asp Tyr
            290                 295                 300

Gly Ala Ala Ile Asp Gly Phe Ile Gly Asp Val Ser Gly Leu Ala Asn
305                 310                 315                 320

Gly Asn Gly Ala Thr Gly Asp Phe Ala Gly Ser Asn Ser Gln Met Ala
                325                 330                 335

Gln Val Gly Glu Gly Asp Asn Ser Pro Leu Met Asn Asn Phe Arg Gln
            340                 345                 350

Tyr Leu Pro Ser Ile Pro Gln Ser Val Glu Cys Arg Pro Phe Val Phe
            355                 360                 365

Gly Ala Gly Lys Pro Tyr Glu Phe Ser Ile Asp Cys Asp Lys Ile Asn
            370                 375                 380

Leu Phe Arg Gly Val Phe Ala Phe Leu Leu Tyr Val Ala Thr Phe Met
385                 390                 395                 400

Tyr Val Phe Ser Thr Phe Ala Asn Ile Leu Arg Asn Lys Glu Ser
                405                 410                 415
```

(2) INFORMATION FOR SEQ ID NO: 281:

(i) SEQUENCE CHARACTERISTICS:
        (A) LENGTH: 502 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene cassette"

(ix) FEATURE:
        (A) NAME/KEY: CDS
        (B) LOCATION: 4..492
        (D) OTHER INFORMATION:/product= "gIIIp ss"

(xi) SEQUENCE DESCRIPTION: SEQ ID NO: 281:

```
CGG GAA TTC GGA GGC GGT TCC GGT GGT GGC TCT GGT TCC GGT GAT TTT        48
    Glu Phe Gly Gly Gly Ser Gly Gly Gly Ser Gly Ser Gly Asp Phe
                        420                 425                 430

GAT TAT GAA AAG ATG GCA AAC GCT AAT AAG GGG GCT ATG ACC GAA AAT        96
Asp Tyr Glu Lys Met Ala Asn Ala Asn Lys Gly Ala Met Thr Glu Asn
                435                 440                 445

GCC GAT GAA AAC GCG CTA CAG TCT GAC GCT AAA GGC AAA CTT GAT TCT       144
Ala Asp Glu Asn Ala Leu Gln Ser Asp Ala Lys Gly Lys Leu Asp Ser
            450                 455                 460

GTC GCT ACT GAT TAC GGT GCT GCT ATC GAT GGT TTC ATT GGT GAC GTT       192
Val Ala Thr Asp Tyr Gly Ala Ala Ile Asp Gly Phe Ile Gly Asp Val
            465                 470                 475

TCC GGC CTT GCT AAT GGT AAT GGT GCT ACT GGT GAT TTT GCT GGC TCT       240
Ser Gly Leu Ala Asn Gly Asn Gly Ala Thr Gly Asp Phe Ala Gly Ser
            480                 485                 490

AAT TCC CAA ATG GCT CAA GTC GGT GAC GGT GAT AAT TCA CCT TTA ATG       288
Asn Ser Gln Met Ala Gln Val Gly Asp Gly Asp Asn Ser Pro Leu Met
495                 500                 505                 510

AAT AAT TTC CGT CAA TAT TTA CCT TCC CTC CCT CAA TCG GTT GAA TGT       336
Asn Asn Phe Arg Gln Tyr Leu Pro Ser Leu Pro Gln Ser Val Glu Cys
                515                 520                 525

CGC CCT TTT GTC TTT GGC GCT GGT AAA CCA TAT GAA TTT TCT ATT GAT       384
Arg Pro Phe Val Phe Gly Ala Gly Lys Pro Tyr Glu Phe Ser Ile Asp
```

-continued

```
                    530             535             540
TGT GAC AAA ATA AAC TTA TTC CGT GGT GTC TTT GCG TTT CTT TTA TAT    432
Cys Asp Lys Ile Asn Leu Phe Arg Gly Val Phe Ala Phe Leu Leu Tyr
            545             550             555

GTT GCC ACC TTT ATG TAT GTA TTT TCT ACG TTT GCT AAC ATA CTG CGT    480
Val Ala Thr Phe Met Tyr Val Phe Ser Thr Phe Ala Asn Ile Leu Arg
    560             565             570

AAT AAG GAG TCT TGATAAGCTT                                         502
Asn Lys Glu Ser
575
```

(2) INFORMATION FOR SEQ ID NO: 282:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO: 282:

```
Glu Phe Gly Gly Gly Ser Gly Gly Ser Gly Ser Gly Asp Phe Asp
 1               5                  10                  15

Tyr Glu Lys Met Ala Asn Ala Asn Lys Gly Ala Met Thr Glu Asn Ala
                20                  25                  30

Asp Glu Asn Ala Leu Gln Ser Asp Ala Lys Gly Lys Leu Asp Ser Val
            35                  40                  45

Ala Thr Asp Tyr Gly Ala Ala Ile Asp Gly Phe Ile Gly Asp Val Ser
        50                  55                  60

Gly Leu Ala Asn Gly Asn Gly Ala Thr Gly Asp Phe Ala Gly Ser Asn
65                  70                  75                  80

Ser Gln Met Ala Gln Val Gly Asp Gly Asp Asn Ser Pro Leu Met Asn
                85                  90                  95

Asn Phe Arg Gln Tyr Leu Pro Ser Leu Pro Gln Ser Val Glu Cys Arg
                100                 105                 110

Pro Phe Val Phe Gly Ala Gly Lys Pro Tyr Glu Phe Ser Ile Asp Cys
            115                 120                 125

Asp Lys Ile Asn Leu Phe Arg Gly Val Phe Ala Phe Leu Leu Tyr Val
    130                 135                 140

Ala Thr Phe Met Tyr Val Phe Ser Thr Phe Ala Asn Ile Leu Arg Asn
145                 150                 155                 160

Lys Glu Ser
```

(2) INFORMATION FOR SEQ ID NO: 283:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 283:

```
GCATGCCATA ACTTCGTATA ATGTACGCTA TACGAAGTTA TAAGCTT               47
```

(2) INFORMATION FOR SEQ ID NO: 284:

(i) SEQUENCE CHARACTERISTICS:
        (A) LENGTH: 1163 base pairs (B) TYPE: nucleic acid
(C) STRANDEDNESS: double
(D) TOPOLOGY: linear (ii) MOLECULE TYPE: other nucleic acid
(A) DESCRIPTION: /desc = "synthetic gene cassette"

(ix) FEATURE:
(A) NAME/KEY: CDS
(B) LOCATION:82..978
(D) OTHER INFORMATION:/product= "bla resistance"

(xi) SEQUENCE DESCRIPTION: SEQ ID NO: 284:

```
GGGGGTGTAC ATTCAAATAT GTATCCGCTC ATGAGACAAT AACCCTGATA AATGCTTCAA        60

TAATATTGAA AAAGGAAGAG T ATG AGT ATT CAA CAT TTC CGT GTC GCC CTT        111
                        Met Ser Ile Gln His Phe Arg Val Ala Leu
                        165                 170

ATT CCC TTT TTT GCG GCA TTT TGC CTT CCT GTT TTT GCT CAC CCA GAA        159
Ile Pro Phe Phe Ala Ala Phe Cys Leu Pro Val Phe Ala His Pro Glu
    175                 180                 185

ACG CTG GTG AAA GTA AAA GAT GCT GAG GAT CAG TTG GGT GCG CGA GTG        207
Thr Leu Val Lys Val Lys Asp Ala Glu Asp Gln Leu Gly Ala Arg Val
190                 195                 200                 205

GGT TAC ATC GAA CTG GAT CTC AAC AGC GGT AAG ATC CTT GAG AGT TTT        255
Gly Tyr Ile Glu Leu Asp Leu Asn Ser Gly Lys Ile Leu Glu Ser Phe
                210                 215                 220

CGC CCC GAA GAA CGT TTT CCA ATG ATG AGC ACT TTT AAA GTT CTG CTA        303
Arg Pro Glu Glu Arg Phe Pro Met Met Ser Thr Phe Lys Val Leu Leu
        225                 230                 235

TGT GGC GCG GTA TTA TCC CGT ATT GAC GCC GGG CAA GAG CAA CTC GGT        351
Cys Gly Ala Val Leu Ser Arg Ile Asp Ala Gly Gln Glu Gln Leu Gly
            240                 245                 250

CGC CGC ATA CAC TAT TCT CAG AAT GAC TTG GTT GAG TAC TCA CCA GTC        399
Arg Arg Ile His Tyr Ser Gln Asn Asp Leu Val Glu Tyr Ser Pro Val
255                 260                 265

ACA GAA AAG CAT CTT ACG GAT GGC ATG ACA GTA AGA GAA TTA TGC AGT        447
Thr Glu Lys His Leu Thr Asp Gly Met Thr Val Arg Glu Leu Cys Ser
270                 275                 280                 285

GCT GCC ATA ACC ATG AGT GAT AAC ACT GCG GCC AAC TTA CTT CTG ACA        495
Ala Ala Ile Thr Met Ser Asp Asn Thr Ala Ala Asn Leu Leu Leu Thr
                290                 295                 300

ACG ATC GGA GGA CCG AAG GAG CTA ACC GCT TTT TTG CAC AAC ATG GGG        543
Thr Ile Gly Gly Pro Lys Glu Leu Thr Ala Phe Leu His Asn Met Gly
        305                 310                 315

GAT CAT GTA ACT CGC CTT GAT CGT TGG GAA CCG GAG CTG AAT GAA GCC        591
Asp His Val Thr Arg Leu Asp Arg Trp Glu Pro Glu Leu Asn Glu Ala
            320                 325                 330

ATA CCA AAC GAC GAG CGT GAC ACC ACG ATG CCT GTA GCA ATG GCA ACA        639
Ile Pro Asn Asp Glu Arg Asp Thr Thr Met Pro Val Ala Met Ala Thr
335                 340                 345

ACG TTG CGC AAA CTA TTA ACT GGC GAA CTA CTT ACT CTA GCT TCC CGG        687
Thr Leu Arg Lys Leu Leu Thr Gly Glu Leu Leu Thr Leu Ala Ser Arg
350                 355                 360                 365

CAA CAG TTA ATA GAC TGG ATG GAG GCG GAT AAA GTT GCA GGA CCA CTT        735
Gln Gln Leu Ile Asp Trp Met Glu Ala Asp Lys Val Ala Gly Pro Leu
                370                 375                 380

CTG CGC TCG GCC CTT CCG GCT GGC TGG TTT ATT GCT GAT AAA TCT GGA        783
Leu Arg Ser Ala Leu Pro Ala Gly Trp Phe Ile Ala Asp Lys Ser Gly
            385                 390                 395

GCC GGT GAG CGT GGG TCT CGC GGT ATC ATT GCA GCA CTG GGG CCA GAT        831
Ala Gly Glu Arg Gly Ser Arg Gly Ile Ile Ala Ala Leu Gly Pro Asp
```

```
                 400             405              410
GGT AAG CCC TCC CGT ATC GTA GTT ATC TAC ACG ACG GGG AGT CAG GCA         879
Gly Lys Pro Ser Arg Ile Val Val Ile Tyr Thr Thr Gly Ser Gln Ala
        415                 420                 425

ACT ATG GAT GAA CGA AAT AGA CAG ATC GCT GAG ATA GGT GCC TCA CTG         927
Thr Met Asp Glu Arg Asn Arg Gln Ile Ala Glu Ile Gly Ala Ser Leu
430                 435                 440                 445

ATT AAG CAT TGG GTA ACT GTC AGA CCA AGT TTA CTC ATA TAT ACT TTA         975
Ile Lys His Trp Val Thr Val Arg Pro Ser Leu Leu Ile Tyr Thr Leu
                450                 455                 460

GAT TGATTTAAAA CTTCATTTTT AATTTAAAAG GATCTAGGTG AAGATCCTTT             1028
Asp

TTGATAATCT CATGACCAAA ATCCCTTAAC GTGAGTTTTC GTTCCACTGA GCGTCAGACC      1088

CCGTAGAAAA GATCAAAGGA TCTTCTTGAG ATCCTTTTTG ATAATGGCCG GCCCCCCCCC      1148

TTAATTAAGG GGGGG                                                       1163

(2) INFORMATION FOR SEQ ID NO: 285:

(i) SEQUENCE CHARACTERISTICS:
        (A) LENGTH: 299 amino acids
        (B) TYPE: amino acid
        (D) TOPOLOGY: linear (ii) MOLECULE TYPE: protein (xi) SEQUENCE DESCRIPTION: SEQ ID NO: 285:

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240
```

```
Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp Val Thr
            275                 280                 285

Val Arg Pro Ser Leu Leu Ile Tyr Thr Leu Asp
        290                 295

(2) INFORMATION FOR SEQ ID NO: 286:

(i) SEQUENCE CHARACTERISTICS:
        (A) LENGTH: 470 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 286:

GCTAGCACGC GCCCTGTAGC GGCGCATTAA GCGCGGCGGG TGTGGTGGTT ACGCGCAGCG      60

TGACCGCTAC ACTTGCCAGC GCCCTAGCGC CCGCTCCTTT CGCTTTCTTC CCTTCCTTTC     120

TCGCCACGTT CGCCGGCTTT CCCCGTCAAG CTCTAAATCG GGGGCTCCCT TTAGGGTTCC     180

GATTTAGTGC TTTACGGCAC CTCGACCCCA AAAAACTTGA TTAGGGTGAT GGTTCTCGTA     240

GTGGGCCATC GCCCTGATAG ACGGTTTTTC GCCCTTTGAC GTTGGAGTCC ACGTTCTTTA     300

ATAGTGGACT CTTGTTCCAA ACTGGAACAA CACTCAACCC TATCTCGGTC TATTCTTTTG     360

ATTTATAAGG GATTTTGCCG ATTTCGGCCT ATTGGTTAAA AAATGAGCTG ATTTAACAAA     420

AATTTAACGC GAATTTTAAC AAAATATTAA CGTTTACAAT TTCATGTACA                470

(2) INFORMATION FOR SEQ ID NO: 287:

(i) SEQUENCE CHARACTERISTICS:
        (A) LENGTH: 832 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 287:

AGATCTAATA AGATGATCTT CTTGAGATCG TTTTGGTCTG CGCGTAATCT CTTGCTCTGA      60

AAACGAAAAA ACCGCCTTGC AGGGCGGTTT TTCGTAGGTT CTCTGAGCTA CCAACTCTTT     120

GAACCGAGGT AACTGGCTTG GAGGAGCGCA GTCACTAAAA CTTGTCCTTT CAGTTTAGCC     180

TTAACCGGCG CATGACTTCA AGACTAACTC CTCTAAATCA ATTACCAGTG GCTGCTGCCA     240

GTGGTGCTTT TGCATGTCTT TCCGGGTTGG ACTCAAGACG ATAGTTACCG GATAAGGCGC     300

AGCGGTCGGA CTGAACGGGG GGTTCGTGCA TACAGTCCAG CTTGGAGCGA ACTGCCTACC     360

CGGAACTGAG TGTCAGGCGT GGAATGAGAC AAACGCGGCC ATAACAGCGG AATGACACCG     420

GTAAACCGAA AGGCAGGAAC AGGAGAGCGC AGGAGGGAGC CGCCAGGGGG AAACGCCTGG     480

TATCTTTATA GTCCTGTCGG GTTTCGCCAC CACTGATTTG AGCGTCAGAT TTCGTGATGC     540

TTGTCAGGGG GGCGGAGCCT ATGGAAAAAC GGCTTTGCCG CGGCCCTCTC ACTTCCCTGT     600

TAAGTATCTT CCTGGCATCT TCCAGGAAAT CTCCGCCCCG TTCGTAAGCC ATTTCCGCTC     660
```

```
GCCGCAGTCG AACGACCGAG CGTAGCGAGT CAGTGAGCGA GGAAGCGGAA TATATCCTGT      720

ATCACATATT CTGCTGACGC ACCGGTGCAG CCTTTTTTCT CCTGCCACAT GAAGCACTTC      780

ACTGACACCC TCATCAGTGC AACATAGTA AGCCAGTATA CACTCCGCTA GC               832
```

(2) INFORMATION FOR SEQ ID NO: 288:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 288:

```
AGATCTCATA ACTTCGTATA ATGTATGCTA TACGAAGTTA TTCAGATCT                  49
```

(2) INFORMATION FOR SEQ ID NO: 289:

(i) SEQUENCE CHARACTERISTICS:
        (A) LENGTH: 96 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 289:

```
TCTAGAGCAT GCGTAGGAGA AAATAAAATG AAACAAAGCA CTATTGCACT GGCACTCTTA      60

CCGTTGCTCT TCACCCCTGT TACCAAAGCC GAATTC                                96
```

(2) INFORMATION FOR SEQ ID NO: 290:

(i) SEQUENCE CHARACTERISTICS:
        (A) LENGTH: 120 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 290:

```
TCTAGAGCAT GCGTAGGAGA AAATAAAATG AAACAAAGCA CTATTGCACT GGCACTCTTA      60

CCGTTGCTCT TCACCCCTGT TACCAAAGCC GACTACAAAG ATGAAGTGCA ATTGGAATTC     120
```

(2) INFORMATION FOR SEQ ID NO: 291:

(i) SEQUENCE CHARACTERISTICS:
        (A) LENGTH: 96 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA cassette"

(xi) SEQUENCE DESCRIPTION: SEQ ID NO: 291:

```
TCTAGAGGTT GAGGTGATTT TATGAAAAAG AATATCGCAT TTCTTCTTGC ATCTATGTTC      60

GTTTTTTCTA TTGCTACAAA TGCATACGCT GAATTC                                96
```

(2) INFORMATION FOR SEQ ID NO: 292:

(i) SEQUENCE CHARACTERISTICS:
    (A) LENGTH: 1221 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc = "synthetic gene cassette"

(ix) FEATURE:
    (A) NAME/KEY: CDS
    (B) LOCATION:79..1158
    (D) OTHER INFORMATION:/product= "lacI"

(xi) SEQUENCE DESCRIPTION: SEQ ID NO: 292:

```
GCTAGCATCG AATGGCGCAA AACCTTTCGC GGTATGGCAT GATAGCGCCC GGAAGAGAGT         60

CAATTCAGGG TGGTGAAT GTG AAA CCA GTA ACG TTA TAC GAT GTC GCA GAG          111
                    Val Lys Pro Val Thr Leu Tyr Asp Val Ala Glu
                    300             305                 310

TAT GCC GGT GTC TCT TAT CAG ACC GTT TCC CGC GTG GTG AAC CAG GCC          159
Tyr Ala Gly Val Ser Tyr Gln Thr Val Ser Arg Val Val Asn Gln Ala
            315                 320                 325

AGC CAC GTT TCT GCG AAA ACG CGG GAA AAA GTG GAA GCG GCG ATG GCG          207
Ser His Val Ser Ala Lys Thr Arg Glu Lys Val Glu Ala Ala Met Ala
        330                 335                 340

GAG CTG AAT TAC ATT CCT AAC CGC GTG GCA CAA CAA CTG GCG GGC AAA          255
Glu Leu Asn Tyr Ile Pro Asn Arg Val Ala Gln Gln Leu Ala Gly Lys
            345                 350                 355

CAG TCG TTG CTG ATT GGC GTT GCC ACC TCC AGT CTG GCC CTG CAC GCG          303
Gln Ser Leu Leu Ile Gly Val Ala Thr Ser Ser Leu Ala Leu His Ala
360                 365                 370

CCG TCG CAA ATT GTC GCG GCG ATT AAA TCT CGC GCC GAT CAA CTG GGT          351
Pro Ser Gln Ile Val Ala Ala Ile Lys Ser Arg Ala Asp Gln Leu Gly
375                 380                 385                 390

GCC AGC GTG GTC GTG TCG ATG GTA GAA CGA AGC GGC GTC GAA GCC TGT          399
Ala Ser Val Val Val Ser Met Val Glu Arg Ser Gly Val Glu Ala Cys
                395                 400                 405

AAA GCG GCG GTG CAC AAT CTT CTC GCG CAA CGT GTC AGT GGG CTG ATT          447
Lys Ala Ala Val His Asn Leu Leu Ala Gln Arg Val Ser Gly Leu Ile
            410                 415                 420

ATT AAC TAT CCG CTG GAT GAC CAG GAT GCT ATT GCT GTG GAA GCT GCC          495
Ile Asn Tyr Pro Leu Asp Asp Gln Asp Ala Ile Ala Val Glu Ala Ala
            425                 430                 435

TGC ACT AAT GTT CCG GCG TTA TTT CTT GAT GTC TCT GAC CAG ACA CCC          543
Cys Thr Asn Val Pro Ala Leu Phe Leu Asp Val Ser Asp Gln Thr Pro
440                 445                 450

ATC AAC AGT ATT ATT TTC TCC CAT GAG GAC GGT ACG CGA CTG GGC GTG          591
Ile Asn Ser Ile Ile Phe Ser His Glu Asp Gly Thr Arg Leu Gly Val
455                 460                 465                 470

GAG CAT CTG GTC GCA TTG GGC CAC CAG CAA ATC GCG CTG TTA GCT GGC          639
Glu His Leu Val Ala Leu Gly His Gln Gln Ile Ala Leu Leu Ala Gly
                475                 480                 485

CCA TTA AGT TCT GTC TCG GCG CGT CTG CGT CTG GCT GGC TGG CAT AAA          687
Pro Leu Ser Ser Val Ser Ala Arg Leu Arg Leu Ala Gly Trp His Lys
            490                 495                 500

TAT CTC ACT CGC AAT CAA ATT CAG CCG ATA GCG GAA CGG GAA GGC GAC          735
Tyr Leu Thr Arg Asn Gln Ile Gln Pro Ile Ala Glu Arg Glu Gly Asp
        505                 510                 515

TGG AGT GCC ATG TCC GGT TTT CAA CAA ACC ATG CAA ATG CTG AAT GAG          783
Trp Ser Ala Met Ser Gly Phe Gln Gln Thr Met Gln Met Leu Asn Glu
        520                 525                 530
```

```
GGC ATC GTT CCC ACT GCG ATG CTG GTT GCC AAC GAT CAG ATG GCG CTG      831
Gly Ile Val Pro Thr Ala Met Leu Val Ala Asn Asp Gln Met Ala Leu
535                 540                 545                 550

GGC GCA ATG CGT GCC ATT ACC GAG TCC GGG CTG CGC GTT GGT GCG GAC      879
Gly Ala Met Arg Ala Ile Thr Glu Ser Gly Leu Arg Val Gly Ala Asp
                555                 560                 565

ATC TCG GTA GTG GGA TAC GAC GAT ACC GAG GAC AGC TCA TGT TAT ATC      927
Ile Ser Val Val Gly Tyr Asp Asp Thr Glu Asp Ser Ser Cys Tyr Ile
            570                 575                 580

CCG CCG CTG ACC ACC ATC AAA CAG GAT TTT CGC CTG CTG GGG CAA ACC      975
Pro Pro Leu Thr Thr Ile Lys Gln Asp Phe Arg Leu Leu Gly Gln Thr
585                 590                 595

AGC GTG GAC CGC TTG CTG CAA CTC TCT CAG GGC CAG GCG GTG AAG GGC     1023
Ser Val Asp Arg Leu Leu Gln Leu Ser Gln Gly Gln Ala Val Lys Gly
    600                 605                 610

AAT CAG CTG TTG CCC GTC TCA CTG GTG AAA AGA AAA ACC ACC CTG GCT     1071
Asn Gln Leu Leu Pro Val Ser Leu Val Lys Arg Lys Thr Thr Leu Ala
615                 620                 625                 630

CCC AAT ACG CAA ACC GCC TCT CCC CGC GCG TTG GCC GAT TCA CTG ATG     1119
Pro Asn Thr Gln Thr Ala Ser Pro Arg Ala Leu Ala Asp Ser Leu Met
                635                 640                 645

CAG CTG GCA CGA CAG GTT TCC CGA CTG GAA AGC GGG CAG TGAGGCTACC      1168
Gln Leu Ala Arg Gln Val Ser Arg Leu Glu Ser Gly Gln
            650                 655

CGATAAAAGC GGCTTCCTGA CAGGAGGCCG TTTTGTTTTG CAGCCCACTT AAG          1221

(2) INFORMATION FOR SEQ ID NO: 293:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO: 293:

Val Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
                20                  25                  30

Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
        50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
                100                 105                 110

Asn Leu Leu Ala Gln Arg Val Ser Gly Leu Ile Ile Asn Tyr Pro Leu
            115                 120                 125

Asp Asp Gln Asp Ala Ile Ala Val Glu Ala Ala Cys Thr Asn Val Pro
        130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175
```

```
Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
            245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
            325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

(2) INFORMATION FOR SEQ ID NO: 294:

(i) SEQUENCE CHARACTERISTICS:
        (A) LENGTH: 2380 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "synthetic vector"

(ix) FEATURE:
        (A) NAME/KEY: CDS
        (B) LOCATION:complement (51..707)
        (D) OTHER INFORMATION:/product= "cat resistance"

(xi) SEQUENCE DESCRIPTION: SEQ ID NO: 294:

GATCTAGCAC CAGGCGTTTA AGGGCACCAA TAACTGCCTT AAAAAAATTA CGCCCCGCCC      60

TGCCACTCAT CGCAGTACTG TTGTAATTCA TTAAGCATTC TGCCGACATG GAAGCCATCA    120

CAAACGGCAT GATGAACCTG AATCGCCAGC GGCATCAGCA CCTTGTCGCC TTGCGTATAA    180

TATTTGCCCA TAGTGAAAAC GGGGGCGAAG AAGTTGTCCA TATTGGCTAC GTTTAAATCA    240

AAACTGGTGA AACTCACCCA GGGATTGGCT GAGACGAAAA ACATATTCTC AATAAACCCT    300

TTAGGGAAAT AGGCCAGGTT TTCACCGTAA CACGCCACAT CTTGCGAATA TATGTGTAGA    360

AACTGCCGGA AATCGTCGTG GTATTCACTC CAGAGCGATG AAAACGTTTC AGTTTGCTCA    420

TGGAAAACGG TGTAACAAGG GTGAACACTA TCCCATATCA CCAGCTCACC GTCTTTCATT    480

GCCATACGGA ACTCCGGGTG AGCATTCATC AGGCGGGCAA GAATGTGAAT AAAGGCCGGA    540

TAAAACTTGT GCTTATTTTT CTTTACGGTC TTTAAAAAGG CCGTAATATC CAGCTGAACG    600

GTCTGGTTAT AGGTACATTG AGCAACTGAC TGAAATGCCT CAAAATGTTC TTTACGATGC    660

CATTGGGATA TATCAACGGT GGTATATCCA GTGATTTTTT CTCCATTTT AGCTTCCTTA    720
```

```
GCTCCTGAAA ATCTCGATAA CTCAAAAAAT ACGCCCGGTA GTGATCTTAT TTCATTATGG      780

TGAAAGTTGG AACCTCACCC GACGTCTAAT GTGAGTTAGC TCACTCATTA GGCACCCCAG      840

GCTTTACACT TTATGCTTCC GGCTCGTATG TTGTGTGGAA TTGTGAGCGG ATAACAATTT      900

CACACAGGAA ACAGCTATGA CCATGATTAC GAATTTCTAG ACCCCCCCCC CGCATGCCAT      960

AACTTCGTAT AATGTACGCT ATACGAAGTT ATAAGCTTGA CCTGTGAAGT GAAAAATGGC     1020

GCAGATTGTG CGACATTTTT TTTGTCTGCC GTTTAATTAA AGGGGGGGGG GGGCCGGCCT     1080

GGGGGGGGGT GTACATGAAA TTGTAAACGT TAATATTTTG TTAAAATTCG CGTTAAATTT     1140

TTGTTAAATC AGCTCATTTT TTAACCAATA GGCCGAAATC GGCAAAATCC CTTATAAATC     1200

AAAAGAATAG ACCGAGATAG GGTTGAGTGT TGTTCCAGTT TGGAACAAGA GTCCACTATT     1260

AAAGAACGTG GACTCCAACG TCAAAGGGCG AAAAACCGTC TATCAGGGCG ATGGCCCACT     1320

ACGAGAACCA TCACCCTAAT CAAGTTTTTT GGGGTCGAGG TGCCGTAAAG CACTAAATCG     1380

GAACCCTAAA GGGAGCCCCC GATTTAGAGC TTGACGGGGA AAGCCGGCGA ACGTGGCGAG     1440

AAAGGAAGGG AAGAAAGCGA AAGGAGCGGG CGCTAGGGCG CTGGCAAGTG TAGCGGTCAC     1500

GCTGCGCGTA ACCACCACAC CCGCCGCGCT TAATGCGCCG CTACAGGGCG CGTGCTAGCG     1560

GAGTGTATAC TGGCTTACTA TGTTGGCACT GATGAGGGTG TCAGTGAAGT GCTTCATGTG     1620

GCAGGAGAAA AAAGGCTGCA CCGGTGCGTC AGCAGAATAT GTGATACAGG ATATATTCCG     1680

CTTCCTCGCT CACTGACTCG CTACGCTCGG TCGTTCGACT GCGGCGAGCG GAAATGGCTT     1740

ACGAACGGGG CGGAGATTTC CTGGAAGATG CCAGGAAGAT ACTTAACAGG GAAGTGAGAG     1800

GGCCGCGGCA AAGCCGTTTT TCCATAGGCT CCGCCCCCCT GACAAGCATC ACGAAATCTG     1860

ACGCTCAAAT CAGTGGTGGC GAAACCCGAC AGGACTATAA AGATACCAGG CGTTTCCCCC     1920

TGGCGGCTCC CTCCTGCGCT CTCCTGTTCC TGCCTTTCGG TTTACCGGTG TCATTCCGCT     1980

GTTATGGCCG CGTTTGTCTC ATTCCACGCC TGACACTCAG TTCCGGGTAG GCAGTTCGCT     2040

CCAAGCTGGA CTGTATGCAC GAACCCCCCG TTCAGTCCGA CCGCTGCGCC TTATCCGGTA     2100

ACTATCGTCT TGAGTCCAAC CCGGAAAGAC ATGCAAAAGC ACCACTGGCA GCAGCCACTG     2160

GTAATTGATT TAGAGGAGTT AGTCTTGAAG TCATGCGCCG GTTAAGGCTA AACTGAAAGG     2220

ACAAGTTTTA GTGACTGCGC TCCTCCAAGC CAGTTACCTC GGTTCAAAGA GTTGGTAGCT     2280

CAGAGAACCT ACGAAAAACC GCCCTGCAAG GCGGTTTTTT CGTTTTCAGA GCAAGAGATT     2340

ACGCGCAGAC CAAAACGATC TCAAGAAGAT CATCTTATTA                          2380
```

(2) INFORMATION FOR SEQ ID NO: 295:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO: 295:

```
Met Glu Lys Lys Ile Thr Gly Tyr Thr Thr Val Asp Ile Ser Gln Trp
 1               5                  10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
            35                  40                  45

Lys Lys Asn Lys His Lys Phe Tyr Pro Ala Phe Ile His Ile Leu Ala
        50                  55                  60
```

```
Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

(2) INFORMATION FOR SEQ ID NO: 296:

(i) SEQUENCE CHARACTERISTICS:
        (A) LENGTH: 3488 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "synthetic vector"

(ix) FEATURE:
        (A) NAME/KEY: CDS
        (B) LOCATION:complement (1341..1997)
        (D) OTHER INFORMATION:/product= "cat resistance"

(ix) FEATURE:
        (A) NAME/KEY: CDS
        (B) LOCATION:complement (2521..3417)
        (D) OTHER INFORMATION:/product= "bla resistance"

(xi) SEQUENCE DESCRIPTION: SEQ ID NO: 296:

```
GTACATGAAA TTGTAAACGT TAATATTTTG TTAAAATTCG CGTTAAATTT TTGTTAAATC    60

AGCTCATTTT TTAACCAATA GGCCGAAATC GGCAAAATCC CTTATAAATC AAAAGAATAG   120

ACCGAGATAG GGTTGAGTGT TGTTCCAGTT TGGAACAAGA GTCCACTATT AAAGAACGTG   180

GACTCCAACG TCAAAGGGCG AAAAACCGTC TATCAGGGCG ATGGCCCACT ACGAGAACCA   240

TCACCCTAAT CAAGTTTTTT GGGGTCGAGG TGCCGTAAAG CACTAAATCG AACCCTAAA    300

GGGAGCCCCC GATTTAGAGC TTGACGGGGA AGCCGGCGA ACGTGGCGAG AAAGGAAGGG   360

AAGAAAGCGA AAGGAGCGGG CGCTAGGGCG CTGGCAAGTG TAGCGGTCAC GCTGCGCGTA   420

ACCACCACAC CCGCCGCGCT TAATGCGCCG CTACAGGGCG CGTGCTAGCG GAGTGTATAC   480

TGGCTTACTA TGTTGGCACT GATGAGGGTG TCAGTGAAGT GCTTCATGTG GCAGGAGAAA   540

AAAGGCTGCA CCGGTGCGTC AGCAGAATAT GTGATACAGG ATATATTCCG CTTCCTCGCT   600

CACTGACTCG CTACGCTCGG TCGTTCGACT GCGGCGAGCG GAAATGGCTT ACGAACGGGG   660

CGGAGATTTC CTGGAAGATG CCAGGAAGAT ACTTAACAGG GAAGTGAGAG GGCCGCGGCA   720
```

-continued

| | | | | | |
|---|---|---|---|---|---|
| AAGCCGTTTT | TCCATAGGCT | CCGCCCCCCT | GACAAGCATC | ACGAAATCTG | ACGCTCAAAT | 780 |
| CAGTGGTGGC | GAAACCCGAC | AGGACTATAA | AGATACCAGG | CGTTTCCCCC | TGGCGGCTCC | 840 |
| CTCCTGCGCT | CTCCTGTTCC | TGCCTTTCGG | TTTACCGGTG | TCATTCCGCT | GTTATGGCCG | 900 |
| CGTTTGTCTC | ATTCCACGCC | TGACACTCAG | TTCCGGGTAG | GCAGTTCGCT | CCAAGCTGGA | 960 |
| CTGTATGCAC | GAACCCCCCG | TTCAGTCCGA | CCGCTGCGCC | TTATCCGGTA | ACTATCGTCT | 1020 |
| TGAGTCCAAC | CCGGAAAGAC | ATGCAAAAGC | ACCACTGGCA | GCAGCCACTG | GTAATTGATT | 1080 |
| TAGAGGAGTT | AGTCTTGAAG | TCATGCGCCG | GTTAAGGCTA | AACTGAAAGG | ACAAGTTTTA | 1140 |
| GTGACTGCGC | TCCTCCAAGC | CAGTTACCTC | GGTTCAAAGA | GTTGGTAGCT | CAGAGAACCT | 1200 |
| ACGAAAAACC | GCCCTGCAAG | GCGGTTTTTT | CGTTTTCAGA | GCAAGAGATT | ACGCGCAGAC | 1260 |
| CAAAACGATC | TCAAGAAGAT | CATCTTATTA | GATCTAGCAC | CAGGCGTTTA | AGGGCACCAA | 1320 |
| TAACTGCCTT | AAAAAAATTA | CGCCCCGCCC | TGCCACTCAT | CGCAGTACTG | TTGTAATTCA | 1380 |
| TTAAGCATTC | TGCCGACATG | GAAGCCATCA | CAAACGGCAT | GATGAACCTG | AATCGCCAGC | 1440 |
| GGCATCAGCA | CCTTGTCGCC | TTGCGTATAA | TATTTGCCCA | TAGTGAAAAC | GGGGGCGAAG | 1500 |
| AAGTTGTCCA | TATTGGCTAC | GTTTAAATCA | AAACTGGTGA | AACTCACCCA | GGGATTGGCT | 1560 |
| GAGACGAAAA | ACATATTCTC | AATAAACCCT | TTAGGGAAAT | AGGCCAGGTT | TTCACCGTAA | 1620 |
| CACGCCACAT | CTTGCGAATA | TATGTGTAGA | AACTGCCGGA | AATCGTCGTG | GTATTCACTC | 1680 |
| CAGAGCGATG | AAAACGTTTC | AGTTTGCTCA | TGGAAAACGG | TGTAACAAGG | GTGAACACTA | 1740 |
| TCCCATATCA | CCAGCTCACC | GTCTTTCATT | GCCATACGGA | ACTCCGGGTG | AGCATTCATC | 1800 |
| AGGCGGGCAA | GAATGTGAAT | AAAGGCCGGA | TAAAACTTGT | GCTTATTTTT | CTTTACGGTC | 1860 |
| TTTAAAAAGG | CCGTAATATC | CAGCTGAACG | GTCTGGTTAT | AGGTACATTG | AGCAACTGAC | 1920 |
| TGAAATGCCT | CAAAATGTTC | TTTACGATGC | CATTGGGATA | TATCAACGGT | GGTATATCCA | 1980 |
| GTGATTTTTT | TCTCCATTTT | AGCTTCCTTA | GCTCCTGAAA | ATCTCGATAA | CTCAAAAAAT | 2040 |
| ACGCCCGGTA | GTGATCTTAT | TTCATTATGG | TGAAAGTTGG | AACCTCACCC | GACGTCTAAT | 2100 |
| GTGAGTTAGC | TCACTCATTA | GGCACCCCAG | GCTTTACACT | TTATGCTTCC | GGCTCGTATG | 2160 |
| TTGTGTGGAA | TTGTGAGCGG | ATAACAATTT | CACACAGGAA | ACAGCTATGA | CCATGATTAC | 2220 |
| GAATTTCTAG | ACCCCCCCCC | CGCATGCCAT | AACTTCGTAT | AATGTACGCT | ATACGAAGTT | 2280 |
| ATAAGCTTGA | CCTGTGAAGT | GAAAAATGGC | GCAGATTGTG | CGACATTTTT | TTTGTCTGCC | 2340 |
| GTTTAATTAA | GGGGGGGGGC | CGGCCATTAT | CAAAAAGGAT | CTCAAGAAGA | TCCTTTGATC | 2400 |
| TTTTCTACGG | GGTCTGACGC | TCAGTGGAAC | GAAAACTCAC | GTTAAGGGAT | TTTGGTCATG | 2460 |
| AGATTATCAA | AAAGGATCTT | CACCTAGATC | CTTTTAAATT | AAAAATGAAG | TTTTAAATCA | 2520 |
| ATCTAAAGTA | TATATGAGTA | AACTTGGTCT | GACAGTTACC | AATGCTTAA | TCAGTGAGGC | 2580 |
| ACCTATCTCA | GCGATCTGTC | TATTTCGTTC | ATCCATAGTT | GCCTGACTCC | CCGTCGTGTA | 2640 |
| GATAACTACG | ATACGGGAGG | GCTTACCATC | TGGCCCCAGT | GCTGCAATGA | TACCGCGAGA | 2700 |
| CCCACGCTCA | CCGGCTCCAG | ATTTATCAGC | AATAAACCAG | CCAGCCGGAA | GGGCCGAGCG | 2760 |
| CAGAAGTGGT | CCTGCAACTT | TATCCGCCTC | CATCCAGTCT | ATTAACTGTT | GCCGGGAAGC | 2820 |
| TAGAGTAAGT | AGTTCGCCAG | TTAATAGTTT | GCGCAACGTT | GTTGCCATTG | CTACAGGCAT | 2880 |
| CGTGGTGTCA | CGCTCGTCGT | TTGGTATGGC | TTCATTCAGC | TCCGGTTCCC | AACGATCAAG | 2940 |
| GCGAGTTACA | TGATCCCCCA | TGTTGTGCAA | AAAAGCGGTT | AGCTCCTTCG | GTCCTCCGAT | 3000 |
| CGTTGTCAGA | AGTAAGTTGG | CCGCAGTGTT | ATCACTCATG | GTTATGGCAG | CACTGCATAA | 3060 |
| TTCTCTTACT | GTCATGCCAT | CCGTAAGATG | CTTTTCTGTG | ACTGGTGAGT | ACTCAACCAA | 3120 |

```
GTCATTCTGA GAATAGTGTA TGCGGCGACC GAGTTGCTCT TGCCCGGCGT CAATACGGGA      3180

TAATACCGCG CCACATAGCA GAACTTTAAA AGTGCTCATC ATTGGAAAAC GTTCTTCGGG      3240

GCGAAAACTC TCAAGGATCT TACCGCTGTT GAGATCCAGT TCGATGTAAC CCACTCGCGC      3300

ACCCAACTGA TCCTCAGCAT CTTTTACTTT CACCAGCGTT TCTGGGTGAG CAAAAACAGG      3360

AAGGCAAAAT GCCGCAAAAA AGGGAATAAG GGCGACACGG AAATGTTGAA TACTCATACT      3420

CTTCCTTTTT CAATATTATT GAAGCATTTA TCAGGGTTAT TGTCTCATGA GCGGATACAT      3480

ATTTGAAT                                                              3488
```

(2) INFORMATION FOR SEQ ID NO: 297:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO: 297:

```
Met Glu Lys Lys Ile Thr Gly Tyr Thr Thr Val Asp Ile Ser Gln Trp
 1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

(2) INFORMATION FOR SEQ ID NO: 298:

(i) SEQUENCE CHARACTERISTICS:
        (A) LENGTH: 299 amino acids
        (B) TYPE: amino acid
        (D) TOPOLOGY: linear (ii) MOLECULE TYPE: protein -continued (xi) SEQUENCE DESCRIPTION: SEQ ID NO: 298:

| Met | Ser | Ile | Gln | His | Phe | Arg | Val | Ala | Leu | Ile | Pro | Phe | Phe | Ala | Ala |
| 1 | | | | 5 | | | | | 10 | | | | | 15 | |

| Phe | Cys | Leu | Pro | Val | Phe | Ala | His | Pro | Glu | Thr | Leu | Val | Lys | Val | Lys |
| | | | 20 | | | | | 25 | | | | | 30 | | |

| Asp | Ala | Glu | Asp | Gln | Leu | Gly | Ala | Arg | Val | Gly | Tyr | Ile | Glu | Leu | Asp |
| | | | 35 | | | | | 40 | | | | | 45 | | |

| Leu | Asn | Ser | Gly | Lys | Ile | Leu | Glu | Ser | Phe | Arg | Pro | Glu | Glu | Arg | Phe |
| | 50 | | | | | 55 | | | | | 60 | | | | |

| Pro | Met | Met | Ser | Thr | Phe | Lys | Val | Leu | Leu | Cys | Gly | Ala | Val | Leu | Ser |
| 65 | | | | | 70 | | | | | 75 | | | | | 80 |

| Arg | Ile | Asp | Ala | Gly | Gln | Glu | Gln | Leu | Gly | Arg | Arg | Ile | His | Tyr | Ser |
| | | | | 85 | | | | | 90 | | | | | 95 | |

| Gln | Asn | Asp | Leu | Val | Glu | Tyr | Ser | Pro | Val | Thr | Glu | Lys | His | Leu | Thr |
| | | | | 100 | | | | | 105 | | | | | 110 | |

| Asp | Gly | Met | Thr | Val | Arg | Glu | Leu | Cys | Ser | Ala | Ala | Ile | Thr | Met | Ser |
| | | | 115 | | | | | 120 | | | | | 125 | | |

| Asp | Asn | Thr | Ala | Ala | Asn | Leu | Leu | Leu | Thr | Thr | Ile | Gly | Gly | Pro | Lys |
| | 130 | | | | | 135 | | | | | 140 | | | | |

| Glu | Leu | Thr | Ala | Phe | Leu | His | Asn | Met | Gly | Asp | His | Val | Thr | Arg | Leu |
| 145 | | | | | 150 | | | | | 155 | | | | | 160 |

| Asp | Arg | Trp | Glu | Pro | Glu | Leu | Asn | Glu | Ala | Ile | Pro | Asn | Asp | Glu | Arg |
| | | | | 165 | | | | | 170 | | | | | 175 | |

| Asp | Thr | Thr | Met | Pro | Val | Ala | Met | Ala | Thr | Thr | Leu | Arg | Lys | Leu | Leu |
| | | | 180 | | | | | 185 | | | | | 190 | | |

| Thr | Gly | Glu | Leu | Leu | Thr | Leu | Ala | Ser | Arg | Gln | Gln | Leu | Ile | Asp | Trp |
| | | | 195 | | | | | 200 | | | | | 205 | | |

| Met | Glu | Ala | Asp | Lys | Val | Ala | Gly | Pro | Leu | Leu | Arg | Ser | Ala | Leu | Pro |
| 210 | | | | | 215 | | | | | 220 | | | | | |

| Ala | Gly | Trp | Phe | Ile | Ala | Asp | Lys | Ser | Gly | Ala | Gly | Glu | Arg | Gly | Ser |
| 225 | | | | | 230 | | | | | 235 | | | | | 240 |

| Arg | Gly | Ile | Ile | Ala | Ala | Leu | Gly | Pro | Asp | Gly | Lys | Pro | Ser | Arg | Ile |
| | | | | 245 | | | | | 250 | | | | | 255 | |

| Val | Val | Ile | Tyr | Thr | Thr | Gly | Ser | Gln | Ala | Thr | Met | Asp | Glu | Arg | Asn |
| | | | | 260 | | | | | 265 | | | | | 270 | |

| Arg | Gln | Ile | Ala | Glu | Ile | Gly | Ala | Ser | Leu | Ile | Lys | His | Trp | Val | Thr |
| | | 275 | | | | | 280 | | | | | 285 | | | |

| Val | Arg | Pro | Ser | Leu | Leu | Ile | Tyr | Thr | Leu | Asp | | | | | |
| | 290 | | | | | 295 | | | | | | | | | |

(2) INFORMATION FOR SEQ ID NO: 299:

(i) SEQUENCE CHARACTERISTICS:
        (A) LENGTH: 2728 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "synthetic vector"

(ix) FEATURE:
        (A) NAME/KEY: CDS
        (B) LOCATION:complement (471..1367)
        (D) OTHER INFORMATION:/product= "bla resistance"

(xi) SEQUENCE DESCRIPTION: SEQ ID NO: 299:

GATCTCATAA CTTCGTATAA TGTATGCTAT ACGAAGTTAT GACGTCTAAT GTGAGTTAGC    60

```
TCACTCATTA GGCACCCCAG GCTTTACACT TTATGCTTCC GGCTCGTATG TTGTGTGGAA    120

TTGTGAGCGG ATAACAATTT CACACAGGAA ACAGCTATGA CCATGATTAC GAATTTCTAG    180

ACCCCCCCCC CGCATGCCAT AACTTCGTAT AATGTACGCT ATACGAAGTT ATAAGCTTGA    240

CCTGTGAAGT GAAAAATGGC GCAGATTGTG CGACATTTTT TTTGTCTGCC GTTTAATTAA    300

GGGGGGGGGC CGGCCATTAT CAAAAAGGAT CTCAAGAAGA TCCTTTGATC TTTTCTACGG    360

GGTCTGACGC TCAGTGGAAC GAAAACTCAC GTTAAGGGAT TTTGGTCATG AGATTATCAA    420

AAAGGATCTT CACCTAGATC CTTTTAAATT AAAAATGAAG TTTTAAATCA ATCTAAAGTA    480

TATATGAGTA AACTTGGTCT GACAGTTACC CAATGCTTAA TCAGTGAGGC ACCTATCTCA    540

GCGATCTGTC TATTTCGTTC ATCCATAGTT GCCTGACTCC CCGTCGTGTA GATAACTACG    600

ATACGGGAGG GCTTACCATC TGGCCCCAGT GCTGCAATGA TACCGCGAGA CCCACGCTCA    660

CCGGCTCCAG ATTTATCAGC AATAAACCAG CCAGCCGGAA GGGCCGAGCG CAGAAGTGGT    720

CCTGCAACTT TATCCGCCTC CATCCAGTCT ATTAACTGTT GCCGGGAAGC TAGAGTAAGT    780

AGTTCGCCAG TTAATAGTTT GCGCAACGTT GTTGCCATTG CTACAGGCAT CGTGGTGTCA    840

CGCTCGTCGT TTGGTATGGC TTCATTCAGC TCCGGTTCCC AACGATCAAG GCGAGTTACA    900

TGATCCCCCA TGTTGTGCAA AAAAGCGGTT AGCTCCTTCG GTCCTCCGAT CGTTGTCAGA    960

AGTAAGTTGG CCGCAGTGTT ATCACTCATG GTTATGGCAG CACTGCATAA TTCTCTTACT   1020

GTCATGCCAT CCGTAAGATG CTTTTCTGTG ACTGGTGAGT ACTCAACCAA GTCATTCTGA   1080

GAATAGTGTA TGCGGCGACC GAGTTGCTCT TGCCCGGCGT CAATACGGGA TAATACCGCG   1140

CCACATAGCA GAACTTTAAA AGTGCTCATC ATTGGAAAAC GTTCTTCGGG GCGAAAACTC   1200

TCAAGGATCT TACCGCTGTT GAGATCCAGT TCGATGTAAC CCACTCGCGC ACCCAACTGA   1260

TCCTCAGCAT CTTTTACTTT CACCAGCGTT TCTGGGTGAG CAAAAACAGG AAGGCAAAAT   1320

GCCGCAAAAA AGGGAATAAG GGCGACACGG AAATGTTGAA TACTCATACT CTTCCTTTTT   1380

CAATATTATT GAAGCATTTA TCAGGGTTAT TGTCTCATGA GCGGATACAT ATTTGAATGT   1440

ACATGAAATT GTAAACGTTA ATATTTTGTT AAAATTCGCG TTAAATTTTT GTTAAATCAG   1500

CTCATTTTTT AACCAATAGG CCGAAATCGG CAAAATCCCT TATAAATCAA AGAATAGAC   1560

CGAGATAGGG TTGAGTGTTG TTCCAGTTTG GAACAAGAGT CCACTATTAA AGAACGTGGA   1620

CTCCAACGTC AAAGGGCGAA AAACCGTCTA TCAGGGCGAT GGCCCACTAC GAGAACCATC   1680

ACCCTAATCA AGTTTTTTGG GGTCGAGGTG CCGTAAAGCA CTAAATCGGA ACCCTAAAGG   1740

GAGCCCCCGA TTTAGAGCTT GACGGGGAAA GCCGGCGAAC GTGGCGAGAA AGGAAGGGAA   1800

GAAAGCGAAA GGAGCGGGCG CTAGGGCGCT GGCAAGTGTA GCGGTCACGC TGCGCGTAAC   1860

CACCACACCC GCCGCGCTTA ATGCGCCGCT ACAGGGCGCG TGCTAGCGGA GTGTATACTG   1920

GCTTACTATG TTGGCACTGA TGAGGGTGTC AGTGAAGTGC TTCATGTGGC AGGAGAAAAA   1980

AGGCTGCACC GGTGCGTCAG CAGAATATGT GATACAGGAT ATATTCCGCT TCCTCGCTCA   2040

CTGACTCGCT ACGCTCGGTC GTTCGACTGC GGCGAGCGGA AATGGCTTAC GAACGGGGCG   2100

GAGATTTCCT GGAAGATGCC AGGAAGATAC TTAACAGGGA AGTGAGAGGG CCGCGGCAAA   2160

GCCGTTTTTC CATAGGCTCC GCCCCCCTGA CAAGCATCAC GAAATCTGAC GCTCAAATCA   2220

GTGGTGGCGA AACCCGACAG GACTATAAAG ATACCAGGCG TTTCCCCCTG GCGGCTCCCT   2280

CCTGCGCTCT CCTGTTCCTG CCTTTCGGTT TACCGGTGTC ATTCCGCTGT TATGGCCGCG   2340

TTTGTCTCAT TCCACGCCTG ACACTCAGTT CCGGGTAGGC AGTTCGCTCC AAGCTGGACT   2400
```

```
GTATGCACGA ACCCCCCGTT CAGTCCGACC GCTGCGCCTT ATCCGGTAAC TATCGTCTTG    2460

AGTCCAACCC GGAAAGACAT GCAAAAGCAC CACTGGCAGC AGCCACTGGT AATTGATTTA    2520

GAGGAGTTAG TCTTGAAGTC ATGCGCCGGT TAAGGCTAAA CTGAAAGGAC AAGTTTTAGT    2580

GACTGCGCTC CTCCAAGCCA GTTACCTCGG TTCAAAGAGT TGGTAGCTCA GAGAACCTAC    2640

GAAAAACCGC CCTGCAAGGC GGTTTTTTCG TTTTCAGAGC AAGAGATTAC GCGCAGACCA    2700

AAACGATCTC AAGAAGATCA TCTTATTA                                       2728
```

(2) INFORMATION FOR SEQ ID NO: 300:

(i) SEQUENCE CHARACTERISTICS:
        (A) LENGTH: 299 amino acids
        (B) TYPE: amino acid
        (D) TOPOLOGY: linear (ii) MOLECULE TYPE: protein (xi) SEQUENCE DESCRIPTION: SEQ ID NO: 300:

```
Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285

Val Arg Pro Ser Leu Leu Ile Tyr Thr Leu Asp
    290                 295
```

```
        290             295

(2) INFORMATION FOR SEQ ID NO: 301:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 301:

TATGAGATCT CATAACTTCG TATAATGTAC GCTATACGAA GTTAT            45

(2) INFORMATION FOR SEQ ID NO: 302:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 302:

TAATAACTTC GTATAGCATA CATTATACGA AGTTATGAGA TCTCA             45

(2) INFORMATION FOR SEQ ID NO: 303:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 303:

CATTTTTTGC CCTCGTTATC TACGCATGCG ATAACTTCGT ATAGCGTACA TTATACGAAG    60

TTATTCTAGA CATGGTCATA GCTGTTTCCT G                           91

(2) INFORMATION FOR SEQ ID NO: 304:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 304:

GGGGGGAATT CGGTGGTGGT GGATCTGCGT GCGCTGAAAC GGTTGAAAGT TG     52

(2) INFORMATION FOR SEQ ID NO: 305:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"
```

(xi) SEQUENCE DESCRIPTION: SEQ ID NO: 305:

CCCCCCCAAG CTTATCAAGA CTCCTTATTA CG         32

(2) INFORMATION FOR SEQ ID NO: 306:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 306:

GGGGGGGGAA TTCGGAGGCG GTTCCGGTGG TGGC         34

(2) INFORMATION FOR SEQ ID NO: 307:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 307:

GGGGGGGGAA TTCGAGCAGA AGCTGATCTC TGAGGAGGAT CTGTAGGGTG GTGGCTCTGG         60

TTCCGGTGAT TTTG         74

(2) INFORMATION FOR SEQ ID NO: 308:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 308:

CCATAACTTC GTATAATGTA CGCTATACGA AGTTATA         37

(2) INFORMATION FOR SEQ ID NO: 309:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 309:

AGCTTATAAC TTCGTATAGC GTACATTATA CGAAGTTATG GCATG         45

(2) INFORMATION FOR SEQ ID NO: 310:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "synthetic oligonucleotide"

(xi) SEQUENCE DESCRIPTION: SEQ ID NO: 310:

AGCTTGACCT GTGAAGTGAA AAATGGCGCA GATTGTGCGA CATTTTTTTT GTCTGCCGTT    60

TAATTAAAGG GGGGGT    76

(2) INFORMATION FOR SEQ ID NO: 311:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 311:

GTACACCCCC CCCCAGGCCG GCCCCCCCCC CCCTTTAATT AAACGGCAGA CAAAAAAAT    60

GTCGCACAAT CTGCG    75

(2) INFORMATION FOR SEQ ID NO: 312:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 312:

GGGGGGGTGT ACATTCAAAT ATGTATCCGC TCATG    35

(2) INFORMATION FOR SEQ ID NO: 313:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 313:

GGGTTACATC GAACTGGATC TC    22

(2) INFORMATION FOR SEQ ID NO: 314:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 314:

CCAGTTCGAT GTAACCCACT CGCGCACCCA ACTGATCCTC AGCATCTTTT ACTTTCACC    59

(2) INFORMATION FOR SEQ ID NO: 315:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic oligonucleotide"

(xi) SEQUENCE DESCRIPTION: SEQ ID NO: 315:

ACTCTAGCTT CCCGGCAACA GTTAATAGAC TGGATGGAGG CGG                43

(2) INFORMATION FOR SEQ ID NO: 316:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 316:

CTGTTGCCGG GAAGCTAGAG TAAG                                    24

(2) INFORMATION FOR SEQ ID NO: 317:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 317:

CCCCCCCTTA ATTAAGGGGG GGGGCCGGCC ATTATCAAAA AGGATCTCAA GAAGATCC    58

(2) INFORMATION FOR SEQ ID NO: 318:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 318:

GGGGGGGGCT AGCACGCGCC CTGTAGCGGC GCATTAA                      37

(2) INFORMATION FOR SEQ ID NO: 319:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 319:

CCCCCCCTGT ACATGAAATT GTAAACGTTA ATATTTTG                     38

(2) INFORMATION FOR SEQ ID NO: 320:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 320:

GGGCGATGGC CCACTACGAG AACCATCACC CTAATC                                36

(2) INFORMATION FOR SEQ ID NO: 321:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 321:

GGGGGGAGAT CTAATAAGAT GATCTTCTTG AG                                    32

(2) INFORMATION FOR SEQ ID NO: 322:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 322:

GAGTTGGTAG CTCAGAGAAC CTACGAAAAA CCGCCCTGCA AGGCG                      45

(2) INFORMATION FOR SEQ ID NO: 323:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 323:

GTAGGTTCTC TGAGCTACCA ACTC                                             24

(2) INFORMATION FOR SEQ ID NO: 324:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 324:

GTTTCCCCCT GGCGGCTCCC TCCTGCGCTC TCCTGTTCCT GCC                        43

-continued (2) INFORMATION FOR SEQ ID NO: 325:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 325:

```
AGGAGGGAGC CGCCAGGGGG AAAC                                    24
```

(2) INFORMATION FOR SEQ ID NO: 326:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 326:

```
GACATCAGCG CTAGCGGAGT GTATAC                                  26
```

(2) INFORMATION FOR SEQ ID NO: 327:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 327:

```
GATCTCATAA CTTCGTATAA TGTATGCTAT ACGAAGTTAT TCA               43
```

(2) INFORMATION FOR SEQ ID NO: 328:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 328:

```
GATCTGAATA ACTTCGTATA GCATACATTA TACGAAGTTA TGAGA             45
```

(2) INFORMATION FOR SEQ ID NO: 329:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 329:

```
GGGGGGGAGA TCTGACCAAA ATCCCTTAAC GTGAG                        35
```

(2) INFORMATION FOR SEQ ID NO: 330:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 330:

GGTATCTGCG CTCTGCTGTA GCCAGTTACC TTCGG                35

(2) INFORMATION FOR SEQ ID NO: 331:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 331:

CCCCCCCGCT AGCCATGTGA GCAAAAGGCC AGCAA                35

(2) INFORMATION FOR SEQ ID NO: 332:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 332:

GGGACGTCGG GTGAGGTTCC AAC                             23

(2) INFORMATION FOR SEQ ID NO: 333:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 333:

CCATACGGAA CTCCGGGTGA GCATTCATC                       29

(2) INFORMATION FOR SEQ ID NO: 334:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 334:

CCGGAGTTCC GTATGG                                     16

(2) INFORMATION FOR SEQ ID NO: 335:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 335:

ACGTTTAAAT CAAAACTGG                                              19

(2) INFORMATION FOR SEQ ID NO: 336:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 336:

CCAGTTTTGA TTTAAACGTA GCCAATATGG ACAACTTCTT CGCCCCCGTT TTCACTATGG      60

GCAAATATT                                                              69

(2) INFORMATION FOR SEQ ID NO: 337:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 337:

GGAAGATCTA GCACCAGGCG TTTAAG                                    26

(2) INFORMATION FOR SEQ ID NO: 338:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 338:

GAGGCCGGCC ATCGAATGGC GCAAAAC                                  27

(2) INFORMATION FOR SEQ ID NO: 339:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 339:

CGCGTACCGT CCTCATGGGA GAAAATAATA C                                        31

(2) INFORMATION FOR SEQ ID NO: 340:

(i) SEQUENCE CHARACTERISTICS:
      (A) LENGTH: 83 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO: 340:

CCATGAGGAC GGTACGCGAC TGGGCGTGGA GCATCTGGTC GCATTGGGTC ACCAGCAAAT        60

CCGCTGTTAG CTGGCCCATT AAG                                                83

(2) INFORMATION FOR SEQ ID NO: 341:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO: 341:

GTCAGCGGCG GGATATAACA TGAGCTGTCC TCGGTATCGT CG                            42

(2) INFORMATION FOR SEQ ID NO: 342:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO: 342:

GTTATATCCC GCCGCTGACC ACCATCAAAC                                          30

(2) INFORMATION FOR SEQ ID NO: 343:

(i) SEQUENCE CHARACTERISTICS:
      (A) LENGTH: 65 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(ix) FEATURE:
      (A) NAME/KEY: conflict
      (B) LOCATION:replace(42..44, "")
      (D) OTHER INFORMATION:/note= "in Fig.35b, M41, LAC6: T4T;
        but see Fig.35a, M41: LAC6 pos.1055-1119 on complementary
        strand, 1076 to 1078: TAT"

(xi) SEQUENCE DESCRIPTION: SEQ ID NO: 343:

CATCAGTGAA TCGGCCAACG CGCGGGGAGA GGCGGTTTGC GTATTGGGAG CCAGGGTGGT        60

TTTTC                                                                    65

(2) INFORMATION FOR SEQ ID NO: 344:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 344:

```
GGTTAATTAA CCTCACTGCC CGCTTTCCAG TCGGGAAACC TGTCGTGCCA GCTGCATCAG      60

TGAATCGGCC AAC                                                        73
```

(2) INFORMATION FOR SEQ ID NO: 345:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 345:

```
CTAGACTAGT GTTTAAACCG GACCGGGGGG GGGCTTAAGG GGGGGGGGGG                 50
```

(2) INFORMATION FOR SEQ ID NO: 346:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 346:

```
CTAGCCCCCC CCCCCCTTAA GCCCCCCCCC GGTCCGGTTT AAACACTAGT                 50
```

(2) INFORMATION FOR SEQ ID NO: 347:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 347:

```
CTAGACTAGT GTTTAAACCG GACCGGGGGG GGGCTTAAGG GGGGGGGGGG                 50
```

(2) INFORMATION FOR SEQ ID NO: 348:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 348:

CCCCCCCTTA AGTGGGCTGC AAAACAAAAC GGCCTCCTGT CAGGAAGCCG CTTTTATCGG        60

GTAGCCTCAC TGCCCGCTTT CC        82

(2) INFORMATION FOR SEQ ID NO: 349:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 349:

GTTGTTGTGC CACGCGGTTA GGAATGTAAT TCAGCTCCGC        40

(2) INFORMATION FOR SEQ ID NO: 350:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 350:

AACCGCGTGG CACAACAAC        19

(2) INFORMATION FOR SEQ ID NO: 351:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 351:

CTTCGTTCTA CCATCGACAC GACCACGCTG GCACCCAGTT G        41

(2) INFORMATION FOR SEQ ID NO: 352:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 352:

GTGTCGATGG TAGAACGAAG        20

(2) INFORMATION FOR SEQ ID NO: 353:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "synthetic oligonucleotide"

(xi) SEQUENCE DESCRIPTION: SEQ ID NO: 353:

CCACAGCAAT AGCATCCTGG TCATCCAGCG GATAGTTAAT AATCAGCCCA CTGACACGTT      60

GCGCGAG      67

(2) INFORMATION FOR SEQ ID NO: 354:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 354:

GACCAGGATG CTATTGCTGT GG      22

(2) INFORMATION FOR SEQ ID NO: 355:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 355:

CAGCGCGATT TGCTGGTGGC CCAATGCGAC CAGATGC      37

(2) INFORMATION FOR SEQ ID NO: 356:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 356:

CACCAGCAAA TCGCGCTG      18

(2) INFORMATION FOR SEQ ID NO: 357:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 357:

CCCGGACTCG GTAATGGCAC GCATTGCGCC CAGCGCC      37

(2) INFORMATION FOR SEQ ID NO: 358:

(i) SEQUENCE CHARACTERISTICS:
        (A) LENGTH: 18 base pairs
        (B) TYPE: nucleic acid
        (C) STRANDEDNESS: single

```
            (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 358:

GCCATTACCG AGTCCGGG                                                       18

(2) INFORMATION FOR SEQ ID NO: 359:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 359:

AATTCCACCA TCATCACCAT TGACGTCTA                                           29

(2) INFORMATION FOR SEQ ID NO: 360:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 360:

AGCTTAGACG TCAATGGTGA TGATGGTGG                                           29

(2) INFORMATION FOR SEQ ID NO: 361:

(i) SEQUENCE CHARACTERISTICS:
        (A) LENGTH: 1289 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic gene cassette"

(ix) FEATURE:
        (A) NAME/KEY: CDS
        (B) LOCATION:complement (280..1137)
        (D) OTHER INFORMATION:/product= "bla resistance"

(xi) SEQUENCE DESCRIPTION: SEQ ID NO: 361:

CGCGTTAACC TCAGGTGACC AAGCCCCTGG CCAAGGTCCC GTACGTTCGA AGATTACCAT          60

CACGTGGATC CGGTACCAGG CCGGCCATTA TCAAAAAGGA TCTCAAGAAG ATCCTTTGAT         120

CTTTTCTACG GGGTCTGACG CTCAGTGGAA CGAAAACTCA CGTTAAGGGA TTTTGGTCAT         180

GAGATTATCA AAAAGGATCT TCACCTAGAT CCTTTTAAAT TAAAAATGAA GTTTTAAATC         240

AATCTAAAGT ATATATGAGT AAACTTGGTC TGACAGTTAC CAATGCTTAA TCAGTGAGGC         300

ACCTATCTCA GCGATCTGTC TATTTCGTTC ATCCATAGTT GCCTGACTCC CCGTCGTGTA         360

GATAACTACG ATACGGGAGG GCTTACCATC TGGCCCCAGT GCTGCAATGA TACCGCGAGA         420

CCCACGCTCA CCGGCTCCAG ATTTATCAGC AATAAACCAG CCAGCCGGAA GGGCCGAGCG         480

CAGAAGTGGT CCTGCAACTT TATCCGCCTC CATCCAGTCT ATTAACTGTT GCCGGGAAGC         540

TAGAGTAAGT AGTTCGCCAG TTAATAGTTT GCGCAACGTT GTTGCCATTG CTACAGGCAT         600
```

-continued

```
CGTGGTGTCA CGCTCGTCGT TTGGTATGGC TTCATTCAGC TCCGGTTCCC AACGATCAAG    660

GCGAGTTACA TGATCCCCCA TGTTGTGCAA AAAAGCGGTT AGCTCCTTCG GTCCTCCGAT    720

CGTTGTCAGA AGTAAGTTGG CCGCAGTGTT ATCACTCATG GTTATGGCAG CACTGCATAA    780

TTCTCTTACT GTCATGCCAT CCGTAAGATG CTTTTCTGTG ACTGGTGAGT ACTCAACCAA    840

GTCATTCTGA GAATAGTGTA TGCGGCGACC GAGTTGCTCT TGCCCGGCGT CAATACGGGA    900

TAATACCGCG CCACATAGCA GAACTTTAAA AGTGCTCATC ATTGGAAAAC GTTCTTCGGG    960

GCGAAAACTC TCAAGGATCT TACCGCTGTT GAGATCCAGT TCGATGTAAC CCACTCGTGC   1020

ACCCAACTGA TCTTCAGCAT CTTTTACTTT CACCAGCGTT TCTGGGTGAG CAAAAACAGG   1080

AAGGCAAAAT GCCGCAAAAA AGGGAATAAG GGCGACACGG AAATGTTGAA TACTCATACT   1140

CTTCCTTTTT CAATATTATT GAAGCATTTA TCAGGGTTAT TGTCTCATGA GCGGATACAT   1200

ATTTGAATGT ACTCGGCCGC ACGAGCTGCA GGCGCCATTA ATGGCTCGAG CGCGCTTCAG   1260

CGCTTTGTCT TCCGGATGTA CATGAAATT                                    1289
```

(2) INFORMATION FOR SEQ ID NO: 362:

(i) SEQUENCE CHARACTERISTICS:
        (A) LENGTH: 286 amino acids
        (B) TYPE: amino acid
        (D) TOPOLOGY: linear (ii) MOLECULE TYPE: protein (xi) SEQUENCE DESCRIPTION: SEQ ID NO: 362:

```
Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220
```

```
Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
            275                 280                 285
```

(2) INFORMATION FOR SEQ ID NO: 363:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 363:

```
GCCCTGCAAG CGGAAGAC                                                    18
```

(2) INFORMATION FOR SEQ ID NO: 364:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 364:

```
GGCTTTCGAA TGGCCAAAGG                                                  20
```

(2) INFORMATION FOR SEQ ID NO: 365:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
        (A) NAME/KEY: misc_feature
        (B) LOCATION:25..27
        (D) OTHER INFORMATION:/product= "random codon by
            trinucleotide mutagenesis (ACT/GTT)"

(ix) FEATURE:
        (A) NAME/KEY: misc_feature
        (B) LOCATION:37..39
        (D) OTHER INFORMATION:/product= "random codon by
            trinucleotides (TTT,CAT,CTT,ATG,CAG)"

(ix) FEATURE:
        (A) NAME/KEY: misc_feature
        (B) LOCATION:43..45
        (D) OTHER INFORMATION:/product= "random codon by
            trinucleotides (18 codons, no Pro, no Cys)"

(ix) FEATURE:
        (A) NAME/KEY: misc_feature
        (B) LOCATION:46..48
        (D) OTHER INFORMATION:/product= "random codon by
            trinucleotides (GAT, GGT, AAT, TCT, TAT)"

```
    (ix) FEATURE:
        (A) NAME/KEY: misc_feature
        (B) LOCATION:49..51
        (D) OTHER INFORMATION:/product= "random codon by
            trinucleotides (GAT, GGT, AAT, TCT)"

(ix) FEATURE:
        (A) NAME/KEY: misc_feature
        (B) LOCATION:52..54
        (D) OTHER INFORMATION:/product= "random codon by
            trinucleotide mutagenesis (19aa, no Cys)"

(ix) FEATURE:
        (A) NAME/KEY: misc_feature
        (B) LOCATION:55..57
        (D) OTHER INFORMATION:/product= "random codon by
            trinucleotides (CCT/TCT)"

(ix) FEATURE:
        (A) NAME/KEY: misc_feature
        (B) LOCATION:58..60
        (D) OTHER INFORMATION:/product= "random codon by
            trinucleotide mutagenesis (19 aa, no Cys)"

(xi) SEQUENCE DESCRIPTION: SEQ ID NO: 365:

GCCCTGCAAG CGGAAGACTT TGCGRYTTAT TATTGCHWKC AGNNKDVTDV TNNKYCTNNK    60

ACCTTTGGCC ATTCGAAAGC C                                              81

(2) INFORMATION FOR SEQ ID NO: 366:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
        (A) NAME/KEY: misc_feature
        (B) LOCATION:37..39
        (D) OTHER INFORMATION:/product= "random codon by
            trinucleotides (TTT,CAT,CTT,ATG,CAG)"

(ix) FEATURE:
        (A) NAME/KEY: misc_feature
        (B) LOCATION:43..45
        (D) OTHER INFORMATION:/product= "random codon by
            trinucleotides (18 codons, no Pro, no Cys)"

(ix) FEATURE:
        (A) NAME/KEY: misc_feature
        (B) LOCATION:46..48
        (D) OTHER INFORMATION:/product= "random codon by
            trinucleotides (GAT, GGT, AAT, TCT, TAT)"

(ix) FEATURE:
        (A) NAME/KEY: misc_feature
        (B) LOCATION:49..51
        (D) OTHER INFORMATION:/product= "random codon by
            trinucleotides (GAT, GGT, AAT, TCT)"

(ix) FEATURE:
        (A) NAME/KEY: misc_feature
        (B) LOCATION:52..54
        (D) OTHER INFORMATION:/product= "random codon by
            trinucleotide mutagenesis (19aa, no Cys)"

(ix) FEATURE:
        (A) NAME/KEY: misc_feature
        (B) LOCATION:55..57
        (D) OTHER INFORMATION:/product= "random codon by
            trinucleotides (CCT/TCT)"

(ix) FEATURE:
```

(A) NAME/KEY: misc_feature
            (B) LOCATION:58..60
            (D) OTHER INFORMATION:/product= "random codon by
                trinucleotide mutagenesis (19 aa, no Cys)"

(xi) SEQUENCE DESCRIPTION: SEQ ID NO: 366:

GCCCTGCAAG CGGAAGACGT GGGCGTGTAT TATTGCHWKC AGNNKDVTDV TNNKYCTNNK      60

ACCTTTGGCC ATTCGAAAGC C                                                81

(2) INFORMATION FOR SEQ ID NO: 367:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide (ix) FEATURE:
            (A) NAME/KEY: misc_feature
            (B) LOCATION:37..39
            (D) OTHER INFORMATION:/product= "random codon by
                trinucleotides (TTT,CAT,CTT,ATG,CAG)"

(ix) FEATURE:
            (A) NAME/KEY: misc_feature
            (B) LOCATION:43..45
            (D) OTHER INFORMATION:/product= "random codon by
                trinucleotides (18 codons, no Pro, no Cys)"

(ix) FEATURE:
            (A) NAME/KEY: misc_feature
            (B) LOCATION:46..48
            (D) OTHER INFORMATION:/product= "random codon by
                trinucleotides (GAT, GGT, AAT, TCT, TAT)"

(ix) FEATURE:
            (A) NAME/KEY: misc_feature
            (B) LOCATION:49..51
            (D) OTHER INFORMATION:/product= "random codon by
                trinucleotides (GAT, GGT, AAT, TCT)"

(ix) FEATURE:
            (A) NAME/KEY: misc_feature
            (B) LOCATION:52..54
            (D) OTHER INFORMATION:/product= "random codon by
                trinucleotide mutagenesis (19aa, no Cys)"

(ix) FEATURE:
            (A) NAME/KEY: misc_feature
            (B) LOCATION:55..57
            (D) OTHER INFORMATION:/product= "random codon by
                trinucleotides (CCT/TCT)"

(ix) FEATURE:
            (A) NAME/KEY: misc_feature
            (B) LOCATION:58..60
            (D) OTHER INFORMATION:/product= "random codon by
                trinucleotide mutagenesis (19 aa, no Cys)"

(xi) SEQUENCE DESCRIPTION: SEQ ID NO: 367:

GCCCTGCAAG CGGAAGACGT GGCGGTGTAT TATTGCHWKC AGNNKDVTDV TNNKYCTNNK      60

ACCTTTGGCC ATTCGAAAGC C                                                81

(2) INFORMATION FOR SEQ ID NO: 368:

(i) SEQUENCE CHARACTERISTICS:
            (A) LENGTH: 108 base pairs
            (B) TYPE: nucleic acid
            (C) STRANDEDNESS: single
            (D) TOPOLOGY: linear (ii) MOLECULE TYPE: other nucleic acid
    (A) DESCRIPTION: /desc = "synthetic oligonucleotide (ix) FEATURE:
    (A) NAME/KEY: misc_feature
    (B) LOCATION:41..43
    (D) OTHER INFORMATION:/product= "random codon by
         trinucleotides (CGT, TGG, TAT)"

(ix) FEATURE:
    (A) NAME/KEY: misc_feature
    (B) LOCATION:47..61
    (D) OTHER INFORMATION:/product= "random codons by
         trinucleotides (18 aa, no Trp, no Cys)"

(ix) FEATURE:
    (A) NAME/KEY: misc_feature
    (B) LOCATION:62..64
    (D) OTHER INFORMATION:/product= "random codon by
         trinucleotide mutagenesis (19aa, no Cys)"

(xi) SEQUENCE DESCRIPTION: SEQ ID NO: 368:

CCTGCAAGCG GAAGACGAAG CGGATTATTA TTGCCAGAGC YRKGACNNKN NKNNKNNKNN      60

KNNKGGCGGC GGCACGAAGT TAACCGTTCT TGGCCAGGAA TTCGAGCC                 108

(2) INFORMATION FOR SEQ ID NO: 369:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
        (A) NAME/KEY: misc_feature
        (B) LOCATION:41..43
        (D) OTHER INFORMATION:/product= "random codon by
             trinucleotides (CGT, TGG, TAT)"

(ix) FEATURE:
        (A) NAME/KEY: misc_feature
        (B) LOCATION:47..58
        (D) OTHER INFORMATION:/product= "random codons by
             trinucleotides (18 aa, no Trp, no Cys)"

(ix) FEATURE:
        (A) NAME/KEY: misc_feature
        (B) LOCATION:59..61
        (D) OTHER INFORMATION:/product= "random codon by
             trinucleotide mutagenesis (19aa, no Cys)"

(xi) SEQUENCE DESCRIPTION: SEQ ID NO: 369:

CCTGCAAGCG GAAGACGAAG CGGATTATTA TTGCCAGAGC YRKGACNNKN NKNNKNNKNN      60

KGGCGGCGGC ACGAAGTTAA CCGTTCTTGG CCAGGAATTC GAGCC                    105

(2) INFORMATION FOR SEQ ID NO: 370:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide (ix) FEATURE:
        (A) NAME/KEY: misc_feature
        (B) LOCATION:41..43

(D) OTHER INFORMATION:/product= "random codon by
            trinucleotides (CGT, TGG, TAT)"

(ix) FEATURE:
        (A) NAME/KEY: misc_feature
        (B) LOCATION:47..55
        (D) OTHER INFORMATION:/product= "random codons by
            trinucleotides (18 aa, no Trp, no Cys)"

(ix) FEATURE:
        (A) NAME/KEY: misc_feature
        (B) LOCATION:56..58
        (D) OTHER INFORMATION:/product= "random codon by
            trinucleotide mutagenesis (19aa, no Cys)"

(xi) SEQUENCE DESCRIPTION: SEQ ID NO: 370:

CCTGCAAGCG GAAGACGAAG CGGATTATTA TTGCCAGAGC YRKGACNNKN NKNNKNNKGG         60

CGGCGGCACG AAGTTAACCG TTCTTGGCCA GGAATTCGAG CC                           102

(2) INFORMATION FOR SEQ ID NO: 371:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO: 371:

GGCTCGAATT CCTGGCC                                                       17

(2) INFORMATION FOR SEQ ID NO: 372:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO: 372:

Gly Gly Gly Ser Gly Ser Gly Asp Phe Asp Tyr Glu Lys Met Ala Asn
 1               5                  10                  15

Ala Asn Lys Gly Ala Met Thr Glu Asn Ala Asp Glu Asn Ala Leu Gln
            20                  25                  30

Ser Asp Ala Lys Gly Lys Leu Asp Ser Val Ala Thr Asp Tyr Gly Ala
        35                  40                  45

Ala Ile Asp Gly Phe Ile Gly Asp Val Ser Gly Leu Ala Asn Gly Asn
    50                  55                  60

Gly Ala Thr Gly Asp Phe Ala Gly Ser Asn Ser Gln Met Ala Gln Val
65                  70                  75                  80

Gly Asp Gly Asp Asn Ser Pro Leu Met Asn Asn Phe Arg Gln Tyr Leu
                85                  90                  95

Pro Ser Leu Pro Gln Ser Val Glu Cys Arg Pro Phe Val Phe Gly Ala
            100                 105                 110

Gly Lys Pro Tyr Glu Phe Ser Ile Asp Cys Asp Lys Ile Asn Leu Phe
        115                 120                 125

Arg Gly Val Phe Ala Phe Leu Leu Tyr Val Ala Thr Phe Met Tyr Val
    130                 135                 140

Phe Ser Thr Phe Ala Asn Ile Leu Arg Asn Lys Glu Ser
145                 150                 155

-continued (2) INFORMATION FOR SEQ ID NO: 373:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO: 373:

```
Gly Gly Gly Ser Gly Ser Gly Asp Phe Asp Tyr Glu Lys Met Ala Asn
 1               5                  10                  15

Ala Asn Lys Gly Ala Met Thr Glu Asn Ala Asp Glu Asn Ala Leu Gln
            20                  25                  30

Ser Asp Ala Lys Gly Lys Leu Asp Ser Val Ala Thr Asp Tyr Gly Ala
            35                  40                  45

Ala Ile Asp Gly Phe Ile Gly Asp Val Ser Gly Leu Ala Asn Gly Asn
        50                  55                  60

Gly Ala Thr Gly Asp Phe Ala Gly Ser Asn Ser Gln Met Ala Gln Val
65                  70                  75                  80

Gly Asp Gly Asp Asn Ser Pro Leu Met Asn Asn Phe Arg Gln Tyr Leu
                85                  90                  95

Pro Ser Leu Pro Gln Ser Val Glu Cys Arg Pro Phe Val Phe Gly Ala
            100                 105                 110

Gly Lys Pro Tyr Glu Phe Ser Ile Asp Cys Asp Lys Ile Asn Leu Phe
            115                 120                 125

Arg Gly Val Phe Ala Phe Leu Leu Tyr Val Ala Thr Phe Met Tyr Val
            130                 135                 140

Phe Ser Thr Phe Ala Asn Ile Leu Arg Asn Lys Glu Ser
145                 150                 155
```

What is claimed is:

1. An immunoglobulin polypepide comprising four amino acid consensus framework sub-elements and having interspaced complementarity determining region (CDR) sub-elements, wherein said polypeptide is produced by the steps of: (i) aligning a plurality of known human immunoglobulin sequences; (ii) identifying the conserved framework sub-elements of said known and ligned human immunoglobulin sequences; (iii) comparing amino acids at each corresponding position of said conserved framework sub-elements; (iv) deducing consensus sequences for the framework sub-elements based on said comparing step (iii); (v) synthesizing a nucleic acid molecule capable of encoding said polypeptide, wherein said nucleic acid molecule comprises DNA cleavage sites at the boundary between each consensus framework sub-element and CDR sub-elements; and (vi) allowing the expression of said synthesized DNA molecule as said immunoglobulin polypeptide.

2. A collection of (poly)peptides comprising a plurality of (poly)peptides wherein each member of said plurality is a polypeptide according to claim 1.

3. A colectlion of (poly)peptides according to claim 2, comprising specific (poly)peptides wherein the genes encoding said specific (poly)peptides
    (a) are either homologous, or represent consensus gene sequences derived from at least three homologous genes, and
    (b) wherein said cleavage sites are unique within each gene sequence,
    (bb) do not form compatible sites with respect to any single sub-sequence, and
    (bc) are common to all homologous sub-sequences.

4. A kit comprising a collection of nucleic acids that ncode a collection of (poly)peptides according to claim 3 and suitable host cells therefor.

5. A kit comprising a nucleic acid that encodes a (poly) peptide according to claim 1 and a suitable host cell therefor.

6. A kit comprising a plurality of nucleic acids wherein each member of said plurality is a nucleic acid that encodes a polypeptide according to claim 1 and suitable host cells therefor.

7. The Immunoglobulin polypeptide according to claim 1, wherein said plurality of known human immunoglobulin sequences are human Vκ immunoglobulin sequences.

8. The immunoglobulin polypeptide according to claim 1, wherein said plurality of known human immunoglobulin sequences are human Vλ immunoglobulin sequences.

9. The immunoglobulin polypeptide according to claim 1, wherein said plurality of known human immunoglobulin sequences are human VH immunoglobulin sequences.

10. A synthetic antibody molecule comprising a variable heavy chain polypeptide sequence and a variable light chain polypeptide sequence, wherein each of said variable polypeptide sequences comprise four framework regions and three complementarity determining regions, wherein the four framework regions of said variable heavy chain comprise the corresponding framework regions of a sequence selected from the group consisting of VH1A (SEQ ID NO:57), VH1B (SEQ ID NO:59), VH2 (SEQ ID NO:61), VH3 (SEQ ID NO:63), VH4 (SEQ ID NO:65), VH5 (SEQ ID NO:67), and VH6 (SEQ ID NO:69), and wherein the four framework regions of said variable light chain comprise the corresponding framework regions of a sequence selected from the group consisting of Vκ1 (SEQ I NO: 43), Vκ2 (SEQ ID NO: 45), Vκ3 (SEQ ID NO: 47), Vκ4 (SEQ ID NO: 49), Vλ1 (SEQ ID NO: 51), Vλ2 (SEQ ID NO: 53), and Vλ3 (SEQ ID NO: 55).

11. The synthetic antibody molecule according to claim 10, wherein the four framework regions of said variable heavy chain comprise the corresponding framework regions of VH1A (SEQ ID NO:57), and wherein the four framework regions of said variable light chain comprise the corresponding framework regions of Vκ1 (SEQ ID NO: 43).

12. The synthetic antibody molecule according to claim 10, wherein the four framework regions of said variable heavy chain comprise the corresponding framework regions of VH1A (SEQ ID NO:57), and wherein the four framework regions of said variable light chain comprise the corresponding framework regions of Vκ2 (SEQ ID NO: 45).

13. The synthetic antibody molecule according to claim 10, wherein the four framework regions of said variable heavy chain comprise the corresponding framework regions of VH1A (SEQ ID NO:57), and wherein the four framework regions of said variable light chain comprise the corresponding framework regions of Vκ3 (SEQ ID NO: 47).

14. The synthetic antibody molecule according to claim 10, wherein the four framework regions of said variable heavy chain comprise the corresponding framework regions of VH1A (SEQ ID NO:57), and wherein the four framework regions of said variable light chain comprise the corresponding framework regions of Vκ4 (SEQ ID NO: 49).

15. The synthetic antibody molecule according to claim 10, wherein the four framework regions of said variable heavy chain comprise the corresponding framework regions of VH1A (SEQ ID NO:57), and wherein the four framework regions of said variable light chain comprise the corresponding framework regions of Vλ1 (SEQ ID NO: 51).

16. The synthetic antibody molecule according to claim 10, wherein the four framework regions of said variable heavy chain comprise the corresponding framework regions of VH1A (SEQ ID NO:57), and wherein the four framework regions of said variable light chain comprise the corresponding framework regions of Vλ2 (SEQ ID NO: 53).

17. The synthetic antibody molecule according to claim 10, wherein the four framework regions of said variable heavy chain comprise the corresponding framework regions of VH1A (SEQ ID NO:57), and wherein the four framework regions of said variable light chain comprise the corresponding framework regions of Vλ3 (SEQ ID NO: 55).

18. The synthetic antibody molecule according to claim 10, wherein the four framework regions of said variable heavy chain comprise the corresponding framework regions of VH1A (SEQ ID NO:59), and wherein the four framework regions of said variable light chain comprise the corresponding framework regions of Vκ1 (SEQ ID NO: 43).

19. The synthetic antibody molecule according to claim 10, wherein the four framework regions of said variable heavy chain comprise the corresponding framework regions of VH1B (SEQ ID NO:59), and wherein the four framework regions of said variable light chain comprise the corresponding framework regions of Vκ2 (SEQ ID NO: 45).

20. The synthetic antibody molecule according to claim 10, wherein the four framework regions of said variable heavy chain comprise the corresponding framework regions of VH1B (SEQ ID NO:59), and wherein the four framework regions of said variable light chain comprise the corresponding framework regions of Vκ3 (SEQ ID NO: 47).

21. The synthetic antibody molecule according to claim 10, wherein the four framework regions of said variable heavy chain comprise the corresponding framework regions of VH1B (SEQ ID NO:59), and wherein the four framework regions of said variable light chain comprise the corresponding framework regions of Vκ4 (SEQ ID NO: 49).

22. The synthetic antibody molecule according to claim 10, wherein the four framework regions of said variable heavy chain comprise the corresponding framework regions of VH1B (SEQ ID NO:59), and wherein the four framework regions of said variable light chain comprise the corresponding framework regions of Vλ1 (SEQ ID NO: 51).

23. The synthetic antibody molecule according to claim 10, wherein the four framework regions of said variable heavy chain comprise the corresponding framework regions of VH1B (SEQ ID NO:59), and wherein the four framework regions of said variable light chain comprise the corresponding framework regions of Vλ2 (SEQ ID NO: 53).

24. The synthetic antibody molecule according to claim 10, wherein the four framework regions of said variable heavy chain comprise the corresponding framework regions of VH1B (SEQ ID NO:59), and wherein the four framework regions of said variable light chain comprise the corresponding framework regions of Vλ3 (SEQ ID NO: 55).

25. The synthetic antibody molecule according to claim 10, wherein the four framework regions of said variable heavy chain comprise the corresponding framework regions of VH2 (SEQ ID NO:61), and wherein the four framework regions of said variable light chain comprise the corresponding framework regions of Vκ1 (SEQ ID NO: 43).

26. The synthetic antibody molecule according to claim 10, wherein the four framework regions of said variable heavy chain comprise the corresponding framework regions of VH2 (SEQ ID NO:61), and wherein the four framework regions of said variable light chain comprise the corresponding framework regions of Vκ2 (SEQ ID NO: 45).

27. The synthetic antibody molecule according to claim 10, wherein the four framework regions of said variable heavy chain comprise the corresponding framework regions of VH2 (SEQ ID NO:61), and wherein the four framework regions of said variable light chain comprise the corresponding framework regions of Vκ3 (SEQ ID NO: 47).

28. The synthetic antibody molecule according to claim 10, wherein the four framework regions of said variable heavy chain comprise the corresponding framework regions of VH2 (SEQ ID NO:61), and wherein the four framework regions of said variable light chain comprise the corresponding framework regions of Vκ4 (SEQ ID NO: 49).

29. The synthetic antibody molecule according to claim 10, wherein the four framework regions of said variable heavy chain comprise the corresponding framework regions of VH2 (SEQ ID NO:61), and wherein the four framework regions of said variable light chain comprise the corresponding framework regions of Vλ1 (SEQ ID NO: 51).

30. The synthetic antibody molecule according to claim 10, wherein the four framework regions of said variable heavy chain comprise the corresponding framework regions of VH2 (SEQ ID NO:61), and wherein the four framework regions of said variable light chain comprise the corresponding framework regions of Vλ2 (SEQ ID NO: 53).

31. The synthetic antibody molecule according to claim 10, wherein the four framework regions of said variable heavy chain comprise the corresponding framework regions of VH2 (SEQ ID NO:61), and wherein the four framework regions of said variable light chain comprise the corresponding framework regions of Vλ3 (SEQ ID NO: 55).

32. The synthetic antibody molecule according to claim 10, wherein the four framework regions of said variable heavy chain comprise the corresponding framework regions of VH3 (SEQ ID NO:63), and wherein the four framework regions of said variable light chain comprise the corresponding framework regions of Vκ1 (SEQ ID NO: 43).

33. The synthetic antibody molecule according to claim 10, wherein the four framework regions of said variable heavy chain comprise the corresponding framework regions of VH3 (SEQ ID NO:63), and wherein the four framework regions of said variable light chain comprise the corresponding framework regions of Vκ2 (SEQ ID NO: 45).

34. The synthetic antibody molecule according to claim 10, wherein the four framework regions of said variable heavy chain comprise the corresponding framework regions of VH3 (SEQ ID NO:63), and wherein the four framework regions of said variable light chain comprise the corresponding framework regions of Vκ3 (SEQ ID NO: 47).

35. The synthetic antibody molecule according to claim 10, wherein the four framework regions of said variable heavy chain comprise the corresponding framework regions of VH3 (SEQ ID NO:63), and wherein the four framework regions of said variable light chain comprise the corresponding framework regions of Vκ4 (SEQ ID NO: 49).

36. The synthetic antibody molecule according to claim 10, wherein the four framework regions of said variable heavy chain comprise the corresponding framework regions of VH3 (SEQ ID NO:63), and wherein the four framework regions of said variable light chain comprise the corresponding framework regions of Vλ1 (SEQ ID NO: 51).

37. The synthetic antibody molecule according to claim 10, wherein the four framework regions of said variable heavy chain comprise the corresponding framework regions of VH3 (SEQ ID NO:63), and wherein the four framework regions of said variable light chain comprise the corresponding framework regions of Vλ2 (SEQ ID NO: 53).

38. The synthetic antibody molecule according to claim 10, wherein the four framework regions of said variable heavy chain comprise the corresponding framework regions of VH3 (SEQ ID NO:63), and wherein the four framework regions of said variable light chain comprise the corresponding framework regions of Vλ3 (SEQ ID NO: 55).

39. The synthetic antibody molecule according to claim 10, wherein the four framework regions of said variable heavy chain comprise the corresponding framework regions of VH4 (SEQ ID NO:65), and wherein the four framework regions of said variable light chain comprise the corresponding framework regions of Vκ1 (SEQ ID NO: 43).

40. The synthetic antibody molecule according to claim 10, wherein the four framework regions of said variable heavy chain comprise the corresponding framework regions of VH4 (SEQ ID NO:65), and wherein the four framework regions of said variable light chain comprise the corresponding framework regions of Vκ2 (SEQ ID NO: 45).

41. The synthetic antibody molecule according to claim 10, wherein the four framework regions of said variable heavy chain comprise the corresponding framework regions of VH4 (SEQ ID NO:65), and wherein the four framework regions of said variable light chain comprise the corresponding framework regions of Vκ3 (SEQ ID NO: 47).

42. The synthetic antibody molecule according to claim 10, wherein the four framework regions of said variable heavy chain comprise the corresponding framework regions of VH4 (SEQ ID NO:65), and wherein the four framework regions of said variable light chain comprise the corresponding framework regions of Vκ4 (SEQ ID NO: 49).

43. The synthetic antibody molecule according to claim 10, wherein the four framework regions of said variable heavy chain comprise the corresponding framework regions of VH4 (SEQ ID NO:65), and wherein the four framework regions of said variable light chain comprise the corresponding framework regions of Vλ1 (SEQ ID NO: 51).

44. The synthetic antibody molecule according to claim 10, wherein the four framework regions of said variable heavy chain comprise the corresponding framework regions of VH4 (SEQ ID NO:65), and wherein the four framework regions of said variable light chain comprise the corresponding framework regions of Vλ2 (SEQ ID NO: 53).

45. The synthetic antibody molecule according to claim 10, wherein the four framework regions of said variable heavy chain comprise the corresponding framework regions of VH4 (SEQ ID NO:65), and wherein the four framework regions of said variable light chain comprise the corresponding framework regions of Vλ3 (SEQ ID NO: 55).

46. The synthetic antibody molecule according to claim 10, wherein the four framework regions of said variable heavy chain comprise the corresponding framework regions of VH5 (SEQ ID NO:67), and wherein the four framework regions of said variable light chain comprise the corresponding framework regions of Vκ1 (SEQ ID NO: 43).

47. The synthetic antibody molecule according to claim 10, wherein the four framework regions of said variable heavy chain comprise the corresponding framework regions of VH5 (SEQ ID NO:67), and wherein the four framework regions of said variable light chain comprise the corresponding framework regions of Vκ2 (SEQ ID NO: 45).

48. The synthetic antibody molecule according to claim 10, wherein the four framework regions of said variable heavy chain comprise the corresponding framework regions of VH5 (SEQ ID NO:67), and wherein the four framework regions of said variable light chain comprise the corresponding framework regions of Vκ3 (SEQ ID NO: 47).

49. The synthetic antibody molecule according to claim 10, wherein the four framework regions of said variable heavy chain comprise the corresponding framework regions of VH5 (SEQ ID NO:67), and wherein the four framework regions of said variable light chain comprise the corresponding framework regions of Vκ4 (SEQ ID NO: 49).

50. The synthetic antibody molecule according to claim 10, wherein the four framework regions of said variable heavy chain comprise the corresponding framework regions of VH5 (SEQ ID NO:67), and wherein the four framework regions of said variable light chain comprise the corresponding framework regions of Vλ1 (SEQ ID NO: 51).

51. The synthetic antibody molecule according to claim 10, wherein the four framework regions of said variable heavy chain comprise the corresponding framework regions of VH5 (SEQ ID NO:67), and wherein the four framework regions of said variable light chain comprise the corresponding framework regions of Vλ2 (SEQ ID NO: 53).

52. The synthetic antibody molecule according to claim 10, wherein the four framework regions of said variable heavy chain comprise the corresponding framework regions of VH5 (SEQ ID NO:67), and wherein the four framework regions of said variable light chain comprise the corresponding framework regions of Vλ3 (SEQ ID NO: 55).

53. The synthetic antibody molecule according to claim 10, wherein the four framework regions of said variable heavy chain comprise the corresponding framework regions of VH6 (SEQ ID NO:69), and wherein the four framework regions of said variable light chain comprise the corresponding framework regions of Vκ1 (SEQ ID NO: 43).

54. The synthetic antibody molecule according to claim 10, wherein the four framework regions of said variable heavy chain comprise the corresponding framework regions of VH6 (SEQ ID NO:69), and wherein the four framework regions of said variable light chain comprise the corresponding framework regions of Vκ2 (SEQ ID NO: 45).

55. The synthetic antibody molecule according to claim 10, wherein the four framework regions of said variable heavy chain comprise the corresponding framework regions of VH6 (SEQ ID NO:69), and wherein the four framework regions of said variable light chain comprise the corresponding framework regions of Vκ3 (SEQ ID NO: 47).

56. The synthetic antibody molecule according to claim 10, wherein the four framework regions of said variable heavy chain comprise the corresponding framework regions of VH6 (SEQ ID NO:69), and wherein the four framework regions of said variable light chain comprise the corresponding framework regions of Vκ4 (SEQ ID NO: 49).

57. The synthetic antibody molecule according to claim 10, wherein the four framework regions of said variable heavy chain comprise the corresponding framework regions of VH6 (SEQ ID NO:69), and wherein the four framework regions of said variable light chain comprise the corresponding framework regions of Vλ1 (SEQ ID NO: 51).

58. The synthetic antibody molecule according to claim 10, wherein the four framework regions of said variable heavy chain comprise the corresponding framework regions of VH6 (SEQ ID NO:69), and wherein the four framework regions of said variable light chain comprise the corresponding framework regions of Vλ2 (SEQ ID NO: 53).

59. The synthetic antibody molecule according to claim 10, wherein the four framework regions of said variable heavy chain comprise the corresponding framework regions of VH6 (SEQ ID NO:69), and wherein the four framework regions of said variable light chain comprise the corresponding framework regions of Vλ3 (SEQ ID NO: 55).

* * * * *